United States Patent
Meazza et al.

(10) Patent No.: US 7,982,047 B2
(45) Date of Patent: Jul. 19, 2011

(54) DERIVATIVES OF 1,3-DIONES HAVING A HERBICIDAL ACTIVITY

(75) Inventors: Giovanni Meazza, Saronno Varese (IT); Piero Paravidino, Sedriano-Milano (IT); Franco Bettarini, Novara (IT); Daniele Forgia, Casaleggio-Novara (IT); Luca Fornara, Cerro Al Lambro-Milano (IT)

(73) Assignee: Isagro Ricerca S.r.l., Milan (IT)

( * ) Notice: Subject to any disclaimer, the term of this patent is extended or adjusted under 35 U.S.C. 154(b) by 0 days.

(21) Appl. No.: 10/573,052

(22) PCT Filed: Sep. 21, 2004

(86) PCT No.: PCT/EP2004/010653
§ 371 (c)(1),
(2), (4) Date: Mar. 22, 2006

(87) PCT Pub. No.: WO2005/030736
PCT Pub. Date: Apr. 7, 2005

(65) Prior Publication Data
US 2007/0015918 A1    Jan. 18, 2007

(30) Foreign Application Priority Data
Sep. 29, 2003   (IT) .............................. MI2003A1855

(51) Int. Cl.
C07D 271/07    (2006.01)
A61K 31/41     (2006.01)
(52) U.S. Cl. ....................................... 548/132; 514/364
(58) Field of Classification Search .................. 548/132; 514/364
See application file for complete search history.

(56) References Cited

FOREIGN PATENT DOCUMENTS

JP    54-119027 A    9/1979
PL    171529         5/1997

OTHER PUBLICATIONS

Yamada et al. (STN abstract of WO 9933796).*
CAPLUS Abstract (Accession # 1928:615) of: Chichibabin, A. E., Berichte der Deutschen Chemischen Gesellschaft [Abteilung] B: Abhandlungen (1927), 60B, 1607-17.*
McElvain et al. (CAPLUS Abstract (Accession # 1941:42347) of: Journal of the American Chemical Society (1941), 63, 2192-7).*
Lee et al., Pestic. Sci. 1998, 54, 377-384.*
CAPLUS Abstract of: Adamsone et al. (Zhurnal Organicheskoi Khimii (1980), 16(4), 830-4).*
International Search Report.
Harris et al, Pesticide Science, vol. 11, No. 4 (1980), pp. 439-444.
Sawicki et al, Journal of Organic Chemistry, vol. 21, (1956) pp. 183-189.
Baumes et al, Journal of Heterocyclic Chemistry, vol. 10, No. 5, (1973) pp. 763-767.
Ghosh et al, Bioorganic and Medicinal Chemisty, vol. 11, No. 4, (2002) pp. 629-657.
Penning et al, Bioorganic and Medicinal Chemisty Letters, vol. 7, No. 16 (1997) pp. 2121-2124.
Stauffer et al, Bioorganic Chemistry, vol. 9, (2001) pp. 141-150.
Lloris et al, Tetrahedron Letters, vol. 31 No. 51, (1990) pp. 7489-7492.
Shoppee et al, Journal of the Chemical Society, (1961) pp. 1311-1321.

* cited by examiner

Primary Examiner — Robert Havlin
(74) Attorney, Agent, or Firm — Hedman & Costigan, P.C.; James V. Costigan

(57) ABSTRACT

A description follows of 1,3-diones having general formula (I): together with their use as herbicides for the control of weeds in agricultural crops.

6 Claims, No Drawings

DERIVATIVES OF 1,3-DIONES HAVING A HERBICIDAL ACTIVITY

The present invention relates to derivatives of 1,3-diones having a herbicidal activity.

The invention also relates to processes for the preparation of the above derivatives of 1,3-diones and their use as herbicides for the control of weeds in agricultural crops.

Various derivatives of 1,3-diones substituted in position 1 and 2 by aromatic and/or heteroaromatic groups are described in J. Indian. Chem. Soc. (1961), vol. 38, pages 343-345, J. Org. Chem. (1962), vol. 27, pages 1899-1901 and Tetrahedron (1963), vol. 19, pages 413-418.

A herbicidal activity has never been described for any of these compounds.

The Applicant has now surprisingly found that derivatives of 1,3-diones, in which the substituents in position 1 and 2 represent suitably substituted aryl, heteroaryl or heterocyclic groups, have a high herbicidal activity with respect to weeds in crops of agrarian interest.

An object of the present invention therefore relates to derivatives of 1,3-diones having general formula (I):

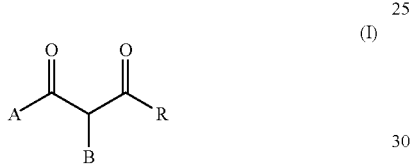

(I)

wherein:

A represents:
an aryl group optionally substituted by one or more substituents selected from halogen, $NO_2$, CN, CHO, OH, linear or branched $C_1$-$C_6$ alkyl, linear or branched $C_1$-$C_6$ haloalkyl, linear or branched $C_1$-$C_6$ alkoxyl, linear or branched $C_1$-$C_6$ haloalkoxyl, $C_1$-$C_6$ cyanoalkyl, $C_2$-$C_6$ alkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ haloalkoxyalkyl, $C_2$-$C_6$ haloalkylthioalkyl, $C_2$-$C_6$ haloalkylsulfinylalkyl, $C_2$-$C_6$ haloalkylsulfonylalkyl, $C_2$-$C_6$ alkoxyalkoxyl or $C_2$-$C_6$ haloalkoxyalkoxyl optionally substituted with a group selected from $C_1$-$C_4$ alkoxyl or $C_1$-$C_4$ haloalkoxyl, $C_2$-$C_6$ alkylthioalkoxyl, $C_2$-$C_6$ haloalkylthioalkoxyl, $C_3$-$C_{12}$ dialkoxyalkyl, $C_3$-$C_{12}$ dialkylthioalkyl, $C_3$-$C_{12}$ dialkylthioalkoxyl, $C_3$-$C_{12}$ dialkoxyalkoxyl, $C_2$-$C_6$ haloalkoxyhaloalkoxyl, $C_3$-$C_{10}$ alkoxyalkoxyalkyl, $C_2$-$C_6$ alkenyl, $C_2$-$C_6$ haloalkenyl, $C_2$-$C_6$ alkenyloxy, $C_2$-$C_6$ haloalkenyloxy, $C_3$-$C_8$ alkenyloxyalkoxyl, $C_3$-$C_8$ haloalkenyloxyalkoxyl, $C_2$-$C_6$ alkynyl, $C_2$-$C_6$ haloalkynyl, $C_2$-$C_6$ alkynyloxy, $C_2$-$C_6$ haloalkynyloxy, $C_3$-$C_8$ alkynyloxyalkoxyl, $C_3$-$C_8$ haloalkynyloxyalkoxyl, $C_3$-$C_{12}$ acylaminoalkoxy, $C_2$-$C_8$ alkoxyiminoalkyl, $C_2$-$C_8$ haloalkoxyiminoalkyl, $C_3$-$C_8$ alkenyloxyiminoalkyl, $C_3$-$C_8$ haloalkenyloxyiminoalkyl, $C_3$-$C_8$ alkynyloxyiminoalkyl, $C_3$-$C_8$ haloalkynyloxyiminoalkyl, $C_5$-$C_{10}$ alkoxyalkynyloxyl, $C_6$-$C_{12}$ cycloalkylideneiminooxyalkyl, $C_6$-$C_{12}$ dialkylideneiminooxyalkyl, —S(O)$_m$R$_1$, —OS(O)$_t$R$_1$, —SO$_2$NR$_2$R$_3$, —CO$_2$R$_4$, —COR$_5$, —CONR$_6$R$_7$, —CSNR$_8$R$_9$, —NR$_{10}$R$_{11}$, —NR$_{12}$COR$_{13}$, —NR$_{14}$CO$_2$R$_{15}$, —NR$_{16}$CONR$_{17}$R$_{18}$, —PO(R$_{19}$)$_2$, -Q, —ZQ$_1$, —(CR$_{20}$R$_{21}$)$_p$Q$_2$, —Z(CR$_{22}$R$_{23}$)$_p$Q$_3$, —(CR$_{24}$R$_{25}$)$_p$ZQ$_4$, —(CR$_{26}$R$_{27}$)$_p$Z(CR$_{28}$R$_{29}$)$_q$Q$_5$, —(CR$_{30}$R$_{31}$)$_p$Z(CR$_{32}$R$_{33}$)$_q$Z$_1$Q$_6$, —Z$_2$(CR$_{34}$R$_{35}$)$_p$(C=Y)T, —Z$_3$(CR$_{36}$R$_{37}$)$_v$(CR$_{38}$R$_{39}$=CR$_{40}$R$_{41}$)(C=Y)T;

or it represents a heterocyclic group selected from pyridyl, pyrimidyl, quinolinyl, pyrazolyl, thiazolyl, oxazolyl, thienyl, furyl, benzothienyl, dihydrobenzothienyl, benzofuranyl, dihydrobenzofuranyl, benzoxazolyl, benzoxazolonyl, benzothiazolyl, benzothiazolonyl, benzoimidazolyl, benzoimidazolonyl, benzotriazolyl, chromanonyl, chromanyl, thiochromanonyl, thiochromanyl, 3a,4-dihydro-3H-indeno[1,2-c]isoxazolyl, 3a,4-dihydro-3H-chromeno[4,3-c]isoxazolyl, 5,5-dioxide-3a,4-dihydro-3H-thiochromeno[4,3-c]isoxazolyl, 2,3,3a,4-tetrahydrochromeno[4,3-c]pyrazolyl, 6,6-dioxide-2,3-dihydro-5H-[1,4]dithiino[2,3-c]thiochromenyl, 5,5-dioxide-2,3,3a,4-tetrahydrothiochromeno[4,3-c]pyrazolyl, 1',1'-dioxide-2',3'-dihydrospiro[1,3-dioxolano-2,4'-thiochromen]-yl, 1,1,4,4-tetraoxide-2,3-dihydro-1,4-benzodithiin-6-yl, 4,4-dioxide-2,3-dihydro-1,4-benzoxathiin-7-yl, 1,1-dioxide-3-oxo-2,3-dihydro-1,2-benzoisothiazol-5-yl, 4-(alkoxyimino)-1,1-dioxide-3,4-dihydro-2H-thiochromen-6-yl, 1,1-dioxide-4-oxo-3,4-dihydro-2H-thiochromen-6-yl, 2,3-dihydro-1,4-benzoxathiin-7-yl, with said groups optionally substituted by one or more substituents selected from halogen, $NO_2$, CN, CHO, OH, linear or branched $C_1$-$C_6$ alkyl, linear or branched $C_1$-$C_6$ haloalkyl, linear or branched $C_1$-$C_6$ alkoxyl, linear or branched $C_1$-$C_6$ haloalkoxyl, $C_1$-$C_6$ cyanoalkyl, $C_2$-$C_6$ alkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ haloalkoxyalkyl, $C_2$-$C_6$ haloalkylthioalkyl, $C_2$-$C_6$ haloalkylsulfinylalkyl, $C_2$-$C_6$ haloalkylsulfonylalkyl, $C_2$-$C_6$ alkoxyalkoxyl or $C_2$-$C_6$ haloalkoxyalkoxyl optionally substituted with a group selected from $C_1$-$C_4$ alkoxyl or $C_1$-$C_4$ haloalkoxyl, $C_2$-$C_6$ alkylthioalkoxyl, $C_2$-$C_6$ haloalkylthioalkoxyl, $C_3$-$C_{12}$ dialkoxyalkyl, $C_3$-$C_{12}$ dialkylthioalkyl, $C_3$-$C_{12}$ dialkylthioalkoxyl, $C_3$-$C_{12}$ dialkoxyalkoxyl, $C_2$-$C_6$ haloalkoxyhaloalkoxyl, $C_3$-$C_{10}$ alkoxyalkoxyalkyl, $C_2$-$C_6$ alkenyl, $C_2$-$C_6$ haloalkenyl, $C_2$-$C_6$ alkenyloxy, $C_2$-$C_6$ haloalkenyloxy, $C_3$-$C_8$ alkenyloxyalkoxyl, $C_3$-$C_8$ haloalkenyloxyalkoxyl, $C_2$-$C_6$ alkynyl, $C_2$-$C_6$ haloalkynyl, $C_2$-$C_6$ alkynyloxy, $C_2$-$C_6$ haloalkynyloxy, $C_3$-$C_8$ alkynyloxyalkoxyl, $C_3$-$C_8$ haloalkynyloxyalkoxyl, $C_3$-$C_{12}$ acylaminoalkoxy, $C_2$-$C_8$ alkoxyiminoalkyl, $C_2$-$C_8$ haloalkoxyiminoalkyl, $C_3$-$C_8$ alkenyloxyiminoalkyl, $C_3$-$C_8$ haloalkenyloxyiminoalkyl, $C_3$-$C_8$ alkynyloxyiminoalkyl, $C_3$-$C_8$ haloalkynyloxyiminoalkyl, $C_5$-$C_{10}$ alkoxyalkynyloxyl, $C_6$-$C_{12}$ cycloalkylideneiminooxyalkyl, $C_6$-$C_{12}$ dialkylideneiminooxyalkyl, —S(O)$_m$R$_1$, —OS(O)$_t$R$_1$, —SO$_2$NR$_2$R$_3$, —CO$_2$R$_4$, —COR$_5$, —CONR$_6$R$_7$, —CSNR$_8$R$_9$, —NR$_{10}$R$_{11}$, —NR$_{12}$COR$_{13}$, —NR$_{14}$CO$_2$R$_{15}$, —NR$_{16}$CONR$_{17}$R$_{18}$, —PO(R$_{19}$)$_2$, -Q, —ZQ$_1$, —(CR$_{20}$R$_{21}$)$_p$Q$_2$, —Z(CR$_{22}$R$_{23}$)$_p$Q$_3$, —(CR$_{24}$R$_{25}$)$_p$ZQ$_4$, —(CR$_{26}$R$_{27}$)$_p$Z(CR$_{28}$R$_{29}$)$_q$Q$_5$, —(CR$_{30}$R$_{31}$)$_p$Z(CR$_{32}$R$_{33}$)$_q$Z$_1$Q$_6$, —Z$_2$(CR$_{34}$R$_{35}$)$_p$(C=Y)T, —Z$_3$(CR$_{36}$R$_{37}$)$_v$(CR$_{38}$R$_{39}$=CR$_{40}$R$_{41}$)(C=Y)T;

B represents a D-(R$_x$)$_n$ group;

R represents a hydrogen atom, a linear or branched $C_1$-$C_6$ alkyl group, a linear or branched $C_1$-$C_6$ haloalkyl group, a $C_3$-$C_6$ cycloalkyl or $C_4$-$C_{12}$ cycloalkylalkyl group optionally substituted with halogen atoms or $C_1$-$C_6$ alkyl or $C_1$-$C_6$ thioalkyl or $C_1$-$C_6$ alkoxyl or $C_2$-$C_6$ alkoxycarbonyl groups, $C_2$-$C_6$ alkenyl groups, $C_2$-$C_6$ alkynyl groups, the latter two groups, in turn, optionally substituted with halogen atoms, a $C_5$-$C_6$ cycloalkenyl group optionally substituted with halogen atoms or $C_1$-$C_6$ alkyl groups, an aryl or arylalkyl group optionally substituted;

$R_1$ and $R_{19}$ represent a $C_1$-$C_6$ alkyl group or a $C_1$-$C_6$ haloalkyl group, a $C_3$-$C_6$ cycloalkyl group, an aryl group optionally substituted by one or more substituents selected from halogen, $NO_2$, CN, CHO, linear or branched $C_1$-$C_6$ alkyl, linear or branched $C_1$-$C_6$ haloalkyl, linear or branched $C_1$-$C_6$ alkoxyl, linear or branched $C_1$-$C_6$ haloalkoxyl, $C_1$-$C_6$ alkylsulfonyl, $C_2$-$C_6$ alkoxycarbonyl;

m is equal to 0, 1 or 2;

t is equal to 1 or 2;

$R_2$, $R_3$, $R_6$, $R_7$, $R_8$, $R_9$, $R_{10}$, $R_{11}$, $R_{17}$ and $R_{18}$, the same or different, represent a hydrogen atom, a linear or branched $C_1$-$C_6$ alkyl group in turn optionally substituted with halogen atoms, a $C_1$-$C_6$ alkoxyl group, a $C_3$-$C_6$ cycloalkyl group, an arylalkyl group or an aryl group, said arylalkyl and aryl groups also optionally substituted by one or more substituents selected from halogen, $NO_2$, CN, CHO, linear or branched $C_1$-$C_6$ alkyl, linear or branched $C_1$-$C_6$ haloalkyl, linear or branched $C_1$-$C_6$ alkoxyl, linear or branched $C_1$-$C_6$ haloalkoxyl, $C_1$-$C_6$ alkylsulfonyl, $C_2$-$C_6$ alkoxycarbonyl, or they jointly represent a $C_2$-$C_5$ alkylene group;

$R_4$, $R_5$ and $R_{42}$ represent a hydrogen atom, a linear or branched $C_1$-$C_6$ alkyl group in turn optionally substituted with halogen atoms, a $C_3$-$C_6$ alkenyl group in turn optionally substituted with halogen atoms, a $Q_7$ group, an arylalkyl group optionally substituted by one or more substituents selected from halogen, $NO_2$, CN, CHO, linear or branched $C_1$-$C_6$ alkyl, linear or branched $C_1$-$C_6$ haloalkyl, linear or branched $C_1$-$C_6$ alkoxyl, linear or branched $C_1$-$C_6$ haloalkoxyl, $C_1$-$C_6$ alkylsulfonyl, $C_2$-$C_6$ alkoxycarbonyl;

$R_{12}$, $R_{14}$ and $R_{16}$ represent a hydrogen atom, a linear or branched $C_1$-$C_6$ alkyl group in turn optionally substituted with halogen atoms, a $C_3$-$C_6$ cycloalkyl group, a $C_1$-$C_6$ alkoxyl group, a $C_1$-$C_6$ haloalkoxyl group;

$R_{13}$ and $R_{15}$ represent a hydrogen atom, a linear or branched $C_1$-$C_6$ alkyl group in turn optionally substituted with halogen atoms, a $C_3$-$C_6$ alkenyl group in turn optionally substituted with halogen atoms, a $Q_7$, $NH_2$, NHCN, $NHNH_2$, NHOH group, an arylalkyl group optionally substituted by one or more substituents selected from halogen, $NO_2$, CN, CHO, linear or branched $C_3$-$C_6$ alkyl, linear or branched $C_1$-$C_6$ haloalkyl, linear or branched $C_1$-$C_6$ alkoxyl, linear or branched $C_1$-$C_6$ haloalkoxyl, $C_1$-$C_6$ alkylsulfonyl, $C_2$-$C_6$ alkoxycarbonyl;

$R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$ and $R_{41}$, the same or different, represent a hydrogen atom, a linear or branched $C_1$-$C_6$ alkyl group in turn optionally substituted with halogen atoms, a $C_1$-$C_6$ alkoxyl group, or the two groups attached to the same carbon atom can be joined to each other by $C_2$-$C_5$ alkylene groups, the alkylene groups can in turn be substituted with $C_1$-$C_3$ alkyl groups;

Q, $Q_1$, $Q_2$, $Q_3$, $Q_4$, $Q_5$, $Q_6$ and $Q_7$ represent an aryl group, a $C_3$-$C_6$ cycloalkyl group, a $C_5$-$C_6$ cycloalkenyl group, a heterocyclic group selected from triazolyl, triazolonyl, pyrazolyl, imidazolyl, imidazolidinonyl, tetrazolyl, tetrazolonyl, isoxazolyl, furyl, thienyl, pyrrolyl, pyrrolidinyl, pyrrolidinonyl, pyridyl, pyrimidinyl, pyrimidinonyl, pyrazinyl, pyridazinyl, oxazolyl, thiazolyl, oxadiazolyl, thiadiazolyl, isothiazolyl, benzoxazolyl, benzothiazolyl, isoxazolinyl, 1,3-dioxanyl, 1,4-dioxanyl, 1,3-dioxolanyl, tetrahydropyranyl, oxethanyl, oxyranyl, thiazolidinyl, oxazolidinyl, piperidinyl, piperidinonyl, piperazinyl, morpholinyl, thiazinyl, tetrahydrofuranyl, dioxazolyl, tetrahydrofuroisoxazolyl, 2-oxa-3-azabicyclo[3.1.0]hex-3-enyl, said groups optionally substituted by one or more substituents selected from halogen, $NO_2$, OH, CN, CHO, linear or branched $C_1$-$C_6$ alkyl, linear or branched $C_1$-$C_6$ haloalkyl, linear or branched $C_3$-$C_6$ alkoxyl, linear or branched $C_1$-$C_6$ haloalkoxyl, $C_1$-$C_6$ cyanoalkyl, $C_2$-$C_6$ alkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ haloalkoxyalkyl, $C_2$-$C_6$ haloalkylthioalkyl, $C_2$-$C_6$ haloalkylsulfinylalkyl, $C_2$-$C_6$ haloalkylsulfonylalkyl, $C_2$-$C_6$ alkoxyalkoxyl or $C_2$-$C_6$ haloalkoxyalkoxyl optionally substituted with a group selected from $C_1$-$C_4$ alkoxyl or $C_1$-$C_4$ haloalkoxyl, $C_2$-$C_6$ alkylthioalkoxyl, $C_2$-$C_6$ haloalkylthioalkoxyl, $C_3$-$C_{12}$ dialkoxyalkyl, $C_3$-$C_{12}$ dialkylthioalkyl, $C_3$-$C_{12}$ dialkylthioalkoxyl, $C_3$-$C_{12}$ dialkoxyalkoxyl, $C_2$-$C_6$ haloalkoxyhaloalkoxyl, $C_3$-$C_{10}$ alkoxyalkoxyalkyl, $C_2$-$C_6$ alkenyl, $C_2$-$C_6$ haloalkenyl, $C_2$-$C_6$ alkenyloxy, $C_2$-$C_6$ haloalkenyloxy, $C_3$-$C_8$ alkenyloxyalkoxyl, $C_3$-$C_8$ haloalkenyloxyalkoxyl, $C_2$-$C_6$ alkynyl, $C_2$-$C_6$ haloalkynyl, $C_2$-$C_6$ alkynyloxy, $C_2$-$C_6$ haloalkynyloxy, $C_3$-$C_8$ alkynyloxyalkoxyl, $C_3$-$C_8$ haloalkynyloxyalkoxyl, $C_3$-$C_{12}$ acylaminoalkoxy, $C_2$-$C_8$ alkoxyiminoalkyl, $C_2$-$C_8$ haloalkoxyiminoalkyl, $C_3$-$C_8$ alkenyloxyiminoalkyl, $C_3$-$C_8$ haloalkenyloxyiminoalkyl, $C_3$-$C_8$ alkynyloxyiminoalkyl, $C_3$-$C_8$ haloalkynyloxyiminoalkyl, $C_5$-$C_{10}$ alkoxyalkynyloxyl, $C_6$-$C_{12}$ cycloalkylideneiminooxyalkyl, $C_6$-$C_{12}$ dialkylideneiminooxyalkyl, aryl optionally substituted, —$S(O)_mR_1$, —$OS(O)_tR_1$, —$SO_2NR_2R_3$, —$CO_2R_4$, —$COR_5$, —$CONR_6R_7$, —$CSNR_8R_9$, —$NR_{10}R_{11}$, —$NR_{12}COR_{13}$, —$NR_{14}CO_2R_{15}$, —$NR_{16}CONR_{17}R_{18}$, —$PO(R_{19})_2$, —$Z_2(CR_{34}R_{35})_p(C=Y)T$, —$Z_3(CR_{36}R_{37})_v(CR_{38}R_{39}=CR_{40}R_{41})(C=Y)T$;

Z, $Z_1$, $Z_2$=O, $S(O)_r$;

Y=O, S;

r is equal to 0, 1 or 2;

p, q are equal to 1, 2, 3 or 4;

v is equal to 0 or 1;

$Z_3$=O, S or a direct bond;

T represents a hydrogen atom, a $Z_4R_{42}$ group, a —$NR_{43}R_{44}$ group, an aryl group or a heterocyclic group selected from triazolyl, triazolonyl, pyrazolyl, imidazolyl, imidazolidinonyl, tetrazolyl, tetrazolonyl, pyrrolyl, pyrrolidinyl, pyrrolidinonyl, pyridyl, pyrimidinyl, piperidinyl, piperidinonyl, piperazinyl, morpholinyl, said groups optionally substituted by one or more substituents selected from halogen, $NO_2$, OH, CN, CHO, linear or branched $C_1$-$C_6$ alkyl, linear or branched $C_1$-$C_6$ haloalkyl, $C_3$-$C_6$ cycloalkyl, $C_5$-$C_6$ cycloalkenyl, linear or branched $C_1$-$C_6$ alkoxyl, linear or branched $C_1$-$C_6$ haloalkoxyl, $C_1$-$C_6$ cyanoalkyl, $C_2$-$C_6$ alkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ haloalkoxyalkyl, $C_2$-$C_6$ haloalkylthioalkyl, $C_2$-$C_6$ haloalkylsulfinylalkyl, $C_2$-$C_6$ haloalkylsulfonylalkyl, —$S(O)_mR_1$;

$Z_4$=O, S or a direct bond;

$R_{43}$ and $R_{44}$, the same or different, represent a hydrogen atom, a linear or branched $C_1$-$C_6$ alkyl group in turn optionally substituted with halogen atoms, a $C_3$-$C_6$ alkenyl group in turn optionally substituted with halogen atoms, a $Q_7$ group, an arylalkyl group optionally substituted by one or more substituents selected from halogen, $NO_2$, CN, CHO, linear or branched $C_1$-$C_6$ alkyl, linear or branched $C_1$-$C_6$ haloalkyl, linear or branched $C_1$-$C_6$ alkoxyl, linear or branched $C_1$-$C_6$ haloalkoxyl, $C_1$-$C_6$ alkylsulfonyl, $C_2$-$C_6$ alkoxycarbonyl, or they jointly represent a $C_2$-$C_5$ alkylene chain;

D represents:
a heterocyclic group of the heteroaryl or heterocyclic type, in all the above cases the heterocycle can be mono or polycyclic and can be connected to the rest of the structure either through one of its carbon atoms or, when possible, through one of its nitrogen atoms;
or it represents a mono or polycyclic aryl group, in this latter case, the group can also be partially saturated;

$R_x$ represents a substituent selected from hydrogen, halogen, $NO_2$, CN, CHO, OH, linear or branched $C_1$-$C_6$ alkyl, linear or branched $C_1$-$C_6$ haloalkyl, linear or branched $C_1$-$C_6$ alkoxyl, linear or branched $C_1$-$C_6$ haloalkoxyl, $C_1$-$C_6$ cyanoalkyl, $C_2$-$C_6$ alkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ haloalkoxyalkyl, $C_2$-$C_6$ haloalkylthioalkyl, $C_2$-$C_6$ haloalkylsulfinylalkyl, $C_2$-$C_6$ haloalkylsulfonylalkyl, $C_2$-$C_6$ alkoxyalkoxyl or $C_2$-$C_6$ haloalkoxyalkoxyl optionally substituted with a group selected from $C_1$-$C_4$ alkoxyl or $C_1$-$C_4$ haloalkoxyl, $C_2$-$C_6$ haloalkylthioalkoxyl, $C_3$-$C_{12}$ dialkoxyalkyl, $C_3$-$C_{12}$ dialkylthioalkyl, $C_3$-$C_{12}$ dialkylthioalkoxyl, $C_3$-$C_{12}$ dialkoxyalkoxyl, $C_2$-$C_6$ haloalkoxyhaloalkoxyl, $C_3$-$C_{10}$ alkoxyalkoxyalkyl, $C_2$-$C_6$ alkenyl, $C_2$-$C_6$ haloalkenyl, $C_2$-$C_6$ alkenyloxy, $C_2$-$C_6$ haloalkenyloxy, $C_3$-$C_8$ alkenyloxyalkoxy, $C_3$-$C_8$ haloalkenyloxyalkoxy, $C_2$-$C_6$ alkynyl, $C_2$-$C_6$ haloalkynyl, $C_2$-$C_6$ alkynyloxy, $C_2$-$C_6$ haloalkynyloxy, $C_3$-$C_8$ alkynyloxyalkoxy, $C_3$-$C_8$ haloalkynyloxyalkoxy, $C_3$-$C_{12}$ acylaminoalkoxy, $C_2$-$C_8$ alkoxyiminoalkyl, $C_2$-$C_8$ haloalkoxyiminoalkyl, $C_3$-$C_8$ alkenyloxyiminoalkyl, $C_3$-$C_8$ haloalkenyloxyiminoalkyl, $C_3$-$C_8$ alkynyloxyiminoalkyl, $C_3$-$C_8$ haloalkynyloxyiminoalkyl, $C_5$-$C_{10}$ alkoxyalkynyloxyl, $C_6$-$C_{12}$ cycloalkylideneiminooxyalkyl, $C_6$-$C_{12}$ dialkylideneiminooxyalkyl, —S(O)$_m$R$_1$, —OS(O)$_t$R$_1$, —SO$_2$NR$_2$R$_3$, —CO$_2$R$_4$, —COR$_5$, —CONR$_6$R$_7$, —CSNR$_8$R$_9$, —NR$_{10}$R$_{11}$, —NR$_{12}$COR$_{13}$, —NR$_{14}$CO$_2$R$_{15}$, —NR$_{16}$CONR$_{17}$R$_{18}$, —PO(R$_{19}$)$_2$, -Q, —ZQ$_1$, —(CR$_{20}$R$_{21}$)$_p$Q$_2$, —Z(CR$_{22}$R$_{23}$)$_p$Q$_3$, —(CR$_{24}$R$_{25}$)$_p$ZQ$_4$, —(CR$_{26}$R$_{27}$)$_p$Z(CR$_{28}$R$_{29}$)$_q$Q$_5$, —(CR$_{30}$R$_{31}$)$_p$Z(CR$_{32}$R$_{33}$)$_q$Z$_1$Q$_6$, -Z$_2$(CR$_{34}$R$_{35}$)$_p$(C=Y)T, —Z$_3$(CR$_{36}$R$_{37}$)$_v$(CR$_{38}$R$_{39}$=CR$_{40}$R$_{41}$)(C=Y)T;
if several $R_x$ groups are present, these can be the same or different;
n=1-9;

excluding the following compounds having general formula (I) wherein A, B and R have the following meanings:
A=4-chlorophenyl, B=1-methylimidazol-2-yl, R=H;
A=4-nitrophenyl, B=1-(2-hydroxyethyl)-5-nitroimidazol-2-yl, R=H;
A=phenyl, B-1H-benzimidazol-2-yl, R=$C_2H_5$;
A=phenyl, B=4H-1-benzopyran-4-yl, R=$CH_3$;
A=4-nitrophenyl, B=3-(4-methylphenyl)-1,2,4-oxadiazol-5-yl, R=$CH_3$;
A=phenyl, B=4-chloro-2,5-dioxo-2,5-dihydro-1H-pyrrol-3-yl, R=$CH_3$;
A=phenyl, B=2-acetyl-1,2,3,4-tetrahydroisoquinolin-1-yl, R=$C_2H_5$;
A=2-hydroxy-4-methoxyphenyl, B=thiazol-4-yl, R=$CH_3$;
A=phenyl, B=2,5-diphenyl-1,3-oxathiol-2-yl, R=$CH_3$;
A=4-nitrophenyl, B=4,6-bis(dimethylamino)-1,3,5-triazin-2-yl, R=$CH_3$;
A=phenyl, B=furan-2-yl, R=$CH_3$;
A=phenyl, B=1,3-dithian-2-yl, R=$CH_3$;
A=phenyl, B=4-chlorothien-2-yl, R=H;
A=phenyl, B=5-bromothien-2-yl, R=H;
A=phenyl, B=5-methylthien-2-yl, R=H;
A=phenyl, B=6-phenylpyrazin-2-yl, R=$CH_3$;
A=phenyl, B=3,4-dihydro-3-methyl-2-oxo-2H-1,3-benzoxazin-4-yl, R=$CH_3$;
A=phenyl, B=benzothiazol-2-yl, R=$CH_3$;
A=2-hydroxy-4-methoxyphenyl, B=2-phenylthiazol-4-yl, R=$CH_3$;
A=phenyl, B=5-methylfuran-2-yl, R=$CH_3$;
A=phenyl, B=3-(4-methylphenyl)-1,2,4-oxadiazol-5-yl, R=$CH_3$;
A=phenyl, B=tetrahydrofuran-2-yl, R=$CH_3$;
A=phenyl, B=2,3-dihydro-3-hydroxy-2-oxo-1H-indol-3-yl, R=$CH_3$,
A=phenyl, B=4-chloro-1-methyl-2,5-dioxo-2,5-dihydropyrrol-3-yl, R=$CH_3$;
A=phenyl, B=2-trifluoroacetyl-1,2,3,4-tetrahydroisoquinolin-1-yl, R=$C_2H_5$;
A=phenyl, B=2-acetyl-1,2,3,4-tetrahydroisoquinolin-1-yl, R=$CH_3$;
A=4-nitrophenyl, B=2-(4-nitrophenyl)-3,5,6-triphenyl-pyridin-4-yl, R=$CH_3$;
A=phenyl, B=4,6-bis(dimethylamino)-1,3,5-triazin-2-yl, R=$CH_3$;
A=phenyl, B=4-methoxy-5-tert-butoxycarbonyl-1H-pyrro-2-yl, R=$CH_3$;
A=phenyl, B=1,3-dihydro-3-oxo-isobenzofuran-1-yl, R=$CH_3$;
A=phenyl, B=(5-methoxycarbonylmethyl)thien-2-yl, R=H;
A=phenyl, B=4-methylthien-2-yl, R=H;
A=phenyl, B=1,4-dihydro-1-methyl-3-nitroquinolin-4-yl, R=H;
A=phenyl, B=thien-2-yl, R=H;
A=phenyl, B=6-methylbenzothiazol-2-yl, R=$CH_3$;
A=2-methoxycarbonylphenyl, B=phenyl, R=$CH_3$;
A=2-benzyloxy-4-methoxyphenyl, B=2,3,4-trimethoxyphenyl, R=H;
A=4,5-dimethoxy-2-nitrophenyl, B=3,4-dimethoxyphenyl, R=H;
A=2-nitrophenyl, B=phenyl, R=H;
A=2,4,5-trimethoxyphenyl, B=4-methoxyphenyl, R=H;
A=4-bromophenyl, B=phenyl, R=H;
A=4-bromophenyl, B=2,4-dinitrophenyl, R=$CH_3$;
A=4-chlorophenyl, B=phenyl, R=H;
A=2,4-dibenzyloxy-5-methoxyphenyl, B=1,3-benzodioxol-5-yl, R=H;
A=2,4-dibenzyloxyphenyl, B=1,3-benzodioxol-5-yl, R=H;
A=4-methoxyphenyl, B=2-carboxyphenyl, R=H;
A=4-methylphenyl, B-2,4-dinitrophenyl, R=$CH_3$;
A=4-hydroxy-3-methoxyphenyl, B=4-hydroxy-3-methoxyphenyl, R=H;
A=2-nitrophenyl, B=4-methylphenyl, R=H;
A=4-chlorophenyl, B=4-chlorophenyl, R=H;
A=2,4-diacetoxyphenyl, B=phenyl, R=$CH_3$;
A=3-methoxyphenyl, B=phenyl, R=$C_2R_5$;
A=4-nitrophenyl, B=phenyl, R=H;
A=2-nitrophenyl, B=4-n-butoxyphenyl, R=H;
A=2-nitro-4-chlorophenyl, B=4-methylphenyl, R=H;
A=phenyl, B=8-carboxynaphthalenyl, R=$CH_3$;
A=2,5-dimethoxyphenyl, B=2-hydroxyphenyl, R=$C_2H_5$;
A=4-fluorophenyl, B=2-nitro-4-trifluoromethylphenyl, R=$CH_3$;
A=3-chloro-4-methylphenyl, B=2,4-dinitrophenyl, R=$CH_3$;
A=2-nitro-4-chlorophenyl, B=phenyl, R=H;
A=4,5-dimethoxy-2-nitrophenyl, B=4-methylphenyl, R=H;

A=2-carboxy-6-nitrophenyl, B=phenyl, R=CH$_3$;
A=2,4,5-trimethoxyphenyl, B=3-methoxyphenyl, R=H;
A=phenyl, B=4-bromophenyl, R=H;
A=6-benzyloxy-2,3,4-trimethoxyphenyl, B=1,3-benzodioxol-5-yl, R=H;
A=4,5-dimethoxy-2-nitrophenyl, B=4-methoxyphenyl, R=H;
A=4,5-dimethoxy-2-nitrophenyl, B=4-chlorophenyl, R=H;
A=2,4-dibenzyloxyphenyl, B=4-methoxyphenyl, R=H;
A=4-methylphenyl, B=4-methylphenyl, R=H;
A=4-dimethylaminophenyl, B=phenyl, R=H;
A=4-methoxyphenyl, B=phenyl, R=H;
A=4,5-dichloro-2-nitrophenyl, B=4-chlorophenyl, R=H;
A=2-nitrophenyl, B=4-methoxyphenyl, R=H;
A=phenyl, B=2,5-dimethoxycarbonylaminophenyl, R=CH$_3$;
A=4-hydroxy-4-methoxyphenyl, B=2-methoxyphenyl, R=H;
A=phenyl, B=4-methylphenyl, R=H;
A=2-nitrophenyl, B=4-ethoxyphenyl, R=H;
A=2-nitro-4-chlorophenyl, B=4-methoxyphenyl, R=H;
A=4-chlorophenyl, B-phenyl, R=C$_2$H$_5$;
A=2-t-butoxycarbonyl-5-ethyl-4-methoxyphenyl, B=2,3-dihydro-7-methyl-1,4-benzodioxin-6-yl, R=t-butyl;
A=phenyl, B=2-nitro-4-trifluoromethylphenyl, R=CH$_3$;
A=3,4-dichlorophenyl, B=2,4-dinitrophenyl, R=CH$_3$;
A=4,5-dichloro-2-nitrophenyl, B=4-methoxyphenyl, R=H;
A=4-methoxy-2-nitrophenyl, B=4-methylphenyl, R=H;
A=phenyl, B=anthracene-9-yl, R=CH$_3$;
A=phenyl, B=4-methoxyphenyl, R=H;
A=2,4,5-trimethoxyphenyl, B=phenyl, R=H;
A=2,4-diacetoxyphenyl, B=2,4,5-trimethoxyphenyl, R=CH$_3$;
A=2-hydroxyphenyl, B=phenyl, R=H;
A=4-methoxy-2-nitrophenyl, B=phenyl, R=H;
A=4,5-dimethoxy-2-nitrophenyl, B=phenyl, R=H;
A=2,4-dinitrophenyl, B=phenyl, R=CH$_3$;
A=phenyl, B=phenyl, R=CH$_3$;
A=phenyl, B=4-dimethylaminophenyl, R=H;
A=phenyl, B=2,4-dinitrophenyl, R=CH$_3$;
A=4,5-dichloro-2-nitrophenyl, B=4-methylphenyl, R=H;
A=4-bromophenyl, B=phenyl, R=CH$_3$;
A=2-(4-methylphenylsulfonyloxy)-6-methoxyphenyl, B=phenyl, R=H;
A=4-methylsulfonylphenyl, B=2-methoxyphenyl, R=CH$_3$;
A=4-methoxyphenyl, B=4-methoxyphenyl, R=CH$_3$;
A=phenyl, B=4-chlorophenyl, R=H;
A=2-nitrophenyl, B=4-nitrophenyl, R=H;
A=phenyl, B=phenyl, R=H;
A=2,4-dimethoxyphenyl, B=4-methoxyphenyl, R=H;
A=2-nitrophenyl, B=4-n-hexyloxyphenyl, R=H;
A=4-methoxy-2-nitrophenyl, B=4-methoxyphenyl, R=H;
A=phenyl, B=9-carboxyphenanthren-10-yl, R=CH$_3$;
A=phenyl, B=phenyl, R=CH$_3$;
A=3,4-dimethoxyphenyl, B=3,4-dimethoxyphenyl, R=H;
A=2,4-dimethoxyphenyl, B=phenyl, R=H;
A=phenyl, B=2-hydroxy-3,4,6-trimethyl-5-methoxyphenyl, R=CH$_3$;
A=4-chloro-2-nitrophenyl, B=4-chlorophenyl, R=H;
A=2-nitrophenyl, B=4-chlorophenyl, R=H;
A=2,4,5-trimethoxyphenyl, B=3,4-dimethoxyphenyl, R=H;
A=4-chlorophenyl, B=2,4-dinitrophenyl, R=CH$_3$;
A=4,5-dichloro-2-nitrophenyl, B=phenyl, R=H;
A=4-methoxyphenyl, B=phenyl, R=CH$_3$;
A=2,4-dibenzyloxyphenyl, B=3,4-dimethoxyphenyl, R=H;
A=4-methylthiophenyl, B-4-methoxyphenyl, R=H;
A=phenyl, B=phenyl, R=C$_2$H$_5$;
A=4-methoxyphenyl, B=2,4-dinitrophenyl, R=CH$_3$;
A=2-nitrophenyl, B=3-chlorophenyl, R=H;
A=2-nitrophenyl, B=3,4-dimethoxyphenyl, R=H;
A=4-methoxyphenyl, B=4-methoxyphenyl, R=H;
A=2-hydroxyphenyl, B=4-methoxyphenyl, R=H;
A=phenyl, B=2,5-bis(phenacylamino)phenyl, R=CH$_3$;
A=4-nitrophenyl, B=4-methylphenyl, R=H;
A=2-nitrophenyl, B=4-n-pentyloxyphenyl, R=H;
A=4-methoxy-2-nitrophenyl, B=4-chlorophenyl, R=H;
A=phenyl, B=2-carboxynaphthalen-1-yl, R=CH$_3$.

A further object of the present invention relates to the use of derivatives of 1,3-diones having general formula (I)

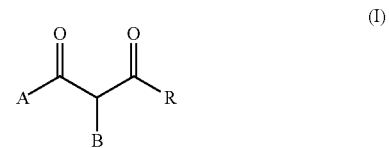

wherein:
A represents:
an aryl group possibly substituted by one or more substituents selected from halogen, NO$_2$, CN, CHO, OH, linear or branched C$_1$-C$_6$ alkyl, linear or branched C$_1$-C$_6$ haloalkyl, linear or branched C$_1$-C$_6$ alkoxyl, linear or branched C$_1$-C$_6$ haloalkoxyl, C$_1$-C$_6$ cyanoalkyl, C$_2$-C$_6$ alkoxyalkyl, C$_2$-C$_6$ alkylthioalkyl, C$_2$-C$_6$ alkylsulfinylalkyl, C$_2$-C$_6$ alkylsulfonylalkyl, C$_2$-C$_6$ haloalkoxyalkyl, C$_2$-C$_6$ haloalkylthioalkyl, C$_2$-C$_6$ haloalkylsulfinylalkyl, C$_2$-C$_6$ haloalkylsulfonylalkyl, C$_2$-C$_6$ alkoxyalkoxyl or C$_2$-C$_6$ haloalkoxyalkoxyl possibly substituted with a C$_1$-C$_4$ alkoxyl or C$_1$-C$_4$ haloalkoxyl group, C$_2$-C$_6$ alkylthioalkoxyl, C$_2$-C$_6$ haloalkylthioalkoxyl, C$_3$-C$_{12}$ dialkoxyalkyl, C$_3$-C$_{12}$ dialkylthioakyl, C$_3$-C$_{12}$ dialkylthioalkoxyl, C$_3$-C$_{12}$ dialkoxyalkoxyl, C$_2$-C$_6$ haloalkoxyhaloalkoxyl, C$_3$-C$_{10}$ alkoxyalkoxyalkyl, C$_2$-C$_6$ alkenyl, C$_2$-C$_6$ haloalkenyl, C$_2$-C$_6$ alkenyloxy, C$_2$-C$_6$ haloalkenyloxy, C$_3$-C$_8$ alkenyloxyalkoxyl, C$_3$-C$_8$ haloalkenyloxyalkoxyl, C$_2$-C$_6$ alkynyl, C$_2$-C$_6$ haloalkynyl, C$_2$-C$_6$ alkynyloxy, C$_2$-C$_6$ haloalkynyloxy, C$_3$-C$_8$ alkynyloxyalkoxyl, C$_3$-C$_8$ haloalkynyloxyalkoxyl, C$_3$-C$_{12}$ acylaminoalkoxy, C$_2$-C$_8$ alkoxyiminoalkyl, C$_2$-C$_8$ haloalkoxyiminoalkyl, C$_3$-C$_8$ alkenyloxyiminoalkyl, C$_3$-C$_8$ haloalkenyloxyiminoalkyl, C$_3$-C$_8$ alkynyloxyiminoalkyl, C$_3$-C$_8$ haloalkynyloxyiminoalkyl, C$_5$-C$_{10}$ alkoxyalkynyloxyl, C$_6$-C$_{12}$ cycloalkylideneiminooxyalkyl, C$_6$-C$_{12}$ dialkylideneiminooxyalkyl, —S(O)$_m$R$_1$, —OS(O)$_t$R$_1$, SO$_2$NR$_2$R$_3$, —CO$_2$R$_4$, —COR$_5$, —CONR$_6$R$_7$, —CSNR$_8$R$_9$, —NR$_{10}$R$_{11}$, —NR$_{12}$COR$_{13}$, —NR$_{14}$CO$_2$R$_{15}$, —NR$_{16}$CONR$_{17}$R$_{18}$, —PO(R$_{19}$)$_2$, -Q, —ZQ$_1$, —(CR$_{20}$R$_{21}$)$_p$Q$_2$, —Z(CR$_{22}$R$_{23}$)$_p$Q$_3$, —(CR$_{24}$R$_{25}$)$_p$ZQ$_4$, —(CR$_{26}$R$_{27}$)$_p$Z(CR$_{28}$R$_{29}$)$_q$Q$_5$, —(CR$_{30}$R$_{31}$)$_p$Z(CR$_{32}$R$_{33}$)$_q$Z$_1$Q$_6$, —Z$_2$(CR$_{34}$R$_{35}$)$_p$(C=Y)T, —Z$_3$(CR$_{36}$R$_{39}$=CR$_{40}$R$_{41}$)(C=Y)T;

or represents a heterocyclic group selected from pyridyl, pyrimidyl, quinolinyl, pyrazolyl, thiazolyl, oxazolyl, thienyl, furyl, benzothienyl, dihydrobenzothienyl, benzofuranyl, dihydrobenzofuranyl, benzoxazolyl, benzoxazolonyl, benzothiazolyl, benzothiazolonyl, benzoimidazolyl, benzoimidazolonyl, benzotriazolyl, chromanonyl, chromanyl, thiochromanonyl, thiochromanyl, 3a,4-dihydro-3H-indeno[1,2-C]isoxazolyl, 3a,4-dihydro-3H-chromeno[4,3-C]isoxazolyl, 5,5-dioxide-3a,4-dihydro-3H-thiochromeno[4,3-C]isoxazolyl, 2,3,3a,4-tetrahydrochromeno[4,3-C]pyrazolyl, 6,6-dioxide-2,3-dihydro-5H-[1,4]dithiino[2,3-C]thiochromenyl, 5,5-dioxide-2,3,3a,4-tetrahydrothiochromeno[4,3-c]pyrazolyl, 1',1'-dioxide-2',3'-dihydrospiro[1,3-dioxolane-2,4'-thiochromen]-yl, 1,1,4,4-tetraoxide-2,3-dihydro-1,4-benzodithiin-6-yl 4,4-dioxide-2,3-dihydro-1,4-benzoxathiin-7-yl, 1,1-dioxide-3-oxo-2,3-dihydro-1,2-benzoisothiazol-5-yl, 4-(alkoxyimino)-1,1-dioxide-3,4-dihydro-2H-thiochromen-6-yl, 1,1-dioxide-4-oxo-3,4-dihydro-2H-thiochromen-6-yl, 2,3-dihydro-1,4-benzoxathiin-7-yl, with all these groups possibly substituted by one or more substituents selected from halogen, $NO_2$, CN, CHO, OH, linear or branched $C_1$-$C_6$ alkyl, linear or branched $C_1$-$C_6$ haloalkyl, linear or branched $C_1$-$C_6$ alkoxyl, linear or branched $C_1$-$C_6$ haloalkoxyl, $C_1$-$C_6$ cyanoalkyl, $C_2$-$C_6$ alkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ haloalkoxyalkyl, $C_2$-$C_6$ haloalkylthioalkyl, $C_2$-$C_6$ haloalkylsulfinylalkyl, $C_2$-$C_6$ haloalkylsulfonylalkyl, $C_2$-$C_6$ alkoxyalkoxyl or $C_2$-$C_6$ haloalkoxyalkoxyl, possibly substituted with a $C_1$-$C_4$ alkoxyl or $C_1$-$C_4$ haloalkoxyl group, $C_2$-$C_6$ alkylthioalkoxyl, $C_2$-$C_6$ haloalkylthioalkoxyl, $C_3$-$C_{12}$ dialkoxyalkyl, $C_3$-$C_{12}$ dialkylthioalkyl, $C_3$-$C_{12}$ dialkylthioalkoxyl, $C_3$-$C_{12}$ dialkoxyalkoxyl, $C_3$-$C_{10}$ haloalkoxyhaloalkoxyl, $C_3$-$C_{10}$ alkoxyalkoxyalkyl, $C_2$-$C_6$ alkenyl, $C_2$-$C_6$ haloalkenyl, $C_2$-$C_6$ alkenyloxy, $C_2$-$C_6$ haloalkenyloxy, $C_3$-$C_8$ alkenyloxyalkoxyl, $C_3$-$C_8$ haloalkenyloxyalkoxyl, $C_2$-$C_6$ alkynyl, $C_2$-$C_6$ haloalkynyl, $C_2$-$C_6$ alkynyloxy, $C_2$-$C_6$ haloalkynyloxy, $C_3$-$C_8$ alkynyloxyalkoxyl, $C_3$-$C_8$ haloalkynyloxyalkoxyl, $C_3$-$C_{12}$ acylaminoalkoxy, $C_2$-$C_8$ alkoxyiminoalkyl, $C_2$-$C_8$ haloalkoxyiminoalkyl, $C_3$-$C_8$ alkenyloxyiminoalkyl, $C_3$-$C_8$ haloalkenyloxyiminoalkyl, $C_3$-$C_8$ alkynyloxyiminoalkyl, $C_3$-$C_8$ haloalkynyloxyiminoalkyl, $C_5$-$C_{10}$ alkoxyalkynyloxyalkyl, $C_6$-$C_{12}$ cycloalkylideneiminooxyalkyl, $C_6$-$C_{12}$ dialkylideneiminooxyalkyl, —S(O)$_m$R$_1$, —OS(O)$_t$R$_1$, —SO$_2$NR$_2$R$_3$, —CO$_2$R$_4$, —COR$_5$, —CONR$_6$R$_7$, —CSNR$_8$R$_9$, —NR$_{10}$R$_{11}$, —NR$_{12}$COR$_{13}$, —NR$_{14}$CO$_2$R$_{15}$, —NR$_{16}$CONR$_{17}$R$_{18}$, —PO(R$_{19}$)$_2$, -Q, —ZQ$_1$, —(CR$_{20}$R$_{21}$)$_p$Q$_2$, —Z(CR$_{22}$R$_{23}$)$_p$Q$_3$, —(CR$_{24}$R$_{25}$)$_p$ZQ$_4$, —(CR$_{26}$R$_{27}$)$_p$Z(CR$_{28}$R$_{29}$)$_p$Q$_5$, —(CR$_{30}$R$_{31}$)$_p$Z(CR$_{32}$R$_{33}$)$_p$Z$_1$Q$_6$, —Z (CR$_{34}$R$_{35}$)$_p$(C=Y)T, —Z(CR$_{36}$R$_{37}$)$_v$(CR$_{38}$R$_{39}$=CR$_{40}$R$_{41}$)(C=Y)T;

B represents a D-(R$_x$)$_n$ group;

R represents a hydrogen atom, a linear or branched $C_1$-$C_6$ alkyl group, a linear or branched $C_1$-$C_6$ haloalkyl group, a $C_3$-$C_6$ cycloalkyl group or a $C_4$-$C_{12}$ cycloalkylalkyl group possibly substituted with halogen atoms or $C_1$-$C_6$ alkyl or $C_1$-$C_6$ thioalkyl or $C_1$-$C_6$ alkoxyl or $C_2$-$C_6$ alkoxycarbonyl groups, alkenyl $C_2$-$C_6$ groups, alkynyl $C_2$-$C_6$ groups, the latter two groups, in turn, possibly substituted with halogen atoms, a $C_5$-$C_6$ cycloalkenyl group possibly substituted with halogen atoms or $C_1$-$C_6$ alkyl groups, an aryl or arylalkyl group optionally substituted;

R$_1$ and R$_{19}$, represent a $C_1$-$C_6$ alkyl or $C_1$-$C_6$ haloalkyl group, a $C_3$-$C_6$ cycloalkyl group, an aryl group optionally substituted by one or more substituents selected from halogen, $NO_2$, CN, CHO, linear or branched $C_1$-$C_6$ alkyl, linear or branched $C_1$-$C_6$ haloalkyl, linear or branched $C_1$-$C_6$ alkoxyl, linear or branched $C_1$-$C_6$ haloalkoxyl, $C_1$-$C_6$ alkylsulfonyl, $C_2$-$C_6$ alkoxycarbonyl;

m is equal to 0, 1 or 2;

t is equal to 1 or 2;

R$_2$, R$_3$, R$_6$, R$_7$, R$_8$, R$_9$, R$_{10}$, R$_{11}$, R$_{17}$ and R$_{18}$, the same or different, represent a hydrogen atom, a linear or branched $C_1$-$C_6$ alkyl group in turn possibly substituted with halogen atoms, a $C_1$-$C_6$ alkoxyl group, a $C_3$-$C_6$ cycloalkyl group, an arylalkyl group or an aryl group, said arylalkyl or aryl groups also optionally substituted with one or more substituents selected from halogen, $NO_2$, CN, CHO, linear or branched $C_1$-$C_6$ alkyl, linear or branched $C_1$-$C_6$ haloalkyl, linear or branched $C_1$-$C_6$ alkoxyl, linear or branched $C_1$-$C_6$ haloalkoxyl, $C_1$-$C_6$ alkylsulfonyl, $C_2$-$C_6$ alkoxycarbonyl or, together, represent a $C_2$-$C_5$ alkylenic chain;

R$_4$, R$_5$ and R$_{42}$, represent a hydrogen atom, a linear or branched $C_1$-$C_6$ alkyl group in turn possibly substituted with halogen atoms, a $C_3$-$C_6$ alkenyl group in turn possibly substituted with halogen atoms, a Q$_7$ group, an arylalkyl group possibly substituted with one or more substituents selected from halogen, $NO_2$, CN, CHO, linear or branched $C_1$-$C_6$ alkyl, linear or branched $C_1$-$C_6$ haloalkyl, linear or branched $C_1$-$C_6$ alkoxyl, linear or branched $C_3$-$C_6$ haloalkoxyl, $C_1$-$C_6$ alkylsulfonyl, $C_2$-$C_6$ alkoxycarbonyl;

R$_{12}$, R$_{14}$ and R$_{16}$, represent a hydrogen atom, a linear or branched $C_1$-$C_6$ alkyl group in turn possibly substituted with halogen atoms, a $C_3$-$C_6$ cycloalkyl group, a $C_1$-$C_6$ alkoxyl group, a $C_1$-$C_6$ haloalkoxyl group;

R$_{13}$ and R$_{15}$, represent a hydrogen atom, a linear or branched $C_1$-$C_6$ alkyl group in turn possibly substituted with halogen atoms, a $C_3$-$C_6$ alkenyl group, in turn possibly substituted with halogen atoms, a Q$_7$ group, NH$_2$, NHCN, NHNH$_2$, NHOH, an arylalkyl group possibly substituted with one or more substituents selected from halogen, $NO_2$, CN, CHO, linear or branched $C_1$-$C_6$ alkyl, linear or branched $C_1$-$C_6$ haloalkyl, linear or branched $C_1$-$C_6$ alkoxyl, linear or branched $C_1$-$C_6$ haloalkoxyl, $C_1$-$C_6$ alkylsulfonyl, $C_2$-$C_6$ alkoxycarbonyl;

R$_{20}$, R$_{21}$, R$_{22}$, R$_{23}$, R$_{24}$, R$_{25}$, R$_{26}$, R$_{27}$, R$_{28}$ R$_{29}$, R$_{30}$, R$_{31}$, R$_{32}$, R$_{33}$, R$_{34}$, R$_{35}$, R$_{36}$, R$_{37}$, R$_{38}$, R$_{39}$, R$_{40}$ and R$_{41}$, the same or different, represent a hydrogen atom, a linear or branched $C_1$-$C_6$ alkyl group in turn possibly substituted with halogen atoms, a $C_1$-$C_6$ alkoxyl group, or the two groups bound to the same carbon atom can be joint by $C_2$-$C_5$ alkylene groups, the alkylene groups can be, in turn, substituted with $C_1$-$C_3$ alkyl groups;

Q, Q$_1$, Q$_2$, Q$_3$, Q$_4$, Q$_5$, Q$_6$ and Q$_7$ represent an aryl group, a $C_3$-$C_6$ cycloalkyl group, $C_5$-$C_6$ cycloalkenyl, a heterocyclic group selected from triazolyl, triazolonyl, pyrazolyl, imidazolyl, imidazolydinonyl, tetrazolyl, tetrazolonyl, isoxazolyl, furyl, thienyl, pyrrolyl, pyrrolidinyl, pyrrolidinonyl, pyridyl, pyrimidinyl, pyrimidinonyl, pyrazinyl, pyridazinyl, oxazolyl, thiazolyl, oxadiazolyl, thiadiazolyl, isothiazolyl, benzoxazolyl, benzothiazolyl, isoxazolinyl, 1,3-dioxanyl, 1,4-dioxanyl, 1,3-dioxolanyl, tetrahydropyranyl, oxethanyl, oxyranyl, thiazolidinyl, oxazolidinyl, piperidinyl, piperidinonyl, piperazinyl, morpholinyl, thiazinyl, tetrahydrofuranyl, dioxazolyl, tetrahydrofuroisoxazolyl, 2-oxa-3-azabicyclo[3.1.0]hex-3-enyl, said groups optionally substituted by one or more substituents selected from halogen, $NO_2$, CN, CHO, linear or branched $C_1$-$C_6$ alkyl, linear or branched $C_1$-$C_6$ haloalkyl, linear or branched $C_1$-$C_6$ alkoxyl, linear or branched $C_1$-$C_6$ haloalkoxyl, $C_1$-$C_6$ cyanoalkyl, $C_2$-$C_6$ alkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ haloalkoxyalkyl, $C_2$-$C_6$ haloalkylthioalkyl, $C_2$-$C_6$ haloalkylsulfinylalkyl, $C_2$-$C_6$ haloalkylsulfonylalkyl, $C_2$-$C_6$ alkoxyalkoxyl or $C_2$-$C_6$ haloalkoxyalkoxyl optionally substituted with a group selected from $C_1$-$C_4$ alkoxyl or $C_1$-$C_4$ haloalkoxyl, $C_2$-$C_6$ alkylthioalkoxyl, $C_2$-$C_6$ haloalkylthioalkoxyl, $C_3$-$C_{12}$ dialkoxyalkyl, $C_3$-$C_{12}$ dialkylthioalkyl, $C_3$-$C_{12}$ dialkylthioalkoxyl, $C_3$-$C_{12}$ dialkoxyalkoxyl, $C_2$-$C_6$ haloalkoxyhaloalkoxyl, $C_3$-$C_{10}$ alkoxyalkoxyalkyl, $C_2$-$C_6$ alkenyl, $C_2$-$C_6$ haloalkenyl, $C_2$-$C_6$ alkenyloxy, $C_2$-$C_6$ haloalkenyloxy, $C_3$-$C_8$ alkenyloxyalkoxyl, $C_3$-$C_8$ haloalkenyloxyalkoxyl, $C_2$-$C_6$ alkynyl, $C_2$-$C_6$ haloalkynyl, $C_2$-$C_6$ alkynyloxy, $C_2$-$C_6$ haloalkynyloxy, $C_3$-$C_8$ alkynyloxyalkoxyl, $C_3$-$C_8$ haloalkynyloxyalkoxyl, $C_3$-$C_{12}$ acylaminoalkoxy, $C_2$-$C_8$ alkoxyiminoalkyl, $C_2$-$C_8$ haloalkoxyiminoalkyl, $C_3$-$C_8$ alkenyloxyiminoalkyl, $C_3$-$C_8$ haloalkenyloxyiminoalkyl, $C_3$-$C_8$ alkynyloxyiminoalkyl, $C_3$-$C_8$ haloalkynyloxyiminoalkyl, $C_5$-$C_{10}$ alkoxyalkynyloxyl, $C_6$-$C_{12}$ cycloalkylideneiminooxyalkyl, $C_6$-$C_{12}$ dialkylideneiminooxyalkyl, aryl optionally substituted, —S(O)$_m$R$_1$, —OS(O)$_r$R$_1$, —SO$_2$NR$_2$R$_3$, —CO$_2$R$_4$, —COR$_5$, —CONR$_6$R$_7$, —CSNR$_8$R$_9$, —NR$_{10}$R$_{11}$, —NR$_{12}$COR$_{13}$, —NR$_{14}$CO$_2$R$_{15}$, —NR$_{16}$CONR$_{17}$R$_{18}$, —PO(R$_{19}$)$_2$, —Z$_2$(CR$_{34}$R$_{35}$)$_p$(C=Y)T, —Z$_3$(CR$_{36}$R$_{37}$)$_v$(CR$_{38}$R$_{39}$=CR$_{40}$R$_{41}$)(C=Y)T;

Z, Z$_1$, Z$_2$=O, S(O)$_r$;

Y=O, S;

r is equal to 0, 1 or 2;

p, q are equal to 1, 2, 3 or 4;

v is equal to 0 or 1;

Z$_3$=O, S or a direct bond;

T represents a hydrogen atom, a Z$_4$R$_{42}$ group, a —NR$_{43}$R$_{44}$ group, an aryl group or a heterocyclic group selected from triazolyl, triazolonyl, pyrazolyl, imidazolyl, imidazolidinonyl, tetrazolyl, tetrazolonyl, pyrrolyl, pyrrolidinyl, pyrrolidinonyl, pyridyl, pyrimidinyl, piperidinyl, piperidinonyl, piperazinyl, morpholinyl, said groups optionally substituted by one or more substituents selected from halogen, NO$_2$, OH, CN, CHO, linear or branched $C_1$-$C_5$ alkyl, linear or branched $C_1$-$C_6$ haloalkyl, $C_3$-$C_6$ cycloalkyl, $C_5$-$C_6$ cycloalkenyl, linear or branched $C_1$-$C_6$ alkoxyl, linear or branched $C_1$-$C_6$ haloalkoxyl, $C_1$-$C_6$ cyanoalkyl, $C_2$-$C_6$ alkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ haloalkoxyalkyl, $C_2$-$C_6$ haloalkylthioalkyl, $C_2$-$C_6$ haloalkylsulfinylalkyl, $C_2$-$C_6$ haloalkylsulfonylalkyl, —S(O)$_m$R$_1$;

Z$_4$=O, S or a direct bond;

R$_{43}$ and R$_{44}$, the same or different, represent a hydrogen atom, a linear or branched $C_1$-$C_6$ alkyl group in turn optionally substituted with halogen atoms, a $C_3$-$C_6$ alkenyl group in turn optionally substituted with halogen atoms, a Q$_7$ group, an arylalkyl group optionally substituted by one or more substituents selected from halogen, NO$_2$, CN, CHO, linear or branched $C_1$-$C_6$ alkyl, linear or branched $C_1$-$C_6$ haloalkyl, linear or branched $C_1$-$C_6$ alkoxyl, linear or branched $C_1$-$C_6$ haloalkoxyl, $C_1$-$C_6$ alkylsulfonyl, $C_2$-$C_6$ alkoxycarbonyl, or they jointly represent a $C_2$-$C_5$ alkylene chain;

D represents:
a heterocyclic group of the heteroaryl or heterocyclic type, in all the above cases the heterocycle can be mono or polycyclic and can be connected to the rest of the structure either through one of its carbon atoms or, when possible, through one of its nitrogen atoms;
or it represents a mono or polycyclic aryl group, in this latter case, the group can also be partially saturated;

R$_x$ represents a substituent selected from hydrogen, halogen, NO$_2$, CN, CHO, OH, linear or branched $C_1$-$C_6$ alkyl, linear or branched $C_1$-$C_6$ haloalkyl, linear or branched $C_1$-$C_6$ alkoxyl, linear or branched $C_1$-$C_6$ haloalkoxyl, $C_1$-$C_6$ cyanoalkyl, $C_2$-$C_6$ alkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ haloalkoxyalkyl, $C_2$-$C_6$ haloalkylthioalkyl, $C_2$-$C_6$ haloalkylsulfinylalkyl, $C_2$-$C_6$ haloalkylsulfonylalkyl, $C_2$-$C_6$ alkoxyalkoxyl or $C_2$-$C_6$ haloalkoxyalkoxyl optionally substituted with a group selected from $C_1$-$C_4$ alkoxyl or $C_1$-$C_4$ haloalkoxyl, $C_2$-$C_6$ alkylthioalkoxyl, $C_2$-$C_6$ haloalkylthioalkoxyl, $C_3$-$C_{12}$ dialkoxyalkyl, $C_3$-$C_{12}$ dialkylthioalkyl, $C_3$-$C_{12}$ dialkylthioalkoxyl, $C_3$-$C_{12}$ dialkoxyalkoxyl, $C_2$-$C_6$ haloalkoxyhaloalkoxyl, $C_3$-$C_{10}$ alkoxyalkoxyalkyl, $C_2$-$C_6$ alkenyl, $C_2$-$C_6$ haloalkenyl, $C_2$-$C_6$ alkenyloxy, $C_2$-$C_6$ haloalkenyloxy, $C_3$-$C_8$ alkenyloxyalkoxyl, $C_3$-$C_8$ haloalkenyloxyalkoxyl, $C_2$-$C_6$ alkynyl, $C_2$-$C_6$ haloalkynyl, $C_2$-$C_6$ alkynyloxy, $C_2$-$C_6$ haloalkynyloxy, $C_3$-$C_8$ alkynyloxyalkoxyl, $C_3$-$C_8$ haloalkynyloxyalkoxyl, $C_3$-$C_{12}$ acylaminoalkoxy, $C_2$-$C_8$ alkoxyiminoalkyl, $C_2$-$C_8$ haloalkoxyiminoalkyl, $C_3$-$C_8$ alkenyloxyiminoalkyl, $C_3$-$C_8$ haloalkenyloxyiminoalkyl, $C_3$-$C_8$ alkynyloxyiminoalkyl, $C_3$-$C_8$ haloalkynyloxyiminoalkyl, $C_5$-$C_{10}$ alkoxyalkynyloxyl, $C_6$-$C_{12}$ cycloalkylideneiminooxyalkyl, $C_6$-$C_{12}$ dialkylideneiminooxyalkyl, —S(O)$_m$R$_1$, —OS(O)$_r$R$_1$, —SO$_2$NR$_2$R$_3$, —CO$_2$R$_4$, —COR$_5$, —CONR$_6$R$_7$, —CSNR$_8$R$_9$, —NR$_{10}$R$_{11}$, —NR$_{12}$COR$_{13}$, —NR$_{14}$CO$_2$R$_{15}$, —NR$_{16}$CONR$_{17}$R$_{18}$, —PO(R$_{19}$)$_2$, -Q, —ZQ$_1$, —(CR$_{20}$R$_{21}$)$_p$Q$_2$, —Z(CR$_{22}$R$_{23}$)$_p$Q$_3$, —(CR$_{24}$R$_{25}$)$_p$ZQ$_4$, —(CR$_{26}$R$_{27}$)$_p$Z(CR$_{28}$R$_{29}$)$_q$Q$_5$, —(CR$_{30}$R$_{31}$)$_p$Z(CR$_{32}$R$_{33}$)$_q$Z$_1$Q$_6$, Z$_2$(CR$_{34}$R$_{35}$)$_p$(C=Y)T, —Z$_3$(CR$_{36}$R$_{37}$)$_v$(CR$_{38}$R$_{39}$=CR$_{40}$R$_{41}$)(C=Y)T;

if several R$_x$ groups are present, these can be the same or different;

n=1-9;

and of the relevant salts having agronomical compatibility, as herbicides.

The use of derivatives of 1,3-diones having general formula (I) is a further object of the present invention:

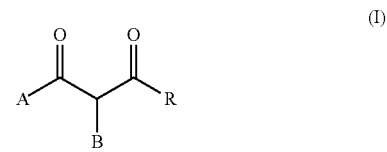

(I)

wherein:
A, B and R have the above-defined meanings, and of relevant salts pharmaceutically acceptable as medicament.

Examples of D groups include: pyrrolyl, pyrrolidinonyl, thienyl, furyl, pyrazolyl, imidazolyl, imidazolidinonyl, triazolyl, triazolonyl, tetrazolyl, tetrazolonyl, thiazolyl, isothiazolyl, dithiol, oxathiol, isoxazolyl, isoxazolinyl, oxazolyl, oxadiazolyl, thiadiazolyl, oxatriazolyl, dioxazolyl, oxathiazolyl, pyridyl, N-oxidopyridyl, pyrimidyl, pyrimidinonyl, pyridazinyl, pyrazinyl, triazinyl, tetrazinyl, piperazinyl, oxazinyl, oxathiazinyl, morfolinyl, benzofuranyl, isobenzofuranyl, benzothienyl, isobenzothienyl, indolyl, isoindolyl, benzoxazolyl, benzothiazolyl, benzimidazolyl, benzopyrazolyl, benzotriazolyl, benzoxadiazolyl, benzothiadiazolyl, quinolinyl, quinazolinyl, quinoxalinyl, pyridopyrimidinyl, oxazolepyridinyl, chromenyl, thiochromenyl, purine, phenyl, naphthyl.

A $C_1$-$C_6$ alkyl group means a linear or branched $C_1$-$C_6$ alkyl group.

Examples of these groups are: methyl, ethyl, propyl, isopropyl, butyl, isobutyl, tert-butyl.

A $C_1$-$C_6$ haloalkyl group means a linear or branched $C_1$-$C_6$ alkyl group, substituted with one or more halogen atoms, the same or different.

Examples of this group are: fluoromethyl, chlorodifluoromethyl, difluoromethyl, trifluoromethyl, dichloromethyl, trichloromethyl, 2,2,2-trifluoroethyl, 2,2,2-trichloroethyl, 1,1,2,2,2-pentafluoroethyl, 1,1,2,2-tetrafluoroethyl, 1,2,2,2-tetrafluoroethyl, 2,2,3,3-tetrafluoropropyl, 2,2,3,3,3-pentafluoropropyl.

A $C_2$-$C_6$ alkenyl group means a linear or branched $C_2$-$C_6$ alkenyl group.

Examples of this group are: ethenyl, propenyl, butenyl.

A $C_2$-$C_6$ haloalkenyl group means a linear or branched $C_2$-$C_6$ alkenyl group, substituted by one or more halogen atoms, the same or different.

Example of this group are: 3,3-dichloroprop-2-enyl, 3,3-difluoroprop-2-enyl, 3,3,3-trifluoropropenyl.

Example of $C_2$-$C_6$ alkynyl groups are: ethynyl, propargyl.

A $C_2$-$C_6$ haloalkynyl group means a linear or branched $C_2$-$C_6$ alkynyl group, substituted by one or more halogen atoms, the same or different.

Example of this group are: 3-chloropropynyl, 3-iodopropynyl.

Halogen atom means a halogen atom selected from fluorine, chlorine, bromine or iodine.

A $C_3$-$C_6$ cycloalkyl group means a cycloalkyl group consisting of 3 to 6 carbon atoms, possibly substituted by one or more substituents the same or different.

Examples of this group are: cyclopropyl, cyclopentyl.

Examples of alkoxy groups are: methoxy, ethoxy.

Examples of haloalkoxyl groups are: difluoromethoxy, trifluoromethoxy, 1,1,2,2-tetrafluoroethoxy, 1,1,2,3,3,3-hexafluoropropoxy.

A heterocyclic group, of the heteroarylic or heterocyclic type, means a ring which can be unsaturated, partially saturated or completely saturated, and can consist of from three to eighteen units containing at least one heteroatom selected from nitrogen, oxygen and sulphur; this group can be condensed with other rings of the heterocyclic or carbocyclic type, which, in turn, can be of the aromatic type, partially saturated or completely saturated.

Mono or polycyclic aryl group means a ring that can be aromatic or partially saturated and consisting exclusively of carbon atoms.

Examples of these groups are: phenyl, naphthyl, tetrahydronaphthalenyl.

The compounds having general formula (I) can exist in different tautomeric and/or isomeric forms, as shown hereinafter:

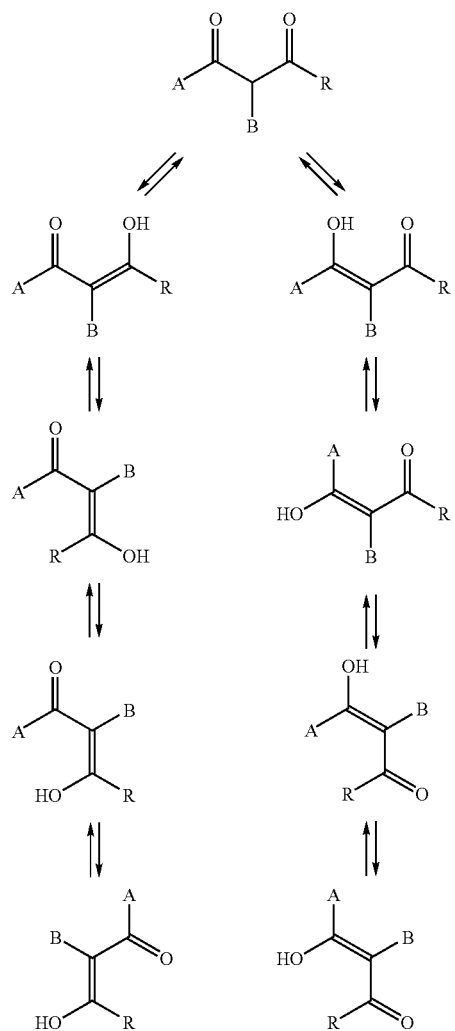

Both the tautomeric and/or isomeric forms of compounds (I) and the mixtures of the same in any possible proportions, are considered included in the present patent application.

If the particular groups A, B and R allow the existence of other tautomeric and/or isomeric forms, these forms are definitely included within the scope of the present invention.

The salts of compounds (I) which have agronomical compatibility are also considered within the spirit of this patent.

As stated before, the derivatives of 1,3-diones having general formula (I) have a high herbicidal activity.

Specific examples of compounds having general formula (I) of interest for their activity are shown in table 1:

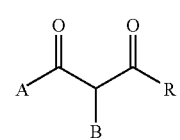
(I)

| A | B | R |
|---|---|---|
| 2-NO$_2$-4-SO$_2$MePh | 1,2,4-oxadiazol-5-yl | H |
| 2-NO$_2$-4-SO$_2$MePh | 1,2,4-oxadiazol-5-yl | methyl |

-continued

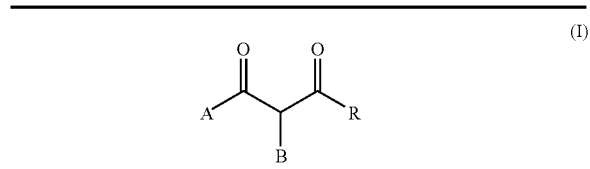
(I)

| A | B | R |
|---|---|---|
| 2-NO$_2$-4-SO$_2$MePh | 1,2,4-oxadiazol-5-yl | i-propyl |
| 2-NO$_2$-4-SO$_2$MePh | 1,2,4-oxadiazol-5-yl | cyclopropyl |
| 2-NO$_2$-4-SO$_2$MePh | 1,2,4-oxadiazol-5-yl | CF$_3$ |
| 2-NO$_2$-4-SO$_2$MePh | 3-methyl-1,2,4-oxadiazol-5-yl | H |
| 2-NO$_2$-4-SO$_2$MePh | 3-methyl-1,2,4-oxadiazol-5-yl | methyl |
| 2-NO$_2$-4-SO$_2$MePh | 3-methyl-1,2,4-oxadiazol-5-yl | i-propyl |
| 2-NO$_2$-4-SO$_2$MePh | 3-methyl-1,2,4-oxadiazol-5-yl | cyclopropyl |
| 2-NO$_2$-4-SO$_2$MePh | 3-methyl-1,2,4-oxadiazol-5-yl | CF$_3$ |
| 2-NO$_2$-4-SO$_2$MePh | 3-trifluoromethyl-1,2,4-oxadiazol-5-yl | H |
| 2-NO$_2$-4-SO$_2$MePh | 3-trifluoromethyl-1,2,4-oxadiazol-5-yl | methyl |
| 2-NO$_2$-4-SO$_2$MePh | 3-trifluoromethyl-1,2,4-oxadiazol-5-yl | i-propyl |
| 2-NO$_2$-4-SO$_2$MePh | 3-trifluoromethyl-1,2,4-oxadiazol-5-yl | cyclopropyl |
| 2-NO$_2$-4-SO$_2$MePh | 3-trifluoromethyl-1,2,4-oxadiazol-5-yl | CF$_3$ |
| 2-NO$_2$-4-SO$_2$MePh | 1,2,4-oxadiazol-3-yl | H |
| 2-NO$_2$-4-SO$_2$MePh | 1,2,4-oxadiazol-3-yl | methyl |
| 2-NO$_2$-4-SO$_2$MePh | 1,2,4-oxadiazol-3-yl | i-propyl |
| 2-NO$_2$-4-SO$_2$MePh | 1,2,4-oxadiazol-3-yl | cyclopropyl |
| 2-NO$_2$-4-SO$_2$MePh | 1,2,4-oxadiazol-3-yl | CF$_3$ |
| 2-NO$_2$-4-SO$_2$MePh | 5-methyl-1,2,4-oxadiazol-3-yl | H |
| 2-NO$_2$-4-SO$_2$MePh | 5-methyl-1,2,4-oxadiazol-3-yl | methyl |
| 2-NO$_2$-4-SO$_2$MePh | 5-methyl-1,2,4-oxadiazol-3-yl | i-propyl |
| 2-NO$_2$-4-SO$_2$MePh | 5-methyl-1,2,4-oxadiazol-3-yl | cyclopropyl |
| 2-NO$_2$-4-SO$_2$MePh | 5-methyl-1,2,4-oxadiazol-3-yl | CF$_3$ |
| 2-NO$_2$-4-SO$_2$MePh | 5-trifluoromethyl-1,2,4-oxadiazol-3-yl | H |
| 2-NO$_2$-4-SO$_2$MePh | 5-trifluoromethyl-1,2,4-oxadiazol-3-yl | methyl |
| 2-NO$_2$-4-SO$_2$MePh | 5-trifluoromethyl-1,2,4-oxadiazol-3-yl | i-propyl |
| 2-NO$_2$-4-SO$_2$MePh | 5-trifluoromethyl-1,2,4-oxadiazol-3-yl | cyclopropyl |
| 2-NO$_2$-4-SO$_2$MePh | 5-trifluoromethyl-1,2,4-oxadiazol-3-yl | CF$_3$ |
| 2-NO$_2$-4-SO$_2$MePh | 5-chloro-1,2,4-oxadiazol-3-yl | H |
| 2-NO$_2$-4-SO$_2$MePh | 5-chloro-1,2,4-oxadiazol-3-yl | methyl |
| 2-NO$_2$-4-SO$_2$MePh | 5-chloro-1,2,4-oxadiazol-3-yl | i-propyl |
| 2-NO$_2$-4-SO$_2$MePh | 5-chloro-1,2,4-oxadiazol-3-yl | cyclopropyl |
| 2-NO$_2$-4-SO$_2$MePh | 5-chloro-1,2,4-oxadiazol-3-yl | CF$_3$ |
| 2-NO$_2$-4-SO$_2$MePh | 1,3,4-oxadiazol-2-yl | H |
| 2-NO$_2$-4-SO$_2$MePh | 1,3,4-oxadiazol-2-yl | methyl |
| 2-NO$_2$-4-SO$_2$MePh | 1,3,4-oxadiazol-2-yl | i-propyl |
| 2-NO$_2$-4-SO$_2$MePh | 1,3,4-oxadiazol-2-yl | cyclopropyl |
| 2-NO$_2$-4-SO$_2$MePh | 1,3,4-oxadiazol-2-yl | CF$_3$ |
| 2-NO$_2$-4-SO$_2$MePh | 5-methylsulfonyl-1,3,4-oxadiazol-2-yl | H |
| 2-NO$_2$-4-SO$_2$MePh | 5-methylsulfonyl-1,3,4-oxadiazol-2-yl | methyl |
| 2-NO$_2$-4-SO$_2$MePh | 5-methylsulfonyl-1,3,4-oxadiazol-2-yl | i-propyl |
| 2-NO$_2$-4-SO$_2$MePh | 5-methylsulfonyl-1,3,4-oxadiazol-2-yl | cyclopropyl |
| 2-NO$_2$-4-SO$_2$MePh | 5-methylsulfonyl-1,3,4-oxadiazol-2-yl | CF$_3$ |
| 2-NO$_2$-4-SO$_2$MePh | 5-methyl-1,3,4-oxadiazol-2-yl | H |
| 2-NO$_2$-4-SO$_2$MePh | 5-methyl-1,3,4-oxadiazol-2-yl | methyl |
| 2-NO$_2$-4-SO$_2$MePh | 5-methyl-1,3,4-oxadiazol-2-yl | i-propyl |
| 2-NO$_2$-4-SO$_2$MePh | 5-methyl-1,3,4-oxadiazol-2-yl | cyclopropyl |
| 2-NO$_2$-4-SO$_2$MePh | 5-methyl-1,3,4-oxadiazol-2-yl | CF$_3$ |
| 2-NO$_2$-4-SO$_2$MePh | 5-trifluoromethyl-1,3,4-oxadiazol-2-yl | H |
| 2-NO$_2$-4-SO$_2$MePh | 5-trifluoromethyl-1,3,4-oxadiazol-2-yl | methyl |
| 2-NO$_2$-4-SO$_2$MePh | 5-trifluoromethyl-1,3,4-oxadiazol-2-yl | i-propyl |
| 2-NO$_2$-4-SO$_2$MePh | 5-trifluoromethyl-1,3,4-oxadiazol-2-yl | cyclopropyl |
| 2-NO$_2$-4-SO$_2$MePh | 5-trifluoromethyl-1,3,4-oxadiazol-2-yl | CF$_3$ |
| 2-NO$_2$-4-SO$_2$MePh | 1,2,3-triazol-4-yl | H |
| 2-NO$_2$-4-SO$_2$MePh | 1,2,3-triazol-4-yl | methyl |
| 2-NO$_2$-4-SO$_2$MePh | 1,2,3-triazol-4-yl | i-propyl |
| 2-NO$_2$-4-SO$_2$MePh | 1,2,3-triazol-4-yl | cyclopropyl |
| 2-NO$_2$-4-SO$_2$MePh | 1,2,3-triazol-4-yl | CF$_3$ |
| 2-NO$_2$-4-SO$_2$MePh | 1-methyl-1,2,3-triazol-4-yl | H |
| 2-NO$_2$-4-SO$_2$MePh | 1-methyl-1,2,3-triazol-4-yl | methyl |
| 2-NO$_2$-4-SO$_2$MePh | 1-methyl-1,2,3-triazol-4-yl | i-propyl |
| 2-NO$_2$-4-SO$_2$MePh | 1-methyl-1,2,3-triazol-4-yl | cyclopropyl |
| 2-NO$_2$-4-SO$_2$MePh | 1-methyl-1,2,3-triazol-4-yl | CF$_3$ |
| 2-NO$_2$-4-SO$_2$MePh | 2-methyl-1,2,3-triazol-4-yl | H |
| 2-NO$_2$-4-SO$_2$MePh | 2-methyl-1,2,3-triazol-4-yl | methyl |
| 2-NO$_2$-4-SO$_2$MePh | 2-methyl-1,2,3-triazol-4-yl | i-propyl |
| 2-NO$_2$-4-SO$_2$MePh | 2-methyl-1,2,3-triazol-4-yl | cyclopropyl |
| 2-NO$_2$-4-SO$_2$MePh | 2-methyl-1,2,3-triazol-4-yl | CF$_3$ |
| 2-NO$_2$-4-SO$_2$MePh | 1,2,3-triazol-1-yl | H |
| 2-NO$_2$-4-SO$_2$MePh | 1,2,3-triazol-1-yl | methyl |
| 2-NO$_2$-4-SO$_2$MePh | 1,2,3-triazol-1-yl | i-propyl |
| 2-NO$_2$-4-SO$_2$MePh | 1,2,3-triazol-1-yl | cyclopropyl |
| 2-NO$_2$-4-SO$_2$MePh | 1,2,3-triazol-1-yl | CF$_3$ |
| 2-NO$_2$-4-SO$_2$MePh | 1,2,3-triazol-2-yl | H |
| 2-NO$_2$-4-SO$_2$MePh | 1,2,3-triazol-2-yl | methyl |
| 2-NO$_2$-4-SO$_2$MePh | 1,2,3-triazol-2-yl | i-propyl |
| 2-NO$_2$-4-SO$_2$MePh | 1,2,3-triazol-2-yl | cyclopropyl |
| 2-NO$_2$-4-SO$_2$MePh | 1,2,3-triazol-2-yl | CF$_3$ |
| 2-NO$_2$-4-SO$_2$MePh | 1,2,4-triazol-1-yl | H |
| 2-NO$_2$-4-SO$_2$MePh | 1,2,4-triazol-1-yl | methyl |
| 2-NO$_2$-4-SO$_2$MePh | 1,2,4-triazol-1-yl | i-propyl |
| 2-NO$_2$-4-SO$_2$MePh | 1,2,4-triazol-1-yl | cyclopropyl |
| 2-NO$_2$-4-SO$_2$MePh | 1,2,4-triazol-1-yl | CF$_3$ |
| 2-NO$_2$-4-SO$_2$MePh | imidazol-2-yl | H |
| 2-NO$_2$-4-SO$_2$MePh | imidazol-2-yl | methyl |
| 2-NO$_2$-4-SO$_2$MePh | imidazol-2-yl | i-propyl |
| 2-NO$_2$-4-SO$_2$MePh | imidazol-2-yl | cyclopropyl |
| 2-NO$_2$-4-SO$_2$MePh | imidazol-2-yl | CF$_3$ |
| 2-NO$_2$-4-SO$_2$MePh | imidazol-1-yl | H |
| 2-NO$_2$-4-SO$_2$MePh | imidazol-1-yl | methyl |
| 2-NO$_2$-4-SO$_2$MePh | imidazol-1-yl | i-propyl |
| 2-NO$_2$-4-SO$_2$MePh | imidazol-1-yl | cyclopropyl |
| 2-NO$_2$-4-SO$_2$MePh | imidazol-1-yl | CF$_3$ |
| 2-NO$_2$-4-SO$_2$MePh | imidazol-4-yl | H |
| 2-NO$_2$-4-SO$_2$MePh | imidazol-4-yl | methyl |
| 2-NO$_2$-4-SO$_2$MePh | imidazol-4-yl | i-propyl |
| 2-NO$_2$-4-SO$_2$MePh | imidazol-4-yl | cyclopropyl |
| 2-NO$_2$-4-SO$_2$MePh | imidazol-4-yl | CF$_3$ |
| 2-NO$_2$-4-SO$_2$MePh | thiazol-2-yl | H |
| 2-NO$_2$-4-SO$_2$MePh | thiazol-2-yl | methyl |
| 2-NO$_2$-4-SO$_2$MePh | thiazol-2-yl | i-propyl |
| 2-NO$_2$-4-SO$_2$MePh | thiazol-2-yl | cyclopropyl |
| 2-NO$_2$-4-SO$_2$MePh | thiazol-2-yl | CF$_3$ |
| 2-NO$_2$-4-SO$_2$MePh | 4-methylthiazol-2-yl | H |
| 2-NO$_2$-4-SO$_2$MePh | 4-methylthiazol-2-yl | methyl |
| 2-NO$_2$-4-SO$_2$MePh | 4-methylthiazol-2-yl | i-propyl |
| 2-NO$_2$-4-SO$_2$MePh | 4-methylthiazol-2-yl | cyclopropyl |
| 2-NO$_2$-4-SO$_2$MePh | 4-methylthiazol-2-yl | CF$_3$ |
| 2-NO$_2$-4-SO$_2$MePh | oxazol-2-yl | H |
| 2-NO$_2$-4-SO$_2$MePh | oxazol-2-yl | methyl |
| 2-NO$_2$-4-SO$_2$MePh | oxazol-2-yl | i-propyl |
| 2-NO$_2$-4-SO$_2$MePh | oxazol-2-yl | cyclopropyl |
| 2-NO$_2$-4-SO$_2$MePh | oxazol-2-yl | CF$_3$ |
| 2-NO$_2$-4-SO$_2$MePh | 4,5-dimethyloxazol-2-yl | H |
| 2-NO$_2$-4-SO$_2$MePh | 4,5-dimethyloxazol-2-yl | methyl |
| 2-NO$_2$-4-SO$_2$MePh | 4,5-dimethyloxazol-2-yl | i-propyl |
| 2-NO$_2$-4-SO$_2$MePh | 4,5-dimethyloxazol-2-yl | cyclopropyl |
| 2-NO$_2$-4-SO$_2$MePh | 4,5-dimethyloxazol-2-yl | CF$_3$ |
| 2-NO$_2$-4-SO$_2$MePh | 2-oxazolin-2-yl | H |
| 2-NO$_2$-4-SO$_2$MePh | 2-oxazolin-2-yl | methyl |

-continued $$\underset{B}{\overset{A}{\underset{\|}{\text{C}}}}\underset{\|}{\overset{O}{\text{C}}}\underset{\|}{\overset{O}{\text{C}}}R \quad (I)$$

| A | B | R |
|---|---|---|
| 2-NO$_2$-4-SO$_2$MePh | 2-oxazolin-2-yl | i-propyl |
| 2-NO$_2$-4-SO$_2$MePh | 2-oxazolin-2-yl | cyclopropyl |
| 2-NO$_2$-4-SO$_2$MePh | 2-oxazolin-2-yl | CF$_3$ |
| 2-NO$_2$-4-SO$_2$MePh | 4,4-dimethyl-2-oxazolin-2-yl | H |
| 2-NO$_2$-4-SO$_2$MePh | 4,4-dimethyl-2-oxazolin-2-yl | methyl |
| 2-NO$_2$-4-SO$_2$MePh | 4,4-dimethyl-2-oxazolin-2-yl | i-propyl |
| 2-NO$_2$-4-SO$_2$MePh | 4,4-dimethyl-2-oxazolin-2-yl | cyclopropyl |
| 2-NO$_2$-4-SO$_2$MePh | 4,4-dimethyl-2-oxazolin-2-yl | CF$_3$ |
| 2-NO$_2$-4-SO$_2$MePh | 1,2,4-thiadiazol-5-yl | H |
| 2-NO$_2$-4-SO$_2$MePh | 1,2,4-thiadiazol-5-yl | methyl |
| 2-NO$_2$-4-SO$_2$MePh | 1,2,4-thiadiazol-5-yl | i-propyl |
| 2-NO$_2$-4-SO$_2$MePh | 1,2,4-thiadiazol-5-yl | cyclopropyl |
| 2-NO$_2$-4-SO$_2$MePh | 1,2,4-thiadiazol-5-yl | CF$_3$ |
| 2-NO$_2$-4-SO$_2$MePh | 3-methyl-1,2,4-thiadiazol-5-yl | H |
| 2-NO$_2$-4-SO$_2$MePh | 3-methyl-1,2,4-thiadiazol-5-yl | methyl |
| 2-NO$_2$-4-SO$_2$MePh | 3-methyl-1,2,4-thiadiazol-5-yl | i-propyl |
| 2-NO$_2$-4-SO$_2$MePh | 3-methyl-1,2,4-thiadiazol-5-yl | cyclopropyl |
| 2-NO$_2$-4-SO$_2$MePh | 3-methyl-1,2,4-thiadiazol-5-yl | CF$_3$ |
| 2-NO$_2$-4-SO$_2$MePh | 3-trifluoromethyl-1,2,4-thiadiazol-5-yl | H |
| 2-NO$_2$-4-SO$_2$MePh | 3-trifluoromethyl-1,2,4-thiadiazol-5-yl | methyl |
| 2-NO$_2$-4-SO$_2$MePh | 3-trifluoromethyl-1,2,4-thiadiazol-5-yl | i-propyl |
| 2-NO$_2$-4-SO$_2$MePh | 3-trifluoromethyl-1,2,4-thiadiazol-5-yl | cyclopropyl |
| 2-NO$_2$-4-SO$_2$MePh | 3-trifluoromethyl-1,2,4-thiadiazol-5-yl | CF$_3$ |
| 2-NO$_2$-4-SO$_2$MePh | 1,2,4-thiadiazol-3-yl | H |
| 2-NO$_2$-4-SO$_2$MePh | 1,2,4-thiadiazol-3-yl | methyl |
| 2-NO$_2$-4-SO$_2$MePh | 1,2,4-thiadiazol-3-yl | i-propyl |
| 2-NO$_2$-4-SO$_2$MePh | 1,2,4-thiadiazol-3-yl | cyclopropyl |
| 2-NO$_2$-4-SO$_2$MePh | 1,2,4-thiadiazol-3-yl | CF$_3$ |
| 2-NO$_2$-4-SO$_2$MePh | 5-methyl-1,2,4-thiadiazol-3-yl | H |
| 2-NO$_2$-4-SO$_2$MePh | 5-methyl-1,2,4-thiadiazol-3-yl | methyl |
| 2-NO$_2$-4-SO$_2$MePh | 5-methyl-1,2,4-thiadiazol-3-yl | i-propyl |
| 2-NO$_2$-4-SO$_2$MePh | 5-methyl-1,2,4-thiadiazol-3-yl | cyclopropyl |
| 2-NO$_2$-4-SO$_2$MePh | 5-methyl-1,2,4-thiadiazol-3-yl | CF$_3$ |
| 2-NO$_2$-4-SO$_2$MePh | 5-trifluoromethyl-1,2,4-thiadiazol-3-yl | H |
| 2-NO$_2$-4-SO$_2$MePh | 5-trifluoromethyl-1,2,4-thiadiazol-3-yl | methyl |
| 2-NO$_2$-4-SO$_2$MePh | 5-trifluoromethyl-1,2,4-thiadiazol-3-yl | i-propyl |
| 2-NO$_2$-4-SO$_2$MePh | 5-trifluoromethyl-1,2,4-thiadiazol-3-yl | cyclopropyl |
| 2-NO$_2$-4-SO$_2$MePh | 5-trifluoromethyl-1,2,4-thiadiazol-3-yl | CF$_3$ |
| 2-NO$_2$-4-SO$_2$MePh | 1,3,4-thiadiazol-2-yl | H |
| 2-NO$_2$-4-SO$_2$MePh | 1,3,4-thiadiazol-2-yl | methyl |
| 2-NO$_2$-4-SO$_2$MePh | 1,3,4-thiadiazol-2-yl | i-propyl |
| 2-NO$_2$-4-SO$_2$MePh | 1,3,4-thiadiazol-2-yl | cyclopropyl |
| 2-NO$_2$-4-SO$_2$MePh | 1,3,4-thiadiazol-2-yl | CF$_3$ |
| 2-NO$_2$-4-SO$_2$MePh | 5-methylsulfonyl-1,3,4-thiadiazol-2-yl | H |
| 2-NO$_2$-4-SO$_2$MePh | 5-methylsulfonyl-1,3,4-thiadiazol-2-yl | methyl |
| 2-NO$_2$-4-SO$_2$MePh | 5-methylsulfonyl-1,3,4-thiadiazol-2-yl | i-propyl |
| 2-NO$_2$-4-SO$_2$MePh | 5-methylsulfonyl-1,3,4-thiadiazol-2-yl | cyclopropyl |
| 2-NO$_2$-4-SO$_2$MePh | 5-methylsulfonyl-1,3,4-thiadiazol-2-yl | CF$_3$ |
| 2-NO$_2$-4-SO$_2$MePh | 5-methyl-1,3,4-thiadiazol-2-yl | H |
| 2-NO$_2$-4-SO$_2$MePh | 5-methyl-1,3,4-thiadiazol-2-yl | methyl |
| 2-NO$_2$-4-SO$_2$MePh | 5-methyl-1,3,4-thiadiazol-2-yl | i-propyl |
| 2-NO$_2$-4-SO$_2$MePh | 5-methyl-1,3,4-thiadiazol-2-yl | cyclopropyl |
| 2-NO$_2$-4-SO$_2$MePh | 5-methyl-1,3,4-thiadiazol-2-yl | CF$_3$ |
| 2-NO$_2$-4-SO$_2$MePh | benzoxazol-2-yl | H |
| 2-NO$_2$-4-SO$_2$MePh | benzoxazol-2-yl | methyl |
| 2-NO$_2$-4-SO$_2$MePh | benzoxazol-2-yl | i-propyl |
| 2-NO$_2$-4-SO$_2$MePh | benzoxazol-2-yl | cyclopropyl |
| 2-NO$_2$-4-SO$_2$MePh | benzoxazol-2-yl | CF$_3$ |
| 2-NO$_2$-4-SO$_2$MePh | 6-methylbenzoxazol-2-yl | H |
| 2-NO$_2$-4-SO$_2$MePh | 6-methylbenzoxazol-2-yl | methyl |
| 2-NO$_2$-4-SO$_2$MePh | 6-methylbenzoxazol-2-yl | i-propyl |
| 2-NO$_2$-4-SO$_2$MePh | 6-methylbenzoxazol-2-yl | cyclopropyl |
| 2-NO$_2$-4-SO$_2$MePh | 6-methylbenzoxazol-2-yl | CF$_3$ |
| 2-NO$_2$-4-SO$_2$MePh | benzothiazol-2-yl | H |
| 2-NO$_2$-4-SO$_2$MePh | benzothiazol-2-yl | methyl |
| 2-NO$_2$-4-SO$_2$MePh | benzothiazol-2-yl | i-propyl |
| 2-NO$_2$-4-SO$_2$MePh | benzothiazol-2-yl | cyclopropyl |
| 2-NO$_2$-4-SO$_2$MePh | benzothiazol-2-yl | CF$_3$ |
| 2-NO$_2$-4-SO$_2$MePh | pyrazol-1-yl | H |
| 2-NO$_2$-4-SO$_2$MePh | pyrazol-1-yl | methyl |
| 2-NO$_2$-4-SO$_2$MePh | pyrazol-1-yl | i-propyl |
| 2-NO$_2$-4-SO$_2$MePh | pyrazol-1-yl | cyclopropyl |
| 2-NO$_2$-4-SO$_2$MePh | pyrazol-1-yl | CF$_3$ |
| 2-NO$_2$-4-SO$_2$MePh | pyrazol-3-yl | H |
| 2-NO$_2$-4-SO$_2$MePh | pyrazol-3-yl | methyl |
| 2-NO$_2$-4-SO$_2$MePh | pyrazol-3-yl | i-propyl |
| 2-NO$_2$-4-SO$_2$MePh | pyrazol-3-yl | cyclopropyl |
| 2-NO$_2$-4-SO$_2$MePh | pyrazol-3-yl | CF$_3$ |
| 2-NO$_2$-4-SO$_2$MePh | 1-methylpyrazol-3-yl | H |
| 2-NO$_2$-4-SO$_2$MePh | 1-methylpyrazol-3-yl | methyl |
| 2-NO$_2$-4-SO$_2$MePh | 1-methylpyrazol-3-yl | i-propyl |
| 2-NO$_2$-4-SO$_2$MePh | 1-methylpyrazol-3-yl | cyclopropyl |
| 2-NO$_2$-4-SO$_2$MePh | 1-methylpyrazol-3-yl | CF$_3$ |
| 2-NO$_2$-4-SO$_2$MePh | tetrazol-1-yl | H |
| 2-NO$_2$-4-SO$_2$MePh | tetrazol-1-yl | methyl |
| 2-NO$_2$-4-SO$_2$MePh | tetrazol-1-yl | i-propyl |
| 2-NO$_2$-4-SO$_2$MePh | tetrazol-1-yl | cyclopropyl |
| 2-NO$_2$-4-SO$_2$MePh | tetrazol-1-yl | CF$_3$ |
| 2-NO$_2$-4-SO$_2$MePh | 5-methyltetrazol-1-yl | H |
| 2-NO$_2$-4-SO$_2$MePh | 5-methyltetrazol-1-yl | methyl |
| 2-NO$_2$-4-SO$_2$MePh | 5-methyltetrazol-1-yl | i-propyl |
| 2-NO$_2$-4-SO$_2$MePh | 5-methyltetrazol-1-yl | cyclopropyl |
| 2-NO$_2$-4-SO$_2$MePh | 5-methyltetrazol-1-yl | CF$_3$ |
| 2-NO$_2$-4-SO$_2$MePh | tetrazol-2-yl | H |
| 2-NO$_2$-4-SO$_2$MePh | tetrazol-2-yl | methyl |
| 2-NO$_2$-4-SO$_2$MePh | tetrazol-2-yl | i-propyl |
| 2-NO$_2$-4-SO$_2$MePh | tetrazol-2-yl | cyclopropyl |
| 2-NO$_2$-4-SO$_2$MePh | tetrazol-2-yl | CF$_3$ |
| 2-NO$_2$-4-SO$_2$MePh | 5-methyltetrazol-2-yl | H |
| 2-NO$_2$-4-SO$_2$MePh | 5-methyltetrazol-2-yl | methyl |
| 2-NO$_2$-4-SO$_2$MePh | 5-methyltetrazol-2-yl | i-propyl |
| 2-NO$_2$-4-SO$_2$MePh | 5-methyltetrazol-2-yl | cyclopropyl |
| 2-NO$_2$-4-SO$_2$MePh | 5-methyltetrazol-2-yl | CF$_3$ |
| 2-NO$_2$-4-SO$_2$MePh | 1-methyltetrazol-5-yl | H |
| 2-NO$_2$-4-SO$_2$MePh | 1-methyltetrazol-5-yl | methyl |
| 2-NO$_2$-4-SO$_2$MePh | 1-methyltetrazol-5-yl | i-propyl |
| 2-NO$_2$-4-SO$_2$MePh | 1-methyltetrazol-5-yl | cyclopropyl |
| 2-NO$_2$-4-SO$_2$MePh | 1-methyltetrazol-5-yl | CF$_3$ |
| 2-NO$_2$-4-SO$_2$MePh | 2-methyltetrazol-5-yl | H |
| 2-NO$_2$-4-SO$_2$MePh | 2-methyltetrazol-5-yl | methyl |
| 2-NO$_2$-4-SO$_2$MePh | 2-methyltetrazol-5-yl | i-propyl |
| 2-NO$_2$-4-SO$_2$MePh | 2-methyltetrazol-5-yl | cyclopropyl |
| 2-NO$_2$-4-SO$_2$MePh | 2-methyltetrazol-5-yl | CF$_3$ |
| 2-NO$_2$-4-SO$_2$MePh | pyridin-2-yl | H |
| 2-NO$_2$-4-SO$_2$MePh | pyridin-2-yl | methyl |
| 2-NO$_2$-4-SO$_2$MePh | pyridin-2-yl | i-propyl |
| 2-NO$_2$-4-SO$_2$MePh | pyridin-2-yl | cyclopropyl |
| 2-NO$_2$-4-SO$_2$MePh | pyridin-2-yl | CF$_3$ |
| 2-NO$_2$-4-SO$_2$MePh | pyridin-4-yl | H |
| 2-NO$_2$-4-SO$_2$MePh | pyridin-4-yl | methyl |
| 2-NO$_2$-4-SO$_2$MePh | pyridin-4-yl | i-propyl |
| 2-NO$_2$-4-SO$_2$MePh | pyridin-4-yl | cyclopropyl |
| 2-NO$_2$-4-SO$_2$MePh | pyridin-4-yl | CF$_3$ |
| 2-NO$_2$-4-SO$_2$MePh | pyridin-3-yl | H |
| 2-NO$_2$-4-SO$_2$MePh | pyridin-3-yl | methyl |

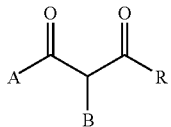

(I)

| A | B | R |
|---|---|---|
| 2-NO₂-4-SO₂MePh | pyridin-3-yl | i-propyl |
| 2-NO₂-4-SO₂MePh | pyridin-3-yl | cyclopropyl |
| 2-NO₂-4-SO₂MePh | pyridin-3-yl | CF₃ |
| 2-NO₂-4-SO₂MePh | 3-nitropyridin-4-yl | H |
| 2-NO₂-4-SO₂MePh | 3-nitropyridin-4-yl | methyl |
| 2-NO₂-4-SO₂MePh | 3-nitropyridin-4-yl | i-propyl |
| 2-NO₂-4-SO₂MePh | 3-nitropyridin-4-yl | cyclopropyl |
| 2-NO₂-4-SO₂MePh | 3-nitropyridin-4-yl | CF₃ |
| 2-NO₂-4-SO₂MePh | 5-cyanopyridin-2-yl | H |
| 2-NO₂-4-SO₂MePh | 5-cyanopyridin-2-yl | methyl |
| 2-NO₂-4-SO₂MePh | 5-cyanopyridin-2-yl | i-propyl |
| 2-NO₂-4-SO₂MePh | 5-cyanopyridin-2-yl | cyclopropyl |
| 2-NO₂-4-SO₂MePh | 5-cyanopyridin-2-yl | CF₃ |
| 2-NO₂-4-SO₂MePh | 5-trifluoromethylpyridin-2-yl | H |
| 2-NO₂-4-SO₂MePh | 5-trifluoromethylpyridin-2-yl | methyl |
| 2-NO₂-4-SO₂MePh | 5-trifluoromethylpyridin-2-yl | i-propyl |
| 2-NO₂-4-SO₂MePh | 5-trifluoromethylpyridin-2-yl | cyclopropyl |
| 2-NO₂-4-SO₂MePh | 5-trifluoromethylpyridin-2-yl | CF₃ |
| 2-NO₂-4-SO₂MePh | pyrimidin-2-yl | H |
| 2-NO₂-4-SO₂MePh | pyrimidin-2-yl | methyl |
| 2-NO₂-4-SO₂MePh | pyrimidin-2-yl | i-propyl |
| 2-NO₂-4-SO₂MePh | pyrimidin-2-yl | cyclopropyl |
| 2-NO₂-4-SO₂MePh | pyrimidin-2-yl | CF₃ |
| 2-NO₂-4-SO₂MePh | pyrimidin-4-yl | H |
| 2-NO₂-4-SO₂MePh | pyrimidin-4-yl | methyl |
| 2-NO₂-4-SO₂MePh | pyrimidin-4-yl | i-propyl |
| 2-NO₂-4-SO₂MePh | pyrimidin-4-yl | cyclopropyl |
| 2-NO₂-4-SO₂MePh | pyrimidin-4-yl | CF₃ |
| 2-NO₂-4-SO₂MePh | 6-chloropyrimidin-4-yl | methyl |
| 2-NO₂-4-SO₂MePh | 6-chloropyrimidin-4-yl | i-propyl |
| 2-NO₂-4-SO₂MePh | 6-chloropyrimidin-4-yl | cyclopropyl |
| 2-NO₂-4-SO₂MePh | 6-chloropyrimidin-4-yl | CF₃ |
| 2-NO₂-4-SO₂MePh | pyridazin-3-yl | H |
| 2-NO₂-4-SO₂MePh | pyridazin-3-yl | methyl |
| 2-NO₂-4-SO₂MePh | pyridazin-3-yl | i-propyl |
| 2-NO₂-4-SO₂MePh | pyridazin-3-yl | cyclopropyl |
| 2-NO₂-4-SO₂MePh | pyridazin-3-yl | CF₃ |
| 2-NO₂-4-SO₂MePh | 6-chloropyridazin-3-yl | methyl |
| 2-NO₂-4-SO₂MePh | 6-chloropyridazin-3-yl | i-propyl |
| 2-NO₂-4-SO₂MePh | 6-chloropyridazin-3-yl | cyclopropyl |
| 2-NO₂-4-SO₂MePh | 6-chloropyridazin-3-yl | CF₃ |
| 2-NO₂-4-SO₂MePh | pyrazin-2-yl | methyl |
| 2-NO₂-4-SO₂MePh | pyrazin-2-yl | i-propyl |
| 2-NO₂-4-SO₂MePh | pyrazin-2-yl | cyclopropyl |
| 2-NO₂-4-SO₂MePh | pyrazin-2-yl | CF₃ |
| 2-NO₂-4-SO₂MePh | triazin-2-yl | methyl |
| 2-NO₂-4-SO₂MePh | triazin-2-yl | i-propyl |
| 2-NO₂-4-SO₂MePh | triazin-2-yl | cyclopropyl |
| 2-NO₂-4-SO₂MePh | triazin-2-yl | CF₃ |
| 2-NO₂-4-SO₂MePh | quinolin-2-yl | methyl |
| 2-NO₂-4-SO₂MePh | quinolin-2-yl | i-propyl |
| 2-NO₂-4-SO₂MePh | quinolin-2-yl | cyclopropyl |
| 2-NO₂-4-SO₂MePh | quinolin-2-yl | CF₃ |
| 2-NO₂-4-SO₂MePh | 4,4,6-trimethyl-5,6-dihydro-1,3(4H)-oxazin-2-yl | H |
| 2-NO₂-4-SO₂MePh | 4,4,6-trimethyl-5,6-dihydro-1,3(4H)-oxazin-2-yl | methyl |
| 2-NO₂-4-SO₂MePh | 4,4,6-trimethyl-5,6-dihydro-1,3(4H)-oxazin-2-yl | i-propyl |
| 2-NO₂-4-SO₂MePh | 4,4,6-trimethyl-5,6-dihydro-1,3(4H)-oxazin-2-yl | cyclopropyl |
| 2-NO₂-4-SO₂MePh | 4,4,6-trimethyl-5,6-dihydro-1,3(4H)-oxazin-2-yl | CF₃ |
| 2-NO₂-4-SO₂MePh | 2-oxazolidinon-3-yl | H |
| 2-NO₂-4-SO₂MePh | 2-oxazolidinon-3-yl | methyl |
| 2-NO₂-4-SO₂MePh | 2-oxazolidinon-3-yl | i-propyl |
| 2-NO₂-4-SO₂MePh | 2-oxazolidinon-3-yl | cyclopropyl |
| 2-NO₂-4-SO₂MePh | 2-oxazolidinon-3-yl | CF₃ |
| 2-NO₂-4-SO₂MePh | 2-pyrrolidinon-1-yl | methyl |
| 2-NO₂-4-SO₂MePh | 2-pyrrolidinon-1-yl | i-propyl |

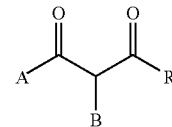

(I)

| A | B | R |
|---|---|---|
| 2-NO₂-4-SO₂MePh | 2-pyrrolidinon-1-yl | cyclopropyl |
| 2-NO₂-4-SO₂MePh | 2-pyrrolidinon-1-yl | CF₃ |
| 2-NO₂-4-SO₂MePh | 3-methylisoxazol-5-yl | methyl |
| 2-NO₂-4-SO₂MePh | 3-methylisoxazol-5-yl | i-propyl |
| 2-NO₂-4-SO₂MePh | 3-methylisoxazol-5-yl | cyclopropyl |
| 2-NO₂-4-SO₂MePh | 3-methylisoxazol-5-yl | CF₃ |
| 2-NO₂-4-SO₂MePh | 2-NO₂-4-SO₂MePh | H |
| 2-NO₂-4-SO₂MePh | 2-NO₂-4-SO₂MePh | methyl |
| 2-NO₂-4-SO₂MePh | 2-NO₂-4-SO₂MePh | i-propyl |
| 2-NO₂-4-SO₂MePh | 2-NO₂-4-SO₂MePh | cyclopropyl |
| 2-NO₂-4-SO₂MePh | 2-NO₂-4-SO₂MePh | CF₃ |
| 2-NO₂-4-SO₂MePh | 2-Cl-4-SO₂MePh | H |
| 2-NO₂-4-SO₂MePh | 2-Cl-4-SO₂MePh | methyl |
| 2-NO₂-4-SO₂MePh | 2-Cl-4-SO₂MePh | i-propyl |
| 2-NO₂-4-SO₂MePh | 2-Cl-4-SO₂MePh | cyclopropyl |
| 2-NO₂-4-SO₂MePh | 2-Cl-4-SO₂MePh | CF₃ |
| 2-NO₂-4-SO₂MePh | 2-NO₂-4-CF₃Ph | H |
| 2-NO₂-4-SO₂MePh | 2-NO₂-4-CF₃Ph | methyl |
| 2-NO₂-4-SO₂MePh | 2-NO₂-4-CF₃Ph | i-propyl |
| 2-NO₂-4-SO₂MePh | 2-NO₂-4-CF₃Ph | cyclopropyl |
| 2-NO₂-4-SO₂MePh | 2-NO₂-4-CF₃Ph | CF₃ |
| 2-NO₂-4-SO₂MePh | 2-NO₂-4-ClPh | H |
| 2-NO₂-4-SO₂MePh | 2-NO₂-4-ClPh | methyl |
| 2-NO₂-4-SO₂MePh | 2-NO₂-4-ClPh | i-propyl |
| 2-NO₂-4-SO₂MePh | 2-NO₂-4-ClPh | cyclopropyl |
| 2-NO₂-4-SO₂MePh | 2-NO₂-4-ClPh | CF₃ |
| 2-NO₂-4-SO₂MePh | 2-Cl-4-NO₂Ph | H |
| 2-NO₂-4-SO₂MePh | 2-Cl-4-NO₂Ph | methyl |
| 2-NO₂-4-SO₂MePh | 2-Cl-4-NO₂Ph | i-propyl |
| 2-NO₂-4-SO₂MePh | 2-Cl-4-NO₂Ph | cyclopropyl |
| 2-NO₂-4-SO₂MePh | 2-Cl-4-NO₂Ph | CF₃ |
| 2-NO₂-4-SO₂MePh | 2,4-(NO₂)₂Ph | H |
| 2-NO₂-4-SO₂MePh | 2,4-(NO₂)₂Ph | methyl |
| 2-NO₂-4-SO₂MePh | 2,4-(NO₂)₂Ph | i-propyl |
| 2-NO₂-4-SO₂MePh | 2,4-(NO₂)₂Ph | cyclopropyl |
| 2-NO₂-4-SO₂MePh | 2,4-(NO₂)₂Ph | CF₃ |
| 2-NO₂-4-SO₂MePh | 4-F-3-NO₂Ph | H |
| 2-NO₂-4-SO₂MePh | 4-F-3-NO₂Ph | methyl |
| 2-NO₂-4-SO₂MePh | 4-F-3-NO₂Ph | i-propyl |
| 2-NO₂-4-SO₂MePh | 4-F-3-NO₂Ph | cyclopropyl |
| 2-NO₂-4-SO₂MePh | 4-F-3-NO₂Ph | CF₃ |
| 2-NO₂-4-SO₂MePh | 3,5-(CF₃)₂Ph | H |
| 2-NO₂-4-SO₂MePh | 3,5-(CF₃)₂Ph | methyl |
| 2-NO₂-4-SO₂MePh | 3,5-(CF₃)₂Ph | i-propyl |
| 2-NO₂-4-SO₂MePh | 3,5-(CF₃)₂Ph | cyclopropyl |
| 2-NO₂-4-SO₂MePh | 3,5-(CF₃)₂Ph | CF₃ |
| 2-NO₂-4-SO₂MePh | 2-SO₂Me-4-CF₃Ph | H |
| 2-NO₂-4-SO₂MePh | 2-SO₂Me-4-CF₃Ph | methyl |
| 2-NO₂-4-SO₂MePh | 2-SO₂Me-4-CF₃Ph | i-propyl |
| 2-NO₂-4-SO₂MePh | 2-SO₂Me-4-CF₃Ph | cyclopropyl |
| 2-NO₂-4-SO₂MePh | 2-SO₂Me-4-CF₃Ph | CF₃ |
| 2-Cl-4-SO₂MePh | 1,2,4-oxadiazol-5-yl | H |
| 2-Cl-4-SO₂MePh | 1,2,4-oxadiazol-5-yl | methyl |
| 2-Cl-4-SO₂MePh | 1,2,4-oxadiazol-5-yl | i-propyl |
| 2-Cl-4-SO₂MePh | 1,2,4-oxadiazol-5-yl | cyclopropyl |
| 2-Cl-4-SO₂MePh | 1,2,4-oxadiazol-5-yl | CF₃ |
| 2-Cl-4-SO₂MePh | 3-methyl-1,2,4-oxadiazol-5-yl | H |
| 2-Cl-4-SO₂MePh | 3-methyl-1,2,4-oxadiazol-5-yl | methyl |
| 2-Cl-4-SO₂MePh | 3-methyl-1,2,4-oxadiazol-5-yl | i-propyl |
| 2-Cl-4-SO₂MePh | 3-methyl-1,2,4-oxadiazol-5-yl | cyclopropyl |
| 2-Cl-4-SO₂MePh | 3-methyl-1,2,4-oxadiazol-5-yl | CF₃ |
| 2-Cl-4-SO₂MePh | 3-trifluoromethyl-1,2,4-oxadiazol-5-yl | H |
| 2-Cl-4-SO₂MePh | 3-trifluoromethyl-1,2,4-oxadiazol-5-yl | methyl |
| 2-Cl-4-SO₂MePh | 3-trifluoromethyl-1,2,4-oxadiazol-5-yl | i-propyl |
| 2-Cl-4-SO₂MePh | 3-trifluoromethyl-1,2,4-oxadiazol-5-yl | cyclopropyl |
| 2-Cl-4-SO₂MePh | 3-trifluoromethyl-1,2,4- | CF₃ |

-continued

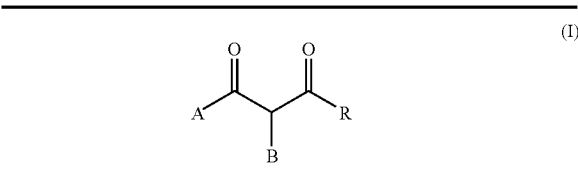
(I)

| A | B | R |
|---|---|---|
| | oxadiazol-5-yl | |
| 2-Cl-4-SO$_2$MePh | 1,2,4-oxadiazol-3-yl | H |
| 2-Cl-4-SO$_2$MePh | 1,2,4-oxadiazol-3-yl | methyl |
| 2-Cl-4-SO$_2$MePh | 1,2,4-oxadiazol-3-yl | i-propyl |
| 2-Cl-4-SO$_2$MePh | 1,2,4-oxadiazol-3-yl | cyclopropyl |
| 2-Cl-4-SO$_2$MePh | 1,2,4-oxadiazol-3-yl | CF$_3$ |
| 2-Cl-4-SO$_2$MePh | 5-methyl-1,2,4-oxadiazol-3-yl | H |
| 2-Cl-4-SO$_2$MePh | 5-methyl-1,2,4-oxadiazol-3-yl | methyl |
| 2-Cl-4-SO$_2$MePh | 5-methyl-1,2,4-oxadiazol-3-yl | i-propyl |
| 2-Cl-4-SO$_2$MePh | 5-methyl-1,2,4-oxadiazol-3-yl | cyclopropyl |
| 2-Cl-4-SO$_2$MePh | 5-methyl-1,2,4-oxadiazol-3-yl | CF$_3$ |
| 2-Cl-4-SO$_2$MePh | 5-trifluoromethyl-1,2,4-oxadiazol-3-yl | H |
| 2-Cl-4-SO$_2$MePh | 5-trifluoromethyl-1,2,4-oxadiazol-3-yl | methyl |
| 2-Cl-4-SO$_2$MePh | 5-trifluoromethyl-1,2,4-oxadiazol-3-yl | i-propyl |
| 2-Cl-4-SO$_2$MePh | 5-trifluoromethyl-1,2,4-oxadiazol-3-yl | cyclopropyl |
| 2-Cl-4-SO$_2$MePh | 5-trifluoromethyl-1,2,4-oxadiazol-3-yl | CF$_3$ |
| 2-Cl-4-SO$_2$MePh | 5-chloro-1,2,4-oxadiazol-3-yl | H |
| 2-Cl-4-SO$_2$MePh | 5-chloro-1,2,4-oxadiazol-3-yl | methyl |
| 2-Cl-4-SO$_2$MePh | 5-chloro-1,2,4-oxadiazol-3-yl | i-propyl |
| 2-Cl-4-SO$_2$MePh | 5-chloro-1,2,4-oxadiazol-3-yl | cyclopropyl |
| 2-Cl-4-SO$_2$MePh | 5-chloro-1,2,4-oxadiazol-3-yl | CF$_3$ |
| 2-Cl-4-SO$_2$MePh | 1,3,4-oxadiazol-2-yl | H |
| 2-Cl-4-SO$_2$MePh | 1,3,4-oxadiazol-2-yl | methyl |
| 2-Cl-4-SO$_2$MePh | 1,3,4-oxadiazol-2-yl | i-propyl |
| 2-Cl-4-SO$_2$MePh | 1,3,4-oxadiazol-2-yl | cyclopropyl |
| 2-Cl-4-SO$_2$MePh | 1,3,4-oxadiazol-2-yl | CF$_3$ |
| 2-Cl-4-SO$_2$MePh | 5-methylsulfonyl-1,3,4-oxadiazol-2-yl | H |
| 2-Cl-4-SO$_2$MePh | 5-methylsulfonyl-1,3,4-oxadiazol-2-yl | methyl |
| 2-Cl-4-SO$_2$MePh | 5-methylsulfonyl-1,3,4-oxadiazol-2-yl | i-propyl |
| 2-Cl-4-SO$_2$MePh | 5-methylsulfonyl-1,3,4-oxadiazol-2-yl | cyclopropyl |
| 2-Cl-4-SO$_2$MePh | 5-methylsulfonyl-1,3,4-oxadiazol-2-yl | CF$_3$ |
| 2-Cl-4-SO$_2$MePh | 5-methyl-1,3,4-oxadiazol-2-yl | H |
| 2-Cl-4-SO$_2$MePh | 5-methyl-1,3,4-oxadiazol-2-yl | methyl |
| 2-Cl-4-SO$_2$MePh | 5-methyl-1,3,4-oxadiazol-2-yl | i-propyl |
| 2-Cl-4-SO$_2$MePh | 5-methyl-1,3,4-oxadiazol-2-yl | cyclopropyl |
| 2-Cl-4-SO$_2$MePh | 5-methyl-1,3,4-oxadiazol-2-yl | CF$_3$ |
| 2-Cl-4-SO$_2$MePh | 5-trifluoromethyl-1,3,4-oxadiazol-2-yl | H |
| 2-Cl-4-SO$_2$MePh | 5-trifluoromethyl-1,3,4-oxadiazol-2-yl | methyl |
| 2-Cl-4-SO$_2$MePh | 5-trifluoromethyl-1,3,4-oxadiazol-2-yl | i-propyl |
| 2-Cl-4-SO$_2$MePh | 5-trifluoromethyl-1,3,4-oxadiazol-2-yl | cyclopropyl |
| 2-Cl-4-SO$_2$MePh | 5-trifluoromethyl-1,3,4-oxadiazol-2-yl | CF$_3$ |
| 2-Cl-4-SO$_2$MePh | 1,2,3-triazol-4-yl | H |
| 2-Cl-4-SO$_2$MePh | 1,2,3-triazol-4-yl | methyl |
| 2-Cl-4-SO$_2$MePh | 1,2,3-triazol-4-yl | i-propyl |
| 2-Cl-4-SO$_2$MePh | 1,2,3-triazol-4-yl | cyclopropyl |
| 2-Cl-4-SO$_2$MePh | 1,2,3-triazol-4-yl | CF$_3$ |
| 2-Cl-4-SO$_2$MePh | 1-methyl-1,2,3-triazol-4-yl | H |
| 2-Cl-4-SO$_2$MePh | 1-methyl-1,2,3-triazol-4-yl | methyl |
| 2-Cl-4-SO$_2$MePh | 1-methyl-1,2,3-triazol-4-yl | i-propyl |
| 2-Cl-4-SO$_2$MePh | 1-methyl-1,2,3-triazol-4-yl | cyclopropyl |
| 2-Cl-4-SO$_2$MePh | 1-methyl-1,2,3-triazol-4-yl | CF$_3$ |
| 2-Cl-4-SO$_2$MePh | 2-methyl-1,2,3-triazol-4-yl | H |
| 2-Cl-4-SO$_2$MePh | 2-methyl-1,2,3-triazol-4-yl | methyl |
| 2-Cl-4-SO$_2$MePh | 2-methyl-1,2,3-triazol-4-yl | i-propyl |
| 2-Cl-4-SO$_2$MePh | 2-methyl-1,2,3-triazol-4-yl | cyclopropyl |

-continued

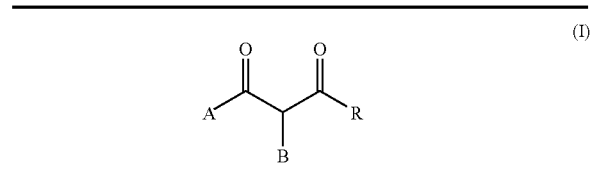
(I)

| A | B | R |
|---|---|---|
| 2-Cl-4-SO$_2$MePh | 2-methyl-1,2,3-triazol-4-yl | CF$_3$ |
| 2-Cl-4-SO$_2$MePh | 1,2,3-triazol-1-yl | H |
| 2-Cl-4-SO$_2$MePh | 1,2,3-triazol-1-yl | methyl |
| 2-Cl-4-SO$_2$MePh | 1,2,3-triazol-1-yl | i-propyl |
| 2-Cl-4-SO$_2$MePh | 1,2,3-triazol-1-yl | cyclopropyl |
| 2-Cl-4-SO$_2$MePh | 1,2,3-triazol-1-yl | CF$_3$ |
| 2-Cl-4-SO$_2$MePh | 1,2,3-triazol-2-yl | H |
| 2-Cl-4-SO$_2$MePh | 1,2,3-triazol-2-yl | methyl |
| 2-Cl-4-SO$_2$MePh | 1,2,3-triazol-2-yl | i-propyl |
| 2-Cl-4-SO$_2$MePh | 1,2,3-triazol-2-yl | cyclopropyl |
| 2-Cl-4-SO$_2$MePh | 1,2,3-triazol-2-yl | CF$_3$ |
| 2-Cl-4-SO$_2$MePh | 1,2,4-triazol-1-yl | H |
| 2-Cl-4-SO$_2$MePh | 1,2,4-triazol-1-yl | methyl |
| 2-Cl-4-SO$_2$MePh | 1,2,4-triazol-1-yl | i-propyl |
| 2-Cl-4-SO$_2$MePh | 1,2,4-triazol-1-yl | cyclopropyl |
| 2-Cl-4-SO$_2$MePh | 1,2,4-triazol-1-yl | CF$_3$ |
| 2-Cl-4-SO$_2$MePh | imidazol-2-yl | H |
| 2-Cl-4-SO$_2$MePh | imidazol-2-yl | methyl |
| 2-Cl-4-SO$_2$MePh | imidazol-2-yl | i-propyl |
| 2-Cl-4-SO$_2$MePh | imidazol-2-yl | cyclopropyl |
| 2-Cl-4-SO$_2$MePh | imidazol-2-yl | CF$_3$ |
| 2-Cl-4-SO$_2$MePh | imidazol-1-yl | H |
| 2-Cl-4-SO$_2$MePh | imidazol-1-yl | methyl |
| 2-Cl-4-SO$_2$MePh | imidazol-1-yl | i-propyl |
| 2-Cl-4-SO$_2$MePh | imidazol-1-yl | cyclopropyl |
| 2-Cl-4-SO$_2$MePh | imidazol-1-yl | CF$_3$ |
| 2-Cl-4-SO$_2$MePh | imidazol-4-yl | H |
| 2-Cl-4-SO$_2$MePh | imidazol-4-yl | methyl |
| 2-Cl-4-SO$_2$MePh | imidazol-4-yl | i-propyl |
| 2-Cl-4-SO$_2$MePh | imidazol-4-yl | cyclopropyl |
| 2-Cl-4-SO$_2$MePh | imidazol-4-yl | CF$_3$ |
| 2-Cl-4-SO$_2$MePh | thiazol-2-yl | H |
| 2-Cl-4-SO$_2$MePh | thiazol-2-yl | methyl |
| 2-Cl-4-SO$_2$MePh | thiazol-2-yl | i-propyl |
| 2-Cl-4-SO$_2$MePh | thiazol-2-yl | cyclopropyl |
| 2-Cl-4-SO$_2$MePh | thiazol-2-yl | CF$_3$ |
| 2-Cl-4-SO$_2$MePh | 4-methylthiazol-2-yl | H |
| 2-Cl-4-SO$_2$MePh | 4-methylthiazol-2-yl | methyl |
| 2-Cl-4-SO$_2$MePh | 4-methylthiazol-2-yl | i-propyl |
| 2-Cl-4-SO$_2$MePh | 4-methylthiazol-2-yl | cyclopropyl |
| 2-Cl-4-SO$_2$MePh | 4-methylthiazol-2-yl | CF$_3$ |
| 2-Cl-4-SO$_2$MePh | oxazol-2-yl | H |
| 2-Cl-4-SO$_2$MePh | oxazol-2-yl | methyl |
| 2-Cl-4-SO$_2$MePh | oxazol-2-yl | i-propyl |
| 2-Cl-4-SO$_2$MePh | oxazol-2-yl | cyclopropyl |
| 2-Cl-4-SO$_2$MePh | oxazol-2-yl | CF$_3$ |
| 2-Cl-4-SO$_2$MePh | 4,5-dimethyloxazol-2-yl | H |
| 2-Cl-4-SO$_2$MePh | 4,5-dimethyloxazol-2-yl | methyl |
| 2-Cl-4-SO$_2$MePh | 4,5-dimethyloxazol-2-yl | i-propyl |
| 2-Cl-4-SO$_2$MePh | 4,5-dimethyloxazol-2-yl | cyclopropyl |
| 2-Cl-4-SO$_2$MePh | 4,5-dimethyloxazol-2-yl | CF$_3$ |
| 2-Cl-4-SO$_2$MePh | 2-oxazolin-2-yl | H |
| 2-Cl-4-SO$_2$MePh | 2-oxazolin-2-yl | methyl |
| 2-Cl-4-SO$_2$MePh | 2-oxazolin-2-yl | i-propyl |
| 2-Cl-4-SO$_2$MePh | 2-oxazolin-2-yl | cyclopropyl |
| 2-Cl-4-SO$_2$MePh | 2-oxazolin-2-yl | CF$_3$ |
| 2-Cl-4-SO$_2$MePh | 4,4-dimethyl-2-oxazolin-2-yl | H |
| 2-Cl-4-SO$_2$MePh | 4,4-dimethyl-2-oxazolin-2-yl | methyl |
| 2-Cl-4-SO$_2$MePh | 4,4-dimethyl-2-oxazolin-2-yl | i-propyl |
| 2-Cl-4-SO$_2$MePh | 4,4-dimethyl-2-oxazolin-2-yl | cyclopropyl |
| 2-Cl-4-SO$_2$MePh | 4,4-dimethyl-2-oxazolin-2-yl | CF$_3$ |
| 2-Cl-4-SO$_2$MePh | 1,2,4-thiadiazol-5-yl | H |
| 2-Cl-4-SO$_2$MePh | 1,2,4-thiadiazol-5-yl | methyl |
| 2-Cl-4-SO$_2$MePh | 1,2,4-thiadiazol-5-yl | i-propyl |
| 2-Cl-4-SO$_2$MePh | 1,2,4-thiadiazol-5-yl | cyclopropyl |
| 2-Cl-4-SO$_2$MePh | 1,2,4-thiadiazol-5-yl | CF$_3$ |
| 2-Cl-4-SO$_2$MePh | 3-methyl-1,2,4-thiadiazol-5-yl | H |
| 2-Cl-4-SO$_2$MePh | 3-methyl-1,2,4-thiadiazol-5-yl | methyl |
| 2-Cl-4-SO$_2$MePh | 3-methyl-1,2,4-thiadiazol-5-yl | i-propyl |
| 2-Cl-4-SO$_2$MePh | 3-methyl-1,2,4-thiadiazol-5-yl | cyclopropyl |

-continued

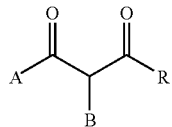

(I)

| A | B | R |
|---|---|---|
| 2-Cl-4-SO$_2$MePh | 3-methyl-1,2,4-thiadiazol-5-yl | CF$_3$ |
| 2-Cl-4-SO$_2$MePh | 3-trifluoromethyl-1,2,4-thiadiazol-5-yl | H |
| 2-Cl-4-SO$_2$MePh | 3-trifluoromethyl-1,2,4-thiadiazol-5-yl | methyl |
| 2-Cl-4-SO$_2$MePh | 3-trifluoromethyl-1,2,4-thiadiazol-5-yl | i-propyl |
| 2-Cl-4-SO$_2$MePh | 3-trifluoromethyl-1,2,4-thiadiazol-5-yl | cyclopropyl |
| 2-Cl-4-SO$_2$MePh | 3-trifluoromethyl-1,2,4-thiadiazol-5-yl | CF$_3$ |
| 2-Cl-4-SO$_2$MePh | 1,2,4-thiadiazol-3-yl | H |
| 2-Cl-4-SO$_2$MePh | 1,2,4-thiadiazol-3-yl | methyl |
| 2-Cl-4-SO$_2$MePh | 1,2,4-thiadiazol-3-yl | i-propyl |
| 2-Cl-4-SO$_2$MePh | 1,2,4-thiadiazol-3-yl | cyclopropyl |
| 2-Cl-4-SO$_2$MePh | 1,2,4-thiadiazol-3-yl | CF$_3$ |
| 2-Cl-4-SO$_2$MePh | 5-methyl-1,2,4-thiadiazol-3-yl | H |
| 2-Cl-4-SO$_2$MePh | 5-methyl-1,2,4-thiadiazol-3-yl | methyl |
| 2-Cl-4-SO$_2$MePh | 5-methyl-1,2,4-thiadiazol-3-yl | i-propyl |
| 2-Cl-4-SO$_2$MePh | 5-methyl-1,2,4-thiadiazol-3-yl | cyclopropyl |
| 2-Cl-4-SO$_2$MePh | 5-methyl-1,2,4-thiadiazol-3-yl | CF$_3$ |
| 2-Cl-4-SO$_2$MePh | 5-trifluoromethyl-1,2,4-thiadiazol-3-yl | H |
| 2-Cl-4-SO$_2$MePh | 5-trifluoromethyl-1,2,4-thiadiazol-3-yl | methyl |
| 2-Cl-4-SO$_2$MePh | 5-trifluoromethyl-1,2,4-thiadiazol-3-yl | i-propyl |
| 2-Cl-4-SO$_2$MePh | 5-trifluoromethyl-1,2,4-thiadiazol-3-yl | cyclopropyl |
| 2-Cl-4-SO$_2$MePh | 5-trifluoromethyl-1,2,4-thiadiazol-3-yl | CF$_3$ |
| 2-Cl-4-SO$_2$MePh | 1,3,4-thiadiazol-2-yl | H |
| 2-Cl-4-SO$_2$MePh | 1,3,4-thiadiazol-2-yl | methyl |
| 2-Cl-4-SO$_2$MePh | 1,3,4-thiadiazol-2-yl | i-propyl |
| 2-Cl-4-SO$_2$MePh | 1,3,4-thiadiazol-2-yl | cyclopropyl |
| 2-Cl-4-SO$_2$MePh | 1,3,4-thiadiazol-2-yl | CF$_3$ |
| 2-Cl-4-SO$_2$MePh | 5-methylsulfonyl-1,3,4-thiadiazol-2-yl | H |
| 2-Cl-4-SO$_2$MePh | 5-methylsulfonyl-1,3,4-thiadiazol-2-yl | methyl |
| 2-Cl-4-SO$_2$MePh | 5-methylsulfonyl-1,3,4-thiadiazol-2-yl | i-propyl |
| 2-Cl-4-SO$_2$MePh | 5-methylsulfonyl-1,3,4-thiadiazol-2-yl | cyclopropyl |
| 2-Cl-4-SO$_2$MePh | 5-methylsulfonyl-1,3,4-thiadiazol-2-yl | CF$_3$ |
| 2-Cl-4-SO$_2$MePh | 5-methyl-1,3,4-thiadiazol-2-yl | H |
| 2-Cl-4-SO$_2$MePh | 5-methyl-1,3,4-thiadiazol-2-yl | methyl |
| 2-Cl-4-SO$_2$MePh | 5-methyl-1,3,4-thiadiazol-2-yl | i-propyl |
| 2-Cl-4-SO$_2$MePh | 5-methyl-1,3,4-thiadiazol-2-yl | cyclopropyl |
| 2-Cl-4-SO$_2$MePh | 5-methyl-1,3,4-thiadiazol-2-yl | CF$_3$ |
| 2-Cl-4-SO$_2$MePh | benzoxazol-2-yl | H |
| 2-Cl-4-SO$_2$MePh | benzoxazol-2-yl | methyl |
| 2-Cl-4-SO$_2$MePh | benzoxazol-2-yl | i-propyl |
| 2-Cl-4-SO$_2$MePh | benzoxazol-2-yl | cyclopropyl |
| 2-Cl-4-SO$_2$MePh | benzoxazol-2-yl | CF$_3$ |
| 2-Cl-4-SO$_2$MePh | 6-methylbenzoxazol-2-yl | H |
| 2-Cl-4-SO$_2$MePh | 6-methylbenzoxazol-2-yl | methyl |
| 2-Cl-4-SO$_2$MePh | 6-methylbenzoxazol-2-yl | i-propyl |
| 2-Cl-4-SO$_2$MePh | 6-methylbenzoxazol-2-yl | cyclopropyl |
| 2-Cl-4-SO$_2$MePh | 6-methylbenzoxazol-2-yl | CF$_3$ |
| 2-Cl-4-SO$_2$MePh | benzothiazol-2-yl | H |
| 2-Cl-4-SO$_2$MePh | benzothiazol-2-yl | methyl |
| 2-Cl-4-SO$_2$MePh | benzothiazol-2-yl | i-propyl |
| 2-Cl-4-SO$_2$MePh | benzothiazol-2-yl | cyclopropyl |
| 2-Cl-4-SO$_2$MePh | benzothiazol-2-yl | CF$_3$ |
| 2-Cl-4-SO$_2$MePh | pyrazol-1-yl | H |
| 2-Cl-4-SO$_2$MePh | pyrazol-1-yl | methyl |
| 2-Cl-4-SO$_2$MePh | pyrazol-1-yl | i-propyl |
| 2-Cl-4-SO$_2$MePh | pyrazol-1-yl | cyclopropyl |

-continued

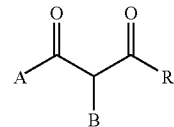

(I)

| A | B | R |
|---|---|---|
| 2-Cl-4-SO$_2$MePh | pyrazol-1-yl | CF$_3$ |
| 2-Cl-4-SO$_2$MePh | pyrazol-3-yl | H |
| 2-Cl-4-SO$_2$MePh | pyrazol-3-yl | methyl |
| 2-Cl-4-SO$_2$MePh | pyrazol-3-yl | i-propyl |
| 2-Cl-4-SO$_2$MePh | pyrazol-3-yl | cyclopropyl |
| 2-Cl-4-SO$_2$MePh | pyrazol-3-yl | CF$_3$ |
| 2-Cl-4-SO$_2$MePh | 1-methylpyrazol-3-yl | H |
| 2-Cl-4-SO$_2$MePh | 1-methylpyrazol-3-yl | methyl |
| 2-Cl-4-SO$_2$MePh | 1-methylpyrazol-3-yl | i-propyl |
| 2-Cl-4-SO$_2$MePh | 1-methylpyrazol-3-yl | cyclopropyl |
| 2-Cl-4-SO$_2$MePh | 1-methylpyrazol-3-yl | CF$_3$ |
| 2-Cl-4-SO$_2$MePh | tetrazol-1-yl | H |
| 2-Cl-4-SO$_2$MePh | tetrazol-1-yl | methyl |
| 2-Cl-4-SO$_2$MePh | tetrazol-1-yl | i-propyl |
| 2-Cl-4-SO$_2$MePh | tetrazol-1-yl | cyclopropyl |
| 2-Cl-4-SO$_2$MePh | tetrazol-1-yl | CF$_3$ |
| 2-Cl-4-SO$_2$MePh | 5-methyltetrazol-1-yl | H |
| 2-Cl-4-SO$_2$MePh | 5-methyltetrazol-1-yl | methyl |
| 2-Cl-4-SO$_2$MePh | 5-methyltetrazol-1-yl | i-propyl |
| 2-Cl-4-SO$_2$MePh | 5-methyltetrazol-1-yl | cyclopropyl |
| 2-Cl-4-SO$_2$MePh | 5-methyltetrazol-1-yl | CF$_3$ |
| 2-Cl-4-SO$_2$MePh | tetrazol-2-yl | H |
| 2-Cl-4-SO$_2$MePh | tetrazol-2-yl | methyl |
| 2-Cl-4-SO$_2$MePh | tetrazol-2-yl | i-propyl |
| 2-Cl-4-SO$_2$MePh | tetrazol-2-yl | cyclopropyl |
| 2-Cl-4-SO$_2$MePh | tetrazol-2-yl | CF$_3$ |
| 2-Cl-4-SO$_2$MePh | 5-methyltetrazol-2-yl | H |
| 2-Cl-4-SO$_2$MePh | 5-methyltetrazol-2-yl | methyl |
| 2-Cl-4-SO$_2$MePh | 5-methyltetrazol-2-yl | i-propyl |
| 2-Cl-4-SO$_2$MePh | 5-methyltetrazol-2-yl | cyclopropyl |
| 2-Cl-4-SO$_2$MePh | 5-methyltetrazol-2-yl | CF$_3$ |
| 2-Cl-4-SO$_2$MePh | 1-methyltetrazol-5-yl | H |
| 2-Cl-4-SO$_2$MePh | 1-methyltetrazol-5-yl | methyl |
| 2-Cl-4-SO$_2$MePh | 1-methyltetrazol-5-yl | i-propyl |
| 2-Cl-4-SO$_2$MePh | 1-methyltetrazol-5-yl | cyclopropyl |
| 2-Cl-4-SO$_2$MePh | 1-methyltetrazol-5-yl | CF$_3$ |
| 2-Cl-4-SO$_2$MePh | 2-methyltetrazol-5-yl | H |
| 2-Cl-4-SO$_2$MePh | 2-methyltetrazol-5-yl | methyl |
| 2-Cl-4-SO$_2$MePh | 2-methyltetrazol-5-yl | i-propyl |
| 2-Cl-4-SO$_2$MePh | 2-methyltetrazol-5-yl | cyclopropyl |
| 2-Cl-4-SO$_2$MePh | 2-methyltetrazol-5-yl | CF$_3$ |
| 2-Cl-4-SO$_2$MePh | pyridin-2-yl | H |
| 2-Cl-4-SO$_2$MePh | pyridin-2-yl | methyl |
| 2-Cl-4-SO$_2$MePh | pyridin-2-yl | i-propyl |
| 2-Cl-4-SO$_2$MePh | pyridin-2-yl | cyclopropyl |
| 2-Cl-4-SO$_2$MePh | pyridin-2-yl | CF$_3$ |
| 2-Cl-4-SO$_2$MePh | pyridin-4-yl | H |
| 2-Cl-4-SO$_2$MePh | pyridin-4-yl | methyl |
| 2-Cl-4-SO$_2$MePh | pyridin-4-yl | i-propyl |
| 2-Cl-4-SO$_2$MePh | pyridin-4-yl | cyclopropyl |
| 2-Cl-4-SO$_2$MePh | pyridin-4-yl | CF$_3$ |
| 2-Cl-4-SO$_2$MePh | pyridin-3-yl | H |
| 2-Cl-4-SO$_2$MePh | pyridin-3-yl | methyl |
| 2-Cl-4-SO$_2$MePh | pyridin-3-yl | i-propyl |
| 2-Cl-4-SO$_2$MePh | pyridin-3-yl | cyclopropyl |
| 2-Cl-4-SO$_2$MePh | pyridin-3-yl | CF$_3$ |
| 2-Cl-4-SO$_2$MePh | 3-nitropyridin-4-yl | H |
| 2-Cl-4-SO$_2$MePh | 3-nitropyridin-4-yl | methyl |
| 2-Cl-4-SO$_2$MePh | 3-nitropyridin-4-yl | i-propyl |
| 2-Cl-4-SO$_2$MePh | 3-nitropyridin-4-yl | cyclopropyl |
| 2-Cl-4-SO$_2$MePh | 3-nitropyridin-4-yl | CF$_3$ |
| 2-Cl-4-SO$_2$MePh | 5-cyanopyridin-2-yl | H |
| 2-Cl-4-SO$_2$MePh | 5-cyanopyridin-2-yl | methyl |
| 2-Cl-4-SO$_2$MePh | 5-cyanopyridin-2-yl | i-propyl |
| 2-Cl-4-SO$_2$MePh | 5-cyanopyridin-2-yl | cyclopropyl |
| 2-Cl-4-SO$_2$MePh | 5-cyanopyridin-2-yl | CF$_3$ |
| 2-Cl-4-SO$_2$MePh | 5-trifluoromethylpyridin-2-yl | H |
| 2-Cl-4-SO$_2$MePh | 5-trifluoromethylpyridin-2-yl | methyl |
| 2-Cl-4-SO$_2$MePh | 5-trifluoromethylpyridin-2-yl | i-propyl |
| 2-Cl-4-SO$_2$MePh | 5-trifluoromethylpyridin-2-yl | cyclopropyl |

-continued

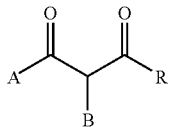

(I)

| A | B | R |
|---|---|---|
| 2-Cl-4-SO$_2$MePh | 5-trifluoromethylpyridin-2-yl | CF$_3$ |
| 2-Cl-4-SO$_2$MePh | pyrimidin-2-yl | H |
| 2-Cl-4-SO$_2$MePh | pyrimidin-2-yl | methyl |
| 2-Cl-4-SO$_2$MePh | pyrimidin-2-yl | i-propyl |
| 2-Cl-4-SO$_2$MePh | pyrimidin-2-yl | cyclopropyl |
| 2-Cl-4-SO$_2$MePh | pyrimidin-2-yl | CF$_3$ |
| 2-Cl-4-SO$_2$MePh | pyrimidin-4-yl | H |
| 2-Cl-4-SO$_2$MePh | pyrimidin-4-yl | methyl |
| 2-Cl-4-SO$_2$MePh | pyrimidin-4-yl | i-propyl |
| 2-Cl-4-SO$_2$MePh | pyrimidin-4-yl | cyclopropyl |
| 2-Cl-4-SO$_2$MePh | pyrimidin-4-yl | CF$_3$ |
| 2-Cl-4-SO$_2$MePh | 6-chloropyrimidin-4-yl | methyl |
| 2-Cl-4-SO$_2$MePh | 6-chloropyrimidin-4-yl | i-propyl |
| 2-Cl-4-SO$_2$MePh | 6-chloropyrimidin-4-yl | cyclopropyl |
| 2-Cl-4-SO$_2$MePh | 6-chloropyrimidin-4-yl | CF$_3$ |
| 2-Cl-4-SO$_2$MePh | pyridazin-3-yl | H |
| 2-Cl-4-SO$_2$MePh | pyridazin-3-yl | methyl |
| 2-Cl-4-SO$_2$MePh | pyridazin-3-yl | i-propyl |
| 2-Cl-4-SO$_2$MePh | pyridazin-3-yl | cyclopropyl |
| 2-Cl-4-SO$_2$MePh | pyridazin-3-yl | CF$_3$ |
| 2-Cl-4-SO$_2$MePh | 6-chloropyridazin-3-yl | methyl |
| 2-Cl-4-SO$_2$MePh | 6-chloropyridazin-3-yl | i-propyl |
| 2-Cl-4-SO$_2$MePh | 6-chloropyridazin-3-yl | cyclopropyl |
| 2-Cl-4-SO$_2$MePh | 6-chloropyridazin-3-yl | CF$_3$ |
| 2-Cl-4-SO$_2$MePh | pyrazin-2-yl | methyl |
| 2-Cl-4-SO$_2$MePh | pyrazin-2-yl | i-propyl |
| 2-Cl-4-SO$_2$MePh | pyrazin-2-yl | cyclopropyl |
| 2-Cl-4-SO$_2$MePh | pyrazin-2-yl | CF$_3$ |
| 2-Cl-4-SO$_2$MePh | triazin-2-yl | methyl |
| 2-Cl-4-SO$_2$MePh | triazin-2-yl | i-propyl |
| 2-Cl-4-SO$_2$MePh | triazin-2-yl | cyclopropyl |
| 2-Cl-4-SO$_2$MePh | triazin-2-yl | CF$_3$ |
| 2-Cl-4-SO$_2$MePh | quinolin-2-yl | methyl |
| 2-Cl-4-SO$_2$MePh | quinolin-2-yl | i-propyl |
| 2-Cl-4-SO$_2$MePh | quinolin-2-yl | cyclopropyl |
| 2-Cl-4-SO$_2$MePh | quinolin-2-yl | CF$_3$ |
| 2-Cl-4-SO$_2$MePh | 4,4,6-trimethyl-5,6-dihydro-1,3(4H)-oxazin-2-yl | H |
| 2-Cl-4-SO$_2$MePh | 4,4,6-trimethyl-5,6-dihydro-1,3(4H)-oxazin-2-yl | methyl |
| 2-Cl-4-SO$_2$MePh | 4,4,6-trimethyl-5,6-dihydro-1,3(4H)-oxazin-2-yl | i-propyl |
| 2-Cl-4-SO$_2$MePh | 4,4,6-trimethyl-5,6-dihydro-1,3(4H)-oxazin-2-yl | cyclopropyl |
| 2-Cl-4-SO$_2$MePh | 4,4,6-trimethyl-5,6-dihydro-1,3(4H)-oxazin-2-yl | CF$_3$ |
| 2-Cl-4-SO$_2$MePh | 2-oxazolidinon-3-yl | H |
| 2-Cl-4-SO$_2$MePh | 2-oxazolidinon-3-yl | methyl |
| 2-Cl-4-SO$_2$MePh | 2-oxazolidinon-3-yl | i-propyl |
| 2-Cl-4-SO$_2$MePh | 2-oxazolidinon-3-yl | cyclopropyl |
| 2-Cl-4-SO$_2$MePh | 2-oxazolidinon-3-yl | CF$_3$ |
| 2-Cl-4-SO$_2$MePh | 2-pyrrolidinon-1-yl | methyl |
| 2-Cl-4-SO$_2$MePh | 2-pyrrolidinon-1-yl | i-propyl |
| 2-Cl-4-SO$_2$MePh | 2-pyrrolidinon-1-yl | cyclopropyl |
| 2-Cl-4-SO$_2$MePh | 2-pyrrolidinon-1-yl | CF$_3$ |
| 2-Cl-4-SO$_2$MePh | 3-methylisoxazol-5-yl | methyl |
| 2-Cl-4-SO$_2$MePh | 3-methylisoxazol-5-yl | i-propyl |
| 2-Cl-4-SO$_2$MePh | 3-methylisoxazol-5-yl | cyclopropyl |
| 2-Cl-4-SO$_2$MePh | 3-methylisoxazol-5-yl | CF$_3$ |
| 2-Cl-4-SO$_2$MePh | 2-NO$_2$-4-SO$_2$MePh | H |
| 2-Cl-4-SO$_2$MePh | 2-NO$_2$-4-SO$_2$MePh | methyl |
| 2-Cl-4-SO$_2$MePh | 2-NO$_2$-4-SO$_2$MePh | i-propyl |
| 2-Cl-4-SO$_2$MePh | 2-NO$_2$-4-SO$_2$MePh | cyclopropyl |
| 2-Cl-4-SO$_2$MePh | 2-NO$_2$-4-SO$_2$MePh | CF$_3$ |
| 2-Cl-4-SO$_2$MePh | 2-Cl-4-SO$_2$MePh | H |
| 2-Cl-4-SO$_2$MePh | 2-Cl-4-SO$_2$MePh | methyl |
| 2-Cl-4-SO$_2$MePh | 2-Cl-4-SO$_2$MePh | i-propyl |
| 2-Cl-4-SO$_2$MePh | 2-Cl-4-SO$_2$MePh | cyclopropyl |
| 2-Cl-4-SO$_2$MePh | 2-Cl-4-SO$_2$MePh | CF$_3$ |
| 2-Cl-4-SO$_2$MePh | 2-NO$_2$-4-CF$_3$Ph | H |

-continued

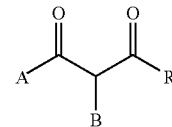

(I)

| A | B | R |
|---|---|---|
| 2-Cl-4-SO$_2$MePh | 2-NO$_2$-4-CF$_3$Ph | methyl |
| 2-Cl-4-SO$_2$MePh | 2-NO$_2$-4-CF$_3$Ph | i-propyl |
| 2-Cl-4-SO$_2$MePh | 2-NO$_2$-4-CF$_3$Ph | cyclopropyl |
| 2-Cl-4-SO$_2$MePh | 2-NO$_2$-4-CF$_3$Ph | CF$_3$ |
| 2-Cl-4-SO$_2$MePh | 2-NO$_2$-4-ClPh | H |
| 2-Cl-4-SO$_2$MePh | 2-NO$_2$-4-ClPh | methyl |
| 2-Cl-4-SO$_2$MePh | 2-NO$_2$-4-ClPh | i-propyl |
| 2-Cl-4-SO$_2$MePh | 2-NO$_2$-4-ClPh | cyclopropyl |
| 2-Cl-4-SO$_2$MePh | 2-NO$_2$-4-ClPh | CF$_3$ |
| 2-Cl-4-SO$_2$MePh | 2-Cl-4-NO$_2$Ph | H |
| 2-Cl-4-SO$_2$MePh | 2-Cl-4-NO$_2$Ph | methyl |
| 2-Cl-4-SO$_2$MePh | 2-Cl-4-NO$_2$Ph | i-propyl |
| 2-Cl-4-SO$_2$MePh | 2-Cl-4-NO$_2$Ph | cyclopropyl |
| 2-Cl-4-SO$_2$MePh | 2-Cl-4-NO$_2$Ph | CF$_3$ |
| 2-Cl-4-SO$_2$MePh | 2,4-(NO$_2$)$_2$Ph | H |
| 2-Cl-4-SO$_2$MePh | 2,4-(NO$_2$)$_2$Ph | methyl |
| 2-Cl-4-SO$_2$MePh | 2,4-(NO$_2$)$_2$Ph | i-propyl |
| 2-Cl-4-SO$_2$MePh | 2,4-(NO$_2$)$_2$Ph | cyclopropyl |
| 2-Cl-4-SO$_2$MePh | 2,4-(NO$_2$)$_2$Ph | CF$_3$ |
| 2-Cl-4-SO$_2$MePh | 4-F-3-NO$_2$Ph | H |
| 2-Cl-4-SO$_2$MePh | 4-F-3-NO$_2$Ph | methyl |
| 2-Cl-4-SO$_2$MePh | 4-F-3-NO$_2$Ph | i-propyl |
| 2-Cl-4-SO$_2$MePh | 4-F-3-NO$_2$Ph | cyclopropyl |
| 2-Cl-4-SO$_2$MePh | 4-F-3-NO$_2$Ph | CF$_3$ |
| 2-Cl-4-SO$_2$MePh | 3,5-(CF$_3$)$_2$Ph | H |
| 2-Cl-4-SO$_2$MePh | 3,5-(CF$_3$)$_2$Ph | methyl |
| 2-Cl-4-SO$_2$MePh | 3,5-(CF$_3$)$_2$Ph | i-propyl |
| 2-Cl-4-SO$_2$MePh | 3,5-(CF$_3$)$_2$Ph | cyclopropyl |
| 2-Cl-4-SO$_2$MePh | 3,5-(CF$_3$)$_2$Ph | CF$_3$ |
| 2-Cl-4-SO$_2$MePh | 2-SO$_2$Me-4-CF$_3$Ph | H |
| 2-Cl-4-SO$_2$MePh | 2-SO$_2$Me-4-CF$_3$Ph | methyl |
| 2-Cl-4-SO$_2$MePh | 2-SO$_2$Me-4-CF$_3$Ph | i-propyl |
| 2-Cl-4-SO$_2$MePh | 2-SO$_2$Me-4-CF$_3$Ph | cyclopropyl |
| 2-Cl-4-SO$_2$MePh | 2-SO$_2$Me-4-CF$_3$Ph | CF$_3$ |
| 4-Cl-2-NO$_2$Ph | 1,2,4-oxadiazol-5-yl | H |
| 4-Cl-2-NO$_2$Ph | 1,2,4-oxadiazol-5-yl | methyl |
| 4-Cl-2-NO$_2$Ph | 1,2,4-oxadiazol-5-yl | i-propyl |
| 4-Cl-2-NO$_2$Ph | 1,2,4-oxadiazol-5-yl | cyclopropyl |
| 4-Cl-2-NO$_2$Ph | 1,2,4-oxadiazol-5-yl | CF$_3$ |
| 4-Cl-2-NO$_2$Ph | 3-methyl-1,2,4-oxadiazol-5-yl | H |
| 4-Cl-2-NO$_2$Ph | 3-methyl-1,2,4-oxadiazol-5-yl | methyl |
| 4-Cl-2-NO$_2$Ph | 3-methyl-1,2,4-oxadiazol-5-yl | i-propyl |
| 4-Cl-2-NO$_2$Ph | 3-methyl-1,2,4-oxadiazol-5-yl | cyclopropyl |
| 4-Cl-2-NO$_2$Ph | 3-methyl-1,2,4-oxadiazol-5-yl | CF$_3$ |
| 4-Cl-2-NO$_2$Ph | 3-trifluoromethyl-1,2,4-oxadiazol-5-yl | H |
| 4-Cl-2-NO$_2$Ph | 3-trifluoromethyl-1,2,4-oxadiazol-5-yl | methyl |
| 4-Cl-2-NO$_2$Ph | 3-trifluoromethyl-1,2,4-oxadiazol-5-yl | i-propyl |
| 4-Cl-2-NO$_2$Ph | 3-trifluoromethyl-1,2,4-oxadiazol-5-yl | cyclopropyl |
| 4-Cl-2-NO$_2$Ph | 3-trifluoromethyl-1,2,4-oxadiazol-5-yl | CF$_3$ |
| 4-Cl-2-NO$_2$Ph | 1,2,4-oxadiazol-3-yl | H |
| 4-Cl-2-NO$_2$Ph | 1,2,4-oxadiazol-3-yl | methyl |
| 4-Cl-2-NO$_2$Ph | 1,2,4-oxadiazol-3-yl | i-propyl |
| 4-Cl-2-NO$_2$Ph | 1,2,4-oxadiazol-3-yl | cyclopropyl |
| 4-Cl-2-NO$_2$Ph | 1,2,4-oxadiazol-3-yl | CF$_3$ |
| 4-Cl-2-NO$_2$Ph | 5-methyl-1,2,4-oxadiazol-3-yl | H |
| 4-Cl-2-NO$_2$Ph | 5-methyl-1,2,4-oxadiazol-3-yl | methyl |
| 4-Cl-2-NO$_2$Ph | 5-methyl-1,2,4-oxadiazol-3-yl | i-propyl |
| 4-Cl-2-NO$_2$Ph | 5-methyl-1,2,4-oxadiazol-3-yl | cyclopropyl |
| 4-Cl-2-NO$_2$Ph | 5-methyl-1,2,4-oxadiazol-3-yl | CF$_3$ |
| 4-Cl-2-NO$_2$Ph | 5-trifluoromethyl-1,2,4-oxadiazol-3-yl | H |
| 4-Cl-2-NO$_2$Ph | 5-trifluoromethyl-1,2,4-oxadiazol-3-yl | methyl |
| 4-Cl-2-NO$_2$Ph | 5-trifluoromethyl-1,2,4-oxadiazol-3-yl | i-propyl |

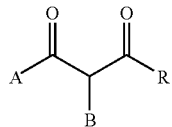

(I)

| A | B | R |
|---|---|---|
| 4-Cl-2-NO₂Ph | 5-trifluoromethyl-1,2,4-oxadiazol-3-yl | cyclopropyl |
| 4-Cl-2-NO₂Ph | 5-trifluoromethyl-1,2,4-oxadiazol-3-yl | CF₃ |
| 4-Cl-2-NO₂Ph | 5-chloro-1,2,4-oxadiazol-3-yl | H |
| 4-Cl-2-NO₂Ph | 5-chloro-1,2,4-oxadiazol-3-yl | methyl |
| 4-Cl-2-NO₂Ph | 5-chloro-1,2,4-oxadiazol-3-yl | i-propyl |
| 4-Cl-2-NO₂Ph | 5-chloro-1,2,4-oxadiazol-3-yl | cyclopropyl |
| 4-Cl-2-NO₂Ph | 5-chloro-1,2,4-oxadiazol-3-yl | CF₃ |
| 4-Cl-2-NO₂Ph | 1,3,4-oxadiazol-2-yl | H |
| 4-Cl-2-NO₂Ph | 1,3,4-oxadiazol-2-yl | methyl |
| 4-Cl-2-NO₂Ph | 1,3,4-oxadiazol-2-yl | i-propyl |
| 4-Cl-2-NO₂Ph | 1,3,4-oxadiazol-2-yl | cyclopropyl |
| 4-Cl-2-NO₂Ph | 1,3,4-oxadiazol-2-yl | CF₃ |
| 4-Cl-2-NO₂Ph | 5-methylsulfonyl-1,3,4-oxadiazol-2-yl | H |
| 4-Cl-2-NO₂Ph | 5-methylsulfonyl-1,3,4-oxadiazol-2-yl | methyl |
| 4-Cl-2-NO₂Ph | 5-methylsulfonyl-1,3,4-oxadiazol-2-yl | i-propyl |
| 4-Cl-2-NO₂Ph | 5-methylsulfonyl-1,3,4-oxadiazol-2-yl | cyclopropyl |
| 4-Cl-2-NO₂Ph | 5-methylsulfonyl-1,3,4-oxadiazol-2-yl | CF₃ |
| 4-Cl-2-NO₂Ph | 5-methyl-1,3,4-oxadiazol-2-yl | H |
| 4-Cl-2-NO₂Ph | 5-methyl-1,3,4-oxadiazol-2-yl | methyl |
| 4-Cl-2-NO₂Ph | 5-methyl-1,3,4-oxadiazol-2-yl | i-propyl |
| 4-Cl-2-NO₂Ph | 5-methyl-1,3,4-oxadiazol-2-yl | cyclopropyl |
| 4-Cl-2-NO₂Ph | 5-methyl-1,3,4-oxadiazol-2-yl | CF₃ |
| 4-Cl-2-NO₂Ph | 5-trifluoromethyl-1,3,4-oxadiazol-2-yl | H |
| 4-Cl-2-NO₂Ph | 5-trifluoromethyl-1,3,4-oxadiazol-2-yl | methyl |
| 4-Cl-2-NO₂Ph | 5-trifluoromethyl-1,3,4-oxadiazol-2-yl | i-propyl |
| 4-Cl-2-NO₂Ph | 5-trifluoromethyl-1,3,4-oxadiazol-2-yl | cyclopropyl |
| 4-Cl-2-NO₂Ph | 5-trifluoromethyl-1,3,4-oxadiazol-2-yl | CF₃ |
| 4-Cl-2-NO₂Ph | 1,2,3-triazol-4-yl | H |
| 4-Cl-2-NO₂Ph | 1,2,3-triazol-4-yl | methyl |
| 4-Cl-2-NO₂Ph | 1,2,3-triazol-4-yl | i-propyl |
| 4-Cl-2-NO₂Ph | 1,2,3-triazol-4-yl | cyclopropyl |
| 4-Cl-2-NO₂Ph | 1,2,3-triazol-4-yl | CF₃ |
| 4-Cl-2-NO₂Ph | 1-methyl-1,2,3-triazol-4-yl | H |
| 4-Cl-2-NO₂Ph | 1-methyl-1,2,3-triazol-4-yl | methyl |
| 4-Cl-2-NO₂Ph | 1-methyl-1,2,3-triazol-4-yl | i-propyl |
| 4-Cl-2-NO₂Ph | 1-methyl-1,2,3-triazol-4-yl | cyclopropyl |
| 4-Cl-2-NO₂Ph | 1-methyl-1,2,3-triazol-4-yl | CF₃ |
| 4-Cl-2-NO₂Ph | 2-methyl-1,2,3-triazol-4-yl | H |
| 4-Cl-2-NO₂Ph | 2-methyl-1,2,3-triazol-4-yl | methyl |
| 4-Cl-2-NO₂Ph | 2-methyl-1,2,3-triazol-4-yl | i-propyl |
| 4-Cl-2-NO₂Ph | 2-methyl-1,2,3-triazol-4-yl | cyclopropyl |
| 4-Cl-2-NO₂Ph | 2-methyl-1,2,3-triazol-4-yl | CF₃ |
| 4-Cl-2-NO₂Ph | 1,2,3-triazol-1-yl | H |
| 4-Cl-2-NO₂Ph | 1,2,3-triazol-1-yl | methyl |
| 4-Cl-2-NO₂Ph | 1,2,3-triazol-1-yl | i-propyl |
| 4-Cl-2-NO₂Ph | 1,2,3-triazol-1-yl | cyclopropyl |
| 4-Cl-2-NO₂Ph | 1,2,3-triazol-1-yl | CF₃ |
| 4-Cl-2-NO₂Ph | 1,2,3-triazol-2-yl | H |
| 4-Cl-2-NO₂Ph | 1,2,3-triazol-2-yl | methyl |
| 4-Cl-2-NO₂Ph | 1,2,3-triazol-2-yl | i-propyl |
| 4-Cl-2-NO₂Ph | 1,2,3-triazol-2-yl | cyclopropyl |
| 4-Cl-2-NO₂Ph | 1,2,3-triazol-2-yl | CF₃ |
| 4-Cl-2-NO₂Ph | 1,2,4-triazol-1-yl | H |
| 4-Cl-2-NO₂Ph | 1,2,4-triazol-1-yl | methyl |
| 4-Cl-2-NO₂Ph | 1,2,4-triazol-1-yl | i-propyl |
| 4-Cl-2-NO₂Ph | 1,2,4-triazol-1-yl | cyclopropyl |
| 4-Cl-2-NO₂Ph | 1,2,4-triazol-1-yl | CF₃ |
| 4-Cl-2-NO₂Ph | imidazol-2-yl | H |

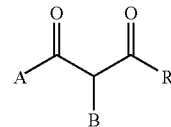

(I)

| A | B | R |
|---|---|---|
| 4-Cl-2-NO₂Ph | imidazol-2-yl | methyl |
| 4-Cl-2-NO₂Ph | imidazol-2-yl | i-propyl |
| 4-Cl-2-NO₂Ph | imidazol-2-yl | cyclopropyl |
| 4-Cl-2-NO₂Ph | imidazol-2-yl | CF₃ |
| 4-Cl-2-NO₂Ph | imidazol-1-yl | H |
| 4-Cl-2-NO₂Ph | imidazol-1-yl | methyl |
| 4-Cl-2-NO₂Ph | imidazol-1-yl | i-propyl |
| 4-Cl-2-NO₂Ph | imidazol-1-yl | cyclopropyl |
| 4-Cl-2-NO₂Ph | imidazol-1-yl | CF₃ |
| 4-Cl-2-NO₂Ph | imidazol-4-yl | H |
| 4-Cl-2-NO₂Ph | imidazol-4-yl | methyl |
| 4-Cl-2-NO₂Ph | imidazol-4-yl | i-propyl |
| 4-Cl-2-NO₂Ph | imidazol-4-yl | cyclopropyl |
| 4-Cl-2-NO₂Ph | imidazol-4-yl | CF₃ |
| 4-Cl-2-NO₂Ph | thiazol-2-yl | H |
| 4-Cl-2-NO₂Ph | thiazol-2-yl | methyl |
| 4-Cl-2-NO₂Ph | thiazol-2-yl | i-propyl |
| 4-Cl-2-NO₂Ph | thiazol-2-yl | cyclopropyl |
| 4-Cl-2-NO₂Ph | thiazol-2-yl | CF₃ |
| 4-Cl-2-NO₂Ph | 4-methylthiazol-2-yl | H |
| 4-Cl-2-NO₂Ph | 4-methylthiazol-2-yl | methyl |
| 4-Cl-2-NO₂Ph | 4-methylthiazol-2-yl | i-propyl |
| 4-Cl-2-NO₂Ph | 4-methylthiazol-2-yl | cyclopropyl |
| 4-Cl-2-NO₂Ph | 4-methylthiazol-2-yl | CF₃ |
| 4-Cl-2-NO₂Ph | oxazol-2-yl | H |
| 4-Cl-2-NO₂Ph | oxazol-2-yl | methyl |
| 4-Cl-2-NO₂Ph | oxazol-2-yl | i-propyl |
| 4-Cl-2-NO₂Ph | oxazol-2-yl | cyclopropyl |
| 4-Cl-2-NO₂Ph | oxazol-2-yl | CF₃ |
| 4-Cl-2-NO₂Ph | 4,5-dimethyloxazol-2-yl | H |
| 4-Cl-2-NO₂Ph | 4,5-dimethyloxazol-2-yl | methyl |
| 4-Cl-2-NO₂Ph | 4,5-dimethyloxazol-2-yl | i-propyl |
| 4-Cl-2-NO₂Ph | 4,5-dimethyloxazol-2-yl | cyclopropyl |
| 4-Cl-2-NO₂Ph | 4,5-dimethyloxazol-2-yl | CF₃ |
| 4-Cl-2-NO₂Ph | 2-oxazolin-2-yl | H |
| 4-Cl-2-NO₂Ph | 2-oxazolin-2-yl | methyl |
| 4-Cl-2-NO₂Ph | 2-oxazolin-2-yl | i-propyl |
| 4-Cl-2-NO₂Ph | 2-oxazolin-2-yl | cyclopropyl |
| 4-Cl-2-NO₂Ph | 2-oxazolin-2-yl | CF₃ |
| 4-Cl-2-NO₂Ph | 4,4-dimethyl-2-oxazolin-2-yl | H |
| 4-Cl-2-NO₂Ph | 4,4-dimethyl-2-oxazolin-2-yl | methyl |
| 4-Cl-2-NO₂Ph | 4,4-dimethyl-2-oxazolin-2-yl | i-propyl |
| 4-Cl-2-NO₂Ph | 4,4-dimethyl-2-oxazolin-2-yl | cyclopropyl |
| 4-Cl-2-NO₂Ph | 4,4-dimethyl-2-oxazolin-2-yl | CF₃ |
| 4-Cl-2-NO₂Ph | 1,2,4-thiadiazol-5-yl | H |
| 4-Cl-2-NO₂Ph | 1,2,4-thiadiazol-5-yl | methyl |
| 4-Cl-2-NO₂Ph | 1,2,4-thiadiazol-5-yl | i-propyl |
| 4-Cl-2-NO₂Ph | 1,2,4-thiadiazol-5-yl | cyclopropyl |
| 4-Cl-2-NO₂Ph | 1,2,4-thiadiazol-5-yl | CF₃ |
| 4-Cl-2-NO₂Ph | 3-methyl-1,2,4-thiadiazol-5-yl | H |
| 4-Cl-2-NO₂Ph | 3-methyl-1,2,4-thiadiazol-5-yl | methyl |
| 4-Cl-2-NO₂Ph | 3-methyl-1,2,4-thiadiazol-5-yl | i-propyl |
| 4-Cl-2-NO₂Ph | 3-methyl-1,2,4-thiadiazol-5-yl | cyclopropyl |
| 4-Cl-2-NO₂Ph | 3-methyl-1,2,4-thiadiazol-5-yl | CF₃ |
| 4-Cl-2-NO₂Ph | 3-trifluoromethyl-1,2,4-thiadiazol-5-yl | H |
| 4-Cl-2-NO₂Ph | 3-trifluoromethyl-1,2,4-thiadiazol-5-yl | methyl |
| 4-Cl-2-NO₂Ph | 3-trifluoromethyl-1,2,4-thiadiazol-5-yl | i-propyl |
| 4-Cl-2-NO₂Ph | 3-trifluoromethyl-1,2,4-thiadiazol-5-yl | cyclopropyl |
| 4-Cl-2-NO₂Ph | 3-trifluoromethyl-1,2,4-thiadiazol-5-yl | CF₃ |
| 4-Cl-2-NO₂Ph | 1,2,4-thiadiazol-3-yl | H |
| 4-Cl-2-NO₂Ph | 1,2,4-thiadiazol-3-yl | methyl |
| 4-Cl-2-NO₂Ph | 1,2,4-thiadiazol-3-yl | i-propyl |
| 4-Cl-2-NO₂Ph | 1,2,4-thiadiazol-3-yl | cyclopropyl |
| 4-Cl-2-NO₂Ph | 1,2,4-thiadiazol-3-yl | CF₃ |
| 4-Cl-2-NO₂Ph | 5-methyl-1,2,4-thiadiazol-3-yl | H |

-continued

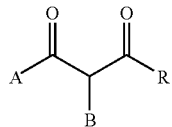

(I)

| A | B | R |
|---|---|---|
| 4-Cl-2-NO$_2$Ph | 5-methyl-1,2,4-thiadiazol-3-yl | methyl |
| 4-Cl-2-NO$_2$Ph | 5-methyl-1,2,4-thiadiazol-3-yl | i-propyl |
| 4-Cl-2-NO$_2$Ph | 5-methyl-1,2,4-thiadiazol-3-yl | cyclopropyl |
| 4-Cl-2-NO$_2$Ph | 5-methyl-1,2,4-thiadiazol-3-yl | CF$_3$ |
| 4-Cl-2-NO$_2$Ph | 5-trifluoromethyl-1,2,4-thiadiazol-3-yl | H |
| 4-Cl-2-NO$_2$Ph | 5-trifluoromethyl-1,2,4-thiadiazol-3-yl | methyl |
| 4-Cl-2-NO$_2$Ph | 5-trifluoromethyl-1,2,4-thiadiazol-3-yl | i-propyl |
| 4-Cl-2-NO$_2$Ph | 5-trifluoromethyl-1,2,4-thiadiazol-3-yl | cyclopropyl |
| 4-Cl-2-NO$_2$Ph | 5-trifluoromethyl-1,2,4-thiadiazol-3-yl | CF$_3$ |
| 4-Cl-2-NO$_2$Ph | 1,3,4-thiadiazol-2-yl | H |
| 4-Cl-2-NO$_2$Ph | 1,3,4-thiadiazol-2-yl | methyl |
| 4-Cl-2-NO$_2$Ph | 1,3,4-thiadiazol-2-yl | i-propyl |
| 4-Cl-2-NO$_2$Ph | 1,3,4-thiadiazol-2-yl | cyclopropyl |
| 4-Cl-2-NO$_2$Ph | 1,3,4-thiadiazol-2-yl | CF$_3$ |
| 4-Cl-2-NO$_2$Ph | 5-methylsulfonyl-1,3,4-thiadiazol-2-yl | H |
| 4-Cl-2-NO$_2$Ph | 5-methylsulfonyl-1,3,4-thiadiazol-2-yl | methyl |
| 4-Cl-2-NO$_2$Ph | 5-methylsulfonyl-1,3,4-thiadiazol-2-yl | i-propyl |
| 4-Cl-2-NO$_2$Ph | 5-methylsulfonyl-1,3,4-thiadiazol-2-yl | cyclopropyl |
| 4-Cl-2-NO$_2$Ph | 5-methylsulfonyl-1,3,4-thiadiazol-2-yl | CF$_3$ |
| 4-Cl-2-NO$_2$Ph | 5-methyl-1,3,4-thiadiazol-2-yl | H |
| 4-Cl-2-NO$_2$Ph | 5-methyl-1,3,4-thiadiazol-2-yl | methyl |
| 4-Cl-2-NO$_2$Ph | 5-methyl-1,3,4-thiadiazol-2-yl | i-propyl |
| 4-Cl-2-NO$_2$Ph | 5-methyl-1,3,4-thiadiazol-2-yl | cyclopropyl |
| 4-Cl-2-NO$_2$Ph | 5-methyl-1,3,4-thiadiazol-2-yl | CF$_3$ |
| 4-Cl-2-NO$_2$Ph | benzoxazol-2-yl | H |
| 4-Cl-2-NO$_2$Ph | benzoxazol-2-yl | methyl |
| 4-Cl-2-NO$_2$Ph | benzoxazol-2-yl | i-propyl |
| 4-Cl-2-NO$_2$Ph | benzoxazol-2-yl | cyclopropyl |
| 4-Cl-2-NO$_2$Ph | benzoxazol-2-yl | CF$_3$ |
| 4-Cl-2-NO$_2$Ph | 6-methylbenzoxazol-2-yl | H |
| 4-Cl-2-NO$_2$Ph | 6-methylbenzoxazol-2-yl | methyl |
| 4-Cl-2-NO$_2$Ph | 6-methylbenzoxazol-2-yl | i-propyl |
| 4-Cl-2-NO$_2$Ph | 6-methylbenzoxazol-2-yl | cyclopropyl |
| 4-Cl-2-NO$_2$Ph | 6-methylbenzoxazol-2-yl | CF$_3$ |
| 4-Cl-2-NO$_2$Ph | benzothiazol-2-yl | H |
| 4-Cl-2-NO$_2$Ph | benzothiazol-2-yl | methyl |
| 4-Cl-2-NO$_2$Ph | benzothiazol-2-yl | i-propyl |
| 4-Cl-2-NO$_2$Ph | benzothiazol-2-yl | cyclopropyl |
| 4-Cl-2-NO$_2$Ph | benzothiazol-2-yl | CF$_3$ |
| 4-Cl-2-NO$_2$Ph | pyrazol-1-yl | H |
| 4-Cl-2-NO$_2$Ph | pyrazol-1-yl | methyl |
| 4-Cl-2-NO$_2$Ph | pyrazol-1-yl | i-propyl |
| 4-Cl-2-NO$_2$Ph | pyrazol-1-yl | cyclopropyl |
| 4-Cl-2-NO$_2$Ph | pyrazol-1-yl | CF$_3$ |
| 4-Cl-2-NO$_2$Ph | pyrazol-3-yl | H |
| 4-Cl-2-NO$_2$Ph | pyrazol-3-yl | methyl |
| 4-Cl-2-NO$_2$Ph | pyrazol-3-yl | i-propyl |
| 4-Cl-2-NO$_2$Ph | pyrazol-3-yl | cyclopropyl |
| 4-Cl-2-NO$_2$Ph | pyrazol-3-yl | CF$_3$ |
| 4-Cl-2-NO$_2$Ph | 1-methylpyrazol-3-yl | H |
| 4-Cl-2-NO$_2$Ph | 1-methylpyrazol-3-yl | methyl |
| 4-Cl-2-NO$_2$Ph | 1-methylpyrazol-3-yl | i-propyl |
| 4-Cl-2-NO$_2$Ph | 1-methylpyrazol-3-yl | cyclopropyl |
| 4-Cl-2-NO$_2$Ph | 1-methylpyrazol-3-yl | CF$_3$ |
| 4-Cl-2-NO$_2$Ph | tetrazol-1-yl | H |
| 4-Cl-2-NO$_2$Ph | tetrazol-1-yl | methyl |
| 4-Cl-2-NO$_2$Ph | tetrazol-1-yl | i-propyl |
| 4-Cl-2-NO$_2$Ph | tetrazol-1-yl | cyclopropyl |
| 4-Cl-2-NO$_2$Ph | tetrazol-1-yl | CF$_3$ |
| 4-Cl-2-NO$_2$Ph | 5-methyltetrazol-1-yl | H |

-continued

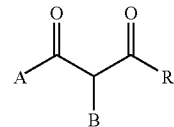

(I)

| A | B | R |
|---|---|---|
| 4-Cl-2-NO$_2$Ph | 5-methyltetrazol-1-yl | methyl |
| 4-Cl-2-NO$_2$Ph | 5-methyltetrazol-1-yl | i-propyl |
| 4-Cl-2-NO$_2$Ph | 5-methyltetrazol-1-yl | cyclopropyl |
| 4-Cl-2-NO$_2$Ph | 5-methyltetrazol-1-yl | CF$_3$ |
| 4-Cl-2-NO$_2$Ph | tetrazol-2-yl | H |
| 4-Cl-2-NO$_2$Ph | tetrazol-2-yl | methyl |
| 4-Cl-2-NO$_2$Ph | tetrazol-2-yl | i-propyl |
| 4-Cl-2-NO$_2$Ph | tetrazol-2-yl | cyclopropyl |
| 4-Cl-2-NO$_2$Ph | tetrazol-2-yl | CF$_3$ |
| 4-Cl-2-NO$_2$Ph | 5-methyltetrazol-2-yl | H |
| 4-Cl-2-NO$_2$Ph | 5-methyltetrazol-2-yl | methyl |
| 4-Cl-2-NO$_2$Ph | 5-methyltetrazol-2-yl | i-propyl |
| 4-Cl-2-NO$_2$Ph | 5-methyltetrazol-2-yl | cyclopropyl |
| 4-Cl-2-NO$_2$Ph | 5-methyltetrazol-2-yl | CF$_3$ |
| 4-Cl-2-NO$_2$Ph | 1-methyltetrazol-5-yl | H |
| 4-Cl-2-NO$_2$Ph | 1-methyltetrazol-5-yl | methyl |
| 4-Cl-2-NO$_2$Ph | 1-methyltetrazol-5-yl | i-propyl |
| 4-Cl-2-NO$_2$Ph | 1-methyltetrazol-5-yl | cyclopropyl |
| 4-Cl-2-NO$_2$Ph | 1-methyltetrazol-5-yl | CF$_3$ |
| 2-Cl-4-NO$_2$Ph | 2-methyltetrazol-5-yl | cyclopropyl |
| 4-Cl-2-NO$_2$Ph | 2-methyltetrazol-5-yl | methyl |
| 4-Cl-2-NO$_2$Ph | 2-methyltetrazol-5-yl | i-propyl |
| 4-Cl-2-NO$_2$Ph | 2-methyltetrazol-5-yl | cyclopropyl |
| 4-Cl-2-NO$_2$Ph | 2-methyltetrazol-5-yl | CF$_3$ |
| 2,4-(NO$_2$)$_2$Ph | 2-methyltetrazol-5-yl | cyclopropyl |
| 4-Cl-2-NO$_2$Ph | pyridin-2-yl | methyl |
| 4-Cl-2-NO$_2$Ph | pyridin-2-yl | i-propyl |
| 4-Cl-2-NO$_2$Ph | pyridin-2-yl | cyclopropyl |
| 4-Cl-2-NO$_2$Ph | pyridin-2-yl | CF$_3$ |
| 4-Cl-2-NO$_2$Ph | pyridin-4-yl | H |
| 4-Cl-2-NO$_2$Ph | pyridin-4-yl | methyl |
| 4-Cl-2-NO$_2$Ph | pyridin-4-yl | i-propyl |
| 4-Cl-2-NO$_2$Ph | pyridin-4-yl | cyclopropyl |
| 4-Cl-2-NO$_2$Ph | pyridin-4-yl | CF$_3$ |
| 4-Cl-2-NO$_2$Ph | pyridin-3-yl | H |
| 4-Cl-2-NO$_2$Ph | pyridin-3-yl | methyl |
| 4-Cl-2-NO$_2$Ph | pyridin-3-yl | i-propyl |
| 4-Cl-2-NO$_2$Ph | pyridin-3-yl | cyclopropyl |
| 4-Cl-2-NO$_2$Ph | pyridin-3-yl | CF$_3$ |
| 4-Cl-2-NO$_2$Ph | 3-nitropyridin-4-yl | H |
| 4-Cl-2-NO$_2$Ph | 3-nitropyridin-4-yl | methyl |
| 4-Cl-2-NO$_2$Ph | 3-nitropyridin-4-yl | i-propyl |
| 4-Cl-2-NO$_2$Ph | 3-nitropyridin-4-yl | cyclopropyl |
| 4-Cl-2-NO$_2$Ph | 3-nitropyridin-4-yl | CF$_3$ |
| 4-Cl-2-NO$_2$Ph | 5-cyanopyridin-2-yl | H |
| 4-Cl-2-NO$_2$Ph | 5-cyanopyridin-2-yl | methyl |
| 4-Cl-2-NO$_2$Ph | 5-cyanopyridin-2-yl | i-propyl |
| 4-Cl-2-NO$_2$Ph | 5-cyanopyridin-2-yl | cyclopropyl |
| 4-Cl-2-NO$_2$Ph | 5-cyanopyridin-2-yl | CF$_3$ |
| 4-Cl-2-NO$_2$Ph | 5-trifluoromethylpyridin-2-yl | H |
| 4-Cl-2-NO$_2$Ph | 5-trifluoromethylpyridin-2-yl | methyl |
| 4-Cl-2-NO$_2$Ph | 5-trifluoromethylpyridin-2-yl | i-propyl |
| 4-Cl-2-NO$_2$Ph | 5-trifluoromethylpyridin-2-yl | cyclopropyl |
| 4-Cl-2-NO$_2$Ph | 5-trifluoromethylpyridin-2-yl | CF$_3$ |
| 4-Cl-2-NO$_2$Ph | pyrimidin-2-yl | H |
| 4-Cl-2-NO$_2$Ph | pyrimidin-2-yl | methyl |
| 4-Cl-2-NO$_2$Ph | pyrimidin-2-yl | i-propyl |
| 4-Cl-2-NO$_2$Ph | pyrimidin-2-yl | cyclopropyl |
| 4-Cl-2-NO$_2$Ph | pyrimidin-2-yl | CF$_3$ |
| 4-Cl-2-NO$_2$Ph | pyrimidin-4-yl | H |
| 4-Cl-2-NO$_2$Ph | pyrimidin-4-yl | methyl |
| 4-Cl-2-NO$_2$Ph | pyrimidin-4-yl | i-propyl |
| 4-Cl-2-NO$_2$Ph | pyrimidin-4-yl | cyclopropyl |
| 4-Cl-2-NO$_2$Ph | pyrimidin-4-yl | CF$_3$ |
| 4-Cl-2-NO$_2$Ph | 6-chloropyrimidin-4-yl | methyl |
| 4-Cl-2-NO$_2$Ph | 6-chloropyrimidin-4-yl | i-propyl |
| 4-Cl-2-NO$_2$Ph | 6-chloropyrimidin-4-yl | cyclopropyl |
| 4-Cl-2-NO$_2$Ph | 6-chloropyrimidin-4-yl | CF$_3$ |
| 2,4-(Cl)$_2$Ph | 1-methyltetrazol-5-yl | t-butil |
| 4-Cl-2-NO$_2$Ph | pyridazin-3-yl | methyl |

-continued

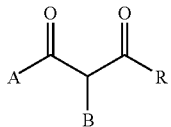

(I)

| A | B | R |
|---|---|---|
| 4-Cl-2-NO$_2$Ph | pyridazin-3-yl | i-propyl |
| 4-Cl-2-NO$_2$Ph | pyridazin-3-yl | cyclopropyl |
| 4-Cl-2-NO$_2$Ph | pyridazin-3-yl | CF$_3$ |
| 4-Cl-2-NO$_2$Ph | 6-chloropyridazin-3-yl | methyl |
| 4-Cl-2-NO$_2$Ph | 6-chloropyridazin-3-yl | i-propyl |
| 4-Cl-2-NO$_2$Ph | 6-chloropyridazin-3-yl | cyclopropyl |
| 4-Cl-2-NO$_2$Ph | 6-chloropyridazin-3-yl | CF$_3$ |
| 4-Cl-2-NO$_2$Ph | pyrazin-2-yl | methyl |
| 4-Cl-2-NO$_2$Ph | pyrazin-2-yl | i-propyl |
| 4-Cl-2-NO$_2$Ph | pyrazin-2-yl | cyclopropyl |
| 4-Cl-2-NO$_2$Ph | pyrazin-2-yl | CF$_3$ |
| 4-Cl-2-NO$_2$Ph | triazin-2-yl | methyl |
| 4-Cl-2-NO$_2$Ph | triazin-2-yl | i-propyl |
| 4-Cl-2-NO$_2$Ph | triazin-2-yl | cyclopropyl |
| 4-Cl-2-NO$_2$Ph | triazin-2-yl | CF$_3$ |
| 4-Cl-2-NO$_2$Ph | quinolin-2-yl | methyl |
| 4-Cl-2-NO$_2$Ph | quinolin-2-yl | i-propyl |
| 4-Cl-2-NO$_2$Ph | quinolin-2-yl | cyclopropyl |
| 4-Cl-2-NO$_2$Ph | quinolin-2-yl | CF$_3$ |
| 4-Cl-2-NO$_2$Ph | 4,4,6-trimethyl-5,6-dihydro-1,3(4H)-oxazin-2-yl | H |
| 4-Cl-2-NO$_2$Ph | 4,4,6-trimethyl-5,6-dihydro-1,3(4H)-oxazin-2-yl | methyl |
| 4-Cl-2-NO$_2$Ph | 4,4,6-trimethyl-5,6-dihydro-1,3(4H)-oxazin-2-yl | i-propyl |
| 4-Cl-2-NO$_2$Ph | 4,4,6-trimethyl-5,6-dihydro-1,3(4H)-oxazin-2-yl | cyclopropyl |
| 4-Cl-2-NO$_2$Ph | 4,4,6-trimethyl-5,6-dihydro-1,3(4H)-oxazin-2-yl | CF$_3$ |
| 4-Cl-2-NO$_2$Ph | 2-oxazolidinon-3-yl | H |
| 4-Cl-2-NO$_2$Ph | 2-oxazolidinon-3-yl | methyl |
| 4-Cl-2-NO$_2$Ph | 2-oxazolidinon-3-yl | i-propyl |
| 4-Cl-2-NO$_2$Ph | 2-oxazolidinon-3-yl | cyclopropyl |
| 4-Cl-2-NO$_2$Ph | 2-oxazolidinon-3-yl | CF$_3$ |
| 4-Cl-2-NO$_2$Ph | 2-pyrrolidinon-1-yl | methyl |
| 4-Cl-2-NO$_2$Ph | 2-pyrrolidinon-1-yl | i-propyl |
| 4-Cl-2-NO$_2$Ph | 2-pyrrolidinon-1-yl | cyclopropyl |
| 4-Cl-2-NO$_2$Ph | 2-pyrrolidinon-1-yl | CF$_3$ |
| 4-Cl-2-NO$_2$Ph | 3-methylisoxazol-5-yl | methyl |
| 4-Cl-2-NO$_2$Ph | 3-methylisoxazol-5-yl | i-propyl |
| 4-Cl-2-NO$_2$Ph | 3-methylisoxazol-5-yl | cyclopropyl |
| 4-Cl-2-NO$_2$Ph | 3-methylisoxazol-5-yl | CF$_3$ |
| 4-Cl-2-NO$_2$Ph | 2-NO$_2$-4-SO$_2$MePh | H |
| 4-Cl-2-NO$_2$Ph | 2-NO$_2$-4-SO$_2$MePh | methyl |
| 4-Cl-2-NO$_2$Ph | 2-NO$_2$-4-SO$_2$MePh | i-propyl |
| 4-Cl-2-NO$_2$Ph | 2-NO$_2$-4-SO$_2$MePh | cyclopropyl |
| 4-Cl-2-NO$_2$Ph | 2-NO$_2$-4-SO$_2$MePh | CF$_3$ |
| 4-Cl-2-NO$_2$Ph | 2-Cl-4-SO$_2$MePh | H |
| 4-Cl-2-NO$_2$Ph | 2-Cl-4-SO$_2$MePh | methyl |
| 4-Cl-2-NO$_2$Ph | 2-Cl-4-SO$_2$MePh | i-propyl |
| 4-Cl-2-NO$_2$Ph | 2-Cl-4-SO$_2$MePh | cyclopropyl |
| 4-Cl-2-NO$_2$Ph | 2-Cl-4-SO$_2$MePh | CF$_3$ |
| 4-Cl-2-NO$_2$Ph | 2-NO$_2$-4-CF$_3$Ph | H |
| 4-Cl-2-NO$_2$Ph | 2-NO$_2$-4-CF$_3$Ph | methyl |
| 4-Cl-2-NO$_2$Ph | 2-NO$_2$-4-CF$_3$Ph | i-propyl |
| 4-Cl-2-NO$_2$Ph | 2-NO$_2$-4-CF$_3$Ph | cyclopropyl |
| 4-Cl-2-NO$_2$Ph | 2-NO$_2$-4-CF$_3$Ph | CF$_3$ |
| 4-Cl-2-NO$_2$Ph | 2-NO$_2$-4-ClPh | H |
| 4-Cl-2-NO$_2$Ph | 2-NO$_2$-4-ClPh | methyl |
| 4-Cl-2-NO$_2$Ph | 2-NO$_2$-4-ClPh | i-propyl |
| 4-Cl-2-NO$_2$Ph | 2-NO$_2$-4-ClPh | cyclopropyl |
| 4-Cl-2-NO$_2$Ph | 2-NO$_2$-4-ClPh | CF$_3$ |
| 4-Cl-2-NO$_2$Ph | 2-Cl-4-NO$_2$Ph | H |
| 4-Cl-2-NO$_2$Ph | 2-Cl-4-NO$_2$Ph | methyl |
| 4-Cl-2-NO$_2$Ph | 2-Cl-4-NO$_2$Ph | i-propyl |
| 4-Cl-2-NO$_2$Ph | 2-Cl-4-NO$_2$Ph | cyclopropyl |
| 4-Cl-2-NO$_2$Ph | 2-Cl-4-NO$_2$Ph | CF$_3$ |
| 4-Cl-2-NO$_2$Ph | 2,4-(NO$_2$)$_2$Ph | H |
| 4-Cl-2-NO$_2$Ph | 2,4-(NO$_2$)$_2$Ph | methyl |
| 4-Cl-2-NO$_2$Ph | 2,4-(NO$_2$)$_2$Ph | i-propyl |

-continued

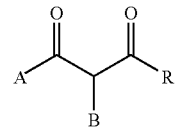

(I)

| A | B | R |
|---|---|---|
| 4-Cl-2-NO$_2$Ph | 2,4-(NO$_2$)$_2$Ph | cyclopropyl |
| 4-Cl-2-NO$_2$Ph | 2,4-(NO$_2$)$_2$Ph | CF$_3$ |
| 4-Cl-2-NO$_2$Ph | 4-F-3-NO$_2$Ph | H |
| 4-Cl-2-NO$_2$Ph | 4-F-3-NO$_2$Ph | methyl |
| 4-Cl-2-NO$_2$Ph | 4-F-3-NO$_2$Ph | i-propyl |
| 4-Cl-2-NO$_2$Ph | 4-F-3-NO$_2$Ph | cyclopropyl |
| 4-Cl-2-NO$_2$Ph | 4-F-3-NO$_2$Ph | CF$_3$ |
| 4-Cl-2-NO$_2$Ph | 3,5-(CF$_3$)$_2$Ph | H |
| 4-Cl-2-NO$_2$Ph | 3,5-(CF$_3$)$_2$Ph | methyl |
| 4-Cl-2-NO$_2$Ph | 3,5-(CF$_3$)$_2$Ph | i-propyl |
| 4-Cl-2-NO$_2$Ph | 3,5-(CF$_3$)$_2$Ph | cyclopropyl |
| 4-Cl-2-NO$_2$Ph | 3,5-(CF$_3$)$_2$Ph | CF$_3$ |
| 4-Cl-2-NO$_2$Ph | 2-SO$_2$Me-4-CF$_3$Ph | H |
| 4-Cl-2-NO$_2$Ph | 2-SO$_2$Me-4-CF$_3$Ph | methyl |
| 4-Cl-2-NO$_2$Ph | 2-SO$_2$Me-4-CF$_3$Ph | i-propyl |
| 4-Cl-2-NO$_2$Ph | 2-SO$_2$Me-4-CF$_3$Ph | cyclopropyl |
| 4-Cl-2-NO$_2$Ph | 2-SO$_2$Me-4-CF$_3$Ph | CF$_3$ |
| 2-SO$_2$Me-4-CF$_3$Ph | 1,2,4-oxadiazol-5-yl | H |
| 2-SO$_2$Me-4-CF$_3$Ph | 1,2,4-oxadiazol-5-yl | methyl |
| 2-SO$_2$Me-4-CF$_3$Ph | 1,2,4-oxadiazol-5-yl | i-propyl |
| 2-SO$_2$Me-4-CF$_3$Ph | 1,2,4-oxadiazol-5-yl | cyclopropyl |
| 2-SO$_2$Me-4-CF$_3$Ph | 1,2,4-oxadiazol-5-yl | CF$_3$ |
| 2-SO$_2$Me-4-CF$_3$Ph | 3-methyl-1,2,4-oxadiazol-5-yl | H |
| 2-SO$_2$Me-4-CF$_3$Ph | 3-methyl-1,2,4-oxadiazol-5-yl | methyl |
| 2-SO$_2$Me-4-CF$_3$Ph | 3-methyl-1,2,4-oxadiazol-5-yl | i-propyl |
| 2-SO$_2$Me-4-CF$_3$Ph | 3-methyl-1,2,4-oxadiazol-5-yl | cyclopropyl |
| 2-SO$_2$Me-4-CF$_3$Ph | 3-methyl-1,2,4-oxadiazol-5-yl | CF$_3$ |
| 2-SO$_2$Me-4-CF$_3$Ph | 3-trifluoromethyl-1,2,4-oxadiazol-5-yl | H |
| 2-SO$_2$Me-4-CF$_3$Ph | 3-trifluoromethyl-1,2,4-oxadiazol-5-yl | methyl |
| 2-SO$_2$Me-4-CF$_3$Ph | 3-trifluoromethyl-1,2,4-oxadiazol-5-yl | i-propyl |
| 2-SO$_2$Me-4-CF$_3$Ph | 3-trifluoromethyl-1,2,4-oxadiazol-5-yl | cyclopropyl |
| 2-SO$_2$Me-4-CF$_3$Ph | 3-trifluoromethyl-1,2,4-oxadiazol-5-yl | CF$_3$ |
| 2-SO$_2$Me-4-CF$_3$Ph | 1,2,4-oxadiazol-3-yl | H |
| 2-SO$_2$Me-4-CF$_3$Ph | 1,2,4-oxadiazol-3-yl | methyl |
| 2-SO$_2$Me-4-CF$_3$Ph | 1,2,4-oxadiazol-3-yl | i-propyl |
| 2-SO$_2$Me-4-CF$_3$Ph | 1,2,4-oxadiazol-3-yl | cyclopropyl |
| 2-SO$_2$Me-4-CF$_3$Ph | 1,2,4-oxadiazol-3-yl | CF$_3$ |
| 2-SO$_2$Me-4-CF$_3$Ph | 5-methyl-1,2,4-oxadiazol-3-yl | H |
| 2-SO$_2$Me-4-CF$_3$Ph | 5-methyl-1,2,4-oxadiazol-3-yl | methyl |
| 2-SO$_2$Me-4-CF$_3$Ph | 5-methyl-1,2,4-oxadiazol-3-yl | i-propyl |
| 2-SO$_2$Me-4-CF$_3$Ph | 5-methyl-1,2,4-oxadiazol-3-yl | cyclopropyl |
| 2-SO$_2$Me-4-CF$_3$Ph | 5-methyl-1,2,4-oxadiazol-3-yl | CF$_3$ |
| 2-SO$_2$Me-4-CF$_3$Ph | 5-trifluoromethyl-1,2,4-oxadiazol-3-yl | H |
| 2-SO$_2$Me-4-CF$_3$Ph | 5-trifluoromethyl-1,2,4-oxadiazol-3-yl | methyl |
| 2-SO$_2$Me-4-CF$_3$Ph | 5-trifluoromethyl-1,2,4-oxadiazol-3-yl | i-propyl |
| 2-SO$_2$Me-4-CF$_3$Ph | 5-trifluoromethyl-1,2,4-oxadiazol-3-yl | cyclopropyl |
| 2-SO$_2$Me-4-CF$_3$Ph | 5-trifluoromethyl-1,2,4-oxadiazol-3-yl | CF$_3$ |
| 2-SO$_2$Me-4-CF$_3$Ph | 5-chloro-1,2,4-oxadiazol-3-yl | H |
| 2-SO$_2$Me-4-CF$_3$Ph | 5-chloro-1,2,4-oxadiazol-3-yl | methyl |
| 2-SO$_2$Me-4-CF$_3$Ph | 5-chloro-1,2,4-oxadiazol-3-yl | i-propyl |
| 2-SO$_2$Me-4-CF$_3$Ph | 5-chloro-1,2,4-oxadiazol-3-yl | cyclopropyl |
| 2-SO$_2$Me-4-CF$_3$Ph | 5-chloro-1,2,4-oxadiazol-3-yl | CF$_3$ |
| 2-SO$_2$Me-4-CF$_3$Ph | 1,3,4-oxadiazol-2-yl | H |
| 2-SO$_2$Me-4-CF$_3$Ph | 1,3,4-oxadiazol-2-yl | methyl |
| 2-SO$_2$Me-4-CF$_3$Ph | 1,3,4-oxadiazol-2-yl | i-propyl |
| 2-SO$_2$Me-4-CF$_3$Ph | 1,3,4-oxadiazol-2-yl | cyclopropyl |
| 2-SO$_2$Me-4-CF$_3$Ph | 1,3,4-oxadiazol-2-yl | CF$_3$ |
| 2-SO$_2$Me-4-CF$_3$Ph | 5-methylsulfonyl-1,3,4-oxadiazol-2-yl | H |
| 2-SO$_2$Me-4-CF$_3$Ph | 5-methylsulfonyl-1,3,4- | methyl |

-continued (I)

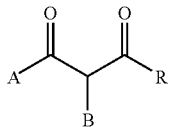

| A | B | R |
|---|---|---|
| 2-SO₂Me-4-CF₃Ph | 5-methylsulfonyl-1,3,4-oxadiazol-2-yl | i-propyl |
| 2-SO₂Me-4-CF₃Ph | 5-methylsulfonyl-1,3,4-oxadiazol-2-yl | cyclopropyl |
| 2-SO₂Me-4-CF₃Ph | 5-methylsulfonyl-1,3,4-oxadiazol-2-yl | CF₃ |
| 2-SO₂Me-4-CF₃Ph | 5-methyl-1,3,4-oxadiazol-2-yl | H |
| 2-SO₂Me-4-CF₃Ph | 5-methyl-1,3,4-oxadiazol-2-yl | methyl |
| 2-SO₂Me-4-CF₃Ph | 5-methyl-1,3,4-oxadiazol-2-yl | i-propyl |
| 2-SO₂Me-4-CF₃Ph | 5-methyl-1,3,4-oxadiazol-2-yl | cyclopropyl |
| 2-SO₂Me-4-CF₃Ph | 5-methyl-1,3,4-oxadiazol-2-yl | CF₃ |
| 2-SO₂Me-4-CF₃Ph | 5-trifluoromethyl-1,3,4-oxadiazol-2-yl | H |
| 2-SO₂Me-4-CF₃Ph | 5-trifluoromethyl-1,3,4-oxadiazol-2-yl | methyl |
| 2-SO₂Me-4-CF₃Ph | 5-trifluoromethyl-1,3,4-oxadiazol-2-yl | i-propyl |
| 2-SO₂Me-4-CF₃Ph | 5-trifluoromethyl-1,3,4-oxadiazol-2-yl | cyclopropyl |
| 2-SO₂Me-4-CF₃Ph | 5-trifluoromethyl-1,3,4-oxadiazol-2-yl | CF₃ |
| 2-SO₂Me-4-CF₃Ph | 1,2,3-triazol-4-yl | H |
| 2-SO₂Me-4-CF₃Ph | 1,2,3-triazol-4-yl | methyl |
| 2-SO₂Me-4-CF₃Ph | 1,2,3-triazol-4-yl | i-propyl |
| 2-SO₂Me-4-CF₃Ph | 1,2,3-triazol-4-yl | cyclopropyl |
| 2-SO₂Me-4-CF₃Ph | 1,2,3-triazol-4-yl | CF₃ |
| 2-SO₂Me-4-CF₃Ph | 1-methyl-1,2,3-triazol-4-yl | H |
| 2-SO₂Me-4-CF₃Ph | 1-methyl-1,2,3-triazol-4-yl | methyl |
| 2-SO₂Me-4-CF₃Ph | 1-methyl-1,2,3-triazol-4-yl | i-propyl |
| 2-SO₂Me-4-CF₃Ph | 1-methyl-1,2,3-triazol-4-yl | cyclopropyl |
| 2-SO₂Me-4-CF₃Ph | 1-methyl-1,2,3-triazol-4-yl | CF₃ |
| 2-SO₂Me-4-CF₃Ph | 2-methyl-1,2,3-triazol-4-yl | H |
| 2-SO₂Me-4-CF₃Ph | 2-methyl-1,2,3-triazol-4-yl | methyl |
| 2-SO₂Me-4-CF₃Ph | 2-methyl-1,2,3-triazol-4-yl | i-propyl |
| 2-SO₂Me-4-CF₃Ph | 2-methyl-1,2,3-triazol-4-yl | cyclopropyl |
| 2-SO₂Me-4-CF₃Ph | 2-methyl-1,2,3-triazol-4-yl | CF₃ |
| 2-SO₂Me-4-CF₃Ph | 1,2,3-triazol-1-yl | H |
| 2-SO₂Me-4-CF₃Ph | 1,2,3-triazol-1-yl | methyl |
| 2-SO₂Me-4-CF₃Ph | 1,2,3-triazol-1-yl | i-propyl |
| 2-SO₂Me-4-CF₃Ph | 1,2,3-triazol-1-yl | cyclopropyl |
| 2-SO₂Me-4-CF₃Ph | 1,2,3-triazol-1-yl | CF₃ |
| 2-SO₂Me-4-CF₃Ph | 1,2,3-triazol-2-yl | H |
| 2-SO₂Me-4-CF₃Ph | 1,2,3-triazol-2-yl | methyl |
| 2-SO₂Me-4-CF₃Ph | 1,2,3-triazol-2-yl | i-propyl |
| 2-SO₂Me-4-CF₃Ph | 1,2,3-triazol-2-yl | cyclopropyl |
| 2-SO₂Me-4-CF₃Ph | 1,2,3-triazol-2-yl | CF₃ |
| 2-SO₂Me-4-CF₃Ph | 1,2,4-triazol-1-yl | H |
| 2-SO₂Me-4-CF₃Ph | 1,2,4-triazol-1-yl | methyl |
| 2-SO₂Me-4-CF₃Ph | 1,2,4-triazol-1-yl | i-propyl |
| 2-SO₂Me-4-CF₃Ph | 1,2,4-triazol-1-yl | cyclopropyl |
| 2-SO₂Me-4-CF₃Ph | 1,2,4-triazol-1-yl | CF₃ |
| 2-SO₂Me-4-CF₃Ph | imidazol-2-yl | H |
| 2-SO₂Me-4-CF₃Ph | imidazol-2-yl | methyl |
| 2-SO₂Me-4-CF₃Ph | imidazol-2-yl | i-propyl |
| 2-SO₂Me-4-CF₃Ph | imidazol-2-yl | cyclopropyl |
| 2-SO₂Me-4-CF₃Ph | imidazol-2-yl | CF₃ |
| 2-SO₂Me-4-CF₃Ph | imidazol-1-yl | H |
| 2-SO₂Me-4-CF₃Ph | imidazol-1-yl | methyl |
| 2-SO₂Me-4-CF₃Ph | imidazol-1-yl | i-propyl |
| 2-SO₂Me-4-CF₃Ph | imidazol-1-yl | cyclopropyl |
| 2-SO₂Me-4-CF₃Ph | imidazol-1-yl | CF₃ |
| 2-SO₂Me-4-CF₃Ph | imidazol-4-yl | H |
| 2-SO₂Me-4-CF₃Ph | imidazol-4-yl | methyl |
| 2-SO₂Me-4-CF₃Ph | imidazol-4-yl | i-propyl |
| 2-SO₂Me-4-CF₃Ph | imidazol-4-yl | cyclopropyl |
| 2-SO₂Me-4-CF₃Ph | imidazol-4-yl | CF₃ |
| 2-SO₂Me-4-CF₃Ph | thiazol-2-yl | H |
| 2-SO₂Me-4-CF₃Ph | thiazol-2-yl | methyl |
| 2-SO₂Me-4-CF₃Ph | thiazol-2-yl | i-propyl |

-continued (I)

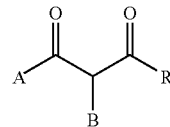

| A | B | R |
|---|---|---|
| 2-SO₂Me-4-CF₃Ph | thiazol-2-yl | cyclopropyl |
| 2-SO₂Me-4-CF₃Ph | thiazol-2-yl | CF₃ |
| 2-SO₂Me-4-CF₃Ph | 4-methylthiazol-2-yl | H |
| 2-SO₂Me-4-CF₃Ph | 4-methylthiazol-2-yl | methyl |
| 2-SO₂Me-4-CF₃Ph | 4-methylthiazol-2-yl | i-propyl |
| 2-SO₂Me-4-CF₃Ph | 4-methylthiazol-2-yl | cyclopropyl |
| 2-SO₂Me-4-CF₃Ph | 4-methylthiazol-2-yl | CF₃ |
| 2-SO₂Me-4-CF₃Ph | oxazol-2-yl | H |
| 2-SO₂Me-4-CF₃Ph | oxazol-2-yl | methyl |
| 2-SO₂Me-4-CF₃Ph | oxazol-2-yl | i-propyl |
| 2-SO₂Me-4-CF₃Ph | oxazol-2-yl | cyclopropyl |
| 2-SO₂Me-4-CF₃Ph | oxazol-2-yl | CF₃ |
| 2-SO₂Me-4-CF₃Ph | 4,5-dimethyloxazol-2-yl | H |
| 2-SO₂Me-4-CF₃Ph | 4,5-dimethyloxazol-2-yl | methyl |
| 2-SO₂Me-4-CF₃Ph | 4,5-dimethyloxazol-2-yl | i-propyl |
| 2-SO₂Me-4-CF₃Ph | 4,5-dimethyloxazol-2-yl | cyclopropyl |
| 2-SO₂Me-4-CF₃Ph | 4,5-dimethyloxazol-2-yl | CF₃ |
| 2-SO₂Me-4-CF₃Ph | 2-oxazolin-2-yl | H |
| 2-SO₂Me-4-CF₃Ph | 2-oxazolin-2-yl | methyl |
| 2-SO₂Me-4-CF₃Ph | 2-oxazolin-2-yl | i-propyl |
| 2-SO₂Me-4-CF₃Ph | 2-oxazolin-2-yl | cyclopropyl |
| 2-SO₂Me-4-CF₃Ph | 2-oxazolin-2-yl | CF₃ |
| 2-SO₂Me-4-CF₃Ph | 4,4-dimethyl-2-oxazolin-2-yl | H |
| 2-SO₂Me-4-CF₃Ph | 4,4-dimethyl-2-oxazolin-2-yl | methyl |
| 2-SO₂Me-4-CF₃Ph | 4,4-dimethyl-2-oxazolin-2-yl | i-propyl |
| 2-SO₂Me-4-CF₃Ph | 4,4-dimethyl-2-oxazolin-2-yl | cyclopropyl |
| 2-SO₂Me-4-CF₃Ph | 4,4-dimethyl-2-oxazolin-2-yl | CF₃ |
| 2-SO₂Me-4-CF₃Ph | 1,2,4-thiadiazol-5-yl | H |
| 2-SO₂Me-4-CF₃Ph | 1,2,4-thiadiazol-5-yl | methyl |
| 2-SO₂Me-4-CF₃Ph | 1,2,4-thiadiazol-5-yl | i-propyl |
| 2-SO₂Me-4-CF₃Ph | 1,2,4-thiadiazol-5-yl | cyclopropyl |
| 2-SO₂Me-4-CF₃Ph | 1,2,4-thiadiazol-5-yl | CF₃ |
| 2-SO₂Me-4-CF₃Ph | 3-methyl-1,2,4-thiadiazol-5-yl | H |
| 2-SO₂Me-4-CF₃Ph | 3-methyl-1,2,4-thiadiazol-5-yl | methyl |
| 2-SO₂Me-4-CF₃Ph | 3-methyl-1,2,4-thiadiazol-5-yl | i-propyl |
| 2-SO₂Me-4-CF₃Ph | 3-methyl-1,2,4-thiadiazol-5-yl | cyclopropyl |
| 2-SO₂Me-4-CF₃Ph | 3-methyl-1,2,4-thiadiazol-5-yl | CF₃ |
| 2-SO₂Me-4-CF₃Ph | 3-trifluoromethyl-1,2,4-thiadiazol-5-yl | H |
| 2-SO₂Me-4-CF₃Ph | 3-trifluoromethyl-1,2,4-thiadiazol-5-yl | methyl |
| 2-SO₂Me-4-CF₃Ph | 3-trifluoromethyl-1,2,4-thiadiazol-5-yl | i-propyl |
| 2-SO₂Me-4-CF₃Ph | 3-trifluoromethyl-1,2,4-thiadiazol-5-yl | cyclopropyl |
| 2-SO₂Me-4-CF₃Ph | 3-trifluoromethyl-1,2,4-thiadiazol-5-yl | CF₃ |
| 2-SO₂Me-4-CF₃Ph | 1,2,4-thiadiazol-3-yl | H |
| 2-SO₂Me-4-CF₃Ph | 1,2,4-thiadiazol-3-yl | methyl |
| 2-SO₂Me-4-CF₃Ph | 1,2,4-thiadiazol-3-yl | i-propyl |
| 2-SO₂Me-4-CF₃Ph | 1,2,4-thiadiazol-3-yl | cyclopropyl |
| 2-SO₂Me-4-CF₃Ph | 1,2,4-thiadiazol-3-yl | CF₃ |
| 2-SO₂Me-4-CF₃Ph | 5-methyl-1,2,4-thiadiazol-3-yl | H |
| 2-SO₂Me-4-CF₃Ph | 5-methyl-1,2,4-thiadiazol-3-yl | methyl |
| 2-SO₂Me-4-CF₃Ph | 5-methyl-1,2,4-thiadiazol-3-yl | i-propyl |
| 2-SO₂Me-4-CF₃Ph | 5-methyl-1,2,4-thiadiazol-3-yl | cyclopropyl |
| 2-SO₂Me-4-CF₃Ph | 5-methyl-1,2,4-thiadiazol-3-yl | CF₃ |
| 2-SO₂Me-4-CF₃Ph | 5-trifluoromethyl-1,2,4-thiadiazol-3-yl | H |
| 2-SO₂Me-4-CF₃Ph | 5-trifluoromethyl-1,2,4-thiadiazol-3-yl | methyl |
| 2-SO₂Me-4-CF₃Ph | 5-trifluoromethyl-1,2,4-thiadiazol-3-yl | i-propyl |
| 2-SO₂Me-4-CF₃Ph | 5-trifluoromethyl-1,2,4-thiadiazol-3-yl | cyclopropyl |
| 2-SO₂Me-4-CF₃Ph | 5-trifluoromethyl-1,2,4-thiadiazol-3-yl | CF₃ |
| 2-SO₂Me-4-CF₃Ph | 1,3,4-thiadiazol-2-yl | H |
| 2-SO₂Me-4-CF₃Ph | 1,3,4-thiadiazol-2-yl | methyl |
| 2-SO₂Me-4-CF₃Ph | 1,3,4-thiadiazol-2-yl | i-propyl |

-continued

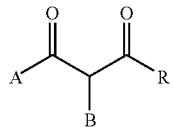

(I)

| A | B | R |
|---|---|---|
| 2-SO$_2$Me-4-CF$_3$Ph | 1,3,4-thiadiazol-2-yl | cyclopropyl |
| 2-SO$_2$Me-4-CF$_3$Ph | 1,3,4-thiadiazol-2-yl | CF$_3$ |
| 2-SO$_2$Me-4-CF$_3$Ph | 5-methylsulfonyl-1,3,4-thiadiazol-2-yl | H |
| 2-SO$_2$Me-4-CF$_3$Ph | 5-methylsulfonyl-1,3,4-thiadiazol-2-yl | methyl |
| 2-SO$_2$Me-4-CF$_3$Ph | 5-methylsulfonyl-1,3,4-thiadiazol-2-yl | i-propyl |
| 2-SO$_2$Me-4-CF$_3$Ph | 5-methylsulfonyl-1,3,4-thiadiazol-2-yl | cyclopropyl |
| 2-SO$_2$Me-4-CF$_3$Ph | 5-methylsulfonyl-1,3,4-thiadiazol-2-yl | CF$_3$ |
| 2-SO$_2$Me-4-CF$_3$Ph | 5-methyl-1,3,4-thiadiazol-2-yl | H |
| 2-SO$_2$Me-4-CF$_3$Ph | 5-methyl-1,3,4-thiadiazol-2-yl | methyl |
| 2-SO$_2$Me-4-CF$_3$Ph | 5-methyl-1,3,4-thiadiazol-2-yl | i-propyl |
| 2-SO$_2$Me-4-CF$_3$Ph | 5-methyl-1,3,4-thiadiazol-2-yl | cyclopropyl |
| 2-SO$_2$Me-4-CF$_3$Ph | 5-methyl-1,3,4-thiadiazol-2-yl | CF$_3$ |
| 2-SO$_2$Me-4-CF$_3$Ph | benzoxazol-2-yl | H |
| 2-SO$_2$Me-4-CF$_3$Ph | benzoxazol-2-yl | methyl |
| 2-SO$_2$Me-4-CF$_3$Ph | benzoxazol-2-yl | i-propyl |
| 2-SO$_2$Me-4-CF$_3$Ph | benzoxazol-2-yl | cyclopropyl |
| 2-SO$_2$Me-4-CF$_3$Ph | benzoxazol-2-yl | CF$_3$ |
| 2-SO$_2$Me-4-CF$_3$Ph | 6-methylbenzoxazol-2-yl | H |
| 2-SO$_2$Me-4-CF$_3$Ph | 6-methylbenzoxazol-2-yl | methyl |
| 2-SO$_2$Me-4-CF$_3$Ph | 6-methylbenzoxazol-2-yl | i-propyl |
| 2-SO$_2$Me-4-CF$_3$Ph | 6-methylbenzoxazol-2-yl | cyclopropyl |
| 2-SO$_2$Me-4-CF$_3$Ph | 6-methylbenzoxazol-2-yl | CF$_3$ |
| 2-SO$_2$Me-4-CF$_3$Ph | benzothiazol-2-yl | H |
| 2-SO$_2$Me-4-CF$_3$Ph | benzothiazol-2-yl | methyl |
| 2-SO$_2$Me-4-CF$_3$Ph | benzothiazol-2-yl | i-propyl |
| 2-SO$_2$Me-4-CF$_3$Ph | benzothiazol-2-yl | cyclopropyl |
| 2-SO$_2$Me-4-CF$_3$Ph | benzothiazol-2-yl | CF$_3$ |
| 2-SO$_2$Me-4-CF$_3$Ph | pyrazol-1-yl | H |
| 2-SO$_2$Me-4-CF$_3$Ph | pyrazol-1-yl | methyl |
| 2-SO$_2$Me-4-CF$_3$Ph | pyrazol-1-yl | i-propyl |
| 2-SO$_2$Me-4-CF$_3$Ph | pyrazol-1-yl | cyclopropyl |
| 2-SO$_2$Me-4-CF$_3$Ph | pyrazol-1-yl | CF$_3$ |
| 2-SO$_2$Me-4-CF$_3$Ph | pyrazol-3-yl | H |
| 2-SO$_2$Me-4-CF$_3$Ph | pyrazol-3-yl | methyl |
| 2-SO$_2$Me-4-CF$_3$Ph | pyrazol-3-yl | i-propyl |
| 2-SO$_2$Me-4-CF$_3$Ph | pyrazol-3-yl | cyclopropyl |
| 2-SO$_2$Me-4-CF$_3$Ph | pyrazol-3-yl | CF$_3$ |
| 2-SO$_2$Me-4-CF$_3$Ph | 1-methylpyrazol-3-yl | H |
| 2-SO$_2$Me-4-CF$_3$Ph | 1-methylpyrazol-3-yl | methyl |
| 2-SO$_2$Me-4-CF$_3$Ph | 1-methylpyrazol-3-yl | i-propyl |
| 2-SO$_2$Me-4-CF$_3$Ph | 1-methylpyrazol-3-yl | cyclopropyl |
| 2-SO$_2$Me-4-CF$_3$Ph | 1-methylpyrazol-3-yl | CF$_3$ |
| 2-SO$_2$Me-4-CF$_3$Ph | tetrazol-1-yl | H |
| 2-SO$_2$Me-4-CF$_3$Ph | tetrazol-1-yl | methyl |
| 2-SO$_2$Me-4-CF$_3$Ph | tetrazol-1-yl | i-propyl |
| 2-SO$_2$Me-4-CF$_3$Ph | tetrazol-1-yl | cyclopropyl |
| 2-SO$_2$Me-4-CF$_3$Ph | tetrazol-1-yl | CF$_3$ |
| 2-SO$_2$Me-4-CF$_3$Ph | 5-methyltetrazol-1-yl | H |
| 2-SO$_2$Me-4-CF$_3$Ph | 5-methyltetrazol-1-yl | methyl |
| 2-SO$_2$Me-4-CF$_3$Ph | 5-methyltetrazol-1-yl | i-propyl |
| 2-SO$_2$Me-4-CF$_3$Ph | 5-methyltetrazol-1-yl | cyclopropyl |
| 2-SO$_2$Me-4-CF$_3$Ph | 5-methyltetrazol-1-yl | CF$_3$ |
| 2-SO$_2$Me-4-CF$_3$Ph | tetrazol-2-yl | H |
| 2-SO$_2$Me-4-CF$_3$Ph | tetrazol-2-yl | methyl |
| 2-SO$_2$Me-4-CF$_3$Ph | tetrazol-2-yl | i-propyl |
| 2-SO$_2$Me-4-CF$_3$Ph | tetrazol-2-yl | cyclopropyl |
| 2-SO$_2$Me-4-CF$_3$Ph | tetrazol-2-yl | CF$_3$ |
| 2-SO$_2$Me-4-CF$_3$Ph | 5-methyltetrazol-2-yl | H |
| 2-SO$_2$Me-4-CF$_3$Ph | 5-methyltetrazol-2-yl | methyl |
| 2-SO$_2$Me-4-CF$_3$Ph | 5-methyltetrazol-2-yl | i-propyl |
| 2-SO$_2$Me-4-CF$_3$Ph | 5-methyltetrazol-2-yl | cyclopropyl |
| 2-SO$_2$Me-4-CF$_3$Ph | 5-methyltetrazol-2-yl | CF$_3$ |
| 2-SO$_2$Me-4-CF$_3$Ph | 1-methyltetrazol-5-yl | H |
| 2-SO$_2$Me-4-CF$_3$Ph | 1-methyltetrazol-5-yl | methyl |
| 2-SO$_2$Me-4-CF$_3$Ph | 1-methyltetrazol-5-yl | i-propyl |

-continued

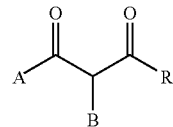

(I)

| A | B | R |
|---|---|---|
| 2-SO$_2$Me-4-CF$_3$Ph | 1-methyltetrazol-5-yl | cyclopropyl |
| 2-SO$_2$Me-4-CF$_3$Ph | 1-methyltetrazol-5-yl | CF$_3$ |
| 2-SO$_2$Me-4-CF$_3$Ph | 2-methyltetrazol-5-yl | H |
| 2-SO$_2$Me-4-CF$_3$Ph | 2-methyltetrazol-5-yl | methyl |
| 2-SO$_2$Me-4-CF$_3$Ph | 2-methyltetrazol-5-yl | i-propyl |
| 2-SO$_2$Me-4-CF$_3$Ph | 2-methyltetrazol-5-yl | cyclopropyl |
| 2-SO$_2$Me-4-CF$_3$Ph | 2-methyltetrazol-5-yl | CF$_3$ |
| 2-SO$_2$Me-4-CF$_3$Ph | pyridin-2-yl | H |
| 2-SO$_2$Me-4-CF$_3$Ph | pyridin-2-yl | methyl |
| 2-SO$_2$Me-4-CF$_3$Ph | pyridin-2-yl | i-propyl |
| 2-SO$_2$Me-4-CF$_3$Ph | pyridin-2-yl | cyclopropyl |
| 2-SO$_2$Me-4-CF$_3$Ph | pyridin-2-yl | CF$_3$ |
| 2-SO$_2$Me-4-CF$_3$Ph | pyridin-4-yl | H |
| 2-SO$_2$Me-4-CF$_3$Ph | pyridin-4-yl | methyl |
| 2-SO$_2$Me-4-CF$_3$Ph | pyridin-4-yl | i-propyl |
| 2-SO$_2$Me-4-CF$_3$Ph | pyridin-4-yl | cyclopropyl |
| 2-SO$_2$Me-4-CF$_3$Ph | pyridin-4-yl | CF$_3$ |
| 2-SO$_2$Me-4-CF$_3$Ph | pyridin-3-yl | H |
| 2-SO$_2$Me-4-CF$_3$Ph | pyridin-3-yl | methyl |
| 2-SO$_2$Me-4-CF$_3$Ph | pyridin-3-yl | i-propyl |
| 2-SO$_2$Me-4-CF$_3$Ph | pyridin-3-yl | cyclopropyl |
| 2-SO$_2$Me-4-CF$_3$Ph | pyridin-3-yl | CF$_3$ |
| 2-SO$_2$Me-4-CF$_3$Ph | 3-nitropyridin-4-yl | H |
| 2-SO$_2$Me-4-CF$_3$Ph | 3-nitropyridin-4-yl | methyl |
| 2-SO$_2$Me-4-CF$_3$Ph | 3-nitropyridin-4-yl | i-propyl |
| 2-SO$_2$Me-4-CF$_3$Ph | 3-nitropyridin-4-yl | cyclopropyl |
| 2-SO$_2$Me-4-CF$_3$Ph | 3-nitropyridin-4-yl | CF$_3$ |
| 2-SO$_2$Me-4-CF$_3$Ph | 5-cyanopyridin-2-yl | H |
| 2-SO$_2$Me-4-CF$_3$Ph | 5-cyanopyridin-2-yl | methyl |
| 2-SO$_2$Me-4-CF$_3$Ph | 5-cyanopyridin-2-yl | i-propyl |
| 2-SO$_2$Me-4-CF$_3$Ph | 5-cyanopyridin-2-yl | cyclopropyl |
| 2-SO$_2$Me-4-CF$_3$Ph | 5-cyanopyridin-2-yl | CF$_3$ |
| 2-SO$_2$Me-4-CF$_3$Ph | 5-trifluoromethylpyridin-2-yl | H |
| 2-SO$_2$Me-4-CF$_3$Ph | 5-trifluoromethylpyridin-2-yl | methyl |
| 2-SO$_2$Me-4-CF$_3$Ph | 5-trifluoromethylpyridin-2-yl | i-propyl |
| 2-SO$_2$Me-4-CF$_3$Ph | 5-trifluoromethylpyridin-2-yl | cyclopropyl |
| 2-SO$_2$Me-4-CF$_3$Ph | 5-trifluoromethylpyridin-2-yl | CF$_3$ |
| 2-SO$_2$Me-4-CF$_3$Ph | pyrimidin-2-yl | H |
| 2-SO$_2$Me-4-CF$_3$Ph | pyrimidin-2-yl | methyl |
| 2-SO$_2$Me-4-CF$_3$Ph | pyrimidin-2-yl | i-propyl |
| 2-SO$_2$Me-4-CF$_3$Ph | pyrimidin-2-yl | cyclopropyl |
| 2-SO$_2$Me-4-CF$_3$Ph | pyrimidin-2-yl | CF$_3$ |
| 2-SO$_2$Me-4-CF$_3$Ph | pyrimidin-4-yl | H |
| 2-SO$_2$Me-4-CF$_3$Ph | pyrimidin-4-yl | methyl |
| 2-SO$_2$Me-4-CF$_3$Ph | pyrimidin-4-yl | i-propyl |
| 2-SO$_2$Me-4-CF$_3$Ph | pyrimidin-4-yl | cyclopropyl |
| 2-SO$_2$Me-4-CF$_3$Ph | pyrimidin-4-yl | CF$_3$ |
| 2-SO$_2$Me-4-CF$_3$Ph | 6-chloropyrimidin-4-yl | methyl |
| 2-SO$_2$Me-4-CF$_3$Ph | 6-chloropyrimidin-4-yl | i-propyl |
| 2-SO$_2$Me-4-CF$_3$Ph | 6-chloropyrimidin-4-yl | cyclopropyl |
| 2-SO$_2$Me-4-CF$_3$Ph | 6-chloropyrimidin-4-yl | CF$_3$ |
| 2-SO$_2$Me-4-CF$_3$Ph | pyridazin-3-yl | H |
| 2-SO$_2$Me-4-CF$_3$Ph | pyridazin-3-yl | methyl |
| 2-SO$_2$Me-4-CF$_3$Ph | pyridazin-3-yl | i-propyl |
| 2-SO$_2$Me-4-CF$_3$Ph | pyridazin-3-yl | cyclopropyl |
| 2-SO$_2$Me-4-CF$_3$Ph | pyridazin-3-yl | CF$_3$ |
| 2-SO$_2$Me-4-CF$_3$Ph | 6-chloropyridazin-3-yl | methyl |
| 2-SO$_2$Me-4-CF$_3$Ph | 6-chloropyridazin-3-yl | i-propyl |
| 2-SO$_2$Me-4-CF$_3$Ph | 6-chloropyridazin-3-yl | cyclopropyl |
| 2-SO$_2$Me-4-CF$_3$Ph | 6-chloropyridazin-3-yl | CF$_3$ |
| 2-SO$_2$Me-4-CF$_3$Ph | pyrazin-2-yl | methyl |
| 2-SO$_2$Me-4-CF$_3$Ph | pyrazin-2-yl | i-propyl |
| 2-SO$_2$Me-4-CF$_3$Ph | pyrazin-2-yl | cyclopropyl |
| 2-SO$_2$Me-4-CF$_3$Ph | pyrazin-2-yl | CF$_3$ |
| 2-SO$_2$Me-4-CF$_3$Ph | triazin-2-yl | methyl |
| 2-SO$_2$Me-4-CF$_3$Ph | triazin-2-yl | i-propyl |
| 2-SO$_2$Me-4-CF$_3$Ph | triazin-2-yl | cyclopropyl |
| 2-SO$_2$Me-4-CF$_3$Ph | triazin-2-yl | CF$_3$ |
| 2-SO$_2$Me-4-CF$_3$Ph | quinolin-2-yl | methyl |
| 2-SO$_2$Me-4-CF$_3$Ph | quinolin-2-yl | i-propyl |

-continued

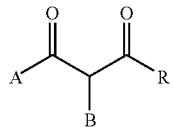
(I)

| A | B | R |
|---|---|---|
| 2-SO₂Me-4-CF₃Ph | quinolin-2-yl | cyclopropyl |
| 2-SO₂Me-4-CF₃Ph | quinolin-2-yl | CF₃ |
| 2-SO₂Me-4-CF₃Ph | 4,4,6-trimethyl-5,6-dihydro-1,3(4H)-oxazin-2-yl | H |
| 2-SO₂Me-4-CF₃Ph | 4,4,6-trimethyl-5,6-dihydro-1,3(4H)-oxazin-2-yl | methyl |
| 2-SO₂Me-4-CF₃Ph | 4,4,6-trimethyl-5,6-dihydro-1,3(4H)-oxazin-2-yl | i-propyl |
| 2-SO₂Me-4-CF₃Ph | 4,4,6-trimethyl-5,6-dihydro-1,3(4H)-oxazin-2-yl | cyclopropyl |
| 2-SO₂Me-4-CF₃Ph | 4,4,6-trimethyl-5,6-dihydro-1,3(4H)-oxazin-2-yl | CF₃ |
| 2-SO₂Me-4-CF₃Ph | 2-oxazolidinon-3-yl | H |
| 2-SO₂Me-4-CF₃Ph | 2-oxazolidinon-3-yl | methyl |
| 2-SO₂Me-4-CF₃Ph | 2-oxazolidinon-3-yl | i-propyl |
| 2-SO₂Me-4-CF₃Ph | 2-oxazolidinon-3-yl | cyclopropyl |
| 2-SO₂Me-4-CF₃Ph | 2-oxazolidinon-3-yl | CF₃ |
| 2-SO₂Me-4-CF₃Ph | 2-pyrrolidinon-1-yl | methyl |
| 2-SO₂Me-4-CF₃Ph | 2-pyrrolidinon-1-yl | i-propyl |
| 2-SO₂Me-4-CF₃Ph | 2-pyrrolidinon-1-yl | cyclopropyl |
| 2-SO₂Me-4-CF₃Ph | 2-pyrrolidinon-1-yl | CF₃ |
| 2-SO₂Me-4-CF₃Ph | 3-methylisoxazol-5-yl | methyl |
| 2-SO₂Me-4-CF₃Ph | 3-methylisoxazol-5-yl | i-propyl |
| 2-SO₂Me-4-CF₃Ph | 3-methylisoxazol-5-yl | cyclopropyl |
| 2-SO₂Me-4-CF₃Ph | 3-methylisoxazol-5-yl | CF₃ |
| 2-SO₂Me-4-CF₃Ph | 2-NO₂-4-SO₂MePh | H |
| 2-SO₂Me-4-CF₃Ph | 2-NO₂-4-SO₂MePh | methyl |
| 2-SO₂Me-4-CF₃Ph | 2-NO₂-4-SO₂MePh | i-propyl |
| 2-SO₂Me-4-CF₃Ph | 2-NO₂-4-SO₂MePh | cyclopropyl |
| 2-SO₂Me-4-CF₃Ph | 2-NO₂-4-SO₂MePh | CF₃ |
| 2-SO₂Me-4-CF₃Ph | 2-Cl-4-SO₂MePh | H |
| 2-SO₂Me-4-CF₃Ph | 2-Cl-4-SO₂MePh | methyl |
| 2-SO₂Me-4-CF₃Ph | 2-Cl-4-SO₂MePh | i-propyl |
| 2-SO₂Me-4-CF₃Ph | 2-Cl-4-SO₂MePh | cyclopropyl |
| 2-SO₂Me-4-CF₃Ph | 2-Cl-4-SO₂MePh | CF₃ |
| 2-SO₂Me-4-CF₃Ph | 2-NO₂-4-CF₃Ph | H |
| 2-SO₂Me-4-CF₃Ph | 2-NO₂-4-CF₃Ph | methyl |
| 2-SO₂Me-4-CF₃Ph | 2-NO₂-4-CF₃Ph | i-propyl |
| 2-SO₂Me-4-CF₃Ph | 2-NO₂-4-CF₃Ph | cyclopropyl |
| 2-SO₂Me-4-CF₃Ph | 2-NO₂-4-CF₃Ph | CF₃ |
| 2-SO₂Me-4-CF₃Ph | 2-NO₂-4-ClPh | H |
| 2-SO₂Me-4-CF₃Ph | 2-NO₂-4-ClPh | methyl |
| 2-SO₂Me-4-CF₃Ph | 2-NO₂-4-ClPh | i-propyl |
| 2-SO₂Me-4-CF₃Ph | 2-NO₂-4-ClPh | cyclopropyl |
| 2-SO₂Me-4-CF₃Ph | 2-NO₂-4-ClPh | CF₃ |
| 2-SO₂Me-4-CF₃Ph | 2-Cl-4-NO₂Ph | H |
| 2-SO₂Me-4-CF₃Ph | 2-Cl-4-NO₂Ph | methyl |
| 2-SO₂Me-4-CF₃Ph | 2-Cl-4-NO₂Ph | i-propyl |
| 2-SO₂Me-4-CF₃Ph | 2-Cl-4-NO₂Ph | cyclopropyl |
| 2-SO₂Me-4-CF₃Ph | 2-Cl-4-NO₂Ph | CF₃ |
| 2-SO₂Me-4-CF₃Ph | 2,4-(NO₂)₂Ph | H |
| 2-SO₂Me-4-CF₃Ph | 2,4-(NO₂)₂Ph | methyl |
| 2-SO₂Me-4-CF₃Ph | 2,4-(NO₂)₂Ph | i-propyl |
| 2-SO₂Me-4-CF₃Ph | 2,4-(NO₂)₂Ph | cyclopropyl |
| 2-SO₂Me-4-CF₃Ph | 2,4-(NO₂)₂Ph | CF₃ |
| 2-SO₂Me-4-CF₃Ph | 4-F-3-NO₂Ph | H |
| 2-SO₂Me-4-CF₃Ph | 4-F-3-NO₂Ph | methyl |
| 2-SO₂Me-4-CF₃Ph | 4-F-3-NO₂Ph | i-propyl |
| 2-SO₂Me-4-CF₃Ph | 4-F-3-NO₂Ph | cyclopropyl |
| 2-SO₂Me-4-CF₃Ph | 4-F-3-NO₂Ph | CF₃ |
| 2-SO₂Me-4-CF₃Ph | 3,5-(CF₃)₂Ph | H |
| 2-SO₂Me-4-CF₃Ph | 3,5-(CF₃)₂Ph | methyl |
| 2-SO₂Me-4-CF₃Ph | 3,5-(CF₃)₂Ph | i-propyl |
| 2-SO₂Me-4-CF₃Ph | 3,5-(CF₃)₂Ph | cyclopropyl |
| 2-SO₂Me-4-CF₃Ph | 3,5-(CF₃)₂Ph | CF₃ |
| 2-SO₂Me-4-CF₃Ph | 2-SO₂Me-4-CF₃Ph | H |
| 2-SO₂Me-4-CF₃Ph | 2-SO₂Me-4-CF₃Ph | methyl |
| 2-SO₂Me-4-CF₃Ph | 2-SO₂Me-4-CF₃Ph | i-propyl |
| 2-SO₂Me-4-CF₃Ph | 2-SO₂Me-4-CF₃Ph | cyclopropyl |
| 2-SO₂Me-4-CF₃Ph | 2-SO₂Me-4-CF₃Ph | CF₃ |
| 3-Cl-5-CF₃Pyridin-2-yl | 1,2,4-oxadiazol-5-yl | H |
| 3-Cl-5-CF₃Pyridin-2-yl | 1,2,4-oxadiazol-5-yl | methyl |
| 3-Cl-5-CF₃Pyridin-2-yl | 1,2,4-oxadiazol-5-yl | i-propyl |
| 3-Cl-5-CF₃Pyridin-2-yl | 1,2,4-oxadiazol-5-yl | cyclopropyl |
| 3-Cl-5-CF₃Pyridin-2-yl | 1,2,4-oxadiazol-5-yl | CF₃ |
| 3-Cl-5-CF₃Pyridin-2-yl | 3-methyl-1,2,4-oxadiazol-5-yl | H |
| 3-Cl-5-CF₃Pyridin-2-yl | 3-methyl-1,2,4-oxadiazol-5-yl | methyl |
| 3-Cl-5-CF₃Pyridin-2-yl | 3-methyl-1,2,4-oxadiazol-5-yl | i-propyl |
| 3-Cl-5-CF₃Pyridin-2-yl | 3-methyl-1,2,4-oxadiazol-5-yl | cyclopropyl |
| 3-Cl-5-CF₃Pyridin-2-yl | 3-methyl-1,2,4-oxadiazol-5-yl | CF₃ |
| 3-Cl-5-CF₃Pyridin-2-yl | 3-trifluoromethyl-1,2,4-oxadiazol-5-yl | H |
| 3-Cl-5-CF₃Pyridin-2-yl | 3-trifluoromethyl-1,2,4-oxadiazol-5-yl | methyl |
| 3-Cl-5-CF₃Pyridin-2-yl | 3-trifluoromethyl-1,2,4-oxadiazol-5-yl | i-propyl |
| 3-Cl-5-CF₃Pyridin-2-yl | 3-trifluoromethyl-1,2,4-oxadiazol-5-yl | cyclopropyl |
| 3-Cl-5-CF₃Pyridin-2-yl | 3-trifluoromethyl-1,2,4-oxadiazol-5-yl | CF₃ |
| 3-Cl-5-CF₃Pyridin-2-yl | 1,2,4-oxadiazol-3-yl | H |
| 3-Cl-5-CF₃Pyridin-2-yl | 1,2,4-oxadiazol-3-yl | methyl |
| 3-Cl-5-CF₃Pyridin-2-yl | 1,2,4-oxadiazol-3-yl | i-propyl |
| 3-Cl-5-CF₃Pyridin-2-yl | 1,2,4-oxadiazol-3-yl | cyclopropyl |
| 3-Cl-5-CF₃Pyridin-2-yl | 1,2,4-oxadiazol-3-yl | CF₃ |
| 3-Cl-5-CF₃Pyridin-2-yl | 5-methyl-1,2,4-oxadiazol-3-yl | H |
| 3-Cl-5-CF₃Pyridin-2-yl | 5-methyl-1,2,4-oxadiazol-3-yl | methyl |
| 3-Cl-5-CF₃Pyridin-2-yl | 5-methyl-1,2,4-oxadiazol-3-yl | i-propyl |
| 3-Cl-5-CF₃Pyridin-2-yl | 5-methyl-1,2,4-oxadiazol-3-yl | cyclopropyl |
| 3-Cl-5-CF₃Pyridin-2-yl | 5-methyl-1,2,4-oxadiazol-3-yl | CF₃ |
| 3-Cl-5-CF₃Pyridin-2-yl | 5-trifluoromethyl-1,2,4-oxadiazol-3-yl | H |
| 3-Cl-5-CF₃Pyridin-2-yl | 5-trifluoromethyl-1,2,4-oxadiazol-3-yl | methyl |
| 3-Cl-5-CF₃Pyridin-2-yl | 5-trifluoromethyl-1,2,4-oxadiazol-3-yl | i-propyl |
| 3-Cl-5-CF₃Pyridin-2-yl | 5-trifluoromethyl-1,2,4-oxadiazol-3-yl | cyclopropyl |
| 3-Cl-5-CF₃Pyridin-2-yl | 5-trifluoromethyl-1,2,4-oxadiazol-3-yl | CF₃ |
| 3-Cl-5-CF₃Pyridin-2-yl | 5-chloro-1,2,4-oxadiazol-3-yl | H |
| 3-Cl-5-CF₃Pyridin-2-yl | 5-chloro-1,2,4-oxadiazol-3-yl | methyl |
| 3-Cl-5-CF₃Pyridin-2-yl | 5-chloro-1,2,4-oxadiazol-3-yl | i-propyl |
| 3-Cl-5-CF₃Pyridin-2-yl | 5-chloro-1,2,4-oxadiazol-3-yl | cyclopropyl |
| 3-Cl-5-CF₃Pyridin-2-yl | 5-chloro-1,2,4-oxadiazol-3-yl | CF₃ |
| 3-Cl-5-CF₃Pyridin-2-yl | 1,3,4-oxadiazol-2-yl | H |
| 3-Cl-5-CF₃Pyridin-2-yl | 1,3,4-oxadiazol-2-yl | methyl |
| 3-Cl-5-CF₃Pyridin-2-yl | 1,3,4-oxadiazol-2-yl | i-propyl |
| 3-Cl-5-CF₃Pyridin-2-yl | 1,3,4-oxadiazol-2-yl | cyclopropyl |
| 3-Cl-5-CF₃Pyridin-2-yl | 1,3,4-oxadiazol-2-yl | CF₃ |
| 3-Cl-5-CF₃Pyridin-2-yl | 5-methylsulfonyl-1,3,4-oxadiazol-2-yl | H |
| 3-Cl-5-CF₃Pyridin-2-yl | 5-methylsulfonyl-1,3,4-oxadiazol-2-yl | methyl |
| 3-Cl-5-CF₃Pyridin-2-yl | 5-methylsulfonyl-1,3,4-oxadiazol-2-yl | i-propyl |
| 3-Cl-5-CF₃Pyridin-2-yl | 5-methylsulfonyl-1,3,4-oxadiazol-2-yl | cyclopropyl |
| 3-Cl-5-CF₃Pyridin-2-yl | 5-methylsulfonyl-1,3,4-oxadiazol-2-yl | CF₃ |
| 3-Cl-5-CF₃Pyridin-2-yl | 5-methyl-1,3,4-oxadiazol-2-yl | H |
| 3-Cl-5-CF₃Pyridin-2-yl | 5-methyl-1,3,4-oxadiazol-2-yl | methyl |
| 3-Cl-5-CF₃Pyridin-2-yl | 5-methyl-1,3,4-oxadiazol-2-yl | i-propyl |
| 3-Cl-5-CF₃Pyridin-2-yl | 5-methyl-1,3,4-oxadiazol-2-yl | cyclopropyl |
| 3-Cl-5-CF₃Pyridin-2-yl | 5-methyl-1,3,4-oxadiazol-2-yl | CF₃ |
| 3-Cl-5-CF₃Pyridin-2-yl | 5-trifluoromethyl-1,3,4-oxadiazol-2-yl | H |
| 3-Cl-5-CF₃Pyridin-2-yl | 5-trifluoromethyl-1,3,4-oxadiazol-2-yl | methyl |
| 3-Cl-5-CF₃Pyridin-2-yl | 5-trifluoromethyl-1,3,4-oxadiazol-2-yl | i-propyl |

-continued

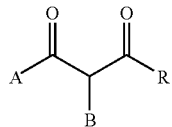

(I)

| A | B | R |
|---|---|---|
| | oxadiazol-2-yl | |
| 3-Cl-5-CF₃Pyridin-2-yl | 5-trifluoromethyl-1,3,4-oxadiazol-2-yl | cyclopropyl |
| 3-Cl-5-CF₃Pyridin-2-yl | 5-trifluoromethyl-1,3,4-oxadiazol-2-yl | CF₃ |
| 3-Cl-5-CF₃Pyridin-2-yl | 1,2,3-triazol-4-yl | H |
| 3-Cl-5-CF₃Pyridin-2-yl | 1,2,3-triazol-4-yl | methyl |
| 3-Cl-5-CF₃Pyridin-2-yl | 1,2,3-triazol-4-yl | i-propyl |
| 3-Cl-5-CF₃Pyridin-2-yl | 1,2,3-triazol-4-yl | cyclopropyl |
| 3-Cl-5-CF₃Pyridin-2-yl | 1,2,3-triazol-4-yl | CF₃ |
| 3-Cl-5-CF₃Pyridin-2-yl | 1-methyl-1,2,3-triazol-4-yl | H |
| 3-Cl-5-CF₃Pyridin-2-yl | 1-methyl-1,2,3-triazol-4-yl | methyl |
| 3-Cl-5-CF₃Pyridin-2-yl | 1-methyl-1,2,3-triazol-4-yl | i-propyl |
| 3-Cl-5-CF₃Pyridin-2-yl | 1-methyl-1,2,3-triazol-4-yl | cyclopropyl |
| 3-Cl-5-CF₃Pyridin-2-yl | 1-methyl-1,2,3-triazol-4-yl | CF₃ |
| 3-Cl-5-CF₃Pyridin-2-yl | 2-methyl-1,2,3-triazol-4-yl | H |
| 3-Cl-5-CF₃Pyridin-2-yl | 2-methyl-1,2,3-triazol-4-yl | methyl |
| 3-Cl-5-CF₃Pyridin-2-yl | 2-methyl-1,2,3-triazol-4-yl | i-propyl |
| 3-Cl-5-CF₃Pyridin-2-yl | 2-methyl-1,2,3-triazol-4-yl | cyclopropyl |
| 3-Cl-5-CF₃Pyridin-2-yl | 2-methyl-1,2,3-triazol-4-yl | CF₃ |
| 3-Cl-5-CF₃Pyridin-2-yl | 1,2,3-triazol-1-yl | H |
| 3-Cl-5-CF₃Pyridin-2-yl | 1,2,3-triazol-1-yl | methyl |
| 3-Cl-5-CF₃Pyridin-2-yl | 1,2,3-triazol-1-yl | i-propyl |
| 3-Cl-5-CF₃Pyridin-2-yl | 1,2,3-triazol-1-yl | cyclopropyl |
| 3-Cl-5-CF₃Pyridin-2-yl | 1,2,3-triazol-1-yl | CF₃ |
| 3-Cl-5-CF₃Pyridin-2-yl | 1,2,3-triazol-2-yl | H |
| 3-Cl-5-CF₃Pyridin-2-yl | 1,2,3-triazol-2-yl | methyl |
| 3-Cl-5-CF₃Pyridin-2-yl | 1,2,3-triazol-2-yl | i-propyl |
| 3-Cl-5-CF₃Pyridin-2-yl | 1,2,3-triazol-2-yl | cyclopropyl |
| 3-Cl-5-CF₃Pyridin-2-yl | 1,2,3-triazol-2-yl | CF₃ |
| 3-Cl-5-CF₃Pyridin-2-yl | 1,2,4-triazol-1-yl | H |
| 3-Cl-5-CF₃Pyridin-2-yl | 1,2,4-triazol-1-yl | methyl |
| 3-Cl-5-CF₃Pyridin-2-yl | 1,2,4-triazol-1-yl | i-propyl |
| 3-Cl-5-CF₃Pyridin-2-yl | 1,2,4-triazol-1-yl | cyclopropyl |
| 3-Cl-5-CF₃Pyridin-2-yl | 1,2,4-triazol-1-yl | CF₃ |
| 3-Cl-5-CF₃Pyridin-2-yl | imidazol-2-yl | H |
| 3-Cl-5-CF₃Pyridin-2-yl | imidazol-2-yl | methyl |
| 3-Cl-5-CF₃Pyridin-2-yl | imidazol-2-yl | i-propyl |
| 3-Cl-5-CF₃Pyridin-2-yl | imidazol-2-yl | cyclopropyl |
| 3-Cl-5-CF₃Pyridin-2-yl | imidazol-2-yl | CF₃ |
| 3-Cl-5-CF₃Pyridin-2-yl | imidazol-1-yl | H |
| 3-Cl-5-CF₃Pyridin-2-yl | imidazol-1-yl | methyl |
| 3-Cl-5-CF₃Pyridin-2-yl | imidazol-1-yl | i-propyl |
| 3-Cl-5-CF₃Pyridin-2-yl | imidazol-1-yl | cyclopropyl |
| 3-Cl-5-CF₃Pyridin-2-yl | imidazol-1-yl | CF₃ |
| 3-Cl-5-CF₃Pyridin-2-yl | imidazol-4-yl | H |
| 3-Cl-5-CF₃Pyridin-2-yl | imidazol-4-yl | methyl |
| 3-Cl-5-CF₃Pyridin-2-yl | imidazol-4-yl | i-propyl |
| 3-Cl-5-CF₃Pyridin-2-yl | imidazol-4-yl | cyclopropyl |
| 3-Cl-5-CF₃Pyridin-2-yl | imidazol-4-yl | CF₃ |
| 3-Cl-5-CF₃Pyridin-2-yl | thiazol-2-yl | H |
| 3-Cl-5-CF₃Pyridin-2-yl | thiazol-2-yl | methyl |
| 3-Cl-5-CF₃Pyridin-2-yl | thiazol-2-yl | i-propyl |
| 3-Cl-5-CF₃Pyridin-2-yl | thiazol-2-yl | cyclopropyl |
| 3-Cl-5-CF₃Pyridin-2-yl | thiazol-2-yl | CF₃ |
| 3-Cl-5-CF₃Pyridin-2-yl | 4-methylthiazol-2-yl | H |
| 3-Cl-5-CF₃Pyridin-2-yl | 4-methylthiazol-2-yl | methyl |
| 3-Cl-5-CF₃Pyridin-2-yl | 4-methylthiazol-2-yl | i-propyl |
| 3-Cl-5-CF₃Pyridin-2-yl | 4-methylthiazol-2-yl | cyclopropyl |
| 3-Cl-5-CF₃Pyridin-2-yl | 4-methylthiazol-2-yl | CF₃ |
| 3-Cl-5-CF₃Pyridin-2-yl | oxazol-2-yl | H |
| 3-Cl-5-CF₃Pyridin-2-yl | oxazol-2-yl | methyl |
| 3-Cl-5-CF₃Pyridin-2-yl | oxazol-2-yl | i-propyl |
| 3-Cl-5-CF₃Pyridin-2-yl | oxazol-2-yl | cyclopropyl |
| 3-Cl-5-CF₃Pyridin-2-yl | oxazol-2-yl | CF₃ |
| 3-Cl-5-CF₃Pyridin-2-yl | 4,5-dimethyloxazol-2-yl | H |
| 3-Cl-5-CF₃Pyridin-2-yl | 4,5-dimethyloxazol-2-yl | methyl |
| 3-Cl-5-CF₃Pyridin-2-yl | 4,5-dimethyloxazol-2-yl | i-propyl |
| 3-Cl-5-CF₃Pyridin-2-yl | 4,5-dimethyloxazol-2-yl | cyclopropyl |
| 3-Cl-5-CF₃Pyridin-2-yl | 4,5-dimethyloxazol-2-yl | CF₃ |

-continued

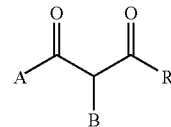

(I)

| A | B | R |
|---|---|---|
| 3-Cl-5-CF₃Pyridin-2-yl | 2-oxazolin-2-yl | H |
| 3-Cl-5-CF₃Pyridin-2-yl | 2-oxazolin-2-yl | methyl |
| 3-Cl-5-CF₃Pyridin-2-yl | 2-oxazolin-2-yl | i-propyl |
| 3-Cl-5-CF₃Pyridin-2-yl | 2-oxazolin-2-yl | cyclopropyl |
| 3-Cl-5-CF₃Pyridin-2-yl | 2-oxazolin-2-yl | CF₃ |
| 3-Cl-5-CF₃Pyridin-2-yl | 4,4-dimethyl-2-oxazolin-2-yl | H |
| 3-Cl-5-CF₃Pyridin-2-yl | 4,4-dimethyl-2-oxazolin-2-yl | methyl |
| 3-Cl-5-CF₃Pyridin-2-yl | 4,4-dimethyl-2-oxazolin-2-yl | i-propyl |
| 3-Cl-5-CF₃Pyridin-2-yl | 4,4-dimethyl-2-oxazolin-2-yl | cyclopropyl |
| 3-Cl-5-CF₃Pyridin-2-yl | 4,4-dimethyl-2-oxazolin-2-yl | CF₃ |
| 3-Cl-5-CF₃Pyridin-2-yl | 1,2,4-thiadiazol-5-yl | H |
| 3-Cl-5-CF₃Pyridin-2-yl | 1,2,4-thiadiazol-5-yl | methyl |
| 3-Cl-5-CF₃Pyridin-2-yl | 1,2,4-thiadiazol-5-yl | i-propyl |
| 3-Cl-5-CF₃Pyridin-2-yl | 1,2,4-thiadiazol-5-yl | cyclopropyl |
| 3-Cl-5-CF₃Pyridin-2-yl | 1,2,4-thiadiazol-5-yl | CF₃ |
| 3-Cl-5-CF₃Pyridin-2-yl | 3-methyl-1,2,4-thiadiazol-5-yl | H |
| 3-Cl-5-CF₃Pyridin-2-yl | 3-methyl-1,2,4-thiadiazol-5-yl | methyl |
| 3-Cl-5-CF₃Pyridin-2-yl | 3-methyl-1,2,4-thiadiazol-5-yl | i-propyl |
| 3-Cl-5-CF₃Pyridin-2-yl | 3-methyl-1,2,4-thiadiazol-5-yl | cyclopropyl |
| 3-Cl-5-CF₃Pyridin-2-yl | 3-methyl-1,2,4-thiadiazol-5-yl | CF₃ |
| 3-Cl-5-CF₃Pyridin-2-yl | 3-trifluoromethyl-1,2,4-thiadiazol-5-yl | H |
| 3-Cl-5-CF₃Pyridin-2-yl | 3-trifluoromethyl-1,2,4-thiadiazol-5-yl | methyl |
| 3-Cl-5-CF₃Pyridin-2-yl | 3-trifluoromethyl-1,2,4-thiadiazol-5-yl | i-propyl |
| 3-Cl-5-CF₃Pyridin-2-yl | 3-trifluoromethyl-1,2,4-thiadiazol-5-yl | cyclopropyl |
| 3-Cl-5-CF₃Pyridin-2-yl | 3-trifluoromethyl-1,2,4-thiadiazol-5-yl | CF₃ |
| 3-Cl-5-CF₃Pyridin-2-yl | 1,2,4-thiadiazol-3-yl | H |
| 3-Cl-5-CF₃Pyridin-2-yl | 1,2,4-thiadiazol-3-yl | methyl |
| 3-Cl-5-CF₃Pyridin-2-yl | 1,2,4-thiadiazol-3-yl | i-propyl |
| 3-Cl-5-CF₃Pyridin-2-yl | 1,2,4-thiadiazol-3-yl | cyclopropyl |
| 3-Cl-5-CF₃Pyridin-2-yl | 1,2,4-thiadiazol-3-yl | CF₃ |
| 3-Cl-5-CF₃Pyridin-2-yl | 5-methyl-1,2,4-thiadiazol-3-yl | H |
| 3-Cl-5-CF₃Pyridin-2-yl | 5-methyl-1,2,4-thiadiazol-3-yl | methyl |
| 3-Cl-5-CF₃Pyridin-2-yl | 5-methyl-1,2,4-thiadiazol-3-yl | i-propyl |
| 3-Cl-5-CF₃Pyridin-2-yl | 5-methyl-1,2,4-thiadiazol-3-yl | cyclopropyl |
| 3-Cl-5-CF₃Pyridin-2-yl | 5-methyl-1,2,4-thiadiazol-3-yl | CF₃ |
| 3-Cl-5-CF₃Pyridin-2-yl | 5-trifluoromethyl-1,2,4-thiadiazol-3-yl | H |
| 3-Cl-5-CF₃Pyridin-2-yl | 5-trifluoromethyl-1,2,4-thiadiazol-3-yl | methyl |
| 3-Cl-5-CF₃Pyridin-2-yl | 5-trifluoromethyl-1,2,4-thiadiazol-3-yl | i-propyl |
| 3-Cl-5-CF₃Pyridin-2-yl | 5-trifluoromethyl-1,2,4-thiadiazol-3-yl | cyclopropyl |
| 3-Cl-5-CF₃Pyridin-2-yl | 5-trifluoromethyl-1,2,4-thiadiazol-3-yl | CF₃ |
| 3-Cl-5-CF₃Pyridin-2-yl | 1,3,4-thiadiazol-2-yl | H |
| 3-Cl-5-CF₃Pyridin-2-yl | 1,3,4-thiadiazol-2-yl | methyl |
| 3-Cl-5-CF₃Pyridin-2-yl | 1,3,4-thiadiazol-2-yl | i-propyl |
| 3-Cl-5-CF₃Pyridin-2-yl | 1,3,4-thiadiazol-2-yl | cyclopropyl |
| 3-Cl-5-CF₃Pyridin-2-yl | 1,3,4-thiadiazol-2-yl | CF₃ |
| 3-Cl-5-CF₃Pyridin-2-yl | 5-methylsulfonyl-1,3,4-thiadiazol-2-yl | H |
| 3-Cl-5-CF₃Pyridin-2-yl | 5-methylsulfonyl-1,3,4-thiadiazol-2-yl | methyl |
| 3-Cl-5-CF₃Pyridin-2-yl | 5-methylsulfonyl-1,3,4-thiadiazol-2-yl | i-propyl |
| 3-Cl-5-CF₃Pyridin-2-yl | 5-methylsulfonyl-1,3,4-thiadiazol-2-yl | cyclopropyl |
| 3-Cl-5-CF₃Pyridin-2-yl | 5-methylsulfonyl-1,3,4-thiadiazol-2-yl | CF₃ |
| 3-Cl-5-CF₃Pyridin-2-yl | 5-methyl-1,3,4-thiadiazol-2-yl | H |
| 3-Cl-5-CF₃Pyridin-2-yl | 5-methyl-1,3,4-thiadiazol-2-yl | methyl |
| 3-Cl-5-CF₃Pyridin-2-yl | 5-methyl-1,3,4-thiadiazol-2-yl | i-propyl |
| 3-Cl-5-CF₃Pyridin-2-yl | 5-methyl-1,3,4-thiadiazol-2-yl | cyclopropyl |
| 3-Cl-5-CF₃Pyridin-2-yl | 5-methyl-1,3,4-thiadiazol-2-yl | CF₃ |

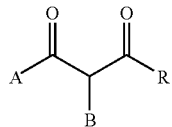

(I)

| A | B | R |
|---|---|---|
| 3-Cl-5-CF₃Pyridin-2-yl | benzoxazol-2-yl | H |
| 3-Cl-5-CF₃Pyridin-2-yl | benzoxazol-2-yl | methyl |
| 3-Cl-5-CF₃Pyridin-2-yl | benzoxazol-2-yl | i-propyl |
| 3-Cl-5-CF₃Pyridin-2-yl | benzoxazol-2-yl | cyclopropyl |
| 3-Cl-5-CF₃Pyridin-2-yl | benzoxazol-2-yl | CF₃ |
| 3-Cl-5-CF₃Pyridin-2-yl | 6-methylbenzoxazol-2-yl | H |
| 3-Cl-5-CF₃Pyridin-2-yl | 6-methylbenzoxazol-2-yl | methyl |
| 3-Cl-5-CF₃Pyridin-2-yl | 6-methylbenzoxazol-2-yl | i-propyl |
| 3-Cl-5-CF₃Pyridin-2-yl | 6-methylbenzoxazol-2-yl | cyclopropyl |
| 3-Cl-5-CF₃Pyridin-2-yl | 6-methylbenzoxazol-2-yl | CF₃ |
| 3-Cl-5-CF₃Pyridin-2-yl | benzothiazol-2-yl | H |
| 3-Cl-5-CF₃Pyridin-2-yl | benzothiazol-2-yl | methyl |
| 3-Cl-5-CF₃Pyridin-2-yl | benzothiazol-2-yl | i-propyl |
| 3-Cl-5-CF₃Pyridin-2-yl | benzothiazol-2-yl | cyclopropyl |
| 3-Cl-5-CF₃Pyridin-2-yl | benzothiazol-2-yl | CF₃ |
| 3-Cl-5-CF₃Pyridin-2-yl | pyrazol-1-yl | H |
| 3-Cl-5-CF₃Pyridin-2-yl | pyrazol-1-yl | methyl |
| 3-Cl-5-CF₃Pyridin-2-yl | pyrazol-1-yl | i-propyl |
| 3-Cl-5-CF₃Pyridin-2-yl | pyrazol-1-yl | cyclopropyl |
| 3-Cl-5-CF₃Pyridin-2-yl | pyrazol-1-yl | CF₃ |
| 3-Cl-5-CF₃Pyridin-2-yl | pyrazol-3-yl | H |
| 3-Cl-5-CF₃Pyridin-2-yl | pyrazol-3-yl | methyl |
| 3-Cl-5-CF₃Pyridin-2-yl | pyrazol-3-yl | i-propyl |
| 3-Cl-5-CF₃Pyridin-2-yl | pyrazol-3-yl | cyclopropyl |
| 3-Cl-5-CF₃Pyridin-2-yl | pyrazol-3-yl | CF₃ |
| 3-Cl-5-CF₃Pyridin-2-yl | 1-methylpyrazol-3-yl | H |
| 3-Cl-5-CF₃Pyridin-2-yl | 1-methylpyrazol-3-yl | methyl |
| 3-Cl-5-CF₃Pyridin-2-yl | 1-methylpyrazol-3-yl | i-propyl |
| 3-Cl-5-CF₃Pyridin-2-yl | 1-methylpyrazol-3-yl | cyclopropyl |
| 3-Cl-5-CF₃Pyridin-2-yl | 1-methylpyrazol-3-yl | CF₃ |
| 3-Cl-5-CF₃Pyridin-2-yl | tetrazol-1-yl | H |
| 3-Cl-5-CF₃Pyridin-2-yl | tetrazol-1-yl | methyl |
| 3-Cl-5-CF₃Pyridin-2-yl | tetrazol-1-yl | i-propyl |
| 3-Cl-5-CF₃Pyridin-2-yl | tetrazol-1-yl | cyclopropyl |
| 3-Cl-5-CF₃Pyridin-2-yl | tetrazol-1-yl | CF₃ |
| 3-Cl-5-CF₃Pyridin-2-yl | 5-methyltetrazol-1-yl | H |
| 3-Cl-5-CF₃Pyridin-2-yl | 5-methyltetrazol-1-yl | methyl |
| 3-Cl-5-CF₃Pyridin-2-yl | 5-methyltetrazol-1-yl | i-propyl |
| 3-Cl-5-CF₃Pyridin-2-yl | 5-methyltetrazol-1-yl | cyclopropyl |
| 3-Cl-5-CF₃Pyridin-2-yl | 5-methyltetrazol-1-yl | CF₃ |
| 3-Cl-5-CF₃Pyridin-2-yl | tetrazol-2-yl | H |
| 3-Cl-5-CF₃Pyridin-2-yl | tetrazol-2-yl | methyl |
| 3-Cl-5-CF₃Pyridin-2-yl | tetrazol-2-yl | i-propyl |
| 3-Cl-5-CF₃Pyridin-2-yl | tetrazol-2-yl | cyclopropyl |
| 3-Cl-5-CF₃Pyridin-2-yl | tetrazol-2-yl | CF₃ |
| 3-Cl-5-CF₃Pyridin-2-yl | 5-methyltetrazol-2-yl | H |
| 3-Cl-5-CF₃Pyridin-2-yl | 5-methyltetrazol-2-yl | methyl |
| 3-Cl-5-CF₃Pyridin-2-yl | 5-methyltetrazol-2-yl | i-propyl |
| 3-Cl-5-CF₃Pyridin-2-yl | 5-methyltetrazol-2-yl | cyclopropyl |
| 3-Cl-5-CF₃Pyridin-2-yl | 5-methyltetrazol-2-yl | CF₃ |
| 3-Cl-5-CF₃Pyridin-2-yl | 1-methyltetrazol-5-yl | H |
| 3-Cl-5-CF₃Pyridin-2-yl | 1-methyltetrazol-5-yl | methyl |
| 3-Cl-5-CF₃Pyridin-2-yl | 1-methyltetrazol-5-yl | i-propyl |
| 3-Cl-5-CF₃Pyridin-2-yl | 1-methyltetrazol-5-yl | cyclopropyl |
| 3-Cl-5-CF₃Pyridin-2-yl | 1-methyltetrazol-5-yl | CF₃ |
| 3-Cl-5-CF₃Pyridin-2-yl | 2-methyltetrazol-5-yl | H |
| 3-Cl-5-CF₃Pyridin-2-yl | 2-methyltetrazol-5-yl | methyl |
| 3-Cl-5-CF₃Pyridin-2-yl | 2-methyltetrazol-5-yl | i-propyl |
| 3-Cl-5-CF₃Pyridin-2-yl | 2-methyltetrazol-5-yl | cyclopropyl |
| 3-Cl-5-CF₃Pyridin-2-yl | 2-methyltetrazol-5-yl | CF₃ |
| 3-Cl-5-CF₃Pyridin-2-yl | pyridin-2-yl | H |
| 3-Cl-5-CF₃Pyridin-2-yl | pyridin-2-yl | methyl |
| 3-Cl-5-CF₃Pyridin-2-yl | pyridin-2-yl | i-propyl |
| 3-Cl-5-CF₃Pyridin-2-yl | pyridin-2-yl | cyclopropyl |
| 3-Cl-5-CF₃Pyridin-2-yl | pyridin-2-yl | CF₃ |
| 3-Cl-5-CF₃Pyridin-2-yl | pyridin-4-yl | H |
| 3-Cl-5-CF₃Pyridin-2-yl | pyridin-4-yl | methyl |
| 3-Cl-5-CF₃Pyridin-2-yl | pyridin-4-yl | i-propyl |
| 3-Cl-5-CF₃Pyridin-2-yl | pyridin-4-yl | cyclopropyl |
| 3-Cl-5-CF₃Pyridin-2-yl | pyridin-4-yl | CF₃ |

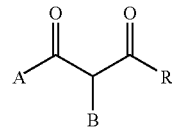

(I)

| A | B | R |
|---|---|---|
| 3-Cl-5-CF₃Pyridin-2-yl | pyridin-3-yl | H |
| 3-Cl-5-CF₃Pyridin-2-yl | pyridin-3-yl | methyl |
| 3-Cl-5-CF₃Pyridin-2-yl | pyridin-3-yl | i-propyl |
| 3-Cl-5-CF₃Pyridin-2-yl | pyridin-3-yl | cyclopropyl |
| 3-Cl-5-CF₃Pyridin-2-yl | pyridin-3-yl | CF₃ |
| 3-Cl-5-CF₃Pyridin-2-yl | 3-nitropyridin-4-yl | H |
| 3-Cl-5-CF₃Pyridin-2-yl | 3-nitropyridin-4-yl | methyl |
| 3-Cl-5-CF₃Pyridin-2-yl | 3-nitropyridin-4-yl | i-propyl |
| 3-Cl-5-CF₃Pyridin-2-yl | 3-nitropyridin-4-yl | cyclopropyl |
| 3-Cl-5-CF₃Pyridin-2-yl | 3-nitropyridin-4-yl | CF₃ |
| 3-Cl-5-CF₃Pyridin-2-yl | 5-cyanopyridin-2-yl | H |
| 3-Cl-5-CF₃Pyridin-2-yl | 5-cyanopyridin-2-yl | methyl |
| 3-Cl-5-CF₃Pyridin-2-yl | 5-cyanopyridin-2-yl | i-propyl |
| 3-Cl-5-CF₃Pyridin-2-yl | 5-cyanopyridin-2-yl | cyclopropyl |
| 3-Cl-5-CF₃Pyridin-2-yl | 5-cyanopyridin-2-yl | CF₃ |
| 3-Cl-5-CF₃Pyridin-2-yl | 5-trifluoromethylpyridin-2-yl | H |
| 3-Cl-5-CF₃Pyridin-2-yl | 5-trifluoromethylpyridin-2-yl | methyl |
| 3-Cl-5-CF₃Pyridin-2-yl | 5-trifluoromethylpyridin-2-yl | i-propyl |
| 3-Cl-5-CF₃Pyridin-2-yl | 5-trifluoromethylpyridin-2-yl | cyclopropyl |
| 3-Cl-5-CF₃Pyridin-2-yl | 5-trifluoromethylpyridin-2-yl | CF₃ |
| 3-Cl-5-CF₃Pyridin-2-yl | pyrimidin-2-yl | H |
| 3-Cl-5-CF₃Pyridin-2-yl | pyrimidin-2-yl | methyl |
| 3-Cl-5-CF₃Pyridin-2-yl | pyrimidin-2-yl | i-propyl |
| 3-Cl-5-CF₃Pyridin-2-yl | pyrimidin-2-yl | cyclopropyl |
| 3-Cl-5-CF₃Pyridin-2-yl | pyrimidin-2-yl | CF₃ |
| 3-Cl-5-CF₃Pyridin-2-yl | pyrimidin-4-yl | H |
| 3-Cl-5-CF₃Pyridin-2-yl | pyrimidin-4-yl | methyl |
| 3-Cl-5-CF₃Pyridin-2-yl | pyrimidin-4-yl | i-propyl |
| 3-Cl-5-CF₃Pyridin-2-yl | pyrimidin-4-yl | cyclopropyl |
| 3-Cl-5-CF₃Pyridin-2-yl | pyrimidin-4-yl | CF₃ |
| 3-Cl-5-CF₃Pyridin-2-yl | 6-chloropyrimidin-4-yl | methyl |
| 3-Cl-5-CF₃Pyridin-2-yl | 6-chloropyrimidin-4-yl | i-propyl |
| 3-Cl-5-CF₃Pyridin-2-yl | 6-chloropyrimidin-4-yl | cyclopropyl |
| 3-Cl-5-CF₃Pyridin-2-yl | 6-chloropyrimidin-4-yl | CF₃ |
| 3-Cl-5-CF₃Pyridin-2-yl | pyridazin-3-yl | H |
| 3-Cl-5-CF₃Pyridin-2-yl | pyridazin-3-yl | methyl |
| 3-Cl-5-CF₃Pyridin-2-yl | pyridazin-3-yl | i-propyl |
| 3-Cl-5-CF₃Pyridin-2-yl | pyridazin-3-yl | cyclopropyl |
| 3-Cl-5-CF₃Pyridin-2-yl | pyridazin-3-yl | CF₃ |
| 3-Cl-5-CF₃Pyridin-2-yl | 6-chloropyridazin-3-yl | methyl |
| 3-Cl-5-CF₃Pyridin-2-yl | 6-chloropyridazin-3-yl | i-propyl |
| 3-Cl-5-CF₃Pyridin-2-yl | 6-chloropyridazin-3-yl | cyclopropyl |
| 3-Cl-5-CF₃Pyridin-2-yl | 6-chloropyridazin-3-yl | CF₃ |
| 3-Cl-5-CF₃Pyridin-2-yl | pyrazin-2-yl | methyl |
| 3-Cl-5-CF₃Pyridin-2-yl | pyrazin-2-yl | i-propyl |
| 3-Cl-5-CF₃Pyridin-2-yl | pyrazin-2-yl | cyclopropyl |
| 3-Cl-5-CF₃Pyridin-2-yl | pyrazin-2-yl | CF₃ |
| 3-Cl-5-CF₃Pyridin-2-yl | triazin-2-yl | methyl |
| 3-Cl-5-CF₃Pyridin-2-yl | triazin-2-yl | i-propyl |
| 3-Cl-5-CF₃Pyridin-2-yl | triazin-2-yl | cyclopropyl |
| 3-Cl-5-CF₃Pyridin-2-yl | triazin-2-yl | CF₃ |
| 3-Cl-5-CF₃Pyridin-2-yl | quinolin-2-yl | methyl |
| 3-Cl-5-CF₃Pyridin-2-yl | quinolin-2-yl | i-propyl |
| 3-Cl-5-CF₃Pyridin-2-yl | quinolin-2-yl | cyclopropyl |
| 3-Cl-5-CF₃Pyridin-2-yl | quinolin-2-yl | CF₃ |
| 3-Cl-5-CF₃Pyridin-2-yl | 4,4,6-trimethyl-5,6-dihydro-1,3(4H)-oxazin-2-yl | H |
| 3-Cl-5-CF₃Pyridin-2-yl | 4,4,6-trimethyl-5,6-dihydro-1,3(4H)-oxazin-2-yl | methyl |
| 3-Cl-5-CF₃Pyridin-2-yl | 4,4,6-trimethyl-5,6-dihydro-1,3(4H)-oxazin-2-yl | i-propyl |
| 3-Cl-5-CF₃Pyridin-2-yl | 4,4,6-trimethyl-5,6-dihydro-1,3(4H)-oxazin-2-yl | cyclopropyl |
| 3-Cl-5-CF₃Pyridin-2-yl | 4,4,6-trimethyl-5,6-dihydro-1,3(4H)-oxazin-2-yl | CF₃ |
| 3-Cl-5-CF₃Pyridin-2-yl | 2-oxazolidinon-3-yl | H |
| 3-Cl-5-CF₃Pyridin-2-yl | 2-oxazolidinon-3-yl | methyl |
| 3-Cl-5-CF₃Pyridin-2-yl | 2-oxazolidinon-3-yl | i-propyl |
| 3-Cl-5-CF₃Pyridin-2-yl | 2-oxazolidinon-3-yl | cyclopropyl |
| 3-Cl-5-CF₃Pyridin-2-yl | 2-oxazolidinon-3-yl | CF₃ |

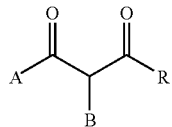

(I)

| A | B | R |
|---|---|---|
| 3-Cl-5-CF$_3$Pyridin-2-yl | 2-pyrrolidinon-1-yl | methyl |
| 3-Cl-5-CF$_3$Pyridin-2-yl | 2-pyrrolidinon-1-yl | i-propyl |
| 3-Cl-5-CF$_3$Pyridin-2-yl | 2-pyrrolidinon-1-yl | cyclopropyl |
| 3-Cl-5-CF$_3$Pyridin-2-yl | 2-pyrrolidinon-1-yl | CF$_3$ |
| 3-Cl-5-CF$_3$Pyridin-2-yl | 3-methylisoxazol-5-yl | methyl |
| 3-Cl-5-CF$_3$Pyridin-2-yl | 3-methylisoxazol-5-yl | i-propyl |
| 3-Cl-5-CF$_3$Pyridin-2-yl | 3-methylisoxazol-5-yl | cyclopropyl |
| 3-Cl-5-CF$_3$Pyridin-2-yl | 3-methylisoxazol-5-yl | CF$_3$ |
| 3-Cl-5-CF$_3$Pyridin-2-yl | 2-NO$_2$-4-SO$_2$MePh | H |
| 3-Cl-5-CF$_3$Pyridin-2-yl | 2-NO$_2$-4-SO$_2$MePh | methyl |
| 3-Cl-5-CF$_3$Pyridin-2-yl | 2-NO$_2$-4-SO$_2$MePh | i-propyl |
| 3-Cl-5-CF$_3$Pyridin-2-yl | 2-NO$_2$-4-SO$_2$MePh | cyclopropyl |
| 3-Cl-5-CF$_3$Pyridin-2-yl | 2-NO$_2$-4-SO$_2$MePh | CF$_3$ |
| 3-Cl-5-CF$_3$Pyridin-2-yl | 2-Cl-4-SO$_2$MePh | H |
| 3-Cl-5-CF$_3$Pyridin-2-yl | 2-Cl-4-SO$_2$MePh | methyl |
| 3-Cl-5-CF$_3$Pyridin-2-yl | 2-Cl-4-SO$_2$MePh | i-propyl |
| 3-Cl-5-CF$_3$Pyridin-2-yl | 2-Cl-4-SO$_2$MePh | cyclopropyl |
| 3-Cl-5-CF$_3$Pyridin-2-yl | 2-Cl-4-SO$_2$MePh | CF$_3$ |
| 3-Cl-5-CF$_3$Pyridin-2-yl | 2-NO$_2$-4-CF$_3$Ph | H |
| 3-Cl-5-CF$_3$Pyridin-2-yl | 2-NO$_2$-4-CF$_3$Ph | methyl |
| 3-Cl-5-CF$_3$Pyridin-2-yl | 2-NO$_2$-4-CF$_3$Ph | i-propyl |
| 3-Cl-5-CF$_3$Pyridin-2-yl | 2-NO$_2$-4-CF$_3$Ph | cyclopropyl |
| 3-Cl-5-CF$_3$Pyridin-2-yl | 2-NO$_2$-4-CF$_3$Ph | CF$_3$ |
| 3-Cl-5-CF$_3$Pyridin-2-yl | 2-NO$_2$-4-ClPh | H |
| 3-Cl-5-CF$_3$Pyridin-2-yl | 2-NO$_2$-4-ClPh | methyl |
| 3-Cl-5-CF$_3$Pyridin-2-yl | 2-NO$_2$-4-ClPh | i-propyl |
| 3-Cl-5-CF$_3$Pyridin-2-yl | 2-NO$_2$-4-ClPh | cyclopropyl |
| 3-Cl-5-CF$_3$Pyridin-2-yl | 2-NO$_2$-4-ClPh | CF$_3$ |
| 3-Cl-5-CF$_3$Pyridin-2-yl | 2-Cl-4-NO$_2$Ph | H |
| 3-Cl-5-CF$_3$Pyridin-2-yl | 2-Cl-4-NO$_2$Ph | methyl |
| 3-Cl-5-CF$_3$Pyridin-2-yl | 2-Cl-4-NO$_2$Ph | i-propyl |
| 3-Cl-5-CF$_3$Pyridin-2-yl | 2-Cl-4-NO$_2$Ph | cyclopropyl |
| 3-Cl-5-CF$_3$Pyridin-2-yl | 2-Cl-4-NO$_2$Ph | CF$_3$ |
| 3-Cl-5-CF$_3$Pyridin-2-yl | 2,4-(NO$_2$)$_2$Ph | H |
| 3-Cl-5-CF$_3$Pyridin-2-yl | 2,4-(NO$_2$)$_2$Ph | methyl |
| 3-Cl-5-CF$_3$Pyridin-2-yl | 2,4-(NO$_2$)$_2$Ph | i-propyl |
| 3-Cl-5-CF$_3$Pyridin-2-yl | 2,4-(NO$_2$)$_2$Ph | cyclopropyl |
| 3-Cl-5-CF$_3$Pyridin-2-yl | 2,4-(NO$_2$)$_2$Ph | CF$_3$ |
| 3-Cl-5-CF$_3$Pyridin-2-yl | 4-F-3-NO$_2$Ph | H |
| 3-Cl-5-CF$_3$Pyridin-2-yl | 4-F-3-NO$_2$Ph | methyl |
| 3-Cl-5-CF$_3$Pyridin-2-yl | 4-F-3-NO$_2$Ph | i-propyl |
| 3-Cl-5-CF$_3$Pyridin-2-yl | 4-F-3-NO$_2$Ph | cyclopropyl |
| 3-Cl-5-CF$_3$Pyridin-2-yl | 4-F-3-NO$_2$Ph | CF$_3$ |
| 3-Cl-5-CF$_3$Pyridin-2-yl | 3,5-(CF$_3$)$_2$Ph | H |
| 3-Cl-5-CF$_3$Pyridin-2-yl | 3,5-(CF$_3$)$_2$Ph | methyl |
| 3-Cl-5-CF$_3$Pyridin-2-yl | 3,5-(CF$_3$)$_2$Ph | i-propyl |
| 3-Cl-5-CF$_3$Pyridin-2-yl | 3,5-(CF$_3$)$_2$Ph | cyclopropyl |
| 3-Cl-5-CF$_3$Pyridin-2-yl | 3,5-(CF$_3$)$_2$Ph | CF$_3$ |
| 3-Cl-5-CF$_3$Pyridin-2-yl | 2-SO$_2$Me-4-CF$_3$Ph | H |
| 3-Cl-5-CF$_3$Pyridin-2-yl | 2-SO$_2$Me-4-CF$_3$Ph | methyl |
| 3-Cl-5-CF$_3$Pyridin-2-yl | 2-SO$_2$Me-4-CF$_3$Ph | i-propyl |
| 3-Cl-5-CF$_3$Pyridin-2-yl | 2-SO$_2$Me-4-CF$_3$Ph | cyclopropyl |
| 3-Cl-5-CF$_3$Pyridin-2-yl | 2-SO$_2$Me-4-CF$_3$Ph | CF$_3$ |
| 2,4-(Me)$_2$Thiazol-5-yl | 1,2,4-oxadiazol-5-yl | H |
| 2,4-(Me)$_2$Thiazol-5-yl | 1,2,4-oxadiazol-5-yl | methyl |
| 2,4-(Me)$_2$Thiazol-5-yl | 1,2,4-oxadiazol-5-yl | i-propyl |
| 2,4-(Me)$_2$Thiazol-5-yl | 1,2,4-oxadiazol-5-yl | cyclopropyl |
| 2,4-(Me)$_2$Thiazol-5-yl | 1,2,4-oxadiazol-5-yl | CF$_3$ |
| 2,4-(Me)$_2$Thiazol-5-yl | 3-methyl-1,2,4-oxadiazol-5-yl | H |
| 2,4-(Me)$_2$Thiazol-5-yl | 3-methyl-1,2,4-oxadiazol-5-yl | methyl |
| 2,4-(Me)$_2$Thiazol-5-yl | 3-methyl-1,2,4-oxadiazol-5-yl | i-propyl |
| 2,4-(Me)$_2$Thiazol-5-yl | 3-methyl-1,2,4-oxadiazol-5-yl | cyclopropyl |
| 2,4-(Me)$_2$Thiazol-5-yl | 3-methyl-1,2,4-oxadiazol-5-yl | CF$_3$ |
| 2,4-(Me)$_2$Thiazol-5-yl | 3-trifluoromethyl-1,2,4-oxadiazol-5-yl | H |
| 2,4-(Me)$_2$Thiazol-5-yl | 3-trifluoromethyl-1,2,4-oxadiazol-5-yl | methyl |
| 2,4-(Me)$_2$Thiazol-5-yl | 3-trifluoromethyl-1,2,4-oxadiazol-5-yl | i-propyl |
| 2,4-(Me)$_2$Thiazol-5-yl | 3-trifluoromethyl-1,2,4-oxadiazol-5-yl | cyclopropyl |

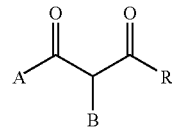

(I)

| A | B | R |
|---|---|---|
| 2,4-(Me)$_2$Thiazol-5-yl | 3-trifluoromethyl-1,2,4-oxadiazol-5-yl | CF$_3$ |
| 2,4-(Me)$_2$Thiazol-5-yl | 1,2,4-oxadiazol-3-yl | H |
| 2,4-(Me)$_2$Thiazol-5-yl | 1,2,4-oxadiazol-3-yl | methyl |
| 2,4-(Me)$_2$Thiazol-5-yl | 1,2,4-oxadiazol-3-yl | i-propyl |
| 2,4-(Me)$_2$Thiazol-5-yl | 1,2,4-oxadiazol-3-yl | cyclopropyl |
| 2,4-(Me)$_2$Thiazol-5-yl | 1,2,4-oxadiazol-3-yl | CF$_3$ |
| 2,4-(Me)$_2$Thiazol-5-yl | 5-methyl-1,2,4-oxadiazol-3-yl | H |
| 2,4-(Me)$_2$Thiazol-5-yl | 5-methyl-1,2,4-oxadiazol-3-yl | methyl |
| 2,4-(Me)$_2$Thiazol-5-yl | 5-methyl-1,2,4-oxadiazol-3-yl | i-propyl |
| 2,4-(Me)$_2$Thiazol-5-yl | 5-methyl-1,2,4-oxadiazol-3-yl | cyclopropyl |
| 2,4-(Me)$_2$Thiazol-5-yl | 5-methyl-1,2,4-oxadiazol-3-yl | CF$_3$ |
| 2,4-(Me)$_2$Thiazol-5-yl | 5-trifluoromethyl-1,2,4-oxadiazol-3-yl | H |
| 2,4-(Me)$_2$Thiazol-5-yl | 5-trifluoromethyl-1,2,4-oxadiazol-3-yl | methyl |
| 2,4-(Me)$_2$Thiazol-5-yl | 5-trifluoromethyl-1,2,4-oxadiazol-3-yl | i-propyl |
| 2,4-(Me)$_2$Thiazol-5-yl | 5-trifluoromethyl-1,2,4-oxadiazol-3-yl | cyclopropyl |
| 2,4-(Me)$_2$Thiazol-5-yl | 5-trifluoromethyl-1,2,4-oxadiazol-3-yl | CF$_3$ |
| 2,4-(Me)$_2$Thiazol-5-yl | 5-chloro-1,2,4-oxadiazol-3-yl | H |
| 2,4-(Me)$_2$Thiazol-5-yl | 5-chloro-1,2,4-oxadiazol-3-yl | methyl |
| 2,4-(Me)$_2$Thiazol-5-yl | 5-chloro-1,2,4-oxadiazol-3-yl | i-propyl |
| 2,4-(Me)$_2$Thiazol-5-yl | 5-chloro-1,2,4-oxadiazol-3-yl | cyclopropyl |
| 2,4-(Me)$_2$Thiazol-5-yl | 5-chloro-1,2,4-oxadiazol-3-yl | CF$_3$ |
| 2,4-(Me)$_2$Thiazol-5-yl | 1,3,4-oxadiazol-2-yl | H |
| 2,4-(Me)$_2$Thiazol-5-yl | 1,3,4-oxadiazol-2-yl | methyl |
| 2,4-(Me)$_2$Thiazol-5-yl | 1,3,4-oxadiazol-2-yl | i-propyl |
| 2,4-(Me)$_2$Thiazol-5-yl | 1,3,4-oxadiazol-2-yl | cyclopropyl |
| 2,4-(Me)$_2$Thiazol-5-yl | 1,3,4-oxadiazol-2-yl | CF$_3$ |
| 2,4-(Me)$_2$Thiazol-5-yl | 5-methylsulfonyl-1,3,4-oxadiazol-2-yl | H |
| 2,4-(Me)$_2$Thiazol-5-yl | 5-methylsulfonyl-1,3,4-oxadiazol-2-yl | methyl |
| 2,4-(Me)$_2$Thiazol-5-yl | 5-methylsulfonyl-1,3,4-oxadiazol-2-yl | i-propyl |
| 2,4-(Me)$_2$Thiazol-5-yl | 5-methylsulfonyl-1,3,4-oxadiazol-2-yl | cyclopropyl |
| 2,4-(Me)$_2$Thiazol-5-yl | 5-methylsulfonyl-1,3,4-oxadiazol-2-yl | CF$_3$ |
| 2,4-(Me)$_2$Thiazol-5-yl | 5-methyl-1,3,4-oxadiazol-2-yl | H |
| 2,4-(Me)$_2$Thiazol-5-yl | 5-methyl-1,3,4-oxadiazol-2-yl | methyl |
| 2,4-(Me)$_2$Thiazol-5-yl | 5-methyl-1,3,4-oxadiazol-2-yl | i-propyl |
| 2,4-(Me)$_2$Thiazol-5-yl | 5-methyl-1,3,4-oxadiazol-2-yl | cyclopropyl |
| 2,4-(Me)$_2$Thiazol-5-yl | 5-methyl-1,3,4-oxadiazol-2-yl | CF$_3$ |
| 2,4-(Me)$_2$Thiazol-5-yl | 5-trifluoromethyl-1,3,4-oxadiazol-2-yl | H |
| 2,4-(Me)$_2$Thiazol-5-yl | 5-trifluoromethyl-1,3,4-oxadiazol-2-yl | methyl |
| 2,4-(Me)$_2$Thiazol-5-yl | 5-trifluoromethyl-1,3,4-oxadiazol-2-yl | i-propyl |
| 2,4-(Me)$_2$Thiazol-5-yl | 5-trifluoromethyl-1,3,4-oxadiazol-2-yl | cyclopropyl |
| 2,4-(Me)$_2$Thiazol-5-yl | 5-trifluoromethyl-1,3,4-oxadiazol-2-yl | CF$_3$ |
| 2,4-(Me)$_2$Thiazol-5-yl | 1,2,3-triazol-4-yl | H |
| 2,4-(Me)$_2$Thiazol-5-yl | 1,2,3-triazol-4-yl | methyl |
| 2,4-(Me)$_2$Thiazol-5-yl | 1,2,3-triazol-4-yl | i-propyl |
| 2,4-(Me)$_2$Thiazol-5-yl | 1,2,3-triazol-4-yl | cyclopropyl |
| 2,4-(Me)$_2$Thiazol-5-yl | 1,2,3-triazol-4-yl | CF$_3$ |
| 2,4-(Me)$_2$Thiazol-5-yl | 1-methyl-1,2,3-triazol-4-yl | H |
| 2,4-(Me)$_2$Thiazol-5-yl | 1-methyl-1,2,3-triazol-4-yl | methyl |
| 2,4-(Me)$_2$Thiazol-5-yl | 1-methyl-1,2,3-triazol-4-yl | i-propyl |
| 2,4-(Me)$_2$Thiazol-5-yl | 1-methyl-1,2,3-triazol-4-yl | cyclopropyl |
| 2,4-(Me)$_2$Thiazol-5-yl | 1-methyl-1,2,3-triazol-4-yl | CF$_3$ |
| 2,4-(Me)$_2$Thiazol-5-yl | 2-methyl-1,2,3-triazol-4-yl | H |
| 2,4-(Me)$_2$Thiazol-5-yl | 2-methyl-1,2,3-triazol-4-yl | methyl |

-continued

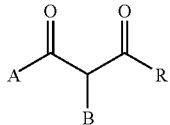
(I)

| A | B | R |
|---|---|---|
| 2,4-(Me)₂Thiazol-5-yl | 2-methyl-1,2,3-triazol-4-yl | i-propyl |
| 2,4-(Me)₂Thiazol-5-yl | 2-methyl-1,2,3-triazol-4-yl | cyclopropyl |
| 2,4-(Me)₂Thiazol-5-yl | 2-methyl-1,2,3-triazol-4-yl | CF₃ |
| 2,4-(Me)₂Thiazol-5-yl | 1,2,3-triazol-1-yl | H |
| 2,4-(Me)₂Thiazol-5-yl | 1,2,3-triazol-1-yl | methyl |
| 2,4-(Me)₂Thiazol-5-yl | 1,2,3-triazol-1-yl | i-propyl |
| 2,4-(Me)₂Thiazol-5-yl | 1,2,3-triazol-1-yl | cyclopropyl |
| 2,4-(Me)₂Thiazol-5-yl | 1,2,3-triazol-1-yl | CF₃ |
| 2,4-(Me)₂Thiazol-5-yl | 1,2,3-triazol-2-yl | H |
| 2,4-(Me)₂Thiazol-5-yl | 1,2,3-triazol-2-yl | methyl |
| 2,4-(Me)₂Thiazol-5-yl | 1,2,3-triazol-2-yl | i-propyl |
| 2,4-(Me)₂Thiazol-5-yl | 1,2,3-triazol-2-yl | cyclopropyl |
| 2,4-(Me)₂Thiazol-5-yl | 1,2,3-triazol-2-yl | CF₃ |
| 2,4-(Me)₂Thiazol-5-yl | 1,2,4-triazol-1-yl | H |
| 2,4-(Me)₂Thiazol-5-yl | 1,2,4-triazol-1-yl | methyl |
| 2,4-(Me)₂Thiazol-5-yl | 1,2,4-triazol-1-yl | i-propyl |
| 2,4-(Me)₂Thiazol-5-yl | 1,2,4-triazol-1-yl | cyclopropyl |
| 2,4-(Me)₂Thiazol-5-yl | 1,2,4-triazol-1-yl | CF₃ |
| 2,4-(Me)₂Thiazol-5-yl | imidazol-2-yl | H |
| 2,4-(Me)₂Thiazol-5-yl | imidazol-2-yl | methyl |
| 2,4-(Me)₂Thiazol-5-yl | imidazol-2-yl | i-propyl |
| 2,4-(Me)₂Thiazol-5-yl | imidazol-2-yl | cyclopropyl |
| 2,4-(Me)₂Thiazol-5-yl | imidazol-2-yl | CF₃ |
| 2,4-(Me)₂Thiazol-5-yl | imidazol-1-yl | H |
| 2,4-(Me)₂Thiazol-5-yl | imidazol-1-yl | methyl |
| 2,4-(Me)₂Thiazol-5-yl | imidazol-1-yl | i-propyl |
| 2,4-(Me)₂Thiazol-5-yl | imidazol-1-yl | cyclopropyl |
| 2,4-(Me)₂Thiazol-5-yl | imidazol-1-yl | CF₃ |
| 2,4-(Me)₂Thiazol-5-yl | imidazol-4-yl | H |
| 2,4-(Me)₂Thiazol-5-yl | imidazol-4-yl | methyl |
| 2,4-(Me)₂Thiazol-5-yl | imidazol-4-yl | i-propyl |
| 2,4-(Me)₂Thiazol-5-yl | imidazol-4-yl | cyclopropyl |
| 2,4-(Me)₂Thiazol-5-yl | imidazol-4-yl | CF₃ |
| 2,4-(Me)₂Thiazol-5-yl | thiazol-2-yl | H |
| 2,4-(Me)₂Thiazol-5-yl | thiazol-2-yl | methyl |
| 2,4-(Me)₂Thiazol-5-yl | thiazol-2-yl | i-propyl |
| 2,4-(Me)₂Thiazol-5-yl | thiazol-2-yl | cyclopropyl |
| 2,4-(Me)₂Thiazol-5-yl | thiazol-2-yl | CF₃ |
| 2,4-(Me)₂Thiazol-5-yl | 4-methylthiazol-2-yl | H |
| 2,4-(Me)₂Thiazol-5-yl | 4-methylthiazol-2-yl | methyl |
| 2,4-(Me)₂Thiazol-5-yl | 4-methylthiazol-2-yl | i-propyl |
| 2,4-(Me)₂Thiazol-5-yl | 4-methylthiazol-2-yl | cyclopropyl |
| 2,4-(Me)₂Thiazol-5-yl | 4-methylthiazol-2-yl | CF₃ |
| 2,4-(Me)₂Thiazol-5-yl | oxazol-2-yl | H |
| 2,4-(Me)₂Thiazol-5-yl | oxazol-2-yl | methyl |
| 2,4-(Me)₂Thiazol-5-yl | oxazol-2-yl | i-propyl |
| 2,4-(Me)₂Thiazol-5-yl | oxazol-2-yl | cyclopropyl |
| 2,4-(Me)₂Thiazol-5-yl | oxazol-2-yl | CF₃ |
| 2,4-(Me)₂Thiazol-5-yl | 4,5-dimethyloxazol-2-yl | H |
| 2,4-(Me)₂Thiazol-5-yl | 4,5-dimethyloxazol-2-yl | methyl |
| 2,4-(Me)₂Thiazol-5-yl | 4,5-dimethyloxazol-2-yl | i-propyl |
| 2,4-(Me)₂Thiazol-5-yl | 4,5-dimethyloxazol-2-yl | cyclopropyl |
| 2,4-(Me)₂Thiazol-5-yl | 4,5-dimethyloxazol-2-yl | CF₃ |
| 2,4-(Me)₂Thiazol-5-yl | 2-oxazolin-2-yl | H |
| 2,4-(Me)₂Thiazol-5-yl | 2-oxazolin-2-yl | methyl |
| 2,4-(Me)₂Thiazol-5-yl | 2-oxazolin-2-yl | i-propyl |
| 2,4-(Me)₂Thiazol-5-yl | 2-oxazolin-2-yl | cyclopropyl |
| 2,4-(Me)₂Thiazol-5-yl | 2-oxazolin-2-yl | CF₃ |
| 2,4-(Me)₂Thiazol-5-yl | 4,4-dimethyl-2-oxazolin-2-yl | H |
| 2,4-(Me)₂Thiazol-5-yl | 4,4-dimethyl-2-oxazolin-2-yl | methyl |
| 2,4-(Me)₂Thiazol-5-yl | 4,4-dimethyl-2-oxazolin-2-yl | i-propyl |
| 2,4-(Me)₂Thiazol-5-yl | 4,4-dimethyl-2-oxazolin-2-yl | cyclopropyl |
| 2,4-(Me)₂Thiazol-5-yl | 4,4-dimethyl-2-oxazolin-2-yl | CF₃ |
| 2,4-(Me)₂Thiazol-5-yl | 1,2,4-thiadiazol-5-yl | H |
| 2,4-(Me)₂Thiazol-5-yl | 1,2,4-thiadiazol-5-yl | methyl |
| 2,4-(Me)₂Thiazol-5-yl | 1,2,4-thiadiazol-5-yl | i-propyl |
| 2,4-(Me)₂Thiazol-5-yl | 1,2,4-thiadiazol-5-yl | cyclopropyl |
| 2,4-(Me)₂Thiazol-5-yl | 1,2,4-thiadiazol-5-yl | CF₃ |
| 2,4-(Me)₂Thiazol-5-yl | 3-methyl-1,2,4-thiadiazol-5-yl | H |
| 2,4-(Me)₂Thiazol-5-yl | 3-methyl-1,2,4-thiadiazol-5-yl | methyl |
| 2,4-(Me)₂Thiazol-5-yl | 3-methyl-1,2,4-thiadiazol-5-yl | i-propyl |
| 2,4-(Me)₂Thiazol-5-yl | 3-methyl-1,2,4-thiadiazol-5-yl | cyclopropyl |
| 2,4-(Me)₂Thiazol-5-yl | 3-methyl-1,2,4-thiadiazol-5-yl | CF₃ |
| 2,4-(Me)₂Thiazol-5-yl | 3-trifluoromethyl-1,2,4-thiadiazol-5-yl | H |
| 2,4-(Me)₂Thiazol-5-yl | 3-trifluoromethyl-1,2,4-thiadiazol-5-yl | methyl |
| 2,4-(Me)₂Thiazol-5-yl | 3-trifluoromethyl-1,2,4-thiadiazol-5-yl | i-propyl |
| 2,4-(Me)₂Thiazol-5-yl | 3-trifluoromethyl-1,2,4-thiadiazol-5-yl | cyclopropyl |
| 2,4-(Me)₂Thiazol-5-yl | 3-trifluoromethyl-1,2,4-thiadiazol-5-yl | CF₃ |
| 2,4-(Me)₂Thiazol-5-yl | 1,2,4-thiadiazol-3-yl | H |
| 2,4-(Me)₂Thiazol-5-yl | 1,2,4-thiadiazol-3-yl | methyl |
| 2,4-(Me)₂Thiazol-5-yl | 1,2,4-thiadiazol-3-yl | i-propyl |
| 2,4-(Me)₂Thiazol-5-yl | 1,2,4-thiadiazol-3-yl | cyclopropyl |
| 2,4-(Me)₂Thiazol-5-yl | 1,2,4-thiadiazol-3-yl | CF₃ |
| 2,4-(Me)₂Thiazol-5-yl | 5-methyl-1,2,4-thiadiazol-3-yl | H |
| 2,4-(Me)₂Thiazol-5-yl | 5-methyl-1,2,4-thiadiazol-3-yl | methyl |
| 2,4-(Me)₂Thiazol-5-yl | 5-methyl-1,2,4-thiadiazol-3-yl | i-propyl |
| 2,4-(Me)₂Thiazol-5-yl | 5-methyl-1,2,4-thiadiazol-3-yl | cyclopropyl |
| 2,4-(Me)₂Thiazol-5-yl | 5-methyl-1,2,4-thiadiazol-3-yl | CF₃ |
| 2,4-(Me)₂Thiazol-5-yl | 5-trifluoromethyl-1,2,4-thiadiazol-3-yl | H |
| 2,4-(Me)₂Thiazol-5-yl | 5-trifluoromethyl-1,2,4-thiadiazol-3-yl | methyl |
| 2,4-(Me)₂Thiazol-5-yl | 5-trifluoromethyl-1,2,4-thiadiazol-3-yl | i-propyl |
| 2,4-(Me)₂Thiazol-5-yl | 5-trifluoromethyl-1,2,4-thiadiazol-3-yl | cyclopropyl |
| 2,4-(Me)₂Thiazol-5-yl | 5-trifluoromethyl-1,2,4-thiadiazol-3-yl | CF₃ |
| 2,4-(Me)₂Thiazol-5-yl | 1,3,4-thiadiazol-2-yl | H |
| 2,4-(Me)₂Thiazol-5-yl | 1,3,4-thiadiazol-2-yl | methyl |
| 2,4-(Me)₂Thiazol-5-yl | 1,3,4-thiadiazol-2-yl | i-propyl |
| 2,4-(Me)₂Thiazol-5-yl | 1,3,4-thiadiazol-2-yl | cyclopropyl |
| 2,4-(Me)₂Thiazol-5-yl | 1,3,4-thiadiazol-2-yl | CF₃ |
| 2,4-(Me)₂Thiazol-5-yl | 5-methylsulfonyl-1,3,4-thiadiazol-2-yl | H |
| 2,4-(Me)₂Thiazol-5-yl | 5-methylsulfonyl-1,3,4-thiadiazol-2-yl | methyl |
| 2,4-(Me)₂Thiazol-5-yl | 5-methylsulfonyl-1,3,4-thiadiazol-2-yl | i-propyl |
| 2,4-(Me)₂Thiazol-5-yl | 5-methylsulfonyl-1,3,4-thiadiazol-2-yl | cyclopropyl |
| 2,4-(Me)₂Thiazol-5-yl | 5-methylsulfonyl-1,3,4-thiadiazol-2-yl | CF₃ |
| 2,4-(Me)₂Thiazol-5-yl | 5-methyl-1,3,4-thiadiazol-2-yl | H |
| 2,4-(Me)₂Thiazol-5-yl | 5-methyl-1,3,4-thiadiazol-2-yl | methyl |
| 2,4-(Me)₂Thiazol-5-yl | 5-methyl-1,3,4-thiadiazol-2-yl | i-propyl |
| 2,4-(Me)₂Thiazol-5-yl | 5-methyl-1,3,4-thiadiazol-2-yl | cyclopropyl |
| 2,4-(Me)₂Thiazol-5-yl | 5-methyl-1,3,4-thiadiazol-2-yl | CF₃ |
| 2,4-(Me)₂Thiazol-5-yl | benzoxazol-2-yl | H |
| 2,4-(Me)₂Thiazol-5-yl | benzoxazol-2-yl | methyl |
| 2,4-(Me)₂Thiazol-5-yl | benzoxazol-2-yl | i-propyl |
| 2,4-(Me)₂Thiazol-5-yl | benzoxazol-2-yl | cyclopropyl |
| 2,4-(Me)₂Thiazol-5-yl | benzoxazol-2-yl | CF₃ |
| 2,4-(Me)₂Thiazol-5-yl | 6-methylbenzoxazol-2-yl | H |
| 2,4-(Me)₂Thiazol-5-yl | 6-methylbenzoxazol-2-yl | methyl |
| 2,4-(Me)₂Thiazol-5-yl | 6-methylbenzoxazol-2-yl | i-propyl |
| 2,4-(Me)₂Thiazol-5-yl | 6-methylbenzoxazol-2-yl | cyclopropyl |
| 2,4-(Me)₂Thiazol-5-yl | 6-methylbenzoxazol-2-yl | CF₃ |
| 2,4-(Me)₂Thiazol-5-yl | benzothiazol-2-yl | H |
| 2,4-(Me)₂Thiazol-5-yl | benzothiazol-2-yl | methyl |
| 2,4-(Me)₂Thiazol-5-yl | benzothiazol-2-yl | i-propyl |
| 2,4-(Me)₂Thiazol-5-yl | benzothiazol-2-yl | cyclopropyl |
| 2,4-(Me)₂Thiazol-5-yl | benzothiazol-2-yl | CF₃ |
| 2,4-(Me)₂Thiazol-5-yl | pyrazol-1-yl | H |
| 2,4-(Me)₂Thiazol-5-yl | pyrazol-1-yl | methyl |

-continued

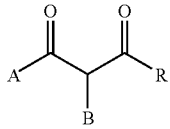
(I)

| A | B | R |
|---|---|---|
| 2,4-(Me)$_2$Thiazol-5-yl | pyrazol-1-yl | i-propyl |
| 2,4-(Me)$_2$Thiazol-5-yl | pyrazol-1-yl | cyclopropyl |
| 2,4-(Me)$_2$Thiazol-5-yl | pyrazol-1-yl | CF$_3$ |
| 2,4-(Me)$_2$Thiazol-5-yl | pyrazol-3-yl | H |
| 2,4-(Me)$_2$Thiazol-5-yl | pyrazol-3-yl | methyl |
| 2,4-(Me)$_2$Thiazol-5-yl | pyrazol-3-yl | i-propyl |
| 2,4-(Me)$_2$Thiazol-5-yl | pyrazol-3-yl | cyclopropyl |
| 2,4-(Me)$_2$Thiazol-5-yl | pyrazol-3-yl | CF$_3$ |
| 2,4-(Me)$_2$Thiazol-5-yl | 1-methylpyrazol-3-yl | H |
| 2,4-(Me)$_2$Thiazol-5-yl | 1-methylpyrazol-3-yl | methyl |
| 2,4-(Me)$_2$Thiazol-5-yl | 1-methylpyrazol-3-yl | i-propyl |
| 2,4-(Me)$_2$Thiazol-5-yl | 1-methylpyrazol-3-yl | cyclopropyl |
| 2,4-(Me)$_2$Thiazol-5-yl | 1-methylpyrazol-3-yl | CF$_3$ |
| 2,4-(Me)$_2$Thiazol-5-yl | tetrazol-1-yl | H |
| 2,4-(Me)$_2$Thiazol-5-yl | tetrazol-1-yl | methyl |
| 2,4-(Me)$_2$Thiazol-5-yl | tetrazol-1-yl | i-propyl |
| 2,4-(Me)$_2$Thiazol-5-yl | tetrazol-1-yl | cyclopropyl |
| 2,4-(Me)$_2$Thiazol-5-yl | tetrazol-1-yl | CF$_3$ |
| 2,4-(Me)$_2$Thiazol-5-yl | 5-methyltetrazol-1-yl | H |
| 2,4-(Me)$_2$Thiazol-5-yl | 5-methyltetrazol-1-yl | methyl |
| 2,4-(Me)$_2$Thiazol-5-yl | 5-methyltetrazol-1-yl | i-propyl |
| 2,4-(Me)$_2$Thiazol-5-yl | 5-methyltetrazol-1-yl | cyclopropyl |
| 2,4-(Me)$_2$Thiazol-5-yl | 5-methyltetrazol-1-yl | CF$_3$ |
| 2,4-(Me)$_2$Thiazol-5-yl | tetrazol-2-yl | H |
| 2,4-(Me)$_2$Thiazol-5-yl | tetrazol-2-yl | methyl |
| 2,4-(Me)$_2$Thiazol-5-yl | tetrazol-2-yl | i-propyl |
| 2,4-(Me)$_2$Thiazol-5-yl | tetrazol-2-yl | cyclopropyl |
| 2,4-(Me)$_2$Thiazol-5-yl | tetrazol-2-yl | CF$_3$ |
| 2,4-(Me)$_2$Thiazol-5-yl | 5-methyltetrazol-2-yl | H |
| 2,4-(Me)$_2$Thiazol-5-yl | 5-methyltetrazol-2-yl | methyl |
| 2,4-(Me)$_2$Thiazol-5-yl | 5-methyltetrazol-2-yl | i-propyl |
| 2,4-(Me)$_2$Thiazol-5-yl | 5-methyltetrazol-2-yl | cyclopropyl |
| 2,4-(Me)$_2$Thiazol-5-yl | 5-methyltetrazol-2-yl | CF$_3$ |
| 2,4-(Me)$_2$Thiazol-5-yl | 1-methyltetrazol-5-yl | H |
| 2,4-(Me)$_2$Thiazol-5-yl | 1-methyltetrazol-5-yl | methyl |
| 2,4-(Me)$_2$Thiazol-5-yl | 1-methyltetrazol-5-yl | i-propyl |
| 2,4-(Me)$_2$Thiazol-5-yl | 1-methyltetrazol-5-yl | cyclopropyl |
| 2,4-(Me)$_2$Thiazol-5-yl | 1-methyltetrazol-5-yl | CF$_3$ |
| 2,4-(Me)$_2$Thiazol-5-yl | 2-methyltetrazol-5-yl | H |
| 2,4-(Me)$_2$Thiazol-5-yl | 2-methyltetrazol-5-yl | methyl |
| 2,4-(Me)$_2$Thiazol-5-yl | 2-methyltetrazol-5-yl | i-propyl |
| 2,4-(Me)$_2$Thiazol-5-yl | 2-methyltetrazol-5-yl | cyclopropyl |
| 2,4-(Me)$_2$Thiazol-5-yl | 2-methyltetrazol-5-yl | CF$_3$ |
| 2,4-(Me)$_2$Thiazol-5-yl | pyridin-2-yl | H |
| 2,4-(Me)$_2$Thiazol-5-yl | pyridin-2-yl | methyl |
| 2,4-(Me)$_2$Thiazol-5-yl | pyridin-2-yl | i-propyl |
| 2,4-(Me)$_2$Thiazol-5-yl | pyridin-2-yl | cyclopropyl |
| 2,4-(Me)$_2$Thiazol-5-yl | pyridin-2-yl | CF$_3$ |
| 2,4-(Me)$_2$Thiazol-5-yl | pyridin-4-yl | H |
| 2,4-(Me)$_2$Thiazol-5-yl | pyridin-4-yl | methyl |
| 2,4-(Me)$_2$Thiazol-5-yl | pyridin-4-yl | i-propyl |
| 2,4-(Me)$_2$Thiazol-5-yl | pyridin-4-yl | cyclopropyl |
| 2,4-(Me)$_2$Thiazol-5-yl | pyridin-4-yl | CF$_3$ |
| 2,4-(Me)$_2$Thiazol-5-yl | pyridin-3-yl | H |
| 2,4-(Me)$_2$Thiazol-5-yl | pyridin-3-yl | methyl |
| 2,4-(Me)$_2$Thiazol-5-yl | pyridin-3-yl | i-propyl |
| 2,4-(Me)$_2$Thiazol-5-yl | pyridin-3-yl | cyclopropyl |
| 2,4-(Me)$_2$Thiazol-5-yl | pyridin-3-yl | CF$_3$ |
| 2,4-(Me)$_2$Thiazol-5-yl | 3-nitropyridin-4-yl | H |
| 2,4-(Me)$_2$Thiazol-5-yl | 3-nitropyridin-4-yl | methyl |
| 2,4-(Me)$_2$Thiazol-5-yl | 3-nitropyridin-4-yl | i-propyl |
| 2,4-(Me)$_2$Thiazol-5-yl | 3-nitropyridin-4-yl | cyclopropyl |
| 2,4-(Me)$_2$Thiazol-5-yl | 3-nitropyridin-4-yl | CF$_3$ |
| 2,4-(Me)$_2$Thiazol-5-yl | 5-cyanopyridin-2-yl | H |
| 2,4-(Me)$_2$Thiazol-5-yl | 5-cyanopyridin-2-yl | methyl |
| 2,4-(Me)$_2$Thiazol-5-yl | 5-cyanopyridin-2-yl | i-propyl |
| 2,4-(Me)$_2$Thiazol-5-yl | 5-cyanopyridin-2-yl | cyclopropyl |
| 2,4-(Me)$_2$Thiazol-5-yl | 5-cyanopyridin-2-yl | CF$_3$ |
| 2,4-(Me)$_2$Thiazol-5-yl | 5-trifluoromethylpyridin-2-yl | H |
| 2,4-(Me)$_2$Thiazol-5-yl | 5-trifluoromethylpyridin-2-yl | methyl |
| 2,4-(Me)$_2$Thiazol-5-yl | 5-trifluoromethylpyridin-2-yl | i-propyl |
| 2,4-(Me)$_2$Thiazol-5-yl | 5-trifluoromethylpyridin-2-yl | cyclopropyl |
| 2,4-(Me)$_2$Thiazol-5-yl | 5-trifluoromethylpyridin-2-yl | CF$_3$ |
| 2,4-(Me)$_2$Thiazol-5-yl | pyrimidin-2-yl | H |
| 2,4-(Me)$_2$Thiazol-5-yl | pyrimidin-2-yl | methyl |
| 2,4-(Me)$_2$Thiazol-5-yl | pyrimidin-2-yl | i-propyl |
| 2,4-(Me)$_2$Thiazol-5-yl | pyrimidin-2-yl | cyclopropyl |
| 2,4-(Me)$_2$Thiazol-5-yl | pyrimidin-2-yl | CF$_3$ |
| 2,4-(Me)$_2$Thiazol-5-yl | pyrimidin-4-yl | H |
| 2,4-(Me)$_2$Thiazol-5-yl | pyrimidin-4-yl | methyl |
| 2,4-(Me)$_2$Thiazol-5-yl | pyrimidin-4-yl | i-propyl |
| 2,4-(Me)$_2$Thiazol-5-yl | pyrimidin-4-yl | cyclopropyl |
| 2,4-(Me)$_2$Thiazol-5-yl | pyrimidin-4-yl | CF$_3$ |
| 2,4-(Me)$_2$Thiazol-5-yl | 6-chloropyrimidin-4-yl | methyl |
| 2,4-(Me)$_2$Thiazol-5-yl | 6-chloropyrimidin-4-yl | i-propyl |
| 2,4-(Me)$_2$Thiazol-5-yl | 6-chloropyrimidin-4-yl | cyclopropyl |
| 2,4-(Me)$_2$Thiazol-5-yl | 6-chloropyrimidin-4-yl | CF$_3$ |
| 2,4-(Me)$_2$Thiazol-5-yl | pyridazin-3-yl | H |
| 2,4-(Me)$_2$Thiazol-5-yl | pyridazin-3-yl | methyl |
| 2,4-(Me)$_2$Thiazol-5-yl | pyridazin-3-yl | i-propyl |
| 2,4-(Me)$_2$Thiazol-5-yl | pyridazin-3-yl | cyclopropyl |
| 2,4-(Me)$_2$Thiazol-5-yl | pyridazin-3-yl | CF$_3$ |
| 2,4-(Me)$_2$Thiazol-5-yl | 6-chloropyridazin-3-yl | methyl |
| 2,4-(Me)$_2$Thiazol-5-yl | 6-chloropyridazin-3-yl | i-propyl |
| 2,4-(Me)$_2$Thiazol-5-yl | 6-chloropyridazin-3-yl | cyclopropyl |
| 2,4-(Me)$_2$Thiazol-5-yl | 6-chloropyridazin-3-yl | CF$_3$ |
| 2,4-(Me)$_2$Thiazol-5-yl | pyrazin-2-yl | methyl |
| 2,4-(Me)$_2$Thiazol-5-yl | pyrazin-2-yl | i-propyl |
| 2,4-(Me)$_2$Thiazol-5-yl | pyrazin-2-yl | cyclopropyl |
| 2,4-(Me)$_2$Thiazol-5-yl | pyrazin-2-yl | CF$_3$ |
| 2,4-(Me)$_2$Thiazol-5-yl | triazin-2-yl | methyl |
| 2,4-(Me)$_2$Thiazol-5-yl | triazin-2-yl | i-propyl |
| 2,4-(Me)$_2$Thiazol-5-yl | triazin-2-yl | cyclopropyl |
| 2,4-(Me)$_2$Thiazol-5-yl | triazin-2-yl | CF$_3$ |
| 2,4-(Me)$_2$Thiazol-5-yl | quinolin-2-yl | methyl |
| 2,4-(Me)$_2$Thiazol-5-yl | quinolin-2-yl | i-propyl |
| 2,4-(Me)$_2$Thiazol-5-yl | quinolin-2-yl | cyclopropyl |
| 2,4-(Me)$_2$Thiazol-5-yl | quinolin-2-yl | CF$_3$ |
| 2,4-(Me)$_2$Thiazol-5-yl | 4,4,6-trimethyl-5,6-dihydro-1,3(4H)-oxazin-2-yl | H |
| 2,4-(Me)$_2$Thiazol-5-yl | 4,4,6-trimethyl-5,6-dihydro-1,3(4H)-oxazin-2-yl | methyl |
| 2,4-(Me)$_2$Thiazol-5-yl | 4,4,6-trimethyl-5,6-dihydro-1,3(4H)-oxazin-2-yl | i-propyl |
| 2,4-(Me)$_2$Thiazol-5-yl | 4,4,6-trimethyl-5,6-dihydro-1,3(4H)-oxazin-2-yl | cyclopropyl |
| 2,4-(Me)$_2$Thiazol-5-yl | 4,4,6-trimethyl-5,6-dihydro-1,3(4H)-oxazin-2-yl | CF$_3$ |
| 2,4-(Me)$_2$Thiazol-5-yl | 2-oxazolidinon-3-yl | H |
| 2,4-(Me)$_2$Thiazol-5-yl | 2-oxazolidinon-3-yl | methyl |
| 2,4-(Me)$_2$Thiazol-5-yl | 2-oxazolidinon-3-yl | i-propyl |
| 2,4-(Me)$_2$Thiazol-5-yl | 2-oxazolidinon-3-yl | cyclopropyl |
| 2,4-(Me)$_2$Thiazol-5-yl | 2-oxazolidinon-3-yl | CF$_3$ |
| 2,4-(Me)$_2$Thiazol-5-yl | 2-pyrrolidinon-1-yl | methyl |
| 2,4-(Me)$_2$Thiazol-5-yl | 2-pyrrolidinon-1-yl | i-propyl |
| 2,4-(Me)$_2$Thiazol-5-yl | 2-pyrrolidinon-1-yl | cyclopropyl |
| 2,4-(Me)$_2$Thiazol-5-yl | 2-pyrrolidinon-1-yl | CF$_3$ |
| 2,4-(Me)$_2$Thiazol-5-yl | 3-methylisoxazol-5-yl | methyl |
| 2,4-(Me)$_2$Thiazol-5-yl | 3-methylisoxazol-5-yl | i-propyl |
| 2,4-(Me)$_2$Thiazol-5-yl | 3-methylisoxazol-5-yl | cyclopropyl |
| 2,4-(Me)$_2$Thiazol-5-yl | 3-methylisoxazol-5-yl | CF$_3$ |
| 2,4-(Me)$_2$Thiazol-5-yl | 2-NO$_2$-4-SO$_2$MePh | H |
| 2,4-(Me)$_2$Thiazol-5-yl | 2-NO$_2$-4-SO$_2$MePh | methyl |
| 2,4-(Me)$_2$Thiazol-5-yl | 2-NO$_2$-4-SO$_2$MePh | i-propyl |
| 2,4-(Me)$_2$Thiazol-5-yl | 2-NO$_2$-4-SO$_2$MePh | cyclopropyl |
| 2,4-(Me)$_2$Thiazol-5-yl | 2-NO$_2$-4-SO$_2$MePh | CF$_3$ |
| 2,4-(Me)$_2$Thiazol-5-yl | 2-Cl-4-SO$_2$MePh | H |
| 2,4-(Me)$_2$Thiazol-5-yl | 2-Cl-4-SO$_2$MePh | methyl |
| 2,4-(Me)$_2$Thiazol-5-yl | 2-Cl-4-SO$_2$MePh | i-propyl |
| 2,4-(Me)$_2$Thiazol-5-yl | 2-Cl-4-SO$_2$MePh | cyclopropyl |

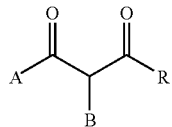

(I)

| A | B | R |
|---|---|---|
| 2,4-(Me)₂Thiazol-5-yl | 2-Cl-4-SO₂MePh | CF₃ |
| 2,4-(Me)₂Thiazol-5-yl | 2-NO₂-4-CF₃Ph | H |
| 2,4-(Me)₂Thiazol-5-yl | 2-NO₂-4-CF₃Ph | methyl |
| 2,4-(Me)₂Thiazol-5-yl | 2-NO₂-4-CF₃Ph | i-propyl |
| 2,4-(Me)₂Thiazol-5-yl | 2-NO₂-4-CF₃Ph | cyclopropyl |
| 2,4-(Me)₂Thiazol-5-yl | 2-NO₂-4-CF₃Ph | CF₃ |
| 2,4-(Me)₂Thiazol-5-yl | 2-NO₂-4-ClPh | H |
| 2,4-(Me)₂Thiazol-5-yl | 2-NO₂-4-ClPh | methyl |
| 2,4-(Me)₂Thiazol-5-yl | 2-NO₂-4-ClPh | i-propyl |
| 2,4-(Me)₂Thiazol-5-yl | 2-NO₂-4-ClPh | cyclopropyl |
| 2,4-(Me)₂Thiazol-5-yl | 2-NO₂-4-ClPh | CF₃ |
| 2,4-(Me)₂Thiazol-5-yl | 2-Cl-4-NO₂Ph | H |
| 2,4-(Me)₂Thiazol-5-yl | 2-Cl-4-NO₂Ph | methyl |
| 2,4-(Me)₂Thiazol-5-yl | 2-Cl-4-NO₂Ph | i-propyl |
| 2,4-(Me)₂Thiazol-5-yl | 2-Cl-4-NO₂Ph | cyclopropyl |
| 2,4-(Me)₂Thiazol-5-yl | 2-Cl-4-NO₂Ph | CF₃ |
| 2,4-(Me)₂Thiazol-5-yl | 2,4-(NO₂)₂Ph | H |
| 2,4-(Me)₂Thiazol-5-yl | 2,4-(NO₂)₂Ph | methyl |
| 2,4-(Me)₂Thiazol-5-yl | 2,4-(NO₂)₂Ph | i-propyl |
| 2,4-(Me)₂Thiazol-5-yl | 2,4-(NO₂)₂Ph | cyclopropyl |
| 2,4-(Me)₂Thiazol-5-yl | 2,4-(NO₂)₂Ph | CF₃ |
| 2,4-(Me)₂Thiazol-5-yl | 4-F-3-NO₂Ph | H |
| 2,4-(Me)₂Thiazol-5-yl | 4-F-3-NO₂Ph | methyl |
| 2,4-(Me)₂Thiazol-5-yl | 4-F-3-NO₂Ph | i-propyl |
| 2,4-(Me)₂Thiazol-5-yl | 4-F-3-NO₂Ph | cyclopropyl |
| 2,4-(Me)₂Thiazol-5-yl | 4-F-3-NO₂Ph | CF₃ |
| 2,4-(Me)₂Thiazol-5-yl | 3,5-(CF₃)₂Ph | H |
| 2,4-(Me)₂Thiazol-5-yl | 3,5-(CF₃)₂Ph | methyl |
| 2,4-(Me)₂Thiazol-5-yl | 3,5-(CF₃)₂Ph | i-propyl |
| 2,4-(Me)₂Thiazol-5-yl | 3,5-(CF₃)₂Ph | cyclopropyl |
| 2,4-(Me)₂Thiazol-5-yl | 3,5-(CF₃)₂Ph | CF₃ |
| 2,4-(Me)₂Thiazol-5-yl | 2-SO₂Me-4-CF₃Ph | H |
| 2,4-(Me)₂Thiazol-5-yl | 2-SO₂Me-4-CF₃Ph | methyl |
| 2,4-(Me)₂Thiazol-5-yl | 2-SO₂Me-4-CF₃Ph | i-propyl |
| 2,4-(Me)₂Thiazol-5-yl | 2-SO₂Me-4-CF₃Ph | cyclopropyl |
| 2,4-(Me)₂Thiazol-5-yl | 2-SO₂Me-4-CF₃Ph | CF₃ |
| 2-Me-4-SO₂Me-3-(4,5-dihydroisoxazol-3-yl)Ph | 1,2,4-oxadiazol-5-yl | H |
| 2-Me-4-SO₂Me-3-(4,5-dihydroisoxazol-3-yl)Ph | 1,2,4-oxadiazol-5-yl | methyl |
| 2-Me-4-SO₂Me-3-(4,5-dihydroisoxazol-3-yl)Ph | 1,2,4-oxadiazol-5-yl | i-propyl |
| 2-Me-4-SO₂Me-3-(4,5-dihydroisoxazol-3-yl)Ph | 1,2,4-oxadiazol-5-yl | cyclopropyl |
| 2-Me-4-SO₂Me-3-(4,5-dihydroisoxazol-3-yl)Ph | 1,2,4-oxadiazol-5-yl | CF₃ |
| 2-Me-4-SO₂Me-3-(4,5-dihydroisoxazol-3-yl)Ph | 3-methyl-1,2,4-oxadiazol-5-yl | H |
| 2-Me-4-SO₂Me-3-(4,5-dihydroisoxazol-3-yl)Ph | 3-methyl-1,2,4-oxadiazol-5-yl | methyl |
| 2-Me-4-SO₂Me-3-(4,5-dihydroisoxazol-3-yl)Ph | 3-methyl-1,2,4-oxadiazol-5-yl | i-propyl |
| 2-Me-4-SO₂Me-3-(4,5-dihydroisoxazol-3-yl)Ph | 3-methyl-1,2,4-oxadiazol-5-yl | cyclopropyl |
| 2-Me-4-SO₂Me-3-(4,5-dihydroisoxazol-3-yl)Ph | 3-methyl-1,2,4-oxadiazol-5-yl | CF₃ |
| 2-Me-4-SO₂Me-3-(4,5-dihydroisoxazol-3-yl)Ph | 3-trifluoromethyl-1,2,4-oxadiazol-5-yl | H |
| 2-Me-4-SO₂Me-3-(4,5-dihydroisoxazol-3-yl)Ph | 3-trifluoromethyl-1,2,4-oxadiazol-5-yl | methyl |
| 2-Me-4-SO₂Me-3-(4,5-dihydroisoxazol-3-yl)Ph | 3-trifluoromethyl-1,2,4-oxadiazol-5-yl | i-propyl |
| 2-Me-4-SO₂Me-3-(4,5-dihydroisoxazol-3-yl)Ph | 3-trifluoromethyl-1,2,4-oxadiazol-5-yl | cyclopropyl |
| 2-Me-4-SO₂Me-3-(4,5-dihydroisoxazol-3-yl)Ph | 3-trifluoromethyl-1,2,4-oxadiazol-5-yl | CF₃ |
| 2-Me-4-SO₂Me-3-(4,5-dihydroisoxazol-3-yl)Ph | 1,2,4-oxadiazol-3-yl | H |
| 2-Me-4-SO₂Me-3-(4,5-dihydroisoxazol-3-yl)Ph | 1,2,4-oxadiazol-3-yl | methyl |
| 2-Me-4-SO₂Me-3-(4,5-dihydroisoxazol-3-yl)Ph | 1,2,4-oxadiazol-3-yl | i-propyl |
| 2-Me-4-SO₂Me-3-(4,5-dihydroisoxazol-3-yl)Ph | 1,2,4-oxadiazol-3-yl | cyclopropyl |
| 2-Me-4-SO₂Me-3-(4,5-dihydroisoxazol-3-yl)Ph | 1,2,4-oxadiazol-3-yl | CF₃ |
| 2-Me-4-SO₂Me-3-(4,5-dihydroisoxazol-3-yl)Ph | 5-methyl-1,2,4-oxadiazol-3-yl | H |
| 2-Me-4-SO₂Me-3-(4,5-dihydroisoxazol-3-yl)Ph | 5-methyl-1,2,4-oxadiazol-3-yl | methyl |
| 2-Me-4-SO₂Me-3-(4,5-dihydroisoxazol-3-yl)Ph | 5-methyl-1,2,4-oxadiazol-3-yl | i-propyl |
| 2-Me-4-SO₂Me-3-(4,5-dihydroisoxazol-3-yl)Ph | 5-methyl-1,2,4-oxadiazol-3-yl | cyclopropyl |
| 2-Me-4-SO₂Me-3-(4,5-dihydroisoxazol-3-yl)Ph | 5-methyl-1,2,4-oxadiazol-3-yl | CF₃ |
| 2-Me-4-SO₂Me-3-(4,5-dihydroisoxazol-3-yl)Ph | 5-trifluoromethyl-1,2,4-oxadiazol-3-yl | H |
| 2-Me-4-SO₂Me-3-(4,5-dihydroisoxazol-3-yl)Ph | 5-trifluoromethyl-1,2,4-oxadiazol-3-yl | methyl |
| 2-Me-4-SO₂Me-3-(4,5-dihydroisoxazol-3-yl)Ph | 5-trifluoromethyl-1,2,4-oxadiazol-3-yl | i-propyl |
| 2-Me-4-SO₂Me-3-(4,5-dihydroisoxazol-3-yl)Ph | 5-trifluoromethyl-1,2,4-oxadiazol-3-yl | cyclopropyl |
| 2-Me-4-SO₂Me-3-(4,5-dihydroisoxazol-3-yl)Ph | 5-trifluoromethyl-1,2,4-oxadiazol-3-yl | CF₃ |
| 2-Me-4-SO₂Me-3-(4,5-dihydroisoxazol-3-yl)Ph | 5-chloro-1,2,4-oxadiazol-3-yl | H |
| 2-Me-4-SO₂Me-3-(4,5-dihydroisoxazol-3-yl)Ph | 5-chloro-1,2,4-oxadiazol-3-yl | methyl |
| 2-Me-4-SO₂Me-3-(4,5-dihydroisoxazol-3-yl)Ph | 5-chloro-1,2,4-oxadiazol-3-yl | i-propyl |
| 2-Me-4-SO₂Me-3-(4,5-dihydroisoxazol-3-yl)Ph | 5-chloro-1,2,4-oxadiazol-3-yl | cyclopropyl |
| 2-Me-4-SO₂Me-3-(4,5-dihydroisoxazol-3-yl)Ph | 5-chloro-1,2,4-oxadiazol-3-yl | CF₃ |
| 2-Me-4-SO₂Me-3-(4,5-dihydroisoxazol-3-yl)Ph | 1,3,4-oxadiazol-2-yl | H |
| 2-Me-4-SO₂Me-3-(4,5-dihydroisoxazol-3-yl)Ph | 1,3,4-oxadiazol-2-yl | methyl |
| 2-Me-4-SO₂Me-3-(4,5-dihydroisoxazol-3-yl)Ph | 1,3,4-oxadiazol-2-yl | i-propyl |
| 2-Me-4-SO₂Me-3-(4,5-dihydroisoxazol-3-yl)Ph | 1,3,4-oxadiazol-2-yl | cyclopropyl |
| 2-Me-4-SO₂Me-3-(4,5-dihydroisoxazol-3-yl)Ph | 1,3,4-oxadiazol-2-yl | CF₃ |
| 2-Me-4-SO₂Me-3-(4,5-dihydroisoxazol-3-yl)Ph | 5-methylsulfonyl-1,3,4-oxadiazol-2-yl | H |
| 2-Me-4-SO₂Me-3-(4,5-dihydroisoxazol-3-yl)Ph | 5-methylsulfonyl-1,3,4-oxadiazol-2-yl | methyl |
| 2-Me-4-SO₂Me-3-(4,5-dihydroisoxazol-3-yl)Ph | 5-methylsulfonyl-1,3,4-oxadiazol-2-yl | i-propyl |
| 2-Me-4-SO₂Me-3-(4,5-dihydroisoxazol-3-yl)Ph | 5-methylsulfonyl-1,3,4-oxadiazol-2-yl | cyclopropyl |
| 2-Me-4-SO₂Me-3-(4,5-dihydroisoxazol-3-yl)Ph | 5-methylsulfonyl-1,3,4-oxadiazol-2-yl | CF₃ |
| 2-Me-4-SO₂Me-3-(4,5-dihydroisoxazol-3-yl)Ph | 5-methyl-1,3,4-oxadiazol-2-yl | H |
| 2-Me-4-SO₂Me-3-(4,5-dihydroisoxazol-3-yl)Ph | 5-methyl-1,3,4-oxadiazol-2-yl | methyl |
| 2-Me-4-SO₂Me-3-(4,5-dihydroisoxazol-3-yl)Ph | 5-methyl-1,3,4-oxadiazol-2-yl | i-propyl |
| 2-Me-4-SO₂Me-3-(4,5-dihydroisoxazol-3-yl)Ph | 5-methyl-1,3,4-oxadiazol-2-yl | cyclopropyl |
| 2-Me-4-SO₂Me-3-(4,5-dihydroisoxazol-3-yl)Ph | 5-methyl-1,3,4-oxadiazol-2-yl | CF₃ |
| 2-Me-4-SO₂Me-3-(4,5-dihydroisoxazol-3-yl)Ph | 5-trifluoromethyl-1,3,4-oxadiazol-2-yl | H |
| 2-Me-4-SO₂Me-3-(4,5-dihydroisoxazol-3-yl)Ph | 5-trifluoromethyl-1,3,4-oxadiazol-2-yl | methyl |

-continued

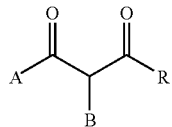
(I)

| A | B | R |
|---|---|---|
| 2-Me-4-SO₂Me-3-(4,5-dihydroisoxazol-3-yl)Ph | 5-trifluoromethyl-1,3,4-oxadiazol-2-yl | i-propyl |
| 2-Me-4-SO₂Me-3-(4,5-dihydroisoxazol-3-yl)Ph | 5-trifluoromethyl-1,3,4-oxadiazol-2-yl | cyclopropyl |
| 2-Me-4-SO₂Me-3-(4,5-dihydroisoxazol-3-yl)Ph | 5-trifluoromethyl-1,3,4-oxadiazol-2-yl | CF₃ |
| 2-Me-4-SO₂Me-3-(4,5-dihydroisoxazol-3-yl)Ph | 1,2,3-triazol-4-yl | H |
| 2-Me-4-SO₂Me-3-(4,5-dihydroisoxazol-3-yl)Ph | 1,2,3-triazol-4-yl | methyl |
| 2-Me-4-SO₂Me-3-(4,5-dihydroisoxazol-3-yl)Ph | 1,2,3-triazol-4-yl | i-propyl |
| 2-Me-4-SO₂Me-3-(4,5-dihydroisoxazol-3-yl)Ph | 1,2,3-triazol-4-yl | cyclopropyl |
| 2-Me-4-SO₂Me-3-(4,5-dihydroisoxazol-3-yl)Ph | 1,2,3-triazol-4-yl | CF₃ |
| 2-Me-4-SO₂Me-3-(4,5-dihydroisoxazol-3-yl)Ph | 1-methyl-1,2,3-triazol-4-yl | H |
| 2-Me-4-SO₂Me-3-(4,5-dihydroisoxazol-3-yl)Ph | 1-methyl-1,2,3-triazol-4-yl | methyl |
| 2-Me-4-SO₂Me-3-(4,5-dihydroisoxazol-3-yl)Ph | 1-methyl-1,2,3-triazol-4-yl | i-propyl |
| 2-Me-4-SO₂Me-3-(4,5-dihydroisoxazol-3-yl)Ph | 1-methyl-1,2,3-triazol-4-yl | cyclopropyl |
| 2-Me-4-SO₂Me-3-(4,5-dihydroisoxazol-3-yl)Ph | 1-methyl-1,2,3-triazol-4-yl | CF₃ |
| 2-Me-4-SO₂Me-3-(4,5-dihydroisoxazol-3-yl)Ph | 2-methyl-1,2,3-triazol-4-yl | H |
| 2-Me-4-SO₂Me-3-(4,5-dihydroisoxazol-3-yl)Ph | 2-methyl-1,2,3-triazol-4-yl | methyl |
| 2-Me-4-SO₂Me-3-(4,5-dihydroisoxazol-3-yl)Ph | 2-methyl-1,2,3-triazol-4-yl | i-propyl |
| 2-Me-4-SO₂Me-3-(4,5-dihydroisoxazol-3-yl)Ph | 2-methyl-1,2,3-triazol-4-yl | cyclopropyl |
| 2-Me-4-SO₂Me-3-(4,5-dihydroisoxazol-3-yl)Ph | 2-methyl-1,2,3-triazol-4-yl | CF₃ |
| 2-Me-4-SO₂Me-3-(4,5-dihydroisoxazol-3-yl)Ph | 1,2,3-triazol-1-yl | H |
| 2-Me-4-SO₂Me-3-(4,5-dihydroisoxazol-3-yl)Ph | 1,2,3-triazol-1-yl | methyl |
| 2-Me-4-SO₂Me-3-(4,5-dihydroisoxazol-3-yl)Ph | 1,2,3-triazol-1-yl | i-propyl |
| 2-Me-4-SO₂Me-3-(4,5-dihydroisoxazol-3-yl)Ph | 1,2,3-triazol-1-yl | cyclopropyl |
| 2-Me-4-SO₂Me-3-(4,5-dihydroisoxazol-3-yl)Ph | 1,2,3-triazol-1-yl | CF₃ |
| 2-Me-4-SO₂Me-3-(4,5-dihydroisoxazol-3-yl)Ph | 1,2,3-triazol-2-yl | H |
| 2-Me-4-SO₂Me-3-(4,5-dihydroisoxazol-3-yl)Ph | 1,2,3-triazol-2-yl | methyl |
| 2-Me-4-SO₂Me-3-(4,5-dihydroisoxazol-3-yl)Ph | 1,2,3-triazol-2-yl | i-propyl |
| 2-Me-4-SO₂Me-3-(4,5-dihydroisoxazol-3-yl)Ph | 1,2,3-triazol-2-yl | cyclopropyl |
| 2-Me-4-SO₂Me-3-(4,5-dihydroisoxazol-3-yl)Ph | 1,2,3-triazol-2-yl | CF₃ |
| 2-Me-4-SO₂Me-3-(4,5-dihydroisoxazol-3-yl)Ph | 1,2,4-triazol-1-yl | H |
| 2-Me-4-SO₂Me-3-(4,5-dihydroisoxazol-3-yl)Ph | 1,2,4-triazol-1-yl | methyl |
| 2-Me-4-SO₂Me-3-(4,5-dihydroisoxazol-3-yl)Ph | 1,2,4-triazol-1-yl | i-propyl |
| 2-Me-4-SO₂Me-3-(4,5-dihydroisoxazol-3-yl)Ph | 1,2,4-triazol-1-yl | cyclopropyl |
| 2-Me-4-SO₂Me-3-(4,5-dihydroisoxazol-3-yl)Ph | 1,2,4-triazol-1-yl | CF₃ |
| 2-Me-4-SO₂Me-3-(4,5-dihydroisoxazol-3-yl)Ph | imidazol-2-yl | H |
| 2-Me-4-SO₂Me-3-(4,5-dihydroisoxazol-3-yl)Ph | imidazol-2-yl | methyl |
| 2-Me-4-SO₂Me-3-(4,5-dihydroisoxazol-3-yl)Ph | imidazol-2-yl | i-propyl |
| 2-Me-4-SO₂Me-3-(4,5-dihydroisoxazol-3-yl)Ph | imidazol-2-yl | cyclopropyl |
| 2-Me-4-SO₂Me-3-(4,5-dihydroisoxazol-3-yl)Ph | imidazol-2-yl | CF₃ |
| 2-Me-4-SO₂Me-3-(4,5-dihydroisoxazol-3-yl)Ph | imidazol-1-yl | H |
| 2-Me-4-SO₂Me-3-(4,5-dihydroisoxazol-3-yl)Ph | imidazol-1-yl | methyl |
| 2-Me-4-SO₂Me-3-(4,5-dihydroisoxazol-3-yl)Ph | imidazol-1-yl | i-propyl |
| 2-Me-4-SO₂Me-3-(4,5-dihydroisoxazol-3-yl)Ph | imidazol-1-yl | cyclopropyl |
| 2-Me-4-SO₂Me-3-(4,5-dihydroisoxazol-3-yl)Ph | imidazol-1-yl | CF₃ |
| 2-Me-4-SO₂Me-3-(4,5-dihydroisoxazol-3-yl)Ph | imidazol-4-yl | H |
| 2-Me-4-SO₂Me-3-(4,5-dihydroisoxazol-3-yl)Ph | imidazol-4-yl | methyl |
| 2-Me-4-SO₂Me-3-(4,5-dihydroisoxazol-3-yl)Ph | imidazol-4-yl | i-propyl |
| 2-Me-4-SO₂Me-3-(4,5-dihydroisoxazol-3-yl)Ph | imidazol-4-yl | cyclopropyl |
| 2-Me-4-SO₂Me-3-(4,5-dihydroisoxazol-3-yl)Ph | imidazol-4-yl | CF₃ |
| 2-Me-4-SO₂Me-3-(4,5-dihydroisoxazol-3-yl)Ph | thiazol-2-yl | H |
| 2-Me-4-SO₂Me-3-(4,5-dihydroisoxazol-3-yl)Ph | thiazol-2-yl | methyl |
| 2-Me-4-SO₂Me-3-(4,5-dihydroisoxazol-3-yl)Ph | thiazol-2-yl | i-propyl |
| 2-Me-4-SO₂Me-3-(4,5-dihydroisoxazol-3-yl)Ph | thiazol-2-yl | cyclopropyl |
| 2-Me-4-SO₂Me-3-(4,5-dihydroisoxazol-3-yl)Ph | thiazol-2-yl | CF₃ |
| 2-Me-4-SO₂Me-3-(4,5-dihydroisoxazol-3-yl)Ph | 4-methylthiazol-2-yl | H |
| 2-Me-4-SO₂Me-3-(4,5-dihydroisoxazol-3-yl)Ph | 4-methylthiazol-2-yl | methyl |
| 2-Me-4-SO₂Me-3-(4,5-dihydroisoxazol-3-yl)Ph | 4-methylthiazol-2-yl | i-propyl |
| 2-Me-4-SO₂Me-3-(4,5-dihydroisoxazol-3-yl)Ph | 4-methylthiazol-2-yl | cyclopropyl |
| 2-Me-4-SO₂Me-3-(4,5-dihydroisoxazol-3-yl)Ph | 4-methylthiazol-2-yl | CF₃ |
| 2-Me-4-SO₂Me-3-(4,5-dihydroisoxazol-3-yl)Ph | oxazol-2-yl | H |
| 2-Me-4-SO₂Me-3-(4,5-dihydroisoxazol-3-yl)Ph | oxazol-2-yl | methyl |
| 2-Me-4-SO₂Me-3-(4,5-dihydroisoxazol-3-yl)Ph | oxazol-2-yl | i-propyl |
| 2-Me-4-SO₂Me-3-(4,5-dihydroisoxazol-3-yl)Ph | oxazol-2-yl | cyclopropyl |
| 2-Me-4-SO₂Me-3-(4,5-dihydroisoxazol-3-yl)Ph | oxazol-2-yl | CF₃ |
| 2-Me-4-SO₂Me-3-(4,5-dihydroisoxazol-3-yl)Ph | 4,5-dimethyloxazol-2-yl | H |
| 2-Me-4-SO₂Me-3-(4,5-dihydroisoxazol-3-yl)Ph | 4,5-dimethyloxazol-2-yl | methyl |
| 2-Me-4-SO₂Me-3-(4,5-dihydroisoxazol-3-yl)Ph | 4,5-dimethyloxazol-2-yl | i-propyl |
| 2-Me-4-SO₂Me-3-(4,5-dihydroisoxazol-3-yl)Ph | 4,5-dimethyloxazol-2-yl | cyclopropyl |
| 2-Me-4-SO₂Me-3-(4,5-dihydroisoxazol-3-yl)Ph | 4,5-dimethyloxazol-2-yl | CF₃ |
| 2-Me-4-SO₂Me-3-(4,5-dihydroisoxazol-3-yl)Ph | 2-oxazolin-2-yl | H |
| 2-Me-4-SO₂Me-3-(4,5-dihydroisoxazol-3-yl)Ph | 2-oxazolin-2-yl | methyl |

-continued $$\underset{B}{\overset{O\quad O}{A \diagdown \diagup R}}$$ (I)

| A | B | R |
|---|---|---|
| 2-Me-4-SO₂Me-3-(4,5-dihydroisoxazol-3-yl)Ph | 2-oxazolin-2-yl | i-propyl |
| 2-Me-4-SO₂Me-3-(4,5-dihydroisoxazol-3-yl)Ph | 2-oxazolin-2-yl | cyclopropyl |
| 2-Me-4-SO₂Me-3-(4,5-dihydroisoxazol-3-yl)Ph | 2-oxazolin-2-yl | CF₃ |
| 2-Me-4-SO₂Me-3-(4,5-dihydroisoxazol-3-yl)Ph | 4,4-dimethyl-2-oxazolin-2-yl | H |
| 2-Me-4-SO₂Me-3-(4,5-dihydroisoxazol-3-yl)Ph | 4,4-dimethyl-2-oxazolin-2-yl | methyl |
| 2-Me-4-SO₂Me-3-(4,5-dihydroisoxazol-3-yl)Ph | 4,4-dimethyl-2-oxazolin-2-yl | i-propyl |
| 2-Me-4-SO₂Me-3-(4,5-dihydroisoxazol-3-yl)Ph | 4,4-dimethyl-2-oxazolin-2-yl | cyclopropyl |
| 2-Me-4-SO₂Me-3-(4,5-dihydroisoxazol-3-yl)Ph | 4,4-dimethyl-2-oxazolin-2-yl | CF₃ |
| 2-Me-4-SO₂Me-3-(4,5-dihydroisoxazol-3-yl)Ph | 1,2,4-thiadiazol-5-yl | H |
| 2-Me-4-SO₂Me-3-(4,5-dihydroisoxazol-3-yl)Ph | 1,2,4-thiadiazol-5-yl | methyl |
| 2-Me-4-SO₂Me-3-(4,5-dihydroisoxazol-3-yl)Ph | 1,2,4-thiadiazol-5-yl | i-propyl |
| 2-Me-4-SO₂Me-3-(4,5-dihydroisoxazol-3-yl)Ph | 1,2,4-thiadiazol-5-yl | cyclopropyl |
| 2-Me-4-SO₂Me-3-(4,5-dihydroisoxazol-3-yl)Ph | 1,2,4-thiadiazol-5-yl | CF₃ |
| 2-Me-4-SO₂Me-3-(4,5-dihydroisoxazol-3-yl)Ph | 3-methyl-1,2,4-thiadiazol-5-yl | H |
| 2-Me-4-SO₂Me-3-(4,5-dihydroisoxazol-3-yl)Ph | 3-methyl-1,2,4-thiadiazol-5-yl | methyl |
| 2-Me-4-SO₂Me-3-(4,5-dihydroisoxazol-3-yl)Ph | 3-methyl-1,2,4-thiadiazol-5-yl | i-propyl |
| 2-Me-4-SO₂Me-3-(4,5-dihydroisoxazol-3-yl)Ph | 3-methyl-1,2,4-thiadiazol-5-yl | cyclopropyl |
| 2-Me-4-SO₂Me-3-(4,5-dihydroisoxazol-3-yl)Ph | 3-methyl-1,2,4-thiadiazol-5-yl | CF₃ |
| 2-Me-4-SO₂Me-3-(4,5-dihydroisoxazol-3-yl)Ph | 3-trifluoromethyl-1,2,4-thiadiazol-5-yl | H |
| 2-Me-4-SO₂Me-3-(4,5-dihydroisoxazol-3-yl)Ph | 3-trifluoromethyl-1,2,4-thiadiazol-5-yl | methyl |
| 2-Me-4-SO₂Me-3-(4,5-dihydroisoxazol-3-yl)Ph | 3-trifluoromethyl-1,2,4-thiadiazol-5-yl | i-propyl |
| 2-Me-4-SO₂Me-3-(4,5-dihydroisoxazol-3-yl)Ph | 3-trifluoromethyl-1,2,4-thiadiazol-5-yl | cyclopropyl |
| 2-Me-4-SO₂Me-3-(4,5-dihydroisoxazol-3-yl)Ph | 3-trifluoromethyl-1,2,4-thiadiazol-5-yl | CF₃ |
| 2-Me-4-SO₂Me-3-(4,5-dihydroisoxazol-3-yl)Ph | 1,2,4-thiadiazol-3-yl | H |
| 2-Me-4-SO₂Me-3-(4,5-dihydroisoxazol-3-yl)Ph | 1,2,4-thiadiazol-3-yl | methyl |
| 2-Me-4-SO₂Me-3-(4,5-dihydroisoxazol-3-yl)Ph | 1,2,4-thiadiazol-3-yl | i-propyl |
| 2-Me-4-SO₂Me-3-(4,5-dihydroisoxazol-3-yl)Ph | 1,2,4-thiadiazol-3-yl | cyclopropyl |
| 2-Me-4-SO₂Me-3-(4,5-dihydroisoxazol-3-yl)Ph | 1,2,4-thiadiazol-3-yl | CF₃ |
| 2-Me-4-SO₂Me-3-(4,5-dihydroisoxazol-3-yl)Ph | 5-methyl-1,2,4-thiadiazol-3-yl | H |
| 2-Me-4-SO₂Me-3-(4,5-dihydroisoxazol-3-yl)Ph | 5-methyl-1,2,4-thiadiazol-3-yl | methyl |
| 2-Me-4-SO₂Me-3-(4,5-dihydroisoxazol-3-yl)Ph | 5-methyl-1,2,4-thiadiazol-3-yl | i-propyl |
| 2-Me-4-SO₂Me-3-(4,5-dihydroisoxazol-3-yl)Ph | 5-methyl-1,2,4-thiadiazol-3-yl | cyclopropyl |
| 2-Me-4-SO₂Me-3-(4,5-dihydroisoxazol-3-yl)Ph | 5-methyl-1,2,4-thiadiazol-3-yl | CF₃ |
| 2-Me-4-SO₂Me-3-(4,5-dihydroisoxazol-3-yl)Ph | 5-trifluoromethyl-1,2,4-thiadiazol-3-yl | H |
| 2-Me-4-SO₂Me-3-(4,5-dihydroisoxazol-3-yl)Ph | 5-trifluoromethyl-1,2,4-thiadiazol-3-yl | methyl |
| 2-Me-4-SO₂Me-3-(4,5-dihydroisoxazol-3-yl)Ph | 5-trifluoromethyl-1,2,4-thiadiazol-3-yl | i-propyl |
| 2-Me-4-SO₂Me-3-(4,5-dihydroisoxazol-3-yl)Ph | 5-trifluoromethyl-1,2,4-thiadiazol-3-yl | cyclopropyl |
| 2-Me-4-SO₂Me-3-(4,5-dihydroisoxazol-3-yl)Ph | 5-trifluoromethyl-1,2,4-thiadiazol-3-yl | CF₃ |
| 2-Me-4-SO₂Me-3-(4,5-dihydroisoxazol-3-yl)Ph | 1,3,4-thiadiazol-2-yl | H |
| 2-Me-4-SO₂Me-3-(4,5-dihydroisoxazol-3-yl)Ph | 1,3,4-thiadiazol-2-yl | methyl |
| 2-Me-4-SO₂Me-3-(4,5-dihydroisoxazol-3-yl)Ph | 1,3,4-thiadiazol-2-yl | i-propyl |
| 2-Me-4-SO₂Me-3-(4,5-dihydroisoxazol-3-yl)Ph | 1,3,4-thiadiazol-2-yl | cyclopropyl |
| 2-Me-4-SO₂Me-3-(4,5-dihydroisoxazol-3-yl)Ph | 1,3,4-thiadiazol-2-yl | CF₃ |
| 2-Me-4-SO₂Me-3-(4,5-dihydroisoxazol-3-yl)Ph | 5-methylsulfonyl-1,3,4-thiadiazol-2-yl | H |
| 2-Me-4-SO₂Me-3-(4,5-dihydroisoxazol-3-yl)Ph | 5-methylsulfonyl-1,3,4-thiadiazol-2-yl | methyl |
| 2-Me-4-SO₂Me-3-(4,5-dihydroisoxazol-3-yl)Ph | 5-methylsulfonyl-1,3,4-thiadiazol-2-yl | i-propyl |
| 2-Me-4-SO₂Me-3-(4,5-dihydroisoxazol-3-yl)Ph | 5-methylsulfonyl-1,3,4-thiadiazol-2-yl | cyclopropyl |
| 2-Me-4-SO₂Me-3-(4,5-dihydroisoxazol-3-yl)Ph | 5-methylsulfonyl-1,3,4-thiadiazol-2-yl | CF₃ |
| 2-Me-4-SO₂Me-3-(4,5-dihydroisoxazol-3-yl)Ph | 5-methyl-1,3,4-thiadiazol-2-yl | H |
| 2-Me-4-SO₂Me-3-(4,5-dihydroisoxazol-3-yl)Ph | 5-methyl-1,3,4-thiadiazol-2-yl | methyl |
| 2-Me-4-SO₂Me-3-(4,5-dihydroisoxazol-3-yl)Ph | 5-methyl-1,3,4-thiadiazol-2-yl | i-propyl |
| 2-Me-4-SO₂Me-3-(4,5-dihydroisoxazol-3-yl)Ph | 5-methyl-1,3,4-thiadiazol-2-yl | cyclopropyl |
| 2-Me-4-SO₂Me-3-(4,5-dihydroisoxazol-3-yl)Ph | 5-methyl-1,3,4-thiadiazol-2-yl | CF₃ |
| 2-Me-4-SO₂Me-3-(4,5-dihydroisoxazol-3-yl)Ph | benzoxazol-2-yl | H |
| 2-Me-4-SO₂Me-3-(4,5-dihydroisoxazol-3-yl)Ph | benzoxazol-2-yl | methyl |
| 2-Me-4-SO₂Me-3-(4,5-dihydroisoxazol-3-yl)Ph | benzoxazol-2-yl | i-propyl |
| 2-Me-4-SO₂Me-3-(4,5-dihydroisoxazol-3-yl)Ph | benzoxazol-2-yl | cyclopropyl |
| 2-Me-4-SO₂Me-3-(4,5-dihydroisoxazol-3-yl)Ph | benzoxazol-2-yl | CF₃ |
| 2-Me-4-SO₂Me-3-(4,5-dihydroisoxazol-3-yl)Ph | 6-methylbenzoxazol-2-yl | H |
| 2-Me-4-SO₂Me-3-(4,5-dihydroisoxazol-3-yl)Ph | 6-methylbenzoxazol-2-yl | methyl |
| 2-Me-4-SO₂Me-3-(4,5-dihydroisoxazol-3-yl)Ph | 6-methylbenzoxazol-2-yl | i-propyl |
| 2-Me-4-SO₂Me-3-(4,5-dihydroisoxazol-3-yl)Ph | 6-methylbenzoxazol-2-yl | cyclopropyl |
| 2-Me-4-SO₂Me-3-(4,5-dihydroisoxazol-3-yl)Ph | 6-methylbenzoxazol-2-yl | CF₃ |
| 2-Me-4-SO₂Me-3-(4,5-dihydroisoxazol-3-yl)Ph | benzothiazol-2-yl | H |
| 2-Me-4-SO₂Me-3-(4,5-dihydroisoxazol-3-yl)Ph | benzothiazol-2-yl | methyl |
| 2-Me-4-SO₂Me-3-(4,5-dihydroisoxazol-3-yl)Ph | benzothiazol-2-yl | i-propyl |
| 2-Me-4-SO₂Me-3-(4,5-dihydroisoxazol-3-yl)Ph | benzothiazol-2-yl | cyclopropyl |
| 2-Me-4-SO₂Me-3-(4,5-dihydroisoxazol-3-yl)Ph | benzothiazol-2-yl | CF₃ |
| 2-Me-4-SO₂Me-3-(4,5-dihydroisoxazol-3-yl)Ph | pyrazol-1-yl | H |
| 2-Me-4-SO₂Me-3-(4,5-dihydroisoxazol-3-yl)Ph | pyrazol-1-yl | methyl |

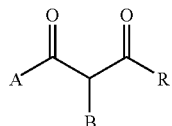 (I)

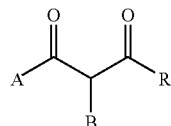 (I)

| A | B | R |
|---|---|---|
| 2-Me-4-SO₂Me-3-(4,5-dihydroisoxazol-3-yl)Ph | pyrazol-1-yl | i-propyl |
| 2-Me-4-SO₂Me-3-(4,5-dihydroisoxazol-3-yl)Ph | pyrazol-1-yl | cyclopropyl |
| 2-Me-4-SO₂Me-3-(4,5-dihydroisoxazol-3-yl)Ph | pyrazol-1-yl | CF₃ |
| 2-Me-4-SO₂Me-3-(4,5-dihydroisoxazol-3-yl)Ph | pyrazol-3-yl | H |
| 2-Me-4-SO₂Me-3-(4,5-dihydroisoxazol-3-yl)Ph | pyrazol-3-yl | methyl |
| 2-Me-4-SO₂Me-3-(4,5-dihydroisoxazol-3-yl)Ph | pyrazol-3-yl | i-propyl |
| 2-Me-4-SO₂Me-3-(4,5-dihydroisoxazol-3-yl)Ph | pyrazol-3-yl | cyclopropyl |
| 2-Me-4-SO₂Me-3-(4,5-dihydroisoxazol-3-yl)Ph | pyrazol-3-yl | CF₃ |
| 2-Me-4-SO₂Me-3-(4,5-dihydroisoxazol-3-yl)Ph | 1-methylpyrazol-3-yl | H |
| 2-Me-4-SO₂Me-3-(4,5-dihydroisoxazol-3-yl)Ph | 1-methylpyrazol-3-yl | methyl |
| 2-Me-4-SO₂Me-3-(4,5-dihydroisoxazol-3-yl)Ph | 1-methylpyrazol-3-yl | i-propyl |
| 2-Me-4-SO₂Me-3-(4,5-dihydroisoxazol-3-yl)Ph | 1-methylpyrazol-3-yl | cyclopropyl |
| 2-Me-4-SO₂Me-3-(4,5-dihydroisoxazol-3-yl)Ph | 1-methylpyrazol-3-yl | CF₃ |
| 2-Me-4-SO₂Me-3-(4,5-dihydroisoxazol-3-yl)Ph | tetrazol-1-yl | H |
| 2-Me-4-SO₂Me-3-(4,5-dihydroisoxazol-3-yl)Ph | tetrazol-1-yl | methyl |
| 2-Me-4-SO₂Me-3-(4,5-dihydroisoxazol-3-yl)Ph | tetrazol-1-yl | i-propyl |
| 2-Me-4-SO₂Me-3-(4,5-dihydroisoxazol-3-yl)Ph | tetrazol-1-yl | cyclopropyl |
| 2-Me-4-SO₂Me-3-(4,5-dihydroisoxazol-3-yl)Ph | tetrazol-1-yl | CF₃ |
| 2-Me-4-SO₂Me-3-(4,5-dihydroisoxazol-3-yl)Ph | 5-methyltetrazol-1-yl | H |
| 2-Me-4-SO₂Me-3-(4,5-dihydroisoxazol-3-yl)Ph | 5-methyltetrazol-1-yl | methyl |
| 2-Me-4-SO₂Me-3-(4,5-dihydroisoxazol-3-yl)Ph | 5-methyltetrazol-1-yl | i-propyl |
| 2-Me-4-SO₂Me-3-(4,5-dihydroisoxazol-3-yl)Ph | 5-methyltetrazol-1-yl | cyclopropyl |
| 2-Me-4-SO₂Me-3-(4,5-dihydroisoxazol-3-yl)Ph | 5-methyltetrazol-1-yl | CF₃ |
| 2-Me-4-SO₂Me-3-(4,5-dihydroisoxazol-3-yl)Ph | tetrazol-2-yl | H |
| 2-Me-4-SO₂Me-3-(4,5-dihydroisoxazol-3-yl)Ph | tetrazol-2-yl | methyl |
| 2-Me-4-SO₂Me-3-(4,5-dihydroisoxazol-3-yl)Ph | tetrazol-2-yl | i-propyl |
| 2-Me-4-SO₂Me-3-(4,5-dihydroisoxazol-3-yl)Ph | tetrazol-2-yl | cyclopropyl |
| 2-Me-4-SO₂Me-3-(4,5-dihydroisoxazol-3-yl)Ph | tetrazol-2-yl | CF₃ |
| 2-Me-4-SO₂Me-3-(4,5-dihydroisoxazol-3-yl)Ph | 5-methyltetrazol-2-yl | H |
| 2-Me-4-SO₂Me-3-(4,5-dihydroisoxazol-3-yl)Ph | 5-methyltetrazol-2-yl | methyl |
| 2-Me-4-SO₂Me-3-(4,5-dihydroisoxazol-3-yl)Ph | 5-methyltetrazol-2-yl | i-propyl |
| 2-Me-4-SO₂Me-3-(4,5-dihydroisoxazol-3-yl)Ph | 5-methyltetrazol-2-yl | cyclopropyl |
| 2-Me-4-SO₂Me-3-(4,5-dihydroisoxazol-3-yl)Ph | 5-methyltetrazol-2-yl | CF₃ |
| 2-Me-4-SO₂Me-3-(4,5-dihydroisoxazol-3-yl)Ph | 1-methyltetrazol-5-yl | H |
| 2-Me-4-SO₂Me-3-(4,5-dihydroisoxazol-3-yl)Ph | 1-methyltetrazol-5-yl | methyl |
| 2-Me-4-SO₂Me-3-(4,5-dihydroisoxazol-3-yl)Ph | 1-methyltetrazol-5-yl | i-propyl |
| 2-Me-4-SO₂Me-3-(4,5-dihydroisoxazol-3-yl)Ph | 1-methyltetrazol-5-yl | cyclopropyl |
| 2-Me-4-SO₂Me-3-(4,5-dihydroisoxazol-3-yl)Ph | 1-methyltetrazol-5-yl | CF₃ |
| 2-Me-4-SO₂Me-3-(4,5-dihydroisoxazol-3-yl)Ph | 2-methyltetrazol-5-yl | H |
| 2-Me-4-SO₂Me-3-(4,5-dihydroisoxazol-3-yl)Ph | 2-methyltetrazol-5-yl | methyl |
| 2-Me-4-SO₂Me-3-(4,5-dihydroisoxazol-3-yl)Ph | 2-methyltetrazol-5-yl | i-propyl |
| 2-Me-4-SO₂Me-3-(4,5-dihydroisoxazol-3-yl)Ph | 2-methyltetrazol-5-yl | cyclopropyl |
| 2-Me-4-SO₂Me-3-(4,5-dihydroisoxazol-3-yl)Ph | 2-methyltetrazol-5-yl | CF₃ |
| 2-Me-4-SO₂Me-3-(4,5-dihydroisoxazol-3-yl)Ph | pyridin-2-yl | H |
| 2-Me-4-SO₂Me-3-(4,5-dihydroisoxazol-3-yl)Ph | pyridin-2-yl | methyl |
| 2-Me-4-SO₂Me-3-(4,5-dihydroisoxazol-3-yl)Ph | pyridin-2-yl | i-propyl |
| 2-Me-4-SO₂Me-3-(4,5-dihydroisoxazol-3-yl)Ph | pyridin-2-yl | cyclopropyl |
| 2-Me-4-SO₂Me-3-(4,5-dihydroisoxazol-3-yl)Ph | pyridin-2-yl | CF₃ |
| 2-Me-4-SO₂Me-3-(4,5-dihydroisoxazol-3-yl)Ph | pyridin-4-yl | H |
| 2-Me-4-SO₂Me-3-(4,5-dihydroisoxazol-3-yl)Ph | pyridin-4-yl | methyl |
| 2-Me-4-SO₂Me-3-(4,5-dihydroisoxazol-3-yl)Ph | pyridin-4-yl | i-propyl |
| 2-Me-4-SO₂Me-3-(4,5-dihydroisoxazol-3-yl)Ph | pyridin-4-yl | cyclopropyl |
| 2-Me-4-SO₂Me-3-(4,5-dihydroisoxazol-3-yl)Ph | pyridin-4-yl | CF₃ |
| 2-Me-4-SO₂Me-3-(4,5-dihydroisoxazol-3-yl)Ph | pyridin-3-yl | H |
| 2-Me-4-SO₂Me-3-(4,5-dihydroisoxazol-3-yl)Ph | pyridin-3-yl | methyl |
| 2-Me-4-SO₂Me-3-(4,5-dihydroisoxazol-3-yl)Ph | pyridin-3-yl | i-propyl |
| 2-Me-4-SO₂Me-3-(4,5-dihydroisoxazol-3-yl)Ph | pyridin-3-yl | cyclopropyl |
| 2-Me-4-SO₂Me-3-(4,5-dihydroisoxazol-3-yl)Ph | pyridin-3-yl | CF₃ |
| 2-Me-4-SO₂Me-3-(4,5-dihydroisoxazol-3-yl)Ph | 3-nitropyridin-4-yl | H |
| 2-Me-4-SO₂Me-3-(4,5-dihydroisoxazol-3-yl)Ph | 3-nitropyridin-4-yl | methyl |
| 2-Me-4-SO₂Me-3-(4,5-dihydroisoxazol-3-yl)Ph | 3-nitropyridin-4-yl | i-propyl |
| 2-Me-4-SO₂Me-3-(4,5-dihydroisoxazol-3-yl)Ph | 3-nitropyridin-4-yl | cyclopropyl |
| 2-Me-4-SO₂Me-3-(4,5-dihydroisoxazol-3-yl)Ph | 3-nitropyridin-4-yl | CF₃ |
| 2-Me-4-SO₂Me-3-(4,5-dihydroisoxazol-3-yl)Ph | 5-cyanopyridin-2-yl | H |
| 2-Me-4-SO₂Me-3-(4,5-dihydroisoxazol-3-yl)Ph | 5-cyanopyridin-2-yl | methyl |
| 2-Me-4-SO₂Me-3-(4,5-dihydroisoxazol-3-yl)Ph | 5-cyanopyridin-2-yl | i-propyl |
| 2-Me-4-SO₂Me-3-(4,5-dihydroisoxazol-3-yl)Ph | 5-cyanopyridin-2-yl | cyclopropyl |
| 2-Me-4-SO₂Me-3-(4,5-dihydroisoxazol-3-yl)Ph | 5-cyanopyridin-2-yl | CF₃ |
| 2-Me-4-SO₂Me-3-(4,5-dihydroisoxazol-3-yl)Ph | 5-trifluoromethylpyridin-2-yl | H |
| 2-Me-4-SO₂Me-3-(4,5-dihydroisoxazol-3-yl)Ph | 5-trifluoromethylpyridin-2-yl | methyl |

-continued

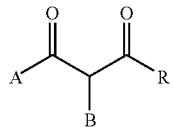

(I)

| A | B | R |
|---|---|---|
| 2-Me-4-SO₂Me-3-(4,5-dihydroisoxazol-3-yl)Ph | 5-trifluoromethylpyridin-2-yl | i-propyl |
| 2-Me-4-SO₂Me-3-(4,5-dihydroisoxazol-3-yl)Ph | 5-trifluoromethylpyridin-2-yl | cyclopropyl |
| 2-Me-4-SO₂Me-3-(4,5-dihydroisoxazol-3-yl)Ph | 5-trifluoromethylpyridin-2-yl | CF₃ |
| 2-Me-4-SO₂Me-3-(4,5-dihydroisoxazol-3-yl)Ph | pyrimidin-2-yl | H |
| 2-Me-4-SO₂Me-3-(4,5-dihydroisoxazol-3-yl)Ph | pyrimidin-2-yl | methyl |
| 2-Me-4-SO₂Me-3-(4,5-dihydroisoxazol-3-yl)Ph | pyrimidin-2-yl | i-propyl |
| 2-Me-4-SO₂Me-3-(4,5-dihydroisoxazol-3-yl)Ph | pyrimidin-2-yl | cyclopropyl |
| 2-Me-4-SO₂Me-3-(4,5-dihydroisoxazol-3-yl)Ph | pyrimidin-2-yl | CF₃ |
| 2-Me-4-SO₂Me-3-(4,5-dihydroisoxazol-3-yl)Ph | pyrimidin-4-yl | H |
| 2-Me-4-SO₂Me-3-(4,5-dihydroisoxazol-3-yl)Ph | pyrimidin-4-yl | methyl |
| 2-Me-4-SO₂Me-3-(4,5-dihydroisoxazol-3-yl)Ph | pyrimidin-4-yl | i-propyl |
| 2-Me-4-SO₂Me-3-(4,5-dihydroisoxazol-3-yl)Ph | pyrimidin-4-yl | cyclopropyl |
| 2-Me-4-SO₂Me-3-(4,5-dihydroisoxazol-3-yl)Ph | pyrimidin-4-yl | CF₃ |
| 2-Me-4-SO₂Me-3-(4,5-dihydroisoxazol-3-yl)Ph | 6-chloropyrimidin-4-yl | methyl |
| 2-Me-4-SO₂Me-3-(4,5-dihydroisoxazol-3-yl)Ph | 6-chloropyrimidin-4-yl | i-propyl |
| 2-Me-4-SO₂Me-3-(4,5-dihydroisoxazol-3-yl)Ph | 6-chloropyrimidin-4-yl | cyclopropyl |
| 2-Me-4-SO₂Me-3-(4,5-dihydroisoxazol-3-yl)Ph | 6-chloropyrimidin-4-yl | CF₃ |
| 2-Me-4-SO₂Me-3-(4,5-dihydroisoxazol-3-yl)Ph | pyridazin-3-yl | H |
| 2-Me-4-SO₂Me-3-(4,5-dihydroisoxazol-3-yl)Ph | pyridazin-3-yl | methyl |
| 2-Me-4-SO₂Me-3-(4,5-dihydroisoxazol-3-yl)Ph | pyridazin-3-yl | i-propyl |
| 2-Me-4-SO₂Me-3-(4,5-dihydroisoxazol-3-yl)Ph | pyridazin-3-yl | cyclopropyl |
| 2-Me-4-SO₂Me-3-(4,5-dihydroisoxazol-3-yl)Ph | pyridazin-3-yl | CF₃ |
| 2-Me-4-SO₂Me-3-(4,5-dihydroisoxazol-3-yl)Ph | 6-chloropyridazin-3-yl | methyl |
| 2-Me-4-SO₂Me-3-(4,5-dihydroisoxazol-3-yl)Ph | 6-chloropyridazin-3-yl | i-propyl |
| 2-Me-4-SO₂Me-3-(4,5-dihydroisoxazol-3-yl)Ph | 6-chloropyridazin-3-yl | cyclopropyl |
| 2-Me-4-SO₂Me-3-(4,5-dihydroisoxazol-3-yl)Ph | 6-chloropyridazin-3-yl | CF₃ |
| 2-Me-4-SO₂Me-3-(4,5-dihydroisoxazol-3-yl)Ph | pyrazin-2-yl | methyl |
| 2-Me-4-SO₂Me-3-(4,5-dihydroisoxazol-3-yl)Ph | pyrazin-2-yl | i-propyl |
| 2-Me-4-SO₂Me-3-(4,5-dihydroisoxazol-3-yl)Ph | pyrazin-2-yl | cyclopropyl |
| 2-Me-4-SO₂Me-3-(4,5-dihydroisoxazol-3-yl)Ph | pyrazin-2-yl | CF₃ |
| 2-Me-4-SO₂Me-3-(4,5-dihydroisoxazol-3-yl)Ph | triazin-2-yl | methyl |
| 2-Me-4-SO₂Me-3-(4,5-dihydroisoxazol-3-yl)Ph | triazin-2-yl | i-propyl |
| 2-Me-4-SO₂Me-3-(4,5-dihydroisoxazol-3-yl)Ph | triazin-2-yl | cyclopropyl |
| 2-Me-4-SO₂Me-3-(4,5-dihydroisoxazol-3-yl)Ph | triazin-2-yl | CF₃ |
| 2-Me-4-SO₂Me-3-(4,5-dihydroisoxazol-3-yl)Ph | quinolin-2-yl | methyl |

-continued

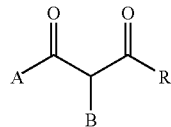

(I)

| A | B | R |
|---|---|---|
| 2-Me-4-SO₂Me-3-(4,5-dihydroisoxazol-3-yl)Ph | quinolin-2-yl | i-propyl |
| 2-Me-4-SO₂Me-3-(4,5-dihydroisoxazol-3-yl)Ph | quinolin-2-yl | cyclopropyl |
| 2-Me-4-SO₂Me-3-(4,5-dihydroisoxazol-3-yl)Ph | quinolin-2-yl | CF₃ |
| 2-Me-4-SO₂Me-3-(4,5-dihydroisoxazol-3-yl)Ph | 4,4,6-trimethyl-5,6-dihydro-1,3(4H)-oxazin-2-yl | H |
| 2-Me-4-SO₂Me-3-(4,5-dihydroisoxazol-3-yl)Ph | 4,4,6-trimethyl-5,6-dihydro-1,3(4H)-oxazin-2-yl | methyl |
| 2-Me-4-SO₂Me-3-(4,5-dihydroisoxazol-3-yl)Ph | 4,4,6-trimethyl-5,6-dihydro-1,3(4H)-oxazin-2-yl | i-propyl |
| 2-Me-4-SO₂Me-3-(4,5-dihydroisoxazol-3-yl)Ph | 4,4,6-trimethyl-5,6-dihydro-1,3(4H)-oxazin-2-yl | cyclopropyl |
| 2-Me-4-SO₂Me-3-(4,5-dihydroisoxazol-3-yl)Ph | 4,4,6-trimethyl-5,6-dihydro-1,3(4H)-oxazin-2-yl | CF₃ |
| 2-Me-4-SO₂Me-3-(4,5-dihydroisoxazol-3-yl)Ph | 2-oxazolidinon-3-yl | H |
| 2-Me-4-SO₂Me-3-(4,5-dihydroisoxazol-3-yl)Ph | 2-oxazolidinon-3-yl | methyl |
| 2-Me-4-SO₂Me-3-(4,5-dihydroisoxazol-3-yl)Ph | 2-oxazolidinon-3-yl | i-propyl |
| 2-Me-4-SO₂Me-3-(4,5-dihydroisoxazol-3-yl)Ph | 2-oxazolidinon-3-yl | cyclopropyl |
| 2-Me-4-SO₂Me-3-(4,5-dihydroisoxazol-3-yl)Ph | 2-oxazolidinon-3-yl | CF₃ |
| 2-Me-4-SO₂Me-3-(4,5-dihydroisoxazol-3-yl)Ph | 2-pyrrolidinon-1-yl | methyl |
| 2-Me-4-SO₂Me-3-(4,5-dihydroisoxazol-3-yl)Ph | 2-pyrrolidinon-1-yl | i-propyl |
| 2-Me-4-SO₂Me-3-(4,5-dihydroisoxazol-3-yl)Ph | 2-pyrrolidinon-1-yl | cyclopropyl |
| 2-Me-4-SO₂Me-3-(4,5-dihydroisoxazol-3-yl)Ph | 2-pyrrolidinon-1-yl | CF₃ |
| 2-Me-4-SO₂Me-3-(4,5-dihydroisoxazol-3-yl)Ph | 3-methylisoxazol-5-yl | methyl |
| 2-Me-4-SO₂Me-3-(4,5-dihydroisoxazol-3-yl)Ph | 3-methylisoxazol-5-yl | i-propyl |
| 2-Me-4-SO₂Me-3-(4,5-dihydroisoxazol-3-yl)Ph | 3-methylisoxazol-5-yl | cyclopropyl |
| 2-Me-4-SO₂Me-3-(4,5-dihydroisoxazol-3-yl)Ph | 3-methylisoxazol-5-yl | CF₃ |
| 2-Me-4-SO₂Me-3-(4,5-dihydroisoxazol-3-yl)Ph | 2-NO₂-4-SO₂MePh | H |
| 2-Me-4-SO₂Me-3-(4,5-dihydroisoxazol-3-yl)Ph | 2-NO₂-4-SO₂MePh | methyl |
| 2-Me-4-SO₂Me-3-(4,5-dihydroisoxazol-3-yl)Ph | 2-NO₂-4-SO₂MePh | i-propyl |
| 2-Me-4-SO₂Me-3-(4,5-dihydroisoxazol-3-yl)Ph | 2-NO₂-4-SO₂MePh | cyclopropyl |
| 2-Me-4-SO₂Me-3-(4,5-dihydroisoxazol-3-yl)Ph | 2-NO₂-4-SO₂MePh | CF₃ |
| 2-Me-4-SO₂Me-3-(4,5-dihydroisoxazol-3-yl)Ph | 2-Cl-4-SO₂MePh | H |
| 2-Me-4-SO₂Me-3-(4,5-dihydroisoxazol-3-yl)Ph | 2-Cl-4-SO₂MePh | methyl |
| 2-Me-4-SO₂Me-3-(4,5-dihydroisoxazol-3-yl)Ph | 2-Cl-4-SO₂MePh | i-propyl |
| 2-Me-4-SO₂Me-3-(4,5-dihydroisoxazol-3-yl)Ph | 2-Cl-4-SO₂MePh | cyclopropyl |
| 2-Me-4-SO₂Me-3-(4,5-dihydroisoxazol-3-yl)Ph | 2-Cl-4-SO₂MePh | CF₃ |
| 2-Me-4-SO₂Me-3-(4,5-dihydroisoxazol-3-yl)Ph | 2-NO₂-4-CF₃Ph | H |
| 2-Me-4-SO₂Me-3-(4,5-dihydroisoxazol-3-yl)Ph | 2-NO₂-4-CF₃Ph | methyl |
| 2-Me-4-SO₂Me-3-(4,5-dihydroisoxazol-3-yl)Ph | 2-NO₂-4-CF₃Ph | i-propyl |
| 2-Me-4-SO₂Me-3-(4,5-dihydroisoxazol-3-yl)Ph | 2-NO₂-4-CF₃Ph | cyclopropyl |

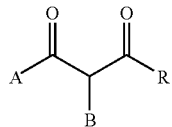

(I)

| A | B | R |
|---|---|---|
| 2-Me-4-SO$_2$Me-3-(4,5-dihydroisoxazol-3-yl)Ph | 2-NO$_2$-4-CF$_3$Ph | CF$_3$ |
| 2-Me-4-SO$_2$Me-3-(4,5-dihydroisoxazol-3-yl)Ph | 2-NO$_2$-4-ClPh | H |
| 2-Me-4-SO$_2$Me-3-(4,5-dihydroisoxazol-3-yl)Ph | 2-NO$_2$-4-ClPh | methyl |
| 2-Me-4-SO$_2$Me-3-(4,5-dihydroisoxazol-3-yl)Ph | 2-NO$_2$-4-ClPh | i-propyl |
| 2-Me-4-SO$_2$Me-3-(4,5-dihydroisoxazol-3-yl)Ph | 2-NO$_2$-4-ClPh | cyclopropyl |
| 2-Me-4-SO$_2$Me-3-(4,5-dihydroisoxazol-3-yl)Ph | 2-NO$_2$-4-ClPh | CF$_3$ |
| 2-Me-4-SO$_2$Me-3-(4,5-dihydroisoxazol-3-yl)Ph | 2-Cl-4-NO$_2$Ph | H |
| 2-Me-4-SO$_2$Me-3-(4,5-dihydroisoxazol-3-yl)Ph | 2-Cl-4-NO$_2$Ph | methyl |
| 2-Me-4-SO$_2$Me-3-(4,5-dihydroisoxazol-3-yl)Ph | 2-Cl-4-NO$_2$Ph | i-propyl |
| 2-Me-4-SO$_2$Me-3-(4,5-dihydroisoxazol-3-yl)Ph | 2-Cl-4-NO$_2$Ph | cyclopropyl |
| 2-Me-4-SO$_2$Me-3-(4,5-dihydroisoxazol-3-yl)Ph | 2-Cl-4-NO$_2$Ph | CF$_3$ |
| 2-Me-4-SO$_2$Me-3-(4,5-dihydroisoxazol-3-yl)Ph | 2,4-(NO$_2$)$_2$Ph | H |
| 2-Me-4-SO$_2$Me-3-(4,5-dihydroisoxazol-3-yl)Ph | 2,4-(NO$_2$)$_2$Ph | methyl |
| 2-Me-4-SO$_2$Me-3-(4,5-dihydroisoxazol-3-yl)Ph | 2,4-(NO$_2$)$_2$Ph | i-propyl |
| 2-Me-4-SO$_2$Me-3-(4,5-dihydroisoxazol-3-yl)Ph | 2,4-(NO$_2$)$_2$Ph | cyclopropyl |
| 2-Me-4-SO$_2$Me-3-(4,5-dihydroisoxazol-3-yl)Ph | 2,4-(NO$_2$)$_2$Ph | CF$_3$ |
| 2-Me-4-SO$_2$Me-3-(4,5-dihydroisoxazol-3-yl)Ph | 4-F-3-NO$_2$Ph | H |
| 2-Me-4-SO$_2$Me-3-(4,5-dihydroisoxazol-3-yl)Ph | 4-F-3-NO$_2$Ph | methyl |
| 2-Me-4-SO$_2$Me-3-(4,5-dihydroisoxazol-3-yl)Ph | 4-F-3-NO$_2$Ph | i-propyl |
| 2-Me-4-SO$_2$Me-3-(4,5-dihydroisoxazol-3-yl)Ph | 4-F-3-NO$_2$Ph | cyclopropyl |
| 2-Me-4-SO$_2$Me-3-(4,5-dihydroisoxazol-3-yl)Ph | 4-F-3-NO$_2$Ph | CF$_3$ |
| 2-Me-4-SO$_2$Me-3-(4,5-dihydroisoxazol-3-yl)Ph | 3,5-(CF$_3$)$_2$Ph | H |
| 2-Me-4-SO$_2$Me-3-(4,5-dihydroisoxazol-3-yl)Ph | 3,5-(CF$_3$)$_2$Ph | methyl |
| 2-Me-4-SO$_2$Me-3-(4,5-dihydroisoxazol-3-yl)Ph | 3,5-(CF$_3$)$_2$Ph | i-propyl |
| 2-Me-4-SO$_2$Me-3-(4,5-dihydroisoxazol-3-yl)Ph | 3,5-(CF$_3$)$_2$Ph | cyclopropyl |
| 2-Me-4-SO$_2$Me-3-(4,5-dihydroisoxazol-3-yl)Ph | 3,5-(CF$_3$)$_2$Ph | CF$_3$ |
| 2-Me-4-SO$_2$Me-3-(4,5-dihydroisoxazol-3-yl)Ph | 2-SO$_2$Me-4-CF$_3$Ph | H |
| 2-Me-4-SO$_2$Me-3-(4,5-dihydroisoxazol-3-yl)Ph | 2-SO$_2$Me-4-CF$_3$Ph | methyl |
| 2-Me-4-SO$_2$Me-3-(4,5-dihydroisoxazol-3-yl)Ph | 2-SO$_2$Me-4-CF$_3$Ph | i-propyl |
| 2-Me-4-SO$_2$Me-3-(4,5-dihydroisoxazol-3-yl)Ph | 2-SO$_2$Me-4-CF$_3$Ph | cyclopropyl |
| 2-Me-4-SO$_2$Me-3-(4,5-dihydroisoxazol-3-yl)Ph | 2-SO$_2$Me-4-CF$_3$Ph | CF$_3$ |
| 4,4-dioxide-8-Me-2,3-dihydro-1,4-benzoxathiin-7-yl | 1,2,4-oxadiazol-5-yl | H |
| 4,4-dioxide-8-Me-2,3-dihydro-1,4-benzoxathiin-7-yl | 1,2,4-oxadiazol-5-yl | methyl |
| 4,4-dioxide-8-Me-2,3-dihydro-1,4-benzoxathiin-7-yl | 1,2,4-oxadiazol-5-yl | i-propyl |

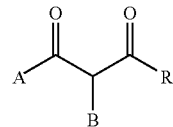

(I)

| A | B | R |
|---|---|---|
| 4,4-dioxide-8-Me-2,3-dihydro-1,4-benzoxathiin-7-yl | 1,2,4-oxadiazol-5-yl | cyclopropyl |
| 4,4-dioxide-8-Me-2,3-dihydro-1,4-benzoxathiin-7-yl | 1,2,4-oxadiazol-5-yl | CF$_3$ |
| 4,4-dioxide-8-Me-2,3-dihydro-1,4-benzoxathiin-7-yl | 3-methyl-1,2,4-oxadiazol-5-yl | H |
| 4,4-dioxide-8-Me-2,3-dihydro-1,4-benzoxathiin-7-yl | 3-methyl-1,2,4-oxadiazol-5-yl | methyl |
| 4,4-dioxide-8-Me-2,3-dihydro-1,4-benzoxathiin-7-yl | 3-methyl-1,2,4-oxadiazol-5-yl | i-propyl |
| 4,4-dioxide-8-Me-2,3-dihydro-1,4-benzoxathiin-7-yl | 3-methyl-1,2,4-oxadiazol-5-yl | cyclopropyl |
| 4,4-dioxide-8-Me-2,3-dihydro-1,4-benzoxathiin-7-yl | 3-methyl-1,2,4-oxadiazol-5-yl | CF$_3$ |
| 4,4-dioxide-8-Me-2,3-dihydro-1,4-benzoxathiin-7-yl | 3-trifluoromethyl-1,2,4-oxadiazol-5-yl | H |
| 4,4-dioxide-8-Me-2,3-dihydro-1,4-benzoxathiin-7-yl | 3-trifluoromethyl-1,2,4-oxadiazol-5-yl | methyl |
| 4,4-dioxide-8-Me-2,3-dihydro-1,4-benzoxathiin-7-yl | 3-trifluoromethyl-1,2,4-oxadiazol-5-yl | i-propyl |
| 4,4-dioxide-8-Me-2,3-dihydro-1,4-benzoxathiin-7-yl | 3-trifluoromethyl-1,2,4-oxadiazol-5-yl | cyclopropyl |
| 4,4-dioxide-8-Me-2,3-dihydro-1,4-benzoxathiin-7-yl | 3-trifluoromethyl-1,2,4-oxadiazol-5-yl | CF$_3$ |
| 4,4-dioxide-8-Me-2,3-dihydro-1,4-benzoxathiin-7-yl | 1,2,4-oxadiazol-3-yl | H |
| 4,4-dioxide-8-Me-2,3-dihydro-1,4-benzoxathiin-7-yl | 1,2,4-oxadiazol-3-yl | methyl |
| 4,4-dioxide-8-Me-2,3-dihydro-1,4-benzoxathiin-7-yl | 1,2,4-oxadiazol-3-yl | i-propyl |
| 4,4-dioxide-8-Me-2,3-dihydro-1,4-benzoxathiin-7-yl | 1,2,4-oxadiazol-3-yl | cyclopropyl |
| 4,4-dioxide-8-Me-2,3-dihydro-1,4-benzoxathiin-7-yl | 1,2,4-oxadiazol-3-yl | CF$_3$ |
| 4,4-dioxide-8-Me-2,3-dihydro-1,4-benzoxathiin-7-yl | 5-methyl-1,2,4-oxadiazol-3-yl | H |
| 4,4-dioxide-8-Me-2,3-dihydro-1,4-benzoxathiin-7-yl | 5-methyl-1,2,4-oxadiazol-3-yl | methyl |
| 4,4-dioxide-8-Me-2,3-dihydro-1,4-benzoxathiin-7-yl | 5-methyl-1,2,4-oxadiazol-3-yl | i-propyl |
| 4,4-dioxide-8-Me-2,3-dihydro-1,4-benzoxathiin-7-yl | 5-methyl-1,2,4-oxadiazol-3-yl | cyclopropyl |
| 4,4-dioxide-8-Me-2,3-dihydro-1,4-benzoxathiin-7-yl | 5-methyl-1,2,4-oxadiazol-3-yl | CF$_3$ |
| 4,4-dioxide-8-Me-2,3-dihydro-1,4-benzoxathiin-7-yl | 5-trifluoromethyl-1,2,4-oxadiazol-3-yl | H |

-continued

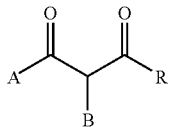

(I)

| A | B | R |
|---|---|---|
| 4,4-dioxide-8-Me-2,3-dihydro-1,4-benzoxathiin-7-yl | 5-trifluoromethyl-1,2,4-oxadiazol-3-yl | methyl |
| 4,4-dioxide-8-Me-2,3-dihydro-1,4-benzoxathiin-7-yl | 5-trifluoromethyl-1,2,4-oxadiazol-3-yl | i-propyl |
| 4,4-dioxide-8-Me-2,3-dihydro-1,4-benzoxathiin-7-yl | 5-trifluoromethyl-1,2,4-oxadiazol-3-yl | cyclopropyl |
| 4,4-dioxide-8-Me-2,3-dihydro-1,4-benzoxathiin-7-yl | 5-trifluoromethyl-1,2,4-oxadiazol-3-yl | CF$_3$ |
| 4,4-dioxide-8-Me-2,3-dihydro-1,4-benzoxathiin-7-yl | 5-chloro-1,2,4-oxadiazol-3-yl | H |
| 4,4-dioxide-8-Me-2,3-dihydro-1,4-benzoxathiin-7-yl | 5-chloro-1,2,4-oxadiazol-3-yl | methyl |
| 4,4-dioxide-8-Me-2,3-dihydro-1,4-benzoxathiin-7-yl | 5-chloro-1,2,4-oxadiazol-3-yl | i-propyl |
| 4,4-dioxide-8-Me-2,3-dihydro-1,4-benzoxathiin-7-yl | 5-chloro-1,2,4-oxadiazol-3-yl | cyclopropyl |
| 4,4-dioxide-8-Me-2,3-dihydro-1,4-benzoxathiin-7-yl | 5-chloro-1,2,4-oxadiazol-3-yl | CF$_3$ |
| 4,4-dioxide-8-Me-2,3-dihydro-1,4-benzoxathiin-7-yl | 1,3,4-oxadiazol-2-yl | H |
| 4,4-dioxide-8-Me-2,3-dihydro-1,4-benzoxathiin-7-yl | 1,3,4-oxadiazol-2-yl | methyl |
| 4,4-dioxide-8-Me-2,3-dihydro-1,4-benzoxathiin-7-yl | 1,3,4-oxadiazol-2-yl | i-propyl |
| 4,4-dioxide-8-Me-2,3-dihydro-1,4-benzoxathiin-7-yl | 1,3,4-oxadiazol-2-yl | cyclopropyl |
| 4,4-dioxide-8-Me-2,3-dihydro-1,4-benzoxathiin-7-yl | 1,3,4-oxadiazol-2-yl | CF$_3$ |
| 4,4-dioxide-8-Me-2,3-dihydro-1,4-benzoxathiin-7-yl | 5-methylsulfonyl-1,3,4-oxadiazol-2-yl | H |
| 4,4-dioxide-8-Me-2,3-dihydro-1,4-benzoxathiin-7-yl | 5-methylsulfonyl-1,3,4-oxadiazol-2-yl | methyl |
| 4,4-dioxide-8-Me-2,3-dihydro-1,4-benzoxathiin-7-yl | 5-methylsulfonyl-1,3,4-oxadiazol-2-yl | i-propyl |
| 4,4-dioxide-8-Me-2,3-dihydro-1,4-benzoxathiin-7-yl | 5-methylsulfonyl-1,3,4-oxadiazol-2-yl | cyclopropyl |
| 4,4-dioxide-8-Me-2,3-dihydro-1,4-benzoxathiin-7-yl | 5-methylsulfonyl-1,3,4-oxadiazol-2-yl | CF$_3$ |
| 4,4-dioxide-8-Me-2,3-dihydro-1,4-benzoxathiin-7-yl | 5-methyl-1,3,4-oxadiazol-2-yl | H |
| 4,4-dioxide-8-Me-2,3-dihydro-1,4-benzoxathiin-7-yl | 5-methyl-1,3,4-oxadiazol-2-yl | methyl |
| 4,4-dioxide-8-Me-2,3-dihydro-1,4-benzoxathiin-7-yl | 5-methyl-1,3,4-oxadiazol-2-yl | i-propyl |
| 4,4-dioxide-8-Me-2,3-dihydro-1,4-benzoxathiin-7-yl | 5-methyl-1,3,4-oxadiazol-2-yl | cyclopropyl |
| 4,4-dioxide-8-Me-2,3-dihydro-1,4-benzoxathiin-7-yl | 5-methyl-1,3,4-oxadiazol-2-yl | CF$_3$ |
| 4,4-dioxide-8-Me-2,3-dihydro-1,4-benzoxathiin-7-yl | 5-trifluoromethyl-1,3,4-oxadiazol-2-yl | H |
| 4,4-dioxide-8-Me-2,3-dihydro-1,4-benzoxathiin-7-yl | 5-trifluoromethyl-1,3,4-oxadiazol-2-yl | methyl |
| 4,4-dioxide-8-Me-2,3-dihydro-1,4-benzoxathiin-7-yl | 5-trifluoromethyl-1,3,4-oxadiazol-2-yl | i-propyl |
| 4,4-dioxide-8-Me-2,3-dihydro-1,4-benzoxathiin-7-yl | 5-trifluoromethyl-1,3,4-oxadiazol-2-yl | cyclopropyl |
| 4,4-dioxide-8-Me-2,3-dihydro-1,4-benzoxathiin-7-yl | 5-trifluoromethyl-1,3,4-oxadiazol-2-yl | CF$_3$ |
| 4,4-dioxide-8-Me-2,3-dihydro-1,4-benzoxathiin-7-yl | 1,2,3-triazol-4-yl | H |
| 4,4-dioxide-8-Me-2,3-dihydro-1,4-benzoxathiin-7-yl | 1,2,3-triazol-4-yl | methyl |
| 4,4-dioxide-8-Me-2,3-dihydro-1,4-benzoxathiin-7-yl | 1,2,3-triazol-4-yl | i-propyl |
| 4,4-dioxide-8-Me-2,3-dihydro-1,4-benzoxathiin-7-yl | 1,2,3-triazol-4-yl | cyclopropyl |
| 4,4-dioxide-8-Me-2,3-dihydro-1,4-benzoxathiin-7-yl | 1,2,3-triazol-4-yl | CF$_3$ |
| 4,4-dioxide-8-Me-2,3-dihydro-1,4-benzoxathiin-7-yl | 1-methyl-1,2,3-triazol-4-yl | H |
| 4,4-dioxide-8-Me-2,3-dihydro-1,4-benzoxathiin-7-yl | 1-methyl-1,2,3-triazol-4-yl | methyl |
| 4,4-dioxide-8-Me-2,3-dihydro-1,4-benzoxathiin-7-yl | 1-methyl-1,2,3-triazol-4-yl | i-propyl |
| 4,4-dioxide-8-Me-2,3-dihydro-1,4-benzoxathiin-7-yl | 1-methyl-1,2,3-triazol-4-yl | cyclopropyl |
| 4,4-dioxide-8-Me-2,3-dihydro-1,4-benzoxathiin-7-yl | 1-methyl-1,2,3-triazol-4-yl | CF$_3$ |
| 4,4-dioxide-8-Me-2,3-dihydro-1,4-benzoxathiin-7-yl | 2-methyl-1,2,3-triazol-4-yl | H |
| 4,4-dioxide-8-Me-2,3-dihydro-1,4-benzoxathiin-7-yl | 2-methyl-1,2,3-triazol-4-yl | methyl |
| 4,4-dioxide-8-Me-2,3-dihydro-1,4-benzoxathiin-7-yl | 2-methyl-1,2,3-triazol-4-yl | i-propyl |
| 4,4-dioxide-8-Me-2,3-dihydro-1,4-benzoxathiin-7-yl | 2-methyl-1,2,3-triazol-4-yl | cyclopropyl |
| 4,4-dioxide-8-Me-2,3-dihydro-1,4-benzoxathiin-7-yl | 2-methyl-1,2,3-triazol-4-yl | CF$_3$ |
| 4,4-dioxide-8-Me-2,3-dihydro-1,4-benzoxathiin-7-yl | 1,2,3-triazol-1-yl | H |
| 4,4-dioxide-8-Me-2,3-dihydro-1,4-benzoxathiin-7-yl | 1,2,3-triazol-1-yl | methyl |
| 4,4-dioxide-8-Me-2,3-dihydro-1,4-benzoxathiin-7-yl | 1,2,3-triazol-1-yl | i-propyl |

-continued

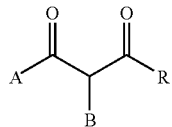

(I)

| A | B | R |
|---|---|---|
| xathiin-7-yl | | |
| 4,4-dioxide-8-Me-2,3-dihydro-1,4-benzo-xathiin-7-yl | 1,2,3-triazol-1-yl | cyclopropyl |
| 4,4-dioxide-8-Me-2,3-dihydro-1,4-benzo-xathiin-7-yl | 1,2,3-triazol-1-yl | CF$_3$ |
| 4,4-dioxide-8-Me-2,3-dihydro-1,4-benzo-xathiin-7-yl | 1,2,3-triazol-2-yl | H |
| 4,4-dioxide-8-Me-2,3-dihydro-1,4-benzo-xathiin-7-yl | 1,2,3-triazol-2-yl | methyl |
| 4,4-dioxide-8-Me-2,3-dihydro-1,4-benzo-xathiin-7-yl | 1,2,3-triazol-2-yl | i-propyl |
| 4,4-dioxide-8-Me-2,3-dihydro-1,4-benzo-xathiin-7-yl | 1,2,3-triazol-2-yl | cyclopropyl |
| 4,4-dioxide-8-Me-2,3-dihydro-1,4-benzo-xathiin-7-yl | 1,2,3-triazol-2-yl | CF$_3$ |
| 4,4-dioxide-8-Me-2,3-dihydro-1,4-benzo-xathiin-7-yl | 1,2,4-triazol-1-yl | H |
| 4,4-dioxide-8-Me-2,3-dihydro-1,4-benzo-xathiin-7-yl | 1,2,4-triazol-1-yl | methyl |
| 4,4-dioxide-8-Me-2,3-dihydro-1,4-benzo-xathiin-7-yl | 1,2,4-triazol-1-yl | i-propyl |
| 4,4-dioxide-8-Me-2,3-dihydro-1,4-benzo-xathiin-7-yl | 1,2,4-triazol-1-yl | cyclopropyl |
| 4,4-dioxide-8-Me-2,3-dihydro-1,4-benzo-xathiin-7-yl | 1,2,4-triazol-1-yl | CF$_3$ |
| 4,4-dioxide-8-Me-2,3-dihydro-1,4-benzo-xathiin-7-yl | imidazol-2-yl | H |
| 4,4-dioxide-8-Me-2,3-dihydro-1,4-benzo-xathiin-7-yl | imidazol-2-yl | methyl |
| 4,4-dioxide-8-Me-2,3-dihydro-1,4-benzo-xathiin-7-yl | imidazol-2-yl | i-propyl |
| 4,4-dioxide-8-Me-2,3-dihydro-1,4-benzo-xathiin-7-yl | imidazol-2-yl | cyclopropyl |
| 4,4-dioxide-8-Me-2,3-dihydro-1,4-benzo-xathiin-7-yl | imidazol-2-yl | CF$_3$ |
| 4,4-dioxide-8-Me-2,3-dihydro-1,4-benzo-xathiin-7-yl | imidazol-1-yl | H |
| 4,4-dioxide-8-Me-2,3-dihydro-1,4-benzo-xathiin-7-yl | imidazol-1-yl | methyl |
| 4,4-dioxide-8-Me-2,3-dihydro-1,4-benzo-xathiin-7-yl | imidazol-1-yl | i-propyl |
| 4,4-dioxide-8-Me-2,3-dihydro-1,4-benzo-xathiin-7-yl | imidazol-1-yl | cyclopropyl |
| 4,4-dioxide-8-Me-2,3-dihydro-1,4-benzo-xathiin-7-yl | imidazol-1-yl | CF$_3$ |
| 4,4-dioxide-8-Me-2,3-dihydro-1,4-benzo-xathiin-7-yl | imidazol-4-yl | H |

-continued

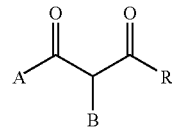

(I)

| A | B | R |
|---|---|---|
| 4,4-dioxide-8-Me-2,3-dihydro-1,4-benzo-xathiin-7-yl | imidazol-4-yl | methyl |
| 4,4-dioxide-8-Me-2,3-dihydro-1,4-benzo-xathiin-7-yl | imidazol-4-yl | i-propyl |
| 4,4-dioxide-8-Me-2,3-dihydro-1,4-benzo-xathiin-7-yl | imidazol-4-yl | cyclopropyl |
| 4,4-dioxide-8-Me-2,3-dihydro-1,4-benzo-xathiin-7-yl | imidazol-4-yl | CF$_3$ |
| 4,4-dioxide-8-Me-2,3-dihydro-1,4-benzo-xathiin-7-yl | thiazol-2-yl | H |
| 4,4-dioxide-8-Me-2,3-dihydro-1,4-benzo-xathiin-7-yl | thiazol-2-yl | methyl |
| 4,4-dioxide-8-Me-2,3-dihydro-1,4-benzo-xathiin-7-yl | thiazol-2-yl | i-propyl |
| 4,4-dioxide-8-Me-2,3-dihydro-1,4-benzo-xathiin-7-yl | thiazol-2-yl | cyclopropyl |
| 4,4-dioxide-8-Me-2,3-dihydro-1,4-benzo-xathiin-7-yl | thiazol-2-yl | CF$_3$ |
| 4,4-dioxide-8-Me-2,3-dihydro-1,4-benzo-xathiin-7-yl | 4-methylthiazol-2-yl | H |
| 4,4-dioxide-8-Me-2,3-dihydro-1,4-benzo-xathiin-7-yl | 4-methylthiazol-2-yl | methyl |
| 4,4-dioxide-8-Me-2,3-dihydro-1,4-benzo-xathiin-7-yl | 4-methylthiazol-2-yl | i-propyl |
| 4,4-dioxide-8-Me-2,3-dihydro-1,4-benzo-xathiin-7-yl | 4-methylthiazol-2-yl | cyclopropyl |
| 4,4-dioxide-8-Me-2,3-dihydro-1,4-benzo-xathiin-7-yl | 4-methylthiazol-2-yl | CF$_3$ |
| 4,4-dioxide-8-Me-2,3-dihydro-1,4-benzo-xathiin-7-yl | oxazol-2-yl | H |
| 4,4-dioxide-8-Me-2,3-dihydro-1,4-benzo-xathiin-7-yl | oxazol-2-yl | methyl |
| 4,4-dioxide-8-Me-2,3-dihydro-1,4-benzo-xathiin-7-yl | oxazol-2-yl | i-propyl |
| 4,4-dioxide-8-Me-2,3-dihydro-1,4-benzo-xathiin-7-yl | oxazol-2-yl | cyclopropyl |
| 4,4-dioxide-8-Me-2,3-dihydro-1,4-benzo-xathiin-7-yl | oxazol-2-yl | CF$_3$ |
| 4,4-dioxide-8-Me-2,3-dihydro-1,4-benzo-xathiin-7-yl | 4,5-dimethyloxazol-2-yl | H |
| 4,4-dioxide-8-Me-2,3-dihydro-1,4-benzo-xathiin-7-yl | 4,5-dimethyloxazol-2-yl | methyl |
| 4,4-dioxide-8-Me-2,3-dihydro-1,4-benzo-xathiin-7-yl | 4,5-dimethyloxazol-2-yl | i-propyl |
| 4,4-dioxide-8-Me-2,3-dihydro-1,4-benzo-xathiin-7-yl | 4,5-dimethyloxazol-2-yl | cyclopropyl |
| 4,4-dioxide-8-Me-2,3- | 4,5-dimethyloxazol-2-yl | CF$_3$ |

-continued

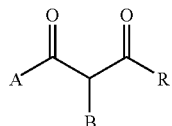

(I)

| A | B | R |
|---|---|---|
| 4,4-dioxide-8-Me-2,3-dihydro-1,4-benzoxathiin-7-yl | 2-oxazolin-2-yl | H |
| 4,4-dioxide-8-Me-2,3-dihydro-1,4-benzoxathiin-7-yl | 2-oxazolin-2-yl | methyl |
| 4,4-dioxide-8-Me-2,3-dihydro-1,4-benzoxathiin-7-yl | 2-oxazolin-2-yl | i-propyl |
| 4,4-dioxide-8-Me-2,3-dihydro-1,4-benzoxathiin-7-yl | 2-oxazolin-2-yl | cyclopropyl |
| 4,4-dioxide-8-Me-2,3-dihydro-1,4-benzoxathiin-7-yl | 2-oxazolin-2-yl | CF$_3$ |
| 4,4-dioxide-8-Me-2,3-dihydro-1,4-benzoxathiin-7-yl | 4,4-dimethyl-2-oxazolin-2-yl | H |
| 4,4-dioxide-8-Me-2,3-dihydro-1,4-benzoxathiin-7-yl | 4,4-dimethyl-2-oxazolin-2-yl | methyl |
| 4,4-dioxide-8-Me-2,3-dihydro-1,4-benzoxathiin-7-yl | 4,4-dimethyl-2-oxazolin-2-yl | i-propyl |
| 4,4-dioxide-8-Me-2,3-dihydro-1,4-benzoxathiin-7-yl | 4,4-dimethyl-2-oxazolin-2-yl | cyclopropyl |
| 4,4-dioxide-8-Me-2,3-dihydro-1,4-benzoxathiin-7-yl | 4,4-dimethyl-2-oxazolin-2-yl | CF$_3$ |
| 4,4-dioxide-8-Me-2,3-dihydro-1,4-benzoxathiin-7-yl | 1,2,4-thiadiazol-5-yl | H |
| 4,4-dioxide-8-Me-2,3-dihydro-1,4-benzoxathiin-7-yl | 1,2,4-thiadiazol-5-yl | methyl |
| 4,4-dioxide-8-Me-2,3-dihydro-1,4-benzoxathiin-7-yl | 1,2,4-thiadiazol-5-yl | i-propyl |
| 4,4-dioxide-8-Me-2,3-dihydro-1,4-benzoxathiin-7-yl | 1,2,4-thiadiazol-5-yl | cyclopropyl |
| 4,4-dioxide-8-Me-2,3-dihydro-1,4-benzoxathiin-7-yl | 1,2,4-thiadiazol-5-yl | CF$_3$ |
| 4,4-dioxide-8-Me-2,3-dihydro-1,4-benzoxathiin-7-yl | 3-methyl-1,2,4-thiadiazol-5-yl | H |
| 4,4-dioxide-8-Me-2,3-dihydro-1,4-benzoxathiin-7-yl | 3-methyl-1,2,4-thiadiazol-5-yl | methyl |
| 4,4-dioxide-8-Me-2,3-dihydro-1,4-benzoxathiin-7-yl | 3-methyl-1,2,4-thiadiazol-5-yl | i-propyl |
| 4,4-dioxide-8-Me-2,3-dihydro-1,4-benzoxathiin-7-yl | 3-methyl-1,2,4-thiadiazol-5-yl | cyclopropyl |
| 4,4-dioxide-8-Me-2,3-dihydro-1,4-benzoxathiin-7-yl | 3-methyl-1,2,4-thiadiazol-5-yl | CF$_3$ |
| 4,4-dioxide-8-Me-2,3-dihydro-1,4-benzoxathiin-7-yl | 3-trifluoromethyl-1,2,4-thiadiazol-5-yl | H |
| 4,4-dioxide-8-Me-2,3-dihydro-1,4-benzoxathiin-7-yl | 3-trifluoromethyl-1,2,4-thiadiazol-5-yl | methyl |
| 4,4-dioxide-8-Me-2,3-dihydro-1,4-benzoxathiin-7-yl | 3-trifluoromethyl-1,2,4-thiadiazol-5-yl | i-propyl |
| 4,4-dioxide-8-Me-2,3-dihydro-1,4-benzoxathiin-7-yl | 3-trifluoromethyl-1,2,4-thiadiazol-5-yl | cyclopropyl |
| 4,4-dioxide-8-Me-2,3-dihydro-1,4-benzoxathiin-7-yl | 3-trifluoromethyl-1,2,4-thiadiazol-5-yl | CF$_3$ |
| 4,4-dioxide-8-Me-2,3-dihydro-1,4-benzoxathiin-7-yl | 1,2,4-thiadiazol-3-yl | H |
| 4,4-dioxide-8-Me-2,3-dihydro-1,4-benzoxathiin-7-yl | 1,2,4-thiadiazol-3-yl | methyl |
| 4,4-dioxide-8-Me-2,3-dihydro-1,4-benzoxathiin-7-yl | 1,2,4-thiadiazol-3-yl | i-propyl |
| 4,4-dioxide-8-Me-2,3-dihydro-1,4-benzoxathiin-7-yl | 1,2,4-thiadiazol-3-yl | cyclopropyl |
| 4,4-dioxide-8-Me-2,3-dihydro-1,4-benzoxathiin-7-yl | 1,2,4-thiadiazol-3-yl | CF$_3$ |
| 4,4-dioxide-8-Me-2,3-dihydro-1,4-benzoxathiin-7-yl | 5-methyl-1,2,4-thiadiazol-3-yl | H |
| 4,4-dioxide-8-Me-2,3-dihydro-1,4-benzoxathiin-7-yl | 5-methyl-1,2,4-thiadiazol-3-yl | methyl |
| 4,4-dioxide-8-Me-2,3-dihydro-1,4-benzoxathiin-7-yl | 5-methyl-1,2,4-thiadiazol-3-yl | i-propyl |
| 4,4-dioxide-8-Me-2,3-dihydro-1,4-benzoxathiin-7-yl | 5-methyl-1,2,4-thiadiazol-3-yl | cyclopropyl |
| 4,4-dioxide-8-Me-2,3-dihydro-1,4-benzoxathiin-7-yl | 5-methyl-1,2,4-thiadiazol-3-yl | CF$_3$ |
| 4,4-dioxide-8-Me-2,3-dihydro-1,4-benzoxathiin-7-yl | 5-trifluoromethyl-1,2,4-thiadiazol-3-yl | H |
| 4,4-dioxide-8-Me-2,3-dihydro-1,4-benzoxathiin-7-yl | 5-trifluoromethyl-1,2,4-thiadiazol-3-yl | methyl |
| 4,4-dioxide-8-Me-2,3-dihydro-1,4-benzoxathiin-7-yl | 5-trifluoromethyl-1,2,4-thiadiazol-3-yl | i-propyl |
| 4,4-dioxide-8-Me-2,3-dihydro-1,4-benzoxathiin-7-yl | 5-trifluoromethyl-1,2,4-thiadiazol-3-yl | cyclopropyl |
| 4,4-dioxide-8-Me-2,3-dihydro-1,4-benzoxathiin-7-yl | 5-trifluoromethyl-1,2,4-thiadiazol-3-yl | CF$_3$ |
| 4,4-dioxide-8-Me-2,3-dihydro-1,4-benzoxathiin-7-yl | 1,3,4-thiadiazol-2-yl | H |
| 4,4-dioxide-8-Me-2,3-dihydro-1,4-benzoxathiin-7-yl | 1,3,4-thiadiazol-2-yl | methyl |
| 4,4-dioxide-8-Me-2,3-dihydro-1,4-benzoxathiin-7-yl | 1,3,4-thiadiazol-2-yl | i-propyl |
| 4,4-dioxide-8-Me-2,3-dihydro-1,4-benzoxathiin-7-yl | 1,3,4-thiadiazol-2-yl | cyclopropyl |
| 4,4-dioxide-8-Me-2,3-dihydro-1,4-benzoxathiin-7-yl | 1,3,4-thiadiazol-2-yl | CF$_3$ |
| 4,4-dioxide-8-Me-2,3-dihydro-1,4-benzoxathiin-7-yl | 5-methylsulfonyl-1,3,4-thiadiazol-2-yl | H |

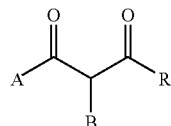

(I)

-continued

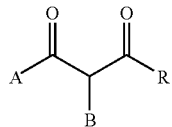
(I)

| A | B | R |
|---|---|---|
| 4,4-dioxide-8-Me-2,3-dihydro-1,4-benzo-xathiin-7-yl | 5-methylsulfonyl-1,3,4-thiadiazol-2-yl | methyl |
| 4,4-dioxide-8-Me-2,3-dihydro-1,4-benzo-xathiin-7-yl | 5-methylsulfonyl-1,3,4-thiadiazol-2-yl | i-propyl |
| 4,4-dioxide-8-Me-2,3-dihydro-1,4-benzo-xathiin-7-yl | 5-methylsulfonyl-1,3,4-thiadiazol-2-yl | cyclopropyl |
| 4,4-dioxide-8-Me-2,3-dihydro-1,4-benzo-xathiin-7-yl | 5-methylsulfonyl-1,3,4-thiadiazol-2-yl | $CF_3$ |
| 4,4-dioxide-8-Me-2,3-dihydro-1,4-benzo-xathiin-7-yl | 5-methyl-1,3,4-thiadiazol-2-yl | H |
| 4,4-dioxide-8-Me-2,3-dihydro-1,4-benzo-xathiin-7-yl | 5-methyl-1,3,4-thiadiazol-2-yl | methyl |
| 4,4-dioxide-8-Me-2,3-dihydro-1,4-benzo-xathiin-7-yl | 5-methyl-1,3,4-thiadiazol-2-yl | i-propyl |
| 4,4-dioxide-8-Me-2,3-dihydro-1,4-benzo-xathiin-7-yl | 5-methyl-1,3,4-thiadiazol-2-yl | cyclopropyl |
| 4,4-dioxide-8-Me-2,3-dihydro-1,4-benzo-xathiin-7-yl | 5-methyl-1,3,4-thiadiazol-2-yl | $CF_3$ |
| 4,4-dioxide-8-Me-2,3-dihydro-1,4-benzo-xathiin-7-yl | benzoxazol-2-yl | H |
| 4,4-dioxide-8-Me-2,3-dihydro-1,4-benzo-xathiin-7-yl | benzoxazol-2-yl | methyl |
| 4,4-dioxide-8-Me-2,3-dihydro-1,4-benzo-xathiin-7-yl | benzoxazol-2-yl | i-propyl |
| 4,4-dioxide-8-Me-2,3-dihydro-1,4-benzo-xathiin-7-yl | benzoxazol-2-yl | cyclopropyl |
| 4,4-dioxide-8-Me-2,3-dihydro-1,4-benzo-xathiin-7-yl | benzoxazol-2-yl | $CF_3$ |
| 4,4-dioxide-8-Me-2,3-dihydro-1,4-benzo-xathiin-7-yl | 6-methylbenzoxazol-2-yl | H |
| 4,4-dioxide-8-Me-2,3-dihydro-1,4-benzo-xathiin-7-yl | 6-methylbenzoxazol-2-yl | methyl |
| 4,4-dioxide-8-Me-2,3-dihydro-1,4-benzo-xathiin-7-yl | 6-methylbenzoxazol-2-yl | i-propyl |
| 4,4-dioxide-8-Me-2,3-dihydro-1,4-benzo-xathiin-7-yl | 6-methylbenzoxazol-2-yl | cyclopropyl |
| 4,4-dioxide-8-Me-2,3-dihydro-1,4-benzo-xathiin-7-yl | 6-methylbenzoxazol-2-yl | $CF_3$ |
| 4,4-dioxide-8-Me-2,3-dihydro-1,4-benzo-xathiin-7-yl | benzothiazol-2-yl | H |
| 4,4-dioxide-8-Me-2,3-dihydro-1,4-benzo-xathiin-7-yl | benzothiazol-2-yl | methyl |
| 4,4-dioxide-8-Me-2,3-dihydro-1,4-benzo-xathiin-7-yl | benzothiazol-2-yl | i-propyl |
| 4,4-dioxide-8-Me-2,3-dihydro-1,4-benzo-xathiin-7-yl | benzothiazol-2-yl | cyclopropyl |
| 4,4-dioxide-8-Me-2,3-dihydro-1,4-benzo-xathiin-7-yl | benzothiazol-2-yl | $CF_3$ |
| 4,4-dioxide-8-Me-2,3-dihydro-1,4-benzo-xathiin-7-yl | pyrazol-1-yl | H |
| 4,4-dioxide-8-Me-2,3-dihydro-1,4-benzo-xathiin-7-yl | pyrazol-1-yl | methyl |
| 4,4-dioxide-8-Me-2,3-dihydro-1,4-benzo-xathiin-7-yl | pyrazol-1-yl | i-propyl |
| 4,4-dioxide-8-Me-2,3-dihydro-1,4-benzo-xathiin-7-yl | pyrazol-1-yl | cyclopropyl |
| 4,4-dioxide-8-Me-2,3-dihydro-1,4-benzo-xathiin-7-yl | pyrazol-1-yl | $CF_3$ |
| 4,4-dioxide-8-Me-2,3-dihydro-1,4-benzo-xathiin-7-yl | pyrazol-3-yl | H |
| 4,4-dioxide-8-Me-2,3-dihydro-1,4-benzo-xathiin-7-yl | pyrazol-3-yl | methyl |
| 4,4-dioxide-8-Me-2,3-dihydro-1,4-benzo-xathiin-7-yl | pyrazol-3-yl | i-propyl |
| 4,4-dioxide-8-Me-2,3-dihydro-1,4-benzo-xathiin-7-yl | pyrazol-3-yl | cyclopropyl |
| 4,4-dioxide-8-Me-2,3-dihydro-1,4-benzo-xathiin-7-yl | pyrazol-3-yl | $CF_3$ |
| 4,4-dioxide-8-Me-2,3-dihydro-1,4-benzo-xathiin-7-yl | 1-methylpyrazol-3-yl | H |
| 4,4-dioxide-8-Me-2,3-dihydro-1,4-benzo-xathiin-7-yl | 1-methylpyrazol-3-yl | methyl |
| 4,4-dioxide-8-Me-2,3-dihydro-1,4-benzo-xathiin-7-yl | 1-methylpyrazol-3-yl | i-propyl |
| 4,4-dioxide-8-Me-2,3-dihydro-1,4-benzo-xathiin-7-yl | 1-methylpyrazol-3-yl | cyclopropyl |
| 4,4-dioxide-8-Me-2,3-dihydro-1,4-benzo-xathiin-7-yl | 1-methylpyrazol-3-yl | $CF_3$ |
| 4,4-dioxide-8-Me-2,3-dihydro-1,4-benzo-xathiin-7-yl | tetrazol-1-yl | H |
| 4,4-dioxide-8-Me-2,3-dihydro-1,4-benzo-xathiin-7-yl | tetrazol-1-yl | methyl |
| 4,4-dioxide-8-Me-2,3-dihydro-1,4-benzo-xathiin-7-yl | tetrazol-1-yl | i-propyl |
| 4,4-dioxide-8-Me-2,3-dihydro-1,4-benzo-xathiin-7-yl | tetrazol-1-yl | cyclopropyl |
| 4,4-dioxide-8-Me-2,3-dihydro-1,4-benzo-xathiin-7-yl | tetrazol-1-yl | $CF_3$ |
| 4,4-dioxide-8-Me-2,3-dihydro-1,4-benzo-xathiin-7-yl | 5-methyltetrazol-1-yl | H |
| 4,4-dioxide-8-Me-2,3-dihydro-1,4-benzo-xathiin-7-yl | 5-methyltetrazol-1-yl | methyl |
| 4,4-dioxide-8-Me-2,3-dihydro-1,4-benzo-xathiin-7-yl | 5-methyltetrazol-1-yl | i-propyl |

-continued

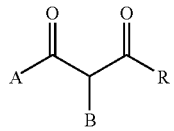
(I)

| A | B | R |
|---|---|---|
| 4,4-dioxide-8-Me-2,3-dihydro-1,4-benzoxathiin-7-yl | 5-methyltetrazol-1-yl | cyclopropyl |
| 4,4-dioxide-8-Me-2,3-dihydro-1,4-benzoxathiin-7-yl | 5-methyltetrazol-1-yl | CF$_3$ |
| 4,4-dioxide-8-Me-2,3-dihydro-1,4-benzoxathiin-7-yl | tetrazol-2-yl | H |
| 4,4-dioxide-8-Me-2,3-dihydro-1,4-benzoxathiin-7-yl | tetrazol-2-yl | methyl |
| 4,4-dioxide-8-Me-2,3-dihydro-1,4-benzoxathiin-7-yl | tetrazol-2-yl | i-propyl |
| 4,4-dioxide-8-Me-2,3-dihydro-1,4-benzoxathiin-7-yl | tetrazol-2-yl | cyclopropyl |
| 4,4-dioxide-8-Me-2,3-dihydro-1,4-benzoxathiin-7-yl | tetrazol-2-yl | CF$_3$ |
| 4,4-dioxide-8-Me-2,3-dihydro-1,4-benzoxathiin-7-yl | 5-methyltetrazol-2-yl | H |
| 4,4-dioxide-8-Me-2,3-dihydro-1,4-benzoxathiin-7-yl | 5-methyltetrazol-2-yl | methyl |
| 4,4-dioxide-8-Me-2,3-dihydro-1,4-benzoxathiin-7-yl | 5-methyltetrazol-2-yl | i-propyl |
| 4,4-dioxide-8-Me-2,3-dihydro-1,4-benzoxathiin-7-yl | 5-methyltetrazol-2-yl | cyclopropyl |
| 4,4-dioxide-8-Me-2,3-dihydro-1,4-benzoxathiin-7-yl | 5-methyltetrazol-2-yl | CF$_3$ |
| 4,4-dioxide-8-Me-2,3-dihydro-1,4-benzoxathiin-7-yl | 1-methyltetrazol-5-yl | H |
| 4,4-dioxide-8-Me-2,3-dihydro-1,4-benzoxathiin-7-yl | 1-methyltetrazol-5-yl | methyl |
| 4,4-dioxide-8-Me-2,3-dihydro-1,4-benzoxathiin-7-yl | 1-methyltetrazol-5-yl | i-propyl |
| 4,4-dioxide-8-Me-2,3-dihydro-1,4-benzoxathiin-7-yl | 1-methyltetrazol-5-yl | cyclopropyl |
| 4,4-dioxide-8-Me-2,3-dihydro-1,4-benzoxathiin-7-yl | 1-methyltetrazol-5-yl | CF$_3$ |
| 4,4-dioxide-8-Me-2,3-dihydro-1,4-benzoxathiin-7-yl | 2-methyltetrazol-5-yl | H |
| 4,4-dioxide-8-Me-2,3-dihydro-1,4-benzoxathiin-7-yl | 2-methyltetrazol-5-yl | methyl |
| 4,4-dioxide-8-Me-2,3-dihydro-1,4-benzoxathiin-7-yl | 2-methyltetrazol-5-yl | i-propyl |
| 4,4-dioxide-8-Me-2,3-dihydro-1,4-benzoxathiin-7-yl | 2-methyltetrazol-5-yl | cyclopropyl |
| 4,4-dioxide-8-Me-2,3-dihydro-1,4-benzoxathiin-7-yl | 2-methyltetrazol-5-yl | CF$_3$ |
| 4,4-dioxide-8-Me-2,3-dihydro-1,4-benzoxathiin-7-yl | pyridin-2-yl | H |

-continued

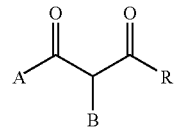
(I)

| A | B | R |
|---|---|---|
| 4,4-dioxide-8-Me-2,3-dihydro-1,4-benzoxathiin-7-yl | pyridin-2-yl | methyl |
| 4,4-dioxide-8-Me-2,3-dihydro-1,4-benzoxathiin-7-yl | pyridin-2-yl | i-propyl |
| 4,4-dioxide-8-Me-2,3-dihydro-1,4-benzoxathiin-7-yl | pyridin-2-yl | cyclopropyl |
| 4,4-dioxide-8-Me-2,3-dihydro-1,4-benzoxathiin-7-yl | pyridin-2-yl | CF$_3$ |
| 4,4-dioxide-8-Me-2,3-dihydro-1,4-benzoxathiin-7-yl | pyridin-4-yl | H |
| 4,4-dioxide-8-Me-2,3-dihydro-1,4-benzoxathiin-7-yl | pyridin-4-yl | methyl |
| 4,4-dioxide-8-Me-2,3-dihydro-1,4-benzoxathiin-7-yl | pyridin-4-yl | i-propyl |
| 4,4-dioxide-8-Me-2,3-dihydro-1,4-benzoxathiin-7-yl | pyridin-4-yl | cyclopropyl |
| 4,4-dioxide-8-Me-2,3-dihydro-1,4-benzoxathiin-7-yl | pyridin-4-yl | CF$_3$ |
| 4,4-dioxide-8-Me-2,3-dihydro-1,4-benzoxathiin-7-yl | pyridin-3-yl | H |
| 4,4-dioxide-8-Me-2,3-dihydro-1,4-benzoxathiin-7-yl | pyridin-3-yl | methyl |
| 4,4-dioxide-8-Me-2,3-dihydro-1,4-benzoxathiin-7-yl | pyridin-3-yl | i-propyl |
| 4,4-dioxide-8-Me-2,3-dihydro-1,4-benzoxathiin-7-yl | pyridin-3-yl | cyclopropyl |
| 4,4-dioxide-8-Me-2,3-dihydro-1,4-benzoxathiin-7-yl | pyridin-3-yl | CF$_3$ |
| 4,4-dioxide-8-Me-2,3-dihydro-1,4-benzoxathiin-7-yl | 3-nitropyridin-4-yl | H |
| 4,4-dioxide-8-Me-2,3-dihydro-1,4-benzoxathiin-7-yl | 3-nitropyridin-4-yl | methyl |
| 4,4-dioxide-8-Me-2,3-dihydro-1,4-benzoxathiin-7-yl | 3-nitropyridin-4-yl | i-propyl |
| 4,4-dioxide-8-Me-2,3-dihydro-1,4-benzoxathiin-7-yl | 3-nitropyridin-4-yl | cyclopropyl |
| 4,4-dioxide-8-Me-2,3-dihydro-1,4-benzoxathiin-7-yl | 3-nitropyridin-4-yl | CF$_3$ |
| 4,4-dioxide-8-Me-2,3-dihydro-1,4-benzoxathiin-7-yl | 5-cyanopyridin-2-yl | H |
| 4,4-dioxide-8-Me-2,3-dihydro-1,4-benzoxathiin-7-yl | 5-cyanopyridin-2-yl | methyl |
| 4,4-dioxide-8-Me-2,3-dihydro-1,4-benzoxathiin-7-yl | 5-cyanopyridin-2-yl | i-propyl |
| 4,4-dioxide-8-Me-2,3-dihydro-1,4-benzoxathiin-7-yl | 5-cyanopyridin-2-yl | cyclopropyl |
| 4,4-dioxide-8-Me-2,3-dihydro-1,4-benzoxathiin-7-yl | 5-cyanopyridin-2-yl | CF$_3$ |

-continued

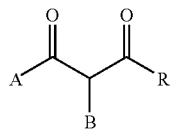

(I)

| A | B | R |
|---|---|---|
| dihydro-1,4-benzo-xathiin-7-yl | | |
| 4,4-dioxide-8-Me-2,3-dihydro-1,4-benzo-xathiin-7-yl | 5-trifluoromethylpyridin-2-yl | H |
| 4,4-dioxide-8-Me-2,3-dihydro-1,4-benzo-xathiin-7-yl | 5-trifluoromethylpyridin-2-yl | methyl |
| 4,4-dioxide-8-Me-2,3-dihydro-1,4-benzo-xathiin-7-yl | 5-trifluoromethylpyridin-2-yl | i-propyl |
| 4,4-dioxide-8-Me-2,3-dihydro-1,4-benzo-xathiin-7-yl | 5-trifluoromethylpyridin-2-yl | cyclopropyl |
| 4,4-dioxide-8-Me-2,3-dihydro-1,4-benzo-xathiin-7-yl | 5-trifluoromethylpyridin-2-yl | $CF_3$ |
| 4,4-dioxide-8-Me-2,3-dihydro-1,4-benzo-xathiin-7-yl | pyrimidin-2-yl | H |
| 4,4-dioxide-8-Me-2,3-dihydro-1,4-benzo-xathiin-7-yl | pyrimidin-2-yl | methyl |
| 4,4-dioxide-8-Me-2,3-dihydro-1,4-benzo-xathiin-7-yl | pyrimidin-2-yl | i-propyl |
| 4,4-dioxide-8-Me-2,3-dihydro-1,4-benzo-xathiin-7-yl | pyrimidin-2-yl | cyclopropyl |
| 4,4-dioxide-8-Me-2,3-dihydro-1,4-benzo-xathiin-7-yl | pyrimidin-2-yl | $CF_3$ |
| 4,4-dioxide-8-Me-2,3-dihydro-1,4-benzo-xathiin-7-yl | pyrimidin-4-yl | H |
| 4,4-dioxide-8-Me-2,3-dihydro-1,4-benzo-xathiin-7-yl | pyrimidin-4-yl | methyl |
| 4,4-dioxide-8-Me-2,3-dihydro-1,4-benzo-xathiin-7-yl | pyrimidin-4-yl | i-propyl |
| 4,4-dioxide-8-Me-2,3-dihydro-1,4-benzo-xathiin-7-yl | pyrimidin-4-yl | cyclopropyl |
| 4,4-dioxide-8-Me-2,3-dihydro-1,4-benzo-xathiin-7-yl | pyrimidin-4-yl | $CF_3$ |
| 4,4-dioxide-8-Me-2,3-dihydro-1,4-benzo-xathiin-7-yl | 6-chloropyrimidin-4-yl | methyl |
| 4,4-dioxide-8-Me-2,3-dihydro-1,4-benzo-xathiin-7-yl | 6-chloropyrimidin-4-yl | i-propyl |
| 4,4-dioxide-8-Me-2,3-dihydro-1,4-benzo-xathiin-7-yl | 6-chloropyrimidin-4-yl | cyclopropyl |
| 4,4-dioxide-8-Me-2,3-dihydro-1,4-benzo-xathiin-7-yl | 6-chloropyrimidin-4-yl | $CF_3$ |
| 4,4-dioxide-8-Me-2,3-dihydro-1,4-benzo-xathiin-7-yl | pyridazin-3-yl | H |
| 4,4-dioxide-8-Me-2,3-dihydro-1,4-benzo-xathiin-7-yl | pyridazin-3-yl | methyl |
| 4,4-dioxide-8-Me-2,3-dihydro-1,4-benzo-xathiin-7-yl | pyridazin-3-yl | i-propyl |
| 4,4-dioxide-8-Me-2,3-dihydro-1,4-benzo-xathiin-7-yl | pyridazin-3-yl | cyclopropyl |

-continued

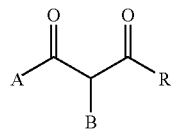

(I)

| A | B | R |
|---|---|---|
| 4,4-dioxide-8-Me-2,3-dihydro-1,4-benzo-xathiin-7-yl | pyridazin-3-yl | $CF_3$ |
| 4,4-dioxide-8-Me-2,3-dihydro-1,4-benzo-xathiin-7-yl | 6-chloropyridazin-3-yl | methyl |
| 4,4-dioxide-8-Me-2,3-dihydro-1,4-benzo-xathiin-7-yl | 6-chloropyridazin-3-yl | i-propyl |
| 4,4-dioxide-8-Me-2,3-dihydro-1,4-benzo-xathiin-7-yl | 6-chloropyridazin-3-yl | cyclopropyl |
| 4,4-dioxide-8-Me-2,3-dihydro-1,4-benzo-xathiin-7-yl | 6-chloropyridazin-3-yl | $CF_3$ |
| 4,4-dioxide-8-Me-2,3-dihydro-1,4-benzo-xathiin-7-yl | pyrazin-2-yl | methyl |
| 4,4-dioxide-8-Me-2,3-dihydro-1,4-benzo-xathiin-7-yl | pyrazin-2-yl | i-propyl |
| 4,4-dioxide-8-Me-2,3-dihydro-1,4-benzo-xathiin-7-yl | pyrazin-2-yl | cyclopropyl |
| 4,4-dioxide-8-Me-2,3-dihydro-1,4-benzo-xathiin-7-yl | pyrazin-2-yl | $CF_3$ |
| 4,4-dioxide-8-Me-2,3-dihydro-1,4-benzo-xathiin-7-yl | triazin-2-yl | methyl |
| 4,4-dioxide-8-Me-2,3-dihydro-1,4-benzo-xathiin-7-yl | triazin-2-yl | i-propyl |
| 4,4-dioxide-8-Me-2,3-dihydro-1,4-benzo-xathiin-7-yl | triazin-2-yl | cyclopropyl |
| 4,4-dioxide-8-Me-2,3-dihydro-1,4-benzo-xathiin-7-yl | triazin-2-yl | $CF_3$ |
| 4,4-dioxide-8-Me-2,3-dihydro-1,4-benzo-xathiin-7-yl | quinolin-2-yl | methyl |
| 4,4-dioxide-8-Me-2,3-dihydro-1,4-benzo-xathiin-7-yl | quinolin-2-yl | i-propyl |
| 4,4-dioxide-8-Me-2,3-dihydro-1,4-benzo-xathiin-7-yl | quinolin-2-yl | cyclopropyl |
| 4,4-dioxide-8-Me-2,3-dihydro-1,4-benzo-xathiin-7-yl | quinolin-2-yl | $CF_3$ |
| 4,4-dioxide-8-Me-2,3-dihydro-1,4-benzo-xathiin-7-yl | 4,4,6-trimethyl-5,6-dihydro-1,3(4H)-oxazin-2-yl | H |
| 4,4-dioxide-8-Me-2,3-dihydro-1,4-benzo-xathiin-7-yl | 4,4,6-trimethyl-5,6-dihydro-1,3(4H)-oxazin-2-yl | methyl |
| 4,4-dioxide-8-Me-2,3-dihydro-1,4-benzo-xathiin-7-yl | 4,4,6-trimethyl-5,6-dihydro-1,3(4H)-oxazin-2-yl | i-propyl |
| 4,4-dioxide-8-Me-2,3-dihydro-1,4-benzo-xathiin-7-yl | 4,4,6-trimethyl-5,6-dihydro-1,3(4H)-oxazin-2-yl | cyclopropyl |
| 4,4-dioxide-8-Me-2,3-dihydro-1,4-benzo-xathiin-7-yl | 4,4,6-trimethyl-5,6-dihydro-1,3(4H)-oxazin-2-yl | $CF_3$ |
| 4,4-dioxide-8-Me-2,3-dihydro-1,4-benzo-xathiin-7-yl | 2-oxazolidinon-3-yl | H |

-continued

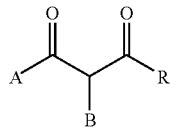
(I)

| A | B | R |
|---|---|---|
| 4,4-dioxide-8-Me-2,3-dihydro-1,4-benzoxathiin-7-yl | 2-oxazolidinon-3-yl | methyl |
| 4,4-dioxide-8-Me-2,3-dihydro-1,4-benzoxathiin-7-yl | 2-oxazolidinon-3-yl | i-propyl |
| 4,4-dioxide-8-Me-2,3-dihydro-1,4-benzoxathiin-7-yl | 2-oxazolidinon-3-yl | cyclopropyl |
| 4,4-dioxide-8-Me-2,3-dihydro-1,4-benzoxathiin-7-yl | 2-oxazolidinon-3-yl | $CF_3$ |
| 4,4-dioxide-8-Me-2,3-dihydro-1,4-benzoxathiin-7-yl | 2-pyrrolidinon-1-yl | methyl |
| 4,4-dioxide-8-Me-2,3-dihydro-1,4-benzoxathiin-7-yl | 2-pyrrolidinon-1-yl | i-propyl |
| 4,4-dioxide-8-Me-2,3-dihydro-1,4-benzoxathiin-7-yl | 2-pyrrolidinon-1-yl | cyclopropyl |
| 4,4-dioxide-8-Me-2,3-dihydro-1,4-benzoxathiin-7-yl | 2-pyrrolidinon-1-yl | $CF_3$ |
| 4,4-dioxide-8-Me-2,3-dihydro-1,4-benzoxathiin-7-yl | 3-methylisoxazol-5-yl | methyl |
| 4,4-dioxide-8-Me-2,3-dihydro-1,4-benzoxathiin-7-yl | 3-methylisoxazol-5-yl | i-propyl |
| 4,4-dioxide-8-Me-2,3-dihydro-1,4-benzoxathiin-7-yl | 3-methylisoxazol-5-yl | cyclopropyl |
| 4,4-dioxide-8-Me-2,3-dihydro-1,4-benzoxathiin-7-yl | 3-methylisoxazol-5-yl | $CF_3$ |
| 4,4-dioxide-8-Me-2,3-dihydro-1,4-benzoxathiin-7-yl | 2-$NO_2$-4-$SO_2$MePh | H |
| 4,4-dioxide-8-Me-2,3-dihydro-1,4-benzoxathiin-7-yl | 2-$NO_2$-4-$SO_2$MePh | methyl |
| 4,4-dioxide-8-Me-2,3-dihydro-1,4-benzoxathiin-7-yl | 2-$NO_2$-4-$SO_2$MePh | i-propyl |
| 4,4-dioxide-8-Me-2,3-dihydro-1,4-benzoxathiin-7-yl | 2-$NO_2$-4-$SO_2$MePh | cyclopropyl |
| 4,4-dioxide-8-Me-2,3-dihydro-1,4-benzoxathiin-7-yl | 2-$NO_2$-4-$SO_2$MePh | $CF_3$ |
| 4,4-dioxide-8-Me-2,3-dihydro-1,4-benzoxathiin-7-yl | 2-Cl-4-$SO_2$MePh | H |
| 4,4-dioxide-8-Me-2,3-dihydro-1,4-benzoxathiin-7-yl | 2-Cl-4-$SO_2$MePh | methyl |
| 4,4-dioxide-8-Me-2,3-dihydro-1,4-benzoxathiin-7-yl | 2-Cl-4-$SO_2$MePh | i-propyl |
| 4,4-dioxide-8-Me-2,3-dihydro-1,4-benzoxathiin-7-yl | 2-Cl-4-$SO_2$MePh | cyclopropyl |
| 4,4-dioxide-8-Me-2,3-dihydro-1,4-benzoxathiin-7-yl | 2-Cl-4-$SO_2$MePh | $CF_3$ |
| 4,4-dioxide-8-Me-2,3-dihydro-1,4-benzoxathiin-7-yl | 2-$NO_2$-4-$CF_3$Ph | H |
| 4,4-dioxide-8-Me-2,3-dihydro-1,4-benzoxathiin-7-yl | 2-$NO_2$-4-$CF_3$Ph | methyl |

-continued

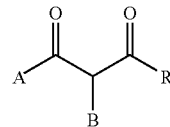
(I)

| A | B | R |
|---|---|---|
| 4,4-dioxide-8-Me-2,3-dihydro-1,4-benzoxathiin-7-yl | 2-$NO_2$-4-$CF_3$Ph | i-propyl |
| 4,4-dioxide-8-Me-2,3-dihydro-1,4-benzoxathiin-7-yl | 2-$NO_2$-4-$CF_3$Ph | cyclopropyl |
| 4,4-dioxide-8-Me-2,3-dihydro-1,4-benzoxathiin-7-yl | 2-$NO_2$-4-$CF_3$Ph | $CF_3$ |
| 4,4-dioxide-8-Me-2,3-dihydro-1,4-benzoxathiin-7-yl | 2-$NO_2$-4-ClPh | H |
| 4,4-dioxide-8-Me-2,3-dihydro-1,4-benzoxathiin-7-yl | 2-$NO_2$-4-ClPh | methyl |
| 4,4-dioxide-8-Me-2,3-dihydro-1,4-benzoxathiin-7-yl | 2-$NO_2$-4-ClPh | i-propyl |
| 4,4-dioxide-8-Me-2,3-dihydro-1,4-benzoxathiin-7-yl | 2-$NO_2$-4-ClPh | cyclopropyl |
| 4,4-dioxide-8-Me-2,3-dihydro-1,4-benzoxathiin-7-yl | 2-$NO_2$-4-ClPh | $CF_3$ |
| 4,4-dioxide-8-Me-2,3-dihydro-1,4-benzoxathiin-7-yl | 2-Cl-4-$NO_2$Ph | H |
| 4,4-dioxide-8-Me-2,3-dihydro-1,4-benzoxathiin-7-yl | 2-Cl-4-$NO_2$Ph | methyl |
| 4,4-dioxide-8-Me-2,3-dihydro-1,4-benzoxathiin-7-yl | 2-Cl-4-$NO_2$Ph | i-propyl |
| 4,4-dioxide-8-Me-2,3-dihydro-1,4-benzoxathiin-7-yl | 2-Cl-4-$NO_2$Ph | cyclopropyl |
| 4,4-dioxide-8-Me-2,3-dihydro-1,4-benzoxathiin-7-yl | 2-Cl-4-$NO_2$Ph | $CF_3$ |
| 4,4-dioxide-8-Me-2,3-dihydro-1,4-benzoxathiin-7-yl | 2,4-$(NO_2)_2$Ph | H |
| 4,4-dioxide-8-Me-2,3-dihydro-1,4-benzoxathiin-7-yl | 2,4-$(NO_2)_2$Ph | methyl |
| 4,4-dioxide-8-Me-2,3-dihydro-1,4-benzoxathiin-7-yl | 2,4-$(NO_2)_2$Ph | i-propyl |
| 4,4-dioxide-8-Me-2,3-dihydro-1,4-benzoxathiin-7-yl | 2,4-$(NO_2)_2$Ph | cyclopropyl |
| 4,4-dioxide-8-Me-2,3-dihydro-1,4-benzoxathiin-7-yl | 2,4-$(NO_2)_2$Ph | $CF_3$ |
| 4,4-dioxide-8-Me-2,3-dihydro-1,4-benzoxathiin-7-yl | 4-F-3-$NO_2$Ph | H |
| 4,4-dioxide-8-Me-2,3-dihydro-1,4-benzoxathiin-7-yl | 4-F-3-$NO_2$Ph | methyl |
| 4,4-dioxide-8-Me-2,3-dihydro-1,4-benzoxathiin-7-yl | 4-F-3-$NO_2$Ph | i-propyl |
| 4,4-dioxide-8-Me-2,3-dihydro-1,4-benzoxathiin-7-yl | 4-F-3-$NO_2$Ph | cyclopropyl |
| 4,4-dioxide-8-Me-2,3-dihydro-1,4-benzoxathiin-7-yl | 4-F-3-$NO_2$Ph | $CF_3$ |

-continued

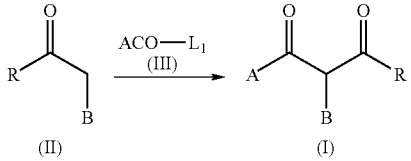
(I)

| A | B | R |
|---|---|---|
| 4,4-dioxide-8-Me-2,3-dihydro-1,4-benzoxathiin-7-yl | 3,5-$(CF_3)_2$Ph | H |
| 4,4-dioxide-8-Me-2,3-dihydro-1,4-benzoxathiin-7-yl | 3,5-$(CF_3)_2$Ph | methyl |
| 4,4-dioxide-8-Me-2,3-dihydro-1,4-benzoxathiin-7-yl | 3,5-$(CF_3)_2$Ph | i-propyl |
| 4,4-dioxide-8-Me-2,3-dihydro-1,4-benzoxathiin-7-yl | 3,5-$(CF_3)_2$Ph | cyclopropyl |
| 4,4-dioxide-8-Me-2,3-dihydro-1,4-benzoxathiin-7-yl | 3,5-$(CF_3)_2$Ph | $CF_3$ |
| 4,4-dioxide-8-Me-2,3-dihydro-1,4-benzoxathiin-7-yl | 2-$SO_2$Me-4-$CF_3$Ph | H |
| 4,4-dioxide-8-Me-2,3-dihydro-1,4-benzoxathiin-7-yl | 2-$SO_2$Me-4-$CF_3$Ph | methyl |
| 4,4-dioxide-8-Me-2,3-dihydro-1,4-benzoxathiin-7-yl | 2-$SO_2$Me-4-$CF_3$Ph | i-propyl |
| 4,4-dioxide-8-Me-2,3-dihydro-1,4-benzoxathiin-7-yl | 2-$SO_2$Me-4-$CF_3$Ph | cyclopropyl |
| 4,4-dioxide-8-Me-2,3-dihydro-1,4-benzoxathiin-7-yl | 2-$SO_2$Me-4-$CF_3$Ph | $CF_3$ |
| 2-Cl-4-$SO_2$MePh | 2-trifluoromethyl-1,3,4-thiadiazol-5-yl | cyclopropyl |
| 2-Cl-4-$SO_2$MePh | 1,1-dioxido-3-oxo-1,2-benzisothiazol-2(3H)-yl | cyclopropyl |
| 4-Cl—Ph | 2-t-butyl-1,3,4-oxadiazol-5-yl | CF3 |
| 2-Me-6-$CF_3$Pyridin-3-yl | 2-methyltetrazol-5-yl | cyclopropyl |
| 2-[(2-methoxyethoxy)methyl]-6-$CF_3$Pyridin-3-yl | 2-methyltetrazol-5-yl | cyclopropyl |
| 2-Cl-4-$SO_2$MePh | 2,5-dioxopyrrolidin-1-yl | cyclopropyl |
| 2-Cl-4-$SO_2$MePh | 2-oxopyridin-1(2H)-yl | cyclopropyl |
| 2-Cl-4-$SO_2$MePh | 2-oxoquinolin-1(2H)-yl | cyclopropyl |
| 2-Cl-4-$SO_2$MePh | 1,2-benzisoxazol-3-yl | cyclopropyl |
| 2-Cl-4-$SO_2$MePh | 2-oxo-1,3-benzoxazol-3(2H)-yl | cyclopropyl |
| 2-Cl-4-$SO_2$MePh | 3-oxo-2,3-dihydro-4H-1,4-benzoxazin-4-yl | cyclopropyl |
| 2-Cl-4-$SO_2$MePh | 2-oxopyrimidin-1(2H)-yl | cyclopropyl |
| 2-Cl-4-$SO_2$MePh | 1H-1,2,3-benzotriazol-1-yl | cyclopropyl |
| 2-$NO_2$-4-$SO_2$MePh | 2,5-dioxopyrrolidin-1-yl | cyclopropyl |
| 2-$NO_2$-4-$SO_2$MePh | 2-oxopyridin-1(2H)-yl | cyclopropyl |
| 2-$NO_2$-4-$SO_2$MePh | 2-oxoquinolin-1(2H)-yl | cyclopropyl |
| 2-$NO_2$-4-$SO_2$MePh | 1,2-benzisoxazol-3-yl | cyclopropyl |
| 2-$NO_2$-4-$SO_2$MePh | 2-oxo-1,3-benzoxazol-3(2H)-yl | cyclopropyl |
| 2-$NO_2$-4-$SO_2$MePh | 3-oxo-2,3-dihydro-4H-1,4-benzoxazin-4-yl | cyclopropyl |
| 2-$NO_2$-4-$SO_2$MePh | 2-oxopyrimidin-1(2H)-yl | cyclopropyl |
| 2-$NO_2$-4-$SO_2$MePh | 1H-1,2,3-benzotriazol-1-yl | cyclopropyl |

The compounds having general formula (I) can be applied in the pharmaceutical field, for example in the treatment of the hereditary disease known as tyrosinemia type 1 (HT-1).

A further object of the present invention relates to processes for the preparation of compounds having general formula (I).

In particular, the compounds having general formula (I) can be prepared by the reaction of a carbonyl compound having general formula (II) with a compound having general formula (III) according to reaction scheme 1.

Scheme 1:

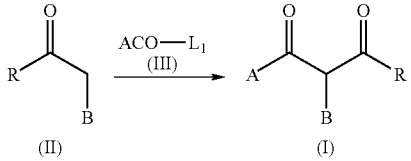

In the general formulae indicated in this reaction scheme:
A, B and R have the meanings previously defined;
$L_1$ represents a suitable leaving group such as, for example, a halogen atom, a CN group, an imidazol-1-yl group, an $R_LO$— group wherein $R_L$ represents a $C_1$-$C_4$ alkyl group or a phenyl group optionally substituted, or it represents an $R_{L1}COO$— group wherein $R_{L1}$ represents a hydrogen atom, a $C_1$-$C_4$ alkyl or haloalkyl group, a phenyl group optionally substituted or an A group.

The reaction between the compounds having general formula (II) and the compounds having general formula (III) is preferably carried out in the presence of an inert organic solvent and in the presence of an organic or inorganic base, at a temperature ranging from −80° C. to the boiling point of the reaction mixture. The reaction can also be carried out in two distinct phases. In the latter case, in the first phase, the compounds having general formula (II) are reacted with a base. The intermediate obtained is reacted, in the subsequent phase, with an acylating compound.

Examples of solvents which can be used for the above reaction comprise aromatic hydrocarbons (benzene, toluene, xylene, chlorobenzene, etc.), ethers (diethyl ether, diisopropyl ether, dimethoxyethane, dioxane, tetrahydrofuran, etc.), aprotic dipolar solvents (dimethylformamide, dimethylacetamide, hexamethylphosphoramide, N-methylpyrrolidone, etc.).

Inorganic bases which can be used for the purpose are, for example, sodium and potassium hydrides, hydroxides and carbonates, sodium amide.

Organic bases which can be used for the purpose are, for example, sodium, potassium and magnesium alcoholates, phenyllithium, butyllithium, lithium diisopropylamide, triethylamine, pyridine, 4-N,N-dimethylaminopyridine, N,N-dimethylaniline, N-methyl piperidine, lutidine, diazabicyclooctane (DABCO), diazabicyclononene (DBN), diazabicycloundecene (DBU).

The compounds having general formula (I) can also be prepared by the reaction of a carbonyl compound having general formula (IV) with a compound having general formula (V) according to reaction, scheme 2.

Scheme 2:

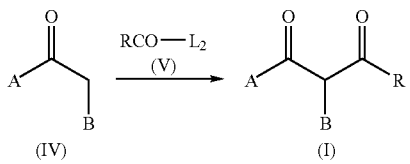

In the general formulae indicated in this reaction scheme:
A, B and R have the meanings previously defined;

L$_2$ represents a suitable leaving group such as, for example, a halogen atom, a CN group, an imidazol-1-yl group, an R$_L$O— group wherein R$_L$ represents a C$_1$-C$_4$ alkyl group or a phenyl group optionally substituted, or it represents an R$_{L1}$COO— group wherein R$_{L1}$ represents a hydrogen atom, a C$_1$-C$_4$ alkyl or haloalkyl group, a phenyl group optionally substituted or an R group.

The reaction between the compounds having general formula (IV) and the compounds having general formula (V) is preferably carried out in the presence of an inert organic solvent and in the presence of an organic or preferably inorganic base, at a temperature ranging from −80° C. to the boiling point of the reaction mixture. The reaction can also be carried out in two distinct phases. In the latter case, in the first phase, the compounds having general formula (IV) are reacted with a base. The intermediate obtained is reacted, in the subsequent phase, with an acylating compound.

Examples of solvents which can be used for the above reaction comprise aromatic hydrocarbons (benzene, toluene, xylene, chlorobenzene, etc.), ethers (diethyl ether, diisopropyl ether, dimethoxyethane, dioxane, tetrahydrofuran, etc.), aprotic dipolar solvents (dimethylformamide, dimethylacetamide, hexamethylphosphoramide, N-methylpyrrolidone, etc.).

Inorganic bases which can be used for the purpose are, for example, sodium and potassium hydrides, hydroxides and carbonates, sodium amide.

Organic bases which can be used for the purpose are, for example, sodium, potassium and magnesium alcoholates, phenyllithium, butyllithium, lithium diisopropylamide, triethylamine, pyridine, 4-N,N-dimethylaminopyridine, N,N-dimethylaniline, N-methyl piperidine, lutidine, diazabicyclooctane (DABCO), diazabicyclononene (DBN), diazabicycloundecene (DBU).

The compounds having general formula (I) can also be prepared by the reaction of a 1,3-dicarbonyl compound having general formula (VI) with a compound having general formula (VII) according to reaction scheme 3.

Scheme 3:

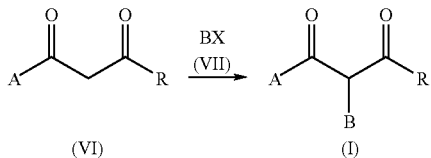

In the general formulae indicated in this reaction scheme:
A, B and R have the meanings previously defined;
X represents a halogen atom, an R$_{L2}$SO$_2$O— group, wherein R$_{L2}$ represents a C$_1$-C$_4$ alkyl or haloalkyl group, a phenyl group optionally substituted by C$_1$-C$_4$ alkyl groups, or it represents an R$_{L3}$SO$_2$— group, wherein R$_{L3}$ represents a C$_1$-C$_4$ alkyl or haloalkyl group.

The reaction between the compounds having general formula (VI) and the compounds having general formula (VII) is preferably carried out in the presence of one or more inert organic solvents and in the presence of an organic or inorganic base, at a temperature ranging from −80° C. to the boiling point of the reaction mixture.

Organic solvents which can be used for the purpose are, for example, aromatic hydrocarbons (benzene, toluene, xylene, chlorobenzene, etc.), ethers (diethyl ether, diisopropyl ether, dimethoxyethane, dioxane, tetrahydrofuran, etc.), alcohols and glycols (methanol, ethanol, methyl cellosolve, ethylene glycol, etc.), ketones (acetone, methyl ethyl ketone, methyl propyl ketone, methyl isobutyl ketone, etc.), nitriles (acetonitrile, benzonitrile, etc.), aprotic dipolar solvents (dimethylformamide, dimethylacetamide, hexamethylphosphoramide, dimethylsulfoxide, sulfolane, N-methylpyrrolidone, etc.).

Organic bases which can be used for the purpose are, for example, sodium, potassium and magnesium alcoholates, phenyllithium, butyllithium, lithium diisopropylamide, triethylamine, pyridine, 4-N,N-dimethylaminopyridine, N,N-dimethylaniline, N-methyl piperidine, lutidine, diazabicyclooctane (DABCO), diazabicyclononene (DBN), diazabicycloundecene (DBU).

Inorganic bases which can be used for the purpose are, for example, sodium or potassium hydrides, hydroxides and carbonates, sodium amide.

The reaction can also be carried out using suitable catalysts based on transition metals, such as, for example, Cu and Pd.

Examples of these reactions are described in Chem. Pharm. Bull. (1987), vol. 35, pages 4972-4976 and J. Chem. Soc., Perkin 1 (1976), vol. 6, pages 592-594.

The 1,3-dicarbonyl compounds having general formula (VI) can be prepared by the acylation of ketones according to what is described, for example, in Organic Reaction (1954), vol. 8, pages 59-196, or in Tetrahedron Letters (2002), vol. 43, pages 2945-2948.

The compounds having general formula (II) can be prepared by the reaction of a compound having general formula (VIII) with an acylating compound having general formula (V) according to reaction scheme 4.

Scheme 4:

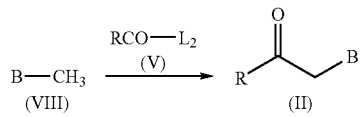

In the general formulae indicated in this reaction scheme:
B and R have the meanings previously defined;
L$_2$ represents a suitable leaving group such as, for example, a halogen atom, a CN group, an imidazol-1-yl group, an R$_L$O— group wherein R$_L$ represents a C$_1$-C$_4$ alkyl group or a phenyl group optionally substituted, or it represents an R$_{L1}$COO— group wherein R$_{L1}$ represents a hydrogen atom, a C$_1$-C$_4$ alkyl or haloalkyl group, a phenyl group optionally substituted or an R group.

The reaction between the compounds having general formula (VIII) and the compounds having general formula (V) is preferably carried out in the presence of an inert organic solvent and in the presence of an organic or preferably inorganic base, at a temperature ranging from −80° C. to the boiling point of the reaction mixture. The reaction can also be carried out in two distinct phases. In the latter case, in the first phase, the compounds having general formula (VIII) are reacted with a base. The intermediate obtained is reacted, in the subsequent phase, with an acylating compound.

Examples of solvents which can be used for the above reaction comprise aromatic hydrocarbons (benzene, toluene, xylene, chlorobenzene, etc.), ethers (diethyl ether, diisopropyl ether, dimethoxyethane, dioxane, tetrahydrofuran, etc.), aprotic dipolar solvents (dimethylformamide, dimethylacetamide, hexamethylphosphoramide, N-methylpyrrolidone, etc.).

Inorganic bases which can be used for the purpose are, for example, sodium and potassium hydrides, hydroxides and carbonates, sodium amide.

Organic bases which can be used for the purpose are, for example, sodium, potassium and magnesium alcoholates, phenyllithium, butyllithium, lithium diisopropylamide, triethylamine, pyridine, 4-N,N-dimethylaminopyridine, N,N-dimethylaniline, N-methyl piperidine, lutidine, diazabicyclooctane (DABCO), diazabicyclononene (DBN), diazabicycloundecene (DBU).

The compounds having general formula (IV) can be prepared by the reaction of a compound having general formula (VIII) with an acylating compound having general formula (III) according to reaction scheme 5.

Scheme 5:

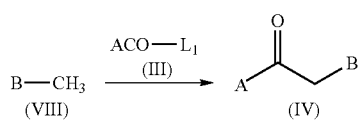

In the general formulae indicated in this reaction scheme:
B and A have the meanings previously defined;
$L_1$ represents a suitable leaving group such as, for example, a halogen atom, a CN group, an imidazol-1-yl group, an $R_LO$— group wherein $R_L$ represents a $C_1$-$C_4$ alkyl group or a phenyl group optionally substituted, or it represents an $R_{L1}COO$— group wherein $R_{L1}$ represents a hydrogen atom, a $C_1$-$C_4$ alkyl or haloalkyl group, a phenyl group optionally substituted or an A group.

The reaction between the compounds having general formula (VIII) and the compounds having general formula (III) is preferably carried out in the presence of an inert organic solvent and in the presence of an organic or inorganic base, at a temperature ranging from $-80°$ C. to the boiling point of the reaction mixture. The reaction can also be carried out in two distinct phases. In the latter case, in the first phase, the compounds having general formula (VIII) are reacted with a base. The intermediate obtained is reacted, in the subsequent phase, with an acylating compound.

Examples of solvents which can be used for the above reaction comprise aromatic hydrocarbons (benzene, toluene, xylene, chlorobenzene, etc.), ethers (diethyl ether, diisopropyl ether, dimethoxyethane, dioxane, tetrahydrofuran, etc.), aprotic dipolar solvents (dimethylformamide, dimethylacetamide, hexamethylphosphoramide, N-methylpyrrolidone, etc.).

Inorganic bases which can be used for the purpose are, for example, sodium and potassium hydrides, hydroxides and carbonates, sodium amide.

Organic bases which can be used for the purpose are, for example, sodium, potassium and magnesium alcoholates, phenyllithium, butyllithium, lithium diisopropylamide, triethylamine, pyridine, 4-N,N-dimethylaminopyridine, N,N-dimethylaniline, N-methyl piperidine, lutidine, diazabicyclooctane (DABCO), diazabicyclononene (DBN), diazabicycloundecene (DBU).

The compounds having general formula (IV) can also be prepared by the reaction of a compound having general formula (IX) with an acylating compound having general formula (III) in the presence of a base. The reaction provides intermediate compounds having general formula (X) which then undergo a hydrolysis and decarboxylation process according to reaction scheme 6.

Scheme 6:

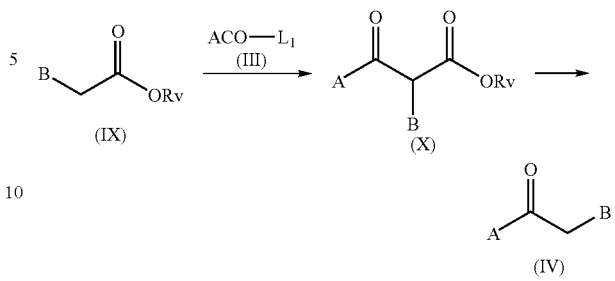

In the general formulae indicated in this reaction scheme:
B and A have the meanings previously defined;
$L_1$ represents a suitable leaving group such as, for example, a halogen atom, a CN group, an imidazol-1-yl group, an $R_LO$— group wherein $R_L$ represents a $C_1$-$C_4$ alkyl group or a phenyl group optionally substituted, or it represents an $R_{L1}COO$— group wherein $R_{L1}$ represents a hydrogen atom, a $C_1$-$C_4$ alkyl or haloalkyl group, a phenyl group optionally substituted or one of the A groups.
Rv represents a $C_1$-$C_5$ alkyl or haloalkyl group, an arylalkyl or aryl group.

The compounds having general formula (II) can also be prepared by the reaction of a compound having general formula (IX) with an acylating compound having general formula (V) in the presence of a base. The reaction provides intermediate compounds having general formula (XI) which then undergo a hydrolysis and decarboxylation process according to reaction scheme 7.

Scheme 7:

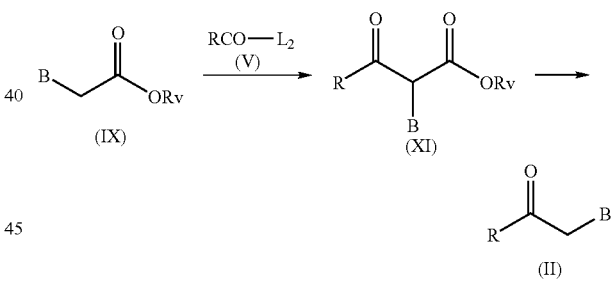

In the general formulae indicated in this reaction scheme:
B and R have the meanings previously defined;
$L_2$ represents a suitable leaving group such as, for example, a halogen atom, a CN group, an imidazol-1-yl group, an $R_LO$— group wherein $R_L$ represents a $C_1$-$C_4$ alkyl group or a phenyl group optionally substituted, or it represents an $R_{L1}COO$— group wherein $R_{L1}$ represents a hydrogen atom, a $C_1$-$C_4$ alkyl or haloalkyl group, a phenyl group optionally substituted or one of the R groups.
Rv represents a $C_1$-$C_5$ alkyl or haloalkyl group, an arylalkyl or aryl group.

The reactions indicated in reaction schemes 6 and 7 can be carried out, for example, according to the methods described in J. Am. Chem. Soc. (1950), vol. 72, pages 1352-1356 and in J. Am. Chem. Soc. (1987), vol. 109, pages 4717-4718.

The compounds having general formula (II) wherein R has the meanings previously defined and B represents a 1,2,4-oxadiazol-5-yl, compounds (IIa), can be prepared, for example, starting from compounds having general formula (XII) by reaction with an amidoxime having general formula (XIII) according to reaction scheme 8.

Scheme 8:

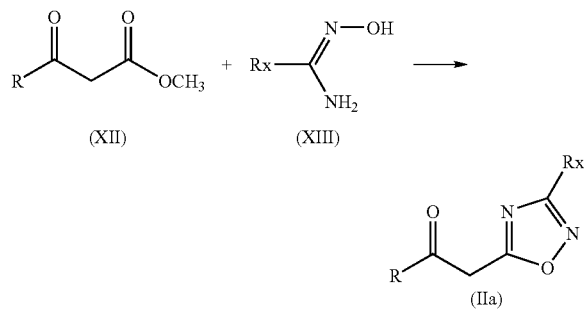

The above reaction can be carried out according to the method described for example in Bull. Soc. Chim. Belges (1949), vol. 58, pages 58-65.

The compounds having general formula (II) wherein R has the meanings previously defined and B represents tetrazol-5-yl (D=tetrazole, $R_x$=H), compounds (IIb), can be prepared, for example, starting from compounds having general formula (XIV) by transforming the cyano group into tetrazole, for example by heating with trimethylsilylazide, in toluene, catalyzed by dibutyltin oxide, according to what is described in J. Org. Chem. (1933), vol. 58, pages 4139-4141, or by heating with sodium azide in water with the catalysis of $ZnBr_2$, as described in J. Org. Chem. (2001), vol. 66, pages 7945-7950.

The above transformation is indicated in reaction scheme 9.

Scheme 9:

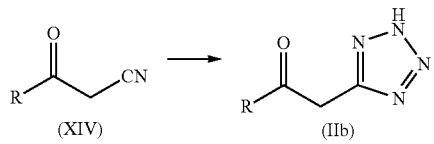

The intermediates having general formulae (III), (V), (VII), (VIII), (IX), (XII), (XIII) and (XIV), when not already known as such, can be easily prepared according to methods known in organic chemistry practice.

In some cases, the compounds having general formula (I) can be obtained in the form of two or more optic or geometric or position isomers. Compounds having general formula (I) which are isomerically pure, and also mixtures of these, possibly obtained during the preparation of the compounds having general formula (I) or deriving from an incomplete separation of the isomers themselves, in any proportion, are therefore considered as being included within the scope of the present invention.

As already mentioned, the compounds having general formula (I) have a high herbicidal activity which makes them suitable for use in the agrarian field in the defense of useful crops from weeds.

In particular, the compounds, object of the present invention, are effective in the control, in both pre-emergence and post-emergence, of numerous monocotyledon and dicotyledon weeds. At the same time, these compounds show compatibility or the absence of toxic effects with respect to useful crops in pre-and/or post-emergence treatments.

The compounds of the present invention can act as total or selective herbicides also in relation to the quantity of active principle used.

Examples of weeds which can be effectively controlled using the compounds having general formula (I) are: *Abutilon theofrasti, Alisma plantago, Amaranthus* spp., *Amni maius, Capsella bursa pastoris, Chenopodium album, Convolvulus sepium, Galium aparine, Geranium dissectum, Ipomea* spp., *Matricaria* spp., *Papaver rhoaes, Phaseolus aureus, Polygonum persicaria, Portulaca oleracea, Sida spinosa, Sinapsis arvensis, Solanum nigrum, Stellaria media, Veronica* spp., *Viola* spp., *Xanthium* spp., *Alopercurus myosuroides, Avena fatua, Cyperus* spp., *Digitaria sanguinalis, Echinocloa* spp., *Heleocaris avicularis, Heranthera* spp., *Panicum* spp., *Poa* spp., *Scirpus* spp., *Sorghum* spp., etc.

With the doses of use suitable for agrarian applications, many of the above compounds showed no toxic effects towards one or more important agrarian crops such as corn (*Zea mays*), wheat (*Triticum* sp.), barley (*Hordeum vulgare*), soybean (*Glycine max*), rice (*Oryza sativa*).

A further object of the present invention relate; to a method for controlling weeds in cultivated areas by the application of the compounds having general formula (I).

The quantity of compound to be applied for obtaining the desired effect can vary in relation to various factors such as, for example, the compound used, the crop to be preserved, the weed to be fought, the degree of infestation, the climatic conditions, the characteristics of the soil, the application method, etc.

Doses of compound ranging from 1 g to 4,000 g per hectare generally provide a sufficient control.

For use in agriculture, it is often advantageous to adopt compositions with a herbicidal activity containing, as active substance, one or more compounds having general formula (I), optionally also as a mixture of tautomers and/or isomers.

Compositions can be used in the form of dry powders, wettable powders, emulsifiable concentrates, micro-emulsions, pastes, granulates, solutions, suspensions, etc.: the selection of the type of composition depends on the specific use.

The compositions are prepared according to known methods, for example by diluting or dissolving the active substance by means of a solvent medium and/or solid diluent, possibly in the presence of surface-active agents.

Kaolin, alumina, silica, talc, bentonite, chalk, quartz, dolomite, attapulgite, montmorillonite, diatomaceous earth, cellulose, starch, etc., can be used as inert solid diluents, or carriers.

Inert liquid diluents which can be used, are water or organic solvents such as aromatic hydrocarbons (xylols, blends of alkyl benzenes, etc.), aliphatic hydrocarbons (hexane, cyclohexane, etc.) halogenated aromatic hydrocarbons (chlorobenzene, etc.), alcohols (methanol, propanol, butanol, octanol, etc.), esters (isobutyl acetate, etc.), ketones (acetone, cyclohexanone, acetophenone, isophorone, ethylamylketone etc.), or vegetable and mineral oils or mixtures thereof, etc.

Surfactants which can be used are wetting and emulsifying agents, of the non-ionic type (polyethoxylated alkyl phenols, polyethoxylated fatty alcohols, etc.), of the anionic type (alkylbenzenesulphonates, alkylsulphonates, etc.), of the cationic type (alkyl ammonium quaternary salts, etc.).

Dispersing agents can also be added (for example lignin and its salts, cellulose derivatives, alginates, etc.), stabilizers (for example antioxidants, UV absorbers, etc.).

In order to enlarge the action range of the above compositions, it is possible to add active ingredients, such as, for example, other herbicides, fungicides, insecticides, acaricides, fertilizers, etc.

Examples of other herbicides which can be added to the compositions containing one or more compounds having general formula (I), are the following: Acetochlor, acifluorfen, aclonifen, AKH-7088, alachlor, alloxydim, ametryn, amicarbazone, amidosulfuron, amitrole, anilofos, asulam, atrazine, azafenidin, azimsulfuron, aziprotryne, BAS 670 H, BAY MKH 6561, beflubutamid, benazolin, benfluralin, benfuresate, bensulfuron, bensulide, bentazone, benzfendizone, benzobicyclon, benzofenap, benzthiazuron, bifenox, bilanafos, bispyribac-sodium, bromacil, bromobutide, bromofenoxim, bromoxynil, butachlor, butafenacil, butamifos, butenachlor, butralin, butroxydim, butylate, cafenstrole, carbetamide, carfentrazone-ethyl, chlomethoxyfen, chloramben, chlorbromuron, chlorbufam, chlorflurenol, chloridazon, chlorimuron, chlornitrofen, chlorotoluron, chloroxuron, chlorpropham, chlorsulfuron, chlorthal, chlorthiamid, cinidon ethyl, cinmethylin, cinosulfuron, clethodim, clodinafop, clomazone, clomeprop, clopyralid, cloransulam-methyl, cumyluron (JC-940), cyanazine, cycloate, cyclosulfamuron, cycloxydim, cyhalofop-butyl, 2,4-D, 2,4-DB, daimuron, dalapon, desmedipham, desmetryn, dicamba, dichlobenil, dichlorprop, dichlorprop-P, diclofop, diclosulam, diethatyl, difenoxuron, difenzoquat, diflufenican, diflufenzopyr, dimefuron, dimepiperate, dimethachlor, dimethametryn, dimethenamid, dinitramine, dinosseb, dinoseb acetate, dinoterb, diphenamid, dipropetryn, diquat, dithiopyr, 1-diuron, eglinazine, endothal, EPTC, espropcarb, ethalfluralin, ethametsulfuron-methyl, ethidimuron, ethiozin (SMY 1500), ethofumesate, ethoxyfen-ethyl (HC-252), ethoxysulfuron, etobenzanid (HW 52), fenoxaprop, fenoxaprop-P, fentrazamide, fenuron, flamprop, flamprop-M, flazasulfuron, florasulam, fluazifop, fluazifop-P, fluazolate (JV 485), flucarbazone-sodium, fluchloralin, flufenacet, flufenpyr ethyl, flumetsulam, flumiclorac-pentyl, flumioxazin, flumipropin, fluometuron, fluoroglycofen, fluoronitrofen, flupoxam, fluproanate, flupyrsulfuron, flurenol, fluridone, flurochloridone, fluroxypyr, flurtamone, fluthiacet-methyl, fomesafen, foramsulfuron, fosamine, furyloxyfen, glufosinate, glyphosate, halosulfuron-methyl, haloxyfop, haloxyfop-P-methyl, hexazinone, imazamethabenz, imazamox, imazapic, imazapyr, imazaquin, imazethapyr, imazosulfuron, indanofan, iodosulfuron, ioxynil, isopropalin, isoproturon, isouron, isoxaben, isoxachlortole, isoxaflutole, isoxapyrifop, KPP-421, lactofen, lenacil, linuron, LS830556, MCPA, MCPA-thioethyl, MCPB, mecoprop, mecoprop-P, mefenacet, mesosulfuron, mesotrione, metamitron, metazachlor, methabenzthiazuron, methazole, methoprotryne, methyldymron, metobenzuron, metobromuron, metolachlor, S-metolachlor, metosulam, metoxuron, metribuzin, metsulfuron, molinate, monalide, monolinuron, naproanilide, napropamide, naptalam, NC-330, neburon, nicosulfuron, nipyraclofen, norflurazon, orbencarb, oryzalin, oxadiargyl, oxadiazon, oxasulfuron, oxaziclomefone, oxyfluorfen, paraquat, pebulate, pendimethalin, penoxsulam, pentanochlor, pentoxazone, pethoxamid, phenmedipham, picloram, picolinafen, piperophos, pretilachlor, primisulfuron, prodiamine, profluazol, proglinazine, prometon, prometryne, propachlor, propanil, propaquizafop, propazine, propham, propisochlor, propyzamide, prosulfocarb, prosulfuron, pyraclonil, pyraflufen-ethyl, pyrazogyl (HAS-961), pyrazolynate, pyrazosulfuron, pyrazoxyfen, pyribenzoxim, pyributicarb, pyridafol, pyridate, pyriftalid, pyriminobac-methyl, pyrithiobac-sodium, quinclorac, quinmerac, quizalofop, quizalofop-P, rimsulfuron, sethoxydim, siduron, simazine, simetryn, sulcotrione, sulfentrazone, sulfometuron-methyl, sulfosulfuron, 2,3,6-TBA, TCA-sodium, tebutam, tebuthiuron, tepraloxydim, terbacil, terbumeton, terbuthyl-azine, terbutryn, thenylchlor, thiazafluron, thiazopyr, thidiazimin, thifensulfuron-methyl, thiobencarb, tiocarbazil, tioclorim, tralkoxydim, triallate, triasulfuron, triaziflam, tribenuron, triclopyr, trietazine, trifloxysulfuron, trifluralin, triflusulfuron-methyl, tritosulfuron, UBI-C4874, vernolate.

The concentration of active substance in the above compositions can vary within a wide range, depending on the active compound, the applications to which they are destined, the environmental conditions and the type of formulation adopted. In general, the concentration of active substance preferably ranges from 1 to 90%.

Some examples are now provided for illustrative and non-limiting purposes of the present invention.

EXAMPLE 1

Synthesis of
3,3-dimethyl-1-(tetrazol-5-yl)butane-2-one

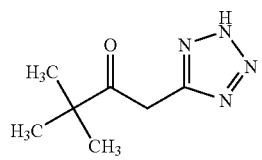

NaN$_3$ (1.71 g) and ZnBr$_2$ (5.40 g) are added to a suspension of 4,4-dimethyl-3-oxopentanenitrile (3.00 g) in 50 ml of water and 4 ml of isopropylic alcohol and the resulting mixture is stirred at 90° C. for 12 hours.

After completion of the reaction, 15 ml of 10% HCl are added, then the mixture is extracted two times with ethyl acetate; the organic phase is then evaporated under reduced pressure. The residue is stirred with 100 ml of 10% NaOH for 20 minutes, then cooled with an ice bath and acidified with concentrated HCl: the white precipitate is extracted two times with ethyl acetate, which is then dried with Na$_2$SO$_4$ and evaporated.

The resulting solid is purified by washing with dichloromethane to obtain 2.75 g of pure product (yield: 68%).

EXAMPLE 2

Synthesis of 3,3-dimethyl-1-(2-methyl-2H-tetrazol-5-yl)butane-2-one and 3,3-dimethyl-1-(1-methyl-1H-tetrazol-5-yl)butane-2---one

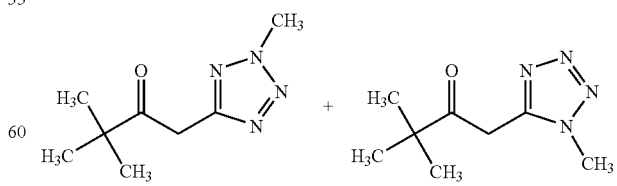

K$_2$CO$_3$ (1.40 g) and CH$_3$I (1.32 g) are added to a solution of 3,3-dimethyl-1-(tetrazol-5-yl)butan-2-one (1.42 g) in 35 ml of acetone under an inert atmosphere, the mixture is stirred at room temperature for 20 hours.

The solvent is then evaporated, the residue is taken up with water and extracted two times with ethyl acetate, which is then washed with water, dried with Na₂SO₄ and evaporated.

The raw product is purified by flash chromatography, isolating the two isomers 3,3-dimethyl-1-(2-methyl-2H-tetrazol-5-yl)butan-2-one (0.60 g, yield: 39%) and 3,3-dimethyl-1-(1-methyl-1H-tetrazol-5-yl)butan-2-one (0.64 g, yield: 42%). The structure of each isomer was assigned according to the NMR spectra.

¹H-NMR (CDCl₃):

(2-methyl isomer) –δ 1.24 (s, 9H, t-butyl), 4.12 (s, 2H, CH₂), 4.32 (s, 3H, N—CH₃)

(1-methyl isomer) –δ 1.19 (s, 9H, t-butyl), 3.90 (s, 3H, N—CH₃), 4.17 (s, 2H, CH₂)

EXAMPLE 3

Synthesis of 1-[2-chloro-4-(methylsulphonyl)phenyl]-4,4-dimethyl-2-(1-methyl-1H-tetrazol-5-yl)pentane-1,3-dione (Compound No 1)

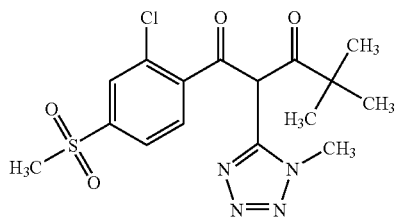

Under an inert atmosphere, Mg(OEt)₂ (0.279 g) is added to a solution of 3,3-dimethyl-1-(1-methyl-1H-tetrazol-5-yl)butan-2-one (0.64 g) in 16 ml of dry tetrahydrofuran; the stirred mixture is refluxed for 3 hours, then completely evaporated under reduced pressure.

The residue is taken up with 16 ml of dry tetrahydrofuran, under an inert atmosphere, then a solution of 2-chloro-4-(methylsulphonyl)benzoyl chloride (1.04 g) in dry tetrahydrofuran is added; the stirred mixture is refluxed for 3 more hours.

After completion of the reaction, the solvent is evaporated and the residue is taken up with water and ethyl acetate; after acidification with 10% HCl the organic phase is recovered and extracted three times with aqueous NaHCO₃ saturated solution. The combined basic aqueous phases are acidified and extracted three times with ethyl acetate, which is then dried with Na₂SO₄ and evaporated, obtaining an off-white solid.

The raw product is purified by filtration over silica gel eluting with dichloromethane/methanol 8:2, then by washing the obtained solid with acetone, thus obtaining 0.60 g of product as a white solid (yield: 45%, m.p. 195-200° C.).

¹H-NMR (CDCl₃): δ 1.07 (s, 9H, t-butyl), 3.01 (s, 3H, SO₂CH₃), 3.76 (s, 3H, N—CH₃), 7.30-7.94 (m, 3H, arom. H's)

EXAMPLE 4

Synthesis of 1-(2,4-dichlorophenyl)-4,4-dimethyl-2-(2-methyl-2H-tetrazol-5-yl)pentane-1,3-dione (Compound No 2)

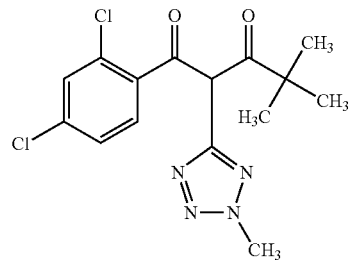

Under an inert atmosphere, Mg(OEt)₂ (0.257 g) is added to a solution of starting 3,3-dimethyl-1-(2-methyl-2H-tetrazol-5-yl)butan-2-one (0.59 g) in 16 ml of dry tetrahydrofuran; the stirred mixture is refluxed for 3 hours, then completely evaporated under reduced pressure.

The residue is taken up with 16 ml of dry tetrahydrofuran, under an inert atmosphere, then a solution of 2,4-dichlorobenzoyl chloride (0.746 g) in dry tetrahydrofuran is added; the stirred mixture is refluxed for 3 more hours.

After completion of the reaction, the solvent is evaporated and the residue is taken up with water and extracted with ethyl acetate; the organic phase is washed with diluted HCl, with brine, then dried with Na₂SO₄ and evaporated.

The raw product is purified by flash chromatography to obtain 0.49 g of product (yield: 43%).

¹H-NMR (CDCl₃): (mixture of two keto-enolic tautomers) δ 1.05, 1.10 (2s, 9H, t-butyl), 4.19, 4.33 (2s, 3H, N—CH₃), 6.62 (s, 1H, CO—CH—CO), 7.04-7.50 (m, 3H, arom. H's)

EXAMPLE 5

Synthesis of 2-(5-tert-butyl-1,3,4-oxadiazol-2-yl)-1-(4-chlorophenyl)-3-(cyclopropyl)propane-1,3-dione (Compound No 3)

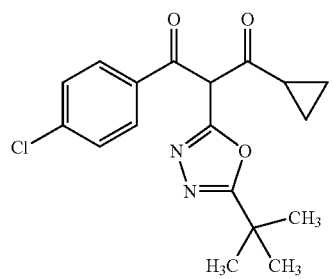

Under an inert atmosphere, Mg(OEt)₂ (0.209 g) is added to a solution of 2-(5-tert-butyl-1,3,4-oxadiazol-2-yl)-1-(4-chlorophenyl)ethanone (0.50 g) in 10 ml of dry tetrahydrofuran; the stirred mixture is refluxed for 3 hours, then completely evaporated under reduced pressure.

The residue is taken up with 10 ml of dry tetrahydrofuran, under an inert atmosphere, then cyclopropanecarbonylchloride (0.208 g) is added; the stirred mixture is refluxed for 3 more hours.

After completion of the reaction, the solvent is evaporated and the residue is taken up with water and extracted with ethyl acetate; the organic phase is washed with diluted HCl, with brine, then dried with $Na_2SO_4$ and evaporated.

The raw product is purified by flash chromatography to obtain 0.28 g of pure product (yield: 44%).

$^1$H-NMR (CDCl$_3$): δ 1.01-1.43 (m, 4H, CH$_2$—CH$_2$), 1.20 (s, 9H, t-butyl), 2.12-2.22 (m, 1H, CH), 7.26 (s, 4H, arom. H's)

EXAMPLE 6

Synthesis of 1-(4-chlorophenyl)-2-(2H-tetrazol-5-yl)ethanone

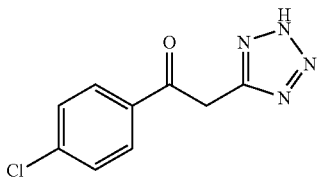

NaN$_3$ (1.19 g) and ZnBr (3.76 g) are added to a suspension of 3-(4-chlorophenyl)-3-oxopropanenitrile (3.00 g) in 30 ml of H$_2$O and 4 ml of isopropylic acid and the resulting mixture is stirred at 90° C. for 12 hours.

After completion of the reaction, 15 ml of 10% HCl are added, then the mixture is extracted two times with ethyl acetate; the combined organic phases are then evaporated under reduced pressure. The residue is stirred with 100 ml of 10% NaOH for 6 hours, then the mixture is cooled with an ice bath and acidified with concentrated HCl: the white precipitate is extracted two times with ethyl acetate, which is then dried with Na$_2$SO$_4$ and evaporated.

The resulting solid is purified by digestion in ethyl acetate to obtain 1.76 g of pure product (yield: 47%)

$^1$H-NMR (acetone-d$_6$): δ 4.98 (s, 2H, CH$_2$), 7.60-8.20 (m, 4H, arom. H's)

EXAMPLE 7

Synthesis of 1-(4-chlorophenyl)-2-(2-methyl-2H-tetrazol-5-yl)ethanone and 1-(4-chlorophenyl)-2-(1-methyl-1H-tetrazol-5-yl)ethanone

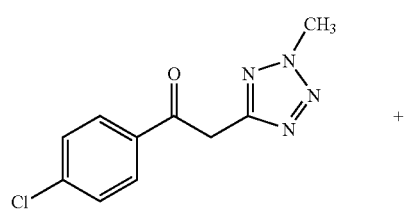

+

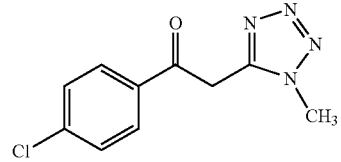

K$_2$CO$_3$ (0.47 g) and CH$_3$I (0.32 g) are added to a solution of 1-(4-chlorophenyl)-2-(2H-tetrazol-5-yl)ethanone (0.50 g) in 15 ml of acetone, under an inert atmosphere; the mixture is stirred at room temperature for 20 hours.

The solvent is then evaporated, the residue is taken up with water and extracted two times with ethyl acetate, which is then washed with water, dried with Na$_2$SO$_4$ and evaporated, thus obtaining a solid raw product (0.56 g) containing the two isomers (1-(4-chlorophenyl)-2-(2-methyl-2H-tetrazol-5-yl)ethanone and 1-(4-chlorophenyl)-2-(1-methyl-1H-tetrazol-5-yl)ethanone), which is used for the following reaction.

EXAMPLE 8

Synthesis of 1-(4-chlorophenyl)-3-cyclopropyl-2-(2-methyl-2H-tetrazol-5-yl)propane-1,3-dione (Compound No 4) and 1-(4-chlorophenyl)-3-cyclopropyl-2-(1-methyl-1H-tetrazol-5-yl)propane-1,3-dione (Compound No 5)

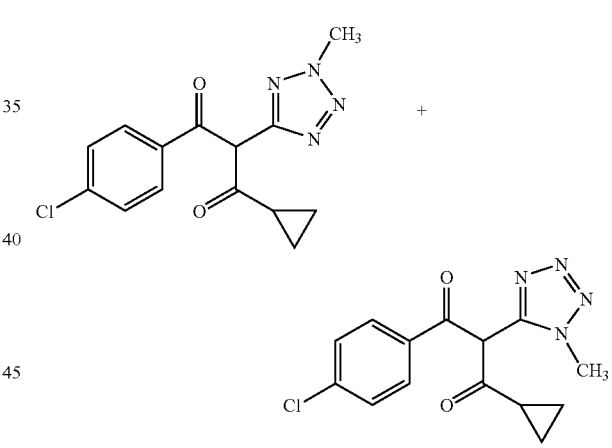

Under an inert atmosphere, Mg(OEt)$_2$ (0.263 g) is added to a solution of the starting mixture of 1-(4-chlorophenyl)-2-(2-methyl-2H-tetrazol-5-yl)ethanone and 1-(4-chlorophenyl)-2-(1-methyl-1H-tetrazol-5-yl)ethanone (0.53 g) in 10 ml of dry tetrahydrofuran; the stirred mixture is refluxed for 3 hours, then completely evaporated under reduced pressure.

The residue is taken up with 10 ml of dry tetrahydrofuran, under an inert atmosphere, then cyclopropanecarbonylchloride (0.235 g) is added; the stirred mixture is refluxed for 3 more hours.

After completion of the reaction, the solvent is evaporated and the residue is taken up with water and extracted with ethyl acetate; the organic phase is washed with diluted HCl, with brine, then dried with Na$_2$SO$_4$ and evaporated.

The raw product is purified by flash chromatography to obtain 0.26 g of 2-methyl isomer (yield: 37%) and 0.17 g of 1-methyl isomer (yield: 24%).

$^1$H-NMR (CDCl$_3$):

(2-methyl isomer) —δ 0.90-1.67 (m, 5H, ciclopropyl), 4.29 (s, 3H, N—CH$_3$), 7.18 (s, 4H, arom. H's)

(1-methyl isomer) —δ 0.9-1.61 (m, 5H, ciclopropyl), 3.49 (s, 3H, N—CH$_3$), 7.12-7.27 (m, 4H, arom. H's)

EXAMPLE 9

Synthesis of 1-cyclopropyl-2-(tetrazol-5-yl)ethanone

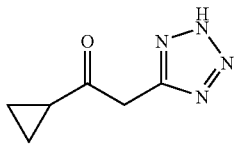

NaN$_3$ (5.0 g) and ZnBr (14.5 g) are added to a suspension of 3-cyclopropyl-3-oxopropanenitrile (7.0 g) in 130 ml of water and 10 ml of isopropylic alcohol and the resulting mixture is stirred at 100° C. for 12 hours.

After completion of the reaction, 60 ml of 10% HCl are added, then the mixture is extracted three times with ethyl acetate; the organic phase is then evaporated under reduced pressure. The residue is stirred with 400 ml of 1% NaOH for 20 hours, cooled with an ice bath and acidified with 10% HCl; the mixture is extracted three times with ethyl acetate, which is then dried with Na$_2$SO$_4$ and evaporated.

The resulting solid is purified by washing with CH$_2$Cl$_2$ to obtain 3.6 g of pure product (yield: 37%).

EXAMPLE 10

Synthesis of 1-cyclopropyl-2-(2-methyl-2H-tetrazol-5-yl)ethanone and 1-cyclopropyl-2-(1-methyl-1H-tetrazol-5-yl)ethanone

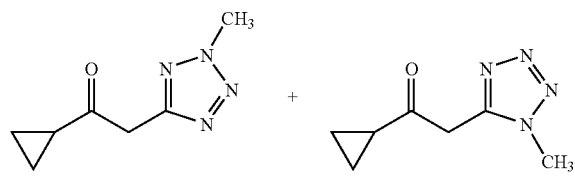

K$_2$CO$_3$ (4.85 g) and CH$_3$I (3.99 g) are added to a solution of 1-cyclopropyl-2-(tetrazol-5-yl)ethanone (3.56 g) in 90 ml of acetone, under an inert atmosphere; the mixture is then stirred at room temperature for 20 hours.

The solvent is then evaporated, the residue is taken up with water/ethyl acetate and the mixture is acidified to pH 1-2 with HCl 10%; the aqueous phase is extracted two more times with ethyl acetate; the combined organic phases are then washed with brine, dried with Na$_2$SO$_4$ and evaporated.

The raw product is purified by flash chromatography, isolating the two isomers 2-methyl (1.95 g, yield: 50%) and 1-methyl (1.13 g, yield: 29%).

$^1$H-NMR (CDCl$_3$):

(2-methyl isomer) —δ 0.90-1.16 (m, 4H, CH$_2$—CH$_2$), 2.06 (m, 1H, COCH), 4.15 (s, 2H, COCH$_2$), 4.33 (s, 3H, N—CH$_3$)

(1-methyl isomer) —δ 0.98-1.18 (m, 4H, CH$_2$—CH$_2$), 2.07 (m, 1H, COCH), 3.96 (s, 2H, COCH$_2$), 4.25 (s, 3H, N—CH$_3$)

EXAMPLE 11

Synthesis of 1-[2-chloro-4-(methylsulphonyl)phenyl]-3-cyclopropyl-2-(2-methyl-2H-tetrazol-5-yl)propane-1,3-dione (Compound No 6, corresponding to compound No 610 in table 2)

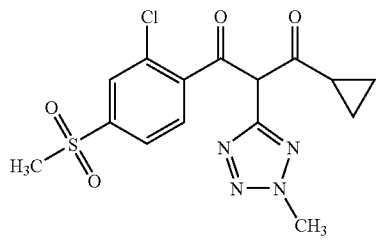

Under an inert atmosphere, Mg(OEt)$_2$ (0.383 g) is added to a solution of 1-cyclopropyl-2-(2-methyl-2H-tetrazol-5-yl)ethanone (0.80 g) in 22 ml of dry tetrahydrofuran; the stirred mixture is refluxed for 3 hours, then completely evaporated under reduced pressure.

The residue is taken up with 15 ml of dry tetarhydrofuran, under an inert atmosphere, then a suspension of 2-chloro-4-(methylsulphonyl)benzoyl chloride (0.96 g) in 20 ml of dry tetrahydrofuran is added ; the stirred mixture is refluxed for 5 more hours.

After completion of the reaction, the solvent is evaporated and the residue is taken up with water and ethyl acetate; after acidification with 10% HCl the organic phase is recovered and extracted three times with aqueous NaHCO$_3$. The combined basic aqueous phases are acidified and extracted three times with ethyl acetate, which is then dried with Na$_2$SO$_4$ and evaporated.

The raw product is purified by washing with warm ethyl acetate, to obtain 0.58 g of product as an orange solid (yield: 40%; m.p.: 220° C.).

$^1$H-NMR (CDCl$_3$): δ 1.02-1.96 (m, 5H, cyclopropyl), 3.03 (s, 3H, SO$_2$CH$_3$), 4.21 (s, 3H, N—CH$_3$), 7.42-7.86 (m, 3H, arom. H's), 17.52 (s, 1H, OH).

EXAMPLE 12

Synthesis of 1-[2-chloro-4-(methylsulphonyl)phenyl]-3-cyclopropyl-2-(1-methyl-1H-tetrazol-5-yl)propane-1,3-dione (Compound No 7, corresponding to compound No 605 in table 2)

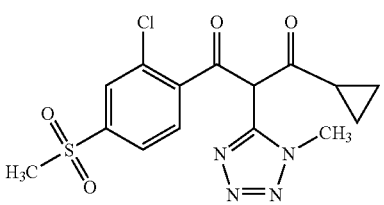

Under an inert atmosphere, Mg(OEt)$_2$ (0.278 g) is added to a solution of starting 1-cyclopropyl-2-(1-methyl-1H-tetrazol5-yl)ethanone (0.58 g) in 15 ml of dry tetrahydrofuran; the stirred mixture is refluxed for 3 hours, then completely evaporated under reduced pressure.

The residue is taken up with 2 ml of dry tetrahydrofuran, under an inert atmosphere, then a suspension of 2-chloro-4-((methylsulphonyl)benzoyl chloride (0.97 g) in 16 ml of dry tetrahydrofuran is added; the stirred mixture is refluxed for 5 more hours.

The solvent is then evaporated and the residue is taken up with water and ethyl acetate; after acidification with 10% HCl the organic phase is collected and extracted two times with aqueous $NaHCO_3$. The combined basic aqueous phases are acidified and extracted three times with ethyl acetate, which is then dried with $Na_2SO_4$ and evaporated.

The raw product is purified by flash chromatography, to obtain 0.81 g of product as an orange solid (yield: 61%; m.p.: 104° C.).

$^1$H-NMR ($CDCl_3$): δ 1.09-1.42 (m, 5H, cyclopropyl), 3.02 (s, 3H, $SO_2CH_3$), 3.91 (s, 3H, N—$CH_3$), 7.47-7.89 (m, 3H, arom. H's), 17.44 (s, 1E, OH).

EXAMPLE 13

Synthesis of 1-(4-chloro-2-nitrophenyl)-2-3-cyclopropyl-(1-methyl-1H-tetrazol-5-yl)propane-1,3-dione (Compound No 8, Corresponding to Compound No 968 in Table 2)

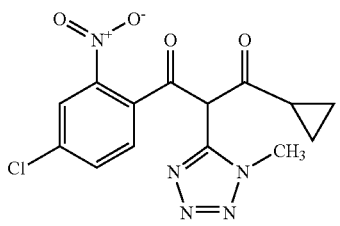

Under an inert atmosphere, $Mg(OEt)_2$ (0.263 g) is added to a solution of 1-cyclopropyl-2-(1-methyl-1H-tetrazol5-yl)ethanone (0.55 g) in 15 ml of dry tetrahydrofuran; the stirred mixture is refluxed for 3 hours, then completely evaporated under reduced pressure.

The residue is taken up with 7 ml of dry tetrahydrofuran, under an inert atmosphere, then a solution of the 4-chloro-2-nitrobenzoyl chloride (0.80 g) in 8 ml of dry tetrahydrofuran is added; the stirred mixture is refluxed for 3 more hours.

The solvent is then evaporated and the residue is taken up with water and ethyl acetate; after acidification with 10% HCl the organic phase is collected and extracted two times with aqueous $NaHCO_3$. The combined basic aqueous phases are acidified and extracted three times with ethyl acetate, which is then dried with $Na_2SO_4$ and evaporated.

The raw product is purified by flash chromatography, to obtain 0.72 g of product as an orange solid (yield: 61%; m.p.: 152° C.).

$^1$H-NMR ($CDCl_3$): δ 1.05-1-52 (m, 5H, cyclopropyl), 3.92 (s, 3H, N—$CH_3$), 7.39-7.93 (m, 3H, arom. H's), 17.07 (s, 1H, OH).

EXAMPLE 14

Synthesis of 3-cyclopropyl-1-[4-(methylsuiphonyl)-2-nitrophenyl]-2-(2-methyl-2H-tetrazol-5-yl)propane-1,3-dione (Compound No 9, Corresponding to Compound No 247 in Table 2)

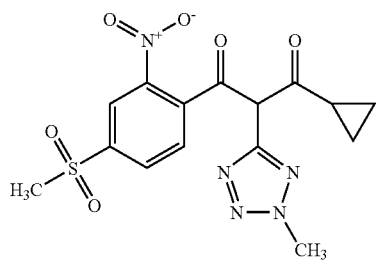

Under an inert atmosphere, $Mg(OEt)_2$ (0.171 g) is added to a solution of 1-cyclopropyl-2-(2-methyl-2H-tetrazol5-yl)ethanone (0.35 g) in 9 ml of dry tetrahydrofuran; the stirred mixture is refluxed for 3 hours, then completely evaporated under reduced pressure.

The residue is taken up with 3 ml of dry tetrahydrofuran, under an inert atmosphere, then a solution of 4-methylsulphonyl-2-nitrobenzoyl chloride (0.61 g) in 6 ml of dry tetrahydrofuran is added; the stirred mixture is refluxed for 3 more hours.

The solvent is then evaporated and the residue is taken up with water and ethyl acetate; after acidification with 10% HCl the organic phase is collected and extracted three times with aqueous $NaHCO_3$. The combined basic aqueous phases are slowly acidified to pH 5 and extracted with ethyl acetate, which is then washed three times with pH 5 buffered solution until all the benzoic acid is eliminated, dried with $Na_2SO_4$ and evaporated.

The resulting solid is purified by filtration over silica gel eluting with ethyl acetate to obtain 0.24 g of pure product as a light brown solid (yield: 61%; m.p 186° C., decomposition).

$^1$H-NMR ($CDCl_3$): δ 1.08-1.99 (m, 5H, cyclopropyl), 3.09 (s; 3H, $SO_2CH_3$), 4.17 (s, 3H, N—$CH_3$), 7.47-8.62 (m, 3H, arom. H's), 17.19 (s, 1H, OH).

EXAMPLE 15

Synthesis of 1-cyclopropyl-2-(4-methyl-1,3-thiazol-2-yl)ethanone

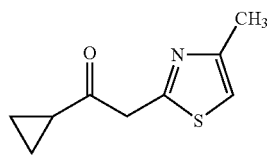

Under an inert atmosphere and in dried glassware, 2,4-dimethyl-1,3-thiazole (3.15 g) is dissolved in 90 ml of anhydrous tetrahydrofuran; 17.4 ml of 1.6 M butyllithium solution in hexanes are then added dropwise: the solution temperature rises to about 40° C.; after the addition, the mixture is stirred for 30 minutes, allowing the temperature to return to about 25° C.

The reaction mixture is then cooled in an ice bath and a solution of ethyl cyclopropanecarboxylate (3.17 g) in 15 ml of anhydrous tetrahydrofuran is quickly added; the ice bath is removed and the resulting solution is stirred at 50° C. for 3 hours.

After completion of the reaction, the solvent is removed at reduced pressure and the residue taken up with 5% HCl, which is washed with a little portion of diethyl ether, then slowly neutralized to pH 7-7.5 and extracted three times with diethyl ether.

The combined organic phases are dried with Na$_2$SO$_4$ and evaporated, yielding a dark oil, which is purified by flash chromatography to obtain 0.72 g of desired product as an oil (yield: 14%).

$^1$H-NMR (CDCl$_3$): δ 0.89-1.24 (m, 4H, CH$_2$CH$_2$), 2.06 (m, 1H, CH), 2.43 (s, 3H, CH$_3$), 4.23 (s, 2H, CH$_2$), 6.83 (s, 1H, thiazole H)

EXAMPLE 16

Synthesis of 1-[2-chloro-4-(methylsulphonyl)phenyl]-3-cyclopropyl-2-(4-methyl-1,3-thiazol-2-yl)propane-1,3-dione (Compound No 10, Corresponding to Compound No 485 in Table 2)

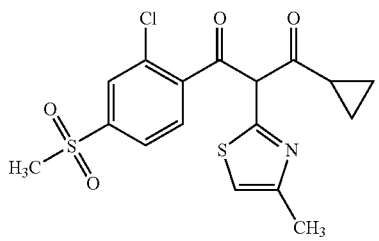

Under an inert atmosphere, Mg(OEt)$_2$ (0.316 g) is added to a solution of 1-cyclopropyl-2-(4-methyl-1,3-thiazol-2-yl)ethanone (0.72 g) in 18 ml of dry tetrahydrofuran; the stirred mixture is refluxed for 3 hours, then completely evaporated under reduced pressure.

The residue is taken up with 3 ml of dry tetrahydrofuran, under an inert atmosphere, then a suspension of 2-chloro-4 (methylsulphonyl)benzoyl chloride (1.11 g) in 15 ml of dry tetrahydrofuran is added; the stirred mixture is refluxed for 3 more hours.

After completion of the reaction, the solvent is evaporated and the residue is taken up with ethyl acetate and 1% HCl, then the mixture is neutralized with NaHCO$_3$ and extracted three times with ethyl acetate; the combined organic phases are washed with brine, dried with Na$_2$SO$_4$ and evaporated.

The resulting solid is purified by washing with diethyl ether to obtain 1.06 g of pure product as an off-white solid (yield: 67%; m.p.: 199° C.)

$^1$H-NMR (CDCl$_3$): δ 0.51-1.35 (m, 5H, cyclopropyl), 2.43 (2s, 3H, Ar—CH$_3$), 3.07 (s, 3H, SO$_2$CH$_3$), 6.59 (2s, 1H, thiazole H), 7.58-8.02 (m, 3H, arom. H's), 14.78 (s, 1H, OH).

MS-DCI: m/z 398 (M+1).

EXAMPLE 17

Synthesis of 1-cyclopropyl-2-(3-methyl-1,2,4-oxadiazol-5-yl)ethanone

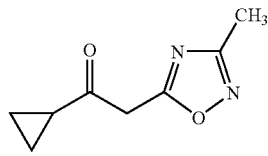

Under an inert atmosphere, acetamidoxime (1.56 g) is added to a solution of methyl 3-cyclopropyl-3-oxopropanoate (3.0 g) in 50 ml of toluene; the stirred mixture is heated to 130° C. while distilling off the solvent and methanol formed in the reaction.

When all the solvent has been removed, 50 ml of toluene and 1.56 g of acetamidoxime are added again to the residue and the distillation continued until all of this second portion of solvent has been removed.

The residue is then purified by flash chromatography to obtain 1.48 g of pure product as a violet oil (yield: 42%).

$^1$H-NMR (CDCl$_3$): δ 0.95-1.18 (m, 4H, CH$_2$CH$_2$), 2.00 (m, 1H, CH), 2.40 (s, 3H, CH$_3$), 4.14 (s, 2H, CH$_2$).

EXAMPLE 18

Synthesis of 1-[2-chloro-4-(methylsulphonyl)phenyl]-3-cyclopropyl-2-(3-methyl-1,2,4-oxadiazol-5-yl)propane-1,3-dione (Compound No 11, Corresponding to Compound No 385 in Table 2)

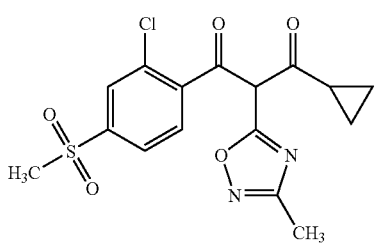

Under an inert atmosphere, Mg(OEt)$_2$ (0.239 g) is added to a solution of 1-cyclopropyl-2-(3-methyl-1,2,4-oxadiazol-5-yl)ethanone (0.50 g) in 13 ml of dry tetrahydrofuran; the stirred mixture is refluxed for 3 hours, then completely evaporated under reduced pressure.

The residue is taken up with 3 ml of dry tetrahydrofuran, under an inert atmosphere, then a suspension of 2-chloro-4-(methylsulphonyl)benzoyl chloride (0.84 g) in 10 ml of dry tetrahydrofuran is added; the stirred mixture is refluxed for 3 more hours.

After completion of the reaction, the solvent is evaporated and the residue is taken up with ethyl acetate and 1% HCl, then neutralized with aqueous NaHCO$_3$ and extracted three times with 5% NaOH; the combined basic aqueous phases are acidified and extracted three times with ethyl acetate, which is then washed with brine, dried with Na$_2$SO$_4$ and evaporated.

The resulting solid is purified by washing with diethyl ether to obtain 0.90 g of pure product as an off-white solid (yield: 78%; m.p.: 188° C.).

$^1$H-NMR (CDCl$_3$): δ 1.19-1.48 (m, 4H, CH$_2$CH$_2$), 2.29 (2s, 3H, Ar—CH$_3$), 2.55 (m, 1H, CH), 3.06 (s, 3H, SO$_2$CH$_3$), 7.46-7.93 (m, 3H, arom. H's), 17.93 (bs, 1H, OH).

EXAMPLE 19

Synthesis of 1-(4-chloro-2-nitrophenil)-3-cyclopropyl-2-(3-methyl-1,2,4-oxadiazol-5-yl)propane-1,3-dione (Compound No 12, Corresponding to Compound No 748 in Table 2)

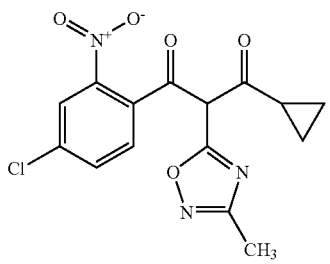

Under an inert atmosphere, Mg(OEt)$_2$ (0.215 g) is added to a solution of 1-ciclopropyl-2-(3-methyl-1,2,4-oxadiazol-5-yl)ethanone (0.45 g) in 12 ml of dry tetrahydrofuran; the stirred mixture is refluxed for 3 hours, then completely evaporated under reduced pressure.

The residue is taken up with 6 ml of dry tetrahydrofuran, under an inert atmosphere, then a solution of 4-chloro-2-nitrobenzoyl chloride (0.66 g) in 6 ml of dry tetrahydrofuran is added; the stirred mixture is refluxed for 3 more hours.

After completion of the reaction, the solvent is evaporated and the residue is taken up with ethyl acetate and 1% HCl, then neutralized with aqueous NaHCO$_3$ and extracted three times with 5% NaOH; the combined basic aqueous phases are acidified and extracted three times with ethyl acetate, which is then washed with brine, dried with Na$_2$SO$_4$ and evaporated.

The resulting solid is purified by washing with a little portion of diethyl ether to obtain 0.51 g of pure product as an off-white solid (yield: 54%; m.p.: 127° C.).

$^1$H-NMR (CDCl$_3$): δ 1.18-1.49 (m, 4H, CH$_2$CH$_2$), 2.25 (2s, 3H, Ar—CH$_3$), 2.47 (m, 1H, CH), 7.16-8.15 (m, 3H, arom. H's), 17.61 (bs, 1H, OH).

EXAMPLE 20

Synthesis of 1-cyclopropyl-2-(pyridin-2-yl)ethanone

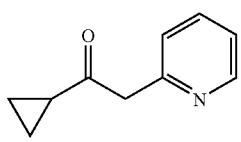

Under an inert atmosphere and in dried glassware, 2-picoline (9.43 g) is dissolved in 95 ml of anhydrous tetrahydrofuran; 63.1 ml of 1.6 M buthyllithium solution in hexanes are then added: the solution temperature rises to about 40° C.; after the addition, the mixture is stirred for 30 minutes at 40° C.

A solution of methyl cyclopropanecarboxylate (5.07 g) in 5 ml of anhydrous tetrahydrofuran is then quickly added and the mixture is stirred for 1 h at 40° C.

The mixture is then cautiously diluted with water and the organic solvent evaporated at reduced pressure; the residue is taken up with ether and a mixture of 10% HCl and ice; the organic phase is extracted 4 times with HCl 10%.

The combined aqueous acid phases are cautiously treated with 50% NaOH until slightly acid, then basified to pH 8 with solid NaHCO$_3$; the mixture is then saturated with NaCl and extracted three times with ethyl acetate, which is then dried with Na$_2$SO$_4$ and evaporated.

The resulting dark oil is purified by flash chromatography to obtain 5.08 g of desired product as a yellow oil (yield: 31%).

$^1$H-NMR (CDCl$_3$): δ 0.82-1.11 (m, 4H, CH$_2$CH$_2$), 2.05 (m, 1H, CH), 4.03 (s, 2H, CH$_2$), 7.19, 7.63, 8.55 (3m, 4H, arom. H's)

EXAMPLE 21

Synthesis of 1-[2-chloro-4-(methylsulphonyl)phenyl]-3-cyclopropyl-2-(pyridin-2-yl)propane-1,3-dione (Compound No 13, Corresponding to Compound No 615 in Table 2)

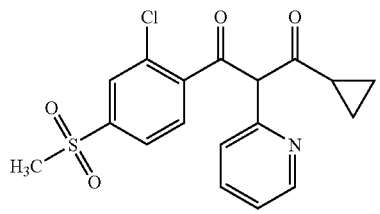

Under an inert atmosphere, Mg(OEt)$_2$ (0.152 g) is added to a solution of 1-ciclopropyl-2-(pyridin-2-yl)ethanone (0.30 g) in 8 ml of dry tetrahydrofuran; the stirred mixture is refluxed for 3 hours, then completely evaporated under reduced pressure.

The residue is taken up with 2 ml of dry tetrahydrofuran, under an inert atmosphere, then a suspension of 2-chloro-4-(methylsulfonyl)benzoyl chloride (0.52 g) in 6 ml of dry tetrahydrofuran is added; the stirred mixture is refluxed for 3 more hours.

After completion of the reaction, the mixture is diluted with methanol to have an homogeneous solution, then the solvent is evaporated. The residue is taken up with water and extracted three times with ethyl acetate, which is then washed with brine, dried with Na$_2$SO$_4$ and evaporated.

The resulting solid is purified by flash chromatography to obtain 0.36 g of product as a yellow amorphous solid (yield: 51%).

¹H-NMR (CDCl₃): δ 0.82-1.70 (m, 5H, cyclopropyl), 3.06 (s, 3H, SO₂CH₃), 7.06-8.21 (m, 7H, arom. H's), 18.05 (bs, 1H, OH).

EXAMPLE 22

Synthesis of 1-[2-chloro-4-(methylsulphonyl)phenyl]-3-(cyclopropyl)propane-1,3-dione

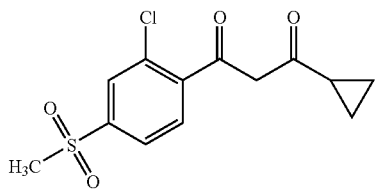

Under an inert atmosphere, Mg(OEt)₂ (1.29 g) is added to a solution of t-butyl 3-cyclopropyl-3-oxopropanoate (3.0 g) in 75 ml of dry tetrahydrofuran; the stirred mixture is refluxed for 3 hours, then completely evaporated under reduced pressure.

The residue is taken up with 20 ml of dry tetrahydrofuran, under an inert atmosphere, then a suspension of 2-chloro-4-(methylsulfonyl)benzoyl chloride (4.52 g) in 55 ml of dry tetrahydrofuran is added; the stirred mixture is refluxed for 3 more hours.

After completion of the reaction, the solvent is evaporated under reduced pressure; the residue is taken up with 30 ml of toluene and p-toluenesulphonic acid (1.13 g) is added, then the stirred mixture is refluxed for 8 hours.

The solid precipitate is filtered off and the solution is evaporated under reduced pressure; the oily residue is purified by flash chromatography to obtain 2.64 g of solid product (yield: 54%).

¹H-NMR (CDCl₃): δ 0.98-1.80 (m, 5H, cyclopropyl), 3.07 (s, 3H, SO₂CH₃), 6.13 (s, 1H, enolic form =CH—), 7.74-8.00 (m, 3H, arom. H's).

EXAMPLE 23

Synthesis of 1-[2-chloro-4-(thylsulphonyl)phenyl]-3-cyclopropyl-2-(5-trifluoromethyl-1,3,4-thiadiazol-2-yl)propane-1,3-dione (Compound No 2918).

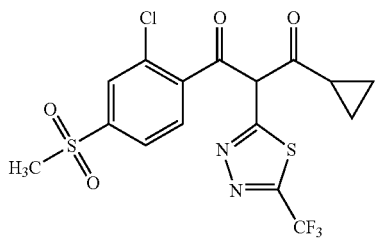

Under an inert atmosphere, NaH (60% suspension in mineral oil, 0.27 g) is suspended in 10 ml of dry tetrahydrofuran; a solution of 1-[2-chloro-4-(methylsulphonyl)phenyl]-3-(cyclopropyl)propan-1,3-dione (1.76 g) in 15 ml of dry tetrahydrofuran is then slowly added dropwise.

The mixture is stirred for 1 hour, then a solution of 2-methylsulphonyl-5-trifluoromethyl-1,3,4-thiadiazole (1.97 g) in 13 ml of dry tetrahydrofuran is added dropwise.

The stirred mixture is refluxed for 3 hours, then the solvent is evaporated under reduced pressure; the residue is taken up with diethyl ether and extracted two times with aqueous NaRCO₃; the combined aqueous phases are slowly acidified to pH 2-3 and extracted with ethyl acetate, which is then dried with Na₂SO₄ and evaporated.

The residue is purified by flash chromatography, then by washing with diethyl ether, to obtain 0.83 g of product as a white solid (yield: 31%; m.p.: 185° C.).

¹H-NMR (CDCl₃): (mixture of two tautomers) δ 0.50-1.40 (m, 5H, cyclopropyl), 3.10 (s, 3H, SO₂CH₃), 7.60-8.06 (m, 3H, arom. H's), 15.23, 15.39 (2 bs, 1H, OH).

¹⁹F-NMR (CDCl₃): (mixture of two tautomers) δ −60.52, −60.68 (2 S, CF₃).

EXAMPLE 24

Synthesis of 1-[2-chloro-4-(methylsulphonyl)phenyl]-3-cyclopropyl-2-(2,4-dinitrophenyl)propane-1,3-dione (Compound No 723)

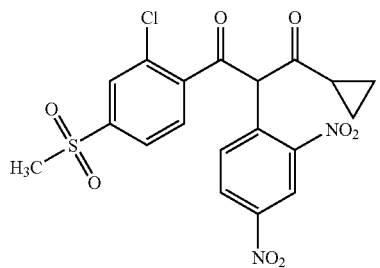

Under an inert atmosphere, NaH (60% suspension in mineral oil, 0.12 g) is suspended in 2 ml of dry tetrahydrofuran; a solution of 1-[2-chloro-4-(methylsulphonyl)phenyl]-3-(cyclopropyl)propan-1,3-dione (0.45 g) in 5 ml of dry tetrahydrofuran is then slowly added dropwise.

The mixture is stirred for 1 hour, then a solution of 2,4-dinitrochlorobenzene (1.52 g) in 2 ml of dry tetrahydrofuran is added dropwise.

The stirred mixture is refluxed for 5 hours, then the solvent is evaporated under reduced pressure; the residue is purified by flash chromatography, then by washing with diethyl ether, to obtain 0.40 g of product (yield: 57%; m.p.: 67° C.).

¹H-NMR (CDCl₃): δ 0.85-1.40 (m, 5H, cyclopropyl), 2.97 (s, 3H, SO₂CH₃), 7.31-8.67 (m, 6H, arom. H's), 16.78 (bs, 1H, OH).

EXAMPLE 25

Synthesis of 2-bromo-1-[2-chloro-4-(methylsulphonyl)phenyl]-3-(cyclopropyl)propane-1,3-dione

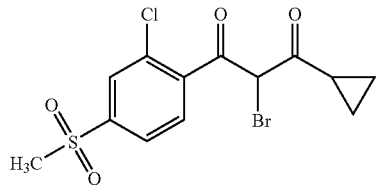

Under an inert atmosphere, bromine (0.24 g) is slowly added dropwise to a solution of (1-[2-chloro-4-(methylsulphonyl)phenyl]-3-(cyclopropyl)propan-1,3-dione (0.43 g) in 25 ml of dichloromethane cooled to 5° C., then the mixture is stirred overnight at room temperature.

The solvent is then completely evaporated under reduced pressure and the residue (0.57 g) is used without purification for the following reaction.

$^1$H-NMR (CDCl$_3$): δ 1.14-1.34 (m, 4H, cyclic CH$_2$—CH$_2$), 2.61 (m, 1H, cyclic CH), 3.10 (s, 3H, SO$_2$CH$_3$), 7.52-8.05 (m, 3H, arom. H's), 16.02 (bs, 1H, OH).

EXAMPLE 26

Synthesis of 1-[2-chloro-4-(methylsulphonyl)phenyl]-3-cyclopropyl-2-(1,2,4-triazol-1-yl)propane-1,3-dione (Compound No 460)

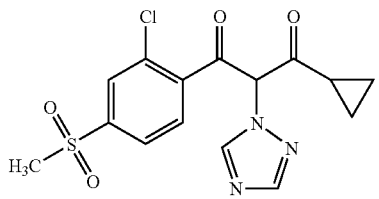

Under an inert atmosphere, NaH (60% suspension in mineral oil, 0.133 g) is suspended in 2 ml of dry tetrahydrofuran cooled in a water bath, then 1,2,4-triazole (0.23 g) is added.

After stirring for 30 minutes at room temperature, a solution of 2-bromo-1-[2-chloro-4-(methylsulphonyl)phenyl]-3-(cyclopropyl)propan-1,3-dione (0.63 g) in 5 ml of dry tetrahydrofuran is added, then the mixture is heated to 50° C. for 8 hours.

After completion of the reaction, the mixture is diluted with water, acidified and extracted three times with ethyl acetate, which is then washed with brine, dried with Na$_2$SO$_4$ and evaporated.

The residue is purified by flash chromatography, then by washing with ethyl ether to obtain 0.23 g of solid product (yield: 38%; m.p.: 162° C.).

$^1$H-NMR (CDCl$_3$): δ 1.09-1.40 (m, 5H, cyclopropyl), 3.01 (s, 3H, SO$_2$CH$_3$), 7.38-8.05 (m, 5H, arom. H's), 16.23 (bs, 1H, OH).

EXAMPLE 27

Synthesis of 1-[2-chloro-4-(methylsulphonyl)phenyl]-3-cyclopropyl-2-[1,1-dioxido-3-oxo-1,2-benzisothiazol-2(3H)-yl]propane-1,3-dione (Compound No 2919)

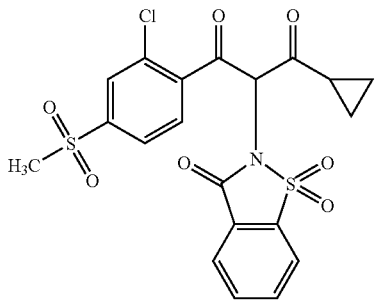

Under an inert atmosphere, NaH (60% suspension in mineral oil, 0.114 g) is suspended in 3 ml of dry tetrahydrofuran cooled in a water bath, then saccharine (0.52 g) is added.

After stirring for 30 minutes at room temperature, a solution of 2-bromo-1-[2-chloro-4-(methylsulphonyl)phenyl]-3-(cyclopropyl)propan-1,3-dione (0.54 g) in 8 ml of dry tetrahydrofuran is added, then the mixture is heated to 50° C. for 6 hours.

After completion of the reaction, the solvent is evaporated; the residue is taken up with water, acidified and extracted three times with ethyl acetate, which is then washed with brine, dried with Na$_2$SO$_4$ and evaporated.

The residue is purified by flash chromatography, then by washing with ethyl ether to obtain 0.31 g of product as an amorphous solid (yield: 45%).

$^1$H-NMR (CDCl$_3$): δ 1.09-1.45 (m, 4H, cyclic CH$_2$—CH$_2$), 1.86 (m, 1H, cyclic CH), 2.99 (s, 3H, SO$_2$CH$_3$), 7.51-8.08 (m, 7H, arom. H's), 17.19 (bs, 1H, OH).

EXAMPLE 28

Synthesis of 1,1,1-trifluoro-3-pyridin-2-ylacetone

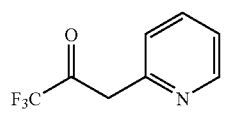

Under an inert atmosphere, 2-picoline (4.72 g) and pyridine (20.0 g) are dissolved in 130 ml of toluene cooled in an ice bath; trifluoroacetic anhydride (31.9 g) is then slowly added dropwise and the mixture is stirred at room temperature for 48 hours.

The mixture is then cautiously poured into 500 ml of 3% Na$_2$CO$_3$, and extracted three times with ethyl acetate; the combined organic phases are extracted two times with 5% NaOH, then these combined basic aqueous phases are acidified to pH 6.5 and extracted with ethyl acetate, which is washed with brine, dried with Na$_2$SO$_4$ and evaporated.

The raw product is purified by flash chromatography, then by washing with diethyl ether to obtain 4.24 g of product as a yellow solid (yield: 44%).

$^1$H-NMR (CDCl$_3$): δ 5.82 (s, 1H, enolic form CH), 6.99-8.10 (m, 4H, arom. H's), 15.88 (bs, 1H, OH).

$^{19}$F-NMR (CDCl$_3$) : δ −74.94 (s, CF$_3$)

EXAMPLE 29

Synthesis of 1-[2-chloro-4-(methylsuiphonyl)phenyl]-2-(pyridin-2-yl)-4,4,4-trifluorobutane-1,3-dione (Compound N-616)

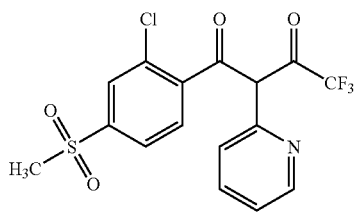

Under an inert atmosphere, Mg(OEt)$_2$ (0.336 g) is added to a solution of 1,1,1-trifluoro-3-pyridin-2-ylacetone (0.80 g) in 17 ml of dry tetrahydrofuran; the stirred mixture is stirred at room temperature for 3 hours, then completely evaporated under reduced pressure.

The residue is taken up with 5 ml of dry tetrahydrofuran, under an inert atmosphere, then a suspension of 2-chloro-4-(methylsulfonyl)benzoyl chloride (1.17 g) in 12 ml of dry tetrahydrofuran is added; the mixture is stirred overnight at room temperature.

After completion of the reaction, the mixture is diluted with ethyl acetate, quickly washed with NH$_4$Cl saturated solution, with brine, then dried with Na$_2$SO$_4$ and evaporated.

The residue is taken up with a mixture of diethyl ether and hexane which causes the product to precipitate: 0.24 g of solid are recovered by filtration (yield: 14%; m.p.: 189° C., with decomposition)

$^1$H-NMR (acetone-d$_6$): δ 3.09 (s, 3H, SO$_2$CH$_3$), 7.07-8.37 (m, 7H, arom. H's).

$^{19}$F-NMR (acetone-d$_6$): δ −67.43 (s, CF$_3$)

EXAMPLE 30

Following the suitable procedures, some of which are detailed in the examples above, the following compounds, listed in Table 2, have been prepared and identified by elemental analysis and/or $^1$H-NMR:

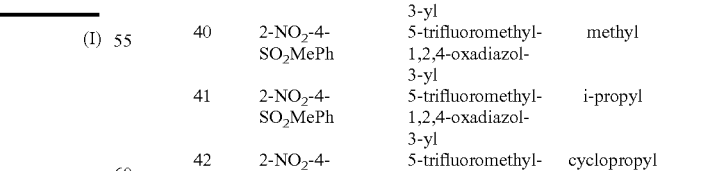

| Compound N | A | B | R | m.p. (° C.) |
|---|---|---|---|---|
| 14 | 2-NO$_2$-4-SO$_2$MePh | 1,2,4-oxadiazol-5-yl | H | |
| 15 | 2-NO$_2$-4-SO$_2$MePh | 1,2,4-oxadiazol-5-yl | methyl | |
| 16 | 2-NO$_2$-4-SO$_2$MePh | 1,2,4-oxadiazol-5-yl | i-propyl | |
| 17 | 2-NO$_2$-4-SO$_2$MePh | 1,2,4-oxadiazol-5-yl | cyclopropyl | |
| 18 | 2-NO$_2$-4-SO$_2$MePh | 1,2,4-oxadiazol-5-yl | CF$_3$ | |
| 19 | 2-NO$_2$-4-SO$_2$MePh | 3-methyl-1,2,4-oxadiazol-5-yl | H | |
| 20 | 2-NO$_2$-4-SO$_2$MePh | 3-methyl-1,2,4-oxadiazol-5-yl | methyl | |
| 21 | 2-NO$_2$-4-SO$_2$MePh | 3-methyl-1,2,4-oxadiazol-5-yl | i-propyl | |
| 22 | 2-NO$_2$-4-SO$_2$MePh | 3-methyl-1,2,4-oxadiazol-5-yl | cyclopropyl | |
| 23 | 2-NO$_2$-4-SO$_2$MePh | 3-methyl-1,2,4-oxadiazol-5-yl | CF$_3$ | |
| 24 | 2-NO$_2$-4-SO$_2$MePh | 3-trifluoromethyl-1,2,4-oxadiazol-5-yl | H | |
| 25 | 2-NO$_2$-4-SO$_2$MePh | 3-trifluoromethyl-1,2,4-oxadiazol-5-yl | methyl | |
| 26 | 2-NO$_2$-4-SO$_2$MePh | 3-trifluoromethyl-1,2,4-oxadiazol-5-yl | i-propyl | |
| 27 | 2-NO$_2$-4-SO$_2$MePh | 3-trifluoromethyl-1,2,4-oxadiazol-5-yl | cyclopropyl | |
| 28 | 2-NO$_2$-4-SO$_2$MePh | 3-trifluoromethyl-1,2,4-oxadiazol-5-yl | CF$_3$ | |
| 29 | 2-NO$_2$-4-SO$_2$MePh | 1,2,4-oxadiazol-3-yl | H | |
| 30 | 2-NO$_2$-4-SO$_2$MePh | 1,2,4-oxadiazol-3-yl | methyl | |
| 31 | 2-NO$_2$-4-SO$_2$MePh | 1,2,4-oxadiazol-3-yl | i-propyl | |
| 32 | 2-NO$_2$-4-SO$_2$MePh | 1,2,4-oxadiazol-3-yl | cyclopropyl | |
| 33 | 2-NO$_2$-4-SO$_2$MePh | 1,2,4-oxadiazol-3-yl | CF$_3$ | |
| 34 | 2-NO$_2$-4-SO$_2$MePh | 5-methyl-1,2,4-oxadiazol-3-yl | H | |
| 35 | 2-NO$_2$-4-SO$_2$MePh | 5-methyl-1,2,4-oxadiazol-3-yl | methyl | |
| 36 | 2-NO$_2$-4-SO$_2$MePh | 5-methyl-1,2,4-oxadiazol-3-yl | i-propyl | |
| 37 | 2-NO$_2$-4-SO$_2$MePh | 5-methyl-1,2,4-oxadiazol-3-yl | cyclopropyl | |
| 38 | 2-NO$_2$-4-SO$_2$MePh | 5-methyl-1,2,4-oxadiazol-3-yl | CF$_3$ | |
| 39 | 2-NO$_2$-4-SO$_2$MePh | 5-trifluoromethyl-1,2,4-oxadiazol-3-yl | H | |
| 40 | 2-NO$_2$-4-SO$_2$MePh | 5-trifluoromethyl-1,2,4-oxadiazol-3-yl | methyl | |
| 41 | 2-NO$_2$-4-SO$_2$MePh | 5-trifluoromethyl-1,2,4-oxadiazol-3-yl | i-propyl | |
| 42 | 2-NO$_2$-4-SO$_2$MePh | 5-trifluoromethyl-1,2,4-oxadiazol-3-yl | cyclopropyl | |
| 43 | 2-NO$_2$-4-SO$_2$MePh | 5-trifluoromethyl-1,2,4-oxadiazol-3-yl | CF$_3$ | |
| 44 | 2-NO$_2$-4-SO$_2$MePh | 5-chloro-1,2,4-oxadiazol-3-yl | H | |
| 45 | 2-NO$_2$-4-SO$_2$MePh | 5-chloro-1,2,4-  | methyl | |

103 -continued

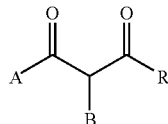
(I)

| Compound N | A | B | R | m.p. (° C.) |
|---|---|---|---|---|
| | SO₂MePh | oxadiazol-3-yl | | |
| 46 | 2-NO₂-4-SO₂MePh | 5-chloro-1,2,4-oxadiazol-3-yl | i-propyl | |
| 47 | 2-NO₂-4-SO₂MePh | 5-chloro-1,2,4-oxadiazol-3-yl | cyclopropyl | |
| 48 | 2-NO₂-4-SO₂MePh | 5-chloro-1,2,4-oxadiazol-3-yl | CF₃ | |
| 49 | 2-NO₂-4-SO₂MePh | 1,3,4-oxadiazol-2-yl | H | |
| 50 | 2-NO₂-4-SO₂MePh | 1,3,4-oxadiazol-2-yl | methyl | |
| 51 | 2-NO₂-4-SO₂MePh | 1,3,4-oxadiazol-2-yl | i-propyl | |
| 52 | 2-NO₂-4-SO₂MePh | 1,3,4-oxadiazol-2-yl | cyclopropyl | |
| 53 | 2-NO₂-4-SO₂MePh | 1,3,4-oxadiazol-2-yl | CF₃ | |
| 54 | 2-NO₂-4-SO₂MePh | 5-methylsulfonyl-1,3,4-oxadiazol-2-yl | H | |
| 55 | 2-NO₂-4-SO₂MePh | 5-methylsulfonyl-1,3,4-oxadiazol-2-yl | methyl | |
| 56 | 2-NO₂-4-SO₂MePh | 5-methylsulfonyl-1,3,4-oxadiazol-2-yl | i-propyl | |
| 57 | 2-NO₂-4-SO₂MePh | 5-methylsulfonyl-1,3,4-oxadiazol-2-yl | cyclopropyl | |
| 58 | 2-NO₂-4-SO₂MePh | 5-methylsulfonyl-1,3,4-oxadiazol-2-yl | CF₃ | |
| 59 | 2-NO₂-4-SO₂MePh | 5-methyl-1,3,4-oxadiazol-2-yl | H | |
| 60 | 2-NO₂-4-SO₂MePh | 5-methyl-1,3,4-oxadiazol-2-yl | methyl | |
| 61 | 2-NO₂-4-SO₂MePh | 5-methyl-1,3,4-oxadiazol-2-yl | i-propyl | |
| 62 | 2-NO₂-4-SO₂MePh | 5-methyl-1,3,4-oxadiazol-2-yl | cyclopropyl | |
| 63 | 2-NO₂-4-SO₂MePh | 5-methyl-1,3,4-oxadiazol-2-yl | CF₃ | |
| 64 | 2-NO₂-4-SO₂MePh | 5-trifluoromethyl-1,3,4-oxadiazol-2-yl | H | |
| 65 | 2-NO₂-4-SO₂MePh | 5-trifluoromethyl-1,3,4-oxadiazol-2-yl | methyl | |
| 66 | 2-NO₂-4-SO₂MePh | 5-trifluoromethyl-1,3,4-oxadiazol-2-yl | i-propyl | |
| 67 | 2-NO₂-4-SO₂MePh | 5-trifluoromethyl-1,3,4-oxadiazol-2-yl | cyclopropyl | |
| 68 | 2-NO₂-4-SO₂MePh | 5-trifluoromethyl-1,3,4-oxadiazol-2-yl | CF₃ | |
| 69 | 2-NO₂-4-SO₂MePh | 1,2,3-triazol-4-yl | H | |
| 70 | 2-NO₂-4-SO₂MePh | 1,2,3-triazol-4-yl | methyl | |
| 71 | 2-NO₂-4-SO₂MePh | 1,2,3-triazol-4-yl | i-propyl | |
| 72 | 2-NO₂-4-SO₂MePh | 1,2,3-triazol-4-yl | cyclopropyl | |
| 73 | 2-NO₂-4-SO₂MePh | 1,2,3-triazol-4-yl | CF₃ | |
| 74 | 2-NO₂-4-SO₂MePh | 1-methyl-1,2,3-triazol-4-yl | H | |

104 -continued

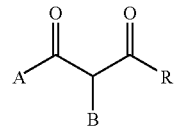
(I)

| Compound N | A | B | R | m.p. (° C.) |
|---|---|---|---|---|
| 75 | 2-NO₂-4-SO₂MePh | 1-methyl-1,2,3-triazol-4-yl | methyl | |
| 76 | 2-NO₂-4-SO₂MePh | 1-methyl-1,2,3-triazol-4-yl | i-propyl | |
| 77 | 2-NO₂-4-SO₂MePh | 1-methyl-1,2,3-triazol-4-yl | cyclopropyl | |
| 78 | 2-NO₂-4-SO₂MePh | 1-methyl-1,2,3-triazol-4-yl | CF₃ | |
| 79 | 2-NO₂-4-SO₂MePh | 2-methyl-1,2,3-triazol-4-yl | H | |
| 80 | 2-NO₂-4-SO₂MePh | 2-methyl-1,2,3-triazol-4-yl | methyl | |
| 81 | 2-NO₂-4-SO₂MePh | 2-methyl-1,2,3-triazol-4-yl | i-propyl | |
| 82 | 2-NO₂-4-SO₂MePh | 2-methyl-1,2,3-triazol-4-yl | cyclopropyl | |
| 83 | 2-NO₂-4-SO₂MePh | 2-methyl-1,2,3-triazol-4-yl | CF₃ | |
| 84 | 2-NO₂-4-SO₂MePh | 1,2,3-triazol-1-yl | H | |
| 85 | 2-NO₂-4-SO₂MePh | 1,2,3-triazol-1-yl | methyl | |
| 86 | 2-NO₂-4-SO₂MePh | 1,2,3-triazol-1-yl | i-propyl | |
| 87 | 2-NO₂-4-SO₂MePh | 1,2,3-triazol-1-yl | cyclopropyl | |
| 88 | 2-NO₂-4-SO₂MePh | 1,2,3-triazol-1-yl | CF₃ | |
| 89 | 2-NO₂-4-SO₂MePh | 1,2,3-triazol-2-yl | H | |
| 90 | 2-NO₂-4-SO₂MePh | 1,2,3-triazol-2-yl | methyl | |
| 91 | 2-NO₂-4-SO₂MePh | 1,2,3-triazol-2-yl | i-propyl | |
| 92 | 2-NO₂-4-SO₂MePh | 1,2,3-triazol-2-yl | cyclopropyl | |
| 93 | 2-NO₂-4-SO₂MePh | 1,2,3-triazol-2-yl | CF₃ | |
| 94 | 2-NO₂-4-SO₂MePh | 1,2,4-triazol-1-yl | H | |
| 95 | 2-NO₂-4-SO₂MePh | 1,2,4-triazol-1-yl | methyl | |
| 96 | 2-NO₂-4-SO₂MePh | 1,2,4-triazol-1-yl | i-propyl | |
| 97 | 2-NO₂-4-SO₂MePh | 1,2,4-triazol-1-yl | cyclopropyl | |
| 98 | 2-NO₂-4-SO₂MePh | 1,2,4-triazol-1-yl | CF₃ | |
| 99 | 2-NO₂-4-SO₂MePh | imidazol-2-yl | H | |
| 100 | 2-NO₂-4-SO₂MePh | imidazol-2-yl | methyl | |
| 101 | 2-NO₂-4-SO₂MePh | imidazol-2-yl | i-propyl | |
| 102 | 2-NO₂-4-SO₂MePh | imidazol-2-yl | cyclopropyl | |
| 103 | 2-NO₂-4-SO₂MePh | imidazol-2-yl | CF₃ | |
| 104 | 2-NO₂-4-SO₂MePh | imidazol-1-yl | H | |
| 105 | 2-NO₂-4-SO₂MePh | imidazol-1-yl | methyl | |
| 106 | 2-NO₂-4-SO₂MePh | imidazol-1-yl | i-propyl | |
| 107 | 2-NO₂-4-SO₂MePh | imidazol-1-yl | cyclopropyl | |
| 108 | 2-NO₂-4-SO₂MePh | imidazol-1-yl | CF₃ | |
| 109 | 2-NO₂-4- | imidazol-4-yl | H | |

-continued

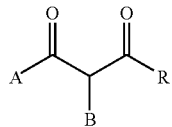

(I)

| Compound N | A | B | R | m.p. (° C.) |
|---|---|---|---|---|
| 110 | 2-NO₂-4-SO₂MePh | imidazol-4-yl | methyl | |
| 111 | 2-NO₂-4-SO₂MePh | imidazol-4-yl | i-propyl | |
| 112 | 2-NO₂-4-SO₂MePh | imidazol-4-yl | cyclopropyl | |
| 113 | 2-NO₂-4-SO₂MePh | imidazol-4-yl | CF₃ | |
| 114 | 2-NO₂-4-SO₂MePh | thiazol-2-yl | H | |
| 115 | 2-NO₂-4-SO₂MePh | thiazol-2-yl | methyl | |
| 116 | 2-NO₂-4-SO₂MePh | thiazol-2-yl | i-propyl | |
| 117 | 2-NO₂-4-SO₂MePh | thiazol-2-yl | cyclopropyl | |
| 118 | 2-NO₂-4-SO₂MePh | thiazol-2-yl | CF₃ | |
| 119 | 2-NO₂-4-SO₂MePh | 4-methylthiazol-2-yl | H | |
| 120 | 2-NO₂-4-SO₂MePh | 4-methylthiazol-2-yl | methyl | |
| 121 | 2-NO₂-4-SO₂MePh | 4-methylthiazol-2-yl | i-propyl | |
| 122 | 2-NO₂-4-SO₂MePh | 4-methylthiazol-2-yl | cyclopropyl | |
| 123 | 2-NO₂-4-SO₂MePh | 4-methylthiazol-2-yl | CF₃ | |
| 124 | 2-NO₂-4-SO₂MePh | oxazol-2-yl | H | |
| 125 | 2-NO₂-4-SO₂MePh | oxazol-2-yl | methyl | |
| 126 | 2-NO₂-4-SO₂MePh | oxazol-2-yl | i-propyl | |
| 127 | 2-NO₂-4-SO₂MePh | oxazol-2-yl | cyclopropyl | |
| 128 | 2-NO₂-4-SO₂MePh | oxazol-2-yl | CF₃ | |
| 129 | 2-NO₂-4-SO₂MePh | 4,5-dimethyl-oxazol-2-yl | H | |
| 130 | 2-NO₂-4-SO₂MePh | 4,5-dimethyl-oxazol-2-yl | methyl | |
| 131 | 2-NO₂-4-SO₂MePh | 4,5-dimethyl-oxazol-2-yl | i-propyl | |
| 132 | 2-NO₂-4-SO₂MePh | 4,5-dimethyl-oxazol-2-yl | cyclopropyl | |
| 133 | 2-NO₂-4-SO₂MePh | 4,5-dimethyl-oxazol-2-yl | CF₃ | |
| 134 | 2-NO₂-4-SO₂MePh | 2-oxazolin-2-yl | H | |
| 135 | 2-NO₂-4-SO₂MePh | 2-oxazolin-2-yl | methyl | |
| 136 | 2-NO₂-4-SO₂MePh | 2-oxazolin-2-yl | i-propyl | |
| 137 | 2-NO₂-4-SO₂MePh | 2-oxazolin-2-yl | cyclopropyl | |
| 138 | 2-NO₂-4-SO₂MePh | 2-oxazolin-2-yl | CF₃ | |
| 139 | 2-NO₂-4-SO₂MePh | 4,4-dimethyl-2-oxazolin-2-yl | H | |
| 140 | 2-NO₂-4-SO₂MePh | 4,4-dimethyl-2-oxazol-2-yl | methyl | |
| 141 | 2-NO₂-4-SO₂MePh | 4,4-dimethyl-2-oxazol-2-yl | i-propyl | |
| 142 | 2-NO₂-4-SO₂MePh | 4,4-dimethyl-2-oxazol-2-yl | cyclopropyl | |
| 143 | 2-NO₂-4-SO₂MePh | 4,4-dimethyl-2-oxazol-2-yl | CF₃ | |

-continued

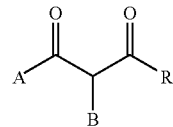

(I)

| Compound N | A | B | R | m.p. (° C.) |
|---|---|---|---|---|
| 144 | 2-NO₂-4-SO₂MePh | 1,2,4-thiadiazol-5-yl | H | |
| 145 | 2-NO₂-4-SO₂MePh | 1,2,4-thiadiazol-5-yl | methyl | |
| 146 | 2-NO₂-4-SO₂MePh | 1,2,4-thiadiazol-5-yl | i-propyl | |
| 147 | 2-NO₂-4-SO₂MePh | 1,2,4-thiadiazol-5-yl | cyclopropyl | |
| 148 | 2-NO₂-4-SO₂MePh | 1,2,4-thiadiazol-5-yl | CF₃ | |
| 149 | 2-NO₂-4-SO₂MePh | 3-methyl-1,2,4-thiadiazol-5-yl | H | |
| 150 | 2-NO₂-4-SO₂MePh | 3-methyl-1,2,4-thiadiazol-5-yl | methyl | |
| 151 | 2-NO₂-4-SO₂MePh | 3-methyl-1,2,4-thiadiazol-5-yl | i-propyl | |
| 152 | 2-NO₂-4-SO₂MePh | 3-methyl-1,2,4-thiadiazol-5-yl | cyclopropyl | |
| 153 | 2-NO₂-4-SO₂MePh | 3-methyl-1,2,4-thiadiazol-5-yl | CF₃ | |
| 154 | 2-NO₂-4-SO₂MePh | 3-trifluoromethyl-1,2,4-thiadiazol-5-yl | H | |
| 155 | 2-NO₂-4-SO₂MePh | 3-trifluoromethyl-1,2,4-thiadiazol-5-yl | methyl | |
| 156 | 2-NO₂-4-SO₂MePh | 3-trifluoromethyl-1,2,4-thiadiazol-5-yl | i-propyl | |
| 157 | 2-NO₂-4-SO₂MePh | 3-trifluoromethyl-1,2,4-thiadiazol-5-yl | cyclopropyl | |
| 158 | 2-NO₂-4-SO₂MePh | 3-trifluoromethyl-1,2,4-thiadiazol-5-yl | CF₃ | |
| 159 | 2-NO₂-4-SO₂MePh | 1,2,4-thiadiazol-3-yl | H | |
| 160 | 2-NO₂-4-SO₂MePh | 1,2,4-thiadiazol-3-yl | methyl | |
| 161 | 2-NO₂-4-SO₂MePh | 1,2,4-thiadiazol-3-yl | i-propyl | |
| 162 | 2-NO₂-4-SO₂MePh | 1,2,4-thiadiazol-3-yl | cyclopropyl | |
| 163 | 2-NO₂-4-SO₂MePh | 1,2,4-thiadiazol-3-yl | CF₃ | |
| 164 | 2-NO₂-4-SO₂MePh | 5-methyl-1,2,4-thiadiazol-3-yl | H | |
| 165 | 2-NO₂-4-SO₂MePh | 5-methyl-1,2,4-thiadiazol-3-yl | methyl | |
| 166 | 2-NO₂-4-SO₂MePh | 5-methyl-1,2,4-thiadiazol-3-yl | i-propyl | |
| 167 | 2-NO₂-4-SO₂MePh | 5-methyl-1,2,4-thiadiazol-3-yl | cyclopropyl | |
| 168 | 2-NO₂-4-SO₂MePh | 5-methyl-1,2,4-thiadiazol-3-yl | CF₃ | |
| 169 | 2-NO₂-4-SO₂MePh | 5-trifluoromethyl-1,2,4-thiadiazol-3-yl | H | |
| 170 | 2-NO₂-4-SO₂MePh | 5-trifluoromethyl-1,2,4-thiadiazol-3-yl | methyl | |
| 171 | 2-NO₂-4-SO₂MePh | 5-trifluoromethyl-1,2,4-thiadiazol-3-yl | i-propyl | |
| 172 | 2-NO₂-4-SO₂MePh | 5-trifluoromethyl-1,2,4-thiadiazol-3-yl | cyclopropyl | |
| 173 | 2-NO₂-4-SO₂MePh | 5-trifluoromethyl-1,2,4-thiadiazol- | CF₃ | |

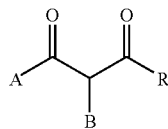

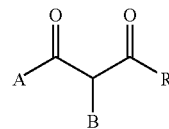

| Compound N | A | B | R | m.p. (°C.) |
|---|---|---|---|---|
| 174 | 2-NO$_2$-4-SO$_2$MePh | 1,3,4-thiadiazol-3-yl 2-yl | H | |
| 175 | 2-NO$_2$-4-SO$_2$MePh | 1,3,4-thiadiazol-2-yl | methyl | |
| 176 | 2-NO$_2$-4-SO$_2$MePh | 1,3,4-thiadiazol-2-yl | i-propyl | |
| 177 | 2-NO$_2$-4-SO$_2$MePh | 1,3,4-thiadiazol-2-yl | cyclopropyl | |
| 178 | 2-NO$_2$-4-SO$_2$MePh | 1,3,4-thiadiazol-2-yl | CF$_3$ | |
| 179 | 2-NO$_2$-4-SO$_2$MePh | 5-methylsulfonyl-1,3,4-thiadiazol-2-yl | H | |
| 180 | 2-NO$_2$-4-SO$_2$MePh | 5-methylsulfonyl-1,3,4-thiadiazol-2-yl | methyl | |
| 181 | 2-NO$_2$-4-SO$_2$MePh | 5-methylsulfonyl-1,3,4-thiadiazol-2-yl | i-propyl | |
| 182 | 2-NO$_2$-4-SO$_2$MePh | 5-methylsulfonyl-1,3,4-thiadiazol-2-yl | cyclopropyl | |
| 183 | 2-NO$_2$-4-SO$_2$MePh | 5-methylsulfonyl-1,3,4-thiadiazol-2-yl | CF$_3$ | |
| 184 | 2-NO$_2$-4-SO$_2$MePh | 5-methyl-1,3,4-thiadiazol-2-yl | H | |
| 185 | 2-NO$_2$-4-SO$_2$MePh | 5-methyl-1,3,4-thiadiazol-2-yl | methyl | |
| 186 | 2-NO$_2$-4-SO$_2$MePh | 5-methyl-1,3,4-thiadiazol-2-yl | i-propyl | |
| 187 | 2-NO$_2$-4-SO$_2$MePh | 5-methyl-1,3,4-thiadiazol-2-yl | cyclopropyl | |
| 188 | 2-NO$_2$-4-SO$_2$MePh | 5-methyl-1,3,4-thiadiazol-2-yl | CF$_3$ | |
| 189 | 2-NO$_2$-4-SO$_2$MePh | benzoxazol-2-yl | H | |
| 190 | 2-NO$_2$-4-SO$_2$MePh | benzoxazol-2-yl | methyl | |
| 191 | 2-NO$_2$-4-SO$_2$MePh | benzoxazol-2-yl | i-propyl | |
| 192 | 2-NO$_2$-4-SO$_2$MePh | benzoxazol-2-yl | cyclopropyl | |
| 193 | 2-NO$_2$-4-SO$_2$MePh | benzoxazol-2-yl | CF$_3$ | |
| 194 | 2-NO$_2$-4-SO$_2$MePh | 6-methyl-benzoxazol-2-yl | H | |
| 195 | 2-NO$_2$-4-SO$_2$MePh | 6-methyl-benzoxazol-2-yl | methyl | |
| 196 | 2-NO$_2$-4-SO$_2$MePh | 6-methyl-benzoxazol-2-yl | i-propyl | |
| 197 | 2-NO$_2$-4-SO$_2$MePh | 6-methyl-benzoxazol-2-yl | cyclopropyl | |
| 198 | 2-NO$_2$-4-SO$_2$MePh | 6-methyl-benzoxazol-2-yl | CF$_3$ | |
| 199 | 2-NO$_2$-4-SO$_2$MePh | benzothiazol-2-yl | H | |
| 200 | 2-NO$_2$-4-SO$_2$MePh | benzothiazol-2-yl | methyl | |
| 201 | 2-NO$_2$-4-SO$_2$MePh | benzothiazol-2-yl | i-propyl | |
| 202 | 2-NO$_2$-4-SO$_2$MePh | benzothiazol-2-yl | cyclopropyl | |
| 203 | 2-NO$_2$-4-SO$_2$MePh | benzothiazol-2-yl | CF$_3$ | |
| 204 | 2-NO$_2$-4-SO$_2$MePh | pyrazol-1-yl | H | |
| 205 | 2-NO$_2$-4-SO$_2$MePh | pyrazol-1-yl | methyl | |
| 206 | 2-NO$_2$-4-SO$_2$MePh | pyrazol-1-yl | i-propyl | |
| 207 | 2-NO$_2$-4-SO$_2$MePh | pyrazol-1-yl | cyclopropyl | |
| 208 | 2-NO$_2$-4-SO$_2$MePh | pyrazol-1-yl | CF$_3$ | |
| 209 | 2-NO$_2$-4-SO$_2$MePh | pyrazol-3-yl | H | |
| 210 | 2-NO$_2$-4-SO$_2$MePh | pyrazol-3-yl | methyl | |
| 211 | 2-NO$_2$-4-SO$_2$MePh | pyrazol-3-yl | i-propyl | |
| 212 | 2-NO$_2$-4-SO$_2$MePh | pyrazol-3-yl | cyclopropyl | |
| 213 | 2-NO$_2$-4-SO$_2$MePh | pyrazol-3-yl | CF$_3$ | |
| 214 | 2-NO$_2$-4-SO$_2$MePh | 1-methylpyrazol-3-yl | H | |
| 215 | 2-NO$_2$-4-SO$_2$MePh | 1-methylpyrazol-3-yl | methyl | |
| 216 | 2-NO$_2$-4-SO$_2$MePh | 1-methylpyrazol-3-yl | i-propyl | |
| 217 | 2-NO$_2$-4-SO$_2$MePh | 1-methylpyrazol-3-yl | cyclopropyl | |
| 218 | 2-NO$_2$-4-SO$_2$MePh | 1-methylpyrazol-3-yl | CF$_3$ | |
| 219 | 2-NO$_2$-4-SO$_2$MePh | tetrazol-1-yl | H | |
| 220 | 2-NO$_2$-4-SO$_2$MePh | tetrazol-1-yl | methyl | |
| 221 | 2-NO$_2$-4-SO$_2$MePh | tetrazol-1-yl | i-propyl | |
| 222 | 2-NO$_2$-4-SO$_2$MePh | tetrazol-1-yl | cyclopropyl | |
| 223 | 2-NO$_2$-4-SO$_2$MePh | tetrazol-1-yl | CF$_3$ | |
| 224 | 2-NO$_2$-4-SO$_2$MePh | 5-methyltetrazol-1-yl | H | |
| 225 | 2-NO$_2$-4-SO$_2$MePh | 5-methyltetrazol-1-yl | methyl | |
| 226 | 2-NO$_2$-4-SO$_2$MePh | 5-methyltetrazol-1-yl | i-propyl | |
| 227 | 2-NO$_2$-4-SO$_2$MePh | 5-methyltetrazol-1-yl | cyclopropyl | |
| 228 | 2-NO$_2$-4-SO$_2$MePh | 5-methyltetrazol-1-yl | CF$_3$ | |
| 229 | 2-NO$_2$-4-SO$_2$MePh | tetrazol-2-yl | H | |
| 230 | 2-NO$_2$-4-SO$_2$MePh | tetrazol-2-yl | methyl | |
| 231 | 2-NO$_2$-4-SO$_2$MePh | tetrazol-2-yl | i-propyl | |
| 232 | 2-NO$_2$-4-SO$_2$MePh | tetrazol-2-yl | cyclopropyl | |
| 233 | 2-NO$_2$-4-SO$_2$MePh | tetrazol-2-yl | CF$_3$ | |
| 234 | 2-NO$_2$-4-SO$_2$MePh | 5-methyltetrazol-2-yl | H | |
| 235 | 2-NO$_2$-4-SO$_2$MePh | 5-methyltetrazol-2-yl | methyl | |
| 236 | 2-NO$_2$-4-SO$_2$MePh | 5-methyltetrazol-2-yl | i-propyl | |
| 237 | 2-NO$_2$-4-SO$_2$MePh | 5-methyltetrazol-2-yl | cyclopropyl | |
| 238 | 2-NO$_2$-4-SO$_2$MePh | 5-methyltetrazol-2-yl | CF$_3$ | |
| 239 | 2-NO$_2$-4-SO$_2$MePh | 1-methyltetrazol-5-yl | H | |

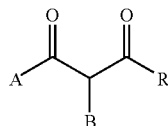

(I)

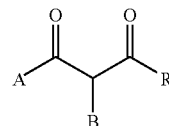

(I)

| Compound N | A | B | R | m.p. (° C.) |
|---|---|---|---|---|
| 240 | 2-NO$_2$-4-SO$_2$MePh | 1-methyltetrazol-5-yl | methyl | |
| 241 | 2-NO$_2$-4-SO$_2$MePh | 1-methyltetrazol-5-yl | i-propyl | |
| 242 | 2-NO$_2$-4-SO$_2$MePh | 1-methyltetrazol-5-yl | cyclopropyl | |
| 243 | 2-NO$_2$-4-SO$_2$MePh | 1-methyltetrazol-5-yl | CF$_3$ | |
| 244 | 2-NO$_2$-4-SO$_2$MePh | 2-methyltetrazol-5-yl | H | |
| 245 | 2-NO$_2$-4-SO$_2$MePh | 2-methyltetrazol-5-yl | methyl | |
| 246 | 2-NO$_2$-4-SO$_2$MePh | 2-methyltetrazol-5-yl | i-propyl | |
| 247 | 2-NO$_2$-4-SO$_2$MePh | 2-methyltetrazol-5-yl | cyclopropyl | 186 |
| 248 | 2-NO$_2$-4-SO$_2$MePh | 2-methyltetrazol-5-yl | CF$_3$ | |
| 249 | 2-NO$_2$-4-SO$_2$MePh | pyridin-2-yl | H | |
| 250 | 2-NO$_2$-4-SO$_2$MePh | pyridin-2-yl | methyl | |
| 251 | 2-NO$_2$-4-SO$_2$MePh | pyridin-2-yl | i-propyl | |
| 252 | 2-NO$_2$-4-SO$_2$MePh | pyridin-2-yl | cyclopropyl | |
| 253 | 2-NO$_2$-4-SO$_2$MePh | pyridin-2-yl | CF$_3$ | |
| 254 | 2-NO$_2$-4-SO$_2$MePh | pyridin-4-yl | H | |
| 255 | 2-NO$_2$-4-SO$_2$MePh | pyridin-4-yl | methyl | |
| 256 | 2-NO$_2$-4-SO$_2$MePh | pyridin-4-yl | i-propyl | |
| 257 | 2-NO$_2$-4-SO$_2$MePh | pyridin-4-yl | cyclopropyl | |
| 258 | 2-NO$_2$-4-SO$_2$MePh | pyridin-4-yl | CF$_3$ | |
| 259 | 2-NO$_2$-4-SO$_2$MePh | pyridin-3-yl | H | |
| 260 | 2-NO$_2$-4-SO$_2$MePh | pyridin-3-yl | methyl | |
| 261 | 2-NO$_2$-4-SO$_2$MePh | pyridin-3-yl | i-propyl | |
| 262 | 2-NO$_2$-4-SO$_2$MePh | pyridin-3-yl | cyclopropyl | |
| 263 | 2-NO$_2$-4-SO$_2$MePh | pyridin-3-yl | CF$_3$ | |
| 264 | 2-NO$_2$-4-SO$_2$MePh | 3-nitropyridin-4-yl | H | |
| 265 | 2-NO$_2$-4-SO$_2$MePh | 3-nitropyridin-4-yl | methyl | |
| 266 | 2-NO$_2$-4-SO$_2$MePh | 3-nitropyridin-4-yl | i-propyl | |
| 267 | 2-NO$_2$-4-SO$_2$MePh | 3-nitropyridin-4-yl | cyclopropyl | |
| 268 | 2-NO$_2$-4-SO$_2$MePh | 3-nitropyridin-4-yl | CF$_3$ | |
| 269 | 2-NO$_2$-4-SO$_2$MePh | 5-cyanopyridin-2-yl | H | |
| 270 | 2-NO$_2$-4-SO$_2$MePh | 5-cyanopyridin-2-yl | methyl | |
| 271 | 2-NO$_2$-4-SO$_2$MePh | 5-cyanopyridin-2-yl | i-propyl | |
| 272 | 2-NO$_2$-4-SO$_2$MePh | 5-cyanopyridin-2-yl | cyclopropyl | |
| 273 | 2-NO$_2$-4-SO$_2$MePh | 5-cyanopyridin-2-yl | CF$_3$ | |
| 274 | 2-NO$_2$-4-SO$_2$MePh | 5-trifluoro-methylpyridin-2-yl | H | |
| 275 | 2-NO$_2$-4-SO$_2$MePh | 5-trifluoro-methylpyridin-2-yl | methyl | |
| 276 | 2-NO$_2$-4-SO$_2$MePh | 5-trifluoro-methylpyridin-2-yl | i-propyl | |
| 277 | 2-NO$_2$-4-SO$_2$MePh | 5-trifluoro-methylpyridin-2-yl | cyclopropyl | |
| 278 | 2-NO$_2$-4-SO$_2$MePh | 5-trifluoro-methylpyridin-2-yl | CF$_3$ | |
| 279 | 2-NO$_2$-4-SO$_2$MePh | pyrimidin-2-yl | H | |
| 280 | 2-NO$_2$-4-SO$_2$MePh | pyrimidin-2-yl | methyl | |
| 281 | 2-NO$_2$-4-SO$_2$MePh | pyrimidin-2-yl | i-propyl | |
| 282 | 2-NO$_2$-4-SO$_2$MePh | pyrimidin-2-yl | cyclopropyl | |
| 283 | 2-NO$_2$-4-SO$_2$MePh | pyrimidin-2-yl | CF$_3$ | |
| 284 | 2-NO$_2$-4-SO$_2$MePh | pyrimidin-4-yl | H | |
| 285 | 2-NO$_2$-4-SO$_2$MePh | pyrimidin-4-yl | methyl | |
| 286 | 2-NO$_2$-4-SO$_2$MePh | pyrimidin-4-yl | i-propyl | |
| 287 | 2-NO$_2$-4-SO$_2$MePh | pyrimidin-4-yl | cyclopropyl | |
| 288 | 2-NO$_2$-4-SO$_2$MePh | pyrimidin-4-yl | CF$_3$ | |
| 289 | 2-NO$_2$-4-SO$_2$MePh | 6-chloro-pyrimidin-4-yl | methyl | |
| 290 | 2-NO$_2$-4-SO$_2$MePh | 6-chloro-pyrimidin-4-yl | i-propyl | |
| 291 | 2-NO$_2$-4-SO$_2$MePh | 6-chloro-pyrimidin-4-yl | cyclopropyl | |
| 292 | 2-NO$_2$-4-SO$_2$MePh | 6-chloro-pyrimidin-4-yl | CF$_3$ | |
| 293 | 2-NO$_2$-4-SO$_2$MePh | pyridazin-3-yl | H | |
| 294 | 2-NO$_2$-4-SO$_2$MePh | pyridazin-3-yl | methyl | |
| 295 | 2-NO$_2$-4-SO$_2$MePh | pyridazin-3-yl | i-propyl | |
| 296 | 2-NO$_2$-4-SO$_2$MePh | pyridazin-3-yl | cyclopropyl | |
| 297 | 2-NO$_2$-4-SO$_2$MePh | pyridazin-3-yl | CF$_3$ | |
| 298 | 2-NO$_2$-4-SO$_2$MePh | 6-chloro-pyridazin-3-yl | methyl | |
| 299 | 2-NO$_2$-4-SO$_2$MePh | 6-chloro-pyridazin-3-yl | i-propyl | |
| 300 | 2-NO$_2$-4-SO$_2$MePh | 6-chloro-pyridazin-3-yl | cyclopropyl | |
| 301 | 2-NO$_2$-4-SO$_2$MePh | 6-chloro-pyridazin-3-yl | CF$_3$ | |
| 302 | 2-NO$_2$-4-SO$_2$MePh | pyrazin-2-yl | methyl | |
| 303 | 2-NO$_2$-4-SO$_2$MePh | pyrazin-2-yl | i-propyl | |
| 304 | 2-NO$_2$-4-SO$_2$MePh | pyrazin-2-yl | cyclopropyl | |
| 305 | 2-NO$_2$-4-SO$_2$MePh | pyrazin-2-yl | CF$_3$ | |
| 306 | 2-NO$_2$-4-SO$_2$MePh | triazin-2-yl | methyl | |

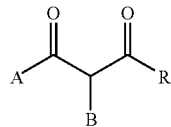

(I)

| Compound N | A | B | R | m.p. (° C.) |
|---|---|---|---|---|
| 307 | 2-NO₂-4-SO₂MePh | triazin-2-yl | i-propyl | |
| 308 | 2-NO₂-4-SO₂MePh | triazin-2-yl | cyclopropyl | |
| 309 | 2-NO₂-4-SO₂MePh | triazin-2-yl | CF₃ | |
| 310 | 2-NO₂-4-SO₂MePh | quinolin-2-yl | methyl | |
| 311 | 2-NO₂-4-SO₂MePh | quinolin-2-yl | i-propyl | |
| 312 | 2-NO₂-4-SO₂MePh | quinolin-2-yl | cyclopropyl | |
| 313 | 2-NO₂-4-SO₂MePh | quinolin-2-yl | CF₃ | |
| 314 | 2-NO₂-4-SO₂MePh | 4,4,6-trimethyl-5,6-dihydro-1,3(4H)-oxazin-2-yl | H | |
| 315 | 2-NO₂-4-SO₂MePh | 4,4,6-trimethyl-5,6-dihydro-1,3(4H)-oxazin-2-yl | methyl | |
| 316 | 2-NO₂-4-SO₂MePh | 4,4,6-trimethyl-5,6-dihydro-1,3(4H)-oxazin-2-yl | i-propyl | |
| 317 | 2-NO₂-4-SO₂MePh | 4,4,6-trimethyl-5,6-dihydro-1,3(4H)-oxazin-2-yl | cyclopropyl | |
| 318 | 2-NO₂-4-SO₂MePh | 4,4,6-trimethyl-5,6-dihydro-1,3(4H)-oxazin-2-yl | CF₃ | |
| 319 | 2-NO₂-4-SO₂MePh | 2-oxazolidinon-3-yl | H | |
| 320 | 2-NO₂-4-SO₂MePh | 2-oxazolidinon-3-yl | methyl | |
| 321 | 2-NO₂-4-SO₂MePh | 2-oxazolidinon-3-yl | i-propyl | |
| 322 | 2-NO₂-4-SO₂MePh | 2-oxazolidinon-3-yl | cyclopropyl | |
| 323 | 2-NO₂-4-SO₂MePh | 2-oxazolidinon-3-yl | CF₃ | |
| 324 | 2-NO₂-4-SO₂MePh | 2-pyrrolidinon-1-yl | methyl | |
| 325 | 2-NO₂-4-SO₂MePh | 2-pyrrolidinon-1-yl | i-propyl | |
| 326 | 2-NO₂-4-SO₂MePh | 2-pyrrolidinon-1-yl | cyclopropyl | |
| 327 | 2-NO₂-4-SO₂MePh | 2-pyrrolidinon-1-yl | CF₃ | |
| 328 | 2-NO₂-4-SO₂MePh | 3-methylisoxazol-5-yl | methyl | |
| 329 | 2-NO₂-4-SO₂MePh | 3-methylisoxazol-5-yl | i-propyl | |
| 330 | 2-NO₂-4-SO₂MePh | 3-methylisoxazol-5-yl | cyclopropyl | |
| 331 | 2-NO₂-4-SO₂MePh | 3-methylisoxazol-5-yl | CF₃ | |
| 332 | 2-NO₂-4-SO₂MePh | 2-NO₂-4-SO₂MePh | H | |
| 333 | 2-NO₂-4-SO₂MePh | 2-NO₂-4-SO₂MePh | methyl | |
| 334 | 2-NO₂-4-SO₂MePh | 2-NO₂-4-SO₂MePh | i-propyl | |
| 335 | 2-NO₂-4-SO₂MePh | 2-NO₂-4-SO₂MePh | cyclopropyl | |
| 336 | 2-NO₂-4-SO₂MePh | 2-NO₂-4-SO₂MePh | CF₃ | |
| 337 | 2-NO₂-4-SO₂MePh | 2-Cl-4-SO₂MePh | H | |
| 338 | 2-NO₂-4-SO₂MePh | 2-Cl-4-SO₂MePh | methyl | |
| 339 | 2-NO₂-4-SO₂MePh | 2-Cl-4-SO₂MePh | i-propyl | |
| 340 | 2-NO₂-4-SO₂MePh | 2-Cl-4-SO₂MePh | cyclopropyl | |
| 341 | 2-NO₂-4-SO₂MePh | 2-Cl-4-SO₂MePh | CF₃ | |
| 342 | 2-NO₂-4-SO₂MePh | 2-NO₂-4-CF₃Ph | H | |
| 343 | 2-NO₂-4-SO₂MePh | 2-NO₂-4-CF₃Ph | methyl | |
| 344 | 2-NO₂-4-SO₂MePh | 2-NO₂-4-CF₃Ph | i-propyl | |
| 345 | 2-NO₂-4-SO₂MePh | 2-NO₂-4-CF₃Ph | cyclopropyl | |
| 346 | 2-NO₂-4-SO₂MePh | 2-NO₂-4-CF₃Ph | CF₃ | |
| 347 | 2-NO₂-4-SO₂MePh | 2-NO₂-4-ClPh | H | |
| 348 | 2-NO₂-4-SO₂MePh | 2-NO₂-4-ClPh | methyl | |
| 349 | 2-NO₂-4-SO₂MePh | 2-NO₂-4-ClPh | i-propyl | |
| 350 | 2-NO₂-4-SO₂MePh | 2-NO₂-4-ClPh | cyclopropyl | |
| 351 | 2-NO₂-4-SO₂MePh | 2-NO₂-4-ClPh | CF₃ | |
| 352 | 2-NO₂-4-SO₂MePh | 2-Cl-4-NO₂Ph | H | |
| 353 | 2-NO₂-4-SO₂MePh | 2-Cl-4-NO₂Ph | methyl | |
| 354 | 2-NO₂-4-SO₂MePh | 2-Cl-4-NO₂Ph | i-propyl | |
| 355 | 2-NO₂-4-SO₂MePh | 2-Cl-4-NO₂Ph | cyclopropyl | |
| 356 | 2-NO₂-4-SO₂MePh | 2-Cl-4-NO₂Ph | CF₃ | |
| 357 | 2-NO₂-4-SO₂MePh | 2,4-(NO₂)₂Ph | H | |
| 358 | 2-NO₂-4-SO₂MePh | 2,4-(NO₂)₂Ph | methyl | |
| 359 | 2-NO₂-4-SO₂MePh | 2,4-(NO₂)₂Ph | i-propyl | |
| 360 | 2-NO₂-4-SO₂MePh | 2,4-(NO₂)₂Ph | cyclopropyl | |
| 361 | 2-NO₂-4-SO₂MePh | 2,4-(NO₂)₂Ph | CF₃ | |
| 362 | 2-NO₂-4-SO₂MePh | 4-F-3-NO₂Ph | H | |
| 363 | 2-NO₂-4-SO₂MePh | 4-F-3-NO₂Ph | methyl | |
| 364 | 2-NO₂-4-SO₂MePh | 4-F-3-NO₂Ph | i-propyl | |
| 365 | 2-NO₂-4-SO₂MePh | 4-F-3-NO₂Ph | cyclopropyl | |
| 366 | 2-NO₂-4-SO₂MePh | 4-F-3-NO₂Ph | CF₃ | |
| 367 | 2-NO₂-4-SO₂MePh | 3,5-(CF₃)₂Ph | H | |
| 368 | 2-NO₂-4-SO₂MePh | 3,5-(CF₃)₂Ph | methyl | |
| 369 | 2-NO₂-4-SO₂MePh | 3,5-(CF₃)₂Ph | i-propyl | |
| 370 | 2-NO₂-4-SO₂MePh | 3,5-(CF₃)₂Ph | cyclopropyl | |
| 371 | 2-NO₂-4-SO₂MePh | 3,5-(CF₃)₂Ph | CF₃ | |
| 372 | 2-NO₂-4-SO₂MePh | 2-SO₂Me-4-CF₃Ph | H | |

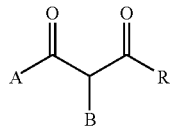

| Compound N | A | B | R | m.p. (° C.) |
|---|---|---|---|---|
| 373 | 2-NO₂-4-SO₂MePh | 2-SO₂Me-4-CF₃Ph | methyl | |
| 374 | 2-NO₂-4-SO₂MePh | 2-SO₂Me-4-CF₃Ph | i-propyl | |
| 375 | 2-NO₂-4-SO₂MePh | 2-SO₂Me-4-CF₃Ph | cyclopropyl | |
| 376 | 2-NO₂-4-SO₂MePh | 2-SO₂Me-4-CF₃Ph | CF₃ | |
| 377 | 2-Cl-4-SO₂MePh | 1,2,4-oxadiazol-5-yl | H | |
| 378 | 2-Cl-4-SO₂MePh | 1,2,4-oxadiazol-5-yl | methyl | |
| 379 | 2-Cl-4-SO₂MePh | 1,2,4-oxadiazol-5-yl | i-propyl | |
| 380 | 2-Cl-4-SO₂MePh | 1,2,4-oxadiazol-5-yl | cyclopropyl | |
| 381 | 2-Cl-4-SO₂MePh | 1,2,4-oxadiazol-5-yl | CF₃ | |
| 382 | 2-Cl-4-SO₂MePh | 3-methyl-1,2,4-oxadiazol-5-yl | H | |
| 383 | 2-Cl-4-SO₂MePh | 3-methyl-1,2,4-oxadiazol-5-yl | methyl | oil |
| 384 | 2-Cl-4-SO₂MePh | 3-methyl-1,2,4-oxadiazol-5-yl | i-propyl | 174 |
| 385 | 2-Cl-4-SO₂MePh | 3-methyl-1,2,4-oxadiazol-5-yl | cyclopropyl | 188 |
| 386 | 2-Cl-4-SO₂MePh | 3-methyl-1,2,4-oxadiazol-5-yl | CF₃ | |
| 387 | 2-Cl-4-SO₂MePh | 3-trifluoromethyl-1,2,4-oxadiazol-5-yl | H | |
| 388 | 2-Cl-4-SO₂MePh | 3-trifluoromethyl-1,2,4-oxadiazol-5-yl | methyl | |
| 389 | 2-Cl-4-SO₂MePh | 3-trifluoromethyl-1,2,4-oxadiazol-5-yl | i-propyl | |
| 390 | 2-Cl-4-SO₂MePh | 3-trifluoromethyl-1,2,4-oxadiazol-5-yl | cyclopropyl | |
| 391 | 2-Cl-4-SO₂MePh | 3-trifluoromethyl-1,2,4-oxadiazol-5-yl | CF₃ | |
| 392 | 2-Cl-4-SO₂MePh | 1,2,4-oxadiazol-3-yl | H | |
| 393 | 2-Cl-4-SO₂MePh | 1,2,4-oxadiazol-3-yl | methyl | |
| 394 | 2-Cl-4-SO₂MePh | 1,2,4-oxadiazol-3-yl | i-propyl | |
| 395 | 2-Cl-4-SO₂MePh | 1,2,4-oxadiazol-3-yl | cyclopropyl | |
| 396 | 2-Cl-4-SO₂MePh | 1,2,4-oxadiazol-3-yl | CF₃ | |
| 397 | 2-Cl-4-SO₂MePh | 5-methyl-1,2,4-oxadiazol-3-yl | H | |
| 398 | 2-Cl-4-SO₂MePh | 5-methyl-1,2,4-oxadiazol-3-yl | methyl | |
| 399 | 2-Cl-4-SO₂MePh | 5-methyl-1,2,4-oxadiazol-3-yl | i-propyl | |
| 400 | 2-Cl-4-SO₂MePh | 5-methyl-1,2,4-oxadiazol-3-yl | cyclopropyl | |
| 401 | 2-Cl-4-SO₂MePh | 5-methyl-1,2,4-oxadiazol-3-yl | CF₃ | |
| 402 | 2-Cl-4-SO₂MePh | 5-trifluoromethyl-1,2,4-oxadiazol-3-yl | H | |
| 403 | 2-Cl-4-SO₂MePh | 5-trifluoromethyl-1,2,4-oxadiazol-3-yl | methyl | |
| 404 | 2-Cl-4-SO₂MePh | 5-trifluoromethyl-1,2,4-oxadiazol-3-yl | i-propyl | |
| 405 | 2-Cl-4-SO₂MePh | 5-trifluoromethyl-1,2,4-oxadiazol-3-yl | cyclopropyl | |
| 406 | 2-Cl-4-SO₂MePh | 5-trifluoromethyl-1,2,4-oxadiazol-3-yl | CF₃ | |
| 407 | 2-Cl-4-SO₂MePh | 5-chloro-1,2,4-oxadiazol-3-yl | H | |
| 408 | 2-Cl-4-SO₂MePh | 5-chloro-1,2,4-oxadiazol-3-yl | methyl | |
| 409 | 2-Cl-4-SO₂MePh | 5-chloro-1,2,4-oxadiazol-3-yl | i-propyl | |
| 410 | 2-Cl-4-SO₂MePh | 5-chloro-1,2,4-oxadiazol-3-yl | cyclopropyl | |
| 411 | 2-Cl-4-SO₂MePh | 5-chloro-1,2,4-oxadiazol-3-yl | CF₃ | |
| 412 | 2-Cl-4-SO₂MePh | 1,3,4-oxadiazol-2-yl | H | |
| 413 | 2-Cl-4-SO₂MePh | 1,3,4-oxadiazol-2-yl | methyl | |
| 414 | 2-Cl-4-SO₂MePh | 1,3,4-oxadiazol-2-yl | i-propyl | |
| 415 | 2-Cl-4-SO₂MePh | 1,3,4-oxadiazol-2-yl | cyclopropyl | |
| 416 | 2-Cl-4-SO₂MePh | 1,3,4-oxadiazol-2-yl | CF₃ | |
| 417 | 2-Cl-4-SO₂MePh | 5-methylsulfonyl-1,3,4-oxadiazol-2-yl | H | |
| 418 | 2-Cl-4-SO₂MePh | 5-methylsulfonyl-1,3,4-oxadiazol-2-yl | methyl | |
| 419 | 2-Cl-4-SO₂MePh | 5-methylsulfonyl-1,3,4-oxadiazol-2-yl | i-propyl | |
| 420 | 2-Cl-4-SO₂MePh | 5-methylsulfonyl-1,3,4-oxadiazol-2-yl | cyclopropyl | |
| 421 | 2-Cl-4-SO₂MePh | 5-methylsulfonyl-1,3,4-oxadiazol-2-yl | CF₃ | |
| 422 | 2-Cl-4-SO₂MePh | 5-methyl-1,3,4-oxadiazol-2-yl | H | |
| 423 | 2-Cl-4-SO₂MePh | 5-methyl-1,3,4-oxadiazol-2-yl | methyl | |
| 424 | 2-Cl-4-SO₂MePh | 5-methyl-1,3,4-oxadiazol-2-yl | i-propyl | |
| 425 | 2-Cl-4-SO₂MePh | 5-methyl-1,3,4-oxadiazol-2-yl | cyclopropyl | |
| 426 | 2-Cl-4-SO₂MePh | 5-methyl-1,3,4-oxadiazol-2-yl | CF₃ | |
| 427 | 2-Cl-4-SO₂MePh | 5-trifluoromethyl-1,3,4-oxadiazol-2-yl | H | |
| 428 | 2-Cl-4-SO₂MePh | 5-trifluoromethyl-1,3,4-oxadiazol-2-yl | methyl | |
| 429 | 2-Cl-4-SO₂MePh | 5-trifluoromethyl-1,3,4-oxadiazol-2-yl | i-propyl | |
| 430 | 2-Cl-4-SO₂MePh | 5-trifluoromethyl-1,3,4-oxadiazol-2-yl | cyclopropyl | |
| 431 | 2-Cl-4-SO₂MePh | 5-trifluoromethyl-1,3,4-oxadiazol-2-yl | CF₃ | |

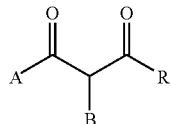 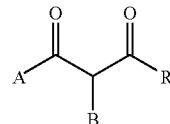

| Compound N | A | B | R | m.p. (° C.) |
|---|---|---|---|---|
| 432 | 2-Cl-4-SO₂MePh | 1,2,3-triazol-4-yl | H | |
| 433 | 2-Cl-4-SO₂MePh | 1,2,3-triazol-4-yl | methyl | |
| 434 | 2-Cl-4-SO₂MePh | 1,2,3-triazol-4-yl | i-propyl | |
| 435 | 2-Cl-4-SO₂MePh | 1,2,3-triazol-4-yl | cyclopropyl | |
| 436 | 2-Cl-4-SO₂MePh | 1,2,3-triazol-4-yl | CF₃ | |
| 437 | 2-Cl-4-SO₂MePh | 1-methyl-1,2,3-triazol-4-yl | H | |
| 438 | 2-Cl-4-SO₂MePh | 1-methyl-1,2,3-triazol-4-yl | methyl | |
| 439 | 2-Cl-4-SO₂MePh | 1-methyl-1,2,3-triazol-4-yl | i-propyl | |
| 440 | 2-Cl-4-SO₂MePh | 1-methyl-1,2,3-triazol-4-yl | cyclopropyl | |
| 441 | 2-Cl-4-SO₂MePh | 1-methyl-1,2,3-triazol-4-yl | CF₃ | |
| 442 | 2-Cl-4-SO₂MePh | 2-methyl-1,2,3-triazol-4-yl | H | |
| 443 | 2-Cl-4-SO₂MePh | 2-methyl-1,2,3-triazol-4-yl | methyl | |
| 444 | 2-Cl-4-SO₂MePh | 2-methyl-1,2,3-triazol-4-yl | i-propyl | |
| 445 | 2-Cl-4-SO₂MePh | 2-methyl-1,2,3-triazol-4-yl | cyclopropyl | |
| 446 | 2-Cl-4-SO₂MePh | 2-methyl-1,2,3-triazol-4-yl | CF₃ | |
| 447 | 2-Cl-4-SO₂MePh | 1,2,3-triazol-1-yl | H | |
| 448 | 2-Cl-4-SO₂MePh | 1,2,3-triazol-1-yl | methyl | |
| 449 | 2-Cl-4-SO₂MePh | 1,2,3-triazol-1-yl | i-propyl | |
| 450 | 2-Cl-4-SO₂MePh | 1,2,3-triazol-1-yl | cyclopropyl | |
| 451 | 2-Cl-4-SO₂MePh | 1,2,3-triazol-1-yl | CF₃ | |
| 452 | 2-Cl-4-SO₂MePh | 1,2,3-triazol-2-yl | H | |
| 453 | 2-Cl-4-SO₂MePh | 1,2,3-triazol-2-yl | methyl | |
| 454 | 2-Cl-4-SO₂MePh | 1,2,3-triazol-2-yl | i-propyl | |
| 455 | 2-Cl-4-SO₂MePh | 1,2,3-triazol-2-yl | cyclopropyl | |
| 456 | 2-Cl-4-SO₂MePh | 1,2,3-triazol-2-yl | CF₃ | |
| 457 | 2-Cl-4-SO₂MePh | 1,2,4-triazol-1-yl | H | |
| 458 | 2-Cl-4-SO₂MePh | 1,2,4-triazol-1-yl | methyl | |
| 459 | 2-Cl-4-SO₂MePh | 1,2,4-triazol-1-yl | i-propyl | |
| 460 | 2-Cl-4-SO₂MePh | 1,2,4-triazol-1-yl | cyclopropyl | 162 |
| 461 | 2-Cl-4-SO₂MePh | 1,2,4-triazol-1-yl | CF₃ | |
| 462 | 2-Cl-4-SO₂MePh | imidazol-2-yl | H | |
| 463 | 2-Cl-4-SO₂MePh | imidazol-2-yl | methyl | |
| 464 | 2-Cl-4-SO₂MePh | imidazol-2-yl | i-propyl | |
| 465 | 2-Cl-4-SO₂MePh | imidazol-2-yl | cyclopropyl | |
| 466 | 2-Cl-4-SO₂MePh | imidazol-2-yl | CF₃ | |
| 467 | 2-Cl-4-SO₂MePh | imidazol-1-yl | H | |
| 468 | 2-Cl-4-SO₂MePh | imidazol-1-yl | methyl | |
| 469 | 2-Cl-4-SO₂MePh | imidazol-1-yl | i-propyl | |
| 470 | 2-Cl-4-SO₂MePh | imidazol-1-yl | cyclopropyl | |
| 471 | 2-Cl-4-SO₂MePh | imidazol-1-yl | CF₃ | |
| 472 | 2-Cl-4-SO₂MePh | imidazol-4-yl | H | |
| 473 | 2-Cl-4-SO₂MePh | imidazol-4-yl | methyl | |
| 474 | 2-Cl-4-SO₂MePh | imidazol-4-yl | i-propyl | |
| 475 | 2-Cl-4-SO₂MePh | imidazol-4-yl | cyclopropyl | |
| 476 | 2-Cl-4-SO₂MePh | imidazol-4-yl | CF₃ | |
| 477 | 2-Cl-4-SO₂MePh | thiazol-2-yl | H | |
| 478 | 2-Cl-4-SO₂MePh | thiazol-2-yl | methyl | |
| 479 | 2-Cl-4-SO₂MePh | thiazol-2-yl | i-propyl | |
| 480 | 2-Cl-4-SO₂MePh | thiazol-2-yl | cyclopropyl | |
| 481 | 2-Cl-4-SO₂MePh | thiazol-2-yl | CF₃ | |
| 482 | 2-Cl-4-SO₂MePh | 4-methylthiazol-2-yl | H | |
| 483 | 2-Cl-4-SO₂MePh | 4-methylthiazol-2-yl | methyl | |
| 484 | 2-Cl-4-SO₂MePh | 4-methylthiazol-2-yl | i-propyl | |
| 485 | 2-Cl-4-SO₂MePh | 4-methylthiazol-2-yl | cyclopropyl | 199 |
| 486 | 2-Cl-4-SO₂MePh | 4-methylthiazol-2-yl | CF₃ | |
| 487 | 2-Cl-4-SO₂MePh | oxazol-2-yl | H | |
| 488 | 2-Cl-4-SO₂MePh | oxazol-2-yl | methyl | |
| 489 | 2-Cl-4-SO₂MePh | oxazol-2-yl | i-propyl | |
| 490 | 2-Cl-4-SO₂MePh | oxazol-2-yl | cyclopropyl | |
| 491 | 2-Cl-4-SO₂MePh | oxazol-2-yl | CF₃ | |
| 492 | 2-Cl-4-SO₂MePh | 4,5-dimethyl-oxazol-2-yl | H | |
| 493 | 2-Cl-4-SO₂MePh | 4,5-dimethyl-oxazol-2-yl | methyl | |
| 494 | 2-Cl-4-SO₂MePh | 4,5-dimethyl-oxazol-2-yl | i-propyl | |
| 495 | 2-Cl-4-SO₂MePh | 4,5-dimethyl-oxazol-2-yl | cyclopropyl | |
| 496 | 2-Cl-4-SO₂MePh | 4,5-dimethyl-oxazol-2-yl | CF₃ | |
| 497 | 2-Cl-4-SO₂MePh | 2-oxazolin-2-yl | H | |
| 498 | 2-Cl-4-SO₂MePh | 2-oxazolin-2-yl | methyl | |
| 499 | 2-Cl-4-SO₂MePh | 2-oxazolin-2-yl | i-propyl | |
| 500 | 2-Cl-4-SO₂MePh | 2-oxazolin-2-yl | cyclopropyl | |
| 501 | 2-Cl-4-SO₂MePh | 2-oxazolin-2-yl | CF₃ | |
| 502 | 2-Cl-4-SO₂MePh | 4,4-dimethyl-2-oxazolin-2-yl | H | |
| 503 | 2-Cl-4-SO₂MePh | 4,4-dimethyl-2-oxazolin-2-yl | methyl | |
| 504 | 2-Cl-4-SO₂MePh | 4,4-dimethyl-2-oxazolin-2-yl | i-propyl | |
| 505 | 2-Cl-4-SO₂MePh | 4,4-dimethyl-2-oxazolin-2-yl | cyclopropyl | |
| 506 | 2-Cl-4-SO₂MePh | 4,4-dimethyl-2-oxazolin-2-yl | CF₃ | |
| 507 | 2-Cl-4-SO₂MePh | 1,2,4-thiadiazol-5-yl | H | |
| 508 | 2-Cl-4-SO₂MePh | 1,2,4-thiadiazol-5-yl | methyl | |
| 509 | 2-Cl-4-SO₂MePh | 1,2,4-thiadiazol-5-yl | i-propyl | |
| 510 | 2-Cl-4-SO₂MePh | 1,2,4-thiadiazol-5-yl | cyclopropyl | |
| 511 | 2-Cl-4-SO₂MePh | 1,2,4-thiadiazol-5-yl | CF₃ | |
| 512 | 2-Cl-4-SO₂MePh | 3-methyl-1,2,4-thiadiazol-5-yl | H | |
| 513 | 2-Cl-4-SO₂MePh | 3-methyl-1,2,4-thiadiazol-5-yl | methyl | |
| 514 | 2-Cl-4-SO₂MePh | 3-methyl-1,2,4-thiadiazol-5-yl | i-propyl | |
| 515 | 2-Cl-4-SO₂MePh | 3-methyl-1,2,4-thiadiazol-5-yl | cyclopropyl | |
| 516 | 2-Cl-4-SO₂MePh | 3-methyl-1,2,4-thiadiazol-5-yl | CF₃ | |
| 517 | 2-Cl-4-SO₂MePh | 3-trifluoromethyl-1,2,4-thiadiazol-5-yl | H | |
| 518 | 2-Cl-4-SO₂MePh | 3-trifluoromethyl-1,2,4-thiadiazol-5-yl | methyl | |
| 519 | 2-Cl-4-SO₂MePh | 3-trifluoromethyl-1,2,4-thiadiazol-5-yl | i-propyl | |
| 520 | 2-Cl-4-SO₂MePh | 3-trifluoromethyl-1,2,4-thiadiazol-5-yl | cyclopropyl | |
| 521 | 2-Cl-4-SO₂MePh | 3-trifluoromethyl-1,2,4-thiadiazol-5-yl | CF₃ | |
| 522 | 2-Cl-4-SO₂MePh | 1,2,4-thiadiazol-3-yl | H | |
| 523 | 2-Cl-4-SO₂MePh | 1,2,4-thiadiazol- | methyl | |

-continued

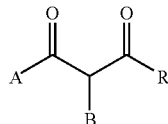

(I)

| Compound N | A | B | R | m.p. (° C.) |
|---|---|---|---|---|
| 524 | 2-Cl-4-SO₂MePh | 1,2,4-thiadiazol-3-yl | i-propyl | |
| 525 | 2-Cl-4-SO₂MePh | 1,2,4-thiadiazol-3-yl | cyclopropyl | |
| 526 | 2-Cl-4-SO₂MePh | 1,2,4-thiadiazol-3-yl | CF₃ | |
| 527 | 2-Cl-4-SO₂MePh | 5-methyl-1,2,4-thiadiazol-3-yl | H | |
| 528 | 2-Cl-4-SO₂MePh | 5-methyl-1,2,4-thiadiazol-3-yl | methyl | |
| 529 | 2-Cl-4-SO₂MePh | 5-methyl-1,2,4-thiadiazol-3-yl | i-propyl | |
| 530 | 2-Cl-4-SO₂MePh | 5-methyl-1,2,4-thiadiazol-3-yl | cyclopropyl | |
| 531 | 2-Cl-4-SO₂MePh | 5-methyl-1,2,4-thiadiazol-3-yl | CF₃ | |
| 532 | 2-Cl-4-SO₂MePh | 5-trifluoromethyl-1,2,4-thiadiazol-3-yl | H | |
| 533 | 2-Cl-4-SO₂MePh | 5-trifluoromethyl-1,2,4-thiadiazol-3-yl | methyl | |
| 534 | 2-Cl-4-SO₂MePh | 5-trifluoromethyl-1,2,4-thiadiazol-3-yl | i-propyl | |
| 535 | 2-Cl-4-SO₂MePh | 5-trifluoromethyl-1,2,4-thiadiazol-3-yl | cyclopropyl | |
| 536 | 2-Cl-4-SO₂MePh | 5-trifluoromethyl-1,2,4-thiadiazol-3-yl | CF₃ | |
| 537 | 2-Cl-4-SO₂MePh | 1,3,4-thiadiazol-2-yl | H | |
| 538 | 2-Cl-4-SO₂MePh | 1,3,4-thiadiazol-2-yl | methyl | |
| 539 | 2-Cl-4-SO₂MePh | 1,3,4-thiadiazol-2-yl | i-propyl | |
| 540 | 2-Cl-4-SO₂MePh | 1,3,4-thiadiazol-2-yl | cyclopropyl | |
| 541 | 2-Cl-4-SO₂MePh | 1,3,4-thiadiazol-2-yl | CF₃ | |
| 542 | 2-Cl-4-SO₂MePh | 5-methylsulfonyl-1,3,4-thiadiazol-2-yl | H | |
| 543 | 2-Cl-4-SO₂MePh | 5-methylsulfonyl-1,3,4-thiadiazol-2-yl | methyl | |
| 544 | 2-Cl-4-SO₂MePh | 5-methylsulfonyl-1,3,4-thiadiazol-2-yl | i-propyl | |
| 545 | 2-Cl-4-SO₂MePh | 5-methylsulfonyl-1,3,4-thiadiazol-2-yl | cyclopropyl | |
| 546 | 2-Cl-4-SO₂MePh | 5-methylsulfonyl-1,3,4-thiadiazol-2-yl | CF₃ | |
| 547 | 2-Cl-4-SO₂MePh | 5-methyl-1,3,4-thiadiazol-2-yl | H | |
| 548 | 2-Cl-4-SO₂MePh | 5-methyl-1,3,4-thiadiazol-2-yl | methyl | |
| 549 | 2-Cl-4-SO₂MePh | 5-methyl-1,3,4-thiadiazol-2-yl | i-propyl | |
| 550 | 2-Cl-4-SO₂MePh | 5-methyl-1,3,4-thiadiazol-2-yl | cyclopropyl | |
| 551 | 2-Cl-4-SO₂MePh | 5-methyl-1,3,4-thiadiazol-2-yl | CF₃ | |
| 552 | 2-Cl-4-SO₂MePh | benzoxazol-2-yl | H | |
| 553 | 2-Cl-4-SO₂MePh | benzoxazol-2-yl | methyl | |

-continued

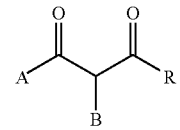

(I)

| Compound N | A | B | R | m.p. (° C.) |
|---|---|---|---|---|
| 554 | 2-Cl-4-SO₂MePh | benzoxazol-2-yl | i-propyl | |
| 555 | 2-Cl-4-SO₂MePh | benzoxazol-2-yl | cyclopropyl | |
| 556 | 2-Cl-4-SO₂MePh | benzoxazol-2-yl | CF₃ | |
| 557 | 2-Cl-4-SO₂MePh | 6-methyl-benzoxazol-2-yl | H | |
| 558 | 2-Cl-4-SO₂MePh | 6-methyl-benzoxazol-2-yl | methyl | |
| 559 | 2-Cl-4-SO₂MePh | 6-methyl-benzoxazol-2-yl | i-propyl | |
| 560 | 2-Cl-4-SO₂MePh | 6-methyl-benzoxazol-2-yl | cyclopropyl | |
| 561 | 2-Cl-4-SO₂MePh | 6-methyl-benzoxazol-2-yl | CF₃ | |
| 562 | 2-Cl-4-SO₂MePh | benzothiazol-2-yl | H | |
| 563 | 2-Cl-4-SO₂MePh | benzothiazol-2-yl | methyl | |
| 564 | 2-Cl-4-SO₂MePh | benzothiazol-2-yl | i-propyl | |
| 565 | 2-Cl-4-SO₂MePh | benzothiazol-2-yl | cyclopropyl | |
| 566 | 2-Cl-4-SO₂MePh | benzothiazol-2-yl | CF₃ | |
| 567 | 2-Cl-4-SO₂MePh | pyrazol-1-yl | H | |
| 568 | 2-Cl-4-SO₂MePh | pyrazol-1-yl | methyl | |
| 569 | 2-Cl-4-SO₂MePh | pyrazol-1-yl | i-propyl | |
| 570 | 2-Cl-4-SO₂MePh | pyrazol-1-yl | cyclopropyl | |
| 571 | 2-Cl-4-SO₂MePh | pyrazol-1-yl | CF₃ | |
| 572 | 2-Cl-4-SO₂MePh | pyrazol-3-yl | H | |
| 573 | 2-Cl-4-SO₂MePh | pyrazol-3-yl | methyl | |
| 574 | 2-Cl-4-SO₂MePh | pyrazol-3-yl | i-propyl | |
| 575 | 2-Cl-4-SO₂MePh | pyrazol-3-yl | cyclopropyl | |
| 576 | 2-Cl-4-SO₂MePh | pyrazol-3-yl | CF₃ | |
| 577 | 2-Cl-4-SO₂MePh | 1-methylpyrazol-3-yl | H | |
| 578 | 2-Cl-4-SO₂MePh | 1-methylpyrazol-3-yl | methyl | |
| 579 | 2-Cl-4-SO₂MePh | 1-methylpyrazol-3-yl | i-propyl | |
| 580 | 2-Cl-4-SO₂MePh | 1-methylpyrazol-3-yl | cyclopropyl | |
| 581 | 2-Cl-4-SO₂MePh | 1-methylpyrazol-3-yl | CF₃ | |
| 582 | 2-Cl-4-SO₂MePh | tetrazol-1-yl | H | |
| 583 | 2-Cl-4-SO₂MePh | tetrazol-1-yl | methyl | |
| 584 | 2-Cl-4-SO₂MePh | tetrazol-1-yl | i-propyl | |
| 585 | 2-Cl-4-SO₂MePh | tetrazol-1-yl | cyclopropyl | |
| 586 | 2-Cl-4-SO₂MePh | tetrazol-1-yl | CF₃ | |
| 587 | 2-Cl-4-SO₂MePh | 5-methyltetrazol-1-yl | H | |
| 588 | 2-Cl-4-SO₂MePh | 5-methyltetrazol-1-yl | methyl | |
| 589 | 2-Cl-4-SO₂MePh | 5-methyltetrazol-1-yl | i-propyl | |
| 590 | 2-Cl-4-SO₂MePh | 5-methyltetrazol-1-yl | cyclopropyl | |
| 591 | 2-Cl-4-SO₂MePh | 5-methyltetrazol-1-yl | CF₃ | |
| 592 | 2-Cl-4-SO₂MePh | tetrazol-2-yl | H | |
| 593 | 2-Cl-4-SO₂MePh | tetrazol-2-yl | methyl | |
| 594 | 2-Cl-4-SO₂MePh | tetrazol-2-yl | i-propyl | |
| 595 | 2-Cl-4-SO₂MePh | tetrazol-2-yl | cyclopropyl | |
| 596 | 2-Cl-4-SO₂MePh | tetrazol-2-yl | CF₃ | |
| 597 | 2-Cl-4-SO₂MePh | 5-methyltetrazol-2-yl | H | |
| 598 | 2-Cl-4-SO₂MePh | 5-methyltetrazol-2-yl | methyl | |
| 599 | 2-Cl-4-SO₂MePh | 5-methyltetrazol-2-yl | i-propyl | |
| 600 | 2-Cl-4-SO₂MePh | 5-methyltetrazol-2-yl | cyclopropyl | |
| 601 | 2-Cl-4-SO₂MePh | 5-methyltetrazol-2-yl | CF₃ | |
| 602 | 2-Cl-4-SO₂MePh | 1-methyltetrazol- | H | |

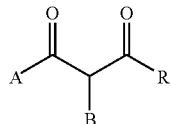

(I)

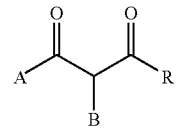

(I)

| Compound N | A | B | R | m.p. (° C.) |
|---|---|---|---|---|
| 603 | 2-Cl-4-SO₂MePh | 1-methyltetrazol-5-yl | methyl | |
| 604 | 2-Cl-4-SO₂MePh | 1-methyltetrazol-5-yl | i-propyl | |
| 605 | 2-Cl-4-SO₂MePh | 1-methyltetrazol-5-yl | cyclopropyl | 104 |
| 606 | 2-Cl-4-SO₂MePh | 1-methyltetrazol-5-yl | CF₃ | |
| 607 | 2-Cl-4-SO₂MePh | 2-methyltetrazol-5-yl | t-butile | oil |
| 608 | 2-Cl-4-SO₂MePh | 2-methyltetrazol-5-yl | methyl | |
| 609 | 2-Cl-4-SO₂MePh | 2-methyltetrazol-5-yl | i-propyl | 210 |
| 610 | 2-Cl-4-SO₂MePh | 2-methyltetrazol-5-yl | cyclopropyl | 220 |
| 611 | 2-Cl-4-SO₂MePh | 2-methyltetrazol-5-yl | CF₃ | |
| 612 | 2-Cl-4-SO₂MePh | pyridin-2-yl | H | |
| 613 | 2-Cl-4-SO₂MePh | pyridin-2-yl | methyl | |
| 614 | 2-Cl-4-SO₂MePh | pyridin-2-yl | i-propyl | |
| 615 | 2-Cl-4-SO₂MePh | pyridin-2-yl | cyclopropyl | |
| 616 | 2-Cl-4-SO₂MePh | pyridin-2-yl | CF₃ | 189 |
| 617 | 2-Cl-4-SO₂MePh | pyridin-4-yl | H | |
| 618 | 2-Cl-4-SO₂MePh | pyridin-4-yl | methyl | |
| 619 | 2-Cl-4-SO₂MePh | pyridin-4-yl | i-propyl | |
| 620 | 2-Cl-4-SO₂MePh | pyridin-4-yl | cyclopropyl | |
| 621 | 2-Cl-4-SO₂MePh | pyridin-4-yl | CF₃ | |
| 622 | 2-Cl-4-SO₂MePh | pyridin-3-yl | H | |
| 623 | 2-Cl-4-SO₂MePh | pyridin-3-yl | methyl | |
| 624 | 2-Cl-4-SO₂MePh | pyridin-3-yl | i-propyl | |
| 625 | 2-Cl-4-SO₂MePh | pyridin-3-yl | cyclopropyl | |
| 626 | 2-Cl-4-SO₂MePh | pyridin-3-yl | CF₃ | |
| 627 | 2-Cl-4-SO₂MePh | 3-nitropyridin-4-yl | H | |
| 628 | 2-Cl-4-SO₂MePh | 3-nitropyridin-4-yl | methyl | |
| 629 | 2-Cl-4-SO₂MePh | 3-nitropyridin-4-yl | i-propyl | |
| 630 | 2-Cl-4-SO₂MePh | 3-nitropyridin-4-yl | cyclopropyl | |
| 631 | 2-Cl-4-SO₂MePh | 3-nitropyridin-4-yl | CF₃ | |
| 632 | 2-Cl-4-SO₂MePh | 5-cyanopyridin-2-yl | H | |
| 633 | 2-Cl-4-SO₂MePh | 5-cyanopyridin-2-yl | methyl | |
| 634 | 2-Cl-4-SO₂MePh | 5-cyanopyridin-2-yl | i-propyl | |
| 635 | 2-Cl-4-SO₂MePh | 5-cyanopyridin-2-yl | cyclopropyl | |
| 636 | 2-Cl-4-SO₂MePh | 5-cyanopyridin-2-yl | CF₃ | |
| 637 | 2-Cl-4-SO₂MePh | 5-trifluoro-methylpyridin-2-yl | H | |
| 638 | 2-Cl-4-SO₂MePh | 5-trifluoro-methylpyridin-2-yl | methyl | |
| 639 | 2-Cl-4-SO₂MePh | 5-trifluoro-methylpyridin-2-yl | i-propyl | |
| 640 | 2-Cl-4-SO₂MePh | 5-trifluoro-methylpyridin-2-yl | cyclopropyl | |
| 641 | 2-Cl-4-SO₂MePh | 5-trifluoro-methylpyridin-2-yl | CF₃ | |
| 642 | 2-Cl-4-SO₂MePh | pyrimidin-2-yl | H | |
| 643 | 2-Cl-4-SO₂MePh | pyrimidin-2-yl | methyl | |
| 644 | 2-Cl-4-SO₂MePh | pyrimidin-2-yl | i-propyl | |
| 645 | 2-Cl-4-SO₂MePh | pyrimidin-2-yl | cyclopropyl | |
| 646 | 2-Cl-4-SO₂MePh | pyrimidin-2-yl | CF₃ | |
| 647 | 2-Cl-4-SO₂MePh | pyrimidin-4-yl | H | |
| 648 | 2-Cl-4-SO₂MePh | pyrimidin-4-yl | methyl | |
| 649 | 2-Cl-4-SO₂MePh | pyrimidin-4-yl | i-propyl | |
| 650 | 2-Cl-4-SO₂MePh | pyrimidin-4-yl | cyclopropyl | |
| 651 | 2-Cl-4-SO₂MePh | pyrimidin-4-yl | CF₃ | |
| 652 | 2-Cl-4-SO₂MePh | 6-chloro-pyrimidin-4-yl | methyl | |
| 653 | 2-Cl-4-SO₂MePh | 6-chloro-pyrimidin-4-yl | i-propyl | |
| 654 | 2-Cl-4-SO₂MePh | 6-chloro-pyrimidin-4-yl | cyclopropyl | |
| 655 | 2-Cl-4-SO₂MePh | 6-chloro-pyrimidin-4-yl | CF₃ | |
| 656 | 2-Cl-4-SO₂MePh | pyridazin-3-yl | H | |
| 657 | 2-Cl-4-SO₂MePh | pyridazin-3-yl | methyl | |
| 658 | 2-Cl-4-SO₂MePh | pyridazin-3-yl | i-propyl | |
| 659 | 2-Cl-4-SO₂MePh | pyridazin-3-yl | cyclopropyl | |
| 660 | 2-Cl-4-SO₂MePh | pyridazin-3-yl | CF₃ | |
| 661 | 2-Cl-4-SO₂MePh | 6-chloro-pyridazin-3-yl | methyl | |
| 662 | 2-Cl-4-SO₂MePh | 6-chloro-pyridazin-3-yl | i-propyl | |
| 663 | 2-Cl-4-SO₂MePh | 6-chloro-pyridazin-3-yl | cyclopropyl | |
| 664 | 2-Cl-4-SO₂MePh | 6-chloro-pyridazin-3-yl | CF₃ | |
| 665 | 2-Cl-4-SO₂MePh | pyrazin-2-yl | methyl | |
| 666 | 2-Cl-4-SO₂MePh | pyrazin-2-yl | i-propyl | |
| 667 | 2-Cl-4-SO₂MePh | pyrazin-2-yl | cyclopropyl | |
| 668 | 2-Cl-4-SO₂MePh | pyrazin-2-yl | CF₃ | |
| 669 | 2-Cl-4-SO₂MePh | triazin-2-yl | methyl | |
| 670 | 2-Cl-4-SO₂MePh | triazin-2-yl | i-propyl | |
| 671 | 2-Cl-4-SO₂MePh | triazin-2-yl | cyclopropyl | |
| 672 | 2-Cl-4-SO₂MePh | triazin-2-yl | CF₃ | |
| 673 | 2-Cl-4-SO₂MePh | quinolin-2-yl | methyl | |
| 674 | 2-Cl-4-SO₂MePh | quinolin-2-yl | i-propyl | |
| 675 | 2-Cl-4-SO₂MePh | quinolin-2-yl | cyclopropyl | |
| 676 | 2-Cl-4-SO₂MePh | quinolin-2-yl | CF₃ | |
| 677 | 2-Cl-4-SO₂MePh | 4,4,6-trimethyl-5,6-dihydro-1,3(4H)-oxazin-2-yl | H | |
| 678 | 2-Cl-4-SO₂MePh | 4,4,6-trimethyl-5,6-dihydro-1,3(4H)-oxazin-2-yl | methyl | |
| 679 | 2-Cl-4-SO₂MePh | 4,4,6-trimethyl-5,6-dihydro-1,3(4H)-oxazin-2-yl | i-propyl | |
| 680 | 2-Cl-4-SO₂MePh | 4,4,6-trimethyl-5,6-dihydro-1,3(4H)-oxazin-2-yl | cyclopropyl | |
| 681 | 2-Cl-4-SO₂MePh | 4,4,6-trimethyl-5,6-dihydro-1,3(4H)-oxazin-2-yl | CF₃ | |
| 682 | 2-Cl-4-SO₂MePh | 2-oxazolidinon-3-yl | H | |
| 683 | 2-Cl-4-SO₂MePh | 2-oxazolidinon-3-yl | methyl | |
| 684 | 2-Cl-4-SO₂MePh | 2-oxazolidinon-3-yl | i-propyl | |
| 685 | 2-Cl-4-SO₂MePh | 2-oxazolidinon-3-yl | cyclopropyl | |
| 686 | 2-Cl-4-SO₂MePh | 2-oxazolidinon-3-yl | CF₃ | |
| 687 | 2-Cl-4-SO₂MePh | 2-pyrrolidinon- | methyl | |

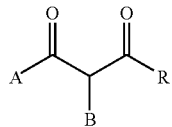

(I)

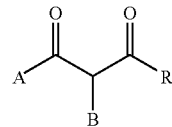

(I)

| Compound N | A | B | R | m.p. (°C.) |
|---|---|---|---|---|
| 688 | 2-Cl-4-SO₂MePh | 2-pyrrolidinon-1-yl | i-propyl | |
| 689 | 2-Cl-4-SO₂MePh | 2-pyrrolidinon-1-yl | cyclopropyl | |
| 690 | 2-Cl-4-SO₂MePh | 2-pyrrolidinon-1-yl | CF₃ | |
| 691 | 2-Cl-4-SO₂MePh | 3-methylisoxazol-5-yl | methyl | |
| 692 | 2-Cl-4-SO₂MePh | 3-methylisoxazol-5-yl | i-propyl | |
| 693 | 2-Cl-4-SO₂MePh | 3-methylisoxazol-5-yl | cyclopropyl | |
| 694 | 2-Cl-4-SO₂MePh | 3-methylisoxazol-5-yl | CF₃ | |
| 695 | 2-Cl-4-SO₂MePh | 2-NO₂-4-SO₂MePh | H | |
| 696 | 2-Cl-4-SO₂MePh | 2-NO₂-4-SO₂MePh | methyl | |
| 697 | 2-Cl-4-SO₂MePh | 2-NO₂-4-SO₂MePh | i-propyl | |
| 698 | 2-Cl-4-SO₂MePh | 2-NO₂-4-SO₂MePh | cyclopropyl | |
| 699 | 2-Cl-4-SO₂MePh | 2-NO₂-4-SO₂MePh | CF₃ | |
| 700 | 2-Cl-4-SO₂MePh | 2-Cl-4-SO₂MePh | H | |
| 701 | 2-Cl-4-SO₂MePh | 2-Cl-4-SO₂MePh | methyl | |
| 702 | 2-Cl-4-SO₂MePh | 2-Cl-4-SO₂MePh | i-propyl | |
| 703 | 2-Cl-4-SO₂MePh | 2-Cl-4-SO₂MePh | cyclopropyl | |
| 704 | 2-Cl-4-SO₂MePh | 2-Cl-4-SO₂MePh | CF₃ | |
| 705 | 2-Cl-4-SO₂MePh | 2-NO₂-4-CF₃Ph | H | |
| 706 | 2-Cl-4-SO₂MePh | 2-NO₂-4-CF₃Ph | methyl | |
| 707 | 2-Cl-4-SO₂MePh | 2-NO₂-4-CF₃Ph | i-propyl | |
| 708 | 2-Cl-4-SO₂MePh | 2-NO₂-4-CF₃Ph | cyclopropyl | |
| 709 | 2-Cl-4-SO₂MePh | 2-NO₂-4-CF₃Ph | CF₃ | |
| 710 | 2-Cl-4-SO₂MePh | 2-NO₂-4-ClPh | H | |
| 711 | 2-Cl-4-SO₂MePh | 2-NO₂-4-ClPh | methyl | |
| 712 | 2-Cl-4-SO₂MePh | 2-NO₂-4-ClPh | i-propyl | |
| 713 | 2-Cl-4-SO₂MePh | 2-NO₂-4-ClPh | cyclopropyl | |
| 714 | 2-Cl-4-SO₂MePh | 2-NO₂-4-ClPh | CF₃ | |
| 715 | 2-Cl-4-SO₂MePh | 2-Cl-4-NO₂Ph | H | |
| 716 | 2-Cl-4-SO₂MePh | 2-Cl-4-NO₂Ph | methyl | |
| 717 | 2-Cl-4-SO₂MePh | 2-Cl-4-NO₂Ph | i-propyl | |
| 718 | 2-Cl-4-SO₂MePh | 2-Cl-4-NO₂Ph | cyclopropyl | |
| 719 | 2-Cl-4-SO₂MePh | 2-Cl-4-NO₂Ph | CF₃ | |
| 720 | 2-Cl-4-SO₂MePh | 2,4-(NO₂)₂Ph | H | |
| 721 | 2-Cl-4-SO₂MePh | 2,4-(NO₂)₂Ph | methyl | |
| 722 | 2-Cl-4-SO₂MePh | 2,4-(NO₂)₂Ph | i-propyl | |
| 723 | 2-Cl-4-SO₂MePh | 2,4-(NO₂)₂Ph | cyclopropyl | 67 |
| 724 | 2-Cl-4-SO₂MePh | 2,4-(NO₂)₂Ph | CF₃ | |
| 725 | 2-Cl-4-SO₂MePh | 4-F-3-NO₂Ph | H | |
| 726 | 2-Cl-4-SO₂MePh | 4-F-3-NO₂Ph | methyl | |
| 727 | 2-Cl-4-SO₂MePh | 4-F-3-NO₂Ph | i-propyl | |
| 728 | 2-Cl-4-SO₂MePh | 4-F-3-NO₂Ph | cyclopropyl | |
| 729 | 2-Cl-4-SO₂MePh | 4-F-3-NO₂Ph | CF₃ | |
| 730 | 2-Cl-4-SO₂MePh | 3,5-(CF₃)₂Ph | H | |
| 731 | 2-Cl-4-SO₂MePh | 3,5-(CF₃)₂Ph | methyl | |
| 732 | 2-Cl-4-SO₂MePh | 3,5-(CF₃)₂Ph | i-propyl | |
| 733 | 2-Cl-4-SO₂MePh | 3,5-(CF₃)₂Ph | cyclopropyl | |
| 734 | 2-Cl-4-SO₂MePh | 3,5-(CF₃)₂Ph | CF₃ | |
| 735 | 2-Cl-4-SO₂MePh | 2-SO₂Me-4-CF₃Ph | H | |
| 736 | 2-Cl-4-SO₂MePh | 2-SO₂Me-4-CF₃Ph | methyl | |
| 737 | 2-Cl-4-SO₂MePh | 2-SO₂Me-4-CF₃Ph | i-propyl | |
| 738 | 2-Cl-4-SO₂MePh | 2-SO₂Me-4-CF₃Ph | cyclopropyl | |
| 739 | 2-Cl-4-SO₂MePh | 2-SO₂Me-4-CF₃Ph | CF₃ | |
| 740 | 4-Cl-2-NO₂Ph | 1,2,4-oxadiazol-5-yl | H | |
| 741 | 4-Cl-2-NO₂Ph | 1,2,4-oxadiazol-5-yl | methyl | |
| 742 | 4-Cl-2-NO₂Ph | 1,2,4-oxadiazol-5-yl | i-propyl | |
| 743 | 4-Cl-2-NO₂Ph | 1,2,4-oxadiazol-5-yl | cyclopropyl | |
| 744 | 4-Cl-2-NO₂Ph | 1,2,4-oxadiazol-5-yl | CF₃ | |
| 745 | 4-Cl-2-NO₂Ph | 3-methyl-1,2,4-oxadiazol-5-yl | H | |
| 746 | 4-Cl-2-NO₂Ph | 3-methyl-1,2,4-oxadiazol-5-yl | methyl | |
| 747 | 4-Cl-2-NO₂Ph | 3-methyl-1,2,4-oxadiazol-5-yl | i-propyl | |
| 748 | 4-Cl-2-NO₂Ph | 3-methyl-1,2,4-oxadiazol-5-yl | cyclopropyl | 127 |
| 749 | 4-Cl-2-NO₂Ph | 3-methyl-1,2,4-oxadiazol-5-yl | CF₃ | |
| 750 | 4-Cl-2-NO₂Ph | 3-trifluoromethyl-1,2,4-oxadiazol-5-yl | H | |
| 751 | 4-Cl-2-NO₂Ph | 3-trifluoromethyl-1,2,4-oxadiazol-5-yl | methyl | |
| 752 | 4-Cl-2-NO₂Ph | 3-trifluoromethyl-1,2,4-oxadiazol-5-yl | i-propyl | |
| 753 | 4-Cl-2-NO₂Ph | 3-trifluoromethyl-1,2,4-oxadiazol-5-yl | cyclopropyl | |
| 754 | 4-Cl-2-NO₂Ph | 3-trifluoromethyl-1,2,4-oxadiazol-5-yl | CF₃ | |
| 755 | 4-Cl-2-NO₂Ph | 1,2,4-oxadiazol-3-yl | H | |
| 756 | 4-Cl-2-NO₂Ph | 1,2,4-oxadiazol-3-yl | methyl | |
| 757 | 4-Cl-2-NO₂Ph | 1,2,4-oxadiazol-3-yl | i-propyl | |
| 758 | 4-Cl-2-NO₂Ph | 1,2,4-oxadiazol-3-yl | cyclopropyl | |
| 759 | 4-Cl-2-NO₂Ph | 1,2,4-oxadiazol-3-yl | CF₃ | |
| 760 | 4-Cl-2-NO₂Ph | 5-methyl-1,2,4-oxadiazol-3-yl | H | |
| 761 | 4-Cl-2-NO₂Ph | 5-methyl-1,2,4-oxadiazol-3-yl | methyl | |
| 762 | 4-Cl-2-NO₂Ph | 5-methyl-1,2,4-oxadiazol-3-yl | i-propyl | |
| 763 | 4-Cl-2-NO₂Ph | 5-methyl-1,2,4-oxadiazol-3-yl | cyclopropyl | |
| 764 | 4-Cl-2-NO₂Ph | 5-methyl-1,2,4-oxadiazol-3-yl | CF₃ | |
| 765 | 4-Cl-2-NO₂Ph | 5-trifluoromethyl-1,2,4-oxadiazol-3-yl | H | |
| 766 | 4-Cl-2-NO₂Ph | 5-trifluoromethyl-1,2,4-oxadiazol-3-yl | methyl | |
| 767 | 4-Cl-2-NO₂Ph | 5-trifluoromethyl-1,2,4-oxadiazol-3-yl | i-propyl | |
| 768 | 4-Cl-2-NO₂Ph | 5-trifluoromethyl-1,2,4-oxadiazol-3-yl | cyclopropyl | |
| 769 | 4-Cl-2-NO₂Ph | 5-trifluoromethyl- | CF₃ | |

-continued

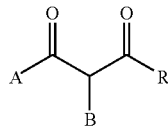
(I)

| Compound N | A | B | R | m.p. (°C.) |
|---|---|---|---|---|
| | | 1,2,4-oxadiazol-3-yl | | |
| 770 | 4-Cl-2-NO$_2$Ph | 5-chloro-1,2,4-oxadiazol-3-yl | H | |
| 771 | 4-Cl-2-NO$_2$Ph | 5-chloro-1,2,4-oxadiazol-3-yl | methyl | |
| 772 | 4-Cl-2-NO$_2$Ph | 5-chloro-1,2,4-oxadiazol-3-yl | i-propyl | |
| 773 | 4-Cl-2-NO$_2$Ph | 5-chloro-1,2,4-oxadiazol-3-yl | cyclopropyl | |
| 774 | 4-Cl-2-NO$_2$Ph | 5-chloro-1,2,4-oxadiazol-3-yl | CF$_3$ | |
| 775 | 4-Cl-2-NO$_2$Ph | 1,3,4-oxadiazol-2-yl | H | |
| 776 | 4-Cl-2-NO$_2$Ph | 1,3,4-oxadiazol-2-yl | methyl | |
| 777 | 4-Cl-2-NO$_2$Ph | 1,3,4-oxadiazol-2-yl | i-propyl | |
| 778 | 4-Cl-2-NO$_2$Ph | 1,3,4-oxadiazol-2-yl | cyclopropyl | |
| 779 | 4-Cl-2-NO$_2$Ph | 1,3,4-oxadiazol-2-yl | CF$_3$ | |
| 780 | 4-Cl-2-NO$_2$Ph | 5-methylsulfonyl-1,3,4-oxadiazol-2-yl | H | |
| 781 | 4-Cl-2-NO$_2$Ph | 5-methylsulfonyl-1,3,4-oxadiazol-2-yl | methyl | |
| 782 | 4-Cl-2-NO$_2$Ph | 5-methylsulfonyl-1,3,4-oxadiazol-2-yl | i-propyl | |
| 783 | 4-Cl-2-NO$_2$Ph | 5-methylsulfonyl-1,3,4-oxadiazol-2-yl | cyclopropyl | |
| 784 | 4-Cl-2-NO$_2$Ph | 5-methylsulfonyl-1,3,4-oxadiazol-2-yl | CF$_3$ | |
| 785 | 4-Cl-2-NO$_2$Ph | 5-methyl-1,3,4-oxadiazol-2-yl | H | |
| 786 | 4-Cl-2-NO$_2$Ph | 5-methyl-1,3,4-oxadiazol-2-yl | methyl | |
| 787 | 4-Cl-2-NO$_2$Ph | 5-methyl-1,3,4-oxadiazol-2-yl | i-propyl | |
| 788 | 4-Cl-2-NO$_2$Ph | 5-methyl-1,3,4-oxadiazol-2-yl | cyclopropyl | |
| 789 | 4-Cl-2-NO$_2$Ph | 5-methyl-1,3,4-oxadiazol-2-yl | CF$_3$ | |
| 790 | 4-Cl-2-NO$_2$Ph | 5-trifluoromethyl-1,3,4-oxadiazol-2-yl | H | |
| 791 | 4-Cl-2-NO$_2$Ph | 5-trifluoromethyl-1,3,4-oxadiazol-2-yl | methyl | |
| 792 | 4-Cl-2-NO$_2$Ph | 5-trifluoromethyl-1,3,4-oxadiazol-2-yl | i-propyl | |
| 793 | 4-Cl-2-NO$_2$Ph | 5-trifluoromethyl-1,3,4-oxadiazol-2-yl | cyclopropyl | |
| 794 | 4-Cl-2-NO$_2$Ph | 5-trifluoromethyl-1,3,4-oxadiazol-2-yl | CF$_3$ | |
| 795 | 4-Cl-2-NO$_2$Ph | 1,2,3-triazol-4-yl | H | |
| 796 | 4-Cl-2-NO$_2$Ph | 1,2,3-triazol-4-yl | methyl | |
| 797 | 4-Cl-2-NO$_2$Ph | 1,2,3-triazol-4-yl | i-propyl | |
| 798 | 4-Cl-2-NO$_2$Ph | 1,2,3-triazol-4-yl | cyclopropyl | |
| 799 | 4-Cl-2-NO$_2$Ph | 1,2,3-triazol-4-yl | CF$_3$ | |
| 800 | 4-Cl-2-NO$_2$Ph | 1-methyl-1,2,3-triazol-4-yl | H | |

-continued

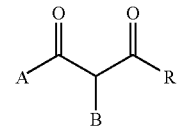
(I)

| Compound N | A | B | R | m.p. (°C.) |
|---|---|---|---|---|
| 801 | 4-Cl-2-NO$_2$Ph | 1-methyl-1,2,3-triazol-4-yl | methyl | |
| 802 | 4-Cl-2-NO$_2$Ph | 1-methyl-1,2,3-triazol-4-yl | i-propyl | |
| 803 | 4-Cl-2-NO$_2$Ph | 1-methyl-1,2,3-triazol-4-yl | cyclopropyl | |
| 804 | 4-Cl-2-NO$_2$Ph | 1-methyl-1,2,3-triazol-4-yl | CF$_3$ | |
| 805 | 4-Cl-2-NO$_2$Ph | 2-methyl-1,2,3-triazol-4-yl | H | |
| 806 | 4-Cl-2-NO$_2$Ph | 2-methyl-1,2,3-triazol-4-yl | methyl | |
| 807 | 4-Cl-2-NO$_2$Ph | 2-methyl-1,2,3-triazol-4-yl | i-propyl | |
| 808 | 4-Cl-2-NO$_2$Ph | 2-methyl-1,2,3-triazol-4-yl | cyclopropyl | |
| 809 | 4-Cl-2-NO$_2$Ph | 2-methyl-1,2,3-triazol-4-yl | CF$_3$ | |
| 810 | 4-Cl-2-NO$_2$Ph | 1,2,3-triazol-1-yl | H | |
| 811 | 4-Cl-2-NO$_2$Ph | 1,2,3-triazol-1-yl | methyl | |
| 812 | 4-Cl-2-NO$_2$Ph | 1,2,3-triazol-1-yl | i-propyl | |
| 813 | 4-Cl-2-NO$_2$Ph | 1,2,3-triazol-1-yl | cyclopropyl | |
| 814 | 4-Cl-2-NO$_2$Ph | 1,2,3-triazol-1-yl | CF$_3$ | |
| 815 | 4-Cl-2-NO$_2$Ph | 1,2,3-triazol-2-yl | H | |
| 816 | 4-Cl-2-NO$_2$Ph | 1,2,3-triazol-2-yl | methyl | |
| 817 | 4-Cl-2-NO$_2$Ph | 1,2,3-triazol-2-yl | i-propyl | |
| 818 | 4-Cl-2-NO$_2$Ph | 1,2,3-triazol-2-yl | cyclopropyl | |
| 819 | 4-Cl-2-NO$_2$Ph | 1,2,3-triazol-2-yl | CF$_3$ | |
| 820 | 4-Cl-2-NO$_2$Ph | 1,2,4-triazol-1-yl | H | |
| 821 | 4-Cl-2-NO$_2$Ph | 1,2,4-triazol-1-yl | methyl | |
| 822 | 4-Cl-2-NO$_2$Ph | 1,2,4-triazol-1-yl | i-propyl | |
| 823 | 4-Cl-2-NO$_2$Ph | 1,2,4-triazol-1-yl | cyclopropyl | |
| 824 | 4-Cl-2-NO$_2$Ph | 1,2,4-triazol-1-yl | CF$_3$ | |
| 825 | 4-Cl-2-NO$_2$Ph | imidazol-2-yl | H | |
| 826 | 4-Cl-2-NO$_2$Ph | imidazol-2-yl | methyl | |
| 827 | 4-Cl-2-NO$_2$Ph | imidazol-2-yl | i-propyl | |
| 828 | 4-Cl-2-NO$_2$Ph | imidazol-2-yl | cyclopropyl | |
| 829 | 4-Cl-2-NO$_2$Ph | imidazol-2-yl | CF$_3$ | |
| 830 | 4-Cl-2-NO$_2$Ph | imidazol-1-yl | H | |
| 831 | 4-Cl-2-NO$_2$Ph | imidazol-1-yl | methyl | |
| 832 | 4-Cl-2-NO$_2$Ph | imidazol-1-yl | i-propyl | |
| 833 | 4-Cl-2-NO$_2$Ph | imidazol-1-yl | cyclopropyl | |
| 834 | 4-Cl-2-NO$_2$Ph | imidazol-1-yl | CF$_3$ | |
| 835 | 4-Cl-2-NO$_2$Ph | imidazol-4-yl | H | |
| 836 | 4-Cl-2-NO$_2$Ph | imidazol-4-yl | methyl | |
| 837 | 4-Cl-2-NO$_2$Ph | imidazol-4-yl | i-propyl | |
| 838 | 4-Cl-2-NO$_2$Ph | imidazol-4-yl | cyclopropyl | |
| 839 | 4-Cl-2-NO$_2$Ph | imidazol-4-yl | CF$_3$ | |
| 840 | 4-Cl-2-NO$_2$Ph | thiazol-2-yl | H | |
| 841 | 4-Cl-2-NO$_2$Ph | thiazol-2-yl | methyl | |
| 842 | 4-Cl-2-NO$_2$Ph | thiazol-2-yl | i-propyl | |
| 843 | 4-Cl-2-NO$_2$Ph | thiazol-2-yl | cyclopropyl | |
| 844 | 4-Cl-2-NO$_2$Ph | thiazol-2-yl | CF$_3$ | |
| 845 | 4-Cl-2-NO$_2$Ph | 4-methylthiazol-2-yl | H | |
| 846 | 4-Cl-2-NO$_2$Ph | 4-methylthiazol-2-yl | methyl | |
| 847 | 4-Cl-2-NO$_2$Ph | 4-methylthiazol-2-yl | i-propyl | |
| 848 | 4-Cl-2-NO$_2$Ph | 4-methylthiazol-2-yl | cyclopropyl | |
| 849 | 4-Cl-2-NO$_2$Ph | 4-methylthiazol-2-yl | CF$_3$ | |
| 850 | 4-Cl-2-NO$_2$Ph | oxazol-2-yl | H | |
| 851 | 4-Cl-2-NO$_2$Ph | oxazol-2-yl | methyl | |
| 852 | 4-Cl-2-NO$_2$Ph | oxazol-2-yl | i-propyl | |
| 853 | 4-Cl-2-NO$_2$Ph | oxazol-2-yl | cyclopropyl | |
| 854 | 4-Cl-2-NO$_2$Ph | oxazol-2-yl | CF$_3$ | |
| 855 | 4-Cl-2-NO$_2$Ph | 4,5-dimethyl- | H | |

-continued

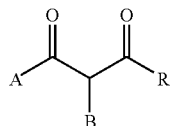

(I)

| Compound N | A | B | R | m.p. (° C.) |
|---|---|---|---|---|
| 856 | 4-Cl-2-NO$_2$Ph | 4,5-dimethyl-oxazol-2-yl | methyl | |
| 857 | 4-Cl-2-NO$_2$Ph | 4,5-dimethyl-oxazol-2-yl | i-propyl | |
| 858 | 4-Cl-2-NO$_2$Ph | 4,5-dimethyl-oxazol-2-yl | cyclopropyl | |
| 859 | 4-Cl-2-NO$_2$Ph | 4,5-dimethyl-oxazol-2-yl | CF$_3$ | |
| 860 | 4-Cl-2-NO$_2$Ph | 2-oxazolin-2-yl | H | |
| 861 | 4-Cl-2-NO$_2$Ph | 2-oxazolin-2-yl | methyl | |
| 862 | 4-Cl-2-NO$_2$Ph | 2-oxazolin-2-yl | i-propyl | |
| 863 | 4-Cl-2-NO$_2$Ph | 2-oxazolin-2-yl | cyclopropyl | |
| 864 | 4-Cl-2-NO$_2$Ph | 2-oxazolin-2-yl | CF$_3$ | |
| 865 | 4-Cl-2-NO$_2$Ph | 4,4-dimethyl-2-oxazolin-2-yl | H | |
| 866 | 4-Cl-2-NO$_2$Ph | 4,4-dimethyl-2-oxazolin-2-yl | methyl | |
| 867 | 4-Cl-2-NO$_2$Ph | 4,4-dimethyl-2-oxazolin-2-yl | i-propyl | |
| 868 | 4-Cl-2-NO$_2$Ph | 4,4-dimethyl-2-oxazolin-2-yl | cyclopropyl | |
| 869 | 4-Cl-2-NO$_2$Ph | 4,4-dimethyl-2-oxazolin-2-yl | CF$_3$ | |
| 870 | 4-Cl-2-NO$_2$Ph | 1,2,4-thiadiazol-5-yl | H | |
| 871 | 4-Cl-2-NO$_2$Ph | 1,2,4-thiadiazol-5-yl | methyl | |
| 872 | 4-Cl-2-NO$_2$Ph | 1,2,4-thiadiazol-5-yl | i-propyl | |
| 873 | 4-Cl-2-NO$_2$Ph | 1,2,4-thiadiazol-5-yl | cyclopropyl | |
| 874 | 4-Cl-2-NO$_2$Ph | 1,2,4-thiadiazol-5-yl | CF$_3$ | |
| 875 | 4-Cl-2-NO$_2$Ph | 3-methyl-1,2,4-thiadiazol-5-yl | H | |
| 876 | 4-Cl-2-NO$_2$Ph | 3-methyl-1,2,4-thiadiazol-5-yl | methyl | |
| 877 | 4-Cl-2-NO$_2$Ph | 3-methyl-1,2,4-thiadiazol-5-yl | i-propyl | |
| 878 | 4-Cl-2-NO$_2$Ph | 3-methyl-1,2,4-thiadiazol-5-yl | cyclopropyl | |
| 879 | 4-Cl-2-NO$_2$Ph | 3-methyl-1,2,4-thiadiazol-5-yl | CF$_3$ | |
| 880 | 4-Cl-2-NO$_2$Ph | 3-trifluoromethyl-1,2,4-thiadiazol-5-yl | H | |
| 881 | 4-Cl-2-NO$_2$Ph | 3-trifluoromethyl-1,2,4-thiadiazol-5-yl | methyl | |
| 882 | 4-Cl-2-NO$_2$Ph | 3-trifluoromethyl-1,2,4-thiadiazol-5-yl | i-propyl | |
| 883 | 4-Cl-2-NO$_2$Ph | 3-trifluoromethyl-1,2,4-thiadiazol-5-yl | cyclopropyl | |
| 884 | 4-Cl-2-NO$_2$Ph | 3-trifluoromethyl-1,2,4-thiadiazol-5-yl | CF$_3$ | |
| 885 | 4-Cl-2-NO$_2$Ph | 1,2,4-thiadiazol-3-yl | H | |
| 886 | 4-Cl-2-NO$_2$Ph | 1,2,4-thiadiazol-3-yl | methyl | |
| 887 | 4-Cl-2-NO$_2$Ph | 1,2,4-thiadiazol-3-yl | i-propyl | |
| 888 | 4-Cl-2-NO$_2$Ph | 1,2,4-thiadiazol-3-yl | cyclopropyl | |
| 889 | 4-Cl-2-NO$_2$Ph | 1,2,4-thiadiazol-3-yl | CF$_3$ | |

-continued

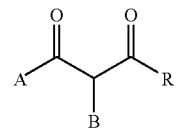

(I)

| Compound N | A | B | R | m.p. (° C.) |
|---|---|---|---|---|
| 890 | 4-Cl-2-NO$_2$Ph | 5-methyl-1,2,4-thiadiazol-3-yl | H | |
| 891 | 4-Cl-2-NO$_2$Ph | 5-methyl-1,2,4-thiadiazol-3-yl | methyl | |
| 892 | 4-Cl-2-NO$_2$Ph | 5-methyl-1,2,4-thiadiazol-3-yl | i-propyl | |
| 893 | 4-Cl-2-NO$_2$Ph | 5-methyl-1,2,4-thiadiazol-3-yl | cyclopropyl | |
| 894 | 4-Cl-2-NO$_2$Ph | 5-methyl-1,2,4-thiadiazol-3-yl | CF$_3$ | |
| 895 | 4-Cl-2-NO$_2$Ph | 5-trifluoromethyl-1,2,4-thiadiazol-3-yl | H | |
| 896 | 4-Cl-2-NO$_2$Ph | 5-trifluoromethyl-1,2,4-thiadiazol-3-yl | methyl | |
| 897 | 4-Cl-2-NO$_2$Ph | 5-trifluoromethyl-1,2,4-thiadiazol-3-yl | i-propyl | |
| 898 | 4-Cl-2-NO$_2$Ph | 5-trifluoromethyl-1,2,4-thiadiazol-3-yl | cyclopropyl | |
| 899 | 4-Cl-2-NO$_2$Ph | 5-trifluoromethyl-1,2,4-thiadiazol-3-yl | CF$_3$ | |
| 900 | 4-Cl-2-NO$_2$Ph | 1,3,4-thiadiazol-2-yl | H | |
| 901 | 4-Cl-2-NO$_2$Ph | 1,3,4-thiadiazol-2-yl | methyl | |
| 902 | 4-Cl-2-NO$_2$Ph | 1,3,4-thiadiazol-2-yl | i-propyl | |
| 903 | 4-Cl-2-NO$_2$Ph | 1,3,4-thiadiazol-2-yl | cyclopropyl | |
| 904 | 4-Cl-2-NO$_2$Ph | 1,3,4-thiadiazol-2-yl | CF$_3$ | |
| 905 | 4-Cl-2-NO$_2$Ph | 5-methylsulfonyl-1,3,4-thiadiazol-2-yl | H | |
| 906 | 4-Cl-2-NO$_2$Ph | 5-methylsulfonyl-1,3,4-thiadiazol-2-yl | methyl | |
| 907 | 4-Cl-2-NO$_2$Ph | 5-methylsulfonyl-1,3,4-thiadiazol-2-yl | i-propyl | |
| 908 | 4-Cl-2-NO$_2$Ph | 5-methylsulfonyl-1,3,4-thiadiazol-2-yl | cyclopropyl | |
| 909 | 4-Cl-2-NO$_2$Ph | 5-methylsulfonyl-1,3,4-thiadiazol-2-yl | CF$_3$ | |
| 910 | 4-Cl-2-NO$_2$Ph | 5-methyl-1,3,4-thiadiazol-2-yl | H | |
| 911 | 4-Cl-2-NO$_2$Ph | 5-methyl-1,3,4-thiadiazol-2-yl | methyl | |
| 912 | 4-Cl-2-NO$_2$Ph | 5-methyl-1,3,4-thiadiazol-2-yl | i-propyl | |
| 913 | 4-Cl-2-NO$_2$Ph | 5-methyl-1,3,4-thiadiazol-2-yl | cyclopropyl | |
| 914 | 4-Cl-2-NO$_2$Ph | 5-methyl-1,3,4-thiadiazol-2-yl | CF$_3$ | |
| 915 | 4-Cl-2-NO$_2$Ph | benzoxazol-2-yl | H | |
| 916 | 4-Cl-2-NO$_2$Ph | benzoxazol-2-yl | methyl | |
| 917 | 4-Cl-2-NO$_2$Ph | benzoxazol-2-yl | i-propyl | |
| 918 | 4-Cl-2-NO$_2$Ph | benzoxazol-2-yl | cyclopropyl | |
| 919 | 4-Cl-2-NO$_2$Ph | benzoxazol-2-yl | CF$_3$ | |
| 920 | 4-Cl-2-NO$_2$Ph | 6-methyl-benzoxazol-2-yl | H | |
| 921 | 4-Cl-2-NO$_2$Ph | 6-methyl-benzoxazol-2-yl | methyl | |

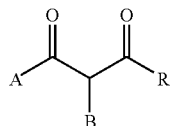

(I)

| Compound N | A | B | R | m.p. (° C.) |
|---|---|---|---|---|
| 922 | 4-Cl-2-NO₂Ph | 6-methyl-benzoxazol-2-yl | i-propyl | |
| 923 | 4-Cl-2-NO₂Ph | 6-methyl-benzoxazol-2-yl | cyclopropyl | |
| 924 | 4-Cl-2-NO₂Ph | 6-methyl-benzoxazol-2-yl | CF₃ | |
| 925 | 4-Cl-2-NO₂Ph | benzothiazol-2-yl | H | |
| 926 | 4-Cl-2-NO₂Ph | benzothiazol-2-yl | methyl | |
| 927 | 4-Cl-2-NO₂Ph | benzothiazol-2-yl | i-propyl | |
| 928 | 4-Cl-2-NO₂Ph | benzothiazol-2-yl | cyclopropyl | |
| 929 | 4-Cl-2-NO₂Ph | benzothiazol-2-yl | CF₃ | |
| 930 | 4-Cl-2-NO₂Ph | pyrazol-1-yl | H | |
| 931 | 4-Cl-2-NO₂Ph | pyrazol-1-yl | methyl | |
| 932 | 4-Cl-2-NO₂Ph | pyrazol-1-yl | i-propyl | |
| 933 | 4-Cl-2-NO₂Ph | pyrazol-1-yl | cyclopropyl | |
| 934 | 4-Cl-2-NO₂Ph | pyrazol-1-yl | CF₃ | |
| 935 | 4-Cl-2-NO₂Ph | pyrazol-3-yl | H | |
| 936 | 4-Cl-2-NO₂Ph | pyrazol-3-yl | methyl | |
| 937 | 4-Cl-2-NO₂Ph | pyrazol-3-yl | i-propyl | |
| 938 | 4-Cl-2-NO₂Ph | pyrazol-3-yl | cyclopropyl | |
| 939 | 4-Cl-2-NO₂Ph | pyrazol-3-yl | CF₃ | |
| 940 | 4-Cl-2-NO₂Ph | 1-methylpyrazol-3-yl | H | |
| 941 | 4-Cl-2-NO₂Ph | 1-methylpyrazol-3-yl | methyl | |
| 942 | 4-Cl-2-NO₂Ph | 1-methylpyrazol-3-yl | i-propyl | |
| 943 | 4-Cl-2-NO₂Ph | 1-methylpyrazol-3-yl | cyclopropyl | |
| 944 | 4-Cl-2-NO₂Ph | 1-methylpyrazol-3-yl | CF₃ | |
| 945 | 4-Cl-2-NO₂Ph | tetrazol-1-yl | H | |
| 946 | 4-Cl-2-NO₂Ph | tetrazol-1-yl | methyl | |
| 947 | 4-Cl-2-NO₂Ph | tetrazol-1-yl | i-propyl | |
| 948 | 4-Cl-2-NO₂Ph | tetrazol-1-yl | cyclopropyl | |
| 949 | 4-Cl-2-NO₂Ph | tetrazol-1-yl | CF₃ | |
| 950 | 4-Cl-2-NO₂Ph | 5-methyltetrazol-1-yl | H | |
| 951 | 4-Cl-2-NO₂Ph | 5-methyltetrazol-1-yl | methyl | |
| 952 | 4-Cl-2-NO₂Ph | 5-methyltetrazol-1-yl | i-propyl | |
| 953 | 4-Cl-2-NO₂Ph | 5-methyltetrazol-1-yl | cyclopropyl | |
| 954 | 4-Cl-2-NO₂Ph | 5-methyltetrazol-1-yl | CF₃ | |
| 955 | 4-Cl-2-NO₂Ph | tetrazol-2-yl | H | |
| 956 | 4-Cl-2-NO₂Ph | tetrazol-2-yl | methyl | |
| 957 | 4-Cl-2-NO₂Ph | tetrazol-2-yl | i-propyl | |
| 958 | 4-Cl-2-NO₂Ph | tetrazol-2-yl | cyclopropyl | |
| 959 | 4-Cl-2-NO₂Ph | tetrazol-2-yl | CF₃ | |
| 960 | 4-Cl-2-NO₂Ph | 5-methyltetrazol-2-yl | H | |
| 961 | 4-Cl-2-NO₂Ph | 5-methyltetrazol-2-yl | methyl | |
| 962 | 4-Cl-2-NO₂Ph | 5-methyltetrazol-2-yl | i-propyl | |
| 963 | 4-Cl-2-NO₂Ph | 5-methyltetrazol-2-yl | cyclopropyl | |
| 964 | 4-Cl-2-NO₂Ph | 5-methyltetrazol-2-yl | CF₃ | |
| 965 | 4-Cl-2-NO₂Ph | 1-methyltetrazol-5-yl | H | |
| 966 | 4-Cl-2-NO₂Ph | 1-methyltetrazol-5-yl | methyl | |
| 967 | 4-Cl-2-NO₂Ph | 1-methyltetrazol-5-yl | i-propyl | |
| 968 | 4-Cl-2-NO₂Ph | 1-methyltetrazol-5-yl | cyclopropyl | 152 |
| 969 | 4-Cl-2-NO₂Ph | 1-methyltetrazol-5-yl | CF₃ | |
| 970 | 2-Cl-4-NO₂Ph | 2-methyltetrazol-5-yl | cyclopropyl | 137 |
| 971 | 4-Cl-2-NO₂Ph | 2-methyltetrazol-5-yl | methyl | |
| 972 | 4-Cl-2-NO₂Ph | 2-methyltetrazol-5-yl | i-propyl | |
| 973 | 4-Cl-2-NO₂Ph | 2-methyltetrazol-5-yl | cyclopropyl | 126 |
| 974 | 4-Cl-2-NO₂Ph | 2-methyltetrazol-5-yl | CF₃ | |
| 975 | 2,4-(NO₂)₂Ph | 2-methyltetrazol-5-yl | cyclopropyl | 144 |
| 976 | 4-Cl-2-NO₂Ph | pyridin-2-yl | methyl | |
| 977 | 4-Cl-2-NO₂Ph | pyridin-2-yl | i-propyl | |
| 978 | 4-Cl-2-NO₂Ph | pyridin-2-yl | cyclopropyl | |
| 979 | 4-Cl-2-NO₂Ph | pyridin-2-yl | CF₃ | |
| 980 | 4-Cl-2-NO₂Ph | pyridin-4-yl | H | |
| 981 | 4-Cl-2-NO₂Ph | pyridin-4-yl | methyl | |
| 982 | 4-Cl-2-NO₂Ph | pyridin-4-yl | i-propyl | |
| 983 | 4-Cl-2-NO₂Ph | pyridin-4-yl | cyclopropyl | |
| 984 | 4-Cl-2-NO₂Ph | pyridin-4-yl | CF₃ | |
| 985 | 4-Cl-2-NO₂Ph | pyridin-3-yl | H | |
| 986 | 4-Cl-2-NO₂Ph | pyridin-3-yl | methyl | |
| 987 | 4-Cl-2-NO₂Ph | pyridin-3-yl | i-propyl | |
| 988 | 4-Cl-2-NO₂Ph | pyridin-3-yl | cyclopropyl | |
| 989 | 4-Cl-2-NO₂Ph | pyridin-3-yl | CF₃ | |
| 990 | 4-Cl-2-NO₂Ph | 3-nitropyridin-4-yl | H | |
| 991 | 4-Cl-2-NO₂Ph | 3-nitropyridin-4-yl | methyl | |
| 992 | 4-Cl-2-NO₂Ph | 3-nitropyridin-4-yl | i-propyl | |
| 993 | 4-Cl-2-NO₂Ph | 3-nitropyridin-4-yl | cyclopropyl | |
| 994 | 4-Cl-2-NO₂Ph | 3-nitropyridin-4-yl | CF₃ | |
| 995 | 4-Cl-2-NO₂Ph | 5-cyanopyridin-2-yl | H | |
| 996 | 4-Cl-2-NO₂Ph | 5-cyanopyridin-2-yl | methyl | |
| 997 | 4-Cl-2-NO₂Ph | 5-cyanopyridin-2-yl | i-propyl | |
| 998 | 4-Cl-2-NO₂Ph | 5-cyanopyridin-2-yl | cyclopropyl | |
| 999 | 4-Cl-2-NO₂Ph | 5-cyanopyridin-2-yl | CF₃ | |
| 1000 | 4-Cl-2-NO₂Ph | 5-trifluoromethylpyridin-2-yl | H | |
| 1001 | 4-Cl-2-NO₂Ph | 5-trifluoromethylpyridin-2-yl | methyl | |
| 1002 | 4-Cl-2-NO₂Ph | 5-trifluoromethylpyridin-2-yl | i-propyl | |
| 1003 | 4-Cl-2-NO₂Ph | 5-trifluoromethylpyridin-2-yl | cyclopropyl | |
| 1004 | 4-Cl-2-NO₂Ph | 5-trifluoromethylpyridin-2-yl | CF₃ | |
| 1005 | 4-Cl-2-NO₂Ph | pyrimidin-2-yl | H | |
| 1006 | 4-Cl-2-NO₂Ph | pyrimidin-2-yl | methyl | |
| 1007 | 4-Cl-2-NO₂Ph | pyrimidin-2-yl | i-propyl | |
| 1008 | 4-Cl-2-NO₂Ph | pyrimidin-2-yl | cyclopropyl | |
| 1009 | 4-Cl-2-NO₂Ph | pyrimidin-2-yl | CF₃ | |
| 1010 | 4-Cl-2-NO₂Ph | pyrimidin-4-yl | H | |

-continued

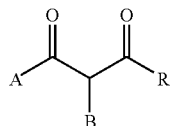

(I)

| Compound N | A | B | R | m.p. (° C.) |
|---|---|---|---|---|
| 1011 | 4-Cl-2-NO₂Ph | pyrimidin-4-yl | methyl | |
| 1012 | 4-Cl-2-NO₂Ph | pyrimidin-4-yl | i-propyl | |
| 1013 | 4-Cl-2-NO₂Ph | pyrimidin-4-yl | cyclopropyl | |
| 1014 | 4-Cl-2-NO₂Ph | pyrimidin-4-yl | CF₃ | |
| 1015 | 4-Cl-2-NO₂Ph | 6-chloro-pyrimidin-4-yl | methyl | |
| 1016 | 4-Cl-2-NO₂Ph | 6-chloro-pyrimidin-4-yl | i-propyl | |
| 1017 | 4-Cl-2-NO₂Ph | 6-chloro-pyrimidin-4-yl | cyclopropyl | |
| 1018 | 4-Cl-2-NO₂Ph | 6-chloro-pyrimidin-4-yl | CF₃ | |
| 1019 | 2,4-(Cl)₂Ph | 1-methyltetrazol-5-yl | t-butil | 124 |
| 1020 | 4-Cl-2-NO₂Ph | pyridazin-3-yl | methyl | |
| 1021 | 4-Cl-2-NO₂Ph | pyridazin-3-yl | i-propyl | |
| 1022 | 4-Cl-2-NO₂Ph | pyridazin-3-yl | cyclopropyl | |
| 1023 | 4-Cl-2-NO₂Ph | pyridazin-3-yl | CF₃ | |
| 1024 | 4-Cl-2-NO₂Ph | 6-chloro-pyridazin-3-yl | methyl | |
| 1025 | 4-Cl-2-NO₂Ph | 6-chloro-pyridazin-3-yl | i-propyl | |
| 1026 | 4-Cl-2-NO₂Ph | 6-chloro-pyridazin-3-yl | cyclopropyl | |
| 1027 | 4-Cl-2-NO₂Ph | 6-chloro-pyridazin-3-yl | CF₃ | |
| 1028 | 4-Cl-2-NO₂Ph | pyrazin-2-yl | methyl | |
| 1029 | 4-Cl-2-NO₂Ph | pyrazin-2-yl | i-propyl | |
| 1030 | 4-Cl-2-NO₂Ph | pyrazin-2-yl | cyclopropyl | |
| 1031 | 4-Cl-2-NO₂Ph | pyrazin-2-yl | CF₃ | |
| 1032 | 4-Cl-2-NO₂Ph | triazin-2-yl | methyl | |
| 1033 | 4-Cl-2-NO₂Ph | triazin-2-yl | i-propyl | |
| 1034 | 4-Cl-2-NO₂Ph | triazin-2-yl | cyclopropyl | |
| 1035 | 4-Cl-2-NO₂Ph | triazin-2-yl | CF₃ | |
| 1036 | 4-Cl-2-NO₂Ph | quinolin-2-yl | methyl | |
| 1037 | 4-Cl-2-NO₂Ph | quinolin-2-yl | i-propyl | |
| 1038 | 4-Cl-2-NO₂Ph | quinolin-2-yl | cyclopropyl | |
| 1039 | 4-Cl-2-NO₂Ph | quinolin-2-yl | CF₃ | |
| 1040 | 4-Cl-2-NO₂Ph | 4,4,6-trimethyl-5,6-dihydro-1,3(4H)-oxazin-2-yl | H | |
| 1041 | 4-Cl-2-NO₂Ph | 4,4,6-trimethyl-5,6-dihydro-1,3(4H)-oxazin-2-yl | methyl | |
| 1042 | 4-Cl-2-NO₂Ph | 4,4,6-trimethyl-5,6-dihydro-1,3(4H)-oxazin-2-yl | i-propyl | |
| 1043 | 4-Cl-2-NO₂Ph | 4,4,6-trimethyl-5,6-dihydro-1,3(4H)-oxazin-2-yl | cyclopropyl | |
| 1044 | 4-Cl-2-NO₂Ph | 4,4,6-trimethyl-5,6-dihydro-1,3(4H)-oxazin-2-yl | CF₃ | |
| 1045 | 4-Cl-2-NO₂Ph | 2-oxazolidinon-3-yl | H | |
| 1046 | 4-Cl-2-NO₂Ph | 2-oxazolidinon-3-yl | methyl | |
| 1047 | 4-Cl-2-NO₂Ph | 2-oxazolidinon-3-yl | i-propyl | |
| 1048 | 4-Cl-2-NO₂Ph | 2-oxazolidinon-3-yl | cyclopropyl | |
| 1049 | 4-Cl-2-NO₂Ph | 2-oxazolidinon-3-yl | CF₃ | |
| 1050 | 4-Cl-2-NO₂Ph | 2-pyrrolidinon-1-yl | methyl | |
| 1051 | 4-Cl-2-NO₂Ph | 2-pyrrolidinon-1-yl | i-propyl | |
| 1052 | 4-Cl-2-NO₂Ph | 2-pyrrolidinon-1-yl | cyclopropyl | |

-continued

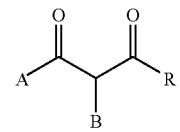

(I)

| Compound N | A | B | R | m.p. (° C.) |
|---|---|---|---|---|
| 1053 | 4-Cl-2-NO₂Ph | 2-pyrrolidinon-1-yl | CF₃ | |
| 1054 | 4-Cl-2-NO₂Ph | 3-methylisoxazol-5-yl | methyl | |
| 1055 | 4-Cl-2-NO₂Ph | 3-methylisoxazol-5-yl | i-propyl | |
| 1056 | 4-Cl-2-NO₂Ph | 3-methylisoxazol-5-yl | cyclopropyl | |
| 1057 | 4-Cl-2-NO₂Ph | 3-methylisoxazol-5-yl | CF₃ | |
| 1058 | 4-Cl-2-NO₂Ph | 2-NO₂-4-SO₂MePh | H | |
| 1059 | 4-Cl-2-NO₂Ph | 2-NO₂-4-SO₂MePh | methyl | |
| 1060 | 4-Cl-2-NO₂Ph | 2-NO₂-4-SO₂MePh | i-propyl | |
| 1061 | 4-Cl-2-NO₂Ph | 2-NO₂-4-SO₂MePh | cyclopropyl | |
| 1062 | 4-Cl-2-NO₂Ph | 2-NO₂-4-SO₂MePh | CF₃ | |
| 1063 | 4-Cl-2-NO₂Ph | 2-Cl-4-SO₂MePH | H | |
| 1064 | 4-Cl-2-NO₂Ph | 2-Cl-4-SO₂MePH | methyl | |
| 1065 | 4-Cl-2-NO₂Ph | 2-Cl-4-SO₂MePH | i-propyl | |
| 1066 | 4-Cl-2-NO₂Ph | 2-Cl-4-SO₂MePH | cyclopropyl | |
| 1067 | 4-Cl-2-NO₂Ph | 2-Cl-4-SO₂MePH | CF₃ | |
| 1068 | 4-Cl-2-NO₂Ph | 2-NO₂-4-CF₃Ph | H | |
| 1069 | 4-Cl-2-NO₂Ph | 2-NO₂-4-CF₃Ph | methyl | |
| 1070 | 4-Cl-2-NO₂Ph | 2-NO₂-4-CF₃Ph | i-propyl | |
| 1071 | 4-Cl-2-NO₂Ph | 2-NO₂-4-CF₃Ph | cyclopropyl | |
| 1072 | 4-Cl-2-NO₂Ph | 2-NO₂-4-CF₃Ph | CF₃ | |
| 1073 | 4-Cl-2-NO₂Ph | 2-NO₂-4-ClPh | H | |
| 1074 | 4-Cl-2-NO₂Ph | 2-NO₂-4-ClPh | methyl | |
| 1075 | 4-Cl-2-NO₂Ph | 2-NO₂-4-ClPh | i-propyl | |
| 1076 | 4-Cl-2-NO₂Ph | 2-NO₂-4-ClPh | cyclopropyl | |
| 1077 | 4-Cl-2-NO₂Ph | 2-NO₂-4-ClPh | CF₃ | |
| 1078 | 4-Cl-2-NO₂Ph | 2-Cl-4-NO₂PH | H | |
| 1079 | 4-Cl-2-NO₂Ph | 2-Cl-4-NO₂PH | methyl | |
| 1080 | 4-Cl-2-NO₂Ph | 2-Cl-4-NO₂PH | i-propyl | |
| 1081 | 4-Cl-2-NO₂Ph | 2-Cl-4-NO₂PH | cyclopropyl | |
| 1082 | 4-Cl-2-NO₂Ph | 2-Cl-4-NO₂PH | CF₃ | |
| 1083 | 4-Cl-2-NO₂Ph | 2,4-(NO₂)₂Ph | H | |
| 1084 | 4-Cl-2-NO₂Ph | 2,4-(NO₂)₂Ph | methyl | |
| 1085 | 4-Cl-2-NO₂Ph | 2,4-(NO₂)₂Ph | i-propyl | |
| 1086 | 4-Cl-2-NO₂Ph | 2,4-(NO₂)₂Ph | cyclopropyl | |
| 1087 | 4-Cl-2-NO₂Ph | 2,4-(NO₂)₂Ph | CF₃ | |
| 1088 | 4-Cl-2-NO₂Ph | 4-F-3-NO₂Ph | H | |
| 1089 | 4-Cl-2-NO₂Ph | 4-F-3-NO₂Ph | methyl | |
| 1090 | 4-Cl-2-NO₂Ph | 4-F-3-NO₂Ph | i-propyl | |
| 1091 | 4-Cl-2-NO₂Ph | 4-F-3-NO₂Ph | cyclopropyl | |
| 1092 | 4-Cl-2-NO₂Ph | 4-F-3-NO₂Ph | CF₃ | |
| 1093 | 4-Cl-2-NO₂Ph | 3,5-(CF₃)₂Ph | H | |
| 1094 | 4-Cl-2-NO₂Ph | 3,5-(CF₃)₂Ph | methyl | |
| 1095 | 4-Cl-2-NO₂Ph | 3,5-(CF₃)₂Ph | i-propyl | |
| 1096 | 4-Cl-2-NO₂Ph | 3,5-(CF₃)₂Ph | cyclopropyl | |
| 1097 | 4-Cl-2-NO₂Ph | 3,5-(CF₃)₂Ph | CF₃ | |
| 1098 | 4-Cl-2-NO₂Ph | 2-SO₂Me-4-CF₃Ph | H | |
| 1099 | 4-Cl-2-NO₂Ph | 2-SO₂Me-4-CF₃Ph | methyl | |
| 1100 | 4-Cl-2-NO₂Ph | 2-SO₂Me-4-CF₃Ph | i-propyl | |
| 1101 | 4-Cl-2-NO₂Ph | 2-SO₂Me-4-CF₃Ph | cyclopropyl | |
| 1102 | 4-Cl-2-NO₂Ph | 2-SO₂Me-4-CF₃Ph | CF₃ | |
| 1103 | 2-SO₂Me-4-CF₃Ph | 1,2,4-oxadiazol-5-yl | H | |
| 1104 | 2-SO₂Me-4-CF₃Ph | 1,2,4-oxadiazol-5-yl | methyl | |

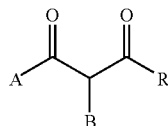

(I)

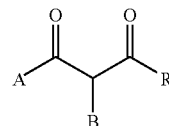

(I)

| Compound N | A | B | R | m.p. (° C.) |
|---|---|---|---|---|
| 1105 | 2-SO₂Me-4-CF₃Ph | 1,2,4-oxadiazol-5-yl | i-propyl | |
| 1106 | 2-SO₂Me-4-CF₃Ph | 1,2,4-oxadiazol-5-yl | cyclopropyl | |
| 1107 | 2-SO₂Me-4-CF₃Ph | 1,2,4-oxadiazol-5-yl | CF₃ | |
| 1108 | 2-SO₂Me-4-CF₃Ph | 3-methyl-1,2,4-oxadiazol-5-yl | H | |
| 1109 | 2-SO₂Me-4-CF₃Ph | 3-methyl-1,2,4-oxadiazol-5-yl | methyl | |
| 1110 | 2-SO₂Me-4-CF₃Ph | 3-methyl-1,2,4-oxadiazol-5-yl | i-propyl | |
| 1111 | 2-SO₂Me-4-CF₃Ph | 3-methyl-1,2,4-oxadiazol-5-yl | cyclopropyl | |
| 1112 | 2-SO₂Me-4-CF₃Ph | 3-methyl-1,2,4-oxadiazol-5-yl | CF₃ | |
| 1113 | 2-SO₂Me-4-CF₃Ph | 3-trifluoromethyl-1,2,4-oxadiazol-5-yl | H | |
| 1114 | 2-SO₂Me-4-CF₃Ph | 3-trifluoromethyl-1,2,4-oxadiazol-5-yl | methyl | |
| 1115 | 2-SO₂Me-4-CF₃Ph | 3-trifluoromethyl-1,2,4-oxadiazol-5-yl | i-propyl | |
| 1116 | 2-SO₂Me-4-CF₃Ph | 3-trifluoromethyl-1,2,4-oxadiazol-5-yl | cyclopropyl | |
| 1117 | 2-SO₂Me-4-CF₃Ph | 3-trifluoromethyl-1,2,4-oxadiazol-5-yl | CF₃ | |
| 1118 | 2-SO₂Me-4-CF₃Ph | 1,2,4-oxadiazol-3-yl | H | |
| 1119 | 2-SO₂Me-4-CF₃Ph | 1,2,4-oxadiazol-3-yl | methyl | |
| 1120 | 2-SO₂Me-4-CF₃Ph | 1,2,4-oxadiazol-3-yl | i-propyl | |
| 1121 | 2-SO₂Me-4-CF₃Ph | 1,2,4-oxadiazol-3-yl | cyclopropyl | |
| 1122 | 2-SO₂Me-4-CF₃Ph | 1,2,4-oxadiazol-3-yl | CF₃ | |
| 1123 | 2-SO₂Me-4-CF₃Ph | 5-methyl-1,2,4-oxadiazol-3-yl | H | |
| 1124 | 2-SO₂Me-4-CF₃Ph | 5-methyl-1,2,4-oxadiazol-3-yl | methyl | |
| 1125 | 2-SO₂Me-4-CF₃Ph | 5-methyl-1,2,4-oxadiazol-3-yl | i-propyl | |
| 1126 | 2-SO₂Me-4-CF₃Ph | 5-methyl-1,2,4-oxadiazol-3-yl | cyclopropyl | |
| 1127 | 2-SO₂Me-4-CF₃Ph | 5-methyl-1,2,4-oxadiazol-3-yl | CF₃ | |
| 1128 | 2-SO₂Me-4-CF₃Ph | 5-trifluoromethyl-1,2,4-oxadiazol-3-yl | H | |
| 1129 | 2-SO₂Me-4-CF₃Ph | 5-trifluoromethyl-1,2,4-oxadiazol-3-yl | methyl | |
| 1130 | 2-SO₂Me-4-CF₃Ph | 5-trifluoromethyl-1,2,4-oxadiazol-3-yl | i-propyl | |
| 1131 | 2-SO₂Me-4-CF₃Ph | 5-trifluoromethyl-1,2,4-oxadiazol-3-yl | cyclopropyl | |
| 1132 | 2-SO₂Me-4-CF₃Ph | 5-trifluoromethyl-1,2,4-oxadiazol-3-yl | CF₃ | |
| 1133 | 2-SO₂Me-4-CF₃Ph | 5-chloro-1,2,4-oxadiazol-3-yl | H | |
| 1134 | 2-SO₂Me-4-CF₃Ph | 5-chloro-1,2,4-oxadiazol-3-yl | methyl | |
| 1135 | 2-SO₂Me-4-CF₃Ph | 5-chloro-1,2,4-oxadiazol-3-yl | i-propyl | |
| 1136 | 2-SO₂Me-4-CF₃Ph | 5-chloro-1,2,4-oxadiazol-3-yl | cyclopropyl | |
| 1137 | 2-SO₂Me-4-CF₃Ph | 5-chloro-1,2,4-oxadiazol-3-yl | CF₃ | |
| 1138 | 2-SO₂Me-4-CF₃Ph | 1,3,4-oxadiazol-2-yl | H | |
| 1139 | 2-SO₂Me-4-CF₃Ph | 1,3,4-oxadiazol-2-yl | methyl | |
| 1140 | 2-SO₂Me-4-CF₃Ph | 1,3,4-oxadiazol-2-yl | i-propyl | |
| 1141 | 2-SO₂Me-4-CF₃Ph | 1,3,4-oxadiazol-2-yl | cyclopropyl | |
| 1142 | 2-SO₂Me-4-CF₃Ph | 1,3,4-oxadiazol-2-yl | CF₃ | |
| 1143 | 2-SO₂Me-4-CF₃Ph | 5-methylsulfonyl-1,3,4-oxadiazol-2-yl | H | |
| 1144 | 2-SO₂Me-4-CF₃Ph | 5-methylsulfonyl-1,3,4-oxadiazol-2-yl | methyl | |
| 1145 | 2-SO₂Me-4-CF₃Ph | 5-methylsulfonyl-1,3,4-oxadiazol-2-yl | i-propyl | |
| 1146 | 2-SO₂Me-4-CF₃Ph | 5-methylsulfonyl-1,3,4-oxadiazol-2-yl | cyclopropyl | |
| 1147 | 2-SO₂Me-4-CF₃Ph | 5-methylsulfonyl-1,3,4-oxadiazol-2-yl | CF₃ | |
| 1148 | 2-SO₂Me-4-CF₃Ph | 5-methyl-1,3,4-oxadiazol-2-yl | H | |
| 1149 | 2-SO₂Me-4-CF₃Ph | 5-methyl-1,3,4-oxadiazol-2-yl | methyl | |
| 1150 | 2-SO₂Me-4-CF₃Ph | 5-methyl-1,3,4-oxadiazol-2-yl | i-propyl | |
| 1151 | 2-SO₂Me-4-CF₃Ph | 5-methyl-1,3,4-oxadiazol-2-yl | cyclopropyl | |
| 1152 | 2-SO₂Me-4-CF₃Ph | 5-methyl-1,3,4-oxadiazol-2-yl | CF₃ | |
| 1153 | 2-SO₂Me-4-CF₃Ph | 5-trifluoromethyl-1,3,4-oxadiazol-2-yl | H | |
| 1154 | 2-SO₂Me-4-CF₃Ph | 5-trifluoromethyl-1,3,4-oxadiazol-2-yl | methyl | |
| 1155 | 2-SO₂Me-4-CF₃Ph | 5-trifluoromethyl-1,3,4-oxadiazol-2-yl | i-propyl | |
| 1156 | 2-SO₂Me-4-CF₃Ph | 5-trifluoromethyl-1,3,4-oxadiazol-2-yl | cyclopropyl | |
| 1157 | 2-SO₂Me-4-CF₃Ph | 5-trifluoromethyl-1,3,4-oxadiazol-2-yl | CF₃ | |
| 1158 | 2-SO₂Me-4-CF₃Ph | 1,2,3-triazol-4-yl | H | |
| 1159 | 2-SO₂Me-4-CF₃Ph | 1,2,3-triazol-4-yl | methyl | |
| 1160 | 2-SO₂Me-4-CF₃Ph | 1,2,3-triazol-4-yl | i-propyl | |
| 1161 | 2-SO₂Me-4-CF₃Ph | 1,2,3-triazol-4-yl | cyclopropyl | |
| 1162 | 2-SO₂Me-4-CF₃Ph | 1,2,3-triazol-4-yl | CF₃ | |
| 1163 | 2-SO₂Me-4-CF₃Ph | 1-methyl-1,2,3-triazol-4-yl | H | |

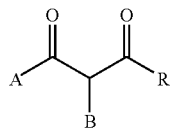
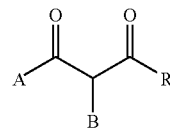

| Compound N | A | B | R | m.p. (°C.) |
|---|---|---|---|---|
| 1164 | 2-SO₂Me-4-CF₃Ph | 1-methyl-1,2,3-triazol-4-yl | methyl | |
| 1165 | 2-SO₂Me-4-CF₃Ph | 1-methyl-1,2,3-triazol-4-yl | i-propyl | |
| 1166 | 2-SO₂Me-4-CF₃Ph | 1-methyl-1,2,3-triazol-4-yl | cyclopropyl | |
| 1167 | 2-SO₂Me-4-CF₃Ph | 1-methyl-1,2,3-triazol-4-yl | CF₃ | |
| 1168 | 2-SO₂Me-4-CF₃Ph | 2-methyl-1,2,3-triazol-4-yl | H | |
| 1169 | 2-SO₂Me-4-CF₃Ph | 2-methyl-1,2,3-triazol-4-yl | methyl | |
| 1170 | 2-SO₂Me-4-CF₃Ph | 2-methyl-1,2,3-triazol-4-yl | i-propyl | |
| 1171 | 2-SO₂Me-4-CF₃Ph | 2-methyl-1,2,3-triazol-4-yl | cyclopropyl | |
| 1172 | 2-SO₂Me-4-CF₃Ph | 2-methyl-1,2,3-triazol-4-yl | CF₃ | |
| 1173 | 2-SO₂Me-4-CF₃Ph | 1,2,3-triazol-1-yl | H | |
| 1174 | 2-SO₂Me-4-CF₃Ph | 1,2,3-triazol-1-yl | methyl | |
| 1175 | 2-SO₂Me-4-CF₃Ph | 1,2,3-triazol-1-yl | i-propyl | |
| 1176 | 2-SO₂Me-4-CF₃Ph | 1,2,3-triazol-1-yl | cyclopropyl | |
| 1177 | 2-SO₂Me-4-CF₃Ph | 1,2,3-triazol-1-yl | CF₃ | |
| 1178 | 2-SO₂Me-4-CF₃Ph | 1,2,3-triazol-2-yl | H | |
| 1179 | 2-SO₂Me-4-CF₃Ph | 1,2,3-triazol-2-yl | methyl | |
| 1180 | 2-SO₂Me-4-CF₃Ph | 1,2,3-triazol-2-yl | i-propyl | |
| 1181 | 2-SO₂Me-4-CF₃Ph | 1,2,3-triazol-2-yl | cyclopropyl | |
| 1182 | 2-SO₂Me-4-CF₃Ph | 1,2,3-triazol-2-yl | CF₃ | |
| 1183 | 2-SO₂Me-4-CF₃Ph | 1,2,4-triazol-1-yl | H | |
| 1184 | 2-SO₂Me-4-CF₃Ph | 1,2,4-triazol-1-yl | methyl | |
| 1185 | 2-SO₂Me-4-CF₃Ph | 1,2,4-triazol-1-yl | i-propyl | |
| 1186 | 2-SO₂Me-4-CF₃Ph | 1,2,4-triazol-1-yl | cyclopropyl | |
| 1187 | 2-SO₂Me-4-CF₃Ph | 1,2,4-triazol-1-yl | CF₃ | |
| 1188 | 2-SO₂Me-4-CF₃Ph | imidazol-2-yl | H | |
| 1189 | 2-SO₂Me-4-CF₃Ph | imidazol-2-yl | methyl | |
| 1190 | 2-SO₂Me-4-CF₃Ph | imidazol-2-yl | i-propyl | |
| 1191 | 2-SO₂Me-4-CF₃Ph | imidazol-2-yl | cyclopropyl | |
| 1192 | 2-SO₂Me-4-CF₃Ph | imidazol-2-yl | CF₃ | |
| 1193 | 2-SO₂Me-4-CF₃Ph | imidazol-1-yl | H | |
| 1194 | 2-SO₂Me-4-CF₃Ph | imidazol-1-yl | methyl | |
| 1195 | 2-SO₂Me-4-CF₃Ph | imidazol-1-yl | i-propyl | |
| 1196 | 2-SO₂Me-4-CF₃Ph | imidazol-1-yl | cyclopropyl | |
| 1197 | 2-SO₂Me-4-CF₃Ph | imidazol-1-yl | CF₃ | |
| 1198 | 2-SO₂Me-4-CF₃Ph | imidazol-4-yl | H | |
| 1199 | 2-SO₂Me-4-CF₃Ph | imidazol-4-yl | methyl | |
| 1200 | 2-SO₂Me-4-CF₃Ph | imidazol-4-yl | i-propyl | |
| 1201 | 2-SO₂Me-4-CF₃Ph | imidazol-4-yl | cyclopropyl | |
| 1202 | 2-SO₂Me-4-CF₃Ph | imidazol-4-yl | CF₃ | |
| 1203 | 2-SO₂Me-4-CF₃Ph | thiazol-2-yl | H | |
| 1204 | 2-SO₂Me-4-CF₃Ph | thiazol-2-yl | methyl | |
| 1205 | 2-SO₂Me-4-CF₃Ph | thiazol-2-yl | i-propyl | |
| 1206 | 2-SO₂Me-4-CF₃Ph | thiazol-2-yl | cyclopropyl | |
| 1207 | 2-SO₂Me-4-CF₃Ph | thiazol-2-yl | CF₃ | |
| 1208 | 2-SO₂Me-4-CF₃Ph | methylthiazol-2-yl | H | |
| 1209 | 2-SO₂Me-4-CF₃Ph | methylthiazol-2-yl | methyl | |
| 1210 | 2-SO₂Me-4-CF₃Ph | methylthiazol-2-yl | i-propyl | |
| 1211 | 2-SO₂Me-4-CF₃Ph | methylthiazol-2-yl | cyclopropyl | |
| 1212 | 2-SO₂Me-4-CF₃Ph | methylthiazol-2-yl | CF₃ | |
| 1213 | 2-SO₂Me-4-CF₃Ph | oxazol-2-yl | H | |
| 1214 | 2-SO₂Me-4-CF₃Ph | oxazol-2-yl | methyl | |
| 1215 | 2-SO₂Me-4-CF₃Ph | oxazol-2-yl | i-propyl | |
| 1216 | 2-SO₂Me-4-CF₃Ph | oxazol-2-yl | cyclopropyl | |
| 1217 | 2-SO₂Me-4-CF₃Ph | oxazol-2-yl | CF₃ | |
| 1218 | 2-SO₂Me-4-CF₃Ph | 4,5-dimethyl-oxazol-2-yl | H | |
| 1219 | 2-SO₂Me-4-CF₃Ph | 4,5-dimethyl-oxazol-2-yl | methyl | |
| 1220 | 2-SO₂Me-4-CF₃Ph | 4,5-dimethyl-oxazol-2-yl | i-propyl | |
| 1221 | 2-SO₂Me-4-CF₃Ph | 4,5-dimethyl-oxazol-2-yl | cyclopropyl | |
| 1222 | 2-SO₂Me-4-CF₃Ph | 4,5-dimethyl-oxazol-2-yl | CF₃ | |
| 1223 | 2-SO₂Me-4-CF₃Ph | 2-oxazolin-2-yl | H | |
| 1224 | 2-SO₂Me-4-CF₃Ph | 2-oxazolin-2-yl | methyl | |
| 1225 | 2-SO₂Me-4-CF₃Ph | 2-oxazolin-2-yl | i-propyl | |
| 1226 | 2-SO₂Me-4-CF₃Ph | 2-oxazolin-2-yl | cyclopropyl | |
| 1227 | 2-SO₂Me-4-CF₃Ph | 2-oxazolin-2-yl | CF₃ | |
| 1228 | 2-SO₂Me-4-CF₃Ph | 4,4-dimethyl-2-oxazolin-2-yl | H | |
| 1229 | 2-SO₂Me-4-CF₃Ph | 4,4-dimethyl-2-oxazolin-2-yl | methyl | |
| 1230 | 2-SO₂Me-4-CF₃Ph | 4,4-dimethyl-2-oxazolin-2-yl | i-propyl | |
| 1231 | 2-SO₂Me-4-CF₃Ph | 4,4-dimethyl-2-oxazolin-2-yl | cyclopropyl | |
| 1232 | 2-SO₂Me-4-CF₃Ph | 4,4-dimethyl-2-oxazolin-2-yl | CF₃ | |

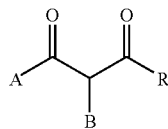

(I)

| Compound N | A | B | R | m.p. (° C.) |
|---|---|---|---|---|
| 1233 | 2-SO$_2$Me-4-CF$_3$Ph | 1,2,4-thiadiazol-5-yl | H | |
| 1234 | 2-SO$_2$Me-4-CF$_3$Ph | 1,2,4-thiadiazol-5-yl | methyl | |
| 1235 | 2-SO$_2$Me-4-CF$_3$Ph | 1,2,4-thiadiazol-5-yl | i-propyl | |
| 1236 | 2-SO$_2$Me-4-CF$_3$Ph | 1,2,4-thiadiazol-5-yl | cyclopropyl | |
| 1237 | 2-SO$_2$Me-4-CF$_3$Ph | 1,2,4-thiadiazol-5-yl | CF$_3$ | |
| 1238 | 2-SO$_2$Me-4-CF$_3$Ph | 3-methyl-1,2,4-thiadiazol-5-yl | H | |
| 1239 | 2-SO$_2$Me-4-CF$_3$Ph | 3-methyl-1,2,4-thiadiazol-5-yl | methyl | |
| 1240 | 2-SO$_2$Me-4-CF$_3$Ph | 3-methyl-1,2,4-thiadiazol-5-yl | i-propyl | |
| 1241 | 2-SO$_2$Me-4-CF$_3$Ph | 3-methyl-1,2,4-thiadiazol-5-yl | cyclopropyl | |
| 1242 | 2-SO$_2$Me-4-CF$_3$Ph | 3-methyl-1,2,4-thiadiazol-5-yl | CF$_3$ | |
| 1243 | 2-SO$_2$Me-4-CF$_3$Ph | 3-trifluoromethyl-1,2,4-thiadiazol-5-yl | H | |
| 1244 | 2-SO$_2$Me-4-CF$_3$Ph | 3-trifluoromethyl-1,2,4-thiadiazol-5-yl | methyl | |
| 1245 | 2-SO$_2$Me-4-CF$_3$Ph | 3-trifluoromethyl-1,2,4-thiadiazol-5-yl | i-propyl | |
| 1246 | 2-SO$_2$Me-4-CF$_3$Ph | 3-trifluoromethyl-1,2,4-thiadiazol-5-yl | cyclopropyl | |
| 1247 | 2-SO$_2$Me-4-CF$_3$Ph | 3-trifluoromethyl-1,2,4-thiadiazol-5-yl | CF$_3$ | |
| 1248 | 2-SO$_2$Me-4-CF$_3$Ph | 1,2,4-thiadiazol-3-yl | H | |
| 1249 | 2-SO$_2$Me-4-CF$_3$Ph | 1,2,4-thiadiazol-3-yl | methyl | |
| 1250 | 2-SO$_2$Me-4-CF$_3$Ph | 1,2,4-thiadiazol-3-yl | i-propyl | |
| 1251 | 2-SO$_2$Me-4-CF$_3$Ph | 1,2,4-thiadiazol-3-yl | cyclopropyl | |
| 1252 | 2-SO$_2$Me-4-CF$_3$Ph | 1,2,4-thiadiazol-3-yl | CF$_3$ | |
| 1253 | 2-SO$_2$Me-4-CF$_3$Ph | 5-methyl-1,2,4-thiadiazol-3-yl | H | |
| 1254 | 2-SO$_2$Me-4-CF$_3$Ph | 5-methyl-1,2,4-thiadiazol-3-yl | methyl | |
| 1255 | 2-SO$_2$Me-4-CF$_3$Ph | 5-methyl-1,2,4-thiadiazol-3-yl | i-propyl | |
| 1256 | 2-SO$_2$Me-4-CF$_3$Ph | 5-methyl-1,2,4-thiadiazol-3-yl | cyclopropyl | |
| 1257 | 2-SO$_2$Me-4-CF$_3$Ph | 5-methyl-1,2,4-thiadiazol-3-yl | CF$_3$ | |
| 1258 | 2-SO$_2$Me-4-CF$_3$Ph | 5-trifluoromethyl-1,2,4-thiadiazol-3-yl | H | |
| 1259 | 2-SO$_2$Me-4-CF$_3$Ph | 5-trifluoromethyl-1,2,4-thiadiazol-3-yl | methyl | |
| 1260 | 2-SO$_2$Me-4-CF$_3$Ph | 5-trifluoromethyl-1,2,4-thiadiazol-3-yl | i-propyl | |
| 1261 | 2-SO$_2$Me-4-CF$_3$Ph | 5-trifluoromethyl-1,2,4-thiadiazol-3-yl | cyclopropyl | |
| 1262 | 2-SO$_2$Me-4-CF$_3$Ph | 5-trifluoromethyl-1,2,4-thiadiazol-3-yl | CF$_3$ | |

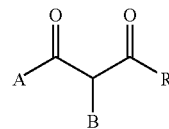

(I)

| Compound N | A | B | R | m.p. (° C.) |
|---|---|---|---|---|
| 1263 | 2-SO$_2$Me-4-CF$_3$Ph | 1,3,4-thiadiazol-2-yl | H | |
| 1264 | 2-SO$_2$Me-4-CF$_3$Ph | 1,3,4-thiadiazol-2-yl | methyl | |
| 1265 | 2-SO$_2$Me-4-CF$_3$Ph | 1,3,4-thiadiazol-2-yl | i-propyl | |
| 1266 | 2-SO$_2$Me-4-CF$_3$Ph | 1,3,4-thiadiazol-2-yl | cyclopropyl | |
| 1267 | 2-SO$_2$Me-4-CF$_3$Ph | 1,3,4-thiadiazol-2-yl | CF$_3$ | |
| 1268 | 2-SO$_2$Me-4-CF$_3$Ph | 5-methylsulfonyl-1,3,4-thiadiazol-2-yl | H | |
| 1269 | 2-SO$_2$Me-4-CF$_3$Ph | 5-methylsulfonyl-1,3,4-thiadiazol-2-yl | methyl | |
| 1270 | 2-SO$_2$Me-4-CF$_3$Ph | 5-methylsulfonyl-1,3,4-thiadiazol-2-yl | i-propyl | |
| 1271 | 2-SO$_2$Me-4-CF$_3$Ph | 5-methylsulfonyl-1,3,4-thiadiazol-2-yl | cyclopropyl | |
| 1272 | 2-SO$_2$Me-4-CF$_3$Ph | 5-methylsulfonyl-1,3,4-thiadiazol-2-yl | CF$_3$ | |
| 1273 | 2-SO$_2$Me-4-CF$_3$Ph | 5-methyl-1,3,4-thiadiazol-2-yl | H | |
| 1274 | 2-SO$_2$Me-4-CF$_3$Ph | 5-methyl-1,3,4-thiadiazol-2-yl | methyl | |
| 1275 | 2-SO$_2$Me-4-CF$_3$Ph | 5-methyl-1,3,4-thiadiazol-2-yl | i-propyl | |
| 1276 | 2-SO$_2$Me-4-CF$_3$Ph | 5-methyl-1,3,4-thiadiazol-2-yl | cyclopropyl | |
| 1277 | 2-SO$_2$Me-4-CF$_3$Ph | 5-methyl-1,3,4-thiadiazol-2-yl | CF$_3$ | |
| 1278 | 2-SO$_2$Me-4-CF$_3$Ph | benzoxazol-2-yl | H | |
| 1279 | 2-SO$_2$Me-4-CF$_3$Ph | benzoxazol-2-yl | methyl | |
| 1280 | 2-SO$_2$Me-4-CF$_3$Ph | benzoxazol-2-yl | i-propyl | |
| 1281 | 2-SO$_2$Me-4-CF$_3$Ph | benzoxazol-2-yl | cyclopropyl | |
| 1282 | 2-SO$_2$Me-4-CF$_3$Ph | benzoxazol-2-yl | CF$_3$ | |
| 1283 | 2-SO$_2$Me-4-CF$_3$Ph | 6-methyl-benzoxazol-2-yl | H | |
| 1284 | 2-SO$_2$Me-4-CF$_3$Ph | 6-methyl-benzoxazol-2-yl | methyl | |
| 1285 | 2-SO$_2$Me-4-CF$_3$Ph | 6-methyl-benzoxazol-2-yl | i-propyl | |
| 1286 | 2-SO$_2$Me-4-CF$_3$Ph | 6-methyl-benzoxazol-2-yl | cyclopropyl | |
| 1287 | 2-SO$_2$Me-4-CF$_3$Ph | 6-methyl-benzoxazol-2-yl | CF$_3$ | |
| 1288 | 2-SO$_2$Me-4-CF$_3$Ph | benzothiazol-2-yl | H | |
| 1289 | 2-SO$_2$Me-4-CF$_3$Ph | benzothiazol-2-yl | methyl | |
| 1290 | 2-SO$_2$Me-4-CF$_3$Ph | benzothiazol-2-yl | i-propyl | |
| 1291 | 2-SO$_2$Me-4-CF$_3$Ph | benzothiazol-2-yl | cyclopropyl | |
| 1292 | 2-SO$_2$Me-4-CF$_3$Ph | benzothiazol-2-yl | CF$_3$ | |
| 1293 | 2-SO$_2$Me-4-CF$_3$Ph | pyrazol-1-yl | H | |
| 1294 | 2-SO$_2$Me-4-CF$_3$Ph | pyrazol-1-yl | methyl | |

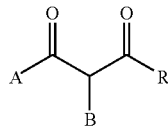

(I)

| Compound N | A | B | R | m.p. (° C.) |
|---|---|---|---|---|
| 1295 | 2-SO₂Me-4-CF₃Ph | pyrazol-1-yl | i-propyl | |
| 1296 | 2-SO₂Me-4-CF₃Ph | pyrazol-1-yl | cyclopropyl | |
| 1297 | 2-SO₂Me-4-CF₃Ph | pyrazol-1-yl | CF₃ | |
| 1298 | 2-SO₂Me-4-CF₃Ph | pyrazol-3-yl | H | |
| 1299 | 2-SO₂Me-4-CF₃Ph | pyrazol-3-yl | methyl | |
| 1300 | 2-SO₂Me-4-CF₃Ph | pyrazol-3-yl | i-propyl | |
| 1301 | 2-SO₂Me-4-CF₃Ph | pyrazol-3-yl | cyclopropyl | |
| 1302 | 2-SO₂Me-4-CF₃Ph | pyrazol-3-yl | CF₃ | |
| 1303 | 2-SO₂Me-4-CF₃Ph | 1-methyl-pyrazol-3-yl | H | |
| 1304 | 2-SO₂Me-4-CF₃Ph | 1-methyl-pyrazol-3-yl | methyl | |
| 1305 | 2-SO₂Me-4-CF₃Ph | 1-methyl-pyrazol-3-yl | i-propyl | |
| 1306 | 2-SO₂Me-4-CF₃Ph | 1-methyl-pyrazol-3-yl | cyclopropyl | |
| 1307 | 2-SO₂Me-4-CF₃Ph | 1-methyl-pyrazol-3-yl | CF₃ | |
| 1308 | 2-SO₂Me-4-CF₃Ph | tetrazol-1-yl | H | |
| 1309 | 2-SO₂Me-4-CF₃Ph | tetrazol-1-yl | methyl | |
| 1310 | 2-SO₂Me-4-CF₃Ph | tetrazol-1-yl | i-propyl | |
| 1311 | 2-SO₂Me-4-CF₃Ph | tetrazol-1-yl | cyclopropyl | |
| 1312 | 2-SO₂Me-4-CF₃Ph | tetrazol-1-yl | CF₃ | |
| 1313 | 2-SO₂Me-4-CF₃Ph | 5-methyltetrazol-1-yl | H | |
| 1314 | 2-SO₂Me-4-CF₃Ph | 5-methyltetrazol-1-yl | methyl | |
| 1315 | 2-SO₂Me-4-CF₃Ph | 5-methyltetrazol-1-yl | i-propyl | |
| 1316 | 2-SO₂Me-4-CF₃Ph | 5-methyltetrazol-1-yl | cyclopropyl | |
| 1317 | 2-SO₂Me-4-CF₃Ph | 5-methyltetrazol-1-yl | CF₃ | |
| 1318 | 2-SO₂Me-4-CF₃Ph | tetrazol-2-yl | H | |
| 1319 | 2-SO₂Me-4-CF₃Ph | tetrazol-2-yl | methyl | |
| 1320 | 2-SO₂Me-4-CF₃Ph | tetrazol-2-yl | i-propyl | |
| 1321 | 2-SO₂Me-4-CF₃Ph | tetrazol-2-yl | cyclopropyl | |
| 1322 | 2-SO₂Me-4-CF₃Ph | tetrazol-2-yl | CF₃ | |
| 1323 | 2-SO₂Me-4-CF₃Ph | 5-methyltetrazol-2-yl | H | |
| 1324 | 2-SO₂Me-4-CF₃Ph | 5-methyltetrazol-2-yl | methyl | |
| 1325 | 2-SO₂Me-4-CF₃Ph | 5-methyltetrazol-2-yl | i-propyl | |
| 1326 | 2-SO₂Me-4-CF₃Ph | 5-methyltetrazol-2-yl | cyclopropyl | |
| 1327 | 2-SO₂Me-4-CF₃Ph | 5-methyltetrazol-2-yl | CF₃ | |
| 1328 | 2-SO₂Me-4-CF₃Ph | 1-methyltetrazol-5-yl | H | |
| 1329 | 2-SO₂Me-4-CF₃Ph | 1-methyltetrazol-5-yl | methyl | |
| 1330 | 2-SO₂Me-4-CF₃Ph | 1-methyltetrazol-5-yl | i-propyl | |
| 1331 | 2-SO₂Me-4-CF₃Ph | 1-methyltetrazol-5-yl | cyclopropyl | |
| 1332 | 2-SO₂Me-4-CF₃Ph | 1-methyltetrazol-5-yl | CF₃ | |
| 1333 | 2-SO₂Me-4-CF₃Ph | 2-methyltetrazol-5-yl | H | |
| 1334 | 2-SO₂Me-4-CF₃Ph | 2-methyltetrazol-5-yl | methyl | |
| 1335 | 2-SO₂Me-4-CF₃Ph | 2-methyltetrazol-5-yl | i-propyl | |
| 1336 | 2-SO₂Me-4-CF₃Ph | 2-methyltetrazol-5-yl | cyclopropyl | 157 |
| 1337 | 2-SO₂Me-4-CF₃Ph | 2-methyltetrazol-5-yl | CF₃ | |
| 1338 | 2-SO₂Me-4-CF₃Ph | pyridin-2-yl | H | |
| 1339 | 2-SO₂Me-4-CF₃Ph | pyridin-2-yl | methyl | |
| 1340 | 2-SO₂Me-4-CF₃Ph | pyridin-2-yl | i-propyl | |
| 1341 | 2-SO₂Me-4-CF₃Ph | pyridin-2-yl | cyclopropyl | |
| 1342 | 2-SO₂Me-4-CF₃Ph | pyridin-2-yl | CF₃ | |
| 1343 | 2-SO₂Me-4-CF₃Ph | pyridin-4-yl | H | |
| 1344 | 2-SO₂Me-4-CF₃Ph | pyridin-4-yl | methyl | |
| 1345 | 2-SO₂Me-4-CF₃Ph | pyridin-4-yl | i-propyl | |
| 1346 | 2-SO₂Me-4-CF₃Ph | pyridin-4-yl | cyclopropyl | |
| 1347 | 2-SO₂Me-4-CF₃Ph | pyridin-4-yl | CF₃ | |
| 1348 | 2-SO₂Me-4-CF₃Ph | pyridin-3-yl | H | |
| 1349 | 2-SO₂Me-4-CF₃Ph | pyridin-3-yl | methyl | |
| 1350 | 2-SO₂Me-4-CF₃Ph | pyridin-3-yl | i-propyl | |
| 1351 | 2-SO₂Me-4-CF₃Ph | pyridin-3-yl | cyclopropyl | |
| 1352 | 2-SO₂Me-4-CF₃Ph | pyridin-3-yl | CF₃ | |
| 1353 | 2-SO₂Me-4-CF₃Ph | 3-nitropyridin-4-yl | H | |
| 1354 | 2-SO₂Me-4-CF₃Ph | 3-nitropyridin-4-yl | methyl | |
| 1355 | 2-SO₂Me-4-CF₃Ph | 3-nitropyridin-4-yl | i-propyl | |
| 1356 | 2-SO₂Me-4-CF₃Ph | 3-nitropyridin-4-yl | cyclopropyl | |
| 1357 | 2-SO₂Me-4-CF₃Ph | 3-nitropyridin-4-yl | CF₃ | |
| 1358 | 2-SO₂Me-4-CF₃Ph | 5-cyanopyridin-2-yl | H | |
| 1359 | 2-SO₂Me-4-CF₃Ph | 5-cyanopyridin-2-yl | methyl | |
| 1360 | 2-SO₂Me-4-CF₃Ph | 5-cyanopyridin-2-yl | i-propyl | |

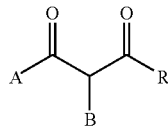

(I)

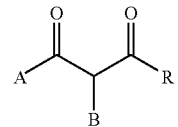

(I)

| Compound N | A | B | R | m.p. (°C.) |
|---|---|---|---|---|
| 1361 | 2-SO$_2$Me-4-CF$_3$Ph | 5-cyanopyridin-2-yl | cyclopropyl | |
| 1362 | 2-SO$_2$Me-4-CF$_3$Ph | 5-cyanopyridin-2-yl | CF$_3$ | |
| 1363 | 2-SO$_2$Me-4-CF$_3$Ph | 5-trifluoromethylpyridin-2-yl | H | |
| 1364 | 2-SO$_2$Me-4-CF$_3$Ph | 5-trifluoromethylpyridin-2-yl | methyl | |
| 1365 | 2-SO$_2$Me-4-CF$_3$Ph | 5-trifluoromethylpyridin-2-yl | i-propyl | |
| 1366 | 2-SO$_2$Me-4-CF$_3$Ph | 5-trifluoromethylpyridin-2-yl | cyclopropyl | |
| 1367 | 2-SO$_2$Me-4-CF$_3$Ph | 5-trifluoromethylpyridin-2-yl | CF$_3$ | |
| 1368 | 2-SO$_2$Me-4-CF$_3$Ph | pyrimidin-2-yl | H | |
| 1369 | 2-SO$_2$Me-4-CF$_3$Ph | pyrimidin-2-yl | methyl | |
| 1370 | 2-SO$_2$Me-4-CF$_3$Ph | pyrimidin-2-yl | i-propyl | |
| 1371 | 2-SO$_2$Me-4-CF$_3$Ph | pyrimidin-2-yl | cyclopropyl | |
| 1372 | 2-SO$_2$Me-4-CF$_3$Ph | pyrimidin-2-yl | CF$_3$ | |
| 1373 | 2-SO$_2$Me-4-CF$_3$Ph | pyrimidin-4-yl | H | |
| 1374 | 2-SO$_2$Me-4-CF$_3$Ph | pyrimidin-4-yl | methyl | |
| 1375 | 2-SO$_2$Me-4-CF$_3$Ph | pyrimidin-4-yl | i-propyl | |
| 1376 | 2-SO$_2$Me-4-CF$_3$Ph | pyrimidin-4-yl | cyclopropyl | |
| 1377 | 2-SO$_2$Me-4-CF$_3$Ph | pyrimidin-4-yl | CF$_3$ | |
| 1378 | 2-SO$_2$Me-4-CF$_3$Ph | 6-chloro-pyrimidin-4-yl | methyl | |
| 1379 | 2-SO$_2$Me-4-CF$_3$Ph | 6-chloro-pyrimidin-4-yl | i-propyl | |
| 1380 | 2-SO$_2$Me-4-CF$_3$Ph | 6-chloro-pyrimidin-4-yl | cyclopropyl | |
| 1381 | 2-SO$_2$Me-4-CF$_3$Ph | 6-chloro-pyrimidin-4-yl | CF$_3$ | |
| 1382 | 2-SO$_2$Me-4-CF$_3$Ph | pyridazin-3-yl | H | |
| 1383 | 2-SO$_2$Me-4-CF$_3$Ph | pyridazin-3-yl | methyl | |
| 1384 | 2-SO$_2$Me-4-CF$_3$Ph | pyridazin-3-yl | i-propyl | |
| 1385 | 2-SO$_2$Me-4-CF$_3$Ph | pyridazin-3-yl | cyclopropyl | |
| 1386 | 2-SO$_2$Me-4-CF$_3$Ph | pyridazin-3-yl | CF$_3$ | |
| 1387 | 2-SO$_2$Me-4-CF$_3$Ph | 6-chloro-pyridazin-3-yl | methyl | |
| 1388 | 2-SO$_2$Me-4-CF$_3$Ph | 6-chloro-pyridazin-3-yl | i-propyl | |
| 1389 | 2-SO$_2$Me-4-CF$_3$Ph | 6-chloro-pyridazin-3-yl | cyclopropyl | |
| 1390 | 2-SO$_2$Me-4-CF$_3$Ph | 6-chloro-pyridazin-3-yl | CF$_3$ | |
| 1391 | 2-SO$_2$Me-4-CF$_3$Ph | pyrazin-2-yl | methyl | |
| 1392 | 2-SO$_2$Me-4-CF$_3$Ph | pyrazin-2-yl | i-propyl | |
| 1393 | 2-SO$_2$Me-4-CF$_3$Ph | pyrazin-2-yl | cyclopropyl | |
| 1394 | 2-SO$_2$Me-4-CF$_3$Ph | pyrazin-2-yl | CF$_3$ | |
| 1395 | 2-SO$_2$Me-4-CF$_3$Ph | triazin-2-yl | methyl | |
| 1396 | 2-SO$_2$Me-4-CF$_3$Ph | triazin-2-yl | i-propyl | |
| 1397 | 2-SO$_2$Me-4-CF$_3$Ph | triazin-2-yl | cyclopropyl | |
| 1398 | 2-SO$_2$Me-4-CF$_3$Ph | triazin-2-yl | CF$_3$ | |
| 1399 | 2-SO$_2$Me-4-CF$_3$Ph | quinolin-2-yl | methyl | |
| 1400 | 2-SO$_2$Me-4-CF$_3$Ph | quinolin-2-yl | i-propyl | |
| 1401 | 2-SO$_2$Me-4-CF$_3$Ph | quinolin-2-yl | cyclopropyl | |
| 1402 | 2-SO$_2$Me-4-CF$_3$Ph | quinolin-2-yl | CF$_3$ | |
| 1403 | 2-SO$_2$Me-4-CF$_3$Ph | 4,4,6-trimethyl-5,6-dihydro-1,3(4H)-oxazin-2-yl | H | |
| 1404 | 2-SO$_2$Me-4-CF$_3$Ph | 4,4,6-trimethyl-5,6-dihydro-1,3(4H)-oxazin-2-yl | methyl | |
| 1405 | 2-SO$_2$Me-4-CF$_3$Ph | 4,4,6-trimethyl-5,6-dihydro-1,3(4H)-oxazin-2-yl | i-propyl | |
| 1406 | 2-SO$_2$Me-4-CF$_3$Ph | 4,4,6-trimethyl-5,6-dihydro-1,3(4H)-oxazin-2-yl | cyclopropyl | |
| 1407 | 2-SO$_2$Me-4-CF$_3$Ph | 4,4,6-trimethyl-5,6-dihydro-1,3(4H)-oxazin-2-yl | CF$_3$ | |
| 1408 | 2-SO$_2$Me-4-CF$_3$Ph | 2-oxazolidinon-3-yl | H | |
| 1409 | 2-SO$_2$Me-4-CF$_3$Ph | 2-oxazolidinon-3-yl | methyl | |
| 1410 | 2-SO$_2$Me-4-CF$_3$Ph | 2-oxazolidinon-3-yl | i-propyl | |
| 1411 | 2-SO$_2$Me-4-CF$_3$Ph | 2-oxazolidinon-3-yl | cyclopropyl | |
| 1412 | 2-SO$_2$Me-4-CF$_3$Ph | 2-oxazolidinon-3-yl | CF$_3$ | |
| 1413 | 2-SO$_2$Me-4-CF$_3$Ph | 2-pyrrolidinon-1-yl | methyl | |
| 1414 | 2-SO$_2$Me-4-CF$_3$Ph | 2-pyrrolidinon-1-yl | i-propyl | |
| 1415 | 2-SO$_2$Me-4-CF$_3$Ph | 2-pyrrolidinon-1-yl | cyclopropyl | |
| 1416 | 2-SO$_2$Me-4-CF$_3$Ph | 2-pyrrolidinon-1-yl | CF$_3$ | |
| 1417 | 2-SO$_2$Me-4-CF$_3$Ph | 3-methylisoxazol-5-yl | methyl | |
| 1418 | 2-SO$_2$Me-4-CF$_3$Ph | 3-methylisoxazol-5-yl | i-propyl | |
| 1419 | 2-SO$_2$Me-4-CF$_3$Ph | 3-methylisoxazol-5-yl | cyclopropyl | |
| 1420 | 2-SO$_2$Me-4-CF$_3$Ph | 3-methylisoxazol-5-yl | CF$_3$ | |
| 1421 | 2-SO$_2$Me-4-CF$_3$Ph | 2-NO$_2$-4-SO$_2$MePh | H | |
| 1422 | 2-SO$_2$Me-4-CF$_3$Ph | 2-NO$_2$-4-SO$_2$MePh | methyl | |
| 1423 | 2-SO$_2$Me-4-CF$_3$Ph | 2-NO$_2$-4-SO$_2$MePh | i-propyl | |
| 1424 | 2-SO$_2$Me-4-CF$_3$Ph | 2-NO$_2$-4-SO$_2$MePh | cyclopropyl | |

-continued

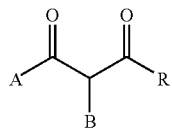

(I)

| Compound N | A | B | R | m.p. (° C.) |
|---|---|---|---|---|
| 1425 | 2-SO$_2$Me-4-CF$_3$Ph | 2-NO$_2$-4-SO$_2$MePh | CF$_3$ | |
| 1426 | 2-SO$_2$Me-4-CF$_3$Ph | 2-Cl-4-SO$_2$MePh | H | |
| 1427 | 2-SO$_2$Me-4-CF$_3$Ph | 2-Cl-4-SO$_2$MePh | methyl | |
| 1428 | 2-SO$_2$Me-4-CF$_3$Ph | 2-Cl-4-SO$_2$MePh | i-propyl | |
| 1429 | 2-SO$_2$Me-4-CF$_3$Ph | 2-Cl-4-SO$_2$MePh | cyclopropyl | |
| 1430 | 2-SO$_2$Me-4-CF$_3$Ph | 2-Cl-4-SO$_2$MePh | CF$_3$ | |
| 1431 | 2-SO$_2$Me-4-CF$_3$Ph | 2-NO$_2$-4-CF$_3$Ph | H | |
| 1432 | 2-SO$_2$Me-4-CF$_3$Ph | 2-NO$_2$-4-CF$_3$Ph | methyl | |
| 1433 | 2-SO$_2$Me-4-CF$_3$Ph | 2-NO$_2$-4-CF$_3$Ph | i-propyl | |
| 1434 | 2-SO$_2$Me-4-CF$_3$Ph | 2-NO$_2$-4-CF$_3$Ph | cyclopropyl | |
| 1435 | 2-SO$_2$Me-4-CF$_3$Ph | 2-NO$_2$-4-CF$_3$Ph | CF$_3$ | |
| 1436 | 2-SO$_2$Me-4-CF$_3$Ph | 2-NO$_2$-4-ClPh | H | |
| 1437 | 2-SO$_2$Me-4-CF$_3$Ph | 2-NO$_2$-4-ClPh | methyl | |
| 1438 | 2-SO$_2$Me-4-CF$_3$Ph | 2-NO$_2$-4-ClPh | i-propyl | |
| 1439 | 2-SO$_2$Me-4-CF$_3$Ph | 2-NO$_2$-4-ClPh | cyclopropyl | |
| 1440 | 2-SO$_2$Me-4-CF$_3$Ph | 2-NO$_2$-4-ClPh | CF$_3$ | |
| 1441 | 2-SO$_2$Me-4-CF$_3$Ph | 2-Cl-4-NO$_2$Ph | H | |
| 1442 | 2-SO$_2$Me-4-CF$_3$Ph | 2-Cl-4-NO$_2$Ph | methyl | |
| 1443 | 2-SO$_2$Me-4-CF$_3$Ph | 2-Cl-4-NO$_2$Ph | i-propyl | |
| 1444 | 2-SO$_2$Me-4-CF$_3$Ph | 2-Cl-4-NO$_2$Ph | cyclopropyl | |
| 1445 | 2-SO$_2$Me-4-CF$_3$Ph | 2-Cl-4-NO$_2$Ph | CF$_3$ | |
| 1446 | 2-SO$_2$Me-4-CF$_3$Ph | 2,4-(NO$_2$)$_2$Ph | H | |
| 1447 | 2-SO$_2$Me-4-CF$_3$Ph | 2,4-(NO$_2$)$_2$Ph | methyl | |
| 1448 | 2-SO$_2$Me-4-CF$_3$Ph | 2,4-(NO$_2$)$_2$Ph | i-propyl | |
| 1449 | 2-SO$_2$Me-4-CF$_3$Ph | 2,4-(NO$_2$)$_2$Ph | cyclopropyl | |
| 1450 | 2-SO$_2$Me-4-CF$_3$Ph | 2,4-(NO$_2$)$_2$Ph | CF$_3$ | |
| 1451 | 2-SO$_2$Me-4-CF$_3$Ph | 4-F-3-NO$_2$Ph | H | |
| 1452 | 2-SO$_2$Me-4-CF$_3$Ph | 4-F-3-NO$_2$Ph | methyl | |
| 1453 | 2-SO$_2$Me-4-CF$_3$Ph | 4-F-3-NO$_2$Ph | i-propyl | |
| 1454 | 2-SO$_2$Me-4-CF$_3$Ph | 4-F-3-NO$_2$Ph | cyclopropyl | |
| 1455 | 2-SO$_2$Me-4-CF$_3$Ph | 4-F-3-NO$_2$Ph | CF$_3$ | |
| 1456 | 2-SO$_2$Me-4-CF$_3$Ph | 3,5-(CF$_3$)$_2$Ph | H | |
| 1457 | 2-SO$_2$Me-4-CF$_3$Ph | 3,5-(CF$_3$)$_2$Ph | methyl | |
| 1458 | 2-SO$_2$Me-4-CF$_3$Ph | 3,5-(CF$_3$)$_2$Ph | i-propyl | |
| 1459 | 2-SO$_2$Me-4-CF$_3$Ph | 3,5-(CF$_3$)$_2$Ph | cyclopropyl | |

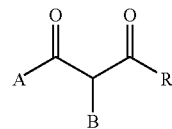

(I)

| Compound N | A | B | R | m.p. (° C.) |
|---|---|---|---|---|
| 1460 | 2-SO$_2$Me-4-CF$_3$Ph | 3,5-(CF$_3$)$_2$Ph | CF$_3$ | |
| 1461 | 2-SO$_2$Me-4-CF$_3$Ph | 2-SO$_2$Me-4-CF$_3$Ph | H | |
| 1462 | 2-SO$_2$Me-4-CF$_3$Ph | 2-SO$_2$Me-4-CF$_3$Ph | methyl | |
| 1463 | 2-SO$_2$Me-4-CF$_3$Ph | 2-SO$_2$Me-4-CF$_3$Ph | i-propyl | |
| 1464 | 2-SO$_2$Me-4-CF$_3$Ph | 2-SO$_2$Me-4-CF$_3$Ph | cyclopropyl | |
| 1465 | 2-SO$_2$Me-4-CF$_3$Ph | 2-SO$_2$Me-4-CF$_3$Ph | CF$_3$ | |
| 1466 | 3-Cl-5-CF$_3$Pyridin-2-yl | 1,2,4-oxadiazol-5-yl | H | |
| 1467 | 3-Cl-5-CF$_3$Pyridin-2-yl | 1,2,4-oxadiazol-5-yl | methyl | |
| 1468 | 3-Cl-5-CF$_3$Pyridin-2-yl | 1,2,4-oxadiazol-5-yl | i-propyl | |
| 1469 | 3-Cl-5-CF$_3$Pyridin-2-yl | 1,2,4-oxadiazol-5-yl | cyclopropyl | |
| 1470 | 3-Cl-5-CF$_3$Pyridin-2-yl | 1,2,4-oxadiazol-5-yl | CF$_3$ | |
| 1471 | 3-Cl-5-CF$_3$Pyridin-2-yl | 3-methyl-1,2,4-oxadiazol-5-yl | H | |
| 1472 | 3-Cl-5-CF$_3$Pyridin-2-yl | 3-methyl-1,2,4-oxadiazol-5-yl | methyl | |
| 1473 | 3-Cl-5-CF$_3$Pyridin-2-yl | 3-methyl-1,2,4-oxadiazol-5-yl | i-propyl | |
| 1474 | 3-Cl-5-CF$_3$Pyridin-2-yl | 3-methyl-1,2,4-oxadiazol-5-yl | cyclopropyl | |
| 1475 | 3-Cl-5-CF$_3$Pyridin-2-yl | 3-methyl-1,2,4-oxadiazol-5-yl | CF$_3$ | |
| 1476 | 3-Cl-5-CF$_3$Pyridin-2-yl | 3-trifluoromethyl-1,2,4-oxadiazol-5-yl | H | |
| 1477 | 3-Cl-5-CF$_3$Pyridin-2-yl | 3-trifluoromethyl-1,2,4-oxadiazol-5-yl | methyl | |
| 1478 | 3-Cl-5-CF$_3$Pyridin-2-yl | 3-trifluoromethyl-1,2,4-oxadiazol-5-yl | i-propyl | |
| 1479 | 3-Cl-5-CF$_3$Pyridin-2-yl | 3-trifluoromethyl-1,2,4-oxadiazol-5-yl | cyclopropyl | |
| 1480 | 3-Cl-5-CF$_3$Pyridin-2-yl | 3-trifluoromethyl-1,2,4-oxadiazol-5-yl | CF$_3$ | |
| 1481 | 3-Cl-5-CF$_3$Pyridin-2-yl | 1,2,4-oxadiazol-3-yl | H | |
| 1482 | 3-Cl-5-CF$_3$Pyridin-2-yl | 1,2,4-oxadiazol-3-yl | methyl | |
| 1483 | 3-Cl-5-CF$_3$Pyridin-2-yl | 1,2,4-oxadiazol-3-yl | i-propyl | |
| 1484 | 3-Cl-5-CF$_3$Pyridin-2-yl | 1,2,4-oxadiazol-3-yl | cyclopropyl | |
| 1485 | 3-Cl-5-CF$_3$Pyridin-2-yl | 1,2,4-oxadiazol-3-yl | CF$_3$ | |
| 1486 | 3-Cl-5-CF$_3$Pyridin-2-yl | 5-methyl-1,2,4-oxadiazol-3-yl | H | |
| 1487 | 3-Cl-5-CF$_3$Pyridin-2-yl | 5-methyl-1,2,4-oxadiazol-3-yl | methyl | |
| 1488 | 3-Cl-5-CF$_3$Pyridin-2-yl | 5-methyl-1,2,4-oxadiazol-3-yl | i-propyl | |
| 1489 | 3-Cl-5-CF$_3$Pyridin-2-yl | 5-methyl-1,2,4-oxadiazol-3-yl | cyclopropyl | |
| 1490 | 3-Cl-5-CF$_3$Pyridin-2-yl | 5-methyl-1,2,4-oxadiazol-3-yl | CF$_3$ | |
| 1491 | 3-Cl-5-CF$_3$Pyridin-2-yl | 5-trifluoromethyl- | H | |

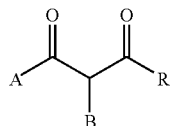

(I)

| Compound N | A | B | R | m.p. (° C.) |
|---|---|---|---|---|
| 1492 | 3-Cl-5-CF₃Pyridin-2-yl | 1,2,4-oxadiazol-3-yl 5-trifluoromethyl-1,2,4-oxadiazol-3-yl | methyl | |
| 1493 | 3-Cl-5-CF₃Pyridin-2-yl | 5-trifluoromethyl-1,2,4-oxadiazol-3-yl | i-propyl | |
| 1494 | 3-Cl-5-CF₃Pyridin-2-yl | 5-trifluoromethyl-1,2,4-oxadiazol-3-yl | cyclopropyl | |
| 1495 | 3-Cl-5-CF₃Pyridin-2-yl | 5-trifluoromethyl-1,2,4-oxadiazol-3-yl | CF₃ | |
| 1496 | 3-Cl-5-CF₃Pyridin-2-yl | 5-chloro-1,2,4-oxadiazol-3-yl | H | |
| 1497 | 3-Cl-5-CF₃Pyridin-2-yl | 5-chloro-1,2,4-oxadiazol-3-yl | methyl | |
| 1498 | 3-Cl-5-CF₃Pyridin-2-yl | 5-chloro-1,2,4-oxadiazol-3-yl | i-propyl | |
| 1499 | 3-Cl-5-CF₃Pyridin-2-yl | 5-chloro-1,2,4-oxadiazol-3-yl | cyclopropyl | |
| 1500 | 3-Cl-5-CF₃Pyridin-2-yl | 5-chloro-1,2,4-oxadiazol-3-yl | CF₃ | |
| 1501 | 3-Cl-5-CF₃Pyridin-2-yl | 1,3,4-oxadiazol-2-yl | H | |
| 1502 | 3-Cl-5-CF₃Pyridin-2-yl | 1,3,4-oxadiazol-2-yl | methyl | |
| 1503 | 3-Cl-5-CF₃Pyridin-2-yl | 1,3,4-oxadiazol-2-yl | i-propyl | |
| 1504 | 3-Cl-5-CF₃Pyridin-2-yl | 1,3,4-oxadiazol-2-yl | cyclopropyl | |
| 1505 | 3-Cl-5-CF₃Pyridin-2-yl | 1,3,4-oxadiazol-2-yl | CF₃ | |
| 1506 | 3-Cl-5-CF₃Pyridin-2-yl | 5-methylsulfonyl-1,3,4-oxadiazol-2-yl | H | |
| 1507 | 3-Cl-5-CF₃Pyridin-2-yl | 5-methylsulfonyl-1,3,4-oxadiazol-2-yl | methyl | |
| 1508 | 3-Cl-5-CF₃Pyridin-2-yl | 5-methylsulfonyl-1,3,4-oxadiazol-2-yl | i-propyl | |
| 1509 | 3-Cl-5-CF₃Pyridin-2-yl | 5-methylsulfonyl-1,3,4-oxadiazol-2-yl | cyclopropyl | |
| 1510 | 3-Cl-5-CF₃Pyridin-2-yl | 5-methylsulfonyl-1,3,4-oxadiazol-2-yl | CF₃ | |
| 1511 | 3-Cl-5-CF₃Pyridin-2-yl | 5-methyl-1,3,4-oxadiazol-2-yl | H | |
| 1512 | 3-Cl-5-CF₃Pyridin-2-yl | 5-methyl-1,3,4-oxadiazol-2-yl | methyl | |
| 1513 | 3-Cl-5-CF₃Pyridin-2-yl | 5-methyl-1,3,4-oxadiazol-2-yl | i-propyl | |
| 1514 | 3-Cl-5-CF₃Pyridin-2-yl | 5-methyl-1,3,4-oxadiazol-2-yl | cyclopropyl | |
| 1515 | 3-Cl-5-CF₃Pyridin-2-yl | 5-methyl-1,3,4-oxadiazol-2-yl | CF₃ | |
| 1516 | 3-Cl-5-CF₃Pyridin-2-yl | 5-trifluoromethyl-1,3,4-oxadiazol-2-yl | H | |
| 1517 | 3-Cl-5-CF₃Pyridin-2-yl | 5-trifluoromethyl-1,3,4-oxadiazol-2-yl | methyl | |
| 1518 | 3-Cl-5-CF₃Pyridin-2-yl | 5-trifluoromethyl-1,3,4-oxadiazol-2-yl | i-propyl | |
| 1519 | 3-Cl-5-CF₃Pyridin-2-yl | 5-trifluoromethyl-1,3,4-oxadiazol-2-yl | cyclopropyl | |

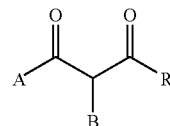

(I)

| Compound N | A | B | R | m.p. (° C.) |
|---|---|---|---|---|
| 1520 | 3-Cl-5-CF₃Pyridin-2-yl | 5-trifluoromethyl-1,3,4-oxadiazol-2-yl | CF₃ | |
| 1521 | 3-Cl-5-CF₃Pyridin-2-yl | 1,2,3-triazol-4-yl | H | |
| 1522 | 3-Cl-5-CF₃Pyridin-2-yl | 1,2,3-triazol-4-yl | methyl | |
| 1523 | 3-Cl-5-CF₃Pyridin-2-yl | 1,2,3-triazol-4-yl | i-propyl | |
| 1524 | 3-Cl-5-CF₃Pyridin-2-yl | 1,2,3-triazol-4-yl | cyclopropyl | |
| 1525 | 3-Cl-5-CF₃Pyridin-2-yl | 1,2,3-triazol-4-yl | CF₃ | |
| 1526 | 3-Cl-5-CF₃Pyridin-2-yl | 1-methyl-1,2,3-triazol-4-yl | H | |
| 1527 | 3-Cl-5-CF₃Pyridin-2-yl | 1-methyl-1,2,3-triazol-4-yl | methyl | |
| 1528 | 3-Cl-5-CF₃Pyridin-2-yl | 1-methyl-1,2,3-triazol-4-yl | i-propyl | |
| 1529 | 3-Cl-5-CF₃Pyridin-2-yl | 1-methyl-1,2,3-triazol-4-yl | cyclopropyl | |
| 1530 | 3-Cl-5-CF₃Pyridin-2-yl | 1-methyl-1,2,3-triazol-4-yl | CF₃ | |
| 1531 | 3-Cl-5-CF₃Pyridin-2-yl | 2-methyl-1,2,3-triazol-4-yl | H | |
| 1532 | 3-Cl-5-CF₃Pyridin-2-yl | 2-methyl-1,2,3-triazol-4-yl | methyl | |
| 1533 | 3-Cl-5-CF₃Pyridin-2-yl | 2-methyl-1,2,3-triazol-4-yl | i-propyl | |
| 1534 | 3-Cl-5-CF₃Pyridin-2-yl | 2-methyl-1,2,3-triazol-4-yl | cyclopropyl | |
| 1535 | 3-Cl-5-CF₃Pyridin-2-yl | 2-methyl-1,2,3-triazol-4-yl | CF₃ | |
| 1536 | 3-Cl-5-CF₃Pyridin-2-yl | 1,2,3-triazol-1-yl | H | |
| 1537 | 3-Cl-5-CF₃Pyridin-2-yl | 1,2,3-triazol-1-yl | methyl | |
| 1538 | 3-Cl-5-CF₃Pyridin-2-yl | 1,2,3-triazol-1-yl | i-propyl | |
| 1539 | 3-Cl-5-CF₃Pyridin-2-yl | 1,2,3-triazol-1-yl | cyclopropyl | |
| 1540 | 3-Cl-5-CF₃Pyridin-2-yl | 1,2,3-triazol-1-yl | CF₃ | |
| 1541 | 3-Cl-5-CF₃Pyridin-2-yl | 1,2,3-triazol-2-yl | H | |
| 1542 | 3-Cl-5-CF₃Pyridin-2-yl | 1,2,3-triazol-2-yl | methyl | |
| 1543 | 3-Cl-5-CF₃Pyridin-2-yl | 1,2,3-triazol-2-yl | i-propyl | |
| 1544 | 3-Cl-5-CF₃Pyridin-2-yl | 1,2,3-triazol-2-yl | cyclopropyl | |
| 1545 | 3-Cl-5-CF₃Pyridin-2-yl | 1,2,3-triazol-2-yl | CF₃ | |
| 1546 | 3-Cl-5-CF₃Pyridin-2-yl | 1,2,4-triazol-1-yl | H | |
| 1547 | 3-Cl-5-CF₃Pyridin-2-yl | 1,2,4-triazol-1-yl | methyl | |
| 1548 | 3-Cl-5-CF₃Pyridin-2-yl | 1,2,4-triazol-1-yl | i-propyl | |
| 1549 | 3-Cl-5-CF₃Pyridin-2-yl | 1,2,4-triazol-1-yl | cyclopropyl | |
| 1550 | 3-Cl-5-CF₃Pyridin-2-yl | 1,2,4-triazol-1-yl | CF₃ | |
| 1551 | 3-Cl-5-CF₃Pyridin-2-yl | imidazol-2-yl | H | |
| 1552 | 3-Cl-5-CF₃Pyridin-2-yl | imidazol-2-yl | methyl | |

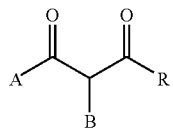

(I)

| Compound N | A | B | R | m.p. (°C.) |
|---|---|---|---|---|
| 1553 | 3-Cl-5-CF₃Pyridin-2-yl | imidazol-2-yl | i-propyl | |
| 1554 | 3-Cl-5-CF₃Pyridin-2-yl | imidazol-2-yl | cyclopropyl | |
| 1555 | 3-Cl-5-CF₃Pyridin-2-yl | imidazol-2-yl | CF₃ | |
| 1556 | 3-Cl-5-CF₃Pyridin-2-yl | imidazol-1-yl | H | |
| 1557 | 3-Cl-5-CF₃Pyridin-2-yl | imidazol-1-yl | methyl | |
| 1558 | 3-Cl-5-CF₃Pyridin-2-yl | imidazol-1-yl | i-propyl | |
| 1559 | 3-Cl-5-CF₃Pyridin-2-yl | imidazol-1-yl | cyclopropyl | |
| 1560 | 3-Cl-5-CF₃Pyridin-2-yl | imidazol-1-yl | CF₃ | |
| 1561 | 3-Cl-5-CF₃Pyridin-2-yl | imidazol-4-yl | H | |
| 1562 | 3-Cl-5-CF₃Pyridin-2-yl | imidazol-4-yl | methyl | |
| 1563 | 3-Cl-5-CF₃Pyridin-2-yl | imidazol-4-yl | i-propyl | |
| 1564 | 3-Cl-5-CF₃Pyridin-2-yl | imidazol-4-yl | cyclopropyl | |
| 1565 | 3-Cl-5-CF₃Pyridin-2-yl | imidazol-4-yl | CF₃ | |
| 1566 | 3-Cl-5-CF₃Pyridin-2-yl | thiazol-2-yl | H | |
| 1567 | 3-Cl-5-CF₃Pyridin-2-yl | thiazol-2-yl | methyl | |
| 1568 | 3-Cl-5-CF₃Pyridin-2-yl | thiazol-2-yl | i-propyl | |
| 1569 | 3-Cl-5-CF₃Pyridin-2-yl | thiazol-2-yl | cyclopropyl | |
| 1570 | 3-Cl-5-CF₃Pyridin-2-yl | thiazol-2-yl | CF₃ | |
| 1571 | 3-Cl-5-CF₃Pyridin-2-yl | 4-methylthiazol-2-yl | H | |
| 1572 | 3-Cl-5-CF₃Pyridin-2-yl | 4-methylthiazol-2-yl | methyl | |
| 1573 | 3-Cl-5-CF₃Pyridin-2-yl | 4-methylthiazol-2-yl | i-propyl | |
| 1574 | 3-Cl-5-CF₃Pyridin-2-yl | 4-methylthiazol-2-yl | cyclopropyl | |
| 1575 | 3-Cl-5-CF₃Pyridin-2-yl | 4-methylthiazol-2-yl | CF₃ | |
| 1576 | 3-Cl-5-CF₃Pyridin-2-yl | oxazol-2-yl | H | |
| 1577 | 3-Cl-5-CF₃Pyridin-2-yl | oxazol-2-yl | methyl | |
| 1578 | 3-Cl-5-CF₃Pyridin-2-yl | oxazol-2-yl | i-propyl | |
| 1579 | 3-Cl-5-CF₃Pyridin-2-yl | oxazol-2-yl | cyclopropyl | |
| 1580 | 3-Cl-5-CF₃Pyridin-2-yl | oxazol-2-yl | CF₃ | |
| 1581 | 3-Cl-5-CF₃Pyridin-2-yl | 4,5-dimethyl-oxazol-2-yl | H | |
| 1582 | 3-Cl-5-CF₃Pyridin-2-yl | 4,5-dimethyl-oxazol-2-yl | methyl | |
| 1583 | 3-Cl-5-CF₃Pyridin-2-yl | 4,5-dimethyl-oxazol-2-yl | i-propyl | |
| 1584 | 3-Cl-5-CF₃Pyridin-2-yl | 4,5-dimethyl-oxazol-2-yl | cyclopropyl | |
| 1585 | 3-Cl-5-CF₃Pyridin-2-yl | 4,5-dimethyl-oxazol-2-yl | CF₃ | |
| 1586 | 3-Cl-5-CF₃Pyridin-2-yl | 2-oxazolin-2-yl | H | |
| 1587 | 3-Cl-5-CF₃Pyridin-2-yl | 2-oxazolin-2-yl | methyl | |

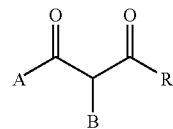

(I)

| Compound N | A | B | R | m.p. (°C.) |
|---|---|---|---|---|
| 1588 | 3-Cl-5-CF₃Pyridin-2-yl | 2-oxazolin-2-yl | i-propyl | |
| 1589 | 3-Cl-5-CF₃Pyridin-2-yl | 2-oxazolin-2-yl | cyclopropyl | |
| 1590 | 3-Cl-5-CF₃Pyridin-2-yl | 2-oxazolin-2-yl | CF₃ | |
| 1591 | 3-Cl-5-CF₃Pyridin-2-yl | 4,4-dimethyl-2-oxazolin-2-yl | H | |
| 1592 | 3-Cl-5-CF₃Pyridin-2-yl | 4,4-dimethyl-2-oxazolin-2-yl | methyl | |
| 1593 | 3-Cl-5-CF₃Pyridin-2-yl | 4,4-dimethyl-2-oxazolin-2-yl | i-propyl | |
| 1594 | 3-Cl-5-CF₃Pyridin-2-yl | 4,4-dimethyl-2-oxazolin-2-yl | cyclopropyl | |
| 1595 | 3-Cl-5-CF₃Pyridin-2-yl | 4,4-dimethyl-2-oxazolin-2-yl | CF₃ | |
| 1596 | 3-Cl-5-CF₃Pyridin-2-yl | 1,2,4-thiadiazol-5-yl | H | |
| 1597 | 3-Cl-5-CF₃Pyridin-2-yl | 1,2,4-thiadiazol-5-yl | methyl | |
| 1598 | 3-Cl-5-CF₃Pyridin-2-yl | 1,2,4-thiadiazol-5-yl | i-propyl | |
| 1599 | 3-Cl-5-CF₃Pyridin-2-yl | 1,2,4-thiadiazol-5-yl | cyclopropyl | |
| 1600 | 3-Cl-5-CF₃Pyridin-2-yl | 1,2,4-thiadiazol-5-yl | CF₃ | |
| 1601 | 3-Cl-5-CF₃Pyridin-2-yl | 3-methyl-1,2,4-thiadiazol-5-yl | H | |
| 1602 | 3-Cl-5-CF₃Pyridin-2-yl | 3-methyl-1,2,4-thiadiazol-5-yl | methyl | |
| 1603 | 3-Cl-5-CF₃Pyridin-2-yl | 3-methyl-1,2,4-thiadiazol-5-yl | i-propyl | |
| 1604 | 3-Cl-5-CF₃Pyridin-2-yl | 3-methyl-1,2,4-thiadiazol-5-yl | cyclopropyl | |
| 1605 | 3-Cl-5-CF₃Pyridin-2-yl | 3-methyl-1,2,4-thiadiazol-5-yl | CF₃ | |
| 1606 | 3-Cl-5-CF₃Pyridin-2-yl | 3-trifluoromethyl-1,2,4-thiadiazol-5-yl | H | |
| 1607 | 3-Cl-5-CF₃Pyridin-2-yl | 3-trifluoromethyl-1,2,4-thiadiazol-5-yl | methyl | |
| 1608 | 3-Cl-5-CF₃Pyridin-2-yl | 3-trifluoromethyl-1,2,4-thiadiazol-5-yl | i-propyl | |
| 1609 | 3-Cl-5-CF₃Pyridin-2-yl | 3-trifluoromethyl-1,2,4-thiadiazol-5-yl | cyclopropyl | |
| 1610 | 3-Cl-5-CF₃Pyridin-2-yl | 3-trifluoromethyl-1,2,4-thiadiazol-5-yl | CF₃ | |
| 1611 | 3-Cl-5-CF₃Pyridin-2-yl | 1,2,4-thiadiazol-3-yl | H | |
| 1612 | 3-Cl-5-CF₃Pyridin-2-yl | 1,2,4-thiadiazol-3-yl | methyl | |
| 1613 | 3-Cl-5-CF₃Pyridin-2-yl | 1,2,4-thiadiazol-3-yl | i-propyl | |
| 1614 | 3-Cl-5-CF₃Pyridin-2-yl | 1,2,4-thiadiazol-3-yl | cyclopropyl | |
| 1615 | 3-Cl-5-CF₃Pyridin-2-yl | 1,2,4-thiadiazol-3-yl | CF₃ | |
| 1616 | 3-Cl-5-CF₃Pyridin-2-yl | 5-methyl-1,2,4-thiadiazol-3-yl | H | |
| 1617 | 3-Cl-5-CF₃Pyridin-2-yl | 5-methyl-1,2,4-thiadiazol-3-yl | methyl | |
| 1618 | 3-Cl-5-CF₃Pyridin-2-yl | 5-methyl-1,2,4-thiadiazol-3-yl | i-propyl | |
| 1619 | 3-Cl-5-CF₃Pyridin-2-yl | 5-methyl-1,2,4-thiadiazol-3-yl | cyclopropyl | |

-continued

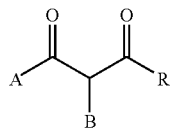
(I)

| Compound N | A | B | R | m.p. (° C.) |
|---|---|---|---|---|
| | CF₃Pyridin-2-yl | thiadiazol-3-yl | | |
| 1620 | 3-Cl-5-CF₃Pyridin-2-yl | 5-methyl-1,2,4-thiadiazol-3-yl | CF₃ | |
| 1621 | 3-Cl-5-CF₃Pyridin-2-yl | 5-trifluoromethyl-1,2,4-thiadiazol-3-yl | H | |
| 1622 | 3-Cl-5-CF₃Pyridin-2-yl | 5-trifluoromethyl-1,2,4-thiadiazol-3-yl | methyl | |
| 1623 | 3-Cl-5-CF₃Pyridin-2-yl | 5-trifluoromethyl-1,2,4-thiadiazol-3-yl | i-propyl | |
| 1624 | 3-Cl-5-CF₃Pyridin-2-yl | 5-trifluoromethyl-1,2,4-thiadiazol-3-yl | cyclopropyl | |
| 1625 | 3-Cl-5-CF₃Pyridin-2-yl | 5-trifluoromethyl-1,2,4-thiadiazol-3-yl | CF₃ | |
| 1626 | 3-Cl-5-CF₃Pyridin-2-yl | 1,3,4-thiadiazol-2-yl | H | |
| 1627 | 3-Cl-5-CF₃Pyridin-2-yl | 1,3,4-thiadiazol-2-yl | methyl | |
| 1628 | 3-Cl-5-CF₃Pyridin-2-yl | 1,3,4-thiadiazol-2-yl | i-propyl | |
| 1629 | 3-Cl-5-CF₃Pyridin-2-yl | 1,3,4-thiadiazol-2-yl | cyclopropyl | |
| 1630 | 3-Cl-5-CF₃Pyridin-2-yl | 1,3,4-thiadiazol-2-yl | CF₃ | |
| 1631 | 3-Cl-5-CF₃Pyridin-2-yl | 5-methylsulfonyl-1,3,4-thiadiazol-2-yl | H | |
| 1632 | 3-Cl-5-CF₃Pyridin-2-yl | 5-methylsulfonyl-1,3,4-thiadiazol-2-yl | methyl | |
| 1633 | 3-Cl-5-CF₃Pyridin-2-yl | 5-methylsulfonyl-1,3,4-thiadiazol-2-yl | i-propyl | |
| 1634 | 3-Cl-5-CF₃Pyridin-2-yl | 5-methylsulfonyl-1,3,4-thiadiazol-2-yl | cyclopropyl | |
| 1635 | 3-Cl-5-CF₃Pyridin-2-yl | 5-methylsulfonyl-1,3,4-thiadiazol-2-yl | CF₃ | |
| 1636 | 3-Cl-5-CF₃Pyridin-2-yl | 5-methyl-1,3,4-thiadiazol-2-yl | H | |
| 1637 | 3-Cl-5-CF₃Pyridin-2-yl | 5-methyl-1,3,4-thiadiazol-2-yl | methyl | |
| 1638 | 3-Cl-5-CF₃Pyridin-2-yl | 5-methyl-1,3,4-thiadiazol-2-yl | i-propyl | |
| 1639 | 3-Cl-5-CF₃Pyridin-2-yl | 5-methyl-1,3,4-thiadiazol-2-yl | cyclopropyl | |
| 1640 | 3-Cl-5-CF₃Pyridin-2-yl | 5-methyl-1,3,4-thiadiazol-2-yl | CF₃ | |
| 1641 | 3-Cl-5-CF₃Pyridin-2-yl | benzoxazol-2-yl | H | |
| 1642 | 3-Cl-5-CF₃Pyridin-2-yl | benzoxazol-2-yl | methyl | |
| 1643 | 3-Cl-5-CF₃Pyridin-2-yl | benzoxazol-2-yl | i-propyl | |
| 1644 | 3-Cl-5-CF₃Pyridin-2-yl | benzoxazol-2-yl | cyclopropyl | |
| 1645 | 3-Cl-5-CF₃Pyridin-2-yl | benzoxazol-2-yl | CF₃ | |
| 1646 | 3-Cl-5-CF₃Pyridin-2-yl | 6-methyl-benzoxazol-2-yl | H | |
| 1647 | 3-Cl-5-CF₃Pyridin-2-yl | 6-methyl-benzoxazol-2-yl | methyl | |
| 1648 | 3-Cl-5-CF₃Pyridin-2-yl | 6-methyl-benzoxazol-2-yl | i-propyl | |

-continued

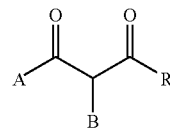
(I)

| Compound N | A | B | R | m.p. (° C.) |
|---|---|---|---|---|
| 1649 | 3-Cl-5-CF₃Pyridin-2-yl | 6-methyl-benzoxazol-2-yl | cyclopropyl | |
| 1650 | 3-Cl-5-CF₃Pyridin-2-yl | 6-methyl-benzoxazol-2-yl | CF₃ | |
| 1651 | 3-Cl-5-CF₃Pyridin-2-yl | benzothiazol-2-yl | H | |
| 1652 | 3-Cl-5-CF₃Pyridin-2-yl | benzothiazol-2-yl | methyl | |
| 1653 | 3-Cl-5-CF₃Pyridin-2-yl | benzothiazol-2-yl | i-propyl | |
| 1654 | 3-Cl-5-CF₃Pyridin-2-yl | benzothiazol-2-yl | cyclopropyl | |
| 1655 | 3-Cl-5-CF₃Pyridin-2-yl | benzothiazol-2-yl | CF₃ | |
| 1656 | 3-Cl-5-CF₃Pyridin-2-yl | pyrazol-1-yl | H | |
| 1657 | 3-Cl-5-CF₃Pyridin-2-yl | pyrazol-1-yl | methyl | |
| 1658 | 3-Cl-5-CF₃Pyridin-2-yl | pyrazol-1-yl | i-propyl | |
| 1659 | 3-Cl-5-CF₃Pyridin-2-yl | pyrazol-1-yl | cyclopropyl | |
| 1660 | 3-Cl-5-CF₃Pyridin-2-yl | pyrazol-1-yl | CF₃ | |
| 1661 | 3-Cl-5-CF₃Pyridin-2-yl | pyrazol-3-yl | H | |
| 1662 | 3-Cl-5-CF₃Pyridin-2-yl | pyrazol-3-yl | methyl | |
| 1663 | 3-Cl-5-CF₃Pyridin-2-yl | pyrazol-3-yl | i-propyl | |
| 1664 | 3-Cl-5-CF₃Pyridin-2-yl | pyrazol-3-yl | cyclopropyl | |
| 1665 | 3-Cl-5-CF₃Pyridin-2-yl | pyrazol-3-yl | CF₃ | |
| 1666 | 3-Cl-5-CF₃Pyridin-2-yl | 1-methylpyrazol-3-yl | H | |
| 1667 | 3-Cl-5-CF₃Pyridin-2-yl | 1-methylpyrazol-3-yl | methyl | |
| 1668 | 3-Cl-5-CF₃Pyridin-2-yl | 1-methylpyrazol-3-yl | i-propyl | |
| 1669 | 3-Cl-5-CF₃Pyridin-2-yl | 1-methylpyrazol-3-yl | cyclopropyl | |
| 1670 | 3-Cl-5-CF₃Pyridin-2-yl | 1-methylpyrazol-3-yl | CF₃ | |
| 1671 | 3-Cl-5-CF₃Pyridin-2-yl | tetrazol-1-yl | H | |
| 1672 | 3-Cl-5-CF₃Pyridin-2-yl | tetrazol-1-yl | methyl | |
| 1673 | 3-Cl-5-CF₃Pyridin-2-yl | tetrazol-1-yl | i-propyl | |
| 1674 | 3-Cl-5-CF₃Pyridin-2-yl | tetrazol-1-yl | cyclopropyl | |
| 1675 | 3-Cl-5-CF₃Pyridin-2-yl | tetrazol-1-yl | CF₃ | |
| 1676 | 3-Cl-5-CF₃Pyridin-2-yl | 5-methyltetrazol-1-yl | H | |
| 1677 | 3-Cl-5-CF₃Pyridin-2-yl | 5-methyltetrazol-1-yl | methyl | |
| 1678 | 3-Cl-5-CF₃Pyridin-2-yl | 5-methyltetrazol-1-yl | i-propyl | |
| 1679 | 3-Cl-5-CF₃Pyridin-2-yl | 5-methyltetrazol-1-yl | cyclopropyl | |
| 1680 | 3-Cl-5-CF₃Pyridin-2-yl | 5-methyltetrazol-1-yl | CF₃ | |
| 1681 | 3-Cl-5-CF₃Pyridin-2-yl | tetrazol-2-yl | H | |
| 1682 | 3-Cl-5-CF₃Pyridin-2-yl | tetrazol-2-yl | methyl | |
| 1683 | 3-Cl-5-CF₃Pyridin-2-yl | tetrazol-2-yl | i-propyl | |

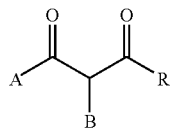

(I)

| Compound N | A | B | R | m.p. (° C.) |
|---|---|---|---|---|
| | CF₃Pyridin-2-yl | | | |
| 1684 | 3-Cl-5-CF₃Pyridin-2-yl | tetrazol-2-yl | cyclopropyl | |
| 1685 | 3-Cl-5-CF₃Pyridin-2-yl | tetrazol-2-yl | CF₃ | |
| 1686 | 3-Cl-5-CF₃Pyridin-2-yl | 5-methyltetrazol-2-yl | H | |
| 1687 | 3-Cl-5-CF₃Pyridin-2-yl | 5-methyltetrazol-2-yl | methyl | |
| 1688 | 3-Cl-5-CF₃Pyridin-2-yl | 5-methyltetrazol-2-yl | i-propyl | |
| 1689 | 3-Cl-5-CF₃Pyridin-2-yl | 5-methyltetrazol-2-yl | cyclopropyl | |
| 1690 | 3-Cl-5-CF₃Pyridin-2-yl | 5-methyltetrazol-2-yl | CF₃ | |
| 1691 | 3-Cl-5-CF₃Pyridin-2-yl | 1-methyltetrazol-5-yl | H | |
| 1692 | 3-Cl-5-CF₃Pyridin-2-yl | 1-methyltetrazol-5-yl | methyl | |
| 1693 | 3-Cl-5-CF₃Pyridin-2-yl | 1-methyltetrazol-5-yl | i-propyl | |
| 1694 | 3-Cl-5-CF₃Pyridin-2-yl | 1-methyltetrazol-5-yl | cyclopropyl | |
| 1695 | 3-Cl-5-CF₃Pyridin-2-yl | 1-methyltetrazol-5-yl | CF₃ | |
| 1696 | 3-Cl-5-CF₃Pyridin-2-yl | 2-methyltetrazol-5-yl | H | |
| 1697 | 3-Cl-5-CF₃Pyridin-2-yl | 2-methyltetrazol-5-yl | methyl | |
| 1698 | 3-Cl-5-CF₃Pyridin-2-yl | 2-methyltetrazol-5-yl | i-propyl | |
| 1699 | 3-Cl-5-CF₃Pyridin-2-yl | 2-methyltetrazol-5-yl | cyclopropyl | |
| 1700 | 3-Cl-5-CF₃Pyridin-2-yl | 2-methyltetrazol-5-yl | CF₃ | |
| 1701 | 3-Cl-5-CF₃Pyridin-2-yl | pyridin-2-yl | H | |
| 1702 | 3-Cl-5-CF₃Pyridin-2-yl | pyridin-2-yl | methyl | |
| 1703 | 3-Cl-5-CF₃Pyridin-2-yl | pyridin-2-yl | i-propyl | |
| 1704 | 3-Cl-5-CF₃Pyridin-2-yl | pyridin-2-yl | cyclopropyl | |
| 1705 | 3-Cl-5-CF₃Pyridin-2-yl | pyridin-2-yl | CF₃ | |
| 1706 | 3-Cl-5-CF₃Pyridin-2-yl | pyridin-4-yl | H | |
| 1707 | 3-Cl-5-CF₃Pyridin-2-yl | pyridin-4-yl | methyl | |
| 1708 | 3-Cl-5-CF₃Pyridin-2-yl | pyridin-4-yl | i-propyl | |
| 1709 | 3-Cl-5-CF₃Pyridin-2-yl | pyridin-4-yl | cyclopropyl | |
| 1710 | 3-Cl-5-CF₃Pyridin-2-yl | pyridin-4-yl | CF₃ | |
| 1711 | 3-Cl-5-CF₃Pyridin-2-yl | pyridin-3-yl | H | |
| 1712 | 3-Cl-5-CF₃Pyridin-2-yl | pyridin-3-yl | methyl | |
| 1713 | 3-Cl-5-CF₃Pyridin-2-yl | pyridin-3-yl | i-propyl | |
| 1714 | 3-Cl-5-CF₃Pyridin-2-yl | pyridin-3-yl | cyclopropyl | |
| 1715 | 3-Cl-5-CF₃Pyridin-2-yl | pyridin-3-yl | CF₃ | |
| 1716 | 3-Cl-5-CF₃Pyridin-2-yl | 3-nitropyridin-4-yl | H | |
| 1717 | 3-Cl-5-CF₃Pyridin-2-yl | 3-nitropyridin-4-yl | methyl | |

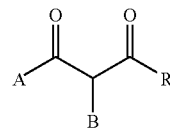

(I)

| Compound N | A | B | R | m.p. (° C.) |
|---|---|---|---|---|
| 1718 | 3-Cl-5-CF₃Pyridin-2-yl | 3-nitropyridin-4-yl | i-propyl | |
| 1719 | 3-Cl-5-CF₃Pyridin-2-yl | 3-nitropyridin-4-yl | cyclopropyl | |
| 1720 | 3-Cl-5-CF₃Pyridin-2-yl | 3-nitropyridin-4-yl | CF₃ | |
| 1721 | 3-Cl-5-CF₃Pyridin-2-yl | 5-cyanopyridin-2-yl | H | |
| 1722 | 3-Cl-5-CF₃Pyridin-2-yl | 5-cyanopyridin-2-yl | methyl | |
| 1723 | 3-Cl-5-CF₃Pyridin-2-yl | 5-cyanopyridin-2-yl | i-propyl | |
| 1724 | 3-Cl-5-CF₃Pyridin-2-yl | 5-cyanopyridin-2-yl | cyclopropyl | |
| 1725 | 3-Cl-5-CF₃Pyridin-2-yl | 5-cyanopyridin-2-yl | CF₃ | |
| 1726 | 3-Cl-5-CF₃Pyridin-2-yl | 5-trifluoromethylpyridin-2-yl | H | |
| 1727 | 3-Cl-5-CF₃Pyridin-2-yl | 5-trifluoromethylpyridin-2-yl | methyl | |
| 1728 | 3-Cl-5-CF₃Pyridin-2-yl | 5-trifluoromethylpyridin-2-yl | i-propyl | |
| 1729 | 3-Cl-5-CF₃Pyridin-2-yl | 5-trifluoromethylpyridin-2-yl | cyclopropyl | |
| 1730 | 3-Cl-5-CF₃Pyridin-2-yl | 5-trifluoromethylpyridin-2-yl | CF₃ | |
| 1731 | 3-Cl-5-CF₃Pyridin-2-yl | pyrimidin-2-yl | H | |
| 1732 | 3-Cl-5-CF₃Pyridin-2-yl | pyrimidin-2-yl | methyl | |
| 1733 | 3-Cl-5-CF₃Pyridin-2-yl | pyrimidin-2-yl | i-propyl | |
| 1734 | 3-Cl-5-CF₃Pyridin-2-yl | pyrimidin-2-yl | cyclopropyl | |
| 1735 | 3-Cl-5-CF₃Pyridin-2-yl | pyrimidin-2-yl | CF₃ | |
| 1736 | 3-Cl-5-CF₃Pyridin-2-yl | pyrimidin-4-yl | H | |
| 1737 | 3-Cl-5-CF₃Pyridin-2-yl | pyrimidin-4-yl | methyl | |
| 1738 | 3-Cl-5-CF₃Pyridin-2-yl | pyrimidin-4-yl | i-propyl | |
| 1739 | 3-Cl-5-CF₃Pyridin-2-yl | pyrimidin-4-yl | cyclopropyl | |
| 1740 | 3-Cl-5-CF₃Pyridin-2-yl | pyrimidin-4-yl | CF₃ | |
| 1741 | 3-Cl-5-CF₃Pyridin-2-yl | 6-chloropyrimidin-4-yl | methyl | |
| 1742 | 3-Cl-5-CF₃Pyridin-2-yl | 6-chloropyrimidin-4-yl | i-propyl | |
| 1743 | 3-Cl-5-CF₃Pyridin-2-yl | 6-chloropyrimidin-4-yl | cyclopropyl | |
| 1744 | 3-Cl-5-CF₃Pyridin-2-yl | 6-chloropyrimidin-4-yl | CF₃ | |
| 1745 | 3-Cl-5-CF₃Pyridin-2-yl | pyridazin-3-yl | H | |
| 1746 | 3-Cl-5-CF₃Pyridin-2-yl | pyridazin-3-yl | methyl | |
| 1747 | 3-Cl-5-CF₃Pyridin-2-yl | pyridazin-3-yl | i-propyl | |
| 1748 | 3-Cl-5-CF₃Pyridin-2-yl | pyridazin-3-yl | cyclopropyl | |
| 1749 | 3-Cl-5-CF₃Pyridin-2-yl | pyridazin-3-yl | CF₃ | |

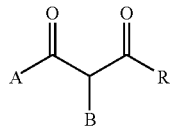

(I)

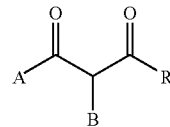

(I)

| Compound N | A | B | R | m.p. (° C.) |
|---|---|---|---|---|
| 1750 | 3-Cl-5-CF₃Pyridin-2-yl | 6-chloro-pyridazin-3-yl | methyl | |
| 1751 | 3-Cl-5-CF₃Pyridin-2-yl | 6-chloro-pyridazin-3-yl | i-propyl | |
| 1752 | 3-Cl-5-CF₃Pyridin-2-yl | 6-chloro-pyridazin-3-yl | cyclopropyl | |
| 1753 | 3-Cl-5-CF₃Pyridin-2-yl | 6-chloro-pyridazin-3-yl | CF₃ | |
| 1754 | 3-Cl-5-CF₃Pyridin-2-yl | pyrazin-2-yl | methyl | |
| 1755 | 3-Cl-5-CF₃Pyridin-2-yl | pyrazin-2-yl | i-propyl | |
| 1756 | 3-Cl-5-CF₃Pyridin-2-yl | pyrazin-2-yl | cyclopropyl | |
| 1757 | 3-Cl-5-CF₃Pyridin-2-yl | pyrazin-2-yl | CF₃ | |
| 1758 | 3-Cl-5-CF₃Pyridin-2-yl | triazin-2-yl | methyl | |
| 1759 | 3-Cl-5-CF₃Pyridin-2-yl | triazin-2-yl | i-propyl | |
| 1760 | 3-Cl-5-CF₃Pyridin-2-yl | triazin-2-yl | cyclopropyl | |
| 1761 | 3-Cl-5-CF₃Pyridin-2-yl | triazin-2-yl | CF₃ | |
| 1762 | 3-Cl-5-CF₃Pyridin-2-yl | quinolin-2-yl | methyl | |
| 1763 | 3-Cl-5-CF₃Pyridin-2-yl | quinolin-2-yl | i-propyl | |
| 1764 | 3-Cl-5-CF₃Pyridin-2-yl | quinolin-2-yl | cyclopropyl | |
| 1765 | 3-Cl-5-CF₃Pyridin-2-yl | quinolin-2-yl | CF₃ | |
| 1766 | 3-Cl-5-CF₃Pyridin-2-yl | 4,4,6-trimethyl-5,6-dihydro-1,3(4H)-oxazin-2-yl | H | |
| 1767 | 3-Cl-5-CF₃Pyridin-2-yl | 4,4,6-trimethyl-5,6-dihydro-1,3(4H)-oxazin-2-yl | methyl | |
| 1768 | 3-Cl-5-CF₃Pyridin-2-yl | 4,4,6-trimethyl-5,6-dihydro-1,3(4H)-oxazin-2-yl | i-propyl | |
| 1769 | 3-Cl-5-CF₃Pyridin-2-yl | 4,4,6-trimethyl-5,6-dihydro-1,3(4H)-oxazin-2-yl | cyclopropyl | |
| 1770 | 3-Cl-5-CF₃Pyridin-2-yl | 4,4,6-trimethyl-5,6-dihydro-1,3(4H)-oxazin-2-yl | CF₃ | |
| 1771 | 3-Cl-5-CF₃Pyridin-2-yl | 2-oxazolidinon-3-yl | H | |
| 1772 | 3-Cl-5-CF₃Pyridin-2-yl | 2-oxazolidinon-3-yl | methyl | |
| 1773 | 3-Cl-5-CF₃Pyridin-2-yl | 2-oxazolidinon-3-yl | i-propyl | |
| 1774 | 3-Cl-5-CF₃Pyridin-2-yl | 2-oxazolidinon-3-yl | cyclopropyl | |
| 1775 | 3-Cl-5-CF₃Pyridin-2-yl | 2-oxazolidinon-3-yl | CF₃ | |
| 1776 | 3-Cl-5-CF₃Pyridin-2-yl | 2-pyrrolidinon-1-yl | methyl | |
| 1777 | 3-Cl-5-CF₃Pyridin-2-yl | 2-pyrrolidinon-1-yl | i-propyl | |
| 1778 | 3-Cl-5-CF₃Pyridin-2-yl | 2-pyrrolidinon-1-yl | cyclopropyl | |
| 1779 | 3-Cl-5-CF₃Pyridin-2-yl | 2-pyrrolidinon-1-yl | CF₃ | |
| 1780 | 3-Cl-5-CF₃Pyridin-2-yl | 3-methylisoxazol-5-yl | methyl | |
| 1781 | 3-Cl-5-CF₃Pyridin-2-yl | 3-methylisoxazol-5-yl | i-propyl | |
| 1782 | 3-Cl-5-CF₃Pyridin-2-yl | 3-methylisoxazol-5-yl | cyclopropyl | |
| 1783 | 3-Cl-5-CF₃Pyridin-2-yl | 3-methylisoxazol-5-yl | CF₃ | |
| 1784 | 3-Cl-5-CF₃Pyridin-2-yl | 2-NO₂-4-SO₂MePh | H | |
| 1785 | 3-Cl-5-CF₃Pyridin-2-yl | 2-NO₂-4-SO₂MePh | methyl | |
| 1786 | 3-Cl-5-CF₃Pyridin-2-yl | 2-NO₂-4-SO₂MePh | i-propyl | |
| 1787 | 3-Cl-5-CF₃Pyridin-2-yl | 2-NO₂-4-SO₂MePh | cyclopropyl | |
| 1788 | 3-Cl-5-CF₃Pyridin-2-yl | 2-NO₂-4-SO₂MePh | CF₃ | |
| 1789 | 3-Cl-5-CF₃Pyridin-2-yl | 2-Cl-4-SO₂MePh | H | |
| 1790 | 3-Cl-5-CF₃Pyridin-2-yl | 2-Cl-4-SO₂MePh | methyl | |
| 1791 | 3-Cl-5-CF₃Pyridin-2-yl | 2-Cl-4-SO₂MePh | i-propyl | |
| 1792 | 3-Cl-5-CF₃Pyridin-2-yl | 2-Cl-4-SO₂MePh | cyclopropyl | |
| 1793 | 3-Cl-5-CF₃Pyridin-2-yl | 2-Cl-4-SO₂MePh | CF₃ | |
| 1794 | 3-Cl-5-CF₃Pyridin-2-yl | 2-NO₂-4-CF₃Ph | H | |
| 1795 | 3-Cl-5-CF₃Pyridin-2-yl | 2-NO₂-4-CF₃Ph | methyl | |
| 1796 | 3-Cl-5-CF₃Pyridin-2-yl | 2-NO₂-4-CF₃Ph | i-propyl | |
| 1797 | 3-Cl-5-CF₃Pyridin-2-yl | 2-NO₂-4-CF₃Ph | cyclopropyl | |
| 1798 | 3-Cl-5-CF₃Pyridin-2-yl | 2-NO₂-4-CF₃Ph | CF₃ | |
| 1799 | 3-Cl-5-CF₃Pyridin-2-yl | 2-NO₂-4-ClPh | H | |
| 1800 | 3-Cl-5-CF₃Pyridin-2-yl | 2-NO₂-4-ClPh | methyl | |
| 1801 | 3-Cl-5-CF₃Pyridin-2-yl | 2-NO₂-4-ClPh | i-propyl | |
| 1802 | 3-Cl-5-CF₃Pyridin-2-yl | 2-NO₂-4-ClPh | cyclopropyl | |
| 1803 | 3-Cl-5-CF₃Pyridin-2-yl | 2-NO₂-4-ClPh | CF₃ | |
| 1804 | 3-Cl-5-CF₃Pyridin-2-yl | 2-Cl-4-NO₂Ph | H | |
| 1805 | 3-Cl-5-CF₃Pyridin-2-yl | 2-Cl-4-NO₂Ph | methyl | |
| 1806 | 3-Cl-5-CF₃Pyridin-2-yl | 2-Cl-4-NO₂Ph | i-propyl | |
| 1807 | 3-Cl-5-CF₃Pyridin-2-yl | 2-Cl-4-NO₂Ph | cyclopropyl | |
| 1808 | 3-Cl-5-CF₃Pyridin-2-yl | 2-Cl-4-NO₂Ph | CF₃ | |
| 1809 | 3-Cl-5-CF₃Pyridin-2-yl | 2,4-(NO₂)₂Ph | H | |
| 1810 | 3-Cl-5-CF₃Pyridin-2-yl | 2,4-(NO₂)₂Ph | methyl | |
| 1811 | 3-Cl-5-CF₃Pyridin-2-yl | 2,4-(NO₂)₂Ph | i-propyl | |
| 1812 | 3-Cl-5-CF₃Pyridin-2-yl | 2,4-(NO₂)₂Ph | cyclopropyl | |
| 1813 | 3-Cl-5-CF₃Pyridin-2-yl | 2,4-(NO₂)₂Ph | CF₃ | |
| 1814 | 3-Cl-5-CF₃Pyridin-2-yl | 4-F-3-NO₂Ph | H | |
| 1815 | 3-Cl-5-CF₃Pyridin-2-yl | 4-F-3-NO₂Ph | methyl | |
| 1816 | 3-Cl-5-CF₃Pyridin-2-yl | 4-F-3-NO₂Ph | i-propyl | |

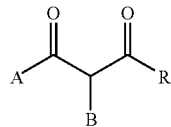

(I)

| Compound N | A | B | R | m.p. (° C.) |
|---|---|---|---|---|
| 1817 | 3-Cl-5-CF₃Pyridin-2-yl | 4-F-3-NO₂Ph | cyclopropyl | |
| 1818 | 3-Cl-5-CF₃Pyridin-2-yl | 4-F-3-NO₂Ph | CF₃ | |
| 1819 | 3-Cl-5-CF₃Pyridin-2-yl | 3,5-(CF₃)₂Ph | H | |
| 1820 | 3-Cl-5-CF₃Pyridin-2-yl | 3,5-(CF₃)₂Ph | methyl | |
| 1821 | 3-Cl-5-CF₃Pyridin-2-yl | 3,5-(CF₃)₂Ph | i-propyl | |
| 1822 | 3-Cl-5-CF₃Pyridin-2-yl | 3,5-(CF₃)₂Ph | cyclopropyl | |
| 1823 | 3-Cl-5-CF₃Pyridin-2-yl | 3,5-(CF₃)₂Ph | CF₃ | |
| 1824 | 3-Cl-5-CF₃Pyridin-2-yl | 2-SO₂Me-4-CF₃Ph | H | |
| 1825 | 3-Cl-5-CF₃Pyridin-2-yl | 2-SO₂Me-4-CF₃Ph | methyl | |
| 1826 | 3-Cl-5-CF₃Pyridin-2-yl | 2-SO₂Me-4-CF₃Ph | i-propyl | |
| 1827 | 3-Cl-5-CF₃Pyridin-2-yl | 2-SO₂Me-4-CF₃Ph | cyclopropyl | |
| 1828 | 3-Cl-5-CF₃Pyridin-2-yl | 2-SO₂Me-4-CF₃Ph | CF₃ | |
| 1829 | 2,4-(Me)₂Thiazol-5-yl | 1,2,4-oxadiazol-5-yl | H | |
| 1830 | 2,4-(Me)₂Thiazol-5-yl | 1,2,4-oxadiazol-5-yl | methyl | |
| 1331 | 2,4-(Me)₂Thiazol-5-yl | 1,2,4-oxadiazol-5-yl | i-propyl | |
| 1832 | 2,4-(Me)₂Thiazol-5-yl | 1,2,4-oxadiazol-5-yl | cyclopropyl | |
| 1833 | 2,4-(Me)₂Thiazol-5-yl | 1,2,4-oxadiazol-5-yl | CF₃ | |
| 1834 | 2,4-(Me)₂Thiazol-5-yl | 3-methyl-1,2,4-oxadiazol-5-yl | H | |
| 1835 | 2,4-(Me)₂Thiazol-5-yl | 3-methyl-1,2,4-oxadiazol-5-yl | methyl | |
| 1836 | 2,4-(Me)₂Thiazol-5-yl | 3-methyl-1,2,4-oxadiazol-5-yl | i-propyl | |
| 1837 | 2,4-(Me)₂Thiazol-5-yl | 3-methyl-1,2,4-oxadiazol-5-yl | cyclopropyl | |
| 1838 | 2,4-(Me)₂Thiazol-5-yl | 3-methyl-1,2,4-oxadiazol-5-yl | CF₃ | |
| 1839 | 2,4-(Me)₂Thiazol-5-yl | 3-trifluoromethyl-1,2,4-oxadiazol-5-yl | H | |
| 1840 | 2,4-(Me)₂Thiazol-5-yl | 3-trifluoromethyl-1,2,4-oxadiazol-5-yl | methyl | |
| 1841 | 2,4-(Me)₂Thiazol-5-yl | 3-trifluoromethyl-1,2,4-oxadiazol-5-yl | i-propyl | |
| 1842 | 2,4-(Me)₂Thiazol-5-yl | 3-trifluoromethyl-1,2,4-oxadiazol-5-yl | cyclopropyl | |
| 1843 | 2,4-(Me)₂Thiazol-5-yl | 3-trifluoromethyl-1,2,4-oxadiazol-5-yl | CF₃ | |
| 1844 | 2,4-(Me)₂Thiazol-5-yl | 1,2,4-oxadiazol-3-yl | H | |
| 1845 | 2,4-(Me)₂Thiazol-5-yl | 1,2,4-oxadiazol-3-yl | methyl | |
| 1846 | 2,4-(Me)₂Thiazol-5-yl | 1,2,4-oxadiazol-3-yl | i-propyl | |
| 1847 | 2,4-(Me)₂Thiazol-5-yl | 1,2,4-oxadiazol-3-yl | cyclopropyl | |
| 1848 | 2,4-(Me)₂Thiazol-5-yl | 1,2,4-oxadiazol-3-yl | CF₃ | |
| 1849 | 2,4-(Me)₂Thiazol-5-yl | 5-methyl-1,2,4-oxadiazol-3-yl | H | |
| 1850 | 2,4-(Me)₂Thiazol-5-yl | 5-methyl-1,2,4-oxadiazol-3-yl | methyl | |
| 1851 | 2,4-(Me)₂Thiazol-5-yl | 5-methyl-1,2,4-oxadiazol-3-yl | i-propyl | |
| 1852 | 2,4-(Me)₂Thiazol-5-yl | 5-methyl-1,2,4-oxadiazol-3-yl | cyclopropyl | |
| 1853 | 2,4-(Me)₂Thiazol-5-yl | 5-methyl-1,2,4-oxadiazol-3-yl | CF₃ | |
| 1854 | 2,4-(Me)₂Thiazol-5-yl | 5-trifluoromethyl-1,2,4-oxadiazol-3-yl | H | |
| 1855 | 2,4-(Me)₂Thiazol-5-yl | 5-trifluoromethyl-1,2,4-oxadiazol-3-yl | methyl | |
| 1856 | 2,4-(Me)₂Thiazol-5-yl | 5-trifluoromethyl-1,2,4-oxadiazol-3-yl | i-propyl | |
| 1857 | 2,4-(Me)₂Thiazol-5-yl | 5-trifluoromethyl-1,2,4-oxadiazol-3-yl | cyclopropyl | |
| 1858 | 2,4-(Me)₂Thiazol-5-yl | 5-trifluoromethyl-1,2,4-oxadiazol-3-yl | CF₃ | |
| 1859 | 2,4-(Me)₂Thiazol-5-yl | 5-chloro-1,2,4-oxadiazol-3-yl | H | |
| 1860 | 2,4-(Me)₂Thiazol-5-yl | 5-chloro-1,2,4-oxadiazol-3-yl | methyl | |
| 1861 | 2,4-(Me)₂Thiazol-5-yl | 5-chloro-1,2,4-oxadiazol-3-yl | i-propyl | |
| 1862 | 2,4-(Me)₂Thiazol-5-yl | 5-chloro-1,2,4-oxadiazol-3-yl | cyclopropyl | |
| 1863 | 2,4-(Me)₂Thiazol-5-yl | 5-chloro-1,2,4-oxadiazol-3-yl | CF₃ | |
| 1864 | 2,4-(Me)₂Thiazol-5-yl | 1,3,4-oxadiazol-2-yl | H | |
| 1865 | 2,4-(Me)₂Thiazol-5-yl | 1,3,4-oxadiazol-2-yl | methyl | |
| 1866 | 2,4-(Me)₂Thiazol-5-yl | 1,3,4-oxadiazol-2-yl | i-propyl | |
| 1867 | 2,4-(Me)₂Thiazol-5-yl | 1,3,4-oxadiazol-2-yl | cyclopropyl | |
| 1868 | 2,4-(Me)₂Thiazol-5-yl | 1,3,4-oxadiazol-2-yl | CF₃ | |
| 1869 | 2,4-(Me)₂Thiazol-5-yl | 5-methylsulfonyl-1,3,4-oxadiazol-2-yl | H | |
| 1870 | 2,4-(Me)₂Thiazol-5-yl | 5-methylsulfonyl-1,3,4-oxadiazol-2-yl | methyl | |
| 1871 | 2,4-(Me)₂Thiazol-5-yl | 5-methylsulfonyl-1,3,4-oxadiazol-2-yl | i-propyl | |
| 1872 | 2,4-(Me)₂Thiazol-5-yl | 5-methylsulfonyl-1,3,4-oxadiazol-2-yl | cyclopropyl | |
| 1873 | 2,4-(Me)₂Thiazol-5-yl | 5-methylsulfonyl-1,3,4-oxadiazol-2-yl | CF₃ | |
| 1874 | 2,4-(Me)₂Thiazol-5-yl | 5-methyl-1,3,4-oxadiazol-2-yl | H | |
| 1875 | 2,4-(Me)₂Thiazol-5-yl | 5-methyl-1,3,4-oxadiazol-2-yl | methyl | |
| 1876 | 2,4-(Me)₂Thiazol-5-yl | 5-methyl-1,3,4-oxadiazol-2-yl | i-propyl | |
| 1877 | 2,4-(Me)₂Thiazol-5-yl | 5-methyl-1,3,4-oxadiazol-2-yl | cyclopropyl | |

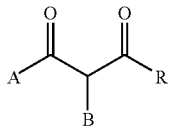

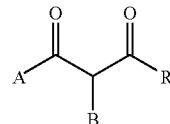

| Compound N | A | B | R | m.p. (° C.) |
|---|---|---|---|---|
| 1878 | 2,4-(Me)₂Thiazol-5-yl | 5-methyl-1,3,4-oxadiazol-2-yl | CF₃ | |
| 1879 | 2,4-(Me)₂Thiazol-5-yl | 5-trifluoromethyl-1,3,4-oxadiazol-2-yl | H | |
| 1880 | 2,4-(Me)₂Thiazol-5-yl | 5-trifluoromethyl-1,3,4-oxadiazol-2-yl | methyl | |
| 1881 | 2,4-(Me)₂Thiazol-5-yl | 5-trifluoromethyl-1,3,4-oxadiazol-2-yl | i-propyl | |
| 1882 | 2,4-(Me)₂Thiazol-5-yl | 5-trifluoromethyl-1,3,4-oxadiazol-2-yl | cyclopropyl | |
| 1883 | 2,4-(Me)₂Thiazol-5-yl | 5-trifluoromethyl-1,3,4-oxadiazol-2-yl | CF₃ | |
| 1884 | 2,4-(Me)₂Thiazol-5-yl | 1,2,3-triazol-4-yl | H | |
| 1885 | 2,4-(Me)₂Thiazol-5-yl | 1,2,3-triazol-4-yl | methyl | |
| 1886 | 2,4-(Me)₂Thiazol-5-yl | 1,2,3-triazol-4-yl | i-propyl | |
| 1887 | 2,4-(Me)₂Thiazol-5-yl | 1,2,3-triazol-4-yl | cyclopropyl | |
| 1888 | 2,4-(Me)₂Thiazol-5-yl | 1,2,3-triazol-4-yl | CF₃ | |
| 1889 | 2,4-(Me)₂Thiazol-5-yl | 1-methyl-1,2,3-triazol-4-yl | H | |
| 1890 | 2,4-(Me)₂Thiazol-5-yl | 1-methyl-1,2,3-triazol-4-yl | methyl | |
| 1891 | 2,4-(Me)₂Thiazol-5-yl | 1-methyl-1,2,3-triazol-4-yl | i-propyl | |
| 1892 | 2,4-(Me)₂Thiazol-5-yl | 1-methyl-1,2,3-triazol-4-yl | cyclopropyl | |
| 1893 | 2,4-(Me)₂Thiazol-5-yl | 1-methyl-1,2,3-triazol-4-yl | CF₃ | |
| 1894 | 2,4-(Me)₂Thiazol-5-yl | 2-methyl-1,2,3-triazol-4-yl | H | |
| 1895 | 2,4-(Me)₂Thiazol-5-yl | 2-methyl-1,2,3-triazol-4-yl | methyl | |
| 1896 | 2,4-(Me)₂Thiazol-5-yl | 2-methyl-1,2,3-triazol-4-yl | i-propyl | |
| 1897 | 2,4-(Me)₂Thiazol-5-yl | 2-methyl-1,2,3-triazol-4-yl | cyclopropyl | |
| 1898 | 2,4-(Me)₂Thiazol-5-yl | 2-methyl-1,2,3-triazol-4-yl | CF₃ | |
| 1899 | 2,4-(Me)₂Thiazol-5-yl | 1,2,3-triazol-1-yl | H | |
| 1900 | 2,4-(Me)₂Thiazol-5-yl | 1,2,3-triazol-1-yl | methyl | |
| 1901 | 2,4-(Me)₂Thiazol-5-yl | 1,2,3-triazol-1-yl | i-propyl | |
| 1902 | 2,4-(Me)₂Thiazol-5-yl | 1,2,3-triazol-1-yl | cyclopropyl | |
| 1903 | 2,4-(Me)₂Thiazol-5-yl | 1,2,3-triazol-1-yl | CF₃ | |
| 1904 | 2,4-(Me)₂Thiazol-5-yl | 1,2,3-triazol-2-yl | H | |
| 1905 | 2,4-(Me)₂Thiazol-5-yl | 1,2,3-triazol-2-yl | methyl | |
| 1906 | 2,4-(Me)₂Thiazol-5-yl | 1,2,3-triazol-2-yl | i-propyl | |
| 1907 | 2,4-(Me)₂Thiazol-5-yl | 1,2,3-triazol-2-yl | cyclopropyl | |
| 1908 | 2,4-(Me)₂Thiazol-5-yl | 1,2,3-triazol-2-yl | CF₃ | |
| 1909 | 2,4-(Me)₂Thiazol-5-yl | 1,2,4-triazol-1-yl | H | |
| 1910 | 2,4-(Me)₂Thiazol-5-yl | 1,2,4-triazol-1-yl | methyl | |
| 1911 | 2,4-(Me)₂Thiazol-5-yl | 1,2,4-triazol-1-yl | i-propyl | |
| 1912 | 2,4-(Me)₂Thiazol-5-yl | 1,2,4-triazol-1-yl | cyclopropyl | |
| 1913 | 2,4-(Me)₂Thiazol-5-yl | 1,2,4-triazol-1-yl | CF₃ | |
| 1914 | 2,4-(Me)₂Thiazol-5-yl | imidazol-2-yl | H | |
| 1915 | 2,4-(Me)₂Thiazol-5-yl | imidazol-2-yl | methyl | |
| 1916 | 2,4-(Me)₂Thiazol-5-yl | imidazol-2-yl | i-propyl | |
| 1917 | 2,4-(Me)₂Thiazol-5-yl | imidazol-2-yl | cyclopropyl | |
| 1918 | 2,4-(Me)₂Thiazol-5-yl | imidazol-2-yl | CF₃ | |
| 1919 | 2,4-(Me)₂Thiazol-5-yl | imidazol-1-yl | H | |
| 1920 | 2,4-(Me)₂Thiazol-5-yl | imidazol-1-yl | methyl | |
| 1921 | 2,4-(Me)₂Thiazol-5-yl | imidazol-1-yl | i-propyl | |
| 1922 | 2,4-(Me)₂Thiazol-5-yl | imidazol-1-yl | cyclopropyl | |
| 1923 | 2,4-(Me)₂Thiazol-5-yl | imidazol-1-yl | CF₃ | |
| 1924 | 2,4-(Me)₂Thiazol-5-yl | imidazol-4-yl | H | |
| 1925 | 2,4-(Me)₂Thiazol-5-yl | imidazol-4-yl | methyl | |
| 1926 | 2,4-(Me)₂Thiazol-5-yl | imidazol-4-yl | i-propyl | |
| 1927 | 2,4-(Me)₂Thiazol-5-yl | imidazol-4-yl | cyclopropyl | |
| 1928 | 2,4-(Me)₂Thiazol-5-yl | imidazol-4-yl | CF₃ | |
| 1929 | 2,4-(Me)₂Thiazol-5-yl | thiazol-2-yl | H | |
| 1930 | 2,4-(Me)₂Thiazol-5-yl | thiazol-2-yl | methyl | |
| 1931 | 2,4-(Me)₂Thiazol-5-yl | thiazol-2-yl | i-propyl | |
| 1932 | 2,4-(Me)₂Thiazol-5-yl | thiazol-2-yl | cyclopropyl | |
| 1933 | 2,4-(Me)₂Thiazol-5-yl | thiazol-2-yl | CF₃ | |
| 1934 | 2,4-(Me)₂Thiazol-5-yl | 4-methylthiazol-2-yl | H | |
| 1935 | 2,4-(Me)₂Thiazol-5-yl | 4-methylthiazol-2-yl | methyl | |
| 1936 | 2,4-(Me)₂Thiazol-5-yl | 4-methylthiazol-2-yl | i-propyl | |
| 1937 | 2,4-(Me)₂Thiazol-5-yl | 4-methylthiazol-2-yl | cyclopropyl | |
| 1938 | 2,4-(Me)₂Thiazol-5-yl | 4-methylthiazol-2-yl | CF₃ | |
| 1939 | 2,4-(Me)₂Thiazol-5-yl | oxazol-2-yl | H | |
| 1940 | 2,4-(Me)₂Thiazol-5-yl | oxazol-2-yl | methyl | |
| 1941 | 2,4-(Me)₂Thiazol-5-yl | oxazol-2-yl | i-propyl | |
| 1942 | 2,4-(Me)₂Thiazol-5-yl | oxazol-2-yl | cyclopropyl | |
| 1943 | 2,4-(Me)₂Thiazol-5-yl | oxazol-2-yl | CF₃ | |
| 1944 | 2,4-(Me)₂Thiazol- | 4,5-dimethyl- | H | |

-continued

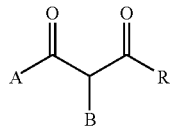
(I)

| Compound N | A | B | R | m.p. (°C.) |
|---|---|---|---|---|
| | 5-yl | oxazol-2-yl | | |
| 1945 | 2,4-(Me)₂Thiazol-5-yl | 4,5-dimethyl-oxazol-2-yl | methyl | |
| 1946 | 2,4-(Me)₂Thiazol-5-yl | 4,5-dimethyl-oxazol-2-yl | i-propyl | |
| 1947 | 2,4-(Me)₂Thiazol-5-yl | 4,5-dimethyl-oxazol-2-yl | cyclopropyl | |
| 1948 | 2,4-(Me)₂Thiazol-5-yl | 4,5-dimethyl-oxazol-2-yl | CF₃ | |
| 1949 | 2,4-(Me)₂Thiazol-5-yl | 2-oxazolin-2-yl | H | |
| 1950 | 2,4-(Me)₂Thiazol-5-yl | 2-oxazolin-2-yl | methyl | |
| 1951 | 2,4-(Me)₂Thiazol-5-yl | 2-oxazolin-2-yl | i-propyl | |
| 1952 | 2,4-(Me)₂Thiazol-5-yl | 2-oxazolin-2-yl | cyclopropyl | |
| 1953 | 2,4-(Me)₂Thiazol-5-yl | 2-oxazolin-2-yl | CF₃ | |
| 1954 | 2,4-(Me)₂Thiazol-5-yl | 4,4-dimethyl-2-oxazolin-2-yl | H | |
| 1955 | 2,4-(Me)₂Thiazol-5-yl | 4,4-dimethyl-2-oxazolin-2-yl | methyl | |
| 1956 | 2,4-(Me)₂Thiazol-5-yl | 4,4-dimethyl-2-oxazolin-2-yl | i-propyl | |
| 1957 | 2,4-(Me)₂Thiazol-5-yl | 4,4-dimethyl-2-oxazolin-2-yl | cyclopropyl | |
| 1958 | 2,4-(Me)₂Thiazol-5-yl | 4,4-dimethyl-2-oxazolin-2-yl | CF₃ | |
| 1959 | 2,4-(Me)₂Thiazol-5-yl | 1,2,4-thiadiazol-5-yl | H | |
| 1960 | 2,4-(Me)₂Thiazol-5-yl | 1,2,4-thiadiazol-5-yl | methyl | |
| 1961 | 2,4-(Me)₂Thiazol-5-yl | 1,2,4-thiadiazol-5-yl | i-propyl | |
| 1962 | 2,4-(Me)₂Thiazol-5-yl | 1,2,4-thiadiazol-5-yl | cyclopropyl | |
| 1963 | 2,4-(Me)₂Thiazol-5-yl | 1,2,4-thiadiazol-5-yl | CF₃ | |
| 1964 | 2,4-(Me)₂Thiazol-5-yl | 3-methyl-1,2,4-thiadiazol-5-yl | H | |
| 1965 | 2,4-(Me)₂Thiazol-5-yl | 3-methyl-1,2,4-thiadiazol-5-yl | methyl | |
| 1966 | 2,4-(Me)₂Thiazol-5-yl | 3-methyl-1,2,4-thiadiazol-5-yl | i-propyl | |
| 1967 | 2,4-(Me)₂Thiazol-5-yl | 3-methyl-1,2,4-thiadiazol-5-yl | cyclopropyl | |
| 1968 | 2,4-(Me)₂Thiazol-5-yl | 3-methyl-1,2,4-thiadiazol-5-yl | CF₃ | |
| 1969 | 2,4-(Me)₂Thiazol-5-yl | 3-trifluoromethyl-1,2,4-thiadiazol-5-yl | H | |
| 1970 | 2,4-(Me)₂Thiazol-5-yl | 3-trifluoromethyl-1,2,4-thiadiazol-5-yl | methyl | |
| 1971 | 2,4-(Me)₂Thiazol-5-yl | 3-trifluoromethyl-1,2,4-thiadiazol-5-yl | i-propyl | |
| 1972 | 2,4-(Me)₂Thiazol-5-yl | 3-trifluoromethyl-1,2,4-thiadiazol-5-yl | cyclopropyl | |
| 1973 | 2,4-(Me)₂Thiazol-5-yl | 3-trifluoromethyl-1,2,4-thiadiazol-5-yl | CF₃ | |
| 1974 | 2,4-(Me)₂Thiazol-5-yl | 1,2,4-thiadiazol-3-yl | H | |
| 1975 | 2,4-(Me)₂Thiazol-5-yl | 1,2,4-thiadiazol-3-yl | methyl | |
| 1976 | 2,4-(Me)₂Thiazol-5-yl | 1,2,4-thiadiazol-3-yl | i-propyl | |

-continued

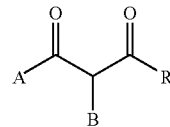
(I)

| Compound N | A | B | R | m.p. (°C.) |
|---|---|---|---|---|
| | 5-yl | 3-yl | | |
| 1977 | 2,4-(Me)₂Thiazol-5-yl | 1,2,4-thiadiazol-3-yl | cyclopropyl | |
| 1978 | 2,4-(Me)₂Thiazol-5-yl | 1,2,4-thiadiazol-3-yl | CF₃ | |
| 1979 | 2,4-(Me)₂Thiazol-5-yl | 5-methyl-1,2,4-thiadiazol-3-yl | H | |
| 1980 | 2,4-(Me)₂Thiazol-5-yl | 5-methyl-1,2,4-thiadiazol-3-yl | methyl | |
| 1981 | 2,4-(Me)₂Thiazol-5-yl | 5-methyl-1,2,4-thiadiazol-3-yl | i-propyl | |
| 1982 | 2,4-(Me)₂Thiazol-5-yl | 5-methyl-1,2,4-thiadiazol-3-yl | cyclopropyl | |
| 1983 | 2,4-(Me)₂Thiazol-5-yl | 5-methyl-1,2,4-thiadiazol-3-yl | CF₃ | |
| 1984 | 2,4-(Me)₂Thiazol-5-yl | 5-trifluoromethyl-1,2,4-thiadiazol-3-yl | H | |
| 1985 | 2,4-(Me)₂Thiazol-5-yl | 5-trifluoromethyl-1,2,4-thiadiazol-3-yl | methyl | |
| 1986 | 2,4-(Me)₂Thiazol-5-yl | 5-trifluoromethyl-1,2,4-thiadiazol-3-yl | i-propyl | |
| 1987 | 2,4-(Me)₂Thiazol-5-yl | 5-trifluoromethyl-1,2,4-thiadiazol-3-yl | cyclopropyl | |
| 1988 | 2,4-(Me)₂Thiazol-5-yl | 5-trifluoromethyl-1,2,4-thiadiazol-3-yl | CF₃ | |
| 1989 | 2,4-(Me)₂Thiazol-5-yl | 1,3,4-thiadiazol-2-yl | H | |
| 1990 | 2,4-(Me)₂Thiazol-5-yl | 1,3,4-thiadiazol-2-yl | methyl | |
| 1991 | 2,4-(Me)₂Thiazol-5-yl | 1,3,4-thiadiazol-2-yl | i-propyl | |
| 1992 | 2,4-(Me)₂Thiazol-5-yl | 1,3,4-thiadiazol-2-yl | cyclopropyl | |
| 1993 | 2,4-(Me)₂Thiazol-5-yl | 1,3,4-thiadiazol-2-yl | CF₃ | |
| 1994 | 2,4-(Me)₂Thiazol-5-yl | 5-methylsulfonyl-1,3,4-thiadiazol-2-yl | H | |
| 1995 | 2,4-(Me)₂Thiazol-5-yl | 5-methylsulfonyl-1,3,4-thiadiazol-2-yl | methyl | |
| 1996 | 2,4-(Me)₂Thiazol-5-yl | 5-methylsulfonyl-1,3,4-thiadiazol-2-yl | i-propyl | |
| 1997 | 2,4-(Me)₂Thiazol-5-yl | 5-methylsulfonyl-1,3,4-thiadiazol-2-yl | cyclopropyl | |
| 1998 | 2,4-(Me)₂Thiazol-5-yl | 5-methylsulfonyl-1,3,4-thiadiazol-2-yl | CF₃ | |
| 1999 | 2,4-(Me)₂Thiazol-5-yl | 5-methyl-1,3,4-thiadiazol-2-yl | H | |
| 2000 | 2,4-(Me)₂Thiazol-5-yl | 5-methyl-1,3,4-thiadiazol-2-yl | methyl | |
| 2001 | 2,4-(Me)₂Thiazol-5-yl | 5-methyl-1,3,4-thiadiazol-2-yl | i-propyl | |
| 2002 | 2,4-(Me)₂Thiazol-5-yl | 5-methyl-1,3,4-thiadiazol-2-yl | cyclopropyl | |
| 2003 | 2,4-(Me)₂Thiazol-5-yl | 5-methyl-1,3,4-thiadiazol-2-yl | CF₃ | |
| 2004 | 2,4-(Me)₂Thiazol-5-yl | benzoxazol-2-yl | H | |
| 2005 | 2,4-(Me)₂Thiazol-5-yl | benzoxazol-2-yl | methyl | |

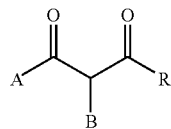 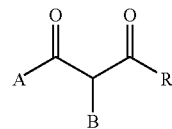

| Compound N | A | B | R | m.p. (°C.) |
|---|---|---|---|---|
| 2006 | 2,4-(Me)$_2$Thiazol-5-yl | benzoxazol-2-yl | i-propyl | |
| 2007 | 2,4-(Me)$_2$Thiazol-5-yl | benzoxazol-2-yl | cyclopropyl | |
| 2008 | 2,4-(Me)$_2$Thiazol-5-yl | benzoxazol-2-yl | CF$_3$ | |
| 2009 | 2,4-(Me)$_2$Thiazol-5-yl | 6-methyl-benzoxazol-2-yl | H | |
| 2010 | 2,4-(Me)$_2$Thiazol-5-yl | 6-methyl-benzoxazol-2-yl | methyl | |
| 2011 | 2,4-(Me)$_2$Thiazol-5-yl | 6-methyl-benzoxazol-2-yl | i-propyl | |
| 2012 | 2,4-(Me)$_2$Thiazol-5-yl | 6-methyl-benzoxazol-2-yl | cyclopropyl | |
| 2013 | 2,4-(Me)$_2$Thiazol-5-yl | 6-methyl-benzoxazol-2-yl | CF$_3$ | |
| 2014 | 2,4-(Me)$_2$Thiazol-5-yl | benzothiazol-2-yl | H | |
| 2015 | 2,4-(Me)$_2$Thiazol-5-yl | benzothiazol-2-yl | methyl | |
| 2016 | 2,4-(Me)$_2$Thiazol-5-yl | benzothiazol-2-yl | i-propyl | |
| 2017 | 2,4-(Me)$_2$Thiazol-5-yl | benzothiazol-2-yl | cyclopropyl | |
| 2018 | 2,4-(Me)$_2$Thiazol-5-yl | benzothiazol-2-yl | CF$_3$ | |
| 2019 | 2,4-(Me)$_2$Thiazol-5-yl | pyrazol-1-yl | H | |
| 2020 | 2,4-(Me)$_2$Thiazol-5-yl | pyrazol-1-yl | methyl | |
| 2021 | 2,4-(Me)$_2$Thiazol-5-yl | pyrazol-1-yl | i-propyl | |
| 2022 | 2,4-(Me)$_2$Thiazol-5-yl | pyrazol-1-yl | cyclopropyl | |
| 2023 | 2,4-(Me)$_2$Thiazol-5-yl | pyrazol-1-yl | CF$_3$ | |
| 2024 | 2,4-(Me)$_2$Thiazol-5-yl | pyrazol-3-yl | H | |
| 2025 | 2,4-(Me)$_2$Thiazol-5-yl | pyrazol-3-yl | methyl | |
| 2026 | 2,4-(Me)$_2$Thiazol-5-yl | pyrazol-3-yl | i-propyl | |
| 2027 | 2,4-(Me)$_2$Thiazol-5-yl | pyrazol-3-yl | cyclopropyl | |
| 2028 | 2,4-(Me)$_2$Thiazol-5-yl | pyrazol-3-yl | CF$_3$ | |
| 2029 | 2,4-(Me)$_2$Thiazol-5-yl | 1-methylpyrazol-3-yl | H | |
| 2030 | 2,4-(Me)$_2$Thiazol-5-yl | 1-methylpyrazol-3-yl | methyl | |
| 2031 | 2,4-(Me)$_2$Thiazol-5-yl | 1-methylpyrazol-3-yl | i-propyl | |
| 2032 | 2,4-(Me)$_2$Thiazol-5-yl | 1-methylpyrazol-3-yl | cyclopropyl | |
| 2033 | 2,4-(Me)$_2$Thiazol-5-yl | 1-methylpyrazol-3-yl | CF$_3$ | |
| 2034 | 2,4-(Me)$_2$Thiazol-5-yl | tetrazol-1-yl | H | |
| 2035 | 2,4-(Me)$_2$Thiazol-5-yl | tetrazol-1-yl | methyl | |
| 2036 | 2,4-(Me)$_2$Thiazol-5-yl | tetrazol-1-yl | i-propyl | |
| 2037 | 2,4-(Me)$_2$Thiazol-5-yl | tetrazol-1-yl | cyclopropyl | |
| 2038 | 2,4-(Me)$_2$Thiazol-5-yl | tetrazol-1-yl | CF$_3$ | |
| 2039 | 2,4-(Me)$_2$Thiazol-5-yl | 5-methyltetrazol-1-yl | H | |
| 2040 | 2,4-(Me)$_2$Thiazol-5-yl | 5-methyltetrazol-1-yl | methyl | |
| 2041 | 2,4-(Me)$_2$Thiazol-5-yl | 5-methyltetrazol-1-yl | i-propyl | |
| 2042 | 2,4-(Me)$_2$Thiazol-5-yl | 5-methyltetrazol-1-yl | cyclopropyl | |
| 2043 | 2,4-(Me)$_2$Thiazol-5-yl | 5-methyltetrazol-1-yl | CF$_3$ | |
| 2044 | 2,4-(Me)$_2$Thiazol-5-yl | tetrazol-2-yl | H | |
| 2045 | 2,4-(Me)$_2$Thiazol-5-yl | tetrazol-2-yl | methyl | |
| 2046 | 2,4-(Me)$_2$Thiazol-5-yl | tetrazol-2-yl | i-propyl | |
| 2047 | 2,4-(Me)$_2$Thiazol-5-yl | tetrazol-2-yl | cyclopropyl | |
| 2048 | 2,4-(Me)$_2$Thiazol-5-yl | tetrazol-2-yl | CF$_3$ | |
| 2049 | 2,4-(Me)$_2$Thiazol-5-yl | 5-methyltetrazol-2-yl | H | |
| 2050 | 2,4-(Me)$_2$Thiazol-5-yl | 5-methyltetrazol-2-yl | methyl | |
| 2051 | 2,4-(Me)$_2$Thiazol-5-yl | 5-methyltetrazol-2-yl | i-propyl | |
| 2052 | 2,4-(Me)$_2$Thiazol-5-yl | 5-methyltetrazol-2-yl | cyclopropyl | |
| 2053 | 2,4-(Me)$_2$Thiazol-5-yl | 5-methyltetrazol-2-yl | CF$_3$ | |
| 2054 | 2,4-(Me)$_2$Thiazol-5-yl | 1-methyltetrazol-5-yl | H | |
| 2055 | 2,4-(Me)$_2$Thiazol-5-yl | 1-methyltetrazol-5-yl | methyl | |
| 2056 | 2,4-(Me)$_2$Thiazol-5-yl | 1-methyltetrazol-5-yl | i-propyl | |
| 2057 | 2,4-(Me)$_2$Thiazol-5-yl | 1-methyltetrazol-5-yl | cyclopropyl | |
| 2058 | 2,4-(Me)$_2$Thiazol-5-yl | 1-methyltetrazol-5-yl | CF$_3$ | |
| 2059 | 2,4-(Me)$_2$Thiazol-5-yl | 2-methyltetrazol-5-yl | H | |
| 2060 | 2,4-(Me)$_2$Thiazol-5-yl | 2-methyltetrazol-5-yl | methyl | |
| 2061 | 2,4-(Me)$_2$Thiazol-5-yl | 2-methyltetrazol-5-yl | i-propyl | |
| 2062 | 2,4-(Me)$_2$Thiazol-5-yl | 2-methyltetrazol-5-yl | cyclopropyl | |
| 2063 | 2,4-(Me)$_2$Thiazol-5-yl | 2-methyltetrazol-5-yl | CF$_3$ | |
| 2064 | 2,4-(Me)$_2$Thiazol-5-yl | pyridin-2-yl | H | |
| 2065 | 2,4-(Me)$_2$Thiazol-5-yl | pyridin-2-yl | methyl | |
| 2066 | 2,4-(Me)$_2$Thiazol-5-yl | pyridin-2-yl | i-propyl | |
| 2067 | 2,4-(Me)$_2$Thiazol-5-yl | pyridin-2-yl | cyclopropyl | |
| 2068 | 2,4-(Me)$_2$Thiazol-5-yl | pyridin-2-yl | CF$_3$ | |
| 2069 | 2,4-(Me)$_2$Thiazol-5-yl | pyridin-4-yl | H | |
| 2070 | 2,4-(Me)$_2$Thiazol-5-yl | pyridin-4-yl | methyl | |
| 2071 | 2,4-(Me)$_2$Thiazol-5-yl | pyridin-4-yl | i-propyl | |
| 2072 | 2,4-(Me)$_2$Thiazol-5-yl | pyridin-4-yl | cyclopropyl | |
| 2073 | 2,4-(Me)$_2$Thiazol-5-yl | pyridin-4-yl | CF$_3$ | |
| 2074 | 2,4-(Me)$_2$Thiazol-5-yl | pyridin-3-yl | H | |

-continued

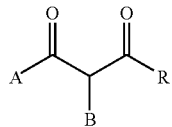

(I)

| Compound N | A | B | R | m.p. (°C.) |
|---|---|---|---|---|
| 2075 | 2,4-(Me)₂Thiazol-5-yl | pyridin-3-yl | methyl | |
| 2076 | 2,4-(Me)₂Thiazol-5-yl | pyridin-3-yl | i-propyl | |
| 2077 | 2,4-(Me)₂Thiazol-5-yl | pyridin-3-yl | cyclopropyl | |
| 2078 | 2,4-(Me)₂Thiazol-5-yl | pyridin-3-yl | CF₃ | |
| 2079 | 2,4-(Me)₂Thiazol-5-yl | 3-nitropyridin-4-yl | H | |
| 2080 | 2,4-(Me)₂Thiazol-5-yl | 3-nitropyridin-4-yl | methyl | |
| 2081 | 2,4-(Me)₂Thiazol-5-yl | 3-nitropyridin-4-yl | i-propyl | |
| 2082 | 2,4-(Me)₂Thiazol-5-yl | 3-nitropyridin-4-yl | cyclopropyl | |
| 2083 | 2,4-(Me)₂Thiazol-5-yl | 3-nitropyridin-4-yl | CF₃ | |
| 2084 | 2,4-(Me)₂Thiazol-5-yl | 5-cyanopyridin-2-yl | H | |
| 2085 | 2,4-(Me)₂Thiazol-5-yl | 5-cyanopyridin-2-yl | methyl | |
| 2086 | 2,4-(Me)₂Thiazol-5-yl | 5-cyanopyridin-2-yl | i-propyl | |
| 2087 | 2,4-(Me)₂Thiazol-5-yl | 5-cyanopyridin-2-yl | cyclopropyl | |
| 2088 | 2,4-(Me)₂Thiazol-5-yl | 5-cyanopyridin-2-yl | CF₃ | |
| 2089 | 2,4-(Me)₂Thiazol-5-yl | 5-trifluoromethylpyridin-2-yl | H | |
| 2090 | 2,4-(Me)₂Thiazol-5-yl | 5-trifluoromethylpyridin-2-yl | methyl | |
| 2091 | 2,4-(Me)₂Thiazol-5-yl | 5-trifluoromethylpyridin-2-yl | i-propyl | |
| 2092 | 2,4-(Me)₂Thiazol-5-yl | 5-trifluoromethylpyridin-2-yl | cyclopropyl | |
| 2093 | 2,4-(Me)₂Thiazol-5-yl | 5-trifluoromethylpyridin-2-yl | CF₃ | |
| 2094 | 2,4-(Me)₂Thiazol-5-yl | pyrimidin-2-yl | H | |
| 2095 | 2,4-(Me)₂Thiazol-5-yl | pyrimidin-2-yl | methyl | |
| 2096 | 2,4-(Me)₂Thiazol-5-yl | pyrimidin-2-yl | i-propyl | |
| 2097 | 2,4-(Me)₂Thiazol-5-yl | pyrimidin-2-yl | cyclopropyl | |
| 2098 | 2,4-(Me)₂Thiazol-5-yl | pyrimidin-2-yl | CF₃ | |
| 2099 | 2,4-(Me)₂Thiazol-5-yl | pyrimidin-4-yl | H | |
| 2100 | 2,4-(Me)₂Thiazol-5-yl | pyrimidin-4-yl | methyl | |
| 2101 | 2,4-(Me)₂Thiazol-5-yl | pyrimidin-4-yl | i-propyl | |
| 2102 | 2,4-(Me)₂Thiazol-5-yl | pyrimidin-4-yl | cyclopropyl | |
| 2103 | 2,4-(Me)₂Thiazol-5-yl | pyrimidin-4-yl | CF₃ | |
| 2104 | 2,4-(Me)₂Thiazol-5-yl | 6-chloropyrimidin-4-yl | methyl | |
| 2105 | 2,4-(Me)₂Thiazol-5-yl | 6-chloropyrimidin-4-yl | i-propyl | |
| 2106 | 2,4-(Me)₂Thiazol-5-yl | 6-chloropyrimidin-4-yl | cyclopropyl | |
| 2107 | 2,4-(Me)₂Thiazol-5-yl | 6-chloropyrimidin-4-yl | CF₃ | |
| 2108 | 2,4-(Me)₂Thiazol-5-yl | pyridazin-3-yl | H | |
| 2109 | 2,4-(Me)₂Thiazol-5-yl | pyridazin-3-yl | methyl | |
| 2110 | 2,4-(Me)₂Thiazol-5-yl | pyridazin-3-yl | i-propyl | |
| 2111 | 2,4-(Me)₂Thiazol-5-yl | pyridazin-3-yl | cyclopropyl | |
| 2112 | 2,4-(Me)₂Thiazol-5-yl | pyridazin-3-yl | CF₃ | |
| 2113 | 2,4-(Me)₂Thiazol-5-yl | 6-chloropyridazin-3-yl | methyl | |
| 2114 | 2,4-(Me)₂Thiazol-5-yl | 6-chloropyridazin-3-yl | i-propyl | |
| 2115 | 2,4-(Me)₂Thiazol-5-yl | 6-chloropyridazin-3-yl | cyclopropyl | |
| 2116 | 2,4-(Me)₂Thiazol-5-yl | 6-chloropyridazin-3-yl | CF₃ | |
| 2117 | 2,4-(Me)₂Thiazol-5-yl | pyrazin-2-yl | methyl | |
| 2118 | 2,4-(Me)₂Thiazol-5-yl | pyrazin-2-yl | i-propyl | |
| 2119 | 2,4-(Me)₂Thiazol-5-yl | pyrazin-2-yl | cyclopropyl | |
| 2120 | 2,4-(Me)₂Thiazol-5-yl | pyrazin-2-yl | CF₃ | |
| 2121 | 2,4-(Me)₂Thiazol-5-yl | triazin-2-yl | methyl | |
| 2122 | 2,4-(Me)₂Thiazol-5-yl | triazin-2-yl | i-propyl | |
| 2123 | 2,4-(Me)₂Thiazol-5-yl | triazin-2-yl | cyclopropyl | |
| 2124 | 2,4-(Me)₂Thiazol-5-yl | triazin-2-yl | CF₃ | |
| 2125 | 2,4-(Me)₂Thiazol-5-yl | quinolin-2-yl | methyl | |
| 2126 | 2,4-(Me)₂Thiazol-5-yl | quinolin-2-yl | i-propyl | |
| 2127 | 2,4-(Me)₂Thiazol-5-yl | quinolin-2-yl | cyclopropyl | |
| 2128 | 2,4-(Me)₂Thiazol-5-yl | quinolin-2-yl | CF₃ | |
| 2129 | 2,4-(Me)₂Thiazol-5-yl | 4,4,6-trimethyl-5,6-dihydro-1,3(4H)-oxazin-2-yl | H | |
| 2130 | 2,4-(Me)₂Thiazol-5-yl | 4,4,6-trimethyl-5,6-dihydro-1,3(4H)-oxazin-2-yl | methyl | |
| 2131 | 2,4-(Me)₂Thiazol-5-yl | 4,4,6-trimethyl-5,6-dihydro-1,3(4H)-oxazin-2-yl | i-propyl | |
| 2132 | 2,4-(Me)₂Thiazol-5-yl | 4,4,6-trimethyl-5,6-dihydro-1,3(4H)-oxazin-2-yl | cyclopropyl | |
| 2133 | 2,4-(Me)₂Thiazol-5-yl | 4,4,6-trimethyl-5,6-dihydro-1,3(4H)-oxazin-2-yl | CF₃ | |
| 2134 | 2,4-(Me)₂Thiazol-5-yl | 2-oxazolidinon-3-yl | H | |
| 2135 | 2,4-(Me)₂Thiazol-5-yl | 2-oxazolidinon-3-yl | methyl | |
| 2136 | 2,4-(Me)₂Thiazol-5-yl | 2-oxazolidinon-3-yl | i-propyl | |
| 2137 | 2,4-(Me)₂Thiazol-5-yl | 2-oxazolidinon-3-yl | cyclopropyl | |
| 2138 | 2,4-(Me)₂Thiazol-5-yl | 2-oxazolidinon-3-yl | CF₃ | |

-continued

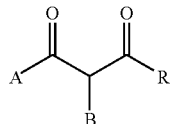
(I)

| Compound N | A | B | R | m.p. (° C.) |
|---|---|---|---|---|
| 2139 | 2,4-(Me)$_2$Thiazol-5-yl | 2-pyrrolidinon-1-yl | methyl | |
| 2140 | 2,4-(Me)$_2$Thiazol-5-yl | 2-pyrrolidinon-1-yl | i-propyl | |
| 2141 | 2,4-(Me)$_2$Thiazol-5-yl | 2-pyrrolidinon-1-yl | cyclopropyl | |
| 2142 | 2,4-(Me)$_2$Thiazol-5-yl | 2-pyrrolidinon-1-yl | CF$_3$ | |
| 2143 | 2,4-(Me)$_2$Thiazol-5-yl | 3-methylisoxazol-5-yl | methyl | |
| 2144 | 2,4-(Me)$_2$Thiazol-5-yl | 3-methylisoxazol-5-yl | i-propyl | |
| 2145 | 2,4-(Me)$_2$Thiazol-5-yl | 3-methylisoxazol-5-yl | cyclopropyl | |
| 2146 | 2,4-(Me)$_2$Thiazol-5-yl | 3-methylisoxazol-5-yl | CF$_3$ | |
| 2147 | 2,4-(Me)$_2$Thiazol-5-yl | 2-NO$_2$-4-SO$_2$MePh | H | |
| 2148 | 2,4-(Me)$_2$Thiazol-5-yl | 2-NO$_2$-4-SO$_2$MePh | methyl | |
| 2149 | 2,4-(Me)$_2$Thiazol-5-yl | 2-NO$_2$-4-SO$_2$MePh | i-propyl | |
| 2150 | 2,4-(Me)$_2$Thiazol-5-yl | 2-NO$_2$-4-SO$_2$MePh | cyclopropyl | |
| 2151 | 2,4-(Me)$_2$Thiazol-5-yl | 2-NO$_2$-4-SO$_2$MePh | CF$_3$ | |
| 2152 | 2,4-(Me)$_2$Thiazol-5-yl | 2-Cl-4-SO$_2$MePH | H | |
| 2153 | 2,4-(Me)$_2$Thiazol-5-yl | 2-Cl-4-SO$_2$MePH | methyl | |
| 2154 | 2,4-(Me)$_2$Thiazol-5-yl | 2-Cl-4-SO$_2$MePH | i-propyl | |
| 2155 | 2,4-(Me)$_2$Thiazol-5-yl | 2-Cl-4-SO$_2$MePH | cyclopropyl | |
| 2156 | 2,4-(Me)$_2$Thiazol-5-yl | 2-Cl-4-SO$_2$MePH | CF$_3$ | |
| 2157 | 2,4-(Me)$_2$Thiazol-5-yl | 2-NO$_2$-4-CF$_3$Ph | H | |
| 2158 | 2,4-(Me)$_2$Thiazol-5-yl | 2-NO$_2$-4-CF$_3$Ph | methyl | |
| 2159 | 2,4-(Me)$_2$Thiazol-5-yl | 2-NO$_2$-4-CF$_3$Ph | i-propyl | |
| 2160 | 2,4-(Me)$_2$Thiazol-5-yl | 2-NO$_2$-4-CF$_3$Ph | cyclopropyl | |
| 2161 | 2,4-(Me)$_2$Thiazol-5-yl | 2-NO$_2$-4-CF$_3$Ph | CF$_3$ | |
| 2162 | 2,4-(Me)$_2$Thiazol-5-yl | 2-NO$_2$-4-ClPh | H | |
| 2163 | 2,4-(Me)$_2$Thiazol-5-yl | 2-NO$_2$-4-ClPh | methyl | |
| 2164 | 2,4-(Me)$_2$Thiazol-5-yl | 2-NO$_2$-4-ClPh | i-propyl | |
| 2165 | 2,4-(Me)$_2$Thiazol-5-yl | 2-NO$_2$-4-ClPh | cyclopropyl | |
| 2166 | 2,4-(Me)$_2$Thiazol-5-yl | 2-NO$_2$-4-ClPh | CF$_3$ | |
| 2167 | 2,4-(Me)$_2$Thiazol-5-yl | 2-Cl-4-NO$_2$Ph | H | |
| 2168 | 2,4-(Me)$_2$Thiazol-5-yl | 2-Cl-4-NO$_2$Ph | methyl | |
| 2169 | 2,4-(Me)$_2$Thiazol-5-yl | 2-Cl-4-NO$_2$Ph | i-propyl | |
| 2170 | 2,4-(Me)$_2$Thiazol-5-yl | 2-Cl-4-NO$_2$Ph | cyclopropyl | |
| 2171 | 2,4-(Me)$_2$Thiazol-5-yl | 2-Cl-4-NO$_2$Ph | CF$_3$ | |
| 2172 | 2,4-(Me)$_2$Thiazol-5-yl | 2,4-(NO$_2$)$_2$Ph | H | |
| 2173 | 2,4-(Me)$_2$Thiazol-5-yl | 2,4-(NO$_2$)$_2$Ph | methyl | |

-continued

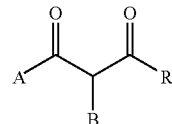
(I)

| Compound N | A | B | R | m.p. (° C.) |
|---|---|---|---|---|
| 2174 | 2,4-(Me)$_2$Thiazol-5-yl | 2,4-(NO$_2$)$_2$Ph | i-propyl | |
| 2175 | 2,4-(Me)$_2$Thiazol-5-yl | 2,4-(NO$_2$)$_2$Ph | cyclopropyl | |
| 2176 | 2,4-(Me)$_2$Thiazol-5-yl | 2,4-(NO$_2$)$_2$Ph | CF$_3$ | |
| 2177 | 2,4-(Me)$_2$Thiazol-5-yl | 4-F-3-NO$_2$Ph | H | |
| 2178 | 2,4-(Me)$_2$Thiazol-5-yl | 4-F-3-NO$_2$Ph | methyl | |
| 2179 | 2,4-(Me)$_2$Thiazol-5-yl | 4-F-3-NO$_2$Ph | i-propyl | |
| 2180 | 2,4-(Me)$_2$Thiazol-5-yl | 4-F-3-NO$_2$Ph | cyclopropyl | |
| 2181 | 2,4-(Me)$_2$Thiazol-5-yl | 4-F-3-NO$_2$Ph | CF$_3$ | |
| 2182 | 2,4-(Me)$_2$Thiazol-5-yl | 3,5-(CF$_3$)$_2$Ph | H | |
| 2183 | 2,4-(Me)$_2$Thiazol-5-yl | 3,5-(CF$_3$)$_2$Ph | methyl | |
| 2184 | 2,4-(Me)$_2$Thiazol-5-yl | 3,5-(CF$_3$)$_2$Ph | i-propyl | |
| 2185 | 2,4-(Me)$_2$Thiazol-5-yl | 3,5-(CF$_3$)$_2$Ph | cyclopropyl | |
| 2186 | 2,4-(Me)$_2$Thiazol-5-yl | 3,5-(CF$_3$)$_2$Ph | CF$_3$ | |
| 2187 | 2,4-(Me)$_2$Thiazol-5-yl | 2-SO$_2$Me-4-CF$_3$Ph | H | |
| 2188 | 2,4-(Me)$_2$Thiazol-5-yl | 2-SO$_2$Me-4-CF$_3$Ph | methyl | |
| 2189 | 2,4-(Me)$_2$Thiazol-5-yl | 2-SO$_2$Me-4-CF$_3$Ph | i-propyl | |
| 2190 | 2,4-(Me)$_2$Thiazol-5-yl | 2-SO$_2$Me-4-CF$_3$Ph | cyclopropyl | |
| 2191 | 2,4-(Me)$_2$Thiazol-5-yl | 2-SO$_2$Me-4-CF$_3$Ph | CF$_3$ | |
| 2192 | 2-Me-4-SO$_2$Me-3-(4,5-dihydro-isoxazol-3-yl)Ph | 1,2,4-oxadiazol-5-yl | H | |
| 2193 | 2-Me-4-SO$_2$Me-3-(4,5-dihydro-isoxazol-3-yl)Ph | 1,2,4-oxadiazol-5-yl | methyl | |
| 2194 | 2-Me-4-SO$_2$Me-3-(4,5-dihydro-isoxazol-3-yl)Ph | 1,2,4-oxadiazol-5-yl | i-propyl | |
| 2195 | 2-Me-4-SO$_2$Me-3-(4,5-dihydro-isoxazol-3-yl)Ph | 1,2,4-oxadiazol-5-yl | cyclopropyl | |
| 2196 | 2-Me-4-SO$_2$Me-3-(4,5-dihydro-isoxazol-3-yl)Ph | 1,2,4-oxadiazol-5-yl | CF$_3$ | |
| 2197 | 2-Me-4-SO$_2$Me-3-(4,5-dihydro-isoxazol-3-yl)Ph | 3-methyl-1,2,4-oxadiazol-5-yl | H | |
| 2198 | 2-Me-4-SO$_2$Me-3-(4,5-dihydro-isoxazol-3-yl)Ph | 3-methyl-1,2,4-oxadiazol-5-yl | methyl | |
| 2199 | 2-Me-4-SO$_2$Me-3-(4,5-dihydro-isoxazol-3-yl)Ph | 3-methyl-1,2,4-oxadiazol-5-yl | i-propyl | |
| 2200 | 2-Me-4-SO$_2$Me-3-(4,5-dihydro-isoxazol-3-yl)Ph | 3-methyl-1,2,4-oxadiazol-5-yl | cyclopropyl | |
| 2201 | 2-Me-4-SO$_2$Me-3-(4,5-dihydro-isoxazol-3-yl)Ph | 3-methyl-1,2,4-oxadiazol-5-yl | CF$_3$ | |
| 2202 | 2-Me-4-SO$_2$Me- | 3-trifluoromethyl- | H | |

-continued

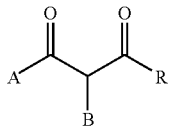
(I)

| Compound N | A | B | R | m.p. (°C.) |
|---|---|---|---|---|
| 2203 | 2-Me-4-SO$_2$Me-3-(4,5-dihydro-isoxazol-3-yl)Ph | 3-trifluoromethyl-1,2,4-oxadiazol-5-yl | methyl | |
| 2204 | 2-Me-4-SO$_2$Me-3-(4,5-dihydro-isoxazol-3-yl)Ph | 3-trifluoromethyl-1,2,4-oxadiazol-5-yl | i-propyl | |
| 2205 | 2-Me-4-SO$_2$Me-3-(4,5-dihydro-isoxazol-3-yl)Ph | 3-trifluoromethyl-1,2,4-oxadiazol-5-yl | cyclopropyl | |
| 2206 | 2-Me-4-SO$_2$Me-3-(4,5-dihydro-isoxazol-3-yl)Ph | 3-trifluoromethyl-1,2,4-oxadiazol-5-yl | CF$_3$ | |
| 2207 | 2-Me-4-SO$_2$Me-3-(4,5-dihydro-isoxazol-3-yl)Ph | 1,2,4-oxadiazol-3-yl | H | |
| 2208 | 2-Me-4-SO$_2$Me-3-(4,5-dihydro-isoxazol-3-yl)Ph | 1,2,4-oxadiazol-3-yl | methyl | |
| 2209 | 2-Me-4-SO$_2$Me-3-(4,5-dihydro-isoxazol-3-yl)Ph | 1,2,4-oxadiazol-3-yl | i-propyl | |
| 2210 | 2-Me-4-SO$_2$Me-3-(4,5-dihydro-isoxazol-3-yl)Ph | 1,2,4-oxadiazol-3-yl | cyclopropyl | |
| 2211 | 2-Me-4-SO$_2$Me-3-(4,5-dihydro-isoxazol-3-yl)Ph | 1,2,4-oxadiazol-3-yl | CF$_3$ | |
| 2212 | 2-Me-4-SO$_2$Me-3-(4,5-dihydro-isoxazol-3-yl)Ph | 5-methyl-1,2,4-oxadiazol-3-yl | H | |
| 2213 | 2-Me-4-SO$_2$Me-3-(4,5-dihydro-isoxazol-3-yl)Ph | 5-methyl-1,2,4-oxadiazol-3-yl | methyl | |
| 2214 | 2-Me-4-SO$_2$Me-3-(4,5-dihydro-isoxazol-3-yl)Ph | 5-methyl-1,2,4-oxadiazol-3-yl | i-propyl | |
| 2215 | 2-Me-4-SO$_2$Me-3-(4,5-dihydro-isoxazol-3-yl)Ph | 5-methyl-1,2,4-oxadiazol-3-yl | cyclopropyl | |
| 2216 | 2-Me-4-SO$_2$Me-3-(4,5-dihydro-isoxazol-3-yl)Ph | 5-methyl-1,2,4-oxadiazol-3-yl | CF$_3$ | |
| 2217 | 2-Me-4-SO$_2$Me-3-(4,5-dihydro-isoxazol-3-yl)Ph | 5-trifluoromethyl-1,2,4-oxadiazol-3-yl | H | |
| 2218 | 2-Me-4-SO$_2$Me-3-(4,5-dihydro-isoxazol-3-yl)Ph | 5-trifluoromethyl-1,2,4-oxadiazol-3-yl | methyl | |
| 2219 | 2-Me-4-SO$_2$Me-3-(4,5-dihydro-isoxazol-3-yl)Ph | 5-trifluoromethyl-1,2,4-oxadiazol-3-yl | i-propyl | |
| 2220 | 2-Me-4-SO$_2$Me-3-(4,5-dihydro-isoxazol-3-yl)Ph | 5-trifluoromethyl-1,2,4-oxadiazol-3-yl | cyclopropyl | |
| 2221 | 2-Me-4-SO$_2$Me-3-(4,5-dihydro-isoxazol-3-yl)Ph | 5-trifluoromethyl-1,2,4-oxadiazol-3-yl | CF$_3$ | |
| 2222 | 2-Me-4-SO$_2$Me-3-(4,5-dihydro-isoxazol-3-yl)Ph | 5-chloro-1,2,4-oxadiazol-3-yl | H | |
| 2223 | 2-Me-4-SO$_2$Me-3-(4,5-dihydro-isoxazol-3-yl)Ph | 5-chloro-1,2,4-oxadiazol-3-yl | methyl | |
| 2224 | 2-Me-4-SO$_2$Me-3-(4,5-dihydro-isoxazol-3-yl)Ph | 5-chloro-1,2,4-oxadiazol-3-yl | i-propyl | |
| 2225 | 2-Me-4-SO$_2$Me-3-(4,5-dihydro-isoxazol-3-yl)Ph | 5-chloro-1,2,4-oxadiazol-3-yl | cyclopropyl | |

-continued

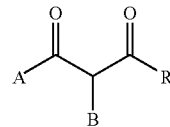
(I)

| Compound N | A | B | R | m.p. (°C.) |
|---|---|---|---|---|
| 2226 | 2-Me-4-SO$_2$Me-3-(4,5-dihydro-isoxazol-3-yl)Ph | 5-chloro-1,2,4-oxadiazol-3-yl | CF$_3$ | |
| 2227 | 2-Me-4-SO$_2$Me-3-(4,5-dihydro-isoxazol-3-yl)Ph | 1,3,4-oxadiazol-2-yl | H | |
| 2228 | 2-Me-4-SO$_2$Me-3-(4,5-dihydro-isoxazol-3-yl)Ph | 1,3,4-oxadiazol-2-yl | methyl | |
| 2229 | 2-Me-4-SO$_2$Me-3-(4,5-dihydro-isoxazol-3-yl)Ph | 1,3,4-oxadiazol-2-yl | i-propyl | |
| 2230 | 2-Me-4-SO$_2$Me-3-(4,5-dihydro-isoxazol-3-yl)Ph | 1,3,4-oxadiazol-2-yl | cyclopropyl | |
| 2231 | 2-Me-4-SO$_2$Me-3-(4,5-dihydro-isoxazol-3-yl)Ph | 1,3,4-oxadiazol-2-yl | CF$_3$ | |
| 2232 | 2-Me-4-SO$_2$Me-3-(4,5-dihydro-isoxazol-3-yl)Ph | 5-methylsulfonyl-1,3,4-oxadiazol-2-yl | H | |
| 2233 | 2-Me-4-SO$_2$Me-3-(4,5-dihydro-isoxazol-3-yl)Ph | 5-methylsulfonyl-1,3,4-oxadiazol-2-yl | methyl | |
| 2234 | 2-Me-4-SO$_2$Me-3-(4,5-dihydro-isoxazol-3-yl)Ph | 5-methylsulfonyl-1,3,4-oxadiazol-2-yl | i-propyl | |
| 2235 | 2-Me-4-SO$_2$Me-3-(4,5-dihydro-isoxazol-3-yl)Ph | 5-methylsulfonyl-1,3,4-oxadiazol-2-yl | cyclopropyl | |
| 2236 | 2-Me-4-SO$_2$Me-3-(4,5-dihydro-isoxazol-3-yl)Ph | 5-methylsulfonyl-1,3,4-oxadiazol-2-yl | CF$_3$ | |
| 2237 | 2-Me-4-SO$_2$Me-3-(4,5-dihydro-isoxazol-3-yl)Ph | 5-methyl-1,3,4-oxadiazol-2-yl | H | |
| 2238 | 2-Me-4-SO$_2$Me-3-(4,5-dihydro-isoxazol-3-yl)Ph | 5-methyl-1,3,4-oxadiazol-2-yl | methyl | |
| 2239 | 2-Me-4-SO$_2$Me-3-(4,5-dihydro-isoxazol-3-yl)Ph | 5-methyl-1,3,4-oxadiazol-2-yl | i-propyl | |
| 2240 | 2-Me-4-SO$_2$Me-3-(4,5-dihydro-isoxazol-3-yl)Ph | 5-methyl-1,3,4-oxadiazol-2-yl | cyclopropyl | |
| 2241 | 2-Me-4-SO$_2$Me-3-(4,5-dihydro-isoxazol-3-yl)Ph | 5-methyl-1,3,4-oxadiazol-2-yl | CF$_3$ | |
| 2242 | 2-Me-4-SO$_2$Me-3-(4,5-dihydro-isoxazol-3-yl)Ph | 5-trifluoromethyl-1,3,4-oxadiazol-2-yl | H | |
| 2243 | 2-Me-4-SO$_2$Me-3-(4,5-dihydro-isoxazol-3-yl)Ph | 5-trifluoromethyl-1,3,4-oxadiazol-2-yl | methyl | |
| 2244 | 2-Me-4-SO$_2$Me-3-(4,5-dihydro-isoxazol-3-yl)Ph | 5-trifluoromethyl-1,3,4-oxadiazol-2-yl | i-propyl | |
| 2245 | 2-Me-4-SO$_2$Me-3-(4,5-dihydro-isoxazol-3-yl)Ph | 5-trifluoromethyl-1,3,4-oxadiazol-2-yl | cyclopropyl | |
| 2246 | 2-Me-4-SO$_2$Me-3-(4,5-dihydro-isoxazol-3-yl)Ph | 5-trifluoromethyl-1,3,4-oxadiazol-2-yl | CF$_3$ | |
| 2247 | 2-Me-4-SO$_2$Me-3-(4,5-dihydro-isoxazol-3-yl)Ph | 1,2,3-triazol-4-yl | H | |
| 2248 | 2-Me-4-SO$_2$Me-3-(4,5-dihydro-isoxazol-3-yl)Ph | 1,2,3-triazol-4-yl | methyl | |

-continued

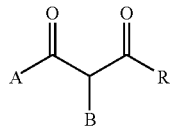

(I)

| Compound N | A | B | R | m.p. (°C.) |
|---|---|---|---|---|
| 2249 | 2-Me-4-SO₂Me-3-(4,5-dihydro-isoxazol-3-yl)Ph | 1,2,3-triazol-4-yl | i-propyl | |
| 2250 | 2-Me-4-SO₂Me-3-(4,5-dihydro-isoxazol-3-yl)Ph | 1,2,3-triazol-4-yl | cyclopropyl | |
| 2251 | 2-Me-4-SO₂Me-3-(4,5-dihydro-isoxazol-3-yl)Ph | 1,2,3-triazol-4-yl | CF₃ | |
| 2252 | 2-Me-4-SO₂Me-3-(4,5-dihydro-isoxazol-3-yl)Ph | 1-methyl-1,2,3-triazol-4-yl | H | |
| 2253 | 2-Me-4-SO₂Me-3-(4,5-dihydro-isoxazol-3-yl)Ph | 1-methyl-1,2,3-triazol-4-yl | methyl | |
| 2254 | 2-Me-4-SO₂Me-3-(4,5-dihydro-isoxazol-3-yl)Ph | 1-methyl-1,2,3-triazol-4-yl | i-propyl | |
| 2255 | 2-Me-4-SO₂Me-3-(4,5-dihydro-isoxazol-3-yl)Ph | 1-methyl-1,2,3-triazol-4-yl | cyclopropyl | |
| 2256 | 2-Me-4-SO₂Me-3-(4,5-dihydro-isoxazol-3-yl)Ph | 1-methyl-1,2,3-triazol-4-yl | CF₃ | |
| 2257 | 2-Me-4-SO₂Me-3-(4,5-dihydro-isoxazol-3-yl)Ph | 2-methyl-1,2,3-triazol-4-yl | H | |
| 2258 | 2-Me-4-SO₂Me-3-(4,5-dihydro-isoxazol-3-yl)Ph | 2-methyl-1,2,3-triazol-4-yl | methyl | |
| 2259 | 2-Me-4-SO₂Me-3-(4,5-dihydro-isoxazol-3-yl)Ph | 2-methyl-1,2,3-triazol-4-yl | i-propyl | |
| 2260 | 2-Me-4-SO₂Me-3-(4,5-dihydro-isoxazol-3-yl)Ph | 2-methyl-1,2,3-triazol-4-yl | cyclopropyl | |
| 2261 | 2-Me-4-SO₂Me-3-(4,5-dihydro-isoxazol-3-yl)Ph | 2-methyl-1,2,3-triazol-4-yl | CF₃ | |
| 2262 | 2-Me-4-SO₂Me-3-(4,5-dihydro-isoxazol-3-yl)Ph | 1,2,3-triazol-1-yl | H | |
| 2263 | 2-Me-4-SO₂Me-3-(4,5-dihydro-isoxazol-3-yl)Ph | 1,2,3-triazol-1-yl | methyl | |
| 2264 | 2-Me-4-SO₂Me-3-(4,5-dihydro-isoxazol-3-yl)Ph | 1,2,3-triazol-1-yl | i-propyl | |
| 2265 | 2-Me-4-SO₂Me-3-(4,5-dihydro-isoxazol-3-yl)Ph | 1,2,3-triazol-1-yl | cyclopropyl | |
| 2266 | 2-Me-4-SO₂Me-3-(4,5-dihydro-isoxazol-3-yl)Ph | 1,2,3-triazol-1-yl | CF₃ | |
| 2267 | 2-Me-4-SO₂Me-3-(4,5-dihydro-isoxazol-3-yl)Ph | 1,2,3-triazol-2-yl | H | |
| 2268 | 2-Me-4-SO₂Me-3-(4,5-dihydro-isoxazol-3-yl)Ph | 1,2,3-triazol-2-yl | methyl | |
| 2269 | 2-Me-4-SO₂Me-3-(4,5-dihydro-isoxazol-3-yl)Ph | 1,2,3-triazol-2-yl | i-propyl | |
| 2270 | 2-Me-4-SO₂Me-3-(4,5-dihydro-isoxazol-3-yl)Ph | 1,2,3-triazol-2-yl | cyclopropyl | |
| 2271 | 2-Me-4-SO₂Me-3-(4,5-dihydro-isoxazol-3-yl)Ph | 1,2,3-triazol-2-yl | CF₃ | |

-continued

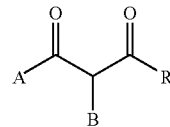

(I)

| Compound N | A | B | R | m.p. (°C.) |
|---|---|---|---|---|
| 2272 | 2-Me-4-SO₂Me-3-(4,5-dihydro-isoxazol-3-yl)Ph | 1,2,4-triazol-1-yl | H | |
| 2273 | 2-Me-4-SO₂Me-3-(4,5-dihydro-isoxazol-3-yl)Ph | 1,2,4-triazol-1-yl | methyl | |
| 2274 | 2-Me-4-SO₂Me-3-(4,5-dihydro-isoxazol-3-yl)Ph | 1,2,4-triazol-1-yl | i-propyl | |
| 2275 | 2-Me-4-SO₂Me-3-(4,5-dihydro-isoxazol-3-yl)Ph | 1,2,4-triazol-1-yl | cyclopropyl | |
| 2276 | 2-Me-4-SO₂Me-3-(4,5-dihydro-isoxazol-3-yl)Ph | 1,2,4-triazol-1-yl | CF₃ | |
| 2277 | 2-Me-4-SO₂Me-3-(4,5-dihydro-isoxazol-3-yl)Ph | imidazol-2-yl | H | |
| 2278 | 2-Me-4-SO₂Me-3-(4,5-dihydro-isoxazol-3-yl)Ph | imidazol-2-yl | methyl | |
| 2279 | 2-Me-4-SO₂Me-3-(4,5-dihydro-isoxazol-3-yl)Ph | imidazol-2-yl | i-propyl | |
| 2280 | 2-Me-4-SO₂Me-3-(4,5-dihydro-isoxazol-3-yl)Ph | imidazol-2-yl | cyclopropyl | |
| 2281 | 2-Me-4-SO₂Me-3-(4,5-dihydro-isoxazol-3-yl)Ph | imidazol-2-yl | CF₃ | |
| 2282 | 2-Me-4-SO₂Me-3-(4,5-dihydro-isoxazol-3-yl)Ph | imidazol-1-yl | H | |
| 2283 | 2-Me-4-SO₂Me-3-(4,5-dihydro-isoxazol-3-yl)Ph | imidazol-1-yl | methyl | |
| 2284 | 2-Me-4-SO₂Me-3-(4,5-dihydro-isoxazol-3-yl)Ph | imidazol-1-yl | i-propyl | |
| 2285 | 2-Me-4-SO₂Me-3-(4,5-dihydro-isoxazol-3-yl)Ph | imidazol-1-yl | cyclopropyl | |
| 2286 | 2-Me-4-SO₂Me-3-(4,5-dihydro-isoxazol-3-yl)Ph | imidazol-1-yl | CF₃ | |
| 2287 | 2-Me-4-SO₂Me-3-(4,5-dihydro-isoxazol-3-yl)Ph | imidazol-4-yl | H | |
| 2288 | 2-Me-4-SO₂Me-3-(4,5-dihydro-isoxazol-3-yl)Ph | imidazol-4-yl | methyl | |
| 2289 | 2-Me-4-SO₂Me-3-(4,5-dihydro-isoxazol-3-yl)Ph | imidazol-4-yl | i-propyl | |
| 2290 | 2-Me-4-SO₂Me-3-(4,5-dihydro-isoxazol-3-yl)Ph | imidazol-4-yl | cyclopropyl | |
| 2291 | 2-Me-4-SO₂Me-3-(4,5-dihydro-isoxazol-3-yl)Ph | imidazol-4-yl | CF₃ | |
| 2292 | 2-Me-4-SO₂Me-3-(4,5-dihydro-isoxazol-3-yl)Ph | thiazol-2-yl | H | |
| 2293 | 2-Me-4-SO₂Me-3-(4,5-dihydro-isoxazol-3-yl)Ph | thiazol-2-yl | methyl | |
| 2294 | 2-Me-4-SO₂Me- | thiazol-2-yl | i-propyl | |

-continued

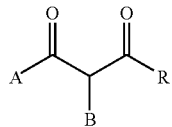

(I)

| Compound N | A | B | R | m.p. (° C.) |
|---|---|---|---|---|
| 2295 | 2-Me-4-SO$_2$Me-3-(4,5-dihydro-isoxazol-3-yl)Ph | thiazol-2-yl | cyclopropyl | |
| 2296 | 2-Me-4-SO$_2$Me-3-(4,5-dihydro-isoxazol-3-yl)Ph | thiazol-2-yl | CF$_3$ | |
| 2297 | 2-Me-4-SO$_2$Me-3-(4,5-dihydro-isoxazol-3-yl)Ph | 4-methylthiazol-2-yl | H | |
| 2298 | 2-Me-4-SO$_2$Me-3-(4,5-dihydro-isoxazol-3-yl)Ph | 4-methylthiazol-2-yl | methyl | |
| 2299 | 2-Me-4-SO$_2$Me-3-(4,5-dihydro-isoxazol-3-yl)Ph | 4-methylthiazol-2-yl | i-propyl | |
| 2300 | 2-Me-4-SO$_2$Me-3-(4,5-dihydro-isoxazol-3-yl)Ph | 4-methylthiazol-2-yl | cyclopropyl | |
| 2301 | 2-Me-4-SO$_2$Me-3-(4,5-dihydro-isoxazol-3-yl)Ph | 4-methylthiazol-2-yl | CF$_3$ | |
| 2302 | 2-Me-4-SO$_2$Me-3-(4,5-dihydro-isoxazol-3-yl)Ph | oxazol-2-yl | H | |
| 2303 | 2-Me-4-SO$_2$Me-3-(4,5-dihydro-isoxazol-3-yl)Ph | oxazol-2-yl | methyl | |
| 2304 | 2-Me-4-SO$_2$Me-3-(4,5-dihydro-isoxazol-3-yl)Ph | oxazol-2-yl | i-propyl | |
| 2305 | 2-Me-4-SO$_2$Me-3-(4,5-dihydro-isoxazol-3-yl)Ph | oxazol-2-yl | cyclopropyl | |
| 2306 | 2-Me-4-SO$_2$Me-3-(4,5-dihydro-isoxazol-3-yl)Ph | oxazol-2-yl | CF$_3$ | |
| 2307 | 2-Me-4-SO$_2$Me-3-(4,5-dihydro-isoxazol-3-yl)Ph | 4,5-dimethyl-oxazol-2-yl | H | |
| 2308 | 2-Me-4-SO$_2$Me-3-(4,5-dihydro-isoxazol-3-yl)Ph | 4,5-dimethyl-oxazol-2-yl | methyl | |
| 2309 | 2-Me-4-SO$_2$Me-3-(4,5-dihydro-isoxazol-3-yl)Ph | 4,5-dimethyl-oxazol-2-yl | i-propyl | |
| 2310 | 2-Me-4-SO$_2$Me-3-(4,5-dihydro-isoxazol-3-yl)Ph | 4,5-dimethyl-oxazol-2-yl | cyclopropyl | |
| 2311 | 2-Me-4-SO$_2$Me-3-(4,5-dihydro-isoxazol-3-yl)Ph | 4,5-dimethyl-oxazol-2-yl | CF$_3$ | |
| 2312 | 2-Me-4-SO$_2$Me-3-(4,5-dihydro-isoxazol-3-yl)Ph | 2-oxazolin-2-yl | H | |
| 2313 | 2-Me-4-SO$_2$Me-3-(4,5-dihydro-isoxazol-3-yl)Ph | 2-oxazolin-2-yl | methyl | |
| 2314 | 2-Me-4-SO$_2$Me-3-(4,5-dihydro-isoxazol-3-yl)Ph | 2-oxazolin-2-yl | i-propyl | |
| 2315 | 2-Me-4-SO$_2$Me-3-(4,5-dihydro-isoxazol-3-yl)Ph | 2-oxazolin-2-yl | cyclopropyl | |
| 2316 | 2-Me-4-SO$_2$Me-3-(4,5-dihydro-isoxazol-3-yl)Ph | 2-oxazolin-2-yl | CF$_3$ | |
| 2317 | 2-Me-4-SO$_2$Me-3-(4,5-dihydro-isoxazol-3-yl)Ph | 4,4-dimethyl-2-oxazolin-2-yl | H | |

-continued

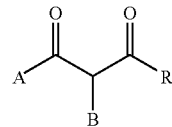

(I)

| Compound N | A | B | R | m.p. (° C.) |
|---|---|---|---|---|
| 2318 | 2-Me-4-SO$_2$Me-3-(4,5-dihydro-isoxazol-3-yl)Ph | 4,4-dimethyl-2-oxazolin-2-yl | methyl | |
| 2319 | 2-Me-4-SO$_2$Me-3-(4,5-dihydro-isoxazol-3-yl)Ph | 4,4-dimethyl-2-oxazolin-2-yl | i-propyl | |
| 2320 | 2-Me-4-SO$_2$Me-3-(4,5-dihydro-isoxazol-3-yl)Ph | 4,4-dimethyl-2-oxazolin-2-yl | cyclopropyl | |
| 2321 | 2-Me-4-SO$_2$Me-3-(4,5-dihydro-isoxazol-3-yl)Ph | 4,4-dimethyl-2-oxazolin-2-yl | CF$_3$ | |
| 2322 | 2-Me-4-SO$_2$Me-3-(4,5-dihydro-isoxazol-3-yl)Ph | 1,2,4-thiadiazol-5-yl | H | |
| 2323 | 2-Me-4-SO$_2$Me-3-(4,5-dihydro-isoxazol-3-yl)Ph | 1,2,4-thiadiazol-5-yl | methyl | |
| 2324 | 2-Me-4-SO$_2$Me-3-(4,5-dihydro-isoxazol-3-yl)Ph | 1,2,4-thiadiazol-5-yl | i-propyl | |
| 2325 | 2-Me-4-SO$_2$Me-3-(4,5-dihydro-isoxazol-3-yl)Ph | 1,2,4-thiadiazol-5-yl | cyclopropyl | |
| 2326 | 2-Me-4-SO$_2$Me-3-(4,5-dihydro-isoxazol-3-yl)Ph | 1,2,4-thiadiazol-5-yl | CF$_3$ | |
| 2327 | 2-Me-4-SO$_2$Me-3-(4,5-dihydro-isoxazol-3-yl)Ph | 3-methyl-1,2,4-thiadiazol-5-yl | H | |
| 2328 | 2-Me-4-SO$_2$Me-3-(4,5-dihydro-isoxazol-3-yl)Ph | 3-methyl-1,2,4-thiadiazol-5-yl | methyl | |
| 2329 | 2-Me-4-SO$_2$Me-3-(4,5-dihydro-isoxazol-3-yl)Ph | 3-methyl-1,2,4-thiadiazol-5-yl | i-propyl | |
| 2330 | 2-Me-4-SO$_2$Me-3-(4,5-dihydro-isoxazol-3-yl)Ph | 3-methyl-1,2,4-thiadiazol-5-yl | cyclopropyl | |
| 2331 | 2-Me-4-SO$_2$Me-3-(4,5-dihydro-isoxazol-3-yl)Ph | 3-methyl-1,2,4-thiadiazol-5-yl | CF$_3$ | |
| 2332 | 2-Me-4-SO$_2$Me-3-(4,5-dihydro-isoxazol-3-yl)Ph | 3-trifluoromethyl-1,2,4-thiadiazol-5-yl | H | |
| 2333 | 2-Me-4-SO$_2$Me-3-(4,5-dihydro-isoxazol-3-yl)Ph | 3-trifluoromethyl-1,2,4-thiadiazol-5-yl | methyl | |
| 2134 | 2-Me-4-SO$_2$Me-3-(4,5-dihydro-isoxazol-3-yl)Ph | 3-trifluoromethyl-1,2,4-thiadiazol-5-yl | i-propyl | |
| 2335 | 2-Me-4-SO$_2$Me-3-(4,5-dihydro-isoxazol-3-yl)Ph | 3-trifluoromethyl-1,2,4-thiadiazol-5-yl | cyclopropyl | |
| 2336 | 2-Me-4-SO$_2$Me-3-(4,5-dihydro-isoxazol-3-yl)Ph | 3-trifluoromethyl-1,2,4-thiadiazol-5-yl | CF$_3$ | |
| 2337 | 2-Me-4-SO$_2$Me-3-(4,5-dihydro-isoxazol-3-yl)Ph | 1,2,4-thiadiazol-3-yl | H | |
| 2338 | 2-Me-4-SO$_2$Me-3-(4,5-dihydro-isoxazol-3-yl)Ph | 1,2,4-thiadiazol-3-yl | methyl | |
| 2339 | 2-Me-4-SO$_2$Me-3-(4,5-dihydro-isoxazol-3-yl)Ph | 1,2,4-thiadiazol-3-yl | i-propyl | |
| 2340 | 2-Me-4-SO$_2$Me-3-(4,5-dihydro-isoxazol-3-yl)Ph | 1,2,4-thiadiazol-3-yl | cyclopropyl | |

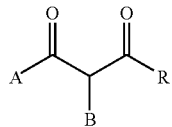

(I)

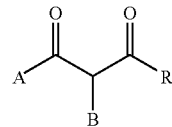

(I)

| Compound N | A | B | R | m.p. (° C.) |
|---|---|---|---|---|
| 2341 | 2-Me-4-SO₂Me-3-(4,5-dihydro-isoxazol-3-yl)Ph | 3-(4,5-dihydro-isoxazol-3-yl)-1,2,4-thiadiazol-3-yl | CF₃ | |
| 2342 | 2-Me-4-SO₂Me-3-(4,5-dihydro-isoxazol-3-yl)Ph | 5-methyl-1,2,4-thiadiazol-3-yl | H | |
| 2343 | 2-Me-4-SO₂Me-3-(4,5-dihydro-isoxazol-3-yl)Ph | 5-methyl-1,2,4-thiadiazol-3-yl | methyl | |
| 2344 | 2-Me-4-SO₂Me-3-(4,5-dihydro-isoxazol-3-yl)Ph | 5-methyl-1,2,4-thiadiazol-3-yl | i-propyl | |
| 2345 | 2-Me-4-SO₂Me-3-(4,5-dihydro-isoxazol-3-yl)Ph | 5-methyl-1,2,4-thiadiazol-3-yl | cyclopropyl | |
| 2346 | 2-Me-4-SO₂Me-3-(4,5-dihydro-isoxazol-3-yl)Ph | 5-methyl-1,2,4-thiadiazol-3-yl | CF₃ | |
| 2347 | 2-Me-4-SO₂Me-3-(4,5-dihydro-isoxazol-3-yl)Ph | 5-trifluoromethyl-1,2,4-thiadiazol-3-yl | H | |
| 2348 | 2-Me-4-SO₂Me-3-(4,5-dihydro-isoxazol-3-yl)Ph | 5-trifluoromethyl-1,2,4-thiadiazol-3-yl | methyl | |
| 2349 | 2-Me-4-SO₂Me-3-(4,5-dihydro-isoxazol-3-yl)Ph | 5-trifluoromethyl-1,2,4-thiadiazol-3-yl | i-propyl | |
| 2350 | 2-Me-4-SO₂Me-3-(4,5-dihydro-isoxazol-3-yl)Ph | 5-trifluoromethyl-1,2,4-thiadiazol-3-yl | cyclopropyl | |
| 2351 | 2-Me-4-SO₂Me-3-(4,5-dihydro-isoxazol-3-yl)Ph | 5-trifluoromethyl-1,2,4-thiadiazol-3-yl | CF₃ | |
| 2352 | 2-Me-4-SO₂Me-3-(4,5-dihydro-isoxazol-3-yl)Ph | 1,3,4-thiadiazol-2-yl | H | |
| 2353 | 2-Me-4-SO₂Me-3-(4,5-dihydro-isoxazol-3-yl)Ph | 1,3,4-thiadiazol-2-yl | methyl | |
| 2354 | 2-Me-4-SO₂Me-3-(4,5-dihydro-isoxazol-3-yl)Ph | 1,3,4-thiadiazol-2-yl | i-propyl | |
| 2355 | 2-Me-4-SO₂Me-3-(4,5-dihydro-isoxazol-3-yl)Ph | 1,3,4-thiadiazol-2-yl | cyclopropyl | |
| 2356 | 2-Me-4-SO₂Me-3-(4,5-dihydro-isoxazol-3-yl)Ph | 1,3,4-thiadiazol-2-yl | CF₃ | |
| 2357 | 2-Me-4-SO₂Me-3-(4,5-dihydro-isoxazol-3-yl)Ph | 5-methylsulfonyl-1,3,4-thiadiazol-2-yl | H | |
| 2358 | 2-Me-4-SO₂Me-3-(4,5-dihydro-isoxazol-3-yl)Ph | 5-methylsulfonyl-1,3,4-thiadiazol-2-yl | methyl | |
| 2359 | 2-Me-4-SO₂Me-3-(4,5-dihydro-isoxazol-3-yl)Ph | 5-methylsulfonyl-1,3,4-thiadiazol-2-yl | i-propyl | |
| 2360 | 2-Me-4-SO₂Me-3-(4,5-dihydro-isoxazol-3-yl)Ph | 5-methylsulfonyl-1,3,4-thiadiazol-2-yl | cyclopropyl | |
| 2361 | 2-Me-4-SO₂Me-3-(4,5-dihydro-isoxazol-3-yl)Ph | 5-methylsulfonyl-1,3,4-thiadiazol-2-yl | CF₃ | |
| 2362 | 2-Me-4-SO₂Me-3-(4,5-dihydro-isoxazol-3-yl)Ph | 5-methyl-1,3,4-thiadiazol-2-yl | H | |
| 2363 | 2-Me-4-SO₂Me- | 5-methyl-1,3,4-thiadiazol-2-yl | methyl | |
| 2364 | 2-Me-4-SO₂Me-3-(4,5-dihydro-isoxazol-3-yl)Ph | 5-methyl-1,3,4-thiadiazol-2-yl | i-propyl | |
| 2365 | 2-Me-4-SO₂Me-3-(4,5-dihydro-isoxazol-3-yl)Ph | 5-methyl-1,3,4-thiadiazol-2-yl | cyclopropyl | |
| 2366 | 2-Me-4-SO₂Me-3-(4,5-dihydro-isoxazol-3-yl)Ph | 5-methyl-1,3,4-thiadiazol-2-yl | CF₃ | |
| 2367 | 2-Me-4-SO₂Me-3-(4,5-dihydro-isoxazol-3-yl)Ph | benzoxazol-2-yl | H | |
| 2368 | 2-Me-4-SO₂Me-3-(4,5-dihydro-isoxazol-3-yl)Ph | benzoxazol-2-yl | methyl | |
| 2369 | 2-Me-4-SO₂Me-3-(4,5-dihydro-isoxazol-3-yl)Ph | benzoxazol-2-yl | i-propyl | |
| 2370 | 2-Me-4-SO₂Me-3-(4,5-dihydro-isoxazol-3-yl)Ph | benzoxazol-2-yl | cyclopropyl | |
| 2371 | 2-Me-4-SO₂Me-3-(4,5-dihydro-isoxazol-3-yl)Ph | benzoxazol-2-yl | CF₃ | |
| 2372 | 2-Me-4-SO₂Me-3-(4,5-dihydro-isoxazol-3-yl)Ph | 6-methyl-benzoxazol-2-yl | H | |
| 2373 | 2-Me-4-SO₂Me-3-(4,5-dihydro-isoxazol-3-yl)Ph | 6-methyl-benzoxazol-2-yl | methyl | |
| 2374 | 2-Me-4-SO₂Me-3-(4,5-dihydro-isoxazol-3-yl)Ph | 6-methyl-benzoxazol-2-yl | i-propyl | |
| 2375 | 2-Me-4-SO₂Me-3-(4,5-dihydro-isoxazol-3-yl)Ph | 6-methyl-benzoxazol-2-yl | cyclopropyl | |
| 2376 | 2-Me-4-SO₂Me-3-(4,5-dihydro-isoxazol-3-yl)Ph | 6-methyl-benzoxazol-2-yl | CF₃ | |
| 2377 | 2-Me-4-SO₂Me-3-(4,5-dihydro-isoxazol-3-yl)Ph | benzothiazol-2-yl | H | |
| 2378 | 2-Me-4-SO₂Me-3-(4,5-dihydro-isoxazol-3-yl)Ph | benzothiazol-2-yl | methyl | |
| 2379 | 2-Me-4-SO₂Me-3-(4,5-dihydro-isoxazol-3-yl)Ph | benzothiazol-2-yl | i-propyl | |
| 2380 | 2-Me-4-SO₂Me-3-(4,5-dihydro-isoxazol-3-yl)Ph | benzothiazol-2-yl | cyclopropyl | |
| 2381 | 2-Me-4-SO₂Me-3-(4,5-dihydro-isoxazol-3-yl)Ph | benzothiazol-2-yl | CF₃ | |
| 2382 | 2-Me-4-SO₂Me-3-(4,5-dihydro-isoxazol-3-yl)Ph | pyrazol-1-yl | H | |
| 2383 | 2-Me-4-SO₂Me-3-(4,5-dihydro-isoxazol-3-yl)Ph | pyrazol-1-yl | methyl | |
| 2385 | 2-Me-4-SO₂Me-3-(4,5-dihydro-isoxazol-3-yl)Ph | pyrazol-1-yl | cyclopropyl | |
| 2386 | 2-Me-4-SO₂Me-3-(4,5-dihydro-isoxazol-3-yl)Ph | pyrazol-1-yl | CF₃ | |
| 2387 | 2-Me-4-SO₂Me- | pyrazol-3-yl | H | |

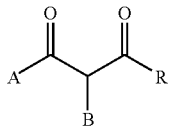

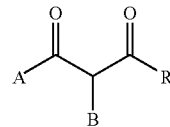

| Compound N | A | B | R | m.p. (°C.) |
|---|---|---|---|---|
| 2388 | 2-Me-4-SO₂Me-3-(4,5-dihydro-isoxazol-3-yl)Ph | pyrazol-3-yl | methyl | |
| 2389 | 2-Me-4-SO₂Me-3-(4,5-dihydro-isoxazol-3-yl)Ph | pyrazol-3-yl | i-propyl | |
| 2390 | 2-Me-4-SO₂Me-3-(4,5-dihydro-isoxazol-3-yl)Ph | pyrazol-3-yl | cyclopropyl | |
| 2391 | 2-Me-4-SO₂Me-3-(4,5-dihydro-isoxazol-3-yl)Ph | pyrazol-3-yl | CF₃ | |
| 2392 | 2-Me-4-SO₂Me-3-(4,5-dihydro-isoxazol-3-yl)Ph | 1-methylpyrazol-3-yl | H | |
| 2393 | 2-Me-4-SO₂Me-3-(4,5-dihydro-isoxazol-3-yl)Ph | 1-methylpyrazol-3-yl | methyl | |
| 2394 | 2-Me-4-SO₂Me-3-(4,5-dihydro-isoxazol-3-yl)Ph | 1-methylpyrazol-3-yl | i-propyl | |
| 2395 | 2-Me-4-SO₂Me-3-(4,5-dihydro-isoxazol-3-yl)Ph | 1-methylpyrazol-3-yl | cyclopropyl | |
| 2396 | 2-Me-4-SO₂Me-3-(4,5-dihydro-isoxazol-3-yl)Ph | 1-methylpyrazol-3-yl | CF₃ | |
| 2397 | 2-Me-4-SO₂Me-3-(4,5-dihydro-isoxazol-3-yl)Ph | tetrazol-1-yl | H | |
| 2398 | 2-Me-4-SO₂Me-3-(4,5-dihydro-isoxazol-3-yl)Ph | tetrazol-1-yl | methyl | |
| 2399 | 2-Me-4-SO₂Me-3-(4,5-dihydro-isoxazol-3-yl)Ph | tetrazol-1-yl | i-propyl | |
| 2400 | 2-Me-4-SO₂Me-3-(4,5-dihydro-isoxazol-3-yl)Ph | tetrazol-1-yl | cyclopropyl | |
| 2401 | 2-Me-4-SO₂Me-3-(4,5-dihydro-isoxazol-3-yl)Ph | tetrazol-1-yl | CF₃ | |
| 2402 | 2-Me-4-SO₂Me-3-(4,5-dihydro-isoxazol-3-yl)Ph | 5-methyltetrazol-1-yl | H | |
| 2403 | 2-Me-4-SO₂Me-3-(4,5-dihydro-isoxazol-3-yl)Ph | 5-methyltetrazol-1-yl | methyl | |
| 2404 | 2-Me-4-SO₂Me-3-(4,5-dihydro-isoxazol-3-yl)Ph | 5-methyltetrazol-1-yl | i-propyl | |
| 2405 | 2-Me-4-SO₂Me-3-(4,5-dihydro-isoxazol-3-yl)Ph | 5-methyltetrazol-1-yl | cyclopropyl | |
| 2406 | 2-Me-4-SO₂Me-3-(4,5-dihydro-isoxazol-3-yl)Ph | 5-methyltetrazol-1-yl | CF₃ | |
| 2407 | 2-Me-4-SO₂Me-3-(4,5-dihydro-isoxazol-3-yl)Ph | tetrazol-2-yl | H | |
| 2408 | 2-Me-4-SO₂Me-3-(4,5-dihydro-isoxazol-3-yl)Ph | tetrazol-2-yl | methyl | |
| 2409 | 2-Me-4-SO₂Me-3-(4,5-dihydro-isoxazol-3-yl)Ph | tetrazol-2-yl | i-propyl | |
| 2410 | 2-Me-4-SO₂Me-3-(4,5-dihydro-isoxazol-3-yl)Ph | tetrazol-2-yl | cyclopropyl | |
| 2411 | 2-Me-4-SO₂Me-3-(4,5-dihydro-isoxazol-3-yl)Ph | tetrazol-2-yl | CF₃ | |
| 2412 | 2-Me-4-SO₂Me-3-(4,5-dihydro-isoxazol-3-yl)Ph | 5-methyltetrazol-2-yl | H | |
| 2413 | 2-Me-4-SO₂Me-3-(4,5-dihydro-isoxazol-3-yl)Ph | 5-methyltetrazol-2-yl | methyl | |
| 2414 | 2-Me-4-SO₂Me-3-(4,5-dihydro-isoxazol-3-yl)Ph | 5-methyltetrazol-2-yl | i-propyl | |
| 2415 | 2-Me-4-SO₂Me-3-(4,5-dihydro-isoxazol-3-yl)Ph | 5-methyltetrazol-2-yl | cyclopropyl | |
| 2416 | 2-Me-4-SO₂Me-3-(4,5-dihydro-isoxazol-3-yl)Ph | 5-methyltetrazol-2-yl | CF₃ | |
| 2417 | 2-Me-4-SO₂Me-3-(4,5-dihydro-isoxazol-3-yl)Ph | 1-methyltetrazol-5-yl | H | |
| 2418 | 2-Me-4-SO₂Me-3-(4,5-dihydro-isoxazol-3-yl)Ph | 1-methyltetrazol-5-yl | methyl | |
| 2419 | 2-Me-4-SO₂Me-3-(4,5-dihydro-isoxazol-3-yl)Ph | 1-methyltetrazol-5-yl | i-propyl | |
| 2420 | 2-Me-4-SO₂Me-3-(4,5-dihydro-isoxazol-3-yl)Ph | 1-methyltetrazol-5-yl | cyclopropyl | |
| 2421 | 2-Me-4-SO₂Me-3-(4,5-dihydro-isoxazol-3-yl)Ph | 1-methyltetrazol-5-yl | CF₃ | |
| 2422 | 2-Me-4-SO₂Me-3-(4,5-dihydro-isoxazol-3-yl)Ph | 2-methyltetrazol-5-yl | H | |
| 2423 | 2-Me-4-SO₂Me-3-(4,5-dihydro-isoxazol-3-yl)Ph | 2-methyltetrazol-5-yl | methyl | |
| 2424 | 2-Me-4-SO₂Me-3-(4,5-dihydro-isoxazol-3-yl)Ph | 2-methyltetrazol-5-yl | i-propyl | |
| 2425 | 2-Me-4-SO₂Me-3-(4,5-dihydro-isoxazol-3-yl)Ph | 2-methyltetrazol-5-yl | cyclopropyl | |
| 2426 | 2-Me-4-SO₂Me-3-(4,5-dihydro-isoxazol-3-yl)Ph | 2-methyltetrazol-5-yl | CF₃ | |
| 2427 | 2-Me-4-SO₂Me-3-(4,5-dihydro-isoxazol-3-yl)Ph | pyridin-2-yl | H | |
| 2428 | 2-Me-4-SO₂Me-3-(4,5-dihydro-isoxazol-3-yl)Ph | pyridin-2-yl | methyl | |
| 2429 | 2-Me-4-SO₂Me-3-(4,5-dihydro-isoxazol-3-yl)Ph | pyridin-2-yl | i-propyl | |
| 2430 | 2-Me-4-SO₂Me-3-(4,5-dihydro-isoxazol-3-yl)Ph | pyridin-2-yl | cyclopropyl | |
| 2431 | 2-Me-4-SO₂Me-3-(4,5-dihydro-isoxazol-3-yl)Ph | pyridin-2-yl | CF₃ | |
| 2432 | 2-Me-4-SO₂Me-3-(4,5-dihydro-isoxazol-3-yl)Ph | pyridin-4-yl | H | |
| 2433 | 2-Me-4-SO₂Me-3-(4,5-dihydro-isoxazol-3-yl)Ph | pyridin-4-yl | methyl | |

-continued

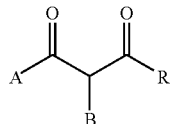

(I)

| Compound N | A | B | R | m.p. (° C.) |
|---|---|---|---|---|
| 2434 | 2-Me-4-SO₂Me-3-(4,5-dihydro-isoxazol-3-yl)Ph | pyridin-4-yl | i-propyl | |
| 2435 | 2-Me-4-SO₂Me-3-(4,5-dihydro-isoxazol-3-yl)Ph | pyridin-4-yl | cyclopropyl | |
| 2436 | 2-Me-4-SO₂Me-3-(4,5-dihydro-isoxazol-3-yl)Ph | pyridin-4-yl | CF₃ | |
| 2437 | 2-Me-4-SO₂Me-3-(4,5-dihydro-isoxazol-3-yl)Ph | pyridin-3-yl | H | |
| 2438 | 2-Me-4-SO₂Me-3-(4,5-dihydro-isoxazol-3-yl)Ph | pyridin-3-yl | methyl | |
| 2439 | 2-Me-4-SO₂Me-3-(4,5-dihydro-isoxazol-3-yl)Ph | pyridin-3-yl | i-propyl | |
| 2440 | 2-Me-4-SO₂Me-3-(4,5-dihydro-isoxazol-3-yl)Ph | pyridin-3-yl | cyclopropyl | |
| 2441 | 2-Me-4-SO₂Me-3-(4,5-dihydro-isoxazol-3-yl)Ph | pyridin-3-yl | CF₃ | |
| 2442 | 2-Me-4-SO₂Me-3-(4,5-dihydro-isoxazol-3-yl)Ph | 3-nitropyridin-4-yl | H | |
| 2443 | 2-Me-4-SO₂Me-3-(4,5-dihydro-isoxazol-3-yl)Ph | 3-nitropyridin-4-yl | methyl | |
| 2444 | 2-Me-4-SO₂Me-3-(4,5-dihydro-isoxazol-3-yl)Ph | 3-nitropyridin-4-yl | i-propyl | |
| 2445 | 2-Me-4-SO₂Me-3-(4,5-dihydro-isoxazol-3-yl)Ph | 3-nitropyridin-4-yl | cyclopropyl | |
| 2446 | 2-Me-4-SO₂Me-3-(4,5-dihydro-isoxazol-3-yl)Ph | 3-nitropyridin-4-yl | CF₃ | |
| 2447 | 2-Me-4-SO₂Me-3-(4,5-dihydro-isoxazol-3-yl)Ph | 5-cyanopyridin-2-yl | H | |
| 2448 | 2-Me-4-SO₂Me-3-(4,5-dihydro-isoxazol-3-yl)Ph | 5-cyanopyridin-2-yl | methyl | |
| 2449 | 2-Me-4-SO₂Me-3-(4,5-dihydro-isoxazol-3-yl)Ph | 5-cyanopyridin-2-yl | i-propyl | |
| 2450 | 2-Me-4-SO₂Me-3-(4,5-dihydro-isoxazol-3-yl)Ph | 5-cyanopyridin-2-yl | cyclopropyl | |
| 2451 | 2-Me-4-SO₂Me-3-(4,5-dihydro-isoxazol-3-yl)Ph | 5-cyanopyridin-2-yl | CF₃ | |
| 2452 | 2-Me-4-SO₂Me-3-(4,5-dihydro-isoxazol-3-yl)Ph | 5-trifluoromethylpyridin-2-yl | H | |
| 2453 | 2-Me-4-SO₂Me-3-(4,5-dihydro-isoxazol-3-yl)Ph | 5-trifluoromethylpyridin-2-yl | methyl | |
| 2454 | 2-Me-4-SO₂Me-3-(4,5-dihydro-isoxazol-3-yl)Ph | 5-trifluoromethylpyridin-2-yl | i-propyl | |
| 2455 | 2-Me-4-SO₂Me-3-(4,5-dihydro-isoxazol-3-yl)Ph | 5-trifluoromethylpyridin-2-yl | cyclopropyl | |
| 2456 | 2-Me-4-SO₂Me-3-(4,5-dihydro-isoxazol-3-yl)Ph | 5-trifluoromethylpyridin-2-yl | CF₃ | |
| 2457 | 2-Me-4-SO₂Me-3-(4,5-dihydro-isoxazol-3-yl)Ph | pyrimidin-2-yl | H | |
| 2458 | 2-Me-4-SO₂Me-3-(4,5-dihydro-isoxazol-3-yl)Ph | pyrimidin-2-yl | methyl | |
| 2459 | 2-Me-4-SO₂Me-3-(4,5-dihydro-isoxazol-3-yl)Ph | pyrimidin-2-yl | i-propyl | |
| 2460 | 2-Me-4-SO₂Me-3-(4,5-dihydro-isoxazol-3-yl)Ph | pyrimidin-2-yl | cyclopropyl | |
| 2461 | 2-Me-4-SO₂Me-3-(4,5-dihydro-isoxazol-3-yl)Ph | pyrimidin-2-yl | CF₃ | |
| 2462 | 2-Me-4-SO₂Me-3-(4,5-dihydro-isoxazol-3-yl)Ph | pyrimidin-4-yl | H | |
| 2463 | 2-Me-4-SO₂Me-3-(4,5-dihydro-isoxazol-3-yl)Ph | pyrimidin-4-yl | methyl | |
| 2464 | 2-Me-4-SO₂Me-3-(4,5-dihydro-isoxazol-3-yl)Ph | pyrimidin-4-yl | i-propyl | |
| 2465 | 2-Me-4-SO₂Me-3-(4,5-dihydro-isoxazol-3-yl)Ph | pyrimidin-4-yl | cyclopropyl | |
| 2466 | 2-Me-4-SO₂Me-3-(4,5-dihydro-isoxazol-3-yl)Ph | pyrimidin-4-yl | CF₃ | |
| 2467 | 2-Me-4-SO₂Me-3-(4,5-dihydro-isoxazol-3-yl)Ph | 6-chloro-pyrimidin-4-yl | methyl | |
| 2468 | 2-Me-4-SO₂Me-3-(4,5-dihydro-isoxazol-3-yl)Ph | 6-chloro-pyrimidin-4-yl | i-propyl | |
| 2469 | 2-Me-4-SO₂Me-3-(4,5-dihydro-isoxazol-3-yl)Ph | 6-chloro-pyrimidin-4-yl | cyclopropyl | |
| 2470 | 2-Me-4-SO₂Me-3-(4,5-dihydro-isoxazol-3-yl)Ph | 6-chloro-pyrimidin-4-yl | CF₃ | |
| 2471 | 2-Me-4-SO₂Me-3-(4,5-dihydro-isoxazol-3-yl)Ph | pyridazin-3-yl | H | |
| 2472 | 2-Me-4-SO₂Me-3-(4,5-dihydro-isoxazol-3-yl)Ph | pyridazin-3-yl | methyl | |
| 2473 | 2-Me-4-SO₂Me-3-(4,5-dihydro-isoxazol-3-yl)Ph | pyridazin-3-yl | i-propyl | |
| 2474 | p2-Me-4-SO₂Me-3-(4,5-dihydro-isoxazol-3-yl)Ph | yridazin-3-yl | cyclopropyl | |
| 2475 | p2-Me-4-SO₂Me-3-(4,5-dihydro-isoxazol-3-yl)Ph | yridazin-3-yl | CF₃ | |
| 2476 | 2-Me-4-SO₂Me-3-(4,5-dihydro-isoxazol-3-yl)Ph | 6-chloro-pyridazin-3-yl | methyl | |
| 2477 | 2-Me-4-SO₂Me-3-(4,5-dihydro-isoxazol-3-yl)Ph | 6-chloro-pyridazin-3-yl | i-propyl | |
| 2478 | 2-Me-4-SO₂Me-3-(4,5-dihydro-isoxazol-3-yl)Ph | 6-chloro-pyridazin-3-yl | cyclopropyl | |
| 2479 | 2-Me-4-SO₂Me- | 6-chloro- | CF₃ | |

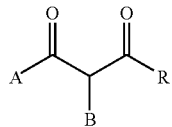

(I)

| Compound N | A | B | R | m.p. (° C.) |
|---|---|---|---|---|
|  | 3-(4,5-dihydro-isoxazol-3-yl)Ph | pyridazin-3-yl |  |  |
| 2480 | 2-Me-4-SO₂Me-3-(4,5-dihydro-isoxazol-3-yl)Ph | pyrazin-2-yl | methyl |  |
| 2481 | 2-Me-4-SO₂Me-3-(4,5-dihydro-isoxazol-3-yl)Ph | pyrazin-2-yl | i-propyl |  |
| 2482 | 2-Me-4-SO₂Me-3-(4,5-dihydro-isoxazol-3-yl)Ph | pyrazin-2-yl | cyclopropyl |  |
| 2483 | 2-Me-4-SO₂Me-3-(4,5-dihydro-isoxazol-3-yl)Ph | pyrazin-2-yl | CF₃ |  |
| 2484 | 2-Me-4-SO₂Me-3-(4,5-dihydro-isoxazol-3-yl)Ph | triazin-2-yl | methyl |  |
| 2485 | 2-Me-4-SO₂Me-3-(4,5-dihydro-isoxazol-3-yl)Ph | triazin-2-yl | i-propyl |  |
| 2486 | 2-Me-4-SO₂Me-3-(4,5-dihydro-isoxazol-3-yl)Ph | triazin-2-yl | cyclopropyl |  |
| 2487 | 2-Me-4-SO₂Me-3-(4,5-dihydro-isoxazol-3-yl)Ph | triazin-2-yl | CF₃ |  |
| 2488 | 2-Me-4-SO₂Me-3-(4,5-dihydro-isoxazol-3-yl)Ph | quinolin-2-yl | methyl |  |
| 2489 | 2-Me-4-SO₂Me-3-(4,5-dihydro-isoxazol-3-yl)Ph | quinolin-2-yl | i-propyl |  |
| 2490 | 2-Me-4-SO₂Me-3-(4,5-dihydro-isoxazol-3-yl)Ph | quinolin-2-yl | cyclopropyl |  |
| 2491 | 2-Me-4-SO₂Me-3-(4,5-dihydro-isoxazol-3-yl)Ph | quinolin-2-yl | CF₃ |  |
| 2492 | 2-Me-4-SO₂Me-3-(4,5-dihydro-isoxazol-3-yl)Ph | 4,4,6-trimethyl-5,6-dihydro-1,3(4H)-oxazin-2-yl | H |  |
| 2493 | 2-Me-4-SO₂Me-3-(4,5-dihydro-isoxazol-3-yl)Ph | 4,4,6-trimethyl-5,6-dihydro-1,3(4H)-oxazin-2-yl | methyl |  |
| 2494 | 2-Me-4-SO₂Me-3-(4,5-dihydro-isoxazol-3-yl)Ph | 4,4,6-trimethyl-5,6-dihydro-1,3(4H)-oxazin-2-yl | i-propyl |  |
| 2495 | 2-Me-4-SO₂Me-3-(4,5-dihydro-isoxazol-3-yl)Ph | 4,4,6-trimethyl-5,6-dihydro-1,3(4H)-oxazin-2-yl | cyclopropyl |  |
| 2496 | 2-Me-4-SO₂Me-3-(4,5-dihydro-isoxazol-3-yl)Ph | 4,4,6-trimethyl-5,6-dihydro-1,3(4H)-oxazin-2-yl | CF₃ |  |
| 2497 | 2-Me-4-SO₂Me-3-(4,5-dihydro-isoxazol-3-yl)Ph | 2-oxazolidinon-3-yl | H |  |
| 2498 | 2-Me-4-SO₂Me-3-(4,5-dihydro-isoxazol-3-yl)Ph | 2-oxazolidinon-3-yl | methyl |  |
| 2499 | 2-Me-4-SO₂Me-3-(4,5-dihydro-isoxazol-3-yl)Ph | 2-oxazolidinon-3-yl | i-propyl |  |
| 2500 | 2-Me-4-SO₂Me-3-(4,5-dihydro-isoxazol-3-yl)Ph | 2-oxazolidinon-3-yl | cyclopropyl |  |
| 2501 | 2-Me-4-SO₂Me-3-(4,5-dihydro-isoxazol-3-yl)Ph | 2-oxazolidinon-3-yl | CF₃ |  |
| 2502 | 2-Me-4-SO₂Me-3-(4,5-dihydro-isoxazol-3-yl)Ph | 2-pyrrolidinon-1-yl | methyl |  |
| 2503 | 2-Me-4-SO₂Me-3-(4,5-dihydro-isoxazol-3-yl)Ph | 2-pyrrolidinon-1-yl | i-propyl |  |
| 2504 | 2-Me-4-SO₂Me-3-(4,5-dihydro-isoxazol-3-yl)Ph | 2-pyrrolidinon-1-yl | cyclopropyl |  |
| 2505 | 2-Me-4-SO₂Me-3-(4,5-dihydro-isoxazol-3-yl)Ph | 2-pyrrolidinon-1-yl | CF₃ |  |
| 2506 | 2-Me-4-SO₂Me-3-(4,5-dihydro-isoxazol-3-yl)Ph | 3-methylisoxazol-5-yl | methyl |  |
| 2507 | 2-Me-4-SO₂Me-3-(4,5-dihydro-isoxazol-3-yl)Ph | 3-methylisoxazol-5-yl | i-propyl |  |
| 2508 | 2-Me-4-SO₂Me-3-(4,5-dihydro-isoxazol-3-yl)Ph | 3-methylisoxazol-5-yl | cyclopropyl |  |
| 2509 | 2-Me-4-SO₂Me-3-(4,5-dihydro-isoxazol-3-yl)Ph | 3-methylisoxazol-5-yl | CF₃ |  |
| 2510 | 2-Me-4-SO₂Me-3-(4,5-dihydro-isoxazol-3-yl)Ph | 2-NO₂-4-SO₂MePh | H |  |
| 2511 | 2-Me-4-SO₂Me-3-(4,5-dihydro-isoxazol-3-yl)Ph | 2-NO₂-4-SO₂MePh | methyl |  |
| 2512 | 2-Me-4-SO₂Me-3-(4,5-dihydro-isoxazol-3-yl)Ph | 2-NO₂-4-SO₂MePh | i-propyl |  |
| 2513 | 2-Me-4-SO₂Me-3-(4,5-dihydro-isoxazol-3-yl)Ph | 2-NO₂-4-SO₂MePh | cyclopropyl |  |
| 2514 | 2-Me-4-SO₂Me-3-(4,5-dihydro-isoxazol-3-yl)Ph | 2-NO₂-4-SO₂MePh | CF₃ |  |
| 2515 | 2-Me-4-SO₂Me-3-(4,5-dihydro-isoxazol-3-yl)Ph | 2-Cl-4-SO₂MePh | H |  |
| 2516 | 2-Me-4-SO₂Me-3-(4,5-dihydro-isoxazol-3-yl)Ph | 2-Cl-4-SO₂MePh | methyl |  |
| 2517 | 2-Me-4-SO₂Me-3-(4,5-dihydro-isoxazol-3-yl)Ph | 2-Cl-4-SO₂MePh | i-propyl |  |
| 2518 | 2-Me-4-SO₂Me-3-(4,5-dihydro-isoxazol-3-yl)Ph | 2-Cl-4-SO₂MePh | cyclopropyl |  |
| 2519 | 2-Me-4-SO₂Me-3-(4,5-dihydro-isoxazol-3-yl)Ph | 2-Cl-4-SO₂MePh | CF₃ |  |
| 2520 | 2-Me-4-SO₂Me-3-(4,5-dihydro-isoxazol-3-yl)Ph | 2-NO₂-4-CF₃Ph | H |  |
| 2521 | 2-Me-4-SO₂Me-3-(4,5-dihydro-isoxazol-3-yl)Ph | 2-NO₂-4-CF₃Ph | methyl |  |
| 2522 | 2-Me-4-SO₂Me-3-(4,5-dihydro-isoxazol-3-yl)Ph | 2-NO₂-4-CF₃Ph | i-propyl |  |
| 2523 | 2-Me-4-SO₂Me-3-(4,5-dihydro-isoxazol-3-yl)Ph | 2-NO₂-4-CF₃Ph | cyclopropyl |  |
| 2524 | 2-Me-4-SO₂Me-3-(4,5-dihydro-isoxazol-3-yl)Ph | 2-NO₂-4-CF₃Ph | CF₃ |  |
| 2525 | 2-Me-4-SO₂Me- | 2-NO₂-4-ClPh | H |  |

-continued

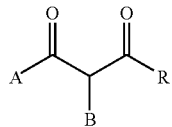

(I)

| Compound N | A | B | R | m.p. (° C.) |
|---|---|---|---|---|
| 2526 | 2-Me-4-SO₂Me-3-(4,5-dihydro-isoxazol-3-yl)Ph | 2-NO₂-4-ClPh | methyl | |
| 2527 | 2-Me-4-SO₂Me-3-(4,5-dihydro-isoxazol-3-yl)Ph | 2-NO₂-4-ClPh | i-propyl | |
| 2528 | 2-Me-4-SO₂Me-3-(4,5-dihydro-isoxazol-3-yl)Ph | 2-NO₂-4-ClPh | cyclopropyl | |
| 2529 | 2-Me-4-SO₂Me-3-(4,5-dihydro-isoxazol-3-yl)Ph | 2-NO₂-4-ClPh | CF₃ | |
| 2530 | 2-Me-4-SO₂Me-3-(4,5-dihydro-isoxazol-3-yl)Ph | 2-Cl-4-NO₂Ph | H | |
| 2531 | 2-Me-4-SO₂Me-3-(4,5-dihydro-isoxazol-3-yl)Ph | 2-Cl-4-NO₂Ph | methyl | |
| 2532 | 2-Me-4-SO₂Me-3-(4,5-dihydro-isoxazol-3-yl)Ph | 2-Cl-4-NO₂Ph | i-propyl | |
| 2533 | 2-Me-4-SO₂Me-3-(4,5-dihydro-isoxazol-3-yl)Ph | 2-Cl-4-NO₂Ph | cyclopropyl | |
| 2534 | 2-Me-4-SO₂Me-3-(4,5-dihydro-isoxazol-3-yl)Ph | 2-Cl-4-NO₂Ph | CF₃ | |
| 2535 | 2-Me-4-SO₂Me-3-(4,5-dihydro-isoxazol-3-yl)Ph | 2,4-(NO₂)₂Ph | H | |
| 2536 | 2-Me-4-SO₂Me-3-(4,5-dihydro-isoxazol-3-yl)Ph | 2,4-(NO₂)₂Ph | methyl | |
| 2537 | 2-Me-4-SO₂Me-3-(4,5-dihydro-isoxazol-3-yl)Ph | 2,4-(NO₂)₂Ph | i-propyl | |
| 2538 | 2-Me-4-SO₂Me-3-(4,5-dihydro-isoxazol-3-yl)Ph | 2,4-(NO₂)₂Ph | cyclopropyl | |
| 2539 | 2-Me-4-SO₂Me-3-(4,5-dihydro-isoxazol-3-yl)Ph | 2,4-(NO₂)₂Ph | CF₃ | |
| 2540 | 2-Me-4-SO₂Me-3-(4,5-dihydro-isoxazol-3-yl)Ph | 4-F-3-NO₂Ph | H | |
| 2541 | 2-Me-4-SO₂Me-3-(4,5-dihydro-isoxazol-3-yl)Ph | 4-F-3-NO₂Ph | methyl | |
| 2542 | 2-Me-4-SO₂Me-3-(4,5-dihydro-isoxazol-3-yl)Ph | 4-F-3-NO₂Ph | i-propyl | |
| 2543 | 2-Me-4-SO₂Me-3-(4,5-dihydro-isoxazol-3-yl)Ph | 4-F-3-NO₂Ph | cyclopropyl | |
| 2544 | 2-Me-4-SO₂Me-3-(4,5-dihydro-isoxazol-3-yl)Ph | 4-F-3-NO₂Ph | CF₃ | |
| 2545 | 2-Me-4-SO₂Me-3-(4,5-dihydro-isoxazol-3-yl)Ph | 3,5-(CF₃)₂Ph | H | |
| 2546 | 2-Me-4-SO₂Me-3-(4,5-dihydro-isoxazol-3-yl)Ph | 3,5-(CF₃)₂Ph | methyl | |
| 2547 | 2-Me-4-SO₂Me-3-(4,5-dihydro-isoxazol-3-yl)Ph | 3,5-(CF₃)₂Ph | i-propyl | |
| 2548 | 2-Me-4-SO₂Me-3-(4,5-dihydro-isoxazol-3-yl)Ph | 3,5-(CF₃)₂Ph | cyclopropyl | |
| 2549 | 2-Me-4-SO₂Me-3-(4,5-dihydro-isoxazol-3-yl)Ph | 3,5-(CF₃)₂Ph | CF₃ | |
| 2550 | 2-Me-4-SO₂Me-3-(4,5-dihydro-isoxazol-3-yl)Ph | 2-SO₂Me-4-CF₃Ph | H | |
| 2551 | 2-Me-4-SO₂Me-3-(4,5-dihydro-isoxazol-3-yl)Ph | 2-SO₂Me-4-CF₃Ph | methyl | |
| 2552 | 2-Me-4-SO₂Me-3-(4,5-dihydro-isoxazol-3-yl)Ph | 2-SO₂Me-4-CF₃Ph | i-propyl | |
| 2553 | 2-Me-4-SO₂Me-3-(4,5-dihydro-isoxazol-3-yl)Ph | 2-SO₂Me-4-CF₃Ph | cyclopropyl | |
| 2554 | 2-Me-4-SO₂Me-3-(4,5-dihydro-isoxazol-3-yl)Ph | 2-SO₂Me-4-CF₃Ph | CF₃ | |
| 2555 | 4,4-dioxide-8-Me-2,3-dihydro-1,4-benzoxathiin-7-yl | 1,2,4-oxadiazol-5-yl | H | |
| 2556 | 4,4-dioxide-8-Me-2,3-dihydro-1,4-benzoxathiin-7-yl | 1,2,4-oxadiazol-5-yl | methyl | |
| 2557 | 4,4-dioxide-8-Me-2,3-dihydro-1,4-benzoxathiin-7-yl | 1,2,4-oxadiazol-5-yl | i-propyl | |
| 2558 | 4,4-dioxide-8-Me-2,3-dihydro-1,4-benzoxathiin-7-yl | 1,2,4-oxadiazol-5-yl | cyclopropyl | |
| 2559 | 4,4-dioxide-8-Me-2,3-dihydro-1,4-benzoxathiin-7-yl | 1,2,4-oxadiazol-5-yl | CF₃ | |
| 2560 | 4,4-dioxide-8-Me-2,3-dihydro-1,4-benzoxathiin-7-yl | 3-methyl-1,2,4-oxadiazol-5-yl | H | |
| 2561 | 4,4-dioxide-8-Me-2,3-dihydro-1,4-benzoxathiin-7-yl | 3-methyl-1,2,4-oxadiazol-5-yl | methyl | |
| 2562 | 4,4-dioxide-8-Me-2,3-dihydro-1,4-benzoxathiin-7-yl | 3-methyl-1,2,4-oxadiazol-5-yl | i-propyl | |
| 2563 | 4,4-dioxide-8-Me-2,3-dihydro-1,4-benzoxathiin-7-yl | 3-methyl-1,2,4-oxadiazol-5-yl | cyclopropyl | |
| 2564 | 4,4-dioxide-8-Me-2,3-dihydro-1,4-benzoxathiin-7-yl | 3-methyl-1,2,4-oxadiazol-5-yl | CF₃ | |
| 2565 | 4,4-dioxide-8-Me-2,3-dihydro-1,4-benzoxathiin-7-yl | 3-trifluoromethyl-1,2,4-oxadiazol-5-yl | H | |
| 2566 | 4,4-dioxide-8-Me-2,3-dihydro-1,4-benzoxathiin-7-yl | 3-trifluoromethyl-1,2,4-oxadiazol-5-yl | methyl | |
| 2567 | 4,4-dioxide-8- | 3-trifluoromethyl- | i-propyl | |

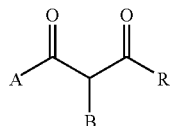

(I)

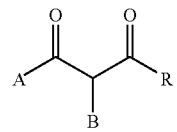

(I)

| Compound N | A | B | R | m.p. (°C.) |
|---|---|---|---|---|
|  | Me-2,3-dihydro-1,4-benzoxathiin-7-yl | 1,2,4-oxadiazol-5-yl |  |  |
| 2568 | 4,4-dioxide-8-Me-2,3-dihydro-1,4-benzoxathiin-7-yl | 3-trifluoromethyl-1,2,4-oxadiazol-5-yl | cyclopro |  |
| 2569 | 4,4-dioxide-8-Me-2,3-dihydro-1,4-benzoxathiin-7-yl | 3-trifluoromethyl-1,2,4-oxadiazol-5-yl | $CF_3$ |  |
| 2570 | 4,4-dioxide-8-Me-2,3-dihydro-1,4-benzoxathiin-7-yl | 1,2,4-oxadiazol-3-yl | H |  |
| 2571 | 4,4-dioxide-8-Me-2,3-dihydro-1,4-benzoxathiin-7-yl | 1,2,4-oxadiazol-3-yl | methyl |  |
| 2572 | 4,4-dioxide-8-Me-2,3-dihydro-1,4-benzoxathiin-7-yl | 1,2,4-oxadiazol-3-yl | i-propyl |  |
| 2573 | 4,4-dioxide-8-Me-2,3-dihydro-1,4-benzoxathiin-7-yl | 1,2,4-oxadiazol-3-yl | cycloprop |  |
| 2574 | 4,4-dioxide-8-Me-2,3-dihydro-1,4-benzoxathiin-7-yl | 1,2,4-oxadiazol-3-yl | $CF_3$ |  |
| 2575 | 4,4-dioxide-8-Me-2,3-dihydro-1,4-benzoxathiin-7-yl | 5-methyl-1,2,4-oxadiazol-3-yl | H |  |
| 2576 | 4,4-dioxide-8-Me-2,3-dihydro-1,4-benzoxathiin-7-yl | 5-methyl-1,2,4-oxadiazol-3-yl | methyl |  |
| 2577 | 4,4-dioxide-8-Me-2,3-dihydro-1,4-benzoxathiin-7-yl | 5-methyl-1,2,4-oxadiazol-3-yl | i-propyl |  |
| 2578 | 4,4-dioxide-8-Me-2,3-dihydro-1,4-benzoxathiin-7-yl | 5-methyl-1,2,4-oxadiazol-3-yl | cycloprop |  |
| 2579 | 4,4-dioxide-8-Me-2,3-dihydro-1,4-benzoxathiin-7-yl | 5-methyl-1,2,4-oxadiazol-3-yl | $CF_3$ |  |
| 2580 | 4,4-dioxide-8-Me-2,3-dihydro-1,4-benzoxathiin-7-yl | 5-trifluoromethyl-1,2,4-oxadiazol-3-yl | H |  |
| 2581 | 4,4-dioxide-8-Me-2,3-dihydro-1,4-benzoxathiin-7-yl | 5-trifluoromethyl-1,2,4-oxadiazol-3-yl | methyl |  |
| 2582 | 4,4-dioxide-8-Me-2,3-dihydro-1,4-benzoxathiin-7-yl | 5-trifluoromethyl-1,2,4-oxadiazol-3-yl | i-propyl |  |
| 2583 | 4,4-dioxide-8-Me-2,3-dihydro-1,4-benzoxathiin-7-yl | 5-trifluoromethyl-1,2,4-oxadiazol-3-yl | cycloprop |  |
| 2584 | 4,4-dioxide-8-Me-2,3-dihydro-1,4-benzoxathiin-7-yl | 5-trifluoromethyl-1,2,4-oxadiazol-3-yl |  |  |
| 2585 | 4,4-dioxide-8-Me-2,3-dihydro-1,4-benzoxathiin-7-yl | 5-chloro-1,2,4-oxadiazol-3-yl | H |  |
| 2586 | 4,4-dioxide-8-Me-2,3-dihydro-1,4-benzoxathiin-7-yl | 5-chloro-1,2,4-oxadiazol-3-yl | methyl |  |
| 2587 | 4,4-dioxide-8-Me-2,3-dihydro-1,4-benzoxathiin-7-yl | 5-chloro-1,2,4-oxadiazol-3-yl | i-propyl |  |
| 2588 | 4,4-dioxide-8-Me-2,3-dihydro-1,4-benzoxathiin-7-yl | 5-chloro-1,2,4-oxadiazol-3-yl | cycloprop |  |
| 2589 | 4,4-dioxide-8-Me-2,3-dihydro-1,4-benzoxathiin-7-yl | 5-chloro-1,2,4-oxadiazol-3-yl | $CF_3$ |  |
| 2590 | 4,4-dioxide-8-Me-2,3-dihydro-1,4-benzoxathiin-7-yl | 1,3,4-oxadiazol-2-yl | H |  |
| 2591 | 4,4-dioxide-8-Me-2,3-dihydro-1,4-benzoxathiin-7-yl | 1,3,4-oxadiazol-2-yl | methyl |  |
| 2592 | 4,4-dioxide-8-Me-2,3-dihydro-1,4-benzoxathiin-7-yl | 1,3,4-oxadiazol-2-yl | i-propyl |  |
| 2593 | 4,4-dioxide-8-Me-2,3-dihydro-1,4-benzoxathiin-7-yl | 1,3,4-oxadiazol-2-yl | cycloprop |  |
| 2594 | 4,4-dioxide-8-Me-2,3-dihydro-1,4-benzoxathiin-7-yl | 1,3,4-oxadiazol-2-yl | $CF_3$ |  |
| 2595 | 4,4-dioxide-8-Me-2,3-dihydro-1,4-benzoxathiin-7-yl | 5-methylsulfonyl-1,3,4-oxadiazol-2-yl | H |  |
| 2596 | 4,4-dioxide-8-Me-2,3-dihydro-1,4-benzoxathiin-7-yl | 5-methylsulfonyl-1,3,4-oxadiazol-2-yl | methyl |  |
| 2597 | 4,4-dioxide-8-Me-2,3-dihydro-1,4-benzoxathiin-7-yl | 5-methylsulfonyl-1,3,4-oxadiazol-2-yl | i-propyl |  |
| 2598 | 4,4-dioxide-8-Me-2,3-dihydro-1,4-benzoxathiin-7-yl | 5-methylsulfonyl-1,3,4-oxadiazol-2-yl | cyclopropyl |  |
| 2599 | 4,4-dioxide-8-Me-2,3-dihydro-1,4-benzoxathiin-7-yl | 5-methylsulfonyl-1,3,4-oxadiazol-2-yl | $CF_3$ |  |
| 2600 | 4,4-dioxide-8-Me-2,3-dihydro-1,4-benzoxathiin-7-yl | 5-methyl-1,3,4-oxadiazol-2-yl | H |  |
| 2601 | 4,4-dioxide-8-Me-2,3-dihydro-1,4-benzoxathiin-7-yl | 5-methyl-1,3,4-oxadiazol-2-yl | methyl |  |

-continued

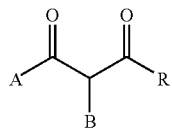
(I)

| Compound N | A | B | R | m.p. (° C.) |
|---|---|---|---|---|
| | 7-yl | | | |
| 2602 | 4,4-dioxide-8-Me-2,3-dihydro-1,4-benzoxathiin-7-yl | 5-methyl-1,3,4-oxadiazol-2-yl | i-propyl | |
| 2603 | 4,4-dioxide-8-Me-2,3-dihydro-1,4-benzoxathiin-7-yl | 5-methyl-1,3,4-oxadiazol-2-yl | cyclopropyl | |
| 2604 | 4,4-dioxide-8-Me-2,3-dihydro-1,4-benzoxathiin-7-yl | 5-methyl-1,3,4-oxadiazol-2-yl | $CF_3$ | |
| 2605 | 4,4-dioxide-8-Me-2,3-dihydro-1,4-benzoxathiin-7-yl | 5-trifluoromethyl-1,3,4-oxadiazol-2-yl | H | |
| 2606 | 4,4-dioxide-8-Me-2,3-dihydro-1,4-benzoxathiin-7-yl | 5-trifluoromethyl-1,3,4-oxadiazol-2-yl | methyl | |
| 2607 | 4,4-dioxide-8-Me-2,3-dihydro-1,4-benzoxathiin-7-yl | 5-trifluoromethyl-1,3,4-oxadiazol-2-yl | i-propyl | |
| 2608 | 4,4-dioxide-8-Me-2,3-dihydro-1,4-benzoxathiin-7-yl | 5-trifluoromethyl-1,3,4-oxadiazol-2-yl | cyclopropyl | |
| 2609 | 4,4-dioxide-8-Me-2,3-dihydro-1,4-benzoxathiin-7-yl | 5-trifluoromethyl-1,3,4-oxadiazol-2-yl | $CF_3$ | |
| 2610 | 4,4-dioxide-8-Me-2,3-dihydro-1,4-benzoxathiin-7-yl | 1,2,3-triazol-4-yl | H | |
| 2611 | 4,4-dioxide-8-Me-2,3-dihydro-1,4-benzoxathiin-7-yl | 1,2,3-triazol-4-yl | methyl | |
| 2612 | 4,4-dioxide-8-Me-2,3-dihydro-1,4-benzoxathiin-7-yl | 1,2,3-triazol-4-yl | i-propyl | |
| 2613 | 4,4-dioxide-8-Me-2,3-dihydro-1,4-benzoxathiin-7-yl | 1,2,3-triazol-4-yl | cyclopropyl | |
| 2614 | 4,4-dioxide-8-Me-2,3-dihydro-1,4-benzoxathiin-7-yl | 1,2,3-triazol-4-yl | $CF_3$ | |
| 2615 | 4,4-dioxide-8-Me-2,3-dihydro-1,4-benzoxathiin-7-yl | 1-methyl-1,2,3-triazol-4-yl | H | |
| 2616 | 4,4-dioxide-8-Me-2,3-dihydro-1,4-benzoxathiin-7-yl | 1-methyl-1,2,3-triazol-4-yl | methyl | |
| 2617 | 4,4-dioxide-8-Me-2,3-dihydro-1,4-benzoxathiin-7-yl | 1-methyl-1,2,3-triazol-4-yl | i-propyl | |
| 2618 | 4,4-dioxide-8-Me-2,3-dihydro-1,4-benzoxathiin-7-yl | 1-methyl-1,2,3-triazol-4-yl | cyclopropyl | |

-continued

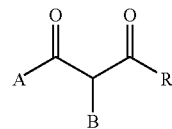
(I)

| Compound N | A | B | R | m.p. (° C.) |
|---|---|---|---|---|
| 2619 | 4,4-dioxide-8-Me-2,3-dihydro-1,4-benzoxathiin-7-yl | 1-methyl-1,2,3-triazol-4-yl | $CF_3$ | |
| 2620 | 4,4-dioxide-8-Me-2,3-dihydro-1,4-benzoxathiin-7-yl | 2-methyl-1,2,3-triazol-4-yl | H | |
| 2621 | 4,4-dioxide-8-Me-2,3-dihydro-1,4-benzoxathiin-7-yl | 2-methyl-1,2,3-triazol-4-yl | methyl | |
| 2622 | 4,4-dioxide-8-Me-2,3-dihydro-1,4-benzoxathiin-7-yl | 2-methyl-1,2,3-triazol-4-yl | i-propyl | |
| 2623 | 4,4-dioxide-8-Me-2,3-dihydro-1,4-benzoxathiin-7-yl | 2-methyl-1,2,3-triazol-4-yl | cyclopropyl | |
| 2624 | 4,4-dioxide-8-Me-2,3-dihydro-1,4-benzoxathiin-7-yl | 2-methyl-1,2,3-triazol-4-yl | $CF_3$ | |
| 2625 | 4,4-dioxide-8-Me-2,3-dihydro-1,4-benzoxathiin-7-yl | 1,2,3-triazol-1-yl | H | |
| 2626 | 4,4-dioxide-8-Me-2,3-dihydro-1,4-benzoxathiin-7-yl | 1,2,3-triazol-1-yl | methyl | |
| 2627 | 4,4-dioxide-8-Me-2,3-dihydro-1,4-benzoxathiin-7-yl | 1,2,3-triazol-1-yl | i-propyl | |
| 2628 | 4,4-dioxide-8-Me-2,3-dihydro-1,4-benzoxathiin-7-yl | 1,2,3-triazol-1-yl | cyclopropyl | |
| 2629 | 4,4-dioxide-8-Me-2,3-dihydro-1,4-benzoxathiin-7-yl | 1,2,3-triazol-1-yl | $CF_3$ | |
| 2630 | 4,4-dioxide-8-Me-2,3-dihydro-1,4-benzoxathiin-7-yl | 1,2,3-triazol-2-yl | H | |
| 2631 | 4,4-dioxide-8-Me-2,3-dihydro-1,4-benzoxathiin-7-yl | 1,2,3-triazol-2-yl | methyl | |
| 2632 | 4,4-dioxide-8-Me-2,3-dihydro-1,4-benzoxathiin-7-yl | 1,2,3-triazol-2-yl | i-propyl | |
| 2633 | 4,4-dioxide-8-Me-2,3-dihydro-1,4-benzoxathiin-7-yl | 1,2,3-triazol-2-yl | cyclopropyl | |
| 2634 | 4,4-dioxide-8-Me-2,3-dihydro-1,4-benzoxathiin-7-yl | 1,2,3-triazol-2-yl | $CF_3$ | |
| 2635 | 4,4-dioxide-8-Me-2,3-dihydro-1,4-benzoxathiin-7-yl | 1,2,4-triazol-1-yl | H | |
| 2636 | 4,4-dioxide-8- | 1,2,4-triazol-1-yl | methyl | |

-continued

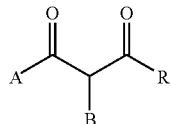

(I)

| Compound N | A | B | R | m.p. (° C.) |
|---|---|---|---|---|
| | Me-2,3-dihydro-1,4-benzoxathiin-7-yl | | | |
| 2637 | 4,4-dioxide-8-Me-2,3-dihydro-1,4-benzoxathiin-7-yl | 1,2,4-triazol-1-yl | i-propyl | |
| 2638 | 4,4-dioxide-8-Me-2,3-dihydro-1,4-benzoxathiin-7-yl | 1,2,4-triazol-1-yl | cyclopropyl | |
| 2639 | 4,4-dioxide-8-Me-2,3-dihydro-1,4-benzoxathiin-7-yl | 1,2,4-triazol-1-yl | CF$_3$ | |
| 2640 | 4,4-dioxide-8-Me-2,3-dihydro-1,4-benzoxathiin-7-yl | imidazol-2-yl | H | |
| 2641 | 4,4-dioxide-8-Me-2,3-dihydro-1,4-benzoxathiin-7-yl | imidazol-2-yl | methyl | |
| 2642 | 4,4-dioxide-8-Me-2,3-dihydro-1,4-benzoxathiin-7-yl | imidazol-2-yl | i-propyl | |
| 2643 | 4,4-dioxide-8-Me-2,3-dihydro-1,4-benzoxathiin-7-yl | imidazol-2-yl | cyclopropyl | |
| 2644 | 4,4-dioxide-8-Me-2,3-dihydro-1,4-benzoxathiin-7-yl | imidazol-2-yl | CF$_3$ | |
| 2645 | 4,4-dioxide-8-Me-2,3-dihydro-1,4-benzoxathiin-7-yl | imidazol-1-yl | H | |
| 2646 | 4,4-dioxide-8-Me-2,3-dihydro-1,4-benzoxathiin-7-yl | imidazol-1-yl | methyl | |
| 2647 | 4,4-dioxide-8-Me-2,3-dihydro-1,4-benzoxathiin-7-yl | imidazol-1-yl | i-propyl | |
| 2648 | 4,4-dioxide-8-Me-2,3-dihydro-1,4-benzoxathiin-7-yl | imidazol-1-yl | cyclopropyl | |
| 2649 | 4,4-dioxide-8-Me-2,3-dihydro-1,4-benzoxathiin-7-yl | imidazol-1-yl | CF$_3$ | |
| 2650 | 4,4-dioxide-8-Me-2,3-dihydro-1,4-benzoxathiin-7-yl | imidazol-4-yl | H | |
| 2651 | 4,4-dioxide-8-Me-2,3-dihydro-1,4-benzoxathiin-7-yl | imidazol-4-yl | methyl | |
| 2652 | 4,4-dioxide-8-Me-2,3-dihydro-1,4-benzoxathiin-7-yl | imidazol-4-yl | i-propyl | |
| 2653 | 4,4-dioxide-8-Me-2,3-dihydro-1,4-benzoxathiin-7-yl | imidazol-4-yl | cyclopropyl | |

-continued

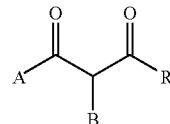

(I)

| Compound N | A | B | R | m.p. (° C.) |
|---|---|---|---|---|
| | 1,4-benzoxathiin-7-yl | | | |
| 2654 | 4,4-dioxide-8-Me-2,3-dihydro-1,4-benzoxathiin-7-yl | imidazol-4-yl | CF$_3$ | |
| 2655 | 4,4-dioxide-8-Me-2,3-dihydro-1,4-benzoxathiin-7-yl | thiazol-2-yl | H | |
| 2656 | 4,4-dioxide-8-Me-2,3-dihydro-1,4-benzoxathiin-7-yl | thiazol-2-yl | methyl | |
| 2657 | 4,4-dioxide-8-Me-2,3-dihydro-1,4-benzoxathiin-7-yl | thiazol-2-yl | i-propyl | |
| 2658 | 4,4-dioxide-8-Me-2,3-dihydro-1,4-benzoxathiin-7-yl | thiazol-2-yl | cyclopropyl | |
| 2659 | 4,4-dioxide-8-Me-2,3-dihydro-1,4-benzoxathiin-7-yl | thiazol-2-yl | CF$_3$ | |
| 2660 | 4,4-dioxide-8-Me-2,3-dihydro-1,4-benzoxathiin-7-yl | 4-methylthiazol-2-yl | H | |
| 2661 | 4,4-dioxide-8-Me-2,3-dihydro-1,4-benzoxathiin-7-yl | 4-methylthiazol-2-yl | methyl | |
| 2662 | 4,4-dioxide-8-Me-2,3-dihydro-1,4-benzoxathiin-7-yl | 4-methylthiazol-2-yl | i-propyl | |
| 2663 | 4,4-dioxide-8-Me-2,3-dihydro-1,4-benzoxathiin-7-yl | 4-methylthiazol-2-yl | cyclopropyl | |
| 2664 | 4,4-dioxide-8-Me-2,3-dihydro-1,4-benzoxathiin-7-yl | 4-methylthiazol-2-yl | CF$_3$ | |
| 2665 | 4,4-dioxide-8-Me-2,3-dihydro-1,4-benzoxathiin-7-yl | oxazol-2-yl | H | |
| 2666 | 4,4-dioxide-8-Me-2,3-dihydro-1,4-benzoxathiin-7-yl | oxazol-2-yl | methyl | |
| 2667 | 4,4-dioxide-8-Me-2,3-dihydro-1,4-benzoxathiin-7-yl | oxazol-2-yl | i-propyl | |
| 2668 | 4,4-dioxide-8-Me-2,3-dihydro-1,4-benzoxathiin-7-yl | oxazol-2-yl | cyclopropyl | |
| 2669 | 4,4-dioxide-8-Me-2,3-dihydro-1,4-benzoxathiin-7-yl | oxazol-2-yl | CF$_3$ | |
| 2670 | 4,4-dioxide-8-Me-2,3-dihydro-1,4-benzoxathiin-7-yl | 4,5-dimethyl-oxazol-2-yl | H | |

-continued

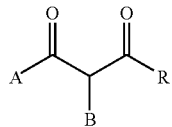

(I)

| Compound N | A | B | R | m.p. (° C.) |
|---|---|---|---|---|
| 2671 | 4,4-dioxide-8-Me-2,3-dihydro-1,4-benzoxathiin-7-yl | 4,5-dimethyl-oxazol-2-yl | methyl | |
| 2672 | 4,4-dioxide-8-Me-2,3-dihydro-1,4-benzoxathiin-7-yl | 4,5-dimethyl-oxazol-2-yl | i-propyl | |
| 2673 | 4,4-dioxide-8-Me-2,3-dihydro-1,4-benzoxathiin-7-yl | 4,5-dimethyl-oxazol-2-yl | cyclopropyl | |
| 2674 | 4,4-dioxide-8-Me-2,3-dihydro-1,4-benzoxathiin-7-yl | 4,5-dimethyl-oxazol-2-yl | $CF_3$ | |
| 2675 | 4,4-dioxide-8-Me-2,3-dihydro-1,4-benzoxathiin-7-yl | 2-oxazolin-2-yl | H | |
| 2676 | 4,4-dioxide-8-Me-2,3-dihydro-1,4-benzoxathiin-7-yl | 2-oxazolin-2-yl | methyl | |
| 2677 | 4,4-dioxide-8-Me-2,3-dihydro-1,4-benzoxathiin-7-yl | 2-oxazolin-2-yl | i-propyl | |
| 2678 | 4,4-dioxide-8-Me-2,3-dihydro-1,4-benzoxathiin-7-yl | 2-oxazolin-2-yl | cyclopropyl | |
| 2679 | 4,4-dioxide-8-Me-2,3-dihydro-1,4-benzoxathiin-7-yl | 2-oxazolin-2-yl | $CF_3$ | |
| 2680 | 4,4-dioxide-8-Me-2,3-dihydro-1,4-benzoxathiin-7-yl | 4,4-dimethyl-2-oxazol-2-yl | H | |
| 2681 | 4,4-dioxide-8-Me-2,3-dihydro-1,4-benzoxathiin-7-yl | 4,4-dimethyl-2-oxazol-2-yl | methyl | |
| 2682 | 4,4-dioxide-8-Me-2,3-dihydro-1,4-benzoxathiin-7-yl | 4,4-dimethyl-2-oxazol-2-yl | i-propyl | |
| 2683 | 4,4-dioxide-8-Me-2,3-dihydro-1,4-benzoxathiin-7-yl | 4,4-dimethyl-2-oxazol-2-yl | cyclopropyl | |
| 2684 | 4,4-dioxide-8-Me-2,3-dihydro-1,4-benzoxathiin-7-yl | 4,4-dimethyl-2-oxazol-2-yl | $CF_3$ | |
| 2685 | 4,4-dioxide-8-Me-2,3-dihydro-1,4-benzoxathiin-7-yl | 1,2,4-thiadiazol-5-yl | H | |
| 2686 | 4,4-dioxide-8-Me-2,3-dihydro-1,4-benzoxathiin-7-yl | 1,2,4-thiadiazol-5-yl | methyl | |
| 2687 | 4,4-dioxide-8-Me-2,3-dihydro-1,4-benzoxathiin-7-yl | 1,2,4-thiadiazol-5-yl | i-propyl | |

-continued

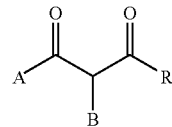

(I)

| Compound N | A | B | R | m.p. (° C.) |
|---|---|---|---|---|
| 2688 | 4,4-dioxide-8-Me-2,3-dihydro-1,4-benzoxathiin-7-yl | 1,2,4-thiadiazol-5-yl | cyclopropyl | |
| 2689 | 4,4-dioxide-8-Me-2,3-dihydro-1,4-benzoxathiin-7-yl | 1,2,4-thiadiazol-5-yl | $CF_3$ | |
| 2690 | 4,4-dioxide-8-Me-2,3-dihydro-1,4-benzoxathiin-7-yl | 3-methyl-1,2,4-thiadiazol-5-yl | H | |
| 2691 | 4,4-dioxide-8-Me-2,3-dihydro-1,4-benzoxathiin-7-yl | 3-methyl-1,2,4-thiadiazol-5-yl | methyl | |
| 2692 | 4,4-dioxide-8-Me-2,3-dihydro-1,4-benzoxathiin-7-yl | 3-methyl-1,2,4-thiadiazol-5-yl | i-propyl | |
| 2693 | 4,4-dioxide-8-Me-2,3-dihydro-1,4-benzoxathiin-7-yl | 3-methyl-1,2,4-thiadiazol-5-yl | cyclopropyl | |
| 2694 | 4,4-dioxide-8-Me-2,3-dihydro-1,4-benzoxathiin-7-yl | 3-methyl-1,2,4-thiadiazol-5-yl | $CF_3$ | |
| 2695 | 4,4-dioxide-8-Me-2,3-dihydro-1,4-benzoxathiin-7-yl | 3-trifluoromethyl-1,2,4-thiadiazol-5-yl | H | |
| 2696 | 4,4-dioxide-8-Me-2,3-dihydro-1,4-benzoxathiin-7-yl | 3-trifluoromethyl-1,2,4-thiadiazol-5-yl | methyl | |
| 2697 | 4,4-dioxide-8-Me-2,3-dihydro-1,4-benzoxathiin-7-yl | 3-trifluoromethyl-1,2,4-thiadiazol-5-yl | i-propyl | |
| 2698 | 4,4-dioxide-8-Me-2,3-dihydro-1,4-benzoxathiin-7-yl | 3-trifluoromethyl-1,2,4-thiadiazol-5-yl | cyclopropyl | |
| 2699 | 4,4-dioxide-8-Me-2,3-dihydro-1,4-benzoxathiin-7-yl | 3-trifluoromethyl-1,2,4-thiadiazol-5-yl | $CF_3$ | |
| 2700 | 4,4-dioxide-8-Me-2,3-dihydro-1,4-benzoxathiin-7-yl | 1,2,4-thiadiazol-3-yl | H | |
| 2701 | 4,4-dioxide-8-Me-2,3-dihydro-1,4-benzoxathiin-7-yl | 1,2,4-thiadiazol-3-yl | methyl | |
| 2702 | 4,4-dioxide-8-Me-2,3-dihydro-1,4-benzoxathiin-7-yl | 1,2,4-thiadiazol-3-yl | i-propyl | |
| 2703 | 4,4-dioxide-8-Me-2,3-dihydro-1,4-benzoxathiin-7-yl | 1,2,4-thiadiazol-3-yl | cyclopropyl | |
| 2704 | 4,4-dioxide-8-Me-2,3-dihydro-1,4-benzoxathiin-7-yl | 1,2,4-thiadiazol-3-yl | $CF_3$ | |
| 2705 | 4,4-dioxide-8- | 5-methyl-1,2,4- | H | |

-continued

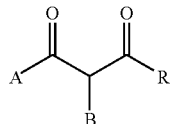

(I)

| Compound N | A | B | R | m.p. (° C.) |
|---|---|---|---|---|
| | Me-2,3-dihydro-1,4-benzoxathiin-7-yl | thiadiazol-3-yl | | |
| 2706 | 4,4-dioxide-8-Me-2,3-dihydro-1,4-benzoxathiin-7-yl | 5-methyl-1,2,4-thiadiazol-3-yl | methyl | |
| 2707 | 4,4-dioxide-8-Me-2,3-dihydro-1,4-benzoxathiin-7-yl | 5-methyl-1,2,4-thiadiazol-3-yl | i-propyl | |
| 2708 | 4,4-dioxide-8-Me-2,3-dihydro-1,4-benzoxathiin-7-yl | 5-methyl-1,2,4-thiadiazol-3-yl | cyclopropyl | |
| 2709 | 4,4-dioxide-8-Me-2,3-dihydro-1,4-benzoxathiin-7-yl | 5-methyl-1,2,4-thiadiazol-3-yl | $CF_3$ | |
| 2710 | 4,4-dioxide-8-Me-2,3-dihydro-1,4-benzoxathiin-7-yl | 5-trifluoromethyl-1,2,4-thiadiazol-3-yl | H | |
| 2711 | 4,4-dioxide-8-Me-2,3-dihydro-1,4-benzoxathiin-7-yl | 5-trifluoromethyl-1,2,4-thiadiazol-3-yl | methyl | |
| 2712 | 4,4-dioxide-8-Me-2,3-dihydro-1,4-benzoxathiin-7-yl | 5-trifluoromethyl-1,2,4-thiadiazol-3-yl | i-propyl | |
| 2713 | 4,4-dioxide-8-Me-2,3-dihydro-1,4-benzoxathiin-7-yl | 5-trifluoromethyl-1,2,4-thiadiazol-3-yl | cyclopropyl | |
| 2714 | 4,4-dioxide-8-Me-2,3-dihydro-1,4-benzoxathiin-7-yl | 5-trifluoromethyl-1,2,4-thiadiazol-3-yl | $CF_3$ | |
| 2715 | 4,4-dioxide-8-Me-2,3-dihydro-1,4-benzoxathiin-7-yl | 1,3,4-thiadiazol-2-yl | H | |
| 2716 | 4,4-dioxide-8-Me-2,3-dihydro-1,4-benzoxathiin-7-yl | 1,3,4-thiadiazol-2-yl | methyl | |
| 2717 | 4,4-dioxide-8-Me-2,3-dihydro-1,4-benzoxathiin-7-yl | 1,3,4-thiadiazol-2-yl | i-propyl | |
| 2718 | 4,4-dioxide-8-Me-2,3-dihydro-1,4-benzoxathiin-7-yl | 1,3,4-thiadiazol-2-yl | cyclopropyl | |
| 2719 | 4,4-dioxide-8-Me-2,3-dihydro-1,4-benzoxathiin-7-yl | 1,3,4-thiadiazol-2-yl | $CF_3$ | |
| 2720 | 4,4-dioxide-8-Me-2,3-dihydro-1,4-benzoxathiin-7-yl | 5-methylsulfonyl-1,3,4-thiadiazol-2-yl | H | |
| 2721 | 4,4-dioxide-8-Me-2,3-dihydro-1,4-benzoxathiin-7-yl | 5-methylsulfonyl-1,3,4-thiadiazol-2-yl | methyl | |
| 2722 | 4,4-dioxide-8-Me-2,3-dihydro-1,4-benzoxathiin-7-yl | 5-methylsulfonyl-1,3,4-thiadiazol-2-yl | i-propyl | |

-continued

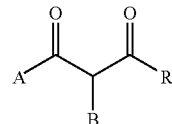

(I)

| Compound N | A | B | R | m.p. (° C.) |
|---|---|---|---|---|
| 2723 | 4,4-dioxide-8-Me-2,3-dihydro-1,4-benzoxathiin-7-yl | 5-methylsulfonyl-1,3,4-thiadiazol-2-yl | cyclopropyl | |
| 2724 | 4,4-dioxide-8-Me-2,3-dihydro-1,4-benzoxathiin-7-yl | 5-methylsulfonyl-1,3,4-thiadiazol-2-yl | $CF_3$ | |
| 2725 | 4,4-dioxide-8-Me-2,3-dihydro-1,4-benzoxathiin-7-yl | 5-methyl-1,3,4-thiadiazol-2-yl | H | |
| 2726 | 4,4-dioxide-8-Me-2,3-dihydro-1,4-benzoxathiin-7-yl | 5-methyl-1,3,4-thiadiazol-2-yl | methyl | |
| 2727 | 4,4-dioxide-8-Me-2,3-dihydro-1,4-benzoxathiin-7-yl | 5-methyl-1,3,4-thiadiazol-2-yl | i-propyl | |
| 2728 | 4,4-dioxide-8-Me-2,3-dihydro-1,4-benzoxathiin-7-yl | 5-methyl-1,3,4-thiadiazol-2-yl | cyclopropyl | |
| 2729 | 4,4-dioxide-8-Me-2,3-dihydro-1,4-benzoxathiin-7-yl | 5-methyl-1,3,4-thiadiazol-2-yl | $CF_3$ | |
| 2730 | 4,4-dioxide-8-Me-2,3-dihydro-1,4-benzoxathiin-7-yl | benzoxazol-2-yl | H | |
| 2731 | 4,4-dioxide-8-Me-2,3-dihydro-1,4-benzoxathiin-7-yl | benzoxazol-2-yl | methyl | |
| 2732 | 4,4-dioxide-8-Me-2,3-dihydro-1,4-benzoxathiin-7-yl | benzoxazol-2-yl | i-propyl | |
| 2733 | 4,4-dioxide-8-Me-2,3-dihydro-1,4-benzoxathiin-7-yl | benzoxazol-2-yl | cyclopropyl | |
| 2734 | 4,4-dioxide-8-Me-2,3-dihydro-1,4-benzoxathiin-7-yl | benzoxazol-2-yl | $CF_3$ | |
| 2735 | 4,4-dioxide-8-Me-2,3-dihydro-1,4-benzoxathiin-7-yl | 6-methyl-benzoxazol-2-yl | H | |
| 2736 | 4,4-dioxide-8-Me-2,3-dihydro-1,4-benzoxathiin-7-yl | 6-methyl-benzoxazol-2-yl | methyl | |
| 2737 | 4,4-dioxide-8-Me-2,3-dihydro-1,4-benzoxathiin-7-yl | 6-methyl-benzoxazol-2-yl | i-propyl | |
| 2738 | 4,4-dioxide-8-Me-2,3-dihydro-1,4-benzoxathiin-7-yl | 6-methyl-benzoxazol-2-yl | cyclopropyl | |
| 2739 | 4,4-dioxide-8-Me-2,3-dihydro-1,4-benzoxathiin- | 6-methyl-benzoxazol-2-yl | $CF_3$ | |

-continued

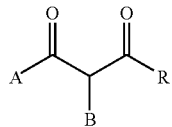

(I)

| Compound N | A | B | R | m.p. (° C.) |
|---|---|---|---|---|
| 2740 | 4,4-dioxide-8-Me-2,3-dihydro-1,4-benzoxathiin-7-yl | benzothiazol-2-yl | H | |
| 2741 | 4,4-dioxide-8-Me-2,3-dihydro-1,4-benzoxathiin-7-yl | benzothiazol-2-yl | methyl | |
| 2742 | 4,4-dioxide-8-Me-2,3-dihydro-1,4-benzoxathiin-7-yl | benzothiazol-2-yl | i-propyl | |
| 2743 | 4,4-dioxide-8-Me-2,3-dihydro-1,4-benzoxathiin-7-yl | benzothiazol-2-yl | cyclopropyl | |
| 2744 | 4,4-dioxide-8-Me-2,3-dihydro-1,4-benzoxathiin-7-yl | benzothiazol-2-yl | $CF_3$ | |
| 2745 | 4,4-dioxide-8-Me-2,3-dihydro-1,4-benzoxathiin-7-yl | pyrazol-1-yl | H | |
| 2746 | 4,4-dioxide-8-Me-2,3-dihydro-1,4-benzoxathiin-7-yl | pyrazol-1-yl | methyl | |
| 2747 | 4,4-dioxide-8-Me-2,3-dihydro-1,4-benzoxathiin-7-yl | pyrazol-1-yl | i-propyl | |
| 2748 | 4,4-dioxide-8-Me-2,3-dihydro-1,4-benzoxathiin-7-yl | pyrazol-1-yl | cyclopropyl | |
| 2749 | 4,4-dioxide-8-Me-2,3-dihydro-1,4-benzoxathiin-7-yl | pyrazol-1-yl | $CF_3$ | |
| 2750 | 4,4-dioxide-8-Me-2,3-dihydro-1,4-benzoxathiin-7-yl | pyrazol-3-yl | H | |
| 2751 | 4,4-dioxide-8-Me-2,3-dihydro-1,4-benzoxathiin-7-yl | pyrazol-3-yl | methyl | |
| 2752 | 4,4-dioxide-8-Me-2,3-dihydro-1,4-benzoxathiin-7-yl | pyrazol-3-yl | i-propyl | |
| 2753 | 4,4-dioxide-8-Me-2,3-dihydro-1,4-benzoxathiin-7-yl | pyrazol-3-yl | cyclopropyl | |
| 2754 | 4,4-dioxide-8-Me-2,3-dihydro-1,4-benzoxathiin-7-yl | pyrazol-3-yl | $CF_3$ | |
| 2755 | 4,4-dioxide-8-Me-2,3-dihydro-1,4-benzoxathiin-7-yl | 1-methylpyrazol-3-yl | H | |
| 2756 | 4,4-dioxide-8-Me-2,3-dihydro-1,4-benzoxathiin-7-yl | 1-methylpyrazol-3-yl | methyl | |

-continued

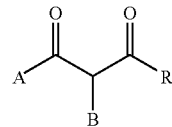

(I)

| Compound N | A | B | R | m.p. (° C.) |
|---|---|---|---|---|
| 2757 | 4,4-dioxide-8-Me-2,3-dihydro-1,4-benzoxathiin-7-yl | 1-methylpyrazol-3-yl | i-propyl | |
| 2758 | 4,4-dioxide-8-Me-2,3-dihydro-1,4-benzoxathiin-7-yl | 1-methylpyrazol-3-yl | cyclopropyl | |
| 2759 | 4,4-dioxide-8-Me-2,3-dihydro-1,4-benzoxathiin-7-yl | 1-methylpyrazol-3-yl | $CF_3$ | |
| 2760 | 4,4-dioxide-8-Me-2,3-dihydro-1,4-benzoxathiin-7-yl | tetrazol-1-yl | H | |
| 2761 | 4,4-dioxide-8-Me-2,3-dihydro-1,4-benzoxathiin-7-yl | tetrazol-1-yl | methyl | |
| 2762 | 4,4-dioxide-8-Me-2,3-dihydro-1,4-benzoxathiin-7-yl | tetrazol-1-yl | i-propyl | |
| 2763 | 4,4-dioxide-8-Me-2,3-dihydro-1,4-benzoxathiin-7-yl | tetrazol-1-yl | cyclopropyl | |
| 2764 | 4,4-dioxide-8-Me-2,3-dihydro-1,4-benzoxathiin-7-yl | tetrazol-1-yl | $CF_3$ | |
| 2765 | 4,4-dioxide-8-Me-2,3-dihydro-1,4-benzoxathiin-7-yl | 5-methyltetrazol-1-yl | H | |
| 2766 | 4,4-dioxide-8-Me-2,3-dihydro-1,4-benzoxathiin-7-yl | 5-methyltetrazol-1-yl | methyl | |
| 2767 | 4,4-dioxide-8-Me-2,3-dihydro-1,4-benzoxathiin-7-yl | 5-methyltetrazol-1-yl | i-propyl | |
| 2768 | 4,4-dioxide-8-Me-2,3-dihydro-1,4-benzoxathiin-7-yl | 5-methyltetrazol-1-yl | cyclopropyl | |
| 2769 | 4,4-dioxide-8-Me-2,3-dihydro-1,4-benzoxathiin-7-yl | 5-methyltetrazol-1-yl | $CF_3$ | |
| 2770 | 4,4-dioxide-8-Me-2,3-dihydro-1,4-benzoxathiin-7-yl | tetrazol-2-yl | H | |
| 2771 | 4,4-dioxide-8-Me-2,3-dihydro-1,4-benzoxathiin-7-yl | tetrazol-2-yl | methyl | |
| 2772 | 4,4-dioxide-8-Me-2,3-dihydro-1,4-benzoxathiin-7-yl | tetrazol-2-yl | i-propyl | |
| 2773 | 4,4-dioxide-8-Me-2,3-dihydro-1,4-benzoxathiin-7-yl | tetrazol-2-yl | cyclopropyl | |

-continued

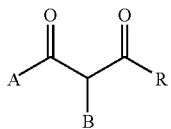 (I)

| Compound N | A | B | R | m.p. (°C.) |
|---|---|---|---|---|
| 2774 | 4,4-dioxide-8-Me-2,3-dihydro-1,4-benzoxathiin-7-yl | tetrazol-2-yl | CF$_3$ | |
| 2775 | 4,4-dioxide-8-Me-2,3-dihydro-1,4-benzoxathiin-7-yl | 5-methyltetrazol-2-yl | H | |
| 2776 | 4,4-dioxide-8-Me-2,3-dihydro-1,4-benzoxathiin-7-yl | 5-methyltetrazol-2-yl | methyl | |
| 2777 | 4,4-dioxide-8-Me-2,3-dihydro-1,4-benzoxathiin-7-yl | 5-methyltetrazol-2-yl | i-propyl | |
| 2778 | 4,4-dioxide-8-Me-2,3-dihydro-1,4-benzoxathiin-7-yl | 5-methyltetrazol-2-yl | cyclopropyl | |
| 2779 | 4,4-dioxide-8-Me-2,3-dihydro-1,4-benzoxathiin-7-yl | 5-methyltetrazol-2-yl | CF$_3$ | |
| 2780 | 4,4-dioxide-8-Me-2,3-dihydro-1,4-benzoxathiin-7-yl | 1-methyltetrazol-5-yl | H | |
| 2781 | 4,4-dioxide-8-Me-2,3-dihydro-1,4-benzoxathiin-7-yl | 1-methyltetrazol-5-yl | methyl | |
| 2782 | 4,4-dioxide-8-Me-2,3-dihydro-1,4-benzoxathiin-7-yl | 1-methyltetrazol-5-yl | i-propyl | |
| 2783 | 4,4-dioxide-8-Me-2,3-dihydro-1,4-benzoxathiin-7-yl | 1-methyltetrazol-5-yl | cyclopropyl | |
| 2784 | 4,4-dioxide-8-Me-2,3-dihydro-1,4-benzoxathiin-7-yl | 1-methyltetrazol-5-yl | CF$_3$ | |
| 2785 | 4,4-dioxide-8-Me-2,3-dihydro-1,4-benzoxathiin-7-yl | 2-methyltetrazol-5-yl | H | |
| 2786 | 4,4-dioxide-8-Me-2,3-dihydro-1,4-benzoxathiin-7-yl | 2-methyltetrazol-5-yl | methyl | |
| 2787 | 4,4-dioxide-8-Me-2,3-dihydro-1,4-benzoxathiin-7-yl | 2-methyltetrazol-5-yl | i-propyl | |
| 2788 | 4,4-dioxide-8-Me-2,3-dihydro-1,4-benzoxathiin-7-yl | 2-methyltetrazol-5-yl | cyclopropyl | |
| 2789 | 4,4-dioxide-8-Me-2,3-dihydro-1,4-benzoxathiin-7-yl | 2-methyltetrazol-5-yl | CF$_3$ | |
| 2790 | 4,4-dioxide-8-Me-2,3-dihydro-1,4-benzoxathiin-7-yl | pyridin-2-yl | H | |
| 2791 | 4,4-dioxide-8-Me-2,3-dihydro-1,4-benzoxathiin-7-yl | pyridin-2-yl | methyl | |

-continued

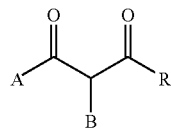 (I)

| Compound N | A | B | R | m.p. (°C.) |
|---|---|---|---|---|
| 2792 | 4,4-dioxide-8-Me-2,3-dihydro-1,4-benzoxathiin-7-yl | pyridin-2-yl | i-propyl | |
| 2793 | 4,4-dioxide-8-Me-2,3-dihydro-1,4-benzoxathiin-7-yl | pyridin-2-yl | cyclopropyl | |
| 2794 | 4,4-dioxide-8-Me-2,3-dihydro-1,4-benzoxathiin-7-yl | pyridin-2-yl | CF$_3$ | |
| 2795 | 4,4-dioxide-8-Me-2,3-dihydro-1,4-benzoxathiin-7-yl | pyridin-4-yl | H | |
| 2796 | 4,4-dioxide-8-Me-2,3-dihydro-1,4-benzoxathiin-7-yl | pyridin-4-yl | methyl | |
| 2797 | 4,4-dioxide-8-Me-2,3-dihydro-1,4-benzoxathiin-7-yl | pyridin-4-yl | i-propyl | |
| 2798 | 4,4-dioxide-8-Me-2,3-dihydro-1,4-benzoxathiin-7-yl | pyridin-4-yl | cyclopropyl | |
| 2799 | 4,4-dioxide-8-Me-2,3-dihydro-1,4-benzoxathiin-7-yl | pyridin-4-yl | CF$_3$ | |
| 2800 | 4,4-dioxide-8-Me-2,3-dihydro-1,4-benzoxathiin-7-yl | pyridin-3-yl | H | |
| 2801 | 4,4-dioxide-8-Me-2,3-dihydro-1,4-benzoxathiin-7-yl | pyridin-3-yl | methyl | |
| 2802 | 4,4-dioxide-8-Me-2,3-dihydro-1,4-benzoxathiin-7-yl | pyridin-3-yl | i-propyl | |
| 2803 | 4,4-dioxide-8-Me-2,3-dihydro-1,4-benzoxathiin-7-yl | pyridin-3-yl | cyclopropyl | |
| 2804 | 4,4-dioxide-8-Me-2,3-dihydro-1,4-benzoxathiin-7-yl | pyridin-3-yl | CF$_3$ | |
| 2805 | 4,4-dioxide-8-Me-2,3-dihydro-1,4-benzoxathiin-7-yl | 3-nitropyridin-4-yl | H | |
| 2806 | 4,4-dioxide-8-Me-2,3-dihydro-1,4-benzoxathiin-7-yl | 3-nitropyridin-4-yl | methyl | |
| 2807 | 4,4-dioxide-8-Me-2,3-dihydro-1,4-benzoxathiin-7-yl | 3-nitropyridin-4-yl | i-propyl | |
| 2808 | 4,4-dioxide-8-Me-2,3-dihydro-1,4-benzoxathiin-7-yl | 3-nitropyridin-4-yl | cyclopropyl | |

-continued

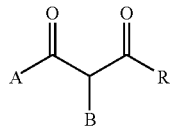

(I)

| Compound N | A | B | R | m.p. (° C.) |
|---|---|---|---|---|
| 2809 | 4,4-dioxide-8-Me-2,3-dihydro-1,4-benzoxathiin-7-yl | 3-nitropyridin-4-yl | CF$_3$ | |
| 2810 | 4,4-dioxide-8-Me-2,3-dihydro-1,4-benzoxathiin-7-yl | 5-cyanopyridin-2-yl | H | |
| 2811 | 4,4-dioxide-8-Me-2,3-dihydro-1,4-benzoxathiin-7-yl | 5-cyanopyridin-2-yl | methyl | |
| 2812 | 4,4-dioxide-8-Me-2,3-dihydro-1,4-benzoxathiin-7-yl | 5-cyanopyridin-2-yl | i-propyl | |
| 2813 | 4,4-dioxide-8-Me-2,3-dihydro-1,4-benzoxathiin-7-yl | 5-cyanopyridin-2-yl | cyclopropyl | |
| 2814 | 4,4-dioxide-8-Me-2,3-dihydro-1,4-benzoxathiin-7-yl | 5-cyanopyridin-2-yl | CF$_3$ | |
| 2815 | 4,4-dioxide-8-Me-2,3-dihydro-1,4-benzoxathiin-7-yl | 5-trifluoro-methylpyridin-2-yl | H | |
| 2816 | 4,4-dioxide-8-Me-2,3-dihydro-1,4-benzoxathiin-7-yl | 5-trifluoro-methylpyridin-2-yl | methyl | |
| 2817 | 4,4-dioxide-8-Me-2,3-dihydro-1,4-benzoxathiin-7-yl | 5-trifluoro-methylpyridin-2-yl | i-propyl | |
| 2818 | 4,4-dioxide-8-Me-2,3-dihydro-1,4-benzoxathiin-7-yl | 5-trifluoro-methylpyridin-2-yl | cyclopropyl | |
| 2819 | 4,4-dioxide-8-Me-2,3-dihydro-1,4-benzoxathiin-7-yl | 5-trifluoro-methylpyridin-2-yl | CF$_3$ | |
| 2820 | 4,4-dioxide-8-Me-2,3-dihydro-1,4-benzoxathiin-7-yl | pyrimidin-2-yl | H | |
| 2821 | 4,4-dioxide-8-Me-2,3-dihydro-1,4-benzoxathiin-7-yl | pyrimidin-2-yl | methyl | |
| 2822 | 4,4-dioxide-8-Me-2,3-dihydro-1,4-benzoxathiin-7-yl | pyrimidin-2-yl | i-propyl | |
| 2823 | 4,4-dioxide-8-Me-2,3-dihydro-1,4-benzoxathiin-7-yl | pyrimidin-2-yl | cyclopropyl | |
| 2824 | 4,4-dioxide-8-Me-2,3-dihydro-1,4-benzoxathiin-7-yl | pyrimidin-2-yl | CF$_3$ | |
| 2825 | 4,4-dioxide-8-Me-2,3-dihydro-1,4-benzoxathiin-7-yl | pyrimidin-4-yl | H | |

-continued

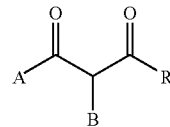

(I)

| Compound N | A | B | R | m.p. (° C.) |
|---|---|---|---|---|
| 2826 | 4,4-dioxide-8-Me-2,3-dihydro-1,4-benzoxathiin-7-yl | pyrimidin-4-yl | methyl | |
| 2827 | 4,4-dioxide-8-Me-2,3-dihydro-1,4-benzoxathiin-7-yl | pyrimidin-4-yl | i-propyl | |
| 2828 | 4,4-dioxide-8-Me-2,3-dihydro-1,4-benzoxathiin-7-yl | pyrimidin-4-yl | cyclopropyl | |
| 2829 | 4,4-dioxide-8-Me-2,3-dihydro-1,4-benzoxathiin-7-yl | pyrimidin-4-yl | CF$_3$ | |
| 2830 | 4,4-dioxide-8-Me-2,3-dihydro-1,4-benzoxathiin-7-yl | 6-chloro-pyrimidin-4-yl | methyl | |
| 2831 | 4,4-dioxide-8-Me-2,3-dihydro-1,4-benzoxathiin-7-yl | 6-chloro-pyrimidin-4-yl | i-propyl | |
| 2832 | 4,4-dioxide-8-Me-2,3-dihydro-1,4-benzoxathiin-7-yl | 6-chloro-pyrimidin-4-yl | cyclopropyl | |
| 2833 | 4,4-dioxide-8-Me-2,3-dihydro-1,4-benzoxathiin-7-yl | 6-chloro-pyrimidin-4-yl | CF$_3$ | |
| 2834 | 4,4-dioxide-8-Me-2,3-dihydro-1,4-benzoxathiin-7-yl | pyridazin-3-yl | H | |
| 2835 | 4,4-dioxide-8-Me-2,3-dihydro-1,4-benzoxathiin-7-yl | pyridazin-3-yl | methyl | |
| 2836 | 4,4-dioxide-8-Me-2,3-dihydro-1,4-benzoxathiin-7-yl | pyridazin-3-yl | i-propy | |
| 2837 | 4,4-dioxide-8-Me-2,3-dihydro-1,4-benzoxathiin-7-yl | pyridazin-3-yl | cyclopropyl | |
| 2838 | 4,4-dioxide-8-Me-2,3-dihydro-1,4-benzoxathiin-7-yl | pyridazin-3-yl | CF$_3$ | |
| 2839 | 4,4-dioxide-8-Me-2,3-dihydro-1,4-benzoxathiin-7-yl | 6-chloro-pyridazin-3-yl | methyl | |
| 2840 | 4,4-dioxide-8-Me-2,3-dihydro-1,4-benzoxathiin-7-yl | 6-chloro-pyridazin-3-yl | i-propyl | |
| 2841 | 4,4-dioxide-8-Me-2,3-dihydro-1,4-benzoxathiin-7-yl | 6-chloro-pyridazin-3-yl | cyclopropyl | |
| 2842 | 4,4-dioxide-8-Me-2,3-dihydro-1,4-benzoxathiin-7-yl | 6-chloro-pyridazin-3-yl | CF$_3$ | |

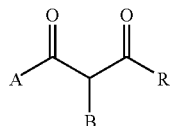 (I)

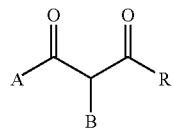 (I)

| Compound N | A | B | R | m.p. (°C.) |
|---|---|---|---|---|
| 2843 | 4,4-dioxide-8-Me-2,3-dihydro-1,4-benzoxathiin-7-yl | pyrazin-2-yl | methyl | |
| 2844 | 4,4-dioxide-8-Me-2,3-dihydro-1,4-benzoxathiin-7-yl | pyrazin-2-yl | i-propyl | |
| 2845 | 4,4-dioxide-8-Me-2,3-dihydro-1,4-benzoxathiin-7-yl | pyrazin-2-yl | cyclopropyl | |
| 2846 | 4,4-dioxide-8-Me-2,3-dihydro-1,4-benzoxathiin-7-yl | pyrazin-2-yl | $CF_3$ | |
| 2847 | 4,4-dioxide-8-Me-2,3-dihydro-1,4-benzoxathiin-7-yl | triazin-2-yl | methyl | |
| 2848 | 4,4-dioxide-8-Me-2,3-dihydro-1,4-benzoxathiin-7-yl | triazin-2-yl | i-propyl | |
| 2849 | 4,4-dioxide-8-Me-2,3-dihydro-1,4-benzoxathiin-7-yl | triazin-2-yl | cyclopropyl | |
| 2850 | 4,4-dioxide-8-Me-2,3-dihydro-1,4-benzoxathiin-7-yl | triazin-2-yl | $CF_3$ | |
| 2851 | 4,4-dioxide-8-Me-2,3-dihydro-1,4-benzoxathiin-7-yl | quinolin-2-yl | methyl | |
| 2852 | 4,4-dioxide-8-Me-2,3-dihydro-1,4-benzoxathiin-7-yl | quinolin-2-yl | i-propyl | |
| 2853 | 4,4-dioxide-8-Me-2,3-dihydro-1,4-benzoxathiin-7-yl | quinolin-2-yl | cyclopropyl | |
| 2854 | 4,4-dioxide-8-Me-2,3-dihydro-1,4-benzoxathiin-7-yl | quinolin-2-yl | $CF_3$ | |
| 2855 | 4,4-dioxide-8-Me-2,3-dihydro-1,4-benzoxathiin-7-yl | 4,4,6-trimethyl-5,6-dihydro-1,3(4H)-oxazin-2-yl | H | |
| 2856 | 4,4-dioxide-8-Me-2,3-dihydro-1,4-benzoxathiin-7-yl | 4,4,6-trimethyl-5,6-dihydro-1,3(4H)-oxazin-2-yl | methyl | |
| 2857 | 4,4-dioxide-8-Me-2,3-dihydro-1,4-benzoxathiin-7-yl | 4,4,6-trimethyl-5,6-dihydro-1,3(4H)-oxazin-2-yl | i-propyl | |
| 2858 | 4,4-dioxide-8-Me-2,3-dihydro-1,4-benzoxathiin-7-yl | 4,4,6-trimethyl-5,6-dihydro-1,3(4H)-oxazin-2-yl | cyclopropyl | |
| 2859 | 4,4-dioxide-8-Me-2,3-dihydro-1,4-benzoxathiin-7-yl | 4,4,6-trimethyl-5,6-dihydro-1,3(4H)-oxazin-2-yl | $CF_3$ | |
| 2860 | 4,4-dioxide-8-Me-2,3-dihydro-1,4-benzoxathiin-7-yl | 2-oxazolidinon-3-yl | H | |
| 2861 | 4,4-dioxide-8-Me-2,3-dihydro-1,4-benzoxathiin-7-yl | 2-oxazolidinon-3-yl | methyl | |
| 2862 | 4,4-dioxide-8-Me-2,3-dihydro-1,4-benzoxathiin-7-yl | 2-oxazolidinon-3-yl | i-propyl | |
| 2863 | 4,4-dioxide-8-Me-2,3-dihydro-1,4-benzoxathiin-7-yl | 2-oxazolidinon-3-yl | cyclopropyl | |
| 2864 | 4,4-dioxide-8-Me-2,3-dihydro-1,4-benzoxathiin-7-yl | 2-oxazolidinon-3-yl | $CF_3$ | |
| 2865 | 4,4-dioxide-8-Me-2,3-dihydro-1,4-benzoxathiin-7-yl | 2-pyrrolidinon-1-yl | methyl | |
| 2866 | 4,4-dioxide-8-Me-2,3-dihydro-1,4-benzoxathiin-7-yl | 2-pyrrolidinon-1-yl | i-propyl | |
| 2867 | 4,4-dioxide-8-Me-2,3-dihydro-1,4-benzoxathiin-7-yl | 2-pyrrolidinon-1-yl | cyclopropyl | |
| 2868 | 4,4-dioxide-8-Me-2,3-dihydro-1,4-benzoxathiin-7-yl | 2-pyrrolidinon-1-yl | $CF_3$ | |
| 2869 | 4,4-dioxide-8-Me-2,3-dihydro-1,4-benzoxathiin-7-yl | 3-methylisoxazol-5-yl | methyl | |
| 2870 | 4,4-dioxide-8-Me-2,3-dihydro-1,4-benzoxathiin-7-yl | 3-methylisoxazol-5-yl | i-propyl | |
| 2871 | 4,4-dioxide-8-Me-2,3-dihydro-1,4-benzoxathiin-7-yl | 3-methylisoxazol-5-yl | cyclopropyl | |
| 2872 | 4,4-dioxide-8-Me-2,3-dihydro-1,4-benzoxathiin-7-yl | 3-methylisoxazol-5-yl | $CF_3$ | |
| 2873 | 4,4-dioxide-8-Me-2,3-dihydro-1,4-benzoxathiin-7-yl | 2-$NO_2$-4-$SO_2$MePh | H | |
| 2874 | 4,4-dioxide-8-Me-2,3-dihydro-1,4-benzoxathiin-7-yl | 2-$NO_2$-4-$SO_2$MePh | methyl | |
| 2875 | 4,4-dioxide-8-Me-2,3-dihydro-1,4-benzoxathiin-7-yl | 2-$NO_2$-4-$SO_2$MePh | i-propyl | |
| 2876 | 4,4-dioxide-8-Me-2,3-dihydro-1,4-benzoxathiin-7-yl | 2-$NO_2$-4-$SO_2$MePh | cyclopropyl | |
| 2877 | 4,4-dioxide-8-Me-2,3-dihydro-1,4-benzoxathiin-7-yl | 2-$NO_2$-4-$SO_2$MePh | $CF_3$ | |

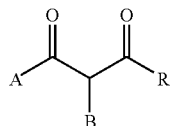

(I)

| Compound N | A | B | R | m.p. (° C.) |
|---|---|---|---|---|
| 2878 | 1,4-benzoxathiin-7-yl 4,4-dioxide-8-Me-2,3-dihydro-1,4-benzoxathiin-7-yl | 2-Cl-4-SO₂MePh | H | |
| 2879 | 4,4-dioxide-8-Me-2,3-dihydro-1,4-benzoxathiin-7-yl | 2-Cl-4-SO₂MePh | methyl | |
| 2880 | 4,4-dioxide-8-Me-2,3-dihydro-1,4-benzoxathiin-7-yl | 2-Cl-4-SO₂MePh | i-propyl | |
| 2881 | 4,4-dioxide-8-Me-2,3-dihydro-1,4-benzoxathiin-7-yl | 2-Cl-4-SO₂MePh | cyclopropyl | |
| 2882 | 4,4-dioxide-8-Me-2,3-dihydro-1,4-benzoxathiin-7-yl | 2-Cl-4-SO₂MePh | CF₃ | |
| 2883 | 4,4-dioxide-8-Me-2,3-dihydro-1,4-benzoxathiin-7-yl | 2-NO₂-4-CF₃Ph | H | |
| 2884 | 4,4-dioxide-8-Me-2,3-dihydro-1,4-benzoxathiin-7-yl | 2-NO₂-4-CF₃Ph | methyl | |
| 2885 | 4,4-dioxide-8-Me-2,3-dihydro-1,4-benzoxathiin-7-yl | 2-NO₂-4-CF₃Ph | i-propyl | |
| 2886 | 4,4-dioxide-8-Me-2,3-dihydro-1,4-benzoxathiin-7-yl | 2-NO₂-4-CF₃Ph | cyclopropyl | |
| 2887 | 4,4-dioxide-8-Me-2,3-dihydro-1,4-benzoxathiin-7-yl | 2-NO₂-4-CF₃Ph | CF₃ | |
| 2888 | 4,4-dioxide-8-Me-2,3-dihydro-1,4-benzoxathiin-7-yl | 2-NO₂-4-ClPh | H | |
| 2889 | 4,4-dioxide-8-Me-2,3-dihydro-1,4-benzoxathiin-7-yl | 2-NO₂-4-ClPh | methyl | |
| 2890 | 4,4-dioxide-8-Me-2,3-dihydro-1,4-benzoxathiin-7-yl | 2-NO₂-4-ClPh | i-propyl | |
| 2891 | 4,4-dioxide-8-Me-2,3-dihydro-1,4-benzoxathiin-7-yl | 2-NO₂-4-ClPh | cyclopropyl | |
| 2892 | 4,4-dioxide-8-Me-2,3-dihydro-1,4-benzoxathiin-7-yl | 2-NO₂-4-ClPh | CF₃ | |
| 2893 | 4,4-dioxide-8-Me-2,3-dihydro-1,4-benzoxathiin-7-yl | 2-Cl-4-NO₂Ph | H | |
| 2894 | 4,4-dioxide-8-Me-2,3-dihydro-1,4-benzoxathiin-7-yl | 2-Cl-4-NO₂Ph | methyl | |

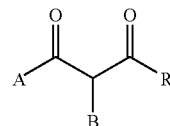

(I)

| Compound N | A | B | R | m.p. (° C.) |
|---|---|---|---|---|
| 2895 | 4,4-dioxide-8-Me-2,3-dihydro-1,4-benzoxathiin-7-yl | 2-Cl-4-NO₂Ph | i-propyl | |
| 2896 | 4,4-dioxide-8-Me-2,3-dihydro-1,4-benzoxathiin-7-yl | 2-Cl-4-NO₂Ph | cyclopropyl | |
| 2897 | 4,4-dioxide-8-Me-2,3-dihydro-1,4-benzoxathiin-7-yl | 2-Cl-4-NO₂Ph | CF₃ | |
| 2898 | 4,4-dioxide-8-Me-2,3-dihydro-1,4-benzoxathiin-7-yl | 2,4-(NO₂)₂Ph | H | |
| 2899 | 4,4-dioxide-8-Me-2,3-dihydro-1,4-benzoxathiin-7-yl | 2,4-(NO₂)₂Ph | methyl | |
| 2900 | 4,4-dioxide-8-Me-2,3-dihydro-1,4-benzoxathiin-7-yl | 2,4-(NO₂)₂Ph | i-propyl | |
| 2901 | 4,4-dioxide-8-Me-2,3-dihydro-1,4-benzoxathiin-7-yl | 2,4-(NO₂)₂Ph | cyclopropyl | |
| 2902 | 4,4-dioxide-8-Me-2,3-dihydro-1,4-benzoxathiin-7-yl | 2,4-(NO₂)₂Ph | CF₃ | |
| 2903 | 4,4-dioxide-8-Me-2,3-dihydro-1,4-benzoxathiin-7-yl | 4-F-3-NO₂Ph | H | |
| 2904 | 4,4-dioxide-8-Me-2,3-dihydro-1,4-benzoxathiin-7-yl | 4-F-3-NO₂Ph | methyl | |
| 2905 | 4,4-dioxide-8-Me-2,3-dihydro-1,4-benzoxathiin-7-yl | 4-F-3-NO₂Ph | i-propyl | |
| 2906 | 4,4-dioxide-8-Me-2,3-dihydro-1,4-benzoxathiin-7-yl | 4-F-3-NO₂Ph | cyclopropyl | |
| 2907 | 4,4-dioxide-8-Me-2,3-dihydro-1,4-benzoxathiin-7-yl | 4-F-3-NO₂Ph | CF₃ | |
| 2908 | 4,4-dioxide-8-Me-2,3-dihydro-1,4-benzoxathiin-7-yl | 3,5-(CF₃)₂Ph | H | |
| 2909 | 4,4-dioxide-8-Me-2,3-dihydro-1,4-benzoxathiin-7-yl | 3,5-(CF₃)₂Ph | methyl | |
| 2910 | 4,4-dioxide-8-Me-2,3-dihydro-1,4-benzoxathiin-7-yl | 3,5-(CF₃)₂Ph | i-propyl | |
| 2911 | 4,4-dioxide-8-Me-2,3-dihydro-1,4-benzoxathiin-7-yl | 3,5-(CF₃)₂Ph | cyclopropyl | |

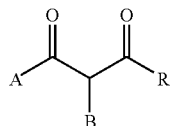

(I)

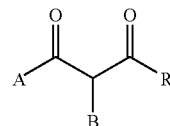

(I)

| Compound N | A | B | R | m.p. (° C.) |
|---|---|---|---|---|
| 2912 | 4,4-dioxide-8-Me-2,3-dihydro-1,4-benzoxathiin-7-yl | 3,5-(CF₃)₂Ph | CF₃ | |
| 2913 | 4,4-dioxide-8-Me-2,3-dihydro-1,4-benzoxathiin-7-yl | 2-SO₂Me-4-CF₃Ph | H | |
| 2914 | 4,4-dioxide-8-Me-2,3-dihydro-1,4-benzoxathiin-7-yl | 2-SO₂Me-4-CF₃Ph | methyl | |
| 2915 | 4,4-dioxide-8-Me-2,3-dihydro-1,4-benzoxathiin-7-yl | 2-SO₂Me-4-CF₃Ph | i-propyl | |
| 2916 | 4,4-dioxide-8-Me-2,3-dihydro-1,4-benzoxathiin-7-yl | 2-SO₂Me-4-CF₃Ph | cyclopropyl | |
| 2917 | 4,4-dioxide-8-Me-2,3-dihydro-1,4-benzoxathiin-7-yl | 2-SO₂Me-4-CF₃Ph | CF₃ | |
| 2918 | 2-Cl-4-SO₂MePh | 2-trifluoro-methyl-1,3,4-thiadiazol-5-yl | cyclopropyl | 185 |
| 2919 | 2-Cl-4-SO₂MePh | 1,1-dioxido-3-oxo-1,2-benzisothiazol-2(3H)-yl | cyclopropyl | |
| 2920 | 4-Cl-Ph | 2-t-butyl-1,3,4-oxadiazol-5-yl | CF₃ | 166 |
| 2921 | 2-Me-6-CF₃pyridin-3-yl | 2-methyltetrazol-5-yl | cyclopropyl | |
| 2922 | 2-[(2-methoxyethoxy)methyl]-6-CF₃ pyridin-3-yl | 2-methyltetrazol-5-yl | cyclopropyl | oil |
| 2923 | 2-Cl-4-SO₂MePh | 2,5-dioxopyrrolidin-1-yl | cyclopropyl | |
| 2924 | 2-Cl-4-SO₂MePh | 2-oxopyridin-1(2H)-yl | cyclopropyl | |
| 2925 | 2-Cl-4-SO₂MePh | 2-oxoquinolin-1(2H)-yl | cyclopropyl | |
| 2926 | 2-Cl-4-SO₂MePh | 1,2-benzisoxazol-3-yl | cyclopropyl | |
| 2927 | 2-Cl-4-SO₂MePh | 2-oxo-1,3-benzoxazol-3(2H)-yl | cyclopropyl | |
| 2928 | 2-Cl-4-SO₂MePh | 3-oxo-2,3-dihydro-4H-1,4-benzoxazin-4-yl | cyclopropyl | |
| 2929 | 2-Cl-4-SO₂MePh | 2-oxopyrimidin-1(2H)-yl | cyclopropyl | |
| 2930 | 2-Cl-4-SO₂MePh | 1H-1,2,3-benzotriazol-1-yl | cyclopropyl | |
| 2931 | 2-NO₂-4-SO₂MePH | 2,5-dioxopyrrolidin-1-yl | cyclopropyl | |
| 2932 | 2-NO₂-4-SO₂MePH | 2-oxopyridin-1(2H)-yl | cyclopropyl | |
| 2933 | 2-NO₂-4-SO₂MePH | 2-oxoquinolin-1(2H)-yl | cyclopropyl | |
| 2934 | 2-NO₂-4-SO₂MePH | 1,2,-benzisoxazol-3-yl | cyclopropyl | |
| 2935 | 2-NO₂-4-SO₂MePH | 2-oxo-1,3-benzoxazol-3(2H)-yl | cyclopropyl | |
| 2936 | 2-NO₂-4-SO₂MePH | 3-oxo-2,3-dihydro-4H-1,4-benzoxazin-4-yl | cyclopropyl | |
| 2937 | 2-NO₂-4-SO₂MePH | 2-oxopyrimidin-1(2H)-yl | cyclopropyl | |
| 2938 | 2-NO₂-4-SO₂MePH | 1H-1,2,3-benzotriazol-1-yl | cyclopropyl | |

EXAMPLE 31

Determination of the Herbicidal Activity and Phyto-Toxicity in Pre-Emergence The herbicidal activity of the compounds of the invention in pre-emergence was evaluated according to the following operative procedures.

The plant species of interest (weeds or crops) were sown in pots with an upper diameter of 10 cm, a height of 10 cm and containing sandy soil. 10 pots were used for each plant species.

Water was added to each pot in such a quantity as to germinate the seeds. The pots were divided into two groups, each containing 5 pots for each weed or crop.

After one day from the sowing, the first set of pots was treated with a hydro-acetonic dispersion containing acetone at 10% in volume, the product under evaluation at the desired concentration and Tween 20 at 0.5%.

The second set was treated with a hydro-acetonic solution only, containing acetone at 10% in volume and Tween 20 at 0.5%, and was used as comparison (blank).

All pots were kept under observation in a conditioned environment under the following conditions:
temperature: 24° C.;
relative humidity: 60%;
photoperiod: 16 hours;
light intensity: 10000 lux.

The pots were uniformly watered in order to ensure a sufficient humidity degree for a good development of the plants.

Fifteen days after the treatment, the herbicidal activity was evaluated on the basis of the following values, which refer to the damage percentage tested on the treated plants, with respect to the non-treated plants (blank):

| | |
|---|---|
| 0 = | 0-10% damage; |
| 1 = | 11-30% damage; |
| 2 = | 31-50% damage; |
| 3 = | 51-70% damage; |
| 4 = | 71-90% damage; |
| 5 = | 91% damage - death of the plant. |

Table 3 shows the results obtained by treating the plant species listed below with compounds 6, 7 and 11 with a dosage of 500 g/ha:

*Abutilon theofrasti* (AT); *Amaranthus retroflexus* (AR); *Chenopodium album* (CA); *Galium aparine* (GA); *Ipomea purpurea* (IP); *Portulaca oleracea* (PO); *Solanum nigrum* (SN); *Stellaria media* (SM).

TABLE 3

Pre-emergence herbicidal activity at rate of 500 g/ha

| | Plant species: | | | | | | | |
|---|---|---|---|---|---|---|---|---|
| | AT | AR | CA | GA | IP | PO | SN | SM |
| Compound N° 6: | 5 | 5 | 5 | 5 | 5 | 5 | 5 | 5 |
| Compound N° 7: | 5 | 5 | 5 | — | — | 5 | 5 | 5 |
| Compound N° 11: | 5 | — | 5 | — | 5 | 5 | — | — |

EXAMPLE 32

Determination of the Herbicidal Activity and Phyto-Toxicity in Post-emergence

The herbicidal activity of the compounds of the invention in post-emergence was evaluated according to the following operative procedures.

The plant species of interest (weeds or crops) were sown in pots with an upper diameter of 10 cm, a height of 10 cm and containing sandy soil. 10 pots were used for each plant species.

Water was added to each pot in such a quantity as to germinate the seeds. The pots were divided into two groups, each containing 5 pots for each weed or crop.

Fifteen days after sowing (ten, in the case of wheat), when the weeds and crops, according to the species, were 10-15 cm high, the first set of pots was treated with a hydro-acetonic dispersion containing acetone at 10% in volume, the product under evaluation at the desired concentration and Tween 20 at 0.5%.

The second set was treated with a hydro-acetonic solution only, containing acetone at 10% in volume and Tween 20 at 0.5%, and was used as comparison (blank).

All pots were kept under observation in a conditioned environment under the following conditions:
temperature: 24° C.;
relative humidity: 60%;
photo-period: 16 hours;
light intensity: 10000 lux.

The pots were uniformly watered every other day so as to ensure a humidity degree sufficient for a good development of the plants.

The herbicidal activity was evaluated fifteen days after the treatment, on the basis of the following values which refer to the percentage of damage tested on the treated plants with respect to the non-treated plants (blank):

| 0 = | 0-10% damage; |
|---|---|
| 1 = | 11-30% damage; |
| 2 = | 31-50% damage; |
| 3 = | 51-70% damage; |
| 4 = | 71-90% damage; |
| 5 = | 91% damage - death of the plant. |

Table 4 shows the results obtained by treating the plant species listed below with compounds 6 and 11 with a dosage of 500 g/ha:

*Abutilon theofrasti* (AT); *Chenopodium album* (CA); *Galium aparine* (GA); *Portulaca oleracea* (PO); *Solanum nigrum* (SN); *Stellaria media* (SM).

TABLE 4

Post-emergence herbicidal activity at rate of 500 g/ha

| | Plant species: | | | | | |
|---|---|---|---|---|---|---|
| | AT | CA | GA | PO | SN | SM |
| Compound N° 6: | 5 | 5 | 5 | 5 | 5 | 5 |
| Compound N° 11: | 5 | 5 | — | — | 5 | — |

The invention claimed is:

1. Compounds having general formula (I)

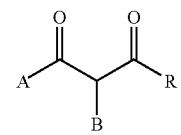

wherein:
A represents a phenyl or a pyridyl group substituted by one or more substituents selected from halogen, $NO_2$, CN, CHO, OH, linear or branched $C_1$-$C_6$ alkyl, linear or branched $C_1$-$C_6$ haloalkyl, linear or branched $C_1$-$C_6$ alkoxy, linear or branched $C_1$-$C_6$ haloalkoxy, $C_1$-$C_6$ cyanoalkyl, $C_2$-$C_6$ alkoxyalkyl, $C_2$-$C_6$ alkylthioalkyl, $C_2$-$C_6$ alkylsulfinyl -alkyl, $C_2$-$C_6$ alkylsulfonylalkyl, $C_2$-$C_6$ haloalkoxyalkyl, $C_2$-$C_6$ haloalkyl -thioalkyl, $C_2$-$C_6$ haloalkylsulfinylalkyl, $C_2$-$C_6$ haloalkylsulfonylalkyl, $C_2$-$C_6$ alkoxyalkoxy, $C_2$-$C_6$ haloalkoxyalkoxy, $C_2$-$C_6$ alkylthioalkoxy, $C_2$-$C_6$ haloalkylthioalkoxy, $C_3$-$C_{12}$ dialkoxyalkyl, $C_3$-$C_{12}$ dialkylthioalkyl, $C_3$-$C_{12}$ dialkylthioalkoxy, $C_3$-$C_{12}$ dialkoxyalkoxy, $C_2$-$C_6$ haloalkoxyhaloalkoxy, $C_3$-$C_{10}$ alkoxyalkoxyalkyl, —S(O)$_m$ $R_1$, —OS(O)$_t$$R_1$, —SO$_2$NR$_2$R$_3$, -Q, —ZQ$_1$;
B represents a D-(R$_x$)$_n$ group;
R represents a cyclopropyl group;
R$_1$ represents a $C_1$-$C_6$ alkyl group or a $C_1$-$C_6$ haloalkyl group;
m is equal to 0, 1 or 2;
t is equal to 1 or 2;
R$_2$ and R$_3$, the same or different, represent a hydrogen atom, a linear or branched $C_1$-$C_6$ alkyl group in turn optionally substituted with halogen atoms;
Q and Q$_1$, represent an aryl group, a $C_3$-$C_6$ cycloalkyl group, or a heterocyclic group selected from pyrazolyl, tetrazolyl, tetrazolonyl oxazolyl, thiazolyl, oxadiazolyl, thiadiazolyl, isothiazolyl, isoxazolinyl, 1,3-dioxolanyl, tetrahydropyranyl, oxethanyl, oxyranyl, thiazolidinyl, oxazolidinyl; said groups optionally substituted by one or more substituents selected from halogen, $NO_2$, OH, CN, CHO, linear or branched $C_1$-$C_6$ alkyl, linear or branched $C_1$-$C_6$ haloalkyl, linear or branched $C_1$-$C_6$ alkoxy, linear or branched $C_1$-$C_6$ haloalkoxy
Z is O, S(O)$_r$;
r is equal to 0, 1 or 2;
D represents a monocyclic heteroaryl group selected from 1,2,4-oxadiazolyl, tetrazolyl, thiazolyl or 2- pyridyl;
R$_x$ represents a substituent selected from: hydrogen, halogen, $NO_2$, CN, CHO, OH, linear or branched $C_1$-$C_6$ alkyl, linear or branched $C_1$-$C_6$ haloalkyl, linear or branched $C_1$-$C_6$ alkoxy, linear or branched $C_1$-$C_6$ haloalkoxy, $C_1$-$C_6$ cyanoalkyl, $C_2$-$C_6$ alkoxyalky, $C_2$-$C_6$ alkylthioalkyl, $C_2$-$C_6$ alkylsulfinylalkyl, $C_2$-$C_6$ alkylsulfonylalkyl, $C_2$-$C_6$ haloalkoxyalky, $C_2$-$C_6$ haloalkylthioalkyl, $C_2$-$C_6$ haloalkylsulfinylalkyl, $C_2$-$C_6$ haloalkylsulfonylalkyl, $C_2$-$C_6$ alkoxyalkoxy or $C_2$-$C_6$ haloalkoxyalkoxy, $C_2$-$C_6$ haloalkylthioalkoxy, $C_3$-$C_{12}$ dialkoxyalkyl, $C_3$-$C_{12}$ dialkylthioalkyl, $C_3$-$C_{12}$ dialkylthioalkoxy, $C_3$-$C_{12}$ dialkoxyalkoxy, $C_2$-$C_6$ haloalkoxyhalo-alkoxy, $C_3$-$C_{10}$ alkoxyalkoxyalkyl;

if several $R_x$ groups are present, these can be the same or different;

n =1-4.

2. A compound according to claims 1, characterized in that the compounds having formula (I) are present as tautomeric forms, pure or as blends of tautomeric forms, in any proportion whatsoever.

3. Herbicidal compositions containing, one or more compounds having general formula (I):

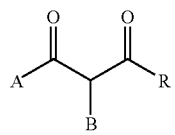

(I)

wherein A, B and R have the meanings according to claim 1.

4. The herbicidal compositions according to claim 3, including other herbicides, fungicides, insecticides, acaricides, fertilizers, compatible with the compounds having general formula (I).

5. The herbicidal compositions according to claim 4, characterized in that the additional herbicides are selected from:
acetochlor, acifluorfen, aclonifen, AKH-7088, alachlor, alloxydim, ametryn, amicarbazone, amidosulfuron, amitrole, anilofos, asulam, atrazine, azafenidin, azimsulfuron, aziprotryne, BAS 670 H, BAY MKH 6561, beflubutamid, benazolin, benfluralin, benfuresate, bensulfuron, bensulide, bentazone, benzfendizone, benzobicyclon, benzofenap, benzthiazuron, bifenox, bilanafos, bispyribac-sodium, bromacil, bromobutide, bromofenoxim, bromoxynil, butachlor, butafenacil, butamifos, butenachlor, butralin, butroxydim, butylate, cafenstrole, carbetamide, carfentrazone-ethyl, chlomethoxyfen, chloramben, chlorbromuron, chlorbufam, chlorflurenol, chloridazon, chlorimuron, chlornitrofen, chlorotoluron, chloroxuron, chlorpropham, chlorsulfuron, chlorthal, chlorthiamid, cinidon ethyl, cinmethylin, cinosulfuron, clethodim, clodinafop, clomazone, clomeprop, clopyralid, cloransulam -methyl, cumyluron (JC-940), cyanazine, cycloate, cyclosulfamuron, cycloxydim, cyhalofop-butyl, 2,4-D, 2,4-DB, daimuron, dalapon, desmedipham, desmetryn, dicamba, dichlobenil, dichlorprop, dichlorprop-P, diclofop, diclosulam, diethatyl, difenoxuron, difenzoquat, diflufenican, diflufenzopyr, dimefuron, dimepiperate, dimethachlor, dimethametryn, dimethenamid, dinitramine, dinosseb, dinoseb acetate, dinoterb, diphenamid, dipropetryn, diquat, dithiopyr, 1-diuron, eglinazine, endothal, EPTC, espropcarb, ethalfluralin, ethametsulfuron-methyl, ethidimuron, ethiozin (SMY 1500), ethofumesate, ethoxyfen-ethyl (HC-252), ethoxysulfuron, etobenzanid (HW 52), fenoxaprop, fenoxaprop-P, fentrazamide, fenuron, flamprop, flamprop-M, flazasulfuron, florasulam, fluazifop, fluazifop-P, fluazolate (JV 485), flucarbazone-sodium, fluchloralin, flufenacet, flufenpyr ethyl, flumetsulam, flumiclorac-pentyl, flumioxazin, flumipropin, fluometuron, fluoroglycofen, fluoronitrofen, flupoxam, flupproanate, flupyrsulfuron, flurenol, fluridone, flurochloridone, fluroxypyr, flurtamone, fluthiacet-methyl, fomesafen, foramsulfuron, fosamine, furyloxyfen, glufosinate, glyphosate, halosulfuron-methyl, haloxyfop, haloxyfop-P-methyl, hexazinone, imazamethabenz, imazamox, imazapic, imazapyr, imazaquin, imazethapyr, imazosulfuron, indanofan, iodosulfuron, ioxynil, isopropalin, isoproturon, isouron, isoxaben, isoxachlortole, isoxaflutole, isoxapyrifop, KPP-421, lactofen, lenacil, linuron, LS830556, MCPA, MCPA-thioethyl, MCPB, mecoprop, mecoprop-P, mefenacet, mesosulfuron, mesotrione, metamitron, metazachlor, methabenzthiazuron, methazole, methoprotryne, methyldymron, metobenzuron, metobromuron, metolachlor, S-metolachlor, metosulam, metoxuron, metribuzin, metsulfuron, molinate, monalide, monolinuron, naproanilide, napropamide, naptalam, NC-330, neburon, nicosulfuron, nipyraclofen, norflurazon, orbencarb, oryzalin, oxadiargyl, oxadiazon, oxasulfuron, oxaziclomefone, oxyfluorfen, paraquat, pebulate, pendimethalin, penoxsulam, pentanochlor, pentoxazone, pethoxamid, phenmedipham, picloram, picolinafen, piperophos, pretilachlor, primisulfuron, prodiamine, profluazol, proglinazine, prometon, prometryne, propachlor, propanil, propaquizafop, propazine, propham, propisochlor, propyzamide, prosulfocarb, prosulfuron, pyraclonil, pyraflufen-ethyl, pyrazogyl (HAS-961), pyrazolynate, pyrazosulfuron, pyrazoxyfen, pyribenzoxim, pyributicarb, pyridafol, pyridate, pyriftalid, pyriminobac-methyl, pyrithiobac-sodium, quinclorac, quinmerac, quizalofop, quizalofop-P, rimsulfuron, sethoxydim, siduron, simazine, simetryn, sulcotrione, sulfentrazone, sulfometuron-methyl, sulfosulfuron, 2,3, 6-TBA, TCA-sodium, tebutam, tebuthiuron, tepraloxydim, terbacil, terbumeton, terbuthyl-azine, terbutryn, thenylchlor, thiazafluron, thiazopyr, thidiazimin, thifensulfuron -methyl, thiobencarb, tiocarbazil, tioclorim, tralkoxydim, tri-allate, triasulfuron, triaziflam, tribenuron, triclopyr, trietazine, trifloxysulfuron, trifluralin, triflusulfuron-methyl, tritosulfuron, UBI-C4874, vernolate.

6. The compositions according to any of the claims 3-5, characterized in that the concentration of active substance ranges from 1 to 90%.

* * * * *